United States Patent
Hagedorn et al.

(10) Patent No.: US 12,163,131 B2
(45) Date of Patent: *Dec. 10, 2024

(54) OLIGONUCLEOTIDES FOR MODULATING TAU EXPRESSION

(71) Applicant: HOFFMANN-LA ROCHE INC., Little Falls, NJ (US)

(72) Inventors: Peter Hagedorn, Hørsholm (DK); Anja Mølhart Høg, Hillerød (DK); Marianne L. Jensen, Køge (DK); Richard E. Olson, Wallingford, CT (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/581,855

(22) Filed: Jan. 21, 2022

(65) Prior Publication Data

US 2022/0177884 A1 Jun. 9, 2022

Related U.S. Application Data

(63) Continuation of application No. 16/503,340, filed on Jul. 3, 2019, now Pat. No. 11,279,929.

(60) Provisional application No. 62/726,005, filed on Aug. 31, 2018, provisional application No. 62/693,851, filed on Jul. 3, 2018.

(51) Int. Cl.
*C07H 21/04* (2006.01)
*C12N 15/113* (2010.01)

(52) U.S. Cl.
CPC .... *C12N 15/113* (2013.01); *C12Y 301/26004* (2013.01); *C12N 2310/11* (2013.01); *C12N 2310/315* (2013.01); *C12N 2310/32* (2013.01); *C12N 2310/321* (2013.01); *C12N 2310/3231* (2013.01); *C12N 2310/341* (2013.01); *C12N 2310/351* (2013.01); *C12N 2330/30* (2013.01)

(58) Field of Classification Search
None
See application file for complete search history.

(56) References Cited

U.S. PATENT DOCUMENTS

| | | |
|---|---|---|
| 4,711,955 A | 12/1987 | Ward et al. |
| 5,525,711 A | 6/1996 | Hawkins et al. |
| 5,792,608 A | 8/1998 | Swaminathan et al. |
| 5,885,968 A | 3/1999 | Biessen et al. |
| 8,090,542 B2 | 1/2012 | Khvorova et al. |
| 8,349,809 B2 | 1/2013 | Brown |
| 8,513,207 B2 | 8/2013 | Brown |
| 9,458,153 B2 | 10/2016 | Han et al. |
| 9,683,235 B2 | 6/2017 | Freier |
| 10,093,671 B2 | 10/2018 | Han et al. |
| 11,279,929 B2 | 3/2022 | Hagedorn et al. |
| 2005/0026164 A1 | 2/2005 | Zhou |
| 2005/0244851 A1 | 11/2005 | Blume et al. |
| 2005/0272080 A1 | 12/2005 | Palma et al. |
| 2006/0257851 A1 | 11/2006 | Bentwich |
| 2010/0173974 A1 | 7/2010 | Brown |
| 2010/0197762 A1 | 8/2010 | Swayze |
| 2011/0118337 A1 | 5/2011 | Chau et al. |
| 2012/0040460 A1 | 2/2012 | Rigoutsos et al. |
| 2013/0253036 A1 | 9/2013 | Collard et al. |
| 2015/0191722 A1 | 7/2015 | Krieg et al. |
| 2015/0275205 A1 | 10/2015 | Miller et al. |
| 2019/0111073 A1 | 4/2019 | Kammler et al. |
| 2019/0211339 A1 | 7/2019 | Agarwal et al. |
| 2020/0010831 A1 | 1/2020 | Hagedorn et al. |
| 2020/0147123 A1 | 5/2020 | Kammler et al. |
| 2021/0123054 A1 | 4/2021 | Høg et al. |
| 2022/0177884 A1 | 6/2022 | Hagedorn et al. |

FOREIGN PATENT DOCUMENTS

| | | |
|---|---|---|
| CL | 2017001956 A1 | 6/2018 |
| CL | 2020003457 A1 | 6/2021 |
| CL | 2021/001072 A1 | 10/2021 |
| CL | 2021001071 A1 | 10/2021 |
| EP | 0302175 A2 | 2/1989 |
| EP | 1013661 A1 | 6/2000 |
| EP | 1152009 A1 | 11/2001 |
| EP | 1752536 A1 | 2/2007 |
| EP | 2213738 B1 | 10/2012 |
| EP | 2742136 B1 | 9/2017 |
| JP | 2015-516953 A | 6/2015 |

(Continued)

OTHER PUBLICATIONS

Kalbfuss et al., "Correction of alternative splicing of tau in frontotemporal dementia and Parkinsonism linked to chromosome 17," Journal of Biological Chemistry 276(46) 42986-42993 (Nov. 16, 2001).

Carmona. S et al., "The Role of TREM2 in Alzheimer's disease and other neurodegenerative disorders," Lancet Neurology, vol. 17, 2018, pp. 721-730.

(Continued)

*Primary Examiner* — Kimberly Chong

(74) *Attorney, Agent, or Firm* — Clark & Elbing LLP; Thomas J. Takara

(57) ABSTRACT

The present invention relates to antisense oligonucleotides that are capable of modulating expression of Tau in a target cell. The oligonucleotides hybridize to MAPT mRNA. The present invention further relates to conjugates of the oligonucleotide and pharmaceutical compositions and methods for treatment of Tauopathies, Alzheimer's disease, frontotemporal dementia (FTD), FTDP-17, progressive supranuclear palsy (PSP), chronic traumatic encephalopathy (CTE), corticobasal ganglionic degeneration (CBD), epilepsy, Dravet syndrome, depression, seizure disorders and movement disorders.

15 Claims, 6 Drawing Sheets

Specification includes a Sequence Listing.

(56) References Cited

FOREIGN PATENT DOCUMENTS

| | | |
|---|---|---|
| RU | 2645259 C2 | 2/2018 |
| WO | 93/07883 A1 | 4/1993 |
| WO | 98/39352 A1 | 9/1998 |
| WO | 99/14226 A2 | 3/1999 |
| WO | 00/47599 A1 | 8/2000 |
| WO | 00/66604 A2 | 11/2000 |
| WO | 01/23613 A1 | 4/2001 |
| WO | 03/22987 A2 | 3/2003 |
| WO | 2004/046160 A2 | 6/2004 |
| WO | 2005/014806 A2 | 2/2005 |
| WO | 2007/031091 A2 | 3/2007 |
| WO | 2007/090071 A2 | 8/2007 |
| WO | 2007/106407 A2 | 9/2007 |
| WO | 2007/134181 A2 | 11/2007 |
| WO | 2007/146511 A2 | 12/2007 |
| WO | 2008/049085 A1 | 4/2008 |
| WO | 2008/113832 A2 | 9/2008 |
| WO | 2008/150729 A2 | 12/2008 |
| WO | 2008/154401 A2 | 12/2008 |
| WO | 2009/006478 A2 | 1/2009 |
| WO | 2009/067647 A1 | 5/2009 |
| WO | 2009/090182 A1 | 7/2009 |
| WO | 2009/124238 A1 | 10/2009 |
| WO | 2010/036698 A1 | 4/2010 |
| WO | 2010/040571 A2 | 4/2010 |
| WO | 2010/077578 A1 | 7/2010 |
| WO | 2010/093788 A2 | 8/2010 |
| WO | 2010/142423 A2 | 12/2010 |
| WO | 2011/017521 A2 | 2/2011 |
| WO | 2011/156202 A1 | 12/2011 |
| WO | 2012/024170 A2 | 2/2012 |
| WO | 2012/055362 A1 | 5/2012 |
| WO | 2012/109395 A1 | 8/2012 |
| WO | 2012/143379 A1 | 10/2012 |
| WO | 2012/145697 A1 | 10/2012 |
| WO | 2013/003520 A1 | 1/2013 |
| WO | 2013/022984 A1 | 2/2013 |
| WO | 2013/036868 A1 | 3/2013 |
| WO | 2013/041962 A1 | 3/2013 |
| WO | 2013/148260 A1 | 10/2013 |
| WO | 2013/154798 A1 | 10/2013 |
| WO | 2013/159109 A1 | 10/2013 |
| WO | WO-2013/148283 A1 | 10/2013 |
| WO | 2013/166264 A2 | 11/2013 |
| WO | 2014/012081 A2 | 1/2014 |
| WO | 2014/036429 A1 | 3/2014 |
| WO | 2014/076195 A1 | 5/2014 |
| WO | 2014/076196 A1 | 5/2014 |
| WO | 2014/153236 A1 | 9/2014 |
| WO | 2014/179620 A1 | 11/2014 |
| WO | 2014/179629 A2 | 11/2014 |
| WO | 2014/207232 A1 | 12/2014 |
| WO | 2015/002971 A2 | 1/2015 |
| WO | 2015/010135 A2 | 1/2015 |
| WO | 2015/031694 A2 | 3/2015 |
| WO | WO-2014/207232 A4 | 3/2015 |
| WO | 2015/113922 A1 | 8/2015 |
| WO | 2015/113990 A1 | 8/2015 |
| WO | 2015/173164 A1 | 11/2015 |
| WO | 2015/173208 A2 | 11/2015 |
| WO | 2016/019063 A1 | 2/2016 |
| WO | 2016/055601 A1 | 4/2016 |
| WO | 2016/079181 A1 | 5/2016 |
| WO | 2016/126995 A1 | 8/2016 |
| WO | 2016/127002 A1 | 8/2016 |
| WO | 2016/151523 A1 | 9/2016 |
| WO | 2016/177655 A1 | 11/2016 |
| WO | 2017/015175 A1 | 1/2017 |
| WO | 2017/027350 A2 | 2/2017 |
| WO | 2017/066712 A2 | 4/2017 |
| WO | 2017/106370 A1 | 6/2017 |
| WO | 2017/109679 A1 | 6/2017 |
| WO | 2017/178656 A1 | 10/2017 |
| WO | 2017/216390 A1 | 12/2017 |
| WO | 2017/216391 A1 | 12/2017 |
| WO | 2018/059718 A1 | 4/2018 |
| WO | 2018/064593 A1 | 4/2018 |
| WO | 2019/145543 A1 | 8/2019 |
| WO | WO-2020/007892 A1 | 1/2020 |

OTHER PUBLICATIONS

Evers. M.M. et al., "Antisense oligonucleotides in therapy for neurodegenerative disorders," Advanced Drug Delivery Review, vol. 87, 2015, pp. 90-103.

Morley. J.E et al., "Alzheimer Disease," Clin Geriatric Med, vol. 34, 2018, pp. 591-601.

Andorfer et al., "Hyperphosphorylation and aggregation of tau in mice expressing normal human tau isoforms," J Neurochem. 86(3): 582-590 (2003) (9 pages).

Ansel et al., "Pharmaceutical Dosage Forms and Drug Delivery Systems," Williams & Wilkins, 6th Edition. pp. 105-116, 194-200; 1456-1457 (1995) (41 pages).

Bastin et al., "Salt Selection and Optimisation Procedures for Pharmaceutical New Chemical Entities," Organic Process Research & Development. 4:427-435 (2000) (9 pages).

Bergstrom DE, "Unnatural Nucleosides with Unusual Base Pairing Properties," Curr Protoc Nucleic Acid Chem. Chapter 1: Unit 1.4 (2009) (1 paqe).

Caruthers et al., "Chemical Synthesis of Deoxyoligonucleotides by the Phosphoramidite Method," Methods Enzymol. 154: 287-313 (1987) (27 pages).

Chambers et al., "Highly Efficient Neural Conversion of Human ES and IPS Cells by Dual Inhibition of SMAD Siqnalinq," Nat Biotechnol. 27(3):275-280 (2009) (13 pages).

Collin et al., "Neuronal Uptake of Tau/Ps422 Antibody and Reduced Progression of Tau Pathology in a Mouse Model of Alzheimer's Disease," Brain. 137(Pt 10):2834-2846 (2014) (13 pages).

Deleavey et al., "Designing Chemically Modified Oligonucleotides for Targeted Gene Silencing," Chem Biol. 19(8):937-954 (2012) (18 pages).

DeVos et al., "Antisense Reduction of Tau in Adult Mice Protects against Seizures," The Journal of Neuroscience, 2013, vol. 33, pp. 12887-12897.

DeVos SL, Miller RL, Schoch KM, et al. Tau reduction prevents neuronal loss and reverses pathological tau deposition and seeding in mice with tauopathy. Sci Transl Med. 2017;9(374):eaag0481. doi:10.1126/scitranslmed.aag0481, 30 pgs.

Fluiter et al., "Filling the Gap in LNA Antisense Oligo Gapmers: The Effects of Unlocked Nucleic Acid (UNA) and 4?-C-Hydroxymethyl-DNA Modifications on Rnase H Recruitment and Efficacy of an LNA Gapmer," Mol Biosyst. 5(8):838-843 (2009) (6 pages).

Freier et al., "The Ups and Downs of Nucleic Acid Duplex Stability: Structure-Stability Studies on Chemically-Modified DNA:RNA Duplexes," Nucleic Acid Res. 25(22):4429-4443 (1997) (15 pages).

Gennaro et al., "Remington's Pharmaceutical Sciences," Mack Publishing Company. 17th ed., (1985) (9 pages).

Gong et al., "Multifactorial Hypothesis and Multi-targets for Alzheimer's Disease," J Alzheimers Dis. 64(s1); S107-S117 (2018) (11 pages).

Greene et al., "Protective Groups in Organic Synthesis," 3rd Ed., Wiley, N.Y. (1999) (6 pages).

Grueninger et al., "Phosphorylation of Tau at S422 is Enhanced by Abeta in TauPS2APP Triple Transgenic Mice," Neurobiol Dis. 37(2):294-306 (2010) (13 pages).

Hansen et al., "Entropy titration. A Calorimetric Method for the Determination of t..G0 (K), t..H0 and t..S0 1," Chemical Communications. 36-38, (1965) (3 pages).

Hirao et al., "Natural versus Artificial Creation of Base Pairs in DNA: Origin of Nucleobases from the Perspectives of Unnatural Base Pair Studies," Ace Chem Res. 45(12): 2055-2065 (2012) (11 pages).

Holdgate et al., "Measurements of Binding Thermodynamics in Drug Discovery," Drug Discov Today. 10(22):1543-1550 (2005) (8 pages).

(56) References Cited

OTHER PUBLICATIONS

International Preliminary Report on Patentability received for PCT Patent Application No. PCT/EP2019/067799, mailed on Jan. 14, 2021, 11 pages.

International Search Report and Written Opinion received for PCT Patent Application No. PCT/EP2019/067799, mailed on Dec. 20, 2019, 16 pages.

Langer, "New Methods of Drua Delivery," Science. 249(4976): 1527-1533 (1990) (7 pages).

Mangos et al., "Efficient RNase H-directed Cleavage of RNA Promoted by Antisense DNA or 2'F-ANA Constructs Containing Acyclic Nucleotide Inserts," J Am Chem Soc. 125(3):654-661 (2003) (8 pages).

Manoharan, "Oligonucleotide Conjugates as Potential Antisense Drugs with Improved Uptake, Biodistribution, Targeted Delivery, and Mechanism of Action," Antisense and Nucleic Acid Drug Dev. 12(2):103-128 (2004) (26 pages).

Manoharan, M., "Oligonucleolide Conjugates in Antisense Technology," Antisense Drug Technology, Marcel Dekker, Inc., 2001, Ch. 16, pp. 391-469, 81 pages.

McTigue et al., "Sequence-Dependent Thermodynamic Parameters for Locked Nucleic Acid (LNA)-DNA Duplex Formation," Biochemistry. 43(18):5388-5405 (2004) (18 pages).

Mergny et al., "Analysis of Thermal Melting Curves," Oligonucleotides. 13(6):515-537 (2003) (23 pages).

Mitsuoka et al., "A Bridged Nucleic Acid, 2',4'-BNA COC: Synthesis of Fully Modified Oligonucleotides Bearing Thymine, 5-Methylcytosine, Adenine and Guanine 2',4'-BNA COC Monomers and RNA-selective Nucleic-Acid Recognition," Nucleic Acids Res. 37(4):1225-1238 (2009) (14 pages).

Morita et al., "2'-O,4'-C-Ethylene-Bridged Nucleic Acids (ENA): Highly Nuclease-Resistant and Thermodynamically Stable Oligonucleotides for Antisense Drug," Bioorg Med Chem Lett. 12(1): 73-76 (2002) (4 pages).

Office Action received for Japanese Patent Application No. 2020-573180, mailed on Feb. 8, 2022, 7 pages (4 pages of English Translation and 3 pages of Original Document).

Polydoro et al., "Age-Dependent Impairment of Cognitive and Synaptic Function in the htau Mouse Model of Tau Patholoqy," J Neurosci. 29(34):10741-10749 (2009) (9 pages).

Remington: Pharmaceutical Sciences: The Science and Practice of Pharmacy, Dec. 2000, abstract, 1 pg.

Rukov et al., "Dissecting the Target Specificity of RNase H Recruiting Oligonucleotides Using Massively Parallel Reporter Analysis of Short RNA Motifs," Nucleic Acids Res. 43(17):8476-8487 (2015) (12 pages).

Santalucia J Jr., "A Unified View of Polymer, Dumbbell, and Oligonucleotide DNA Nearest-neiqhbor Thermodynamics," Proc Natl Acad Sci US A. 95(4):1460-1465 (1998) (6 pages).

Schoch et al., "Antisense Oligonucleotides: Translation from Mouse Models to Human Neurodeqenerative Diseases," Neuron. 94(6): 1056-1070 (2017) (15 pages).

Seth et al., "Synthesis and Biophysical Evaluation of 2',4'-Constrained 2'O-Methoxyethyl and 2',4'-Constrained 2'O-Ethvl Nucleic Acid Analoques," J Orq Chem. 75(5): 1569-1581 (2010) (7 pages).

Sud et al., "Antisense-mediated Exon Skipping Decreases Tau Protein Expression: A Potential Therapy for Tauopathies," Molecular Therapy-Nucleic Acids, 2014, vol. 3, e180, pp. 1-11.

Sugimoto et al., "Thermodynamic Parameters to Predict Stability of RNA/DNA Hybrid Duplexes," Biochemistry. 34(35): 11211-11216 (1995) (6 pages).

Uhlmann, "Recent advances in the medicinal chemistry of antisense olignonucleotides," Curr Opin Druq Discov Devel. 3(2): 203-213 (2000) (11 pages).

Vester et al., "Chemically Modified Oligonucleotides with Efficient RNase H Response," Bioorg Med Chem Lett. 18(7): 2296-2300 (2008) (5 pages).

Wan et al., "The Medicinal Chemistry of Therapeutic Oligonucleotides," J Med Chem. 59(21):9645-9667 (2016) (23 pages).

CMP ID NO: 9_103

CMP ID NO: 9_104

CMP ID NO: 11_1

CMP ID NO: 49_38

CMP ID NO: 49_189

OLIGONUCLEOTIDES FOR MODULATING TAU EXPRESSION

CROSS-REFERENCE TO RELATED APPLICATION

This application is a continuation of U.S. patent application Ser. No. 16/503,340 filed 3 Jul. 2019, which claims the benefit of U.S. Provisional Patent Application No. 62/693,851, entitled "OLIGONUCLEOTIDES FOR MODULATING TAU EXPRESSION," filed on 3 Jul. 2018, and U.S. Provisional Patent Application No. 62/726,005, entitled "OLIGONUCLEOTIDES FOR MODULATING TAU EXPRESSION," filed on 31 Aug. 2018, each of which is specifically incorporated by reference in its entirety for all that each discloses and teaches.

REFERENCE TO A SEQUENCE LISTING SUBMITTED VIA EFS-WEB

The content of the ASCII text file of the sequence listing named "103135-0294_Tau-hotspot.txt" which was created on 21 Jan. 2022, and is 359,556 bytes in size submitted electronically via EFS-Web with this U.S. application is incorporated by reference in its entirety.

FIELD OF INVENTION

The present invention relates to oligonucleotides (oligomers) that are complementary to microtubule-associated protein Tau (MAPT) transcript, leading to reduction of the expression of Tau. Reduction of MAPT transcripts and/or Tau protein expression is beneficial for a range of medical disorders, such as such as Tauopathies, Alzheimer's disease, fronto-temporal dementia (FTD), FTDP-17, progressive supranuclear palsy (PSP), chronic traumatic encephalopathy (CTE), corticobasal ganglionic degeneration (CBD), epilepsy, Dravet syndrome, depression, seizure disorders and movement disorders.

BACKGROUND

Tau is a microtubule-associated protein (MAP) that interacts with tubulin and is involved in microtubule assembly and stabilization. Microtubules are critical structural components of the cellular cytoskeleton and are involved in various cellular processes, including mitosis, cytokinesis, and vesicular transport. Tau protein is present in multiple cell and tissue types, but is particularly abundant in neurons where it plays a critical role in regulating axonal transport and function.

Alterations in Tau expression levels and/or function contribute to the pathophysiology of various neurodegenerative disorders. For example, aggregates of misfolded and hyperphosphorylated Tau are found in the neurofibrillary inclusions associated with Alzheimer's disease (AD) and related Tauopathies such as progressive supranuclear palsy (PSP), corticobasal ganglionic degeneration (CBD), chronic traumatic encephalopathy (CTE), fronto-temporal dementia FTD) and FTD with parkinsonism linked to chromosome 17 (FTDP-17), Pick's disease (PiD), argyrophilic grain disease (AGD), tangle-predominant senile dementia (TPSD), primary age-related Tauopathy (PART), Down syndrome and lytico-bodig disease. Upregulation of pathological Tau is associated with infantile Tauopathies including hemimegalencephaly (HME), tuberous sclerosis complex; focal cortical dysplasia type 2b; and ganglioglioma. In addition, abnormal Tau expression and/or function may also be associated with other diseases such as Hallervorden-Spatz syndrome, also known as neurodegeneration with brain iron accumulation type 1 (NBIA1), gangliocytomas, and subacute sclerosing panencephalitis. Tau may also play a role in seizure disorders (e.g., epilepsy), network dysfunction (e.g., depression), and movement disorders (e.g., Parkinson's disease).

Antisense molecules as well as siRNA molecules have that can reduce Tau protein levels by targeting MAPT pre-mRNA or mRNA transcripts have been described, see for example De Vos et al 2013 Journal of Neuroscience Vol 33 pp 12887, WO2013/148260, WO2014/153236, WO2015/010135, WO2016/126995, WO2016/151523, WO2017/09679 and WO2018/064593. Antisense oligonucleotides than can induce splice modulation of the MAPT transcript have also been described in Sud et al 2014 Mol Ther Nucl Acid 3 e180 and WO2016/019063.

Tau-associated disorders such as AD are the most common cause of dementia in the elderly, and robust and effective agents for the treatment of AD and related neurodegenerative diseases, including Tauopathies, seizure disorders, and movement disorders, are greatly needed.

OBJECTIVE OF THE INVENTION

The present invention provides antisense oligonucleotides which reduce Tau both in vivo and in vitro. The invention identified three specific target regions in the MAPT pre-mRNA located in intron 1 or 2 of the human MAPT pre-mRNA which may be targeted by antisense oligonucleotides to give effective Tau inhibition. In particular targeting position 12051 to 12111, 39562 to 39593 and or 72837 to 72940 of SEQ ID NO: 1 is advantageous in terms of reducing Tau. The invention also provides effective antisense oligonucleotide sequences and compounds which are capable of reducing Tau, and their use in treatment of diseases or disorders such as neurodegenerative diseases including Tauopathies, Alzheimer's disease, FTDP-17, seizure disorders and movement disorders.

SUMMARY OF INVENTION

The present invention relates to oligonucleotides targeting a Tau encoding nucleic acid which is capable of modulating the expression of Tau and the use of the oligonucleotide to treat or prevent diseases related to the functioning of the Tau.

Accordingly, in a first aspect the invention provides oligonucleotides 10 to 30 nucleotides in length which comprise a contiguous nucleotide sequence of at least 10 nucleotides in length with at least 90% complementarity to specific regions of MAPT represented by SEQ ID NO: 3, 4 and 5.

The oligonucleotide can be an antisense oligonucleotide, preferably with a gapmer design. Preferably, the oligonucleotide is capable of inhibiting the expression of Tau by cleavage of a target nucleic acid. The cleavage is preferably achieved via nuclease recruitment.

In a further aspect, the invention provides pharmaceutical compositions comprising the oligonucleotides of the invention and pharmaceutically acceptable diluents, carriers, salts and/or adjuvants.

In a further aspect, the invention provides methods for in vivo or in vitro method for modulation of Tau expression in a target cell which is expressing Tau, by administering an oligonucleotide or composition of the invention in an effective amount to said cell.

In a further aspect the invention provides methods for treating or preventing a disease, disorder or dysfunction associated with in vivo activity of Tau comprising administering a therapeutically or prophylactically effective amount of the oligonucleotide of the invention to a subject suffering from or susceptible to the disease, disorder or dysfunction.

In a further aspect the oligonucleotide or composition of the invention is used for the treatment or prevention of Alzheimer's disease (AD), progressive supranuclear palsy (PSP), fronto-temporal dementia (FTD) or FTDP-17.

Figure 1:
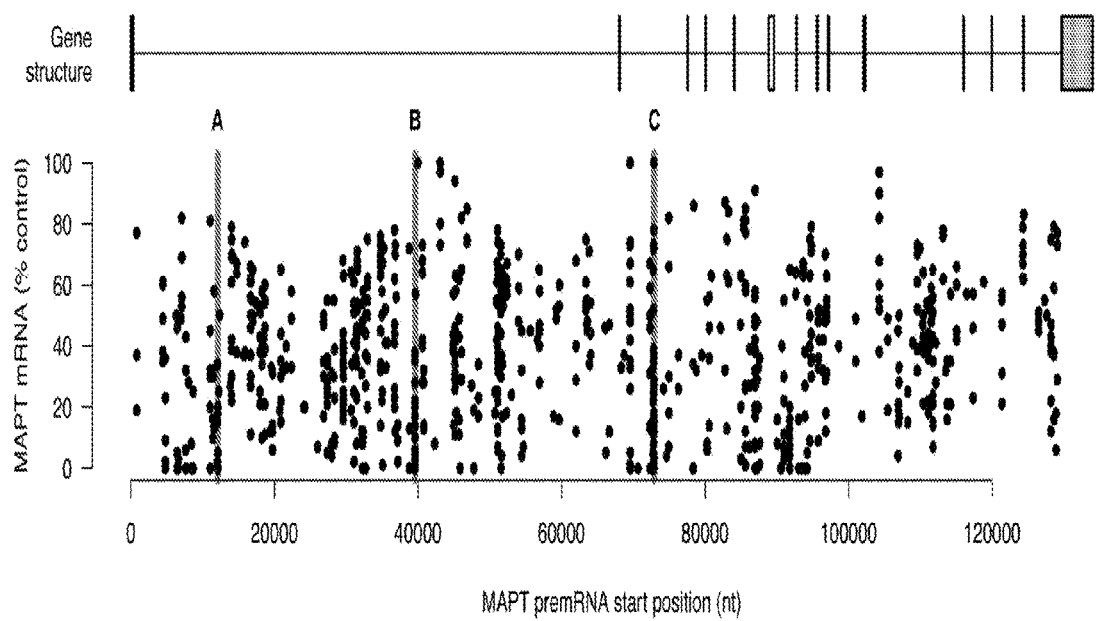
FIG. 1: Screening result from oligonucleotide library (example 1) covering all intron regions on MAPT. Each dot represents an oligonucleotide compound, the x-axis illustrates its position on the MAPT transcript and the y-axis shows the amount of MAPT mRNA remaining when compared to control (low number correspond to large reduction of MAPT). A, B and C indicate three regions on the MAPT transcript selected as target regions for further oligonucleotide compounds.

The compounds illustrated in FIGS. 2, 3, 4, 5 and 6 are shown in the protonated form—the S atom on the phosphorothioate linkage is protonated—it will be understood that the presence of the proton will depend on the acidity of the environment of the molecule, and the presence of an alternative cation (e.g. when the oligonucleotide is in salt form). Protonated phosphorothioates exist in tautomeric forms.

DEFINITIONS

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers.

Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides, such as 2' sugar modified nucleosides.
Antisense Oligonucleotides The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

Advantageously, the single stranded antisense oligonucleotide of the invention does not contain RNA nucleosides, since this will decrease nuclease resistance.

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides.
Contiguous Nucleotide Sequence The term "contiguous nucleotide sequence" refers to the region of the oligonucleotide which is complementary to the target nucleic acid or target sequence. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as a F-G-F' gapmer region, and may optionally comprise further nucleotide(s), for example a nucleotide linker region which may be used to attach a functional group to the contiguous nucleotide sequence. The nucleotide linker region may or may not be complementary to the target nucleic acid. It is understood that the contiguous nucleotide sequence of the oligonucleotide cannot be longer than the oligonucleotide as such and that the oligonucleotide cannot be shorter than the contiguous nucleotide sequence.
Nucleotides Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".
Modified Nucleoside The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprises a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.
Modified Internucleoside Linkage The term "modified internucleoside linkage" is defined as generally understood by the skilled person as linkages other than phosphodiester (PO) linkages, that covalently couples two nucleosides together. The oligonucleotides of the invention may therefore comprise modified internucleoside linkages. In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region G of a gapmer oligonucleotide, as well as in regions of modified nucleosides, such as region F and F'.

In an embodiment, the oligonucleotide comprises one or more internucleoside linkages modified from the natural phosphodiester, such as one or more modified internucleoside linkages that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 75%, such as at least 80% or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

With the oligonucleotides of the invention it is advantageous to use phosphorothioate internucleoside linkages.

Phosphorothioate internucleoside linkages are particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide of the invention comprises both phosphorothioate internucleoside linkages and at least one phosphodiester linkage, such as 2, 3 or 4 phosphodiester linkages, in addition to the phosphorodithioate linkage(s). In a gapmer oligonucleotide, phosphodiester linkages, when present, are suitably not located between contiguous DNA nucleosides in the gap region G.

In some embodiments, the oligonucleotide comprises one or more neutral internucleoside linkage, particularly an internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O, —NR$^H$—CO—O—, —NR$^H$—CO—NR$^H$—, and/or the internucleoside linker may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C1-4-alkyl.

Nuclease resistant linkages, such as phosphorothioate linkages, are particularly useful in oligonucleotide regions capable of recruiting nuclease when forming a duplex with the target nucleic acid, such as region G for gapmers. Phosphorothioate linkages may, however, also be useful in non-nuclease recruiting regions and/or affinity enhancing regions such as regions F and F' for gapmers. Gapmer oligonucleotides may, in some embodiments comprise one or more phosphodiester linkages in region F or F', or both region F and F', where all the internucleoside linkages in region G may be phosphorothioate.

Advantageously, all the internucleoside linkages of the contiguous nucleotide sequence of the oligonucleotide are phosphorothioate, or all the internucleoside linkages of the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012)

Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pair) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

The term "fully complementary", refers to 100% complementarity.

The following is an example of an oligonucleotide that is fully complementary to the target nucleic acid.

The following is an example of an oligonucleotide (SEQ ID NO: 49) that is fully complementary to the target nucleic acid (SEQ ID NO: 4).

```
                                              (SEQ ID NO: 4)
     5' gaaggttgaaatgagaattgatttgagttaaa 3'

(SEQ ID NO: 49)
     3' actcttaactaaactcaatt 5'
```

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity= (Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy $\Delta G°$ is a more accurate representation of binding affinity and is related to the dissociation constant ($K_d$) of the reaction by $\Delta G°=-RT \ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for ΔG° measurements. ΔG° can also be estimated numerically by using the nearest neighbor model as described by SantaLucia, 1998, *Proc Natl Acad Sci USA.* 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Nucleic Acid

According to the present invention, the target nucleic acid is a nucleic acid which encodes mammalian Tau and may for example be a gene, a RNA, a mRNA, and pre-mRNA, a mature mRNA or a cDNA sequence. The target may therefore be referred to as a Tau target nucleic acid or MAPT target nucleic acid, these terms can be used interchangeably. The oligonucleotide of the invention may for example target exon regions of a mammalian MAPT, or may for example target intron region in the MAPT pre-mRNA (see Table 1).

TABLE 1 human MAPT Exons and Introns

| Exonic regions in the human Tau premRNA (SEQ ID NO 2) | | | Intronic regions in the human Tau premRNA (SEQ ID NO 2) | | |
|---|---|---|---|---|---|
| ID | start | end | ID | start | end |
| e1 | 1 | 303 | i1 | 304 | 67979 |
| e2 | 67980 | 68129 | i2 | 68130 | 77517 |
| e3 | 77518 | 77604 | i3 | 77605 | 80043 |

TABLE 1-continued human MAPT Exons and Introns

| Exonic regions in the human Tau premRNA (SEQ ID NO 2) | | | Intronic regions in the human Tau premRNA (SEQ ID NO 2) | | |
|---|---|---|---|---|---|
| ID | start | end | ID | start | end |
| e4 | 80044 | 80130 | i4 | 80131 | 84033 |
| e5 | 84034 | 84099 | i5 | 84100 | 88837 |
| e6 | 88838 | 89590 | i6 | 89591 | 92699 |
| e7 | 92700 | 92755 | i7 | 92756 | 95537 |
| e8 | 95538 | 95735 | i8 | 95736 | 97119 |
| e9 | 97120 | 97246 | i8 | 97247 | 102058 |
| e10 | 102059 | 102324 | i9 | 102325 | 115969 |
| e11 | 115970 | 116062 | i10 | 116063 | 119902 |
| e12 | 119903 | 119984 | i11 | 119985 | 124287 |
| e13 | 124288 | 124400 | i12 | 124401 | 129623 |
| e14 | 129624 | 134004 | | | |

Suitably, the target nucleic acid encodes a Tau protein, in particular mammalian Tau, such as human Tau (See for example tables 2 and 3) which provides pre-mRNA sequences for human, and monkey Tau).

In some embodiments, the target nucleic acid is selected from the group consisting of SEQ ID NO: 1 and 2 or naturally occurring variants thereof (e.g. sequences encoding a mammalian Tau protein. If employing the oligonucleotide of the invention in research or diagnostics the target nucleic acid may be a cDNA or a synthetic nucleic acid derived from DNA or RNA.

For in vivo or in vitro application, the oligonucleotide of the invention is typically capable of inhibiting the expression of the Tau protein in a cell which is expressing the MAPT target nucleic acid. The contiguous sequence of nucleobases of the oligonucleotide of the invention is typically complementary to the MAPT target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). The target nucleic acid may, in some embodiments, be a RNA or DNA, such as a messenger RNA, such as a mature mRNA or a pre-mRNA.

In some embodiments the target nucleic acid is a RNA or DNA which encodes mammalian Tau protein, such as human Tau, e.g. the human MAPTpre-mRNA sequence, such as that disclosed as SEQ ID NO 1. Further information on exemplary target nucleic acids is provided in tables 2 and 3.

TABLE 2

Genome and assembly information for Tau across species.

| Species | Chr. | Strand | Genomic coordinates | | Assembly | NCBI reference sequence* accession number for mRNA |
|---|---|---|---|---|---|---|
| | | | Start | End | | |
| Human | 17 | fwd | 45894382 | 46028334 | GRCh38.p12 | NG_007398.1 |
| Cynomolgus monkey | 16 | fwd | 58257786 | 58390183 | Macaca_ fascicularis_ 5.0 | From 58257786 to 58390183 in NC_022287.1 |

Fwd = forward strand. The genome coordinates provide the pre-mRNA sequence (genomic sequence). The NCBI reference provides the mRNA sequence (cDNA sequence).
*The National Center for Biotechnology Information reference sequence database is a comprehensive, integrated, non-redundant, well-annotated set of reference sequences including genomic, transcript, and protein. It is hosted at www.ncbi.nlm.nih.gov/refseq.

TABLE 3

Sequence details for Tau/MAPT across species.

| Species | RNA type | Length (nt) | SEQ ID NO |
|---|---|---|---|
| Human | premRNA | 134004 | 1 |
| Monkey | premRNA | 132218 | 2 |

Target Sequence

The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid with a nucleobase sequence that is complementary to the contiguous nucleotide sequence of the oligonucleotide of the invention. This region of the target nucleic acid may interchangeably be referred to as the target nucleotide sequence, target sequence or target region. In some embodiments the target sequence is longer than the complementary sequence of a single oligonucleotide, and may, for example represent a preferred region of the target nucleic acid which may be targeted by several oligonucleotides of the invention.

In some embodiments the target sequence is a sequence selected from any region in table 4 (R_1-R_2254). In particular, the target sequence may be selected from one of the region within the group of regions consisting of R_223, R_738 or R_1298.

TABLE 4

Regions (reg.) on SEQ ID NO: 1 which may be targeted using an oligonucleotide of the invention

| Reg. | length (nt) | Position on SEQ ID NO: 1 start | end |
|---|---|---|---|
| R_1 | 32 | 4 | 35 |
| R_2 | 32 | 37 | 68 |
| R_3 | 32 | 70 | 101 |
| R_4 | 25 | 103 | 127 |
| R_5 | 187 | 156 | 342 |
| R_6 | 33 | 344 | 376 |
| R_7 | 37 | 385 | 421 |
| R_8 | 47 | 440 | 486 |
| R_9 | 22 | 488 | 509 |
| R_10 | 38 | 511 | 548 |
| R_11 | 63 | 580 | 642 |
| R_12 | 20 | 649 | 668 |
| R_13 | 32 | 710 | 741 |
| R_14 | 37 | 743 | 779 |
| R_15 | 27 | 792 | 818 |
| R_16 | 23 | 814 | 836 |
| R_17 | 115 | 839 | 953 |
| R_18 | 25 | 955 | 979 |
| R_19 | 80 | 981 | 1060 |
| R_20 | 23 | 1071 | 1093 |
| R_21 | 26 | 1095 | 1120 |
| R_22 | 32 | 1177 | 1208 |
| R_23 | 78 | 1239 | 1316 |
| R_24 | 34 | 1334 | 1367 |
| R_25 | 68 | 1401 | 1468 |
| R_26 | 82 | 1470 | 1551 |
| R_27 | 95 | 1566 | 1660 |
| R_28 | 43 | 1708 | 1750 |
| R_29 | 71 | 1762 | 1832 |
| R_30 | 37 | 1841 | 1877 |
| R_31 | 26 | 1878 | 1903 |
| R_32 | 21 | 1960 | 1980 |
| R_33 | 20 | 1982 | 2001 |

TABLE 4-continued

Regions (reg.) on SEQ ID NO: 1 which may be targeted using an oligonucleotide of the invention

| Reg. | length (nt) | Position on SEQ ID NO: 1 start | end |
|---|---|---|---|
| R_34 | 27 | 2018 | 2044 |
| R_35 | 22 | 2061 | 2082 |
| R_36 | 24 | 2196 | 2219 |
| R_37 | 30 | 2237 | 2266 |
| R_38 | 27 | 2334 | 2360 |
| R_39 | 22 | 2362 | 2383 |
| R_40 | 22 | 2419 | 2440 |
| R_41 | 31 | 2472 | 2502 |
| R_42 | 21 | 2506 | 2526 |
| R_43 | 21 | 2541 | 2561 |
| R_44 | 31 | 2565 | 2595 |
| R_45 | 21 | 2598 | 2618 |
| R_46 | 28 | 2725 | 2752 |
| R_47 | 38 | 2769 | 2806 |
| R_48 | 59 | 2915 | 2973 |
| R_49 | 50 | 2978 | 3027 |
| R_50 | 21 | 3035 | 3055 |
| R_51 | 24 | 3072 | 3095 |
| R_52 | 22 | 3171 | 3192 |
| R_53 | 28 | 3207 | 3234 |
| R_54 | 25 | 3236 | 3260 |
| R_55 | 33 | 3262 | 3294 |
| R_56 | 58 | 3302 | 3359 |
| R_57 | 21 | 3364 | 3384 |
| R_58 | 36 | 3417 | 3452 |
| R_59 | 56 | 3476 | 3531 |
| R_60 | 20 | 3533 | 3552 |
| R_61 | 20 | 3554 | 3573 |
| R_62 | 22 | 3648 | 3669 |
| R_63 | 21 | 3681 | 3701 |
| R_64 | 20 | 3756 | 3775 |
| R_65 | 24 | 3808 | 3831 |
| R_66 | 35 | 3833 | 3867 |
| R_67 | 46 | 3869 | 3914 |
| R_68 | 27 | 3916 | 3942 |
| R_69 | 21 | 3956 | 3976 |
| R_70 | 41 | 4009 | 4049 |
| R_71 | 29 | 4069 | 4097 |
| R_72 | 37 | 4117 | 4153 |
| R_73 | 23 | 4160 | 4182 |
| R_74 | 38 | 4191 | 4228 |
| R_75 | 24 | 4263 | 4286 |
| R_76 | 75 | 4288 | 4362 |
| R_77 | 40 | 4388 | 4427 |
| R_78 | 46 | 4429 | 4474 |
| R_79 | 44 | 4525 | 4568 |
| R_80 | 28 | 4600 | 4627 |
| R_81 | 38 | 4646 | 4683 |
| R_82 | 26 | 4696 | 4721 |
| R_83 | 32 | 4732 | 4763 |
| R_84 | 35 | 4787 | 4821 |
| R_85 | 20 | 4837 | 4856 |
| R_86 | 36 | 4900 | 4935 |
| R_87 | 27 | 5033 | 5059 |
| R_88 | 28 | 5066 | 5093 |
| R_89 | 46 | 5098 | 5143 |
| R_90 | 24 | 5145 | 5168 |
| R_91 | 20 | 5184 | 5203 |
| R_92 | 40 | 5205 | 5244 |
| R_93 | 28 | 5246 | 5273 |
| R_94 | 20 | 5329 | 5348 |
| R_95 | 58 | 5366 | 5423 |
| R_96 | 41 | 5425 | 5465 |
| R_97 | 58 | 5524 | 5581 |
| R_98 | 20 | 5583 | 5602 |
| R_99 | 30 | 5635 | 5664 |
| R_100 | 51 | 5694 | 5744 |
| R_101 | 42 | 5775 | 5816 |
| R_102 | 53 | 5838 | 5890 |
| R_103 | 32 | 5892 | 5923 |
| R_104 | 53 | 5925 | 5977 |
| R_105 | 28 | 6001 | 6028 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_106 | 21 | 6039 | 6059 |
| R_107 | 64 | 6106 | 6169 |
| R_108 | 65 | 6176 | 6240 |
| R_109 | 35 | 6242 | 6276 |
| R_110 | 29 | 6276 | 6304 |
| R_111 | 38 | 6306 | 6343 |
| R_112 | 22 | 6374 | 6395 |
| R_113 | 22 | 6422 | 6443 |
| R_114 | 28 | 6464 | 6491 |
| R_115 | 23 | 6524 | 6546 |
| R_116 | 23 | 6574 | 6596 |
| R_117 | 54 | 6615 | 6668 |
| R_118 | 28 | 6725 | 6752 |
| R_119 | 49 | 6738 | 6786 |
| R_120 | 25 | 6788 | 6812 |
| R_121 | 59 | 6819 | 6877 |
| R_122 | 22 | 6908 | 6929 |
| R_123 | 26 | 6931 | 6956 |
| R_124 | 24 | 6958 | 6981 |
| R_125 | 35 | 6984 | 7018 |
| R_126 | 32 | 7020 | 7051 |
| R_127 | 23 | 7097 | 7119 |
| R_128 | 83 | 7121 | 7203 |
| R_129 | 21 | 7205 | 7225 |
| R_130 | 32 | 7242 | 7273 |
| R_131 | 20 | 7289 | 7308 |
| R_132 | 21 | 7376 | 7396 |
| R_133 | 20 | 7397 | 7416 |
| R_134 | 23 | 7439 | 7461 |
| R_135 | 23 | 7463 | 7485 |
| R_136 | 28 | 7492 | 7519 |
| R_137 | 26 | 7569 | 7594 |
| R_138 | 38 | 7622 | 7659 |
| R_139 | 25 | 7705 | 7729 |
| R_140 | 20 | 7705 | 7724 |
| R_141 | 28 | 7774 | 7801 |
| R_142 | 20 | 7855 | 7874 |
| R_143 | 23 | 7885 | 7907 |
| R_144 | 35 | 7933 | 7967 |
| R_145 | 21 | 7937 | 7957 |
| R_146 | 20 | 7937 | 7956 |
| R_147 | 23 | 7948 | 7970 |
| R_148 | 26 | 7952 | 7977 |
| R_149 | 25 | 7953 | 7977 |
| R_150 | 30 | 8009 | 8038 |
| R_151 | 31 | 8043 | 8073 |
| R_152 | 20 | 8125 | 8144 |
| R_153 | 21 | 8146 | 8166 |
| R_154 | 36 | 8168 | 8203 |
| R_155 | 44 | 8245 | 8288 |
| R_156 | 29 | 8324 | 8352 |
| R_157 | 43 | 8355 | 8397 |
| R_158 | 23 | 8399 | 8421 |
| R_159 | 26 | 8457 | 8482 |
| R_160 | 54 | 8486 | 8539 |
| R_161 | 43 | 8541 | 8583 |
| R_162 | 26 | 8585 | 8610 |
| R_163 | 26 | 8637 | 8662 |
| R_164 | 37 | 8678 | 8714 |
| R_165 | 24 | 8742 | 8765 |
| R_166 | 37 | 8812 | 8848 |
| R_167 | 37 | 8868 | 8904 |
| R_168 | 21 | 9015 | 9035 |
| R_169 | 28 | 9065 | 9092 |
| R_170 | 20 | 9180 | 9199 |
| R_171 | 23 | 9191 | 9213 |
| R_172 | 24 | 9203 | 9226 |
| R_173 | 28 | 9215 | 9242 |
| R_174 | 21 | 9244 | 9264 |
| R_175 | 23 | 9260 | 9282 |
| R_176 | 25 | 9266 | 9290 |
| R_177 | 23 | 9266 | 9288 |
| R_178 | 24 | 9267 | 9290 |
| R_179 | 21 | 9267 | 9287 |
| R_180 | 22 | 9267 | 9288 |
| R_181 | 23 | 9268 | 9290 |
| R_182 | 21 | 9270 | 9290 |
| R_183 | 23 | 9289 | 9311 |
| R_184 | 20 | 9292 | 9311 |
| R_185 | 22 | 9330 | 9351 |
| R_186 | 20 | 9334 | 9353 |
| R_187 | 22 | 10083 | 10104 |
| R_188 | 23 | 10092 | 10114 |
| R_189 | 38 | 10119 | 10156 |
| R_190 | 20 | 10255 | 10274 |
| R_191 | 21 | 10257 | 10277 |
| R_192 | 28 | 10305 | 10332 |
| R_193 | 63 | 10358 | 10420 |
| R_194 | 28 | 10498 | 10525 |
| R_195 | 27 | 10597 | 10623 |
| R_196 | 24 | 10625 | 10648 |
| R_197 | 56 | 10666 | 10721 |
| R_198 | 27 | 10741 | 10767 |
| R_199 | 21 | 10777 | 10797 |
| R_200 | 38 | 10799 | 10836 |
| R_201 | 30 | 10840 | 10869 |
| R_202 | 24 | 10871 | 10894 |
| R_203 | 30 | 10911 | 10940 |
| R_204 | 49 | 10942 | 10990 |
| R_205 | 21 | 10992 | 11012 |
| R_206 | 69 | 11018 | 11086 |
| R_207 | 30 | 11089 | 11118 |
| R_208 | 42 | 11127 | 11168 |
| R_209 | 25 | 11193 | 11217 |
| R_210 | 68 | 11279 | 11346 |
| R_211 | 42 | 11367 | 11408 |
| R_212 | 43 | 11410 | 11452 |
| R_213 | 54 | 11458 | 11511 |
| R_214 | 79 | 11556 | 11634 |
| R_215 | 37 | 11648 | 11684 |
| R_216 | 31 | 11691 | 11721 |
| R_217 | 28 | 11724 | 11751 |
| R_218 | 81 | 11800 | 11880 |
| R_219 | 20 | 11905 | 11924 |
| R_220 | 21 | 11928 | 11948 |
| R_221 | 50 | 11950 | 11999 |
| R_222 | 20 | 12030 | 12049 |
| R_223 | 61 | 12051 | 12111 |
| R_224 | 23 | 12147 | 12169 |
| R_225 | 25 | 12171 | 12195 |
| R_226 | 23 | 12197 | 12219 |
| R_227 | 45 | 12221 | 12265 |
| R_228 | 43 | 12304 | 12346 |
| R_229 | 51 | 12353 | 12403 |
| R_230 | 23 | 12405 | 12427 |
| R_231 | 62 | 12475 | 12536 |
| R_232 | 28 | 12538 | 12565 |
| R_233 | 28 | 12587 | 12614 |
| R_234 | 21 | 12615 | 12635 |
| R_235 | 29 | 12637 | 12665 |
| R_236 | 38 | 12684 | 12721 |
| R_237 | 34 | 12746 | 12779 |
| R_238 | 20 | 12799 | 12818 |
| R_239 | 33 | 12822 | 12854 |
| R_240 | 37 | 12856 | 12892 |
| R_241 | 20 | 12894 | 12913 |
| R_242 | 23 | 12933 | 12955 |
| R_243 | 50 | 13057 | 13106 |
| R_244 | 37 | 13133 | 13169 |
| R_245 | 51 | 13227 | 13277 |
| R_246 | 22 | 13348 | 13369 |
| R_247 | 29 | 13380 | 13408 |
| R_248 | 41 | 13410 | 13450 |
| R_249 | 32 | 13452 | 13483 |

TABLE 4-continued

Regions (reg.) on SEQ ID NO: 1 which may be targeted using an oligonucleotide of the invention

| Reg. | length (nt) | Position on SEQ ID NO: 1 start | end |
|---|---|---|---|
| R_250 | 45 | 13483 | 13527 |
| R_251 | 32 | 13529 | 13560 |
| R_252 | 21 | 13569 | 13589 |
| R_253 | 50 | 13591 | 13640 |
| R_254 | 88 | 13770 | 13857 |
| R_255 | 20 | 13861 | 13880 |
| R_256 | 32 | 13882 | 13913 |
| R_257 | 55 | 13936 | 13990 |
| R_258 | 39 | 13992 | 14030 |
| R_259 | 34 | 14033 | 14066 |
| R_260 | 35 | 14068 | 14102 |
| R_261 | 27 | 14104 | 14130 |
| R_262 | 20 | 14140 | 14159 |
| R_263 | 51 | 14180 | 14230 |
| R_264 | 20 | 14232 | 14251 |
| R_265 | 107 | 14253 | 14359 |
| R_266 | 72 | 14367 | 14438 |
| R_267 | 69 | 14503 | 14571 |
| R_268 | 27 | 14595 | 14621 |
| R_269 | 35 | 14629 | 14663 |
| R_270 | 58 | 14732 | 14789 |
| R_271 | 25 | 14805 | 14829 |
| R_272 | 56 | 14851 | 14906 |
| R_273 | 53 | 14954 | 15006 |
| R_274 | 39 | 15026 | 15064 |
| R_275 | 21 | 15066 | 15086 |
| R_276 | 22 | 15138 | 15159 |
| R_277 | 107 | 15157 | 15263 |
| R_278 | 24 | 15249 | 15272 |
| R_279 | 22 | 15277 | 15298 |
| R_280 | 38 | 15300 | 15337 |
| R_281 | 24 | 15414 | 15437 |
| R_282 | 21 | 15476 | 15496 |
| R_283 | 23 | 15617 | 15639 |
| R_284 | 58 | 15671 | 15728 |
| R_285 | 36 | 15730 | 15765 |
| R_286 | 29 | 15840 | 15868 |
| R_287 | 27 | 15870 | 15896 |
| R_288 | 50 | 15926 | 15975 |
| R_289 | 27 | 16008 | 16034 |
| R_290 | 46 | 16109 | 16154 |
| R_291 | 27 | 16159 | 16185 |
| R_292 | 30 | 16245 | 16274 |
| R_293 | 44 | 16296 | 16339 |
| R_294 | 20 | 16316 | 16335 |
| R_295 | 48 | 16371 | 16418 |
| R_296 | 36 | 16447 | 16482 |
| R_297 | 36 | 16485 | 16520 |
| R_298 | 26 | 16532 | 16557 |
| R_299 | 21 | 16582 | 16602 |
| R_300 | 83 | 16604 | 16686 |
| R_301 | 63 | 16688 | 16750 |
| R_302 | 75 | 16766 | 16840 |
| R_303 | 24 | 16918 | 16941 |
| R_304 | 32 | 16947 | 16978 |
| R_305 | 31 | 17007 | 17037 |
| R_306 | 45 | 17039 | 17083 |
| R_307 | 25 | 17085 | 17109 |
| R_308 | 30 | 17111 | 17140 |
| R_309 | 29 | 17179 | 17207 |
| R_310 | 34 | 17292 | 17325 |
| R_311 | 28 | 17292 | 17319 |
| R_312 | 28 | 17309 | 17336 |
| R_313 | 21 | 17316 | 17336 |
| R_314 | 21 | 17319 | 17339 |
| R_315 | 22 | 17326 | 17347 |
| R_316 | 52 | 17349 | 17400 |
| R_317 | 20 | 17416 | 17435 |
| R_318 | 39 | 17445 | 17483 |
| R_319 | 43 | 17485 | 17527 |
| R_320 | 74 | 17587 | 17660 |
| R_321 | 38 | 17667 | 17704 |
| R_322 | 25 | 17706 | 17730 |
| R_323 | 45 | 17796 | 17840 |
| R_324 | 53 | 17855 | 17907 |
| R_325 | 44 | 17909 | 17952 |
| R_326 | 20 | 17954 | 17973 |
| R_327 | 34 | 17975 | 18008 |
| R_328 | 20 | 18010 | 18029 |
| R_329 | 46 | 18031 | 18076 |
| R_330 | 26 | 18078 | 18103 |
| R_331 | 29 | 18136 | 18164 |
| R_332 | 33 | 18208 | 18240 |
| R_333 | 54 | 18261 | 18314 |
| R_334 | 22 | 18333 | 18354 |
| R_335 | 34 | 18410 | 18443 |
| R_336 | 27 | 18446 | 18472 |
| R_337 | 86 | 18474 | 18559 |
| R_338 | 25 | 18590 | 18614 |
| R_339 | 21 | 18627 | 18647 |
| R_340 | 37 | 18650 | 18686 |
| R_341 | 33 | 18688 | 18720 |
| R_342 | 30 | 18742 | 18771 |
| R_343 | 20 | 18773 | 18792 |
| R_344 | 32 | 18782 | 18813 |
| R_345 | 20 | 18843 | 18862 |
| R_346 | 24 | 18864 | 18887 |
| R_347 | 24 | 18900 | 18923 |
| R_348 | 35 | 18935 | 18969 |
| R_349 | 38 | 18971 | 19008 |
| R_350 | 23 | 19080 | 19102 |
| R_351 | 51 | 19106 | 19156 |
| R_352 | 21 | 19158 | 19178 |
| R_353 | 25 | 19262 | 19286 |
| R_354 | 22 | 19310 | 19331 |
| R_355 | 28 | 19333 | 19360 |
| R_356 | 24 | 19362 | 19385 |
| R_357 | 44 | 19394 | 19437 |
| R_358 | 47 | 19493 | 19539 |
| R_359 | 26 | 19569 | 19594 |
| R_360 | 34 | 19624 | 19657 |
| R_361 | 38 | 19659 | 19696 |
| R_362 | 32 | 19713 | 19744 |
| R_363 | 56 | 19746 | 19801 |
| R_364 | 43 | 19839 | 19881 |
| R_365 | 24 | 19894 | 19917 |
| R_366 | 24 | 19960 | 19983 |
| R_367 | 21 | 19985 | 20005 |
| R_368 | 30 | 20006 | 20035 |
| R_369 | 21 | 20037 | 20057 |
| R_370 | 20 | 20069 | 20088 |
| R_371 | 20 | 20151 | 20170 |
| R_372 | 25 | 20182 | 20206 |
| R_373 | 22 | 20237 | 20258 |
| R_374 | 22 | 20267 | 20288 |
| R_375 | 27 | 20363 | 20389 |
| R_376 | 25 | 20375 | 20399 |
| R_377 | 21 | 20482 | 20502 |
| R_378 | 27 | 20485 | 20511 |
| R_379 | 22 | 20497 | 20518 |
| R_380 | 24 | 20566 | 20589 |
| R_381 | 22 | 20591 | 20612 |
| R_382 | 20 | 20610 | 20629 |
| R_383 | 22 | 20679 | 20700 |
| R_384 | 28 | 20702 | 20729 |
| R_385 | 35 | 20741 | 20775 |
| R_386 | 43 | 20790 | 20832 |
| R_387 | 35 | 20880 | 20914 |
| R_388 | 22 | 20892 | 20913 |
| R_389 | 21 | 21011 | 21031 |
| R_390 | 26 | 21138 | 21163 |
| R_391 | 20 | 21158 | 21177 |
| R_392 | 24 | 21248 | 21271 |
| R_393 | 26 | 21324 | 21349 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_394 | 35 | 21351 | 21385 |
| R_395 | 29 | 21441 | 21469 |
| R_396 | 53 | 21557 | 21609 |
| R_397 | 31 | 21611 | 21641 |
| R_398 | 38 | 21645 | 21682 |
| R_399 | 40 | 21743 | 21782 |
| R_400 | 59 | 21819 | 21877 |
| R_401 | 20 | 21949 | 21968 |
| R_402 | 27 | 22001 | 22027 |
| R_403 | 63 | 22041 | 22103 |
| R_404 | 53 | 22125 | 22177 |
| R_405 | 48 | 22179 | 22226 |
| R_406 | 20 | 22247 | 22266 |
| R_407 | 48 | 22277 | 22324 |
| R_408 | 31 | 22334 | 22364 |
| R_409 | 105 | 22370 | 22474 |
| R_410 | 37 | 22475 | 22511 |
| R_411 | 32 | 22644 | 22675 |
| R_412 | 34 | 22686 | 22719 |
| R_413 | 28 | 22763 | 22790 |
| R_414 | 34 | 22792 | 22825 |
| R_415 | 22 | 22844 | 22865 |
| R_416 | 23 | 22875 | 22897 |
| R_417 | 27 | 22959 | 22985 |
| R_418 | 22 | 22990 | 23011 |
| R_419 | 23 | 23019 | 23041 |
| R_420 | 49 | 23066 | 23114 |
| R_421 | 35 | 23131 | 23165 |
| R_422 | 22 | 23168 | 23189 |
| R_423 | 46 | 23191 | 23236 |
| R_424 | 45 | 23238 | 23282 |
| R_425 | 23 | 23318 | 23340 |
| R_426 | 21 | 23497 | 23517 |
| R_427 | 24 | 23518 | 23541 |
| R_428 | 22 | 23562 | 23583 |
| R_429 | 26 | 23585 | 23610 |
| R_430 | 46 | 23626 | 23671 |
| R_431 | 34 | 23637 | 23670 |
| R_432 | 21 | 23650 | 23670 |
| R_433 | 28 | 23718 | 23745 |
| R_434 | 87 | 23748 | 23834 |
| R_435 | 41 | 23836 | 23876 |
| R_436 | 30 | 23889 | 23918 |
| R_437 | 83 | 23975 | 24057 |
| R_438 | 99 | 24059 | 24157 |
| R_439 | 37 | 24219 | 24255 |
| R_440 | 33 | 24319 | 24351 |
| R_441 | 20 | 24342 | 24361 |
| R_442 | 71 | 24354 | 24424 |
| R_443 | 28 | 24447 | 24474 |
| R_444 | 21 | 24515 | 24535 |
| R_445 | 31 | 24536 | 24566 |
| R_446 | 20 | 24552 | 24571 |
| R_447 | 26 | 24592 | 24617 |
| R_448 | 26 | 24656 | 24681 |
| R_449 | 25 | 24716 | 24740 |
| R_450 | 20 | 24721 | 24740 |
| R_451 | 57 | 24817 | 24873 |
| R_452 | 41 | 24903 | 24943 |
| R_453 | 26 | 24958 | 24983 |
| R_454 | 20 | 24985 | 25004 |
| R_455 | 48 | 25014 | 25061 |
| R_456 | 55 | 25122 | 25176 |
| R_457 | 29 | 25178 | 25206 |
| R_458 | 25 | 25249 | 25273 |
| R_459 | 30 | 25279 | 25308 |
| R_460 | 40 | 25310 | 25349 |
| R_461 | 53 | 25369 | 25421 |
| R_462 | 52 | 25427 | 25478 |
| R_463 | 66 | 25514 | 25579 |
| R_464 | 21 | 25618 | 25638 |
| R_465 | 51 | 25679 | 25729 |
| R_466 | 39 | 25731 | 25769 |
| R_467 | 28 | 25825 | 25852 |
| R_468 | 72 | 25881 | 25952 |
| R_469 | 23 | 25964 | 25986 |
| R_470 | 59 | 25988 | 26046 |
| R_471 | 25 | 26061 | 26085 |
| R_472 | 34 | 26088 | 26121 |
| R_473 | 24 | 26162 | 26185 |
| R_474 | 30 | 26194 | 26223 |
| R_475 | 28 | 26233 | 26260 |
| R_476 | 38 | 26335 | 26372 |
| R_477 | 24 | 26395 | 26418 |
| R_478 | 24 | 26455 | 26478 |
| R_479 | 27 | 26480 | 26506 |
| R_480 | 42 | 26521 | 26562 |
| R_481 | 67 | 26684 | 26750 |
| R_482 | 24 | 26752 | 26775 |
| R_483 | 35 | 26822 | 26856 |
| R_484 | 22 | 26937 | 26958 |
| R_485 | 38 | 26984 | 27021 |
| R_486 | 24 | 27022 | 27045 |
| R_487 | 54 | 27053 | 27106 |
| R_488 | 91 | 27154 | 27244 |
| R_489 | 35 | 27283 | 27317 |
| R_490 | 25 | 27339 | 27363 |
| R_491 | 75 | 27386 | 27460 |
| R_492 | 41 | 27493 | 27533 |
| R_493 | 22 | 27602 | 27623 |
| R_494 | 33 | 27631 | 27663 |
| R_495 | 23 | 27691 | 27713 |
| R_496 | 33 | 27736 | 27768 |
| R_497 | 24 | 27752 | 27775 |
| R_498 | 26 | 27777 | 27802 |
| R_499 | 20 | 27777 | 27796 |
| R_500 | 23 | 27778 | 27800 |
| R_501 | 30 | 27859 | 27888 |
| R_502 | 38 | 27909 | 27946 |
| R_503 | 49 | 27956 | 28004 |
| R_504 | 45 | 28071 | 28115 |
| R_505 | 33 | 28124 | 28156 |
| R_506 | 20 | 28152 | 28171 |
| R_507 | 24 | 28181 | 28204 |
| R_508 | 25 | 28251 | 28275 |
| R_509 | 33 | 28295 | 28327 |
| R_510 | 28 | 28345 | 28372 |
| R_511 | 51 | 28383 | 28433 |
| R_512 | 38 | 28441 | 28478 |
| R_513 | 24 | 28553 | 28576 |
| R_514 | 37 | 28598 | 28634 |
| R_515 | 35 | 28669 | 28703 |
| R_516 | 23 | 28733 | 28755 |
| R_517 | 31 | 28758 | 28788 |
| R_518 | 21 | 28857 | 28877 |
| R_519 | 38 | 28922 | 28959 |
| R_520 | 58 | 29019 | 29076 |
| R_521 | 22 | 29115 | 29136 |
| R_522 | 66 | 29198 | 29263 |
| R_523 | 24 | 29297 | 29320 |
| R_524 | 41 | 29335 | 29375 |
| R_525 | 21 | 29386 | 29406 |
| R_526 | 22 | 29433 | 29454 |
| R_527 | 40 | 29473 | 29512 |
| R_528 | 29 | 29531 | 29559 |
| R_529 | 41 | 29586 | 29626 |
| R_530 | 29 | 29635 | 29663 |
| R_531 | 36 | 29665 | 29700 |
| R_532 | 93 | 29750 | 29842 |
| R_533 | 35 | 29853 | 29887 |
| R_534 | 22 | 29907 | 29928 |
| R_535 | 77 | 29964 | 30040 |
| R_536 | 38 | 30093 | 30130 |
| R_537 | 30 | 30169 | 30198 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_538 | 32 | 30210 | 30241 |
| R_539 | 20 | 30243 | 30262 |
| R_540 | 20 | 30303 | 30322 |
| R_541 | 23 | 30324 | 30346 |
| R_542 | 27 | 30362 | 30388 |
| R_543 | 30 | 30390 | 30419 |
| R_544 | 31 | 30462 | 30492 |
| R_545 | 22 | 30534 | 30555 |
| R_546 | 28 | 30557 | 30584 |
| R_547 | 24 | 30596 | 30619 |
| R_548 | 30 | 30626 | 30655 |
| R_549 | 41 | 30675 | 30715 |
| R_550 | 33 | 30726 | 30758 |
| R_551 | 29 | 30787 | 30815 |
| R_552 | 62 | 30819 | 30880 |
| R_553 | 79 | 30972 | 31050 |
| R_554 | 67 | 31053 | 31119 |
| R_555 | 56 | 31121 | 31176 |
| R_556 | 22 | 31178 | 31199 |
| R_557 | 22 | 31207 | 31228 |
| R_558 | 27 | 31227 | 31253 |
| R_559 | 27 | 31255 | 31281 |
| R_560 | 58 | 31310 | 31367 |
| R_561 | 26 | 31383 | 31408 |
| R_562 | 20 | 31419 | 31438 |
| R_563 | 36 | 31440 | 31475 |
| R_564 | 26 | 31503 | 31528 |
| R_565 | 34 | 31530 | 31563 |
| R_566 | 23 | 31585 | 31607 |
| R_567 | 21 | 31611 | 31631 |
| R_568 | 21 | 31614 | 31634 |
| R_569 | 32 | 31675 | 31706 |
| R_570 | 23 | 31708 | 31730 |
| R_571 | 39 | 31737 | 31775 |
| R_572 | 68 | 31763 | 31830 |
| R_573 | 27 | 31763 | 31789 |
| R_574 | 20 | 31803 | 31822 |
| R_575 | 23 | 31832 | 31854 |
| R_576 | 50 | 31952 | 32001 |
| R_577 | 22 | 32110 | 32131 |
| R_578 | 20 | 32114 | 32133 |
| R_579 | 35 | 32143 | 32177 |
| R_580 | 45 | 32179 | 32223 |
| R_581 | 26 | 32208 | 32233 |
| R_582 | 49 | 32225 | 32273 |
| R_583 | 27 | 32289 | 32315 |
| R_584 | 34 | 32317 | 32350 |
| R_585 | 32 | 32352 | 32383 |
| R_586 | 25 | 32390 | 32414 |
| R_587 | 46 | 32416 | 32461 |
| R_588 | 37 | 32497 | 32533 |
| R_589 | 37 | 32691 | 32727 |
| R_590 | 23 | 32753 | 32775 |
| R_591 | 38 | 32794 | 32831 |
| R_592 | 24 | 32835 | 32858 |
| R_593 | 55 | 32890 | 32944 |
| R_594 | 52 | 32959 | 33010 |
| R_595 | 37 | 33025 | 33061 |
| R_596 | 23 | 33063 | 33085 |
| R_597 | 62 | 33087 | 33148 |
| R_598 | 23 | 33160 | 33182 |
| R_599 | 21 | 33190 | 33210 |
| R_600 | 24 | 33222 | 33245 |
| R_601 | 56 | 33258 | 33313 |
| R_602 | 26 | 33317 | 33342 |
| R_603 | 25 | 33344 | 33368 |
| R_604 | 20 | 33379 | 33398 |
| R_605 | 22 | 33395 | 33416 |
| R_606 | 20 | 33395 | 33414 |
| R_607 | 22 | 33400 | 33421 |
| R_608 | 22 | 33457 | 33478 |
| R_609 | 22 | 33512 | 33533 |
| R_610 | 23 | 33532 | 33554 |
| R_611 | 24 | 33532 | 33555 |
| R_612 | 28 | 33535 | 33562 |
| R_613 | 21 | 33547 | 33567 |
| R_614 | 20 | 33548 | 33567 |
| R_615 | 23 | 33582 | 33604 |
| R_616 | 20 | 33588 | 33607 |
| R_617 | 24 | 33618 | 33641 |
| R_618 | 26 | 33675 | 33700 |
| R_619 | 29 | 33726 | 33754 |
| R_620 | 47 | 33775 | 33821 |
| R_621 | 20 | 33835 | 33854 |
| R_622 | 49 | 33856 | 33904 |
| R_623 | 64 | 33948 | 34011 |
| R_624 | 20 | 34025 | 34044 |
| R_625 | 20 | 34072 | 34091 |
| R_626 | 31 | 34139 | 34169 |
| R_627 | 78 | 34179 | 34256 |
| R_628 | 49 | 34258 | 34306 |
| R_629 | 29 | 34379 | 34407 |
| R_630 | 21 | 34417 | 34437 |
| R_631 | 27 | 34449 | 34475 |
| R_632 | 24 | 34495 | 34518 |
| R_633 | 21 | 34516 | 34536 |
| R_634 | 21 | 34562 | 34582 |
| R_635 | 21 | 34572 | 34592 |
| R_636 | 22 | 34576 | 34597 |
| R_637 | 32 | 34612 | 34643 |
| R_638 | 24 | 34646 | 34669 |
| R_639 | 65 | 34681 | 34745 |
| R_640 | 139 | 34765 | 34903 |
| R_641 | 60 | 34943 | 35002 |
| R_642 | 52 | 35012 | 35063 |
| R_643 | 83 | 35065 | 35147 |
| R_644 | 21 | 35160 | 35180 |
| R_645 | 29 | 35188 | 35216 |
| R_646 | 21 | 35218 | 35238 |
| R_647 | 59 | 35269 | 35327 |
| R_648 | 26 | 35330 | 35355 |
| R_649 | 44 | 35372 | 35415 |
| R_650 | 20 | 35417 | 35436 |
| R_651 | 43 | 35442 | 35484 |
| R_652 | 22 | 35482 | 35503 |
| R_653 | 74 | 35505 | 35578 |
| R_654 | 20 | 35599 | 35618 |
| R_655 | 25 | 35620 | 35644 |
| R_656 | 39 | 35654 | 35692 |
| R_657 | 26 | 35697 | 35722 |
| R_658 | 30 | 35724 | 35753 |
| R_659 | 23 | 35756 | 35778 |
| R_660 | 22 | 35777 | 35798 |
| R_661 | 40 | 35838 | 35877 |
| R_662 | 24 | 35879 | 35902 |
| R_663 | 20 | 35887 | 35906 |
| R_664 | 21 | 35894 | 35914 |
| R_665 | 62 | 35928 | 35989 |
| R_666 | 27 | 36002 | 36028 |
| R_667 | 20 | 36025 | 36044 |
| R_668 | 21 | 36030 | 36050 |
| R_669 | 64 | 36099 | 36162 |
| R_670 | 30 | 36171 | 36200 |
| R_671 | 39 | 36202 | 36240 |
| R_672 | 56 | 36242 | 36297 |
| R_673 | 47 | 36307 | 36353 |
| R_674 | 34 | 36404 | 36437 |
| R_675 | 22 | 36439 | 36460 |
| R_676 | 20 | 36493 | 36512 |
| R_677 | 24 | 36514 | 36537 |
| R_678 | 20 | 36568 | 36587 |
| R_679 | 32 | 36589 | 36620 |
| R_680 | 25 | 36622 | 36646 |
| R_681 | 22 | 36654 | 36675 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_682 | 26 | 36678 | 36703 |
| R_683 | 28 | 36728 | 36755 |
| R_684 | 41 | 36790 | 36830 |
| R_685 | 60 | 36862 | 36921 |
| R_686 | 37 | 36940 | 36976 |
| R_687 | 55 | 37002 | 37056 |
| R_688 | 44 | 37124 | 37167 |
| R_689 | 29 | 37169 | 37197 |
| R_690 | 25 | 37232 | 37256 |
| R_691 | 21 | 37258 | 37278 |
| R_692 | 75 | 37280 | 37354 |
| R_693 | 93 | 37399 | 37491 |
| R_694 | 22 | 37465 | 37486 |
| R_695 | 21 | 37491 | 37511 |
| R_696 | 20 | 37543 | 37562 |
| R_697 | 23 | 37582 | 37604 |
| R_698 | 31 | 37608 | 37638 |
| R_699 | 21 | 37660 | 37680 |
| R_700 | 21 | 37720 | 37740 |
| R_701 | 35 | 37778 | 37812 |
| R_702 | 72 | 37825 | 37896 |
| R_703 | 35 | 37926 | 37960 |
| R_704 | 42 | 37962 | 38003 |
| R_705 | 20 | 38119 | 38138 |
| R_706 | 28 | 38162 | 38189 |
| R_707 | 23 | 38215 | 38237 |
| R_708 | 22 | 38249 | 38270 |
| R_709 | 79 | 38284 | 38362 |
| R_710 | 30 | 38419 | 38448 |
| R_711 | 25 | 38476 | 38500 |
| R_712 | 21 | 38486 | 38506 |
| R_713 | 22 | 38520 | 38541 |
| R_714 | 47 | 38548 | 38594 |
| R_715 | 22 | 38603 | 38624 |
| R_716 | 27 | 38623 | 38649 |
| R_717 | 22 | 38709 | 38730 |
| R_718 | 21 | 38734 | 38754 |
| R_719 | 46 | 38777 | 38822 |
| R_720 | 33 | 38853 | 38885 |
| R_721 | 27 | 38897 | 38923 |
| R_722 | 23 | 38982 | 39004 |
| R_723 | 26 | 39007 | 39032 |
| R_724 | 23 | 39007 | 39029 |
| R_725 | 20 | 39016 | 39035 |
| R_726 | 21 | 39026 | 39046 |
| R_727 | 30 | 39048 | 39077 |
| R_728 | 31 | 39140 | 39170 |
| R_729 | 24 | 39161 | 39184 |
| R_730 | 36 | 39188 | 39223 |
| R_731 | 28 | 39235 | 39262 |
| R_732 | 39 | 39264 | 39302 |
| R_733 | 52 | 39328 | 39379 |
| R_734 | 59 | 39391 | 39449 |
| R_735 | 30 | 39463 | 39492 |
| R_736 | 20 | 39492 | 39511 |
| R_737 | 20 | 39519 | 39538 |
| R_738 | 37 | 39557 | 39593 |
| R_739 | 34 | 39595 | 39628 |
| R_740 | 34 | 39639 | 39672 |
| R_741 | 26 | 39682 | 39707 |
| R_742 | 20 | 39709 | 39728 |
| R_743 | 23 | 39746 | 39768 |
| R_744 | 23 | 39753 | 39775 |
| R_745 | 20 | 39777 | 39796 |
| R_746 | 20 | 39798 | 39817 |
| R_747 | 41 | 39833 | 39873 |
| R_748 | 20 | 39876 | 39895 |
| R_749 | 36 | 39907 | 39942 |
| R_750 | 47 | 39990 | 40036 |
| R_751 | 36 | 40074 | 40109 |
| R_752 | 23 | 40118 | 40140 |
| R_753 | 40 | 40209 | 40248 |
| R_754 | 24 | 40273 | 40296 |
| R_755 | 63 | 40301 | 40363 |
| R_756 | 35 | 40461 | 40495 |
| R_757 | 27 | 40497 | 40523 |
| R_758 | 33 | 40547 | 40579 |
| R_759 | 42 | 40587 | 40628 |
| R_760 | 41 | 40630 | 40670 |
| R_761 | 34 | 40697 | 40730 |
| R_762 | 57 | 40772 | 40828 |
| R_763 | 36 | 40831 | 40866 |
| R_764 | 60 | 40868 | 40927 |
| R_765 | 28 | 40941 | 40968 |
| R_766 | 29 | 40971 | 40999 |
| R_767 | 96 | 41031 | 41126 |
| R_768 | 43 | 41128 | 41170 |
| R_769 | 22 | 41218 | 41239 |
| R_770 | 28 | 41266 | 41293 |
| R_771 | 25 | 41311 | 41335 |
| R_772 | 50 | 41356 | 41405 |
| R_773 | 55 | 41425 | 41479 |
| R_774 | 23 | 41483 | 41505 |
| R_775 | 47 | 41518 | 41564 |
| R_776 | 36 | 41586 | 41621 |
| R_777 | 77 | 41641 | 41717 |
| R_778 | 48 | 41762 | 41809 |
| R_779 | 42 | 41830 | 41871 |
| R_780 | 57 | 41888 | 41944 |
| R_781 | 25 | 41964 | 41988 |
| R_782 | 30 | 42005 | 42034 |
| R_783 | 31 | 42096 | 42126 |
| R_784 | 30 | 42141 | 42170 |
| R_785 | 32 | 42172 | 42203 |
| R_786 | 56 | 42279 | 42334 |
| R_787 | 63 | 42336 | 42398 |
| R_788 | 44 | 42439 | 42482 |
| R_789 | 29 | 42486 | 42514 |
| R_790 | 30 | 42518 | 42547 |
| R_791 | 24 | 42581 | 42604 |
| R_792 | 32 | 42631 | 42662 |
| R_793 | 24 | 42681 | 42704 |
| R_794 | 21 | 42712 | 42732 |
| R_795 | 49 | 42745 | 42793 |
| R_796 | 35 | 42841 | 42875 |
| R_797 | 45 | 42877 | 42921 |
| R_798 | 22 | 42937 | 42958 |
| R_799 | 20 | 42969 | 42988 |
| R_800 | 45 | 42976 | 43020 |
| R_801 | 20 | 43035 | 43054 |
| R_802 | 72 | 43047 | 43118 |
| R_803 | 23 | 43136 | 43158 |
| R_804 | 56 | 43188 | 43243 |
| R_805 | 20 | 43239 | 43258 |
| R_806 | 20 | 43279 | 43298 |
| R_807 | 27 | 43304 | 43330 |
| R_808 | 30 | 43346 | 43375 |
| R_809 | 64 | 43408 | 43471 |
| R_810 | 52 | 43481 | 43532 |
| R_811 | 22 | 43538 | 43559 |
| R_812 | 29 | 43561 | 43589 |
| R_813 | 37 | 43593 | 43629 |
| R_814 | 24 | 43637 | 43660 |
| R_815 | 21 | 43697 | 43717 |
| R_816 | 21 | 43719 | 43739 |
| R_817 | 34 | 43772 | 43805 |
| R_818 | 21 | 43818 | 43838 |
| R_819 | 72 | 43916 | 43987 |
| R_820 | 23 | 44002 | 44024 |
| R_821 | 26 | 44041 | 44066 |
| R_822 | 43 | 44103 | 44145 |
| R_823 | 44 | 44167 | 44210 |
| R_824 | 73 | 44216 | 44288 |
| R_825 | 23 | 44284 | 44306 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_826 | 38 | 44298 | 44335 |
| R_827 | 56 | 44380 | 44435 |
| R_828 | 20 | 44449 | 44468 |
| R_829 | 50 | 44463 | 44512 |
| R_830 | 21 | 44530 | 44550 |
| R_831 | 25 | 44543 | 44567 |
| R_832 | 38 | 44552 | 44589 |
| R_833 | 28 | 44610 | 44637 |
| R_834 | 25 | 44629 | 44653 |
| R_835 | 45 | 44651 | 44695 |
| R_836 | 28 | 44763 | 44790 |
| R_837 | 21 | 44820 | 44840 |
| R_838 | 32 | 44857 | 44888 |
| R_839 | 47 | 44888 | 44934 |
| R_840 | 20 | 44994 | 45013 |
| R_841 | 21 | 45032 | 45052 |
| R_842 | 23 | 45054 | 45076 |
| R_843 | 22 | 45078 | 45099 |
| R_844 | 38 | 45129 | 45166 |
| R_845 | 21 | 45203 | 45223 |
| R_846 | 66 | 45238 | 45303 |
| R_847 | 33 | 45304 | 45336 |
| R_848 | 37 | 45338 | 45374 |
| R_849 | 35 | 45391 | 45425 |
| R_850 | 24 | 45526 | 45549 |
| R_851 | 25 | 45551 | 45575 |
| R_852 | 27 | 45673 | 45699 |
| R_853 | 69 | 45708 | 45776 |
| R_854 | 48 | 45821 | 45868 |
| R_855 | 37 | 45907 | 45943 |
| R_856 | 42 | 45987 | 46028 |
| R_857 | 37 | 46043 | 46079 |
| R_858 | 36 | 46104 | 46139 |
| R_859 | 30 | 46146 | 46175 |
| R_860 | 25 | 46178 | 46202 |
| R_861 | 21 | 46261 | 46281 |
| R_862 | 50 | 46304 | 46353 |
| R_863 | 40 | 46373 | 46412 |
| R_864 | 29 | 46435 | 46463 |
| R_865 | 27 | 46465 | 46491 |
| R_866 | 36 | 46522 | 46557 |
| R_867 | 37 | 46590 | 46626 |
| R_868 | 22 | 46663 | 46684 |
| R_869 | 60 | 46686 | 46745 |
| R_870 | 34 | 46811 | 46844 |
| R_871 | 28 | 46845 | 46872 |
| R_872 | 85 | 46896 | 46980 |
| R_873 | 23 | 47027 | 47049 |
| R_874 | 69 | 47051 | 47119 |
| R_875 | 62 | 47178 | 47239 |
| R_876 | 42 | 47430 | 47471 |
| R_877 | 20 | 47473 | 47492 |
| R_878 | 38 | 47519 | 47556 |
| R_879 | 33 | 47605 | 47637 |
| R_880 | 34 | 47652 | 47685 |
| R_881 | 33 | 47699 | 47731 |
| R_882 | 29 | 47733 | 47761 |
| R_883 | 36 | 47769 | 47804 |
| R_884 | 22 | 47806 | 47827 |
| R_885 | 28 | 47848 | 47875 |
| R_886 | 31 | 47999 | 48029 |
| R_887 | 36 | 48043 | 48078 |
| R_888 | 37 | 48080 | 48116 |
| R_889 | 42 | 48118 | 48159 |
| R_890 | 78 | 48195 | 48272 |
| R_891 | 70 | 48294 | 48363 |
| R_892 | 28 | 48377 | 48404 |
| R_893 | 20 | 48406 | 48425 |
| R_894 | 22 | 48438 | 48459 |
| R_895 | 20 | 48485 | 48504 |
| R_896 | 23 | 48532 | 48554 |
| R_897 | 32 | 48564 | 48595 |
| R_898 | 43 | 48627 | 48669 |
| R_899 | 32 | 48671 | 48702 |
| R_900 | 30 | 48744 | 48773 |
| R_901 | 24 | 48782 | 48805 |
| R_902 | 21 | 48797 | 48817 |
| R_903 | 22 | 48802 | 48823 |
| R_904 | 54 | 48808 | 48861 |
| R_905 | 38 | 48924 | 48961 |
| R_906 | 20 | 48966 | 48985 |
| R_907 | 25 | 49010 | 49034 |
| R_908 | 21 | 49067 | 49087 |
| R_909 | 61 | 49145 | 49205 |
| R_910 | 81 | 49207 | 49287 |
| R_911 | 35 | 49289 | 49323 |
| R_912 | 41 | 49325 | 49365 |
| R_913 | 99 | 49400 | 49498 |
| R_914 | 30 | 49507 | 49536 |
| R_915 | 24 | 49538 | 49561 |
| R_916 | 23 | 49563 | 49585 |
| R_917 | 27 | 49612 | 49638 |
| R_918 | 33 | 49654 | 49686 |
| R_919 | 37 | 49697 | 49733 |
| R_920 | 28 | 49751 | 49778 |
| R_921 | 20 | 49870 | 49889 |
| R_922 | 42 | 49890 | 49931 |
| R_923 | 38 | 49964 | 50001 |
| R_924 | 106 | 50003 | 50108 |
| R_925 | 29 | 50110 | 50138 |
| R_926 | 24 | 50394 | 50417 |
| R_927 | 42 | 50473 | 50514 |
| R_928 | 27 | 50578 | 50604 |
| R_929 | 42 | 50606 | 50647 |
| R_930 | 42 | 50692 | 50733 |
| R_931 | 20 | 50763 | 50782 |
| R_932 | 34 | 50808 | 50841 |
| R_933 | 48 | 50847 | 50894 |
| R_934 | 55 | 50955 | 51009 |
| R_935 | 21 | 51011 | 51031 |
| R_936 | 58 | 51071 | 51128 |
| R_937 | 85 | 51138 | 51222 |
| R_938 | 22 | 51273 | 51294 |
| R_939 | 40 | 51330 | 51369 |
| R_940 | 20 | 51343 | 51362 |
| R_941 | 71 | 51498 | 51568 |
| R_942 | 35 | 51570 | 51604 |
| R_943 | 20 | 51639 | 51658 |
| R_944 | 31 | 51680 | 51710 |
| R_945 | 75 | 51712 | 51786 |
| R_946 | 57 | 51788 | 51844 |
| R_947 | 57 | 51846 | 51902 |
| R_948 | 33 | 51928 | 51960 |
| R_949 | 33 | 51962 | 51994 |
| R_950 | 20 | 52012 | 52031 |
| R_951 | 52 | 52024 | 52075 |
| R_952 | 20 | 52183 | 52202 |
| R_953 | 31 | 52316 | 52346 |
| R_954 | 54 | 52348 | 52401 |
| R_955 | 24 | 52408 | 52431 |
| R_956 | 25 | 52433 | 52457 |
| R_957 | 68 | 52452 | 52519 |
| R_958 | 42 | 52521 | 52562 |
| R_959 | 41 | 52569 | 52609 |
| R_960 | 21 | 52626 | 52646 |
| R_961 | 21 | 52676 | 52696 |
| R_962 | 71 | 52704 | 52774 |
| R_963 | 31 | 52784 | 52814 |
| R_964 | 22 | 52826 | 52847 |
| R_965 | 25 | 52874 | 52898 |
| R_966 | 80 | 52915 | 52994 |
| R_967 | 21 | 53027 | 53047 |
| R_968 | 44 | 53130 | 53173 |
| R_969 | 21 | 53175 | 53195 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_970 | 24 | 53181 | 53204 |
| R_971 | 22 | 53233 | 53254 |
| R_972 | 20 | 53262 | 53281 |
| R_973 | 22 | 53315 | 53336 |
| R_974 | 20 | 53352 | 53371 |
| R_975 | 72 | 53390 | 53461 |
| R_976 | 42 | 53473 | 53514 |
| R_977 | 25 | 53534 | 53558 |
| R_978 | 30 | 53560 | 53589 |
| R_979 | 23 | 53600 | 53622 |
| R_980 | 28 | 53637 | 53664 |
| R_981 | 24 | 53696 | 53719 |
| R_982 | 21 | 53738 | 53758 |
| R_983 | 22 | 53753 | 53774 |
| R_984 | 23 | 53759 | 53781 |
| R_985 | 30 | 53793 | 53822 |
| R_986 | 23 | 53895 | 53917 |
| R_987 | 25 | 53910 | 53934 |
| R_988 | 21 | 53979 | 53999 |
| R_989 | 20 | 53996 | 54015 |
| R_990 | 21 | 54027 | 54047 |
| R_991 | 28 | 54049 | 54076 |
| R_992 | 40 | 54162 | 54201 |
| R_993 | 20 | 54218 | 54237 |
| R_994 | 77 | 54239 | 54315 |
| R_995 | 50 | 54317 | 54366 |
| R_996 | 21 | 54368 | 54388 |
| R_997 | 32 | 54406 | 54437 |
| R_998 | 33 | 54439 | 54471 |
| R_999 | 20 | 54507 | 54526 |
| R_1000 | 55 | 54528 | 54582 |
| R_1001 | 21 | 54584 | 54604 |
| R_1002 | 42 | 54606 | 54647 |
| R_1003 | 118 | 54651 | 54768 |
| R_1004 | 23 | 54833 | 54855 |
| R_1005 | 28 | 54857 | 54884 |
| R_1006 | 57 | 54887 | 54943 |
| R_1007 | 29 | 54973 | 55001 |
| R_1008 | 21 | 55014 | 55034 |
| R_1009 | 28 | 55074 | 55101 |
| R_1010 | 21 | 55134 | 55154 |
| R_1011 | 38 | 55171 | 55208 |
| R_1012 | 31 | 55210 | 55240 |
| R_1013 | 80 | 55248 | 55327 |
| R_1014 | 25 | 55329 | 55353 |
| R_1015 | 23 | 55365 | 55387 |
| R_1016 | 43 | 55424 | 55466 |
| R_1017 | 51 | 55539 | 55589 |
| R_1018 | 27 | 55591 | 55617 |
| R_1019 | 29 | 55619 | 55647 |
| R_1020 | 30 | 55653 | 55682 |
| R_1021 | 29 | 55724 | 55752 |
| R_1022 | 33 | 55778 | 55810 |
| R_1023 | 76 | 55848 | 55923 |
| R_1024 | 33 | 55992 | 56024 |
| R_1025 | 29 | 56026 | 56054 |
| R_1026 | 59 | 56080 | 56138 |
| R_1027 | 26 | 56155 | 56180 |
| R_1028 | 22 | 56196 | 56217 |
| R_1029 | 21 | 56225 | 56245 |
| R_1030 | 31 | 56274 | 56304 |
| R_1031 | 24 | 56338 | 56361 |
| R_1032 | 22 | 56410 | 56431 |
| R_1033 | 36 | 56433 | 56468 |
| R_1034 | 22 | 56521 | 56542 |
| R_1035 | 30 | 56567 | 56596 |
| R_1036 | 55 | 56641 | 56695 |
| R_1037 | 44 | 56697 | 56740 |
| R_1038 | 43 | 56761 | 56803 |
| R_1039 | 72 | 56805 | 56876 |
| R_1040 | 30 | 56885 | 56914 |
| R_1041 | 44 | 56916 | 56959 |
| R_1042 | 67 | 56961 | 57027 |
| R_1043 | 30 | 57033 | 57062 |
| R_1044 | 20 | 57167 | 57186 |
| R_1045 | 49 | 57211 | 57259 |
| R_1046 | 24 | 57348 | 57371 |
| R_1047 | 43 | 57434 | 57476 |
| R_1048 | 73 | 57536 | 57608 |
| R_1049 | 86 | 57641 | 57726 |
| R_1050 | 27 | 57754 | 57780 |
| R_1051 | 20 | 57786 | 57805 |
| R_1052 | 21 | 57807 | 57827 |
| R_1053 | 27 | 57829 | 57855 |
| R_1054 | 41 | 57857 | 57897 |
| R_1055 | 51 | 57899 | 57949 |
| R_1056 | 26 | 57981 | 58006 |
| R_1057 | 48 | 58008 | 58055 |
| R_1058 | 26 | 58057 | 58082 |
| R_1059 | 32 | 58097 | 58128 |
| R_1060 | 40 | 58138 | 58177 |
| R_1061 | 38 | 58192 | 58229 |
| R_1062 | 26 | 58235 | 58260 |
| R_1063 | 57 | 58375 | 58431 |
| R_1064 | 25 | 58444 | 58468 |
| R_1065 | 55 | 58484 | 58538 |
| R_1066 | 26 | 58555 | 58580 |
| R_1067 | 20 | 58582 | 58601 |
| R_1068 | 23 | 58604 | 58626 |
| R_1069 | 32 | 58650 | 58681 |
| R_1070 | 70 | 58740 | 58809 |
| R_1071 | 32 | 58889 | 58920 |
| R_1072 | 25 | 58927 | 58951 |
| R_1073 | 22 | 58953 | 58974 |
| R_1074 | 35 | 58993 | 59027 |
| R_1075 | 48 | 59029 | 59076 |
| R_1076 | 45 | 59079 | 59123 |
| R_1077 | 31 | 59125 | 59155 |
| R_1078 | 31 | 59183 | 59213 |
| R_1079 | 20 | 59243 | 59262 |
| R_1080 | 35 | 59264 | 59298 |
| R_1081 | 24 | 59303 | 59326 |
| R_1082 | 39 | 59328 | 59366 |
| R_1083 | 31 | 59380 | 59410 |
| R_1084 | 20 | 59490 | 59509 |
| R_1085 | 39 | 59551 | 59589 |
| R_1086 | 76 | 59591 | 59666 |
| R_1087 | 46 | 59713 | 59758 |
| R_1088 | 26 | 59837 | 59862 |
| R_1089 | 40 | 59878 | 59917 |
| R_1090 | 23 | 59957 | 59979 |
| R_1091 | 37 | 59998 | 60034 |
| R_1092 | 63 | 60133 | 60195 |
| R_1093 | 22 | 60201 | 60222 |
| R_1094 | 23 | 60281 | 60303 |
| R_1095 | 37 | 60291 | 60327 |
| R_1096 | 27 | 60360 | 60386 |
| R_1097 | 23 | 60429 | 60451 |
| R_1098 | 52 | 60536 | 60587 |
| R_1099 | 24 | 60605 | 60628 |
| R_1100 | 28 | 60656 | 60683 |
| R_1101 | 90 | 60703 | 60792 |
| R_1102 | 48 | 60794 | 60841 |
| R_1103 | 49 | 60841 | 60889 |
| R_1104 | 31 | 60921 | 60951 |
| R_1105 | 21 | 60953 | 60973 |
| R_1106 | 30 | 60979 | 61008 |
| R_1107 | 23 | 61040 | 61062 |
| R_1108 | 20 | 61117 | 61136 |
| R_1109 | 22 | 61148 | 61169 |
| R_1110 | 106 | 61165 | 61270 |
| R_1111 | 21 | 61274 | 61294 |
| R_1112 | 25 | 61392 | 61416 |
| R_1113 | 22 | 61447 | 61468 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_1114 | 25 | 61486 | 61510 |
| R_1115 | 23 | 61495 | 61517 |
| R_1116 | 27 | 61518 | 61544 |
| R_1117 | 23 | 61586 | 61608 |
| R_1118 | 32 | 61646 | 61677 |
| R_1119 | 34 | 61784 | 61817 |
| R_1120 | 23 | 61870 | 61892 |
| R_1121 | 43 | 61904 | 61946 |
| R_1122 | 22 | 61948 | 61969 |
| R_1123 | 33 | 61997 | 62029 |
| R_1124 | 21 | 62076 | 62096 |
| R_1125 | 22 | 62103 | 62124 |
| R_1126 | 20 | 62133 | 62152 |
| R_1127 | 26 | 62162 | 62187 |
| R_1128 | 20 | 62239 | 62258 |
| R_1129 | 24 | 62243 | 62266 |
| R_1130 | 20 | 62266 | 62285 |
| R_1131 | 24 | 62307 | 62330 |
| R_1132 | 27 | 62332 | 62358 |
| R_1133 | 22 | 62433 | 62454 |
| R_1134 | 22 | 62561 | 62582 |
| R_1135 | 50 | 62600 | 62649 |
| R_1136 | 29 | 62678 | 62706 |
| R_1137 | 32 | 62708 | 62739 |
| R_1138 | 20 | 62846 | 62865 |
| R_1139 | 46 | 62871 | 62916 |
| R_1140 | 23 | 62945 | 62967 |
| R_1141 | 52 | 62978 | 63029 |
| R_1142 | 43 | 63043 | 63085 |
| R_1143 | 31 | 63087 | 63117 |
| R_1144 | 35 | 63119 | 63153 |
| R_1145 | 31 | 63155 | 63185 |
| R_1146 | 54 | 63193 | 63246 |
| R_1147 | 23 | 63249 | 63271 |
| R_1148 | 29 | 63362 | 63390 |
| R_1149 | 33 | 63404 | 63436 |
| R_1150 | 33 | 63462 | 63494 |
| R_1151 | 27 | 63501 | 63527 |
| R_1152 | 29 | 63569 | 63597 |
| R_1153 | 36 | 63599 | 63634 |
| R_1154 | 20 | 63634 | 63653 |
| R_1155 | 46 | 63769 | 63814 |
| R_1156 | 20 | 63826 | 63845 |
| R_1157 | 24 | 63848 | 63871 |
| R_1158 | 54 | 63873 | 63926 |
| R_1159 | 48 | 63941 | 63988 |
| R_1160 | 45 | 63990 | 64034 |
| R_1161 | 20 | 64059 | 64078 |
| R_1162 | 20 | 64322 | 64341 |
| R_1163 | 20 | 64382 | 64401 |
| R_1164 | 24 | 64487 | 64510 |
| R_1165 | 34 | 64532 | 64565 |
| R_1166 | 27 | 64550 | 64576 |
| R_1167 | 24 | 65195 | 65218 |
| R_1168 | 20 | 65195 | 65214 |
| R_1169 | 28 | 65736 | 65763 |
| R_1170 | 30 | 65810 | 65839 |
| R_1171 | 26 | 65850 | 65875 |
| R_1172 | 32 | 65877 | 65908 |
| R_1173 | 29 | 65917 | 65945 |
| R_1174 | 55 | 66048 | 66102 |
| R_1175 | 41 | 66123 | 66163 |
| R_1176 | 37 | 66165 | 66201 |
| R_1177 | 66 | 66203 | 66268 |
| R_1178 | 49 | 66291 | 66339 |
| R_1179 | 34 | 66392 | 66425 |
| R_1180 | 45 | 66469 | 66513 |
| R_1181 | 23 | 66545 | 66567 |
| R_1182 | 27 | 66591 | 66617 |
| R_1183 | 24 | 66635 | 66658 |
| R_1184 | 22 | 66660 | 66681 |
| R_1185 | 49 | 66690 | 66738 |
| R_1186 | 29 | 66755 | 66783 |
| R_1187 | 36 | 66789 | 66824 |
| R_1188 | 23 | 66792 | 66814 |
| R_1189 | 23 | 66865 | 66887 |
| R_1190 | 27 | 66889 | 66915 |
| R_1191 | 48 | 66991 | 67038 |
| R_1192 | 24 | 67116 | 67139 |
| R_1193 | 24 | 67155 | 67178 |
| R_1194 | 27 | 67185 | 67211 |
| R_1195 | 35 | 67231 | 67265 |
| R_1196 | 20 | 67316 | 67335 |
| R_1197 | 23 | 67337 | 67359 |
| R_1198 | 31 | 67361 | 67391 |
| R_1199 | 37 | 67467 | 67503 |
| R_1200 | 27 | 67498 | 67524 |
| R_1201 | 23 | 67499 | 67521 |
| R_1202 | 37 | 67517 | 67553 |
| R_1203 | 26 | 67604 | 67629 |
| R_1204 | 25 | 67624 | 67648 |
| R_1205 | 26 | 67708 | 67733 |
| R_1206 | 21 | 67806 | 67826 |
| R_1207 | 27 | 67877 | 67903 |
| R_1208 | 43 | 67905 | 67947 |
| R_1209 | 36 | 67987 | 68022 |
| R_1210 | 50 | 68024 | 68073 |
| R_1211 | 92 | 68092 | 68183 |
| R_1212 | 24 | 68216 | 68239 |
| R_1213 | 52 | 68257 | 68308 |
| R_1214 | 32 | 68390 | 68421 |
| R_1215 | 48 | 68442 | 68489 |
| R_1216 | 20 | 68486 | 68505 |
| R_1217 | 21 | 68546 | 68566 |
| R_1218 | 25 | 68556 | 68580 |
| R_1219 | 20 | 68561 | 68580 |
| R_1220 | 23 | 68610 | 68632 |
| R_1221 | 25 | 68679 | 68703 |
| R_1222 | 35 | 68736 | 68770 |
| R_1223 | 62 | 68806 | 68867 |
| R_1224 | 22 | 68885 | 68906 |
| R_1225 | 22 | 68908 | 68929 |
| R_1226 | 20 | 68931 | 68950 |
| R_1227 | 29 | 68950 | 68978 |
| R_1228 | 34 | 69017 | 69050 |
| R_1229 | 25 | 69053 | 69077 |
| R_1230 | 20 | 69083 | 69102 |
| R_1231 | 27 | 69123 | 69149 |
| R_1232 | 30 | 69160 | 69189 |
| R_1233 | 35 | 69210 | 69244 |
| R_1234 | 53 | 69248 | 69300 |
| R_1235 | 23 | 69304 | 69326 |
| R_1236 | 34 | 69393 | 69426 |
| R_1237 | 29 | 69428 | 69456 |
| R_1238 | 45 | 69458 | 69502 |
| R_1239 | 43 | 69547 | 69589 |
| R_1240 | 20 | 69601 | 69620 |
| R_1241 | 20 | 69633 | 69652 |
| R_1242 | 29 | 69656 | 69684 |
| R_1243 | 39 | 69705 | 69743 |
| R_1244 | 42 | 69769 | 69810 |
| R_1245 | 22 | 69829 | 69850 |
| R_1246 | 28 | 69912 | 69939 |
| R_1247 | 32 | 69941 | 69972 |
| R_1248 | 31 | 70029 | 70059 |
| R_1249 | 41 | 70065 | 70105 |
| R_1250 | 27 | 70162 | 70188 |
| R_1251 | 43 | 70200 | 70242 |
| R_1252 | 20 | 70217 | 70236 |
| R_1253 | 20 | 70345 | 70364 |
| R_1254 | 35 | 70366 | 70400 |
| R_1255 | 57 | 70433 | 70489 |
| R_1256 | 21 | 70515 | 70535 |
| R_1257 | 26 | 70537 | 70562 |

TABLE 4-continued

Regions (reg.) on SEQ ID NO: 1 which may be targeted using an oligonucleotide of the invention

| Reg. | length (nt) | Position on SEQ ID NO: 1 start | end |
|---|---|---|---|
| R_1258 | 40 | 70583 | 70622 |
| R_1259 | 20 | 70657 | 70676 |
| R_1260 | 22 | 70688 | 70709 |
| R_1261 | 34 | 70723 | 70756 |
| R_1262 | 23 | 70758 | 70780 |
| R_1263 | 21 | 70782 | 70802 |
| R_1264 | 21 | 70808 | 70828 |
| R_1265 | 26 | 70818 | 70843 |
| R_1266 | 31 | 70912 | 70942 |
| R_1267 | 22 | 71039 | 71060 |
| R_1268 | 25 | 71104 | 71128 |
| R_1269 | 24 | 71195 | 71218 |
| R_1270 | 43 | 71467 | 71509 |
| R_1271 | 36 | 71519 | 71554 |
| R_1272 | 24 | 71560 | 71583 |
| R_1273 | 30 | 71606 | 71635 |
| R_1274 | 21 | 71637 | 71657 |
| R_1275 | 22 | 71672 | 71693 |
| R_1276 | 56 | 71744 | 71799 |
| R_1277 | 35 | 71827 | 71861 |
| R_1278 | 21 | 71863 | 71883 |
| R_1279 | 32 | 71913 | 71944 |
| R_1280 | 25 | 71946 | 71970 |
| R_1281 | 23 | 72022 | 72044 |
| R_1282 | 28 | 72092 | 72119 |
| R_1283 | 22 | 72095 | 72116 |
| R_1284 | 21 | 72121 | 72141 |
| R_1285 | 50 | 72147 | 72196 |
| R_1286 | 31 | 72204 | 72234 |
| R_1287 | 23 | 72230 | 72252 |
| R_1288 | 36 | 72236 | 72271 |
| R_1289 | 31 | 72285 | 72315 |
| R_1290 | 85 | 72314 | 72398 |
| R_1291 | 52 | 72400 | 72451 |
| R_1292 | 37 | 72443 | 72479 |
| R_1293 | 31 | 72482 | 72512 |
| R_1294 | 40 | 72566 | 72605 |
| R_1295 | 49 | 72607 | 72655 |
| R_1296 | 86 | 72657 | 72742 |
| R_1297 | 63 | 72752 | 72814 |
| R_1298 | 125 | 72816 | 72940 |
| R_1299 | 31 | 72955 | 72985 |
| R_1300 | 20 | 72987 | 73006 |
| R_1301 | 40 | 73008 | 73047 |
| R_1302 | 24 | 73049 | 73072 |
| R_1303 | 37 | 73118 | 73154 |
| R_1304 | 26 | 73163 | 73188 |
| R_1305 | 29 | 73212 | 73240 |
| R_1306 | 22 | 73279 | 73300 |
| R_1307 | 22 | 73315 | 73336 |
| R_1308 | 30 | 73338 | 73367 |
| R_1309 | 23 | 73387 | 73409 |
| R_1310 | 52 | 73411 | 73462 |
| R_1311 | 26 | 73498 | 73523 |
| R_1312 | 24 | 73525 | 73548 |
| R_1313 | 83 | 73562 | 73644 |
| R_1314 | 36 | 73646 | 73681 |
| R_1315 | 20 | 73703 | 73722 |
| R_1316 | 27 | 73725 | 73751 |
| R_1317 | 62 | 73776 | 73837 |
| R_1318 | 20 | 73845 | 73864 |
| R_1319 | 61 | 73894 | 73954 |
| R_1320 | 91 | 73955 | 74045 |
| R_1321 | 32 | 74079 | 74110 |
| R_1322 | 28 | 74115 | 74142 |
| R_1323 | 62 | 74144 | 74205 |
| R_1324 | 27 | 74214 | 74240 |
| R_1325 | 62 | 74244 | 74305 |
| R_1326 | 28 | 74320 | 74347 |
| R_1327 | 24 | 74350 | 74373 |
| R_1328 | 46 | 74386 | 74431 |
| R_1329 | 23 | 74433 | 74455 |
| R_1330 | 31 | 74463 | 74493 |
| R_1331 | 48 | 74497 | 74544 |
| R_1332 | 40 | 74546 | 74585 |
| R_1333 | 20 | 74604 | 74623 |
| R_1334 | 65 | 74648 | 74712 |
| R_1335 | 29 | 74725 | 74753 |
| R_1336 | 35 | 74764 | 74798 |
| R_1337 | 57 | 74805 | 74861 |
| R_1338 | 56 | 74863 | 74918 |
| R_1339 | 37 | 74936 | 74972 |
| R_1340 | 28 | 74974 | 75001 |
| R_1341 | 53 | 75003 | 75055 |
| R_1342 | 22 | 75019 | 75040 |
| R_1343 | 30 | 75097 | 75126 |
| R_1344 | 51 | 75126 | 75176 |
| R_1345 | 28 | 75362 | 75389 |
| R_1346 | 29 | 75417 | 75445 |
| R_1347 | 54 | 75482 | 75535 |
| R_1348 | 27 | 75552 | 75578 |
| R_1349 | 27 | 75580 | 75606 |
| R_1350 | 26 | 75593 | 75618 |
| R_1351 | 41 | 75815 | 75855 |
| R_1352 | 30 | 75919 | 75948 |
| R_1353 | 20 | 75944 | 75963 |
| R_1354 | 37 | 75964 | 76000 |
| R_1355 | 20 | 76123 | 76142 |
| R_1356 | 30 | 76156 | 76185 |
| R_1357 | 80 | 76199 | 76278 |
| R_1358 | 23 | 76296 | 76318 |
| R_1359 | 21 | 76327 | 76347 |
| R_1360 | 24 | 76341 | 76364 |
| R_1361 | 61 | 76366 | 76426 |
| R_1362 | 26 | 76467 | 76492 |
| R_1363 | 35 | 76520 | 76554 |
| R_1364 | 58 | 76571 | 76628 |
| R_1365 | 57 | 76697 | 76753 |
| R_1366 | 22 | 76755 | 76776 |
| R_1367 | 23 | 76822 | 76844 |
| R_1368 | 42 | 76863 | 76904 |
| R_1369 | 26 | 76906 | 76931 |
| R_1370 | 51 | 76944 | 76994 |
| R_1371 | 69 | 77037 | 77105 |
| R_1372 | 26 | 77153 | 77178 |
| R_1373 | 85 | 77180 | 77264 |
| R_1374 | 35 | 77271 | 77305 |
| R_1375 | 41 | 77307 | 77347 |
| R_1376 | 27 | 77433 | 77459 |
| R_1377 | 24 | 77462 | 77485 |
| R_1378 | 30 | 77508 | 77537 |
| R_1379 | 36 | 77561 | 77596 |
| R_1380 | 39 | 77615 | 77653 |
| R_1381 | 50 | 77655 | 77704 |
| R_1382 | 20 | 77719 | 77738 |
| R_1383 | 26 | 77762 | 77787 |
| R_1384 | 29 | 77807 | 77835 |
| R_1385 | 23 | 77837 | 77859 |
| R_1386 | 26 | 77861 | 77886 |
| R_1387 | 22 | 77910 | 77931 |
| R_1388 | 45 | 77933 | 77977 |
| R_1389 | 36 | 78017 | 78052 |
| R_1390 | 24 | 78074 | 78097 |
| R_1391 | 47 | 78136 | 78182 |
| R_1392 | 93 | 78184 | 78276 |
| R_1393 | 24 | 78282 | 78305 |
| R_1394 | 99 | 78319 | 78417 |
| R_1395 | 42 | 78420 | 78461 |
| R_1396 | 23 | 78478 | 78500 |
| R_1397 | 21 | 78647 | 78667 |
| R_1398 | 34 | 78736 | 78769 |
| R_1399 | 20 | 78891 | 78910 |
| R_1400 | 26 | 78926 | 78951 |
| R_1401 | 21 | 78953 | 78973 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
| --- | --- | --- | --- |
| R_1402 | 69 | 78997 | 79065 |
| R_1403 | 21 | 79067 | 79087 |
| R_1404 | 25 | 79091 | 79115 |
| R_1405 | 21 | 79122 | 79142 |
| R_1406 | 24 | 79160 | 79183 |
| R_1407 | 31 | 79187 | 79217 |
| R_1408 | 75 | 79219 | 79293 |
| R_1409 | 27 | 79308 | 79334 |
| R_1410 | 71 | 79366 | 79436 |
| R_1411 | 34 | 79469 | 79502 |
| R_1412 | 41 | 79534 | 79574 |
| R_1413 | 28 | 79576 | 79603 |
| R_1414 | 23 | 79605 | 79627 |
| R_1415 | 24 | 79712 | 79735 |
| R_1416 | 35 | 79738 | 79772 |
| R_1417 | 37 | 79793 | 79829 |
| R_1418 | 38 | 79847 | 79884 |
| R_1419 | 48 | 79924 | 79971 |
| R_1420 | 31 | 80108 | 80138 |
| R_1421 | 34 | 80140 | 80173 |
| R_1422 | 77 | 80211 | 80287 |
| R_1423 | 55 | 80307 | 80361 |
| R_1424 | 26 | 80366 | 80391 |
| R_1425 | 38 | 80419 | 80456 |
| R_1426 | 20 | 80472 | 80491 |
| R_1427 | 21 | 80505 | 80525 |
| R_1428 | 40 | 80527 | 80566 |
| R_1429 | 37 | 80571 | 80607 |
| R_1430 | 40 | 80618 | 80657 |
| R_1431 | 29 | 80671 | 80699 |
| R_1432 | 36 | 80732 | 80767 |
| R_1433 | 39 | 80791 | 80829 |
| R_1434 | 37 | 80830 | 80866 |
| R_1435 | 53 | 80868 | 80920 |
| R_1436 | 30 | 80996 | 81025 |
| R_1437 | 25 | 81027 | 81051 |
| R_1438 | 55 | 81053 | 81107 |
| R_1439 | 68 | 81109 | 81176 |
| R_1440 | 24 | 81225 | 81248 |
| R_1441 | 68 | 81264 | 81331 |
| R_1442 | 23 | 81344 | 81366 |
| R_1443 | 64 | 81377 | 81440 |
| R_1444 | 26 | 81481 | 81506 |
| R_1445 | 31 | 81571 | 81601 |
| R_1446 | 44 | 81608 | 81651 |
| R_1447 | 47 | 81694 | 81740 |
| R_1448 | 27 | 81757 | 81783 |
| R_1449 | 36 | 81780 | 81815 |
| R_1450 | 25 | 81817 | 81841 |
| R_1451 | 46 | 81866 | 81911 |
| R_1452 | 23 | 81916 | 81938 |
| R_1453 | 27 | 81946 | 81972 |
| R_1454 | 20 | 82028 | 82047 |
| R_1455 | 55 | 82049 | 82103 |
| R_1456 | 71 | 82122 | 82192 |
| R_1457 | 32 | 82216 | 82247 |
| R_1458 | 47 | 82278 | 82324 |
| R_1459 | 25 | 82498 | 82522 |
| R_1460 | 27 | 82549 | 82575 |
| R_1461 | 48 | 82606 | 82653 |
| R_1462 | 26 | 82655 | 82680 |
| R_1463 | 27 | 82699 | 82725 |
| R_1464 | 67 | 82735 | 82801 |
| R_1465 | 56 | 82833 | 82888 |
| R_1466 | 29 | 82898 | 82926 |
| R_1467 | 26 | 82928 | 82953 |
| R_1468 | 45 | 82990 | 83034 |
| R_1469 | 73 | 83083 | 83155 |
| R_1470 | 39 | 83180 | 83218 |
| R_1471 | 70 | 83255 | 83324 |
| R_1472 | 35 | 83346 | 83380 |
| R_1473 | 23 | 83409 | 83431 |
| R_1474 | 111 | 83433 | 83543 |
| R_1475 | 39 | 83553 | 83591 |
| R_1476 | 54 | 83628 | 83681 |
| R_1477 | 36 | 83710 | 83745 |
| R_1478 | 32 | 83776 | 83807 |
| R_1479 | 23 | 83809 | 83831 |
| R_1480 | 53 | 83854 | 83906 |
| R_1481 | 20 | 83960 | 83979 |
| R_1482 | 43 | 83995 | 84037 |
| R_1483 | 73 | 84051 | 84123 |
| R_1484 | 40 | 84142 | 84181 |
| R_1485 | 52 | 84217 | 84268 |
| R_1486 | 28 | 84270 | 84297 |
| R_1487 | 20 | 84354 | 84373 |
| R_1488 | 21 | 84440 | 84460 |
| R_1489 | 31 | 84488 | 84518 |
| R_1490 | 22 | 84653 | 84674 |
| R_1491 | 29 | 84727 | 84755 |
| R_1492 | 38 | 84851 | 84888 |
| R_1493 | 21 | 84887 | 84907 |
| R_1494 | 58 | 84932 | 84989 |
| R_1495 | 35 | 84991 | 85025 |
| R_1496 | 24 | 85109 | 85132 |
| R_1497 | 60 | 85135 | 85194 |
| R_1498 | 27 | 85206 | 85232 |
| R_1499 | 26 | 85239 | 85264 |
| R_1500 | 32 | 85327 | 85358 |
| R_1501 | 24 | 85390 | 85413 |
| R_1502 | 24 | 85520 | 85543 |
| R_1503 | 88 | 85545 | 85632 |
| R_1504 | 20 | 85662 | 85681 |
| R_1505 | 75 | 85710 | 85784 |
| R_1506 | 35 | 85786 | 85820 |
| R_1507 | 24 | 85822 | 85845 |
| R_1508 | 24 | 85864 | 85887 |
| R_1509 | 20 | 85879 | 85898 |
| R_1510 | 41 | 85889 | 85929 |
| R_1511 | 25 | 85964 | 85988 |
| R_1512 | 23 | 85994 | 86016 |
| R_1513 | 56 | 86064 | 86119 |
| R_1514 | 71 | 86189 | 86259 |
| R_1515 | 32 | 86266 | 86297 |
| R_1516 | 54 | 86319 | 86372 |
| R_1517 | 38 | 86383 | 86420 |
| R_1518 | 31 | 86427 | 86457 |
| R_1519 | 33 | 86478 | 86510 |
| R_1520 | 36 | 86676 | 86711 |
| R_1521 | 20 | 86715 | 86734 |
| R_1522 | 20 | 86742 | 86761 |
| R_1523 | 29 | 86809 | 86837 |
| R_1524 | 51 | 86873 | 86923 |
| R_1525 | 48 | 86939 | 86986 |
| R_1526 | 21 | 86989 | 87009 |
| R_1527 | 46 | 87080 | 87125 |
| R_1528 | 23 | 87140 | 87162 |
| R_1529 | 24 | 87164 | 87187 |
| R_1530 | 45 | 87209 | 87253 |
| R_1531 | 21 | 87261 | 87281 |
| R_1532 | 37 | 87297 | 87333 |
| R_1533 | 61 | 87367 | 87427 |
| R_1534 | 69 | 87595 | 87663 |
| R_1535 | 29 | 87665 | 87693 |
| R_1536 | 20 | 87679 | 87698 |
| R_1537 | 20 | 87760 | 87779 |
| R_1538 | 21 | 87915 | 87935 |
| R_1539 | 21 | 87952 | 87972 |
| R_1540 | 20 | 87962 | 87981 |
| R_1541 | 47 | 88017 | 88063 |
| R_1542 | 32 | 88099 | 88130 |
| R_1543 | 33 | 88133 | 88165 |
| R_1544 | 22 | 88176 | 88197 |
| R_1545 | 36 | 88216 | 88251 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_1546 | 35 | 88279 | 88313 |
| R_1547 | 30 | 88353 | 88382 |
| R_1548 | 38 | 88384 | 88421 |
| R_1549 | 37 | 88439 | 88475 |
| R_1550 | 54 | 88493 | 88546 |
| R_1551 | 29 | 88561 | 88589 |
| R_1552 | 21 | 88594 | 88614 |
| R_1553 | 23 | 88617 | 88639 |
| R_1554 | 24 | 88648 | 88671 |
| R_1555 | 30 | 88678 | 88707 |
| R_1556 | 27 | 88715 | 88741 |
| R_1557 | 24 | 88774 | 88797 |
| R_1558 | 48 | 88820 | 88867 |
| R_1559 | 35 | 88877 | 88911 |
| R_1560 | 52 | 88919 | 88970 |
| R_1561 | 26 | 88978 | 89003 |
| R_1562 | 32 | 89011 | 89042 |
| R_1563 | 26 | 89044 | 89069 |
| R_1564 | 51 | 89100 | 89150 |
| R_1565 | 34 | 89196 | 89229 |
| R_1566 | 28 | 89231 | 89258 |
| R_1567 | 24 | 89261 | 89284 |
| R_1568 | 24 | 89286 | 89309 |
| R_1569 | 42 | 89374 | 89415 |
| R_1570 | 24 | 89430 | 89453 |
| R_1571 | 48 | 89466 | 89513 |
| R_1572 | 31 | 89528 | 89558 |
| R_1573 | 46 | 89563 | 89608 |
| R_1574 | 24 | 89610 | 89633 |
| R_1575 | 28 | 89725 | 89752 |
| R_1576 | 25 | 89754 | 89778 |
| R_1577 | 21 | 89780 | 89800 |
| R_1578 | 27 | 89802 | 89828 |
| R_1579 | 38 | 89833 | 89870 |
| R_1580 | 23 | 89882 | 89904 |
| R_1581 | 20 | 89961 | 89980 |
| R_1582 | 35 | 89982 | 90016 |
| R_1583 | 44 | 90049 | 90092 |
| R_1584 | 27 | 90129 | 90155 |
| R_1585 | 21 | 90264 | 90284 |
| R_1586 | 35 | 90287 | 90321 |
| R_1587 | 40 | 90444 | 90483 |
| R_1588 | 73 | 90558 | 90630 |
| R_1589 | 20 | 90632 | 90651 |
| R_1590 | 28 | 90702 | 90729 |
| R_1591 | 35 | 90771 | 90805 |
| R_1592 | 27 | 90794 | 90820 |
| R_1593 | 24 | 90814 | 90837 |
| R_1594 | 30 | 90827 | 90856 |
| R_1595 | 21 | 90839 | 90859 |
| R_1596 | 21 | 90876 | 90896 |
| R_1597 | 26 | 90901 | 90926 |
| R_1598 | 29 | 90972 | 91000 |
| R_1599 | 24 | 91032 | 91055 |
| R_1600 | 42 | 91057 | 91098 |
| R_1601 | 30 | 91135 | 91164 |
| R_1602 | 25 | 91189 | 91213 |
| R_1603 | 26 | 91247 | 91272 |
| R_1604 | 21 | 91274 | 91294 |
| R_1605 | 29 | 91296 | 91324 |
| R_1606 | 20 | 91396 | 91415 |
| R_1607 | 31 | 91471 | 91501 |
| R_1608 | 71 | 91521 | 91591 |
| R_1609 | 48 | 91667 | 91714 |
| R_1610 | 23 | 91755 | 91777 |
| R_1611 | 29 | 91788 | 91816 |
| R_1612 | 32 | 91858 | 91889 |
| R_1613 | 28 | 91915 | 91942 |
| R_1614 | 35 | 91965 | 91999 |
| R_1615 | 29 | 92052 | 92080 |
| R_1616 | 20 | 92131 | 92150 |
| R_1617 | 20 | 92152 | 92171 |
| R_1618 | 32 | 92181 | 92212 |
| R_1619 | 43 | 92227 | 92269 |
| R_1620 | 29 | 92271 | 92299 |
| R_1621 | 98 | 92306 | 92403 |
| R_1622 | 22 | 92420 | 92441 |
| R_1623 | 31 | 92463 | 92493 |
| R_1624 | 23 | 92495 | 92517 |
| R_1625 | 27 | 92574 | 92600 |
| R_1626 | 134 | 92643 | 92776 |
| R_1627 | 57 | 92793 | 92849 |
| R_1628 | 43 | 92866 | 92908 |
| R_1629 | 45 | 92910 | 92954 |
| R_1630 | 26 | 92956 | 92981 |
| R_1631 | 23 | 92983 | 93005 |
| R_1632 | 46 | 93007 | 93052 |
| R_1633 | 30 | 93022 | 93051 |
| R_1634 | 22 | 93094 | 93115 |
| R_1635 | 21 | 93117 | 93137 |
| R_1636 | 39 | 93139 | 93177 |
| R_1637 | 117 | 93214 | 93330 |
| R_1638 | 37 | 93359 | 93395 |
| R_1639 | 46 | 93409 | 93454 |
| R_1640 | 32 | 93508 | 93539 |
| R_1641 | 28 | 93541 | 93568 |
| R_1642 | 33 | 93570 | 93602 |
| R_1643 | 22 | 93647 | 93668 |
| R_1644 | 26 | 93674 | 93699 |
| R_1645 | 28 | 93716 | 93743 |
| R_1646 | 72 | 93770 | 93841 |
| R_1647 | 36 | 93897 | 93932 |
| R_1648 | 25 | 94007 | 94031 |
| R_1649 | 25 | 94121 | 94145 |
| R_1650 | 20 | 94227 | 94246 |
| R_1651 | 69 | 94295 | 94363 |
| R_1652 | 49 | 94371 | 94419 |
| R_1653 | 40 | 94426 | 94465 |
| R_1654 | 73 | 94478 | 94550 |
| R_1655 | 35 | 94571 | 94605 |
| R_1656 | 63 | 94607 | 94669 |
| R_1657 | 41 | 94788 | 94828 |
| R_1658 | 73 | 94844 | 94916 |
| R_1659 | 21 | 94929 | 94949 |
| R_1660 | 21 | 94979 | 94999 |
| R_1661 | 31 | 95087 | 95117 |
| R_1662 | 25 | 95173 | 95197 |
| R_1663 | 23 | 95244 | 95266 |
| R_1664 | 38 | 95278 | 95315 |
| R_1665 | 28 | 95355 | 95382 |
| R_1666 | 95 | 95390 | 95484 |
| R_1667 | 159 | 95486 | 95644 |
| R_1668 | 30 | 95646 | 95675 |
| R_1669 | 101 | 95695 | 95795 |
| R_1670 | 33 | 95807 | 95839 |
| R_1671 | 24 | 95863 | 95886 |
| R_1672 | 22 | 95888 | 95909 |
| R_1673 | 31 | 95915 | 95945 |
| R_1674 | 30 | 95951 | 95980 |
| R_1675 | 28 | 96033 | 96060 |
| R_1676 | 37 | 96057 | 96093 |
| R_1677 | 28 | 96159 | 96186 |
| R_1678 | 40 | 96287 | 96326 |
| R_1679 | 43 | 96331 | 96373 |
| R_1680 | 39 | 96450 | 96488 |
| R_1681 | 30 | 96492 | 96521 |
| R_1682 | 44 | 96523 | 96566 |
| R_1683 | 22 | 96589 | 96610 |
| R_1684 | 22 | 96655 | 96676 |
| R_1685 | 52 | 96714 | 96765 |
| R_1686 | 23 | 96776 | 96798 |
| R_1687 | 25 | 96798 | 96822 |
| R_1688 | 36 | 96838 | 96873 |
| R_1689 | 44 | 96895 | 96938 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_1690 | 21 | 96940 | 96960 |
| R_1691 | 24 | 96993 | 97016 |
| R_1692 | 24 | 97038 | 97061 |
| R_1693 | 22 | 97073 | 97094 |
| R_1694 | 25 | 97106 | 97130 |
| R_1695 | 20 | 97132 | 97151 |
| R_1696 | 23 | 97162 | 97184 |
| R_1697 | 38 | 97186 | 97223 |
| R_1698 | 32 | 97225 | 97256 |
| R_1699 | 41 | 97258 | 97298 |
| R_1700 | 34 | 97300 | 97333 |
| R_1701 | 20 | 97342 | 97361 |
| R_1702 | 21 | 97486 | 97506 |
| R_1703 | 24 | 97532 | 97555 |
| R_1704 | 20 | 97592 | 97611 |
| R_1705 | 21 | 97606 | 97626 |
| R_1706 | 20 | 97690 | 97709 |
| R_1707 | 43 | 97694 | 97736 |
| R_1708 | 26 | 97740 | 97765 |
| R_1709 | 28 | 97767 | 97794 |
| R_1710 | 64 | 97820 | 97883 |
| R_1711 | 32 | 97928 | 97959 |
| R_1712 | 40 | 98008 | 98047 |
| R_1713 | 49 | 98103 | 98151 |
| R_1714 | 33 | 98166 | 98198 |
| R_1715 | 26 | 98200 | 98225 |
| R_1716 | 32 | 98324 | 98355 |
| R_1717 | 21 | 98333 | 98353 |
| R_1718 | 21 | 98467 | 98487 |
| R_1719 | 22 | 98506 | 98527 |
| R_1720 | 31 | 98577 | 98607 |
| R_1721 | 32 | 98681 | 98712 |
| R_1722 | 23 | 98751 | 98773 |
| R_1723 | 37 | 98789 | 98825 |
| R_1724 | 37 | 98930 | 98966 |
| R_1725 | 40 | 98969 | 99008 |
| R_1726 | 21 | 99015 | 99035 |
| R_1727 | 45 | 99231 | 99275 |
| R_1728 | 38 | 99345 | 99382 |
| R_1729 | 46 | 99387 | 99432 |
| R_1730 | 25 | 99434 | 99458 |
| R_1731 | 21 | 99515 | 99535 |
| R_1732 | 23 | 99565 | 99587 |
| R_1733 | 21 | 99658 | 99678 |
| R_1734 | 43 | 99718 | 99760 |
| R_1735 | 30 | 99762 | 99791 |
| R_1736 | 62 | 99820 | 99881 |
| R_1737 | 21 | 99933 | 99953 |
| R_1738 | 26 | 99986 | 100011 |
| R_1739 | 29 | 100013 | 100041 |
| R_1740 | 71 | 100063 | 100133 |
| R_1741 | 32 | 100169 | 100200 |
| R_1742 | 21 | 100248 | 100268 |
| R_1743 | 30 | 100263 | 100292 |
| R_1744 | 38 | 100296 | 100333 |
| R_1745 | 22 | 100359 | 100380 |
| R_1746 | 23 | 100375 | 100397 |
| R_1747 | 23 | 100384 | 100406 |
| R_1748 | 24 | 100639 | 100662 |
| R_1749 | 24 | 100645 | 100668 |
| R_1750 | 20 | 100666 | 100685 |
| R_1751 | 23 | 100695 | 100717 |
| R_1752 | 20 | 100746 | 100765 |
| R_1753 | 34 | 100771 | 100804 |
| R_1754 | 21 | 100801 | 100821 |
| R_1755 | 26 | 100823 | 100848 |
| R_1756 | 20 | 100857 | 100876 |
| R_1757 | 34 | 100899 | 100932 |
| R_1758 | 21 | 100965 | 100985 |
| R_1759 | 32 | 101017 | 101048 |
| R_1760 | 21 | 101085 | 101105 |
| R_1761 | 26 | 101195 | 101220 |
| R_1762 | 23 | 101227 | 101249 |
| R_1763 | 30 | 101324 | 101353 |
| R_1764 | 20 | 101357 | 101376 |
| R_1765 | 21 | 101415 | 101435 |
| R_1766 | 20 | 101444 | 101463 |
| R_1767 | 37 | 101465 | 101501 |
| R_1768 | 25 | 101497 | 101521 |
| R_1769 | 42 | 101523 | 101564 |
| R_1770 | 26 | 101576 | 101601 |
| R_1771 | 34 | 101620 | 101653 |
| R_1772 | 36 | 101679 | 101714 |
| R_1773 | 39 | 101734 | 101772 |
| R_1774 | 24 | 101779 | 101802 |
| R_1775 | 71 | 101817 | 101887 |
| R_1776 | 67 | 101913 | 101979 |
| R_1777 | 28 | 101989 | 102016 |
| R_1778 | 28 | 102025 | 102052 |
| R_1779 | 33 | 102054 | 102086 |
| R_1780 | 23 | 102088 | 102110 |
| R_1781 | 44 | 102112 | 102155 |
| R_1782 | 22 | 102161 | 102182 |
| R_1783 | 65 | 102202 | 102266 |
| R_1784 | 23 | 102268 | 102290 |
| R_1785 | 35 | 102292 | 102326 |
| R_1786 | 32 | 102352 | 102383 |
| R_1787 | 29 | 102385 | 102413 |
| R_1788 | 29 | 102526 | 102554 |
| R_1789 | 77 | 102579 | 102655 |
| R_1790 | 39 | 102744 | 102782 |
| R_1791 | 32 | 102841 | 102872 |
| R_1792 | 22 | 103017 | 103038 |
| R_1793 | 20 | 103118 | 103137 |
| R_1794 | 20 | 103196 | 103215 |
| R_1795 | 23 | 103346 | 103368 |
| R_1796 | 24 | 103400 | 103423 |
| R_1797 | 27 | 103456 | 103482 |
| R_1798 | 54 | 103494 | 103547 |
| R_1799 | 21 | 103557 | 103577 |
| R_1800 | 34 | 103637 | 103670 |
| R_1801 | 58 | 103683 | 103740 |
| R_1802 | 25 | 103782 | 103806 |
| R_1803 | 20 | 103851 | 103870 |
| R_1804 | 26 | 103876 | 103901 |
| R_1805 | 21 | 103997 | 104017 |
| R_1806 | 49 | 104093 | 104141 |
| R_1807 | 61 | 104143 | 104203 |
| R_1808 | 28 | 104263 | 104290 |
| R_1809 | 22 | 104331 | 104352 |
| R_1810 | 24 | 104354 | 104377 |
| R_1811 | 36 | 104379 | 104414 |
| R_1812 | 72 | 104416 | 104487 |
| R_1813 | 23 | 104504 | 104526 |
| R_1814 | 54 | 104544 | 104597 |
| R_1815 | 20 | 104599 | 104618 |
| R_1816 | 22 | 104632 | 104653 |
| R_1817 | 25 | 104710 | 104734 |
| R_1818 | 22 | 104738 | 104759 |
| R_1819 | 40 | 104783 | 104822 |
| R_1820 | 42 | 104824 | 104865 |
| R_1821 | 21 | 104919 | 104939 |
| R_1822 | 23 | 105014 | 105036 |
| R_1823 | 58 | 105040 | 105097 |
| R_1824 | 25 | 105111 | 105135 |
| R_1825 | 50 | 105137 | 105186 |
| R_1826 | 22 | 105188 | 105209 |
| R_1827 | 40 | 105283 | 105322 |
| R_1828 | 31 | 105393 | 105423 |
| R_1829 | 29 | 105427 | 105455 |
| R_1830 | 72 | 105457 | 105528 |
| R_1831 | 30 | 105544 | 105573 |
| R_1832 | 39 | 105683 | 105721 |
| R_1833 | 36 | 105732 | 105767 |

TABLE 4-continued

Regions (reg.) on SEQ ID NO: 1 which may be targeted using an oligonucleotide of the invention

| Reg. | length (nt) | Position on SEQ ID NO: 1 start | end |
|---|---|---|---|
| R_1834 | 23 | 106011 | 106033 |
| R_1835 | 45 | 106334 | 106378 |
| R_1836 | 21 | 106380 | 106400 |
| R_1837 | 23 | 106407 | 106429 |
| R_1838 | 23 | 106475 | 106497 |
| R_1839 | 47 | 106562 | 106608 |
| R_1840 | 42 | 106645 | 106686 |
| R_1841 | 44 | 106677 | 106720 |
| R_1842 | 29 | 106677 | 106705 |
| R_1843 | 22 | 106728 | 106749 |
| R_1844 | 40 | 106783 | 106822 |
| R_1845 | 22 | 106824 | 106845 |
| R_1846 | 31 | 106847 | 106877 |
| R_1847 | 31 | 106879 | 106909 |
| R_1848 | 64 | 106923 | 106986 |
| R_1849 | 35 | 106988 | 107022 |
| R_1850 | 35 | 107046 | 107080 |
| R_1851 | 26 | 107085 | 107110 |
| R_1852 | 25 | 107122 | 107146 |
| R_1853 | 40 | 107239 | 107278 |
| R_1854 | 57 | 107338 | 107394 |
| R_1855 | 36 | 107405 | 107440 |
| R_1856 | 22 | 107442 | 107463 |
| R_1857 | 22 | 107465 | 107486 |
| R_1858 | 22 | 107506 | 107527 |
| R_1859 | 28 | 107553 | 107580 |
| R_1860 | 53 | 107582 | 107634 |
| R_1861 | 37 | 107639 | 107675 |
| R_1862 | 34 | 107679 | 107712 |
| R_1863 | 36 | 107775 | 107810 |
| R_1864 | 25 | 107868 | 107892 |
| R_1865 | 24 | 107893 | 107916 |
| R_1866 | 24 | 108016 | 108039 |
| R_1867 | 42 | 108071 | 108112 |
| R_1868 | 21 | 108176 | 108196 |
| R_1869 | 30 | 108213 | 108242 |
| R_1870 | 72 | 108263 | 108334 |
| R_1871 | 32 | 108390 | 108421 |
| R_1872 | 27 | 108441 | 108467 |
| R_1873 | 31 | 108479 | 108509 |
| R_1874 | 21 | 108524 | 108544 |
| R_1875 | 58 | 108546 | 108603 |
| R_1876 | 33 | 108669 | 108701 |
| R_1877 | 26 | 108721 | 108746 |
| R_1878 | 30 | 108822 | 108851 |
| R_1879 | 32 | 108859 | 108890 |
| R_1880 | 30 | 108909 | 108938 |
| R_1881 | 41 | 108996 | 109036 |
| R_1882 | 43 | 109038 | 109080 |
| R_1883 | 22 | 109104 | 109125 |
| R_1884 | 41 | 109145 | 109185 |
| R_1885 | 25 | 109237 | 109261 |
| R_1886 | 41 | 109263 | 109303 |
| R_1887 | 34 | 109306 | 109339 |
| R_1888 | 48 | 109355 | 109402 |
| R_1889 | 20 | 109404 | 109423 |
| R_1890 | 28 | 109425 | 109452 |
| R_1891 | 31 | 109454 | 109484 |
| R_1892 | 20 | 109494 | 109513 |
| R_1893 | 25 | 109519 | 109543 |
| R_1894 | 60 | 109554 | 109613 |
| R_1895 | 34 | 109631 | 109664 |
| R_1896 | 26 | 109666 | 109691 |
| R_1897 | 22 | 109693 | 109714 |
| R_1898 | 23 | 109757 | 109779 |
| R_1899 | 34 | 109822 | 109855 |
| R_1900 | 23 | 109866 | 109888 |
| R_1901 | 140 | 109935 | 110074 |
| R_1902 | 20 | 110077 | 110096 |
| R_1903 | 29 | 110137 | 110165 |
| R_1904 | 29 | 110216 | 110244 |
| R_1905 | 32 | 110254 | 110285 |
| R_1906 | 33 | 110294 | 110326 |
| R_1907 | 31 | 110328 | 110358 |
| R_1908 | 44 | 110383 | 110426 |
| R_1909 | 24 | 110421 | 110444 |
| R_1910 | 20 | 110563 | 110582 |
| R_1911 | 32 | 110584 | 110615 |
| R_1912 | 28 | 110598 | 110625 |
| R_1913 | 54 | 110612 | 110665 |
| R_1914 | 29 | 110781 | 110809 |
| R_1915 | 51 | 110823 | 110873 |
| R_1916 | 22 | 110875 | 110896 |
| R_1917 | 27 | 110899 | 110925 |
| R_1918 | 25 | 110992 | 111016 |
| R_1919 | 38 | 111036 | 111073 |
| R_1920 | 26 | 111108 | 111133 |
| R_1921 | 20 | 111141 | 111160 |
| R_1922 | 21 | 111162 | 111182 |
| R_1923 | 35 | 111184 | 111218 |
| R_1924 | 22 | 111234 | 111255 |
| R_1925 | 20 | 111298 | 111317 |
| R_1926 | 26 | 111319 | 111344 |
| R_1927 | 61 | 111403 | 111463 |
| R_1928 | 57 | 111467 | 111523 |
| R_1929 | 23 | 111525 | 111547 |
| R_1930 | 24 | 111567 | 111590 |
| R_1931 | 26 | 111592 | 111617 |
| R_1932 | 24 | 111631 | 111654 |
| R_1933 | 22 | 111666 | 111687 |
| R_1934 | 21 | 111692 | 111712 |
| R_1935 | 49 | 111732 | 111780 |
| R_1936 | 31 | 111815 | 111845 |
| R_1937 | 21 | 111908 | 111928 |
| R_1938 | 39 | 111934 | 111972 |
| R_1939 | 26 | 111974 | 111999 |
| R_1940 | 58 | 112001 | 112058 |
| R_1941 | 28 | 112064 | 112091 |
| R_1942 | 24 | 112066 | 112089 |
| R_1943 | 21 | 112122 | 112142 |
| R_1944 | 24 | 112157 | 112180 |
| R_1945 | 21 | 112221 | 112241 |
| R_1946 | 26 | 112253 | 112278 |
| R_1947 | 23 | 112428 | 112450 |
| R_1948 | 26 | 112444 | 112469 |
| R_1949 | 30 | 112501 | 112530 |
| R_1950 | 20 | 112511 | 112530 |
| R_1951 | 69 | 112757 | 112825 |
| R_1952 | 20 | 112884 | 112903 |
| R_1953 | 44 | 112905 | 112948 |
| R_1954 | 28 | 112979 | 113006 |
| R_1955 | 62 | 113062 | 113123 |
| R_1956 | 36 | 113141 | 113176 |
| R_1957 | 23 | 113172 | 113194 |
| R_1958 | 26 | 113203 | 113228 |
| R_1959 | 37 | 113277 | 113313 |
| R_1960 | 32 | 113364 | 113395 |
| R_1961 | 43 | 113397 | 113439 |
| R_1962 | 118 | 113452 | 113569 |
| R_1963 | 46 | 113572 | 113617 |
| R_1964 | 21 | 113628 | 113648 |
| R_1965 | 21 | 113662 | 113682 |
| R_1966 | 36 | 113690 | 113725 |
| R_1967 | 32 | 113729 | 113760 |
| R_1968 | 28 | 113782 | 113809 |
| R_1969 | 21 | 113997 | 114017 |
| R_1970 | 22 | 114007 | 114028 |
| R_1971 | 57 | 114039 | 114095 |
| R_1972 | 32 | 114174 | 114205 |
| R_1973 | 28 | 114235 | 114262 |
| R_1974 | 21 | 114349 | 114369 |
| R_1975 | 38 | 114395 | 114432 |
| R_1976 | 31 | 114434 | 114464 |
| R_1977 | 20 | 114529 | 114548 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_1978 | 34 | 114624 | 114657 |
| R_1979 | 65 | 114711 | 114775 |
| R_1980 | 22 | 114904 | 114925 |
| R_1981 | 42 | 114930 | 114971 |
| R_1982 | 22 | 114982 | 115003 |
| R_1983 | 20 | 115005 | 115024 |
| R_1984 | 42 | 115026 | 115067 |
| R_1985 | 28 | 115092 | 115119 |
| R_1986 | 57 | 115121 | 115177 |
| R_1987 | 28 | 115179 | 115206 |
| R_1988 | 31 | 115228 | 115258 |
| R_1989 | 24 | 115263 | 115286 |
| R_1990 | 37 | 115306 | 115342 |
| R_1991 | 44 | 115361 | 115404 |
| R_1992 | 20 | 115467 | 115486 |
| R_1993 | 30 | 115628 | 115657 |
| R_1994 | 26 | 115665 | 115690 |
| R_1995 | 34 | 115687 | 115720 |
| R_1996 | 28 | 115804 | 115831 |
| R_1997 | 26 | 115833 | 115858 |
| R_1998 | 27 | 115937 | 115963 |
| R_1999 | 119 | 115965 | 116083 |
| R_2000 | 23 | 116085 | 116107 |
| R_2001 | 42 | 116121 | 116162 |
| R_2002 | 33 | 116193 | 116225 |
| R_2003 | 24 | 116276 | 116299 |
| R_2004 | 26 | 116356 | 116381 |
| R_2005 | 29 | 116405 | 116433 |
| R_2006 | 46 | 116441 | 116486 |
| R_2007 | 29 | 116488 | 116516 |
| R_2008 | 40 | 116518 | 116557 |
| R_2009 | 46 | 116653 | 116698 |
| R_2010 | 28 | 116700 | 116727 |
| R_2011 | 46 | 116729 | 116774 |
| R_2012 | 43 | 116927 | 116969 |
| R_2013 | 32 | 116997 | 117028 |
| R_2014 | 23 | 117043 | 117065 |
| R_2015 | 35 | 117068 | 117102 |
| R_2016 | 28 | 117148 | 117175 |
| R_2017 | 36 | 117195 | 117230 |
| R_2018 | 20 | 117243 | 117262 |
| R_2019 | 37 | 117273 | 117309 |
| R_2020 | 32 | 117329 | 117360 |
| R_2021 | 59 | 117432 | 117490 |
| R_2022 | 21 | 117509 | 117529 |
| R_2023 | 23 | 117557 | 117579 |
| R_2024 | 65 | 117580 | 117644 |
| R_2025 | 27 | 117646 | 117672 |
| R_2026 | 22 | 117708 | 117729 |
| R_2027 | 47 | 117730 | 117776 |
| R_2028 | 37 | 117778 | 117814 |
| R_2029 | 24 | 117881 | 117904 |
| R_2030 | 40 | 117904 | 117943 |
| R_2031 | 30 | 117945 | 117974 |
| R_2032 | 28 | 117993 | 118020 |
| R_2033 | 48 | 118064 | 118111 |
| R_2034 | 27 | 118113 | 118139 |
| R_2035 | 27 | 118141 | 118167 |
| R_2036 | 29 | 118169 | 118197 |
| R_2037 | 33 | 118210 | 118242 |
| R_2038 | 45 | 118386 | 118430 |
| R_2039 | 48 | 118446 | 118493 |
| R_2040 | 24 | 118532 | 118555 |
| R_2041 | 46 | 118634 | 118679 |
| R_2042 | 44 | 118774 | 118817 |
| R_2043 | 54 | 118841 | 118894 |
| R_2044 | 20 | 118912 | 118931 |
| R_2045 | 21 | 118999 | 119019 |
| R_2046 | 44 | 119283 | 119326 |
| R_2047 | 33 | 119353 | 119385 |
| R_2048 | 39 | 119392 | 119430 |
| R_2049 | 65 | 119441 | 119505 |
| R_2050 | 21 | 119566 | 119586 |
| R_2051 | 55 | 119604 | 119658 |
| R_2052 | 24 | 119660 | 119683 |
| R_2053 | 42 | 119685 | 119726 |
| R_2054 | 33 | 119736 | 119768 |
| R_2055 | 32 | 119770 | 119801 |
| R_2056 | 34 | 119804 | 119837 |
| R_2057 | 116 | 119885 | 120000 |
| R_2058 | 59 | 120128 | 120186 |
| R_2059 | 34 | 120317 | 120350 |
| R_2060 | 24 | 120530 | 120553 |
| R_2061 | 22 | 120571 | 120592 |
| R_2062 | 35 | 120611 | 120645 |
| R_2063 | 98 | 120663 | 120760 |
| R_2064 | 20 | 120924 | 120943 |
| R_2065 | 22 | 121093 | 121114 |
| R_2066 | 29 | 121117 | 121145 |
| R_2067 | 39 | 121244 | 121282 |
| R_2068 | 48 | 121365 | 121412 |
| R_2069 | 37 | 121414 | 121450 |
| R_2070 | 25 | 121649 | 121673 |
| R_2071 | 40 | 121687 | 121726 |
| R_2072 | 45 | 121728 | 121772 |
| R_2073 | 22 | 121795 | 121816 |
| R_2074 | 24 | 121939 | 121962 |
| R_2075 | 28 | 122038 | 122065 |
| R_2076 | 30 | 122218 | 122247 |
| R_2077 | 27 | 122273 | 122299 |
| R_2078 | 21 | 122301 | 122321 |
| R_2079 | 30 | 122318 | 122347 |
| R_2080 | 32 | 122356 | 122387 |
| R_2081 | 21 | 122428 | 122448 |
| R_2082 | 21 | 122432 | 122452 |
| R_2083 | 24 | 123020 | 123043 |
| R_2084 | 30 | 123038 | 123067 |
| R_2085 | 26 | 123052 | 123077 |
| R_2086 | 22 | 123258 | 123279 |
| R_2087 | 28 | 123291 | 123318 |
| R_2088 | 22 | 123402 | 123423 |
| R_2089 | 27 | 123644 | 123670 |
| R_2090 | 20 | 123819 | 123838 |
| R_2091 | 26 | 123841 | 123866 |
| R_2092 | 25 | 123965 | 123989 |
| R_2093 | 24 | 123997 | 124020 |
| R_2094 | 35 | 124034 | 124068 |
| R_2095 | 44 | 124075 | 124118 |
| R_2096 | 50 | 124156 | 124205 |
| R_2097 | 75 | 124247 | 124321 |
| R_2098 | 23 | 124353 | 124375 |
| R_2099 | 34 | 124377 | 124410 |
| R_2100 | 84 | 124472 | 124555 |
| R_2101 | 20 | 124557 | 124576 |
| R_2102 | 32 | 124648 | 124679 |
| R_2103 | 22 | 124688 | 124709 |
| R_2104 | 20 | 124700 | 124719 |
| R_2105 | 35 | 124712 | 124746 |
| R_2106 | 70 | 124748 | 124817 |
| R_2107 | 21 | 124824 | 124844 |
| R_2108 | 23 | 124859 | 124881 |
| R_2109 | 35 | 124883 | 124917 |
| R_2110 | 20 | 124919 | 124938 |
| R_2111 | 57 | 124940 | 124996 |
| R_2112 | 38 | 125015 | 125052 |
| R_2113 | 21 | 125032 | 125052 |
| R_2114 | 29 | 125064 | 125092 |
| R_2115 | 37 | 125107 | 125143 |
| R_2116 | 42 | 125198 | 125239 |
| R_2117 | 50 | 125241 | 125290 |
| R_2118 | 42 | 125292 | 125333 |
| R_2119 | 31 | 125346 | 125376 |
| R_2120 | 22 | 125378 | 125399 |
| R_2121 | 46 | 125401 | 125446 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end |
|---|---|---|---|
| R_2122 | 33 | 125700 | 125732 |
| R_2123 | 32 | 125734 | 125765 |
| R_2124 | 48 | 125803 | 125850 |
| R_2125 | 35 | 125912 | 125946 |
| R_2126 | 45 | 125948 | 125992 |
| R_2127 | 73 | 126012 | 126084 |
| R_2128 | 60 | 126087 | 126146 |
| R_2129 | 32 | 126341 | 126372 |
| R_2130 | 22 | 126374 | 126395 |
| R_2131 | 25 | 126388 | 126412 |
| R_2132 | 20 | 126473 | 126492 |
| R_2133 | 22 | 126484 | 126505 |
| R_2134 | 24 | 126660 | 126683 |
| R_2135 | 23 | 126691 | 126713 |
| R_2136 | 34 | 126715 | 126748 |
| R_2137 | 22 | 126822 | 126843 |
| R_2138 | 20 | 126885 | 126904 |
| R_2139 | 38 | 127054 | 127091 |
| R_2140 | 40 | 127111 | 127150 |
| R_2141 | 30 | 127201 | 127230 |
| R_2142 | 21 | 127232 | 127252 |
| R_2143 | 76 | 127258 | 127333 |
| R_2144 | 59 | 127359 | 127417 |
| R_2145 | 33 | 127419 | 127451 |
| R_2146 | 52 | 127567 | 127618 |
| R_2147 | 38 | 127620 | 127657 |
| R_2148 | 49 | 127656 | 127704 |
| R_2149 | 37 | 127706 | 127742 |
| R_2150 | 60 | 127761 | 127820 |
| R_2151 | 25 | 127953 | 127977 |
| R_2152 | 30 | 128097 | 128126 |
| R_2153 | 40 | 128187 | 128226 |
| R_2154 | 58 | 128237 | 128294 |
| R_2155 | 20 | 128323 | 128342 |
| R_2156 | 32 | 128408 | 128439 |
| R_2157 | 37 | 128425 | 128461 |
| R_2158 | 22 | 128463 | 128484 |
| R_2159 | 56 | 128500 | 128555 |
| R_2160 | 21 | 128565 | 128585 |
| R_2161 | 29 | 128586 | 128614 |
| R_2162 | 53 | 128631 | 128683 |
| R_2163 | 59 | 128685 | 128743 |
| R_2164 | 99 | 128738 | 128836 |
| R_2165 | 23 | 128850 | 128872 |
| R_2166 | 20 | 128896 | 128915 |
| R_2167 | 63 | 128922 | 128984 |
| R_2168 | 25 | 129031 | 129055 |
| R_2169 | 28 | 129071 | 129098 |
| R_2170 | 69 | 129104 | 129172 |
| R_2171 | 27 | 129196 | 129222 |
| R_2172 | 38 | 129235 | 129272 |
| R_2173 | 30 | 129330 | 129359 |
| R_2174 | 33 | 129345 | 129377 |
| R_2175 | 40 | 129401 | 129440 |
| R_2176 | 24 | 129427 | 129450 |
| R_2177 | 22 | 129443 | 129464 |
| R_2178 | 34 | 129488 | 129521 |
| R_2179 | 79 | 129540 | 129618 |
| R_2180 | 69 | 129617 | 129685 |
| R_2181 | 29 | 129705 | 129733 |
| R_2182 | 65 | 129735 | 129799 |
| R_2183 | 48 | 129801 | 129848 |
| R_2184 | 37 | 129884 | 129920 |
| R_2185 | 42 | 129918 | 129959 |
| R_2186 | 38 | 129988 | 130025 |
| R_2187 | 26 | 130084 | 130109 |
| R_2188 | 24 | 130125 | 130148 |
| R_2189 | 36 | 130150 | 130185 |
| R_2190 | 21 | 130247 | 130267 |
| R_2191 | 80 | 130269 | 130348 |
| R_2192 | 30 | 130384 | 130413 |
| R_2193 | 21 | 130424 | 130444 |
| R_2194 | 37 | 130564 | 130600 |
| R_2195 | 21 | 130663 | 130683 |
| R_2196 | 43 | 130690 | 130732 |
| R_2197 | 61 | 130735 | 130795 |
| R_2198 | 109 | 130797 | 130905 |
| R_2199 | 51 | 130941 | 130991 |
| R_2200 | 23 | 131025 | 131047 |
| R_2201 | 21 | 131064 | 131084 |
| R_2202 | 35 | 131119 | 131153 |
| R_2203 | 62 | 131155 | 131216 |
| R_2204 | 39 | 131269 | 131307 |
| R_2205 | 22 | 131309 | 131330 |
| R_2206 | 32 | 131350 | 131381 |
| R_2207 | 52 | 131432 | 131483 |
| R_2208 | 43 | 131501 | 131543 |
| R_2209 | 20 | 131565 | 131584 |
| R_2210 | 90 | 131606 | 131695 |
| R_2211 | 79 | 131697 | 131775 |
| R_2212 | 69 | 131758 | 131826 |
| R_2213 | 20 | 131877 | 131896 |
| R_2214 | 21 | 131898 | 131918 |
| R_2215 | 23 | 131951 | 131973 |
| R_2216 | 37 | 131975 | 132011 |
| R_2217 | 25 | 132017 | 132041 |
| R_2218 | 29 | 132061 | 132089 |
| R_2219 | 22 | 132091 | 132112 |
| R_2220 | 32 | 132138 | 132169 |
| R_2221 | 36 | 132182 | 132217 |
| R_2222 | 26 | 132253 | 132278 |
| R_2223 | 48 | 132280 | 132327 |
| R_2224 | 33 | 132403 | 132435 |
| R_2225 | 58 | 132437 | 132494 |
| R_2226 | 33 | 132496 | 132528 |
| R_2227 | 60 | 132541 | 132600 |
| R_2228 | 22 | 132619 | 132640 |
| R_2229 | 23 | 132656 | 132678 |
| R_2230 | 21 | 132758 | 132778 |
| R_2231 | 39 | 132780 | 132818 |
| R_2232 | 47 | 132827 | 132873 |
| R_2233 | 27 | 132893 | 132919 |
| R_2234 | 65 | 132917 | 132981 |
| R_2235 | 20 | 132983 | 133002 |
| R_2236 | 67 | 133014 | 133080 |
| R_2237 | 46 | 133082 | 133127 |
| R_2238 | 39 | 133129 | 133167 |
| R_2239 | 31 | 133169 | 133199 |
| R_2240 | 34 | 133201 | 133234 |
| R_2241 | 27 | 133251 | 133277 |
| R_2242 | 20 | 133282 | 133301 |
| R_2243 | 37 | 133343 | 133379 |
| R_2244 | 30 | 133404 | 133433 |
| R_2245 | 77 | 133435 | 133511 |
| R_2246 | 48 | 133528 | 133575 |
| R_2247 | 22 | 133676 | 133697 |
| R_2248 | 54 | 133710 | 133763 |
| R_2249 | 20 | 133765 | 133784 |
| R_2250 | 29 | 133786 | 133814 |
| R_2251 | 40 | 133816 | 133855 |
| R_2252 | 42 | 133857 | 133898 |
| R_2253 | 63 | 133900 | 133962 |
| R_2254 | 40 | 133964 | 134003 |

In some embodiments the target sequence is a sequence selected from a human MAPT mRNA intron, such as a Tau human mRNA intron 1 or 2 (see table 1 above).

The oligonucleotide of the invention comprises a contiguous nucleotide sequence which is complementary to or hybridizes to the target nucleic acid, such as a target sequence described herein.

The target sequence to which the oligonucleotide is complementary or hybridizes to generally comprises a contiguous nucleobases sequence of at least 10 nucleotides. The contiguous nucleotide sequence is between 10 to 100 nucleotides, such as 12 to 60, such as 13 to 50, such as 14 to 30, such as 15 to 25, such as 16 to 20 contiguous nucleotides.

In one embodiment of the invention the target sequence is SEQ ID NO: 3, corresponding to region A. In certain embodiments the target sequence is selected from position 12051-12111 of SEQ ID NO: 1 such as position 12051-12079, position 12085-12111 or position 12060-12078 of SEQ ID NO: 1.

In another embodiment of the invention the target sequence is SEQ ID NO: 4, corresponding to region B. In certain embodiments the target sequence is selected from position 39562-39593 of SEQ ID NO: 1 such as position 39573-39592 of SEQ ID NO: 1.

In another embodiment of the invention the target sequence is SEQ ID NO: 5, corresponding to region C. In certain embodiments the target sequence is selected from position 72837-72940 of SEQ ID NO: 1 such as position 72861-72891 or position 72862-72890 of SEQ ID NO: 1.

Target Cell

The term a "target cell" as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell.

In preferred embodiments the target cell expresses Tau mRNA, such as the Tau pre-mRNA or Tau mature mRNA. The poly A tail of Tau mRNA is typically disregarded for antisense oligonucleotide targeting.

Naturally Occurring Variant

The term "naturally occurring variant" refers to variants of MAPT gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms (SNPs), and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian MAPT target nucleic acid, such as a target nucleic acid selected form the group consisting of SEQ ID NO 1 and 2. In some embodiments the naturally occurring variants have at least 99% homology to the human MAPT target nucleic acid of SEQ ID NO: 1.

Modulation of Expression

The term "modulation of expression" as used herein is to be understood as an overall term for an oligonucleotide's ability to alter the amount of Tau when compared to the amount of Tau before administration of the oligonucleotide. Alternatively, modulation of expression may be determined by reference to a control experiment. It is generally understood that the control is an individual or target cell treated with a saline composition or an individual or target cell treated with a non-targeting oligonucleotide (mock).

One type of modulation is the ability of an oligonucleotide to inhibit, down-regulate, reduce, suppress, remove, stop, block, prevent, lessen, lower, avoid or terminate expression of Tau, e.g. by degradation of mRNA or blockage of transcription. Another type of modulation is an oligonucleotide's ability to restore, increase or enhance expression of Tau, e.g. by repair of splice sites or prevention of splicing or removal or blockage of inhibitory mechanisms such as microRNA repression.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Indeed, much focus has been spent on developing 2' sugar substituted nucleosides, and numerous 2' substituted nucleosides have been found to have beneficial properties when incorporated into oligonucleotides. For example, the 2' modified sugar may provide enhanced binding affinity and/ or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

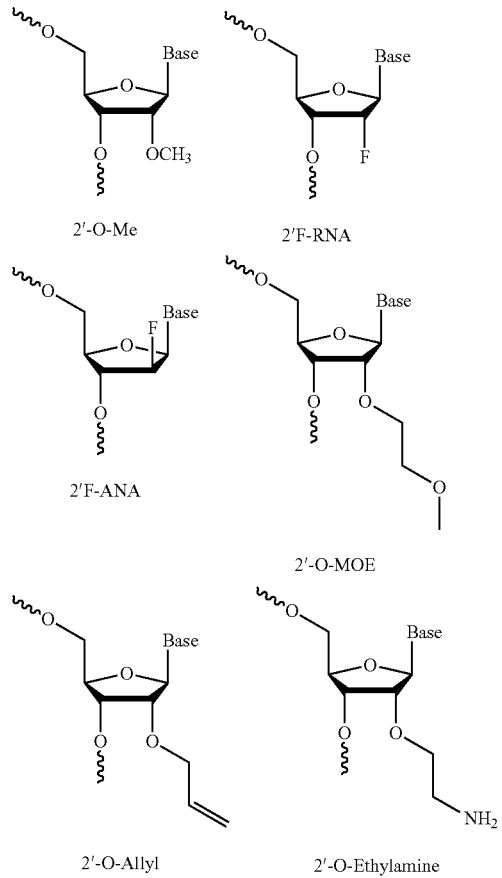

In relation to the present invention 2' substituted sugar modified nucleosides does not include 2' bridged nucleosides like LNA.

Locked Nucleic Acid Nucleosides (LNA Nucleoside)

A "LNA nucleoside" is a 2'-sugar modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, Mitsuoka et al., Nucleic Acids Research 2009, 37(4), 1225-1238, and Wan and Seth, J. Medical Chemistry 2016, 59, 9645-9667.

The 2'-4' bridge comprises 2 to 4 bridging atoms and is in particular of formula —X—Y— wherein X is oxygen, sulfur, —CR$^a$R$^b$—, —C(R$^a$)=C(R$^b$)—, —C(=CR$^a$R$^b$)—, —C(R$^a$)=N—, —Si(R$^a$)$_2$—, —SO$_2$—, —NR$^a$—; —O—NR$^a$—, —NR$^a$—O—, —C(=J)-, Se, —O—NR$^a$—, —NR$^a$—CR$^a$R$^b$—, —N(R$^a$)—O— or —O—CR$^a$R$^b$—;

Y is oxygen, sulfur, —(CR$^a$R$^b$)$_n$—, —CR$^a$R$^b$—O—CR$^a$R$^b$—, —C(R$^a$)=C(R$^b$)—, —C(R$^a$)=N—, —Si(R$^a$)$_2$—, —SO$_2$—, —NR$^a$—, —C(=J)-, Se, —O—NR$^a$—, —NR$^a$—CR$^a$R$^b$—, —N(R$^a$)—O— or —O—CR$^a$R$^b$—;

with the proviso that —X—Y— is not —O—O—, Si(R$^a$)$_2$—Si(R$^a$)$_2$—, —SO$_2$—SO$_2$—, —C(R$^a$)=C(R$^b$)—C(R$^a$)=C(R$^b$), —C(R$^a$)=N—C(R$^a$)=N—, —C(R$^a$)=N—C(R$^a$)=C(R$^b$), —C(R$^a$)=C(R$^b$)—C(R$^a$)=N— or —Se—Se—;

J is oxygen, sulfur, =CH$_2$ or =N(R$^a$);

R$^a$ and R$^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, —OC(=X$^a$)R$^c$, —OC(=X$^a$)NR$^c$R$^d$ and —NR$^e$C(=X$^a$)NR$^c$R$^d$;

or two geminal R$^a$ and R$^b$ together form optionally substituted methylene;

or two geminal R$^a$ and R$^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocyclyl, aryl and heteroaryl;

X$^a$ is oxygen, sulfur or —NR$^c$;

R$^c$, R$^d$ and R$^e$ are independently selected from hydrogen and alkyl; and n is 1, 2 or 3.

In a further particular embodiment of the invention, X is oxygen, sulfur, —NR$^a$—, —CR$^a$R$^b$—or —C(=CR$^a$R$^b$)—, particularly oxygen, sulfur, —NH—, —CH$_2$— or —C(=CH$_2$)—, more particularly oxygen.

In another particular embodiment of the invention, Y is —CR$^a$R$^b$—, —CR$^a$R$^b$—CR$^a$R$^b$— or —CR$^a$R$^b$—CR$^a$R$^b$—CR$^a$R$^b$—, particularly —CH$_2$—CHCH$_3$—, —CHCH$_3$—CH$_2$—, —CH$_2$—CH$_2$— or —CH$_2$—CH$_2$—CH$_2$—.

In a particular embodiment of the invention, —X—Y— is —O—(CR$^a$R$^b$)$_n$—, —S—CR$^a$R$^b$—, —N(R$^a$)CR$^a$R$^b$—, —CR$^a$R$^b$—CR$^a$R$^b$—, —O—CR$^a$R$^b$—O—CR$^a$R$^b$—, —CR$^a$R$^b$—O—CR$^a$R$^b$—, —C(=CR$^a$R$^b$)—CR$^a$R$^b$—, —N(R$^a$)CR$^a$R$^b$—, —O—N(R$^a$)—CR$^a$R$^b$— or —N(R$^a$)—O—CR$^a$R$^b$—.

In a particular embodiment of the invention, R$^a$ and R$^b$ are independently selected from the group consisting of hydrogen, halogen, hydroxyl, alkyl and alkoxyalkyl, in particular hydrogen, halogen, alkyl and alkoxyalkyl.

In another embodiment of the invention, $R^a$ and $R^b$ are independently selected from the group consisting of hydrogen, fluoro, hydroxyl, methyl and —CH$_2$—O—CH$_3$, in particular hydrogen, fluoro, methyl and —CH$_2$—O—CH$_3$.

Advantageously, one of $R^a$ and $R^b$ of —X—Y— is as defined above and the other ones are all hydrogen at the same time.

In a further particular embodiment of the invention, $R^a$ is hydrogen or alkyl, in particular hydrogen or methyl.

In another particular embodiment of the invention, $R^b$ is hydrogen or alkyl, in particular hydrogen or methyl.

In a particular embodiment of the invention, one or both of $R^a$ and $R^b$ are hydrogen.

In a particular embodiment of the invention, only one of $R^a$ and $R^b$ is hydrogen.

In one particular embodiment of the invention, one of $R^a$ and $R^b$ is methyl and the other one is hydrogen.

In a particular embodiment of the invention, $R^a$ and $R^b$ are both methyl at the same time.

In a particular embodiment of the invention, —X—Y— is —O—CH$_2$—, —S—CH$_2$—, —S—CH(CH$_3$)—, —NH—CH$_2$—, —O—CH$_2$CH$_2$—, —O—CH(CH$_2$—O—CH$_3$)—, —O—CH(CH$_2$CH$_3$)—, —O—CH(CH$_3$)—, —O—CH$_2$—O—CH$_2$—, —O—CH$_2$—O—CH$_2$—, —CH$_2$—O—CH$_2$—, —C(=CH$_2$)CH$_2$—, —C(=CH$_2$)CH(CH$_3$)—, —N(OCH$_3$)CH$_2$— or —N(CH$_3$)CH$_2$;

In a particular embodiment of the invention, —X—Y— is —O—CR$^a$R$^b$— wherein $R^a$ and $R^b$ are independently selected from the group consisting of hydrogen, alkyl and alkoxyalkyl, in particular hydrogen, methyl and —CH$_2$—O—CH$_3$.

In a particular embodiment, —X—Y— is —O—CH$_2$— or —O—CH(CH$_3$)—, particularly —O—CH$_2$—.

The 2'-4' bridge may be positioned either below the plane of the ribose ring (beta-D-configuration), or above the plane of the ring (alpha-L-configuration), as illustrated in formula (A) and formula (B) respectively.

The LNA nucleoside according to the invention is in particular of formula (A) or (B)

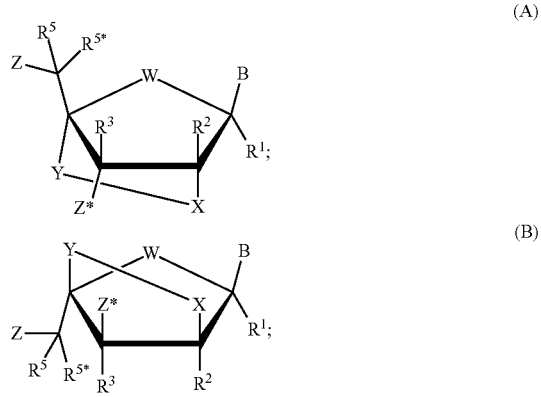

wherein
W is oxygen, sulfur, —N(R$^a$)— or —CR$^a$R$^b$—, in particular oxygen;
B is a nucleobase or a modified nucleobase;
Z is an internucleoside linkage to an adjacent nucleoside or a 5-terminal group;
Z* is an internucleoside linkage to an adjacent nucleoside or a 3'-terminal group;

$R^1$, $R^2$, $R^3$, $R^5$ and $R^{5*}$ are independently selected from hydrogen, halogen, alkyl, haloalkyl, alkenyl, alkynyl, hydroxy, alkoxy, alkoxyalkyl, azido, alkenyloxy, carboxyl, alkoxycarbonyl, alkylcarbonyl, formyl and aryl; and X, Y, $R^a$ and $R^b$ are as defined above.

In a particular embodiment, in the definition of —X—Y—, $R^a$ is hydrogen or alkyl, in particular hydrogen or methyl. In another particular embodiment, in the definition of —X—Y—, $R^b$ is hydrogen or alkyl, in particular hydrogen or methyl. In a further particular embodiment, in the definition of —X—Y—, one or both of $R^a$ and $R^b$ are hydrogen. In a particular embodiment, in the definition of —X—Y—, only one of $R^a$ and $R^b$ is hydrogen. In one particular embodiment, in the definition of —X—Y—, one of $R^a$ and $R^b$ is methyl and the other one is hydrogen. In a particular embodiment, in the definition of —X—Y—, $R^a$ and $R^b$ are both methyl at the same time.

In a further particular embodiment, in the definition of X, $R^a$ is hydrogen or alkyl, in particular hydrogen or methyl. In another particular embodiment, in the definition of X, $R^b$ is hydrogen or alkyl, in particular hydrogen or methyl. In a particular embodiment, in the definition of X, one or both of $R^a$ and $R^b$ are hydrogen. In a particular embodiment, in the definition of X, only one of $R^a$ and $R^b$ is hydrogen. In one particular embodiment, in the definition of X, one of $R^a$ and $R^b$ is methyl and the other one is hydrogen. In a particular embodiment, in the definition of X, $R^a$ and $R^b$ are both methyl at the same time.

In a further particular embodiment, in the definition of Y, $R^a$ is hydrogen or alkyl, in particular hydrogen or methyl. In another particular embodiment, in the definition of Y, $R^b$ is hydrogen or alkyl, in particular hydrogen or methyl. In a particular embodiment, in the definition of Y, one or both of $R^a$ and $R^b$ are hydrogen. In a particular embodiment, in the definition of Y, only one of $R^a$ and $R^b$ is hydrogen. In one particular embodiment, in the definition of Y, one of $R^a$ and $R^b$ is methyl and the other one is hydrogen. In a particular embodiment, in the definition of Y, $R^a$ and $R^b$ are both methyl at the same time.

In a particular embodiment of the invention $R^1$, $R^2$, $R^3$, $R^5$ and $R^{5*}$ are independently selected from hydrogen and alkyl, in particular hydrogen and methyl.

In a further particular advantageous embodiment of the invention, $R^1$, $R^2$, $R^3$, $R^5$ and $R^{5*}$ are all hydrogen at the same time.

In another particular embodiment of the invention, $R^1$, $R^2$, $R^3$, are all hydrogen at the same time, one of $R^5$ and $R^{5*}$ is hydrogen and the other one is as defined above, in particular alkyl, more particularly methyl.

In a particular embodiment of the invention, $R^5$ and $R^{5*}$ are independently selected from hydrogen, halogen, alkyl, alkoxyalkyl and azido, in particular from hydrogen, fluoro, methyl, methoxyethyl and azido. In particular advantageous embodiments of the invention, one of $R^5$ and $R^{5*}$ is hydrogen and the other one is alkyl, in particular methyl, halogen, in particular fluoro, alkoxyalkyl, in particular methoxyethyl or azido; or $R^5$ and $R^{5*}$ are both hydrogen or halogen at the same time, in particular both hydrogen of fluoro at the same time. In such particular embodiments, W can advantageously be oxygen, and —X—Y— advantageously —O—CH$_2$—.

In a particular embodiment of the invention, —X—Y— is —O—CH$_2$—, W is oxygen and $R^1$, $R^2$, $R^3$, $R^5$ and $R^{5*}$ are all hydrogen at the same time. Such LNA nucleosides are disclosed in WO 99/014226, WO 00/66604, WO 98/039352 and WO 2004/046160 which are all hereby incorporated by reference, and include what are commonly known in the art as beta-D-oxy LNA and alpha-L-oxy LNA nucleosides.

In another particular embodiment of the invention, —X—Y— is —S—CH$_2$—, W is oxygen and R$^1$, R$^2$, R$^3$, R$^5$ and R$^{5*}$ are all hydrogen at the same time. Such thio LNA nucleosides are disclosed in WO 99/014226 and WO 2004/046160 which are hereby incorporated by reference.

In another particular embodiment of the invention, —X—Y— is —NH—CH$_2$—, W is oxygen and R$^1$, R$^2$, R$^3$, R$^5$ and R$^{5*}$ are all hydrogen at the same time. Such amino LNA nucleosides are disclosed in WO 99/014226 and WO 2004/046160 which are hereby incorporated by reference.

In another particular embodiment of the invention, —X—Y— is —O—CH$_2$CH$_2$— or —OCH$_2$CH$_2$CH$_2$—, W is oxygen, and R$^1$, R$^2$, R$^3$, R$^5$ and R$^{5*}$ are all hydrogen at the same time. Such LNA nucleosides are disclosed in WO 00/047599 and Morita et al., Bioorganic & Med. Chem. Lett. 12, 73-76, which are hereby incorporated by reference, and include what are commonly known in the art as 2'-O-4'C-ethylene bridged nucleic acids (ENA).

In another particular embodiment of the invention, —X—Y— is —O—CH$_2$—, W is oxygen, R$^1$, R$^2$, R$^3$ are all hydrogen at the same time, one of R$^5$ and R$^{5*}$ is hydrogen and the other one is not hydrogen, such as alkyl, for example methyl. Such 5' substituted LNA nucleosides are disclosed in WO 2007/134181 which is hereby incorporated by reference.

In another particular embodiment of the invention, —X—Y— is —O—CR$^a$R$^b$—, wherein one or both of R$^a$ and R$^b$ are not hydrogen, in particular alkyl such as methyl, W is oxygen, R$^1$, R$^2$, R$^3$ are all hydrogen at the same time, one of R$^5$ and R$^{5*}$ is hydrogen and the other one is not hydrogen, in particular alkyl, for example methyl. Such bis modified LNA nucleosides are disclosed in WO 2010/077578 which is hereby incorporated by reference.

In another particular embodiment of the invention, —X—Y— is —O—CHR$^a$—, W is oxygen and R$^1$, R$^2$, R$^3$, R$^5$ and R$^{5*}$ are all hydrogen at the same time. Such 6'-substituted LNA nucleosides are disclosed in WO 2010/036698 and WO 2007/090071 which are both hereby incorporated by reference. In such 6'-substituted LNA nucleosides, R$^a$ is in particular C1-C$_6$ alkyl, such as methyl.

In another particular embodiment of the invention, —X—Y— is —O—CH(CH$_2$—O—CH$_3$)— ("2' O-methoxyethyl bicyclic nucleic acid", Seth et al. J. Org. Chem. 2010, Vol 75(5) pp. 1569-81).

In another particular embodiment of the invention, —X—Y— is —O—CH(CH$_2$CH$_3$)— ("2'O-ethyl bicyclic nucleic acid", Seth at al., J. Org. Chem. 2010, Vol 75(5) pp. 1569-81).

In another particular embodiment of the invention, —X—Y— is —O—CH(CH$_2$—O—CH$_3$)—, W is oxygen and R$^1$, R$^2$, R$^3$, R$^5$ and R$^{5*}$ are all hydrogen at the same time. Such LNA nucleosides are also known in the art as cyclic MOEs (cMOE) and are disclosed in WO 2007/090071.

In another particular embodiment of the invention, —X—Y— is —O—CH(CH$_3$)—.

In another particular embodiment of the invention, —X—Y— is —O—CH$_2$.O—CH$_2$— (Seth et al., J. Org. Chem 2010 op. cit.)

In another particular embodiment of the invention, —X—Y— is —O—CH(CH$_3$)—, W is oxygen and R$^1$, R$^2$, R$^3$, R$^5$ and R$^{5*}$ are all hydrogen at the same time. Such 6'-methyl LNA nucleosides are also known in the art as cET nucleosides, and may be either (S)-cET or (R)-cET diastereoisomers, as disclosed in WO 2007/090071 (beta-D) and WO 2010/036698 (alpha-L) which are both hereby incorporated by reference.

In another particular embodiment of the invention, —X—Y— is —O—CR$^a$R$^b$—, wherein neither R$^a$ nor R$^b$ is hydrogen, W is oxygen and R$^1$, R$^2$, R$^3$, R$^5$ and R$^{5*}$ are all hydrogen at the same time. In a particular embodiment, R$^a$ and R$^b$ are both alkyl at the same time, in particular both methyl at the same time. Such 6'-di-substituted LNA nucleosides are disclosed in WO 2009/006478 which is hereby incorporated by reference.

In another particular embodiment of the invention, —X—Y— is —S—CHR$^a$—, W is oxygen and R$^1$, R$^2$, R$^3$, R$^5$ and R$^{5*}$ are all hydrogen at the same time. Such 6'-substituted thio LNA nucleosides are disclosed in WO 2011/156202 which is hereby incorporated by reference. In a particular embodiment of such 6'-substituted thio LNA, R$^a$ is alkyl, in particular methyl.

In a particular embodiment of the invention, —X—Y— is —C(=CH$_2$)C(R$^a$R$^b$)—, —C(=CHF)C(R$^a$R$^b$)— or —C(=CF$_2$)C(R$^a$R$^b$)—, W is oxygen and R$^1$, R$^2$, R$^3$, R$^5$ and R$^{5*}$ are all hydrogen at the same time. R$^a$ and R$^b$ are advantageously independently selected from hydrogen, halogen, alkyl and alkoxyalkyl, in particular hydrogen, methyl, fluoro and methoxymethyl. R$^a$ and R$^b$ are in particular both hydrogen or methyl at the same time or one of R$^a$ and R$^b$ is hydrogen and the other one is methyl. Such vinyl carbo LNA nucleosides are disclosed in WO 2008/154401 and WO 2009/067647 which are both hereby incorporated by reference.

In a particular embodiment of the invention, —X—Y— is —N(OR$^a$)—CH$_2$—, W is oxygen and R$^1$, R$^2$, R$^3$, R$^5$ and R$^{5*}$ are all hydrogen at the same time. In a particular embodiment, R$^a$ is alkyl such as methyl. Such LNA nucleosides are also known as N substituted LNAs and are disclosed in WO 2008/150729 which is hereby incorporated by reference.

In a particular embodiment of the invention, —X—Y— is —O—N(R$^a$)—, —N(R$^a$)—O—, —NR$^a$—CR$^a$R$^b$—CR$^a$R$^b$— or —NR$^a$—CR$^a$R$^b$—, W is oxygen and R$^1$, R$^2$, R$^3$, R$^5$ and R$^{5*}$ are all hydrogen at the same time. R$^a$ and R$^b$ are advantageously independently selected from hydrogen, halogen, alkyl and alkoxyalkyl, in particular hydrogen, methyl, fluoro and methoxymethyl. In a particular embodiment, R$^a$ is alkyl, such as methyl, R$^b$ is hydrogen or methyl, in particular hydrogen. (Seth et al., J. Org. Chem 2010 op. cit.).

In a particular embodiment of the invention, —X—Y— is —O—N(CH$_3$)— (Seth et al., J. Org. Chem 2010 op. cit.).

In a particular embodiment of the invention, R$^5$ and R$^{5*}$ are both hydrogen at the same time. In another particular embodiment of the invention, one of R$^5$ and R$^{5*}$ is hydrogen and the other one is alkyl, such as methyl. In such embodiments, R$^1$, R$^2$ and R$^3$ can be in particular hydrogen and —X—Y— can be in particular —O—CH$_2$— or —O—CHC(R$^a$)$_3$—, such as —O—CH(CH$_3$)—.

In a particular embodiment of the invention, —X—Y— is —CR$^a$R$^b$—O—CR$^a$R$^b$—, such as —CH$_2$—O—CH$_2$—, W is oxygen and R$^1$, R$^2$, R$^3$, R$^5$ and R$^{5*}$ are all hydrogen at the same time. In such particular embodiments, R$^a$ can be in particular alkyl such as methyl, R$^b$ hydrogen or methyl, in particular hydrogen. Such LNA nucleosides are also known as conformationally restricted nucleotides (CRNs) and are disclosed in WO 2013/036868 which is hereby incorporated by reference.

In a particular embodiment of the invention, —X—Y— is —O—CR$^a$R$^b$—O—CR$^a$R$^b$—, such as —O—CH$_2$—O—CH$_2$—, W is oxygen and R$^1$, R$^2$, R$^3$, R$^5$ and R$^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. In such a particular embodiment, $R^a$ can be in particular alkyl such as methyl, $R^b$ hydrogen or methyl, in particular hydrogen. Such LNA nucleosides are also known as COC nucleotides and are disclosed in Mitsuoka et al., Nucleic Acids Research 2009, 37(4), 1225-1238, which is hereby incorporated by reference.

It will be recognized than, unless specified, the LNA nucleosides may be in the beta-D or alpha-L stereoisoform.

Particular examples of LNA nucleosides of the invention are presented in Scheme 1 (wherein B is as defined above).

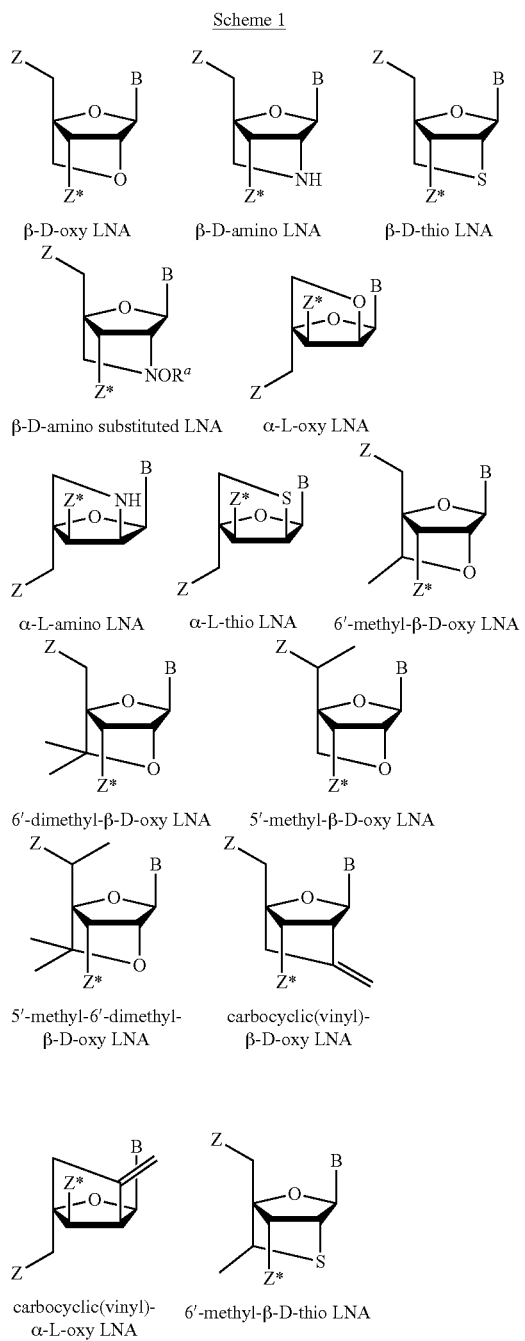

Scheme 1

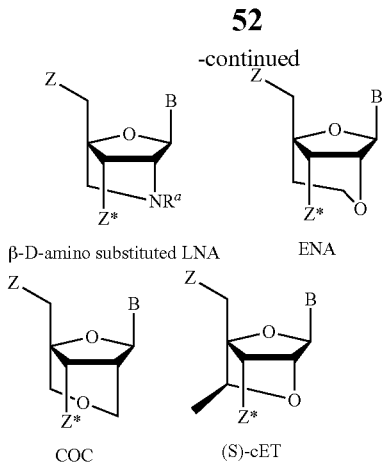

Particular LNA nucleosides are beta-D-oxy-LNA, 6'-methyl-beta-D-oxy LNA such as (S)-6'-methyl-beta-D-oxy-LNA (ScET) and ENA.

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

Chemical Group Definitions

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl, cyclohexyl, cycloheptyl and cyclooctyl, more particularly cyclopropyl and cyclobutyl. A particular example of "cycloalkyl" is cyclopropyl.

The term "alkoxy", alone or in combination, signifies a group of the formula alkyl-O— in which the term "alkyl"

has the previously given significance, such as methoxy, ethoxy, n-propoxy, isopropoxy, n-butoxy, isobutoxy, sec.butoxy and tert.butoxy. Particular "alkoxy" are methoxy and ethoxy. Methoxyethoxy is a particular example of "alkoxyalkoxy".

The term "oxy", alone or in combination, signifies the —O— group.

The term "alkenyl", alone or in combination, signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkynyl", alone or in combination, signifies a straight-chain or branched hydrocarbon residue comprising a triple bond and up to 8, preferably up to 6, particularly preferred up to 4 carbon atoms.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl or trifluoromethyl. Fluoromethyl, difluoromethyl and trifluoromethyl are particular "haloalkyl".

The term "halocycloalkyl", alone or in combination, denotes a cycloalkyl group as defined above substituted with at least one halogen, particularly substituted with one to five halogens, particularly one to three halogens. Particular example of "halocycloalkyl" are halocyclopropyl, in particular fluorocyclopropyl, difluorocyclopropyl and trifluorocyclopropyl.

The terms "hydroxyl" and "hydroxy", alone or in combination, signify the —OH group.

The terms "thiohydroxyl" and "thiohydroxy", alone or in combination, signify the —SH group.

The term "carbonyl", alone or in combination, signifies the —C(O)— group.

The term "carboxy" or "carboxyl", alone or in combination, signifies the —COOH group.

The term "amino", alone or in combination, signifies the primary amino group (—NH$_2$), the secondary amino group (—NH—), or the tertiary amino group (—N—).

The term "alkylamino", alone or in combination, signifies an amino group as defined above substituted with one or two alkyl groups as defined above.

The term "sulfonyl", alone or in combination, means the —SO$_2$ group.

The term "sulfinyl", alone or in combination, signifies the —SO— group.

The term "sulfanyl", alone or in combination, signifies the —S— group.

The term "cyano", alone or in combination, signifies the —CN group.

The term "azido", alone or in combination, signifies the —N$_3$ group.

The term "nitro", alone or in combination, signifies the NO$_2$ group.

The term "formyl", alone or in combination, signifies the —C(O)H group.

The term "carbamoyl", alone or in combination, signifies the —C(O)NH$_2$ group.

The term "carbamido", alone or in combination, signifies the —NH—C(O)—NH$_2$ group.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The term "heteroaryl", alone or in combination, denotes a monovalent aromatic heterocyclic mono- or bicyclic ring system of 5 to 12 ring atoms, comprising 1, 2, 3 or 4 heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl or acridinyl.

The term "heterocyclyl", alone or in combination, signifies a monovalent saturated or partly unsaturated mono- or bicyclic ring system of 4 to 12, in particular 4 to 9 ring atoms, comprising 1, 2, 3 or 4 ring heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl or dihydropyranyl.

Pharmaceutically Acceptable Salts

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition, these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

Protecting Group

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RNase H activity, recombinant human RNase H1 is available from Lubio Science GmbH, Lucerne, Switzerland.

Gapmer

The antisense oligonucleotide of the invention, or contiguous nucleotide sequence thereof, may be a gapmer, also termed gapmer oligonucleotide or gapmer designs. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5→3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further be defined by having at least one sugar modified nucleoside at the end most distant from the gap region, i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides, such as 16 to 20 nucleotides.

By way of example, the gapmer oligonucleotide of the present invention can be represented by the following formulae:

$F_{1-8}$-$G_{6-16}$-$F'_{2-8}$, such as
$F_{2-8}$-$G_{6-14}$-$F'_{2-8}$, such as
$F_{3-8}$-$G_{6-14}$-$F'_{2-8}$ with the proviso that the overall length of the gapmer regions F-G-F' is at least 10, such as at least 12, such as at least 14 nucleotides in length.

In an aspect of the invention the antisense oligonucleotide or contiguous nucleotide sequence thereof consists of or comprises a gapmer of formula 5'-F-G-F'-3', where region F and F' independently comprise or consist of 1-8 nucleosides, of which 2-4 are 2' sugar modified and defines the 5' and 3' end of the F and F' region, and G is a region between 6 and 16 nucleosides which are capable of recruiting RNaseH.

Regions F, G and F' are further defined below and can be incorporated into the F-G-F' formula.

Gapmer—Region G

Region G (gap region) of the gapmer is a region of nucleosides which enables the oligonucleotide to recruit RNaseH, such as human RNase H1, typically DNA nucleosides. RNaseH is a cellular enzyme which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides. Cytosine (C) DNA in the gap region may in some instances be methylated, such residues are either annotated as 5'-methyl-cytosine ($^{me}$C or with an e instead of a c). Methylation of cytosine DNA in the gap is advantageous if cg dinucleotides are present in the gap to reduce potential toxicity, the modification does not have significant impact on efficacy of the oligonucleotides. 5' substituted DNA nucleosides, such as 5' methyl DNA nucleoside have been reported for use in DNA gap regions (EP 2 742 136).

In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages.

Whilst traditional gapmers have a DNA gap region, there are numerous examples of modified nucleosides which allow for RNaseH recruitment when they are used within the gap region. Modified nucleosides which have been reported as being capable of recruiting RNaseH when included within a gap region include, for example, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue. The modified nucleosides used in such gapmers may be nucleosides which adopt a 2' endo (DNA like) structure when introduced into the gap region, i.e. modifications which allow for RNaseH recruitment). In some embodiments the DNA Gap region (G) described herein may optionally contain 1 to 3 sugar modified nucleosides which adopt a 2' endo (DNA like) structure when introduced into the gap region.

Region G—"Gap-Breaker"

Alternatively, there are numerous reports of the insertion of a modified nucleoside which confers a 3' endo conformation into the gap region of gapmers, whilst retaining some RNaseH activity. Such gapmers with a gap region comprising one or more 3'endo modified nucleosides are referred to as "gap-breaker" or "gap-disrupted" gapmers, see for example WO2013/022984. Gap-breaker oligonucleotides retain sufficient region of DNA nucleosides within the gap region to allow for RNaseH recruitment. The ability of gapbreaker oligonucleotide design to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA. Modified nucleosides used within the gap region of gap-breaker oligonucleotides may for example be modified nucleosides which confer a 3'endo confirmation, such 2'-O-methyl (OMe) or 2'-O-MOE (MOE) nucleosides, or beta-D LNA nucleosides (the bridge between C2' and C4' of the ribose sugar ring of a nucleoside is in the beta conformation), such as beta-D-oxy LNA or ScET nucleosides.

As with gapmers containing region G described above, the gap region of gap-breaker or gap-disrupted gapmers, have a DNA nucleosides at the 5' end of the gap (adjacent to the 3' nucleoside of region F), and a DNA nucleoside at the 3' end of the gap (adjacent to the 5' nucleoside of region F'). Gapmers which comprise a disrupted gap typically retain a region of at least 3 or 4 contiguous DNA nucleosides at either the 5' end or 3' end of the gap region.

Exemplary designs for gap-breaker oligonucleotides include $F_{1-8}$-[$D_{3-4}$-$E_1$-$D_{3-4}$]-$F'_{1-8}$
$F_{1-8}$-[$D_{1-4}$-$E_1$-$D_{3-4}$]-$F'_{1-8}$
$F_{1-8}$-[$D_{3-4}$-$E_1$-$D_{1-4}$]-$F'_{1-8}$ wherein region G is within the brackets [$D_n$-$E_r$-$D_m$], D is a contiguous sequence of DNA nucleosides, E is a modified nucleoside (the gap-breaker or gap-disrupting nucleoside), and F and F' are the flanking regions as defined herein, and with the proviso that the overall length of the gapmer regions F-G-F' is at least 12, such as at least 14 nucleotides in length.

In some embodiments, region G of a gap disrupted gapmer comprises at least 6 DNA nucleosides, such as 6, 7, 8, 9, 10, 11, 12, 13, 14, 15 or 16 DNA nucleosides. As described above, the DNA nucleosides may be contiguous or may optionally be interspersed with one or more modified nucleosides, with the proviso that the gap region G is capable of mediating RNaseH recruitment.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 2-6, such as 3-4 contiguous nucleotides in length. Advantageously the 5' most nucleoside of region F is a sugar modified nucleoside. In some embodiments the two 5' most nucleoside of region F are sugar modified nucleoside. In some embodiments the 5' most nucleoside of region F is an LNA nucleoside. In some embodiments the two 5' most nucleoside of region F are LNA nucleosides. In some embodiments the two 5' most nucleoside of region F are 2' substituted nucleoside nucleosides, such as two 3' MOE nucleosides. In some embodiments the 5' most nucleoside of region F is a 2' substituted nucleoside, such as a MOE nucleoside.

Region F' is 2-8 contiguous nucleotides in length, such as 3-6, such as 4-5 contiguous nucleotides in length. Advantageously, embodiments the 3' most nucleoside of region F' is a sugar modified nucleoside. In some embodiments the two 3' most nucleoside of region F' are sugar modified nucleoside. In some embodiments the two 3' most nucleoside of region F' are LNA nucleosides. In some embodiments the 3' most nucleoside of region F' is an LNA nucleoside. In some embodiments the two 3' most nucleoside of region F' are 2' substituted nucleoside nucleosides, such as two 3' MOE nucleosides. In some embodiments the 3' most nucleoside of region F' is a 2' substituted nucleoside, such as a MOE nucleoside.

It should be noted that when the length of region F or F' is one, it is advantageously an LNA nucleoside.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, region F and F' independently comprises both LNA and a 2' substituted modified nucleosides (mixed wing design).

In some embodiments, region F and F' consists of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as independently selected from beta-D-oxy LNA, ENA or ScET nucleosides. In some embodiments region F consists of 1-5, such as 2-4, such as 3-4 such as 1, 2, 3, 4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F', or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

In some embodiments the 5' most and the 3' most nucleosides of region F and F' are LNA nucleosides, such as beta-D-oxy LNA nucleosides or ScET nucleosides.

In some embodiments, the internucleoside linkage between region F and region G is a phosphorothioate internucleoside linkage. In some embodiments, the internucleoside linkage between region F' and region G is a phosphorothioate internucleoside linkage. In some embodiments, the internucleoside linkages between the nucleosides of region F or F', F and F' are phosphorothioate internucleoside linkages.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: [LNA]$_{1-5}$-[region G]-[LNA]$_{1-5}$, wherein region G is as defined in the Gapmer region G definition.

In one embodiment the LNA gapmer is of the formula [LNA]$_4$-[region G]$_{10-12}$-[LNA]$_4$ MOE Gapmers A MOE gapmers is a gapmer wherein regions F and F' consist of MOE nucleosides. In some embodiments the MOE gapmer is of design [MOE]$_{1-8}$-[Region G]$_{5-16}$-[MOE]$_{1-8}$, such as [MOE]$_{2-7}$-[Region G]$_{6-14}$-[MOE]$_{2-7}$, such as [MOE]$_{3-6}$-[Region G]$_{8-12}$-[MOE]$_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as MOE nucleosides. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO2008/049085 and WO2012/109395, both of which are hereby incorporated by reference.

Alternating Flank Gapmers

Flanking regions may comprise both LNA and DNA nucleoside and are referred to as "alternating flanks" as they comprise an alternating motif of LNA-DNA-LNA nucleosides. Gapmers comprising such alternating flanks are referred to as "alternating flank gapmers". "Alternative flank gapmers" are LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

Alternating flank LNA gapmers are disclosed in WO2016/127002.

An alternating flank region may comprise up to 3 contiguous DNA nucleosides, such as 1 to 2 or 1 or 2 or 3 contiguous DNA nucleosides.

The alternating flak can be annotated as a series of integers, representing a number of LNA nucleosides (L) followed by a number of DNA nucleosides (D), for example

[L]$_{1-3}$-[D]$_{1-4}$-[L]$_{1-3}$

[L]$_{1-2}$-[D]$_{1-2}$-[L]$_{1-2}$-[D]$_{1-2}$-[L]$_{1-2}$

In oligonucleotide designs these will often be represented as numbers such that 2-2-1 represents 5' [L]$_2$-[D]$_2$-[L] 3', and 1-1-1-1-1 represents 5' [L]-[D]-[L]-[D]-[L] 3'. The length of the flank (region F and F') in oligonucleotides with alternating flanks may independently be 3 to 10 nucleosides, such as 4 to 8, such as 5 to 6 nucleosides, such as 4, 5, 6 or 7 modified nucleosides. In some embodiments only one of the flanks in the gapmer oligonucleotide is alternating while the other is constituted of LNA nucleotides. It may be advantageous to have at least two LNA nucleosides at the 3' end of the 3' flank (F'), to confer additional exonuclease resistance. In one embodiment the flanks in the alternating flank gapmer have an overall length from 5- to 8 nucleosides of which 3 to 5 are LNA nucleosides. Some examples of oligonucleotides with alternating flanks are:

[L]$_{1-5}$-[D]$_{1-4}$-[L]$_{1-3}$-[G]$_{5-16}$-[L]$_{2-6}$

[L]$_{1-2}$-[D]$_{2-3}$-[L]$_{3-4}$-[G]$_{5-7}$-[L]$_{1-2}$-[D]$_{2-3}$-[L]$_{2-3}$ $[L]_{1-2}$-$[D]_{1-2}$-$[L]_{1-2}$-$[D]_{1-2}$-$[L]_{1-2}$-$[G]_{5-16}$-$[L]_{1-2}$-$[D]_{1-3}$-$[L]_{2-4}$ $[L]_{1-5}$-$[G]_{5-16}$-$[L]$-$[D]$-$[L]$-$[D]$-$[L]_{2}$ $[L]_{4}$-$[G]_{6-10}$-$[L]$-$[D]_{3}$-$[L]_{2}$ with the proviso that the overall length of the gapmer is at least 12, such as at least 14 nucleotides in length.

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group.

When used for joining the contiguous nucleotide sequence with a conjugate moiety is can serve as a biocleavable linker. Alternatively, it may be used to provide exonuclease protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitutes the gapmer.

In some embodiments, the oligonucleotide of the present invention can be represented by the following formulae:

F-G-F'; in particular $F_{2-8}$-$G_{6-16}$-$F'_{2-8}$

D'-F-G-F', in particular $D'_{2-3}$-$F_{1-8}$-$G_{6-16}$-$F'_{2-8}$

F-G-F'-D", in particular $F_{2-8}$-$G_{6-16}$-$F'_{2-8}$-$D''_{1-3}$

D'-F-G-F'-D", in particular $D'_{1-3}$-$F_{2-8}$-$G_{6-16}$-$F'_{2-8}$-$D''_{1-3}$ In some embodiments the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety may modify or enhance the pharmacokinetic properties of the oligonucleotide by improving cellular distribution, bioavailability, metabolism, excretion, permeability, and/or cellular uptake of the oligonucleotide. In particular, the conjugate may target the oligonucleotide to a specific organ, tissue or cell type and thereby enhance the effectiveness of the oligonucleotide in that organ, tissue or cell type. At the same time the conjugate may serve to reduce activity of the oligonucleotide in non-target cell types, tissues or organs, e.g. off target activity or activity in non-target cell types, tissues or organs.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates (e.g. GalNAc), cell surface receptor ligands, drug substances, hormones, lipophilic substances, polymers, proteins, peptides, toxins (e.g. bacterial toxins), vitamins, viral proteins (e.g. capsids) or combinations thereof.

In some embodiments, the conjugate is an antibody or an antibody fragment which has a specific affinity for a transferrin receptor, for example as disclosed in WO 2012/143379 herby incorporated by reference. In some embodiments the non-nucleotide moiety is an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B—Y—C, A-Y—B—C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

In some embodiments treatment is performed on a patient who has been diagnosed with a neurological disorder, such as a neurological disorder selected from the group consisting of neurodegenerative diseases including Tauopathies, Alzheimer's disease (AD), progressive supranuclear palsy (PSP), corticobasal ganglionic degeneration (CBD), chronic traumatic encephalopathy (CTE), fronto-temporal dementia FTD) and FTD with parkinsonism linked to chromosome 17 (FTDP-17), Pick's disease (PiD), argyrophilic grain disease (AGD), tangle-predominant senile dementia (TPSD), primary age-related Tauopathy (PART), Down syndrome and lytico-bodig disease. Upregulation of pathological Tau is associated with infantile Tauopathies including hemimegalencephaly (HME), tuberous sclerosis complex; focal cortical dysplasia type 2b; and ganglioglioma. In addition, abnormal Tau expression and/or function may also be associated with other diseases such as Hallervorden-Spatz syndrome, also known as neurodegeneration with brain iron accumulation type 1 (NBIA1), gangliocytomas, and subacute sclerosing panencephalitis. Tau may also play a role in seizure disorders (e.g., epilepsy), network dysfunction (e.g., depression), and movement disorders (e.g., Parkinson's disease).

DETAILED DESCRIPTION OF THE INVENTION

The Oligonucleotides of the Invention

The invention relates to oligonucleotides capable of modulating expression of Tau, such as inhibiting (down-regulating) Tau. The modulation is achieved by hybridizing to a target nucleic acid encoding Tau. The target nucleic acid may be a mammalian MAPT mRNA sequence, such as a sequence selected from the group consisting of SEQ ID NO: 1 and 2.

The oligonucleotide of the invention is an antisense oligonucleotide which targets MAPT resulting in reduced Tau expression.

In some embodiments the antisense oligonucleotide of the invention is capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target. In some embodiments oligonucleotides of the invention may be capable of inhibiting expression levels of Tau mRNA by at least 60% or 70% in vitro following application of 5 µM oligonucleotide to primary neuronal cells. In some embodiments compounds of the invention may be capable of inhibiting expression levels of Tau protein by at least 50% in vitro following application of 0.5 µM oligonucleotide to primary neuronal cells. Suitably, the examples provide assays which may be used to measure Tau RNA or protein inhibition (e.g. example 1 and 3). The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches hybridization to the target nucleic acid may still be sufficient to show a desired modulation of Tau expression. Reduced binding affinity resulting from mismatches may advantageously be compensated by increased number of nucleotides in the oligonucleotide and/or an increased number of modified nucleosides capable of increasing the binding affinity to the target, such as 2' sugar modified nucleosides, including LNA, present within the oligonucleotide sequence.

An aspect of the present invention relates to an antisense oligonucleotide which comprises a contiguous nucleotide sequence of at least 10 nucleotides in length with at least 90% complementarity to SEQ ID NO: 3, 4 or 5.

In some embodiments, the oligonucleotide comprises a contiguous sequence of 10 to 30 nucleotides in length, which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid or a target sequence.

It is advantageous if the oligonucleotide of the invention, or contiguous nucleotide sequence thereof is fully complementary (100% complementary) to a region of the target nucleic acid, or in some embodiments may comprise one or two mismatches between the oligonucleotide and the target nucleic acid.

In some embodiments the oligonucleotide comprises a contiguous nucleotide sequence of 10 to 30 nucleotides in length with at least 90% complementary, such as fully (or 100%) complementary, to contiguous nucleotides within position 12051 to 12111, 39562 to 39593 or 72837 to 72940 of SEQ ID NO: 1.

In some embodiments the oligonucleotide sequence is 100% complementary to a corresponding target nucleic acid region present in SEQ ID NO: 1 and SEQ ID NO: 2.

It is advantageous if the antisense oligonucleotide is complementary to a target sequence selected from one of the regions listed in table 4. In some embodiments the contiguous nucleotide sequence of the antisense oligonucleotide is at least 90% complementary to, such as fully complementary to a target sequence selected R1-R2254 (table 4) In some embodiments the oligonucleotide sequence is 100% complementary to R_223, R_738 or R_1298 (see table 4).

In some embodiment the oligonucleotide or contiguous nucleotide sequence is 90% complementary, such as fully complementary, to a region of the target nucleic acid, wherein the target nucleic acid region is selected from the group consisting of position 12051-12111 of SEQ ID NO: 1 such as position 12051-12079, position 12085-12111 or position 12060-12078 of SEQ ID NO: 1.

In another embodiment the oligonucleotide or contiguous nucleotide sequence is 90% complementary, such as fully complementary, to a region of the target nucleic acid, wherein the target nucleic acid region is selected from the group consisting of position 39562-39593 of SEQ ID NO: 1 such as position 39573-39592 of SEQ ID NO: 1.

In another embodiment of the oligonucleotide or contiguous nucleotide sequence is 90% complementary, such as fully complementary, to a region of the target nucleic acid, wherein the target nucleic acid region is selected from the group consisting of position 72837-72940 of SEQ ID NO: 1 such as position 72861-72891 or position 72862-72890 of SEQ ID NO: 1.

In some embodiments the oligonucleotide comprises a contiguous nucleotide sequence of 16 to 22 nucleotides, such as 16 to 20 nucleotides, in length with 100% complementary, to contiguous nucleotides within position 12060 to 12078 or 39573 to 39592 or 72862-72890 of SEQ ID NO: 1.

In some embodiments, the oligonucleotide of the invention comprises or consists of 10 to 35 nucleotides in length, such as from 10 to 30, such as 11 to 25, such as from 12 to 22, such as from 14 to 20 or 14 to 18 contiguous nucleotides in length. In one embodiment, the oligonucleotide comprises or consists of 16 to 22 nucleotides in length. In a preferred embodiment, the oligonucleotide comprises or consists of 16 to 20 nucleotides in length.

In some embodiments, the oligonucleotide or contiguous nucleotide sequence thereof comprises or consists of 22 or less nucleotides, such as 20 or less nucleotides, such as 16, 17, 18, 19 or 20 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 10, 11, 12, 13, 14, 15, 16, 17, 18, 19, 20, 21, 22, 23, 24, 25, 26, 27, 28, 29 or 30 contiguous nucleotides in length. In a preferred embodiment, the oligonucleotide comprises or consists of 16, 17, 18, 19 or 20 nucleotides in length.

In some embodiments, the oligonucleotide or contiguous nucleotide sequence comprises or consists of a sequence selected from the group consisting of sequences listed in table 5 (Materials and Method section).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 6 to 65 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 9, 11, 49, 53, 56 and 62 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 6 to 37 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence of SEQ ID NO: 9 or 11 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 38 to 51 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence of SEQ ID NO: 49 or 51 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 52 to 65 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence of SEQ ID NO: 56 or 62 (see motif sequences listed in table 5).

It is understood that the contiguous nucleobase sequences (motif sequence) can be modified to for example increase nuclease resistance and/or binding affinity to the target nucleic acid.

The pattern in which the modified nucleosides (such as high affinity modified nucleosides) are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprises one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In a further embodiment the oligonucleotide comprises at least one modified internucleoside linkage. Suitable internucleoside modifications are described in the "Definitions" section under "Modified internucleoside linkage". It is advantageous if at least 75%, such as 80%, such as all, the internucleoside linkages within the contiguous nucleotide sequence are phosphorothioate or boranophosphate internucleoside linkages. In some embodiments all the inter-nucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 8 LNA nucleosides or 3, 4, 5, 6, 7 or 8 LNA nucleosides. In some embodiments, at least 75% of the modified nucleosides in the oligonucleotide are LNA nucleosides, such as 80%, such as 85%, such as 90% of the modified nucleosides are LNA nucleosides, in particular beta-D-oxy LNA or ScET. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, ScET and/or ENA in either the beta-D or alpha-L configurations or combinations thereof. In a further embodiment, all LNA cytosine units are 5-methyl-cytosine. It is advantageous for the nuclease stability of the oligonucleotide or contiguous nucleotide sequence to have at least 1 LNA nucleoside at the 5' end and at least 2 LNA nucleosides at the 3' end of the nucleotide sequence.

In an embodiment of the invention the oligonucleotide of the invention is capable of recruiting RNase H.

In the current invention an advantageous structural design is a gapmer design as described in the "Definitions" section under for example "Gapmer", "LNA Gapmer", "MOE gapmer" and "Mixed Wing Gapmer" "Alternating Flank Gapmer". The gapmer design includes gapmers with uniform flanks, mixed wing flanks, alternating flanks, and gapbreaker designs. In the present invention it is advantageous if the oligonucleotide of the invention is a gapmer with an F-G-F' design, particular gapmer of formula 5'-F-G-F'-3', where region F and F' independently comprise 1-8 nucleosides, of which 2-5 are 2' sugar modified and defines the 5' and 3' end of the F and F' region, and G is a region between 6 and 16 nucleosides which are capable of recruiting RNaseH, such as a region comprising 6-16 DNA nucleosides.

In some embodiments the gapmer is an LNA gapmer.

In some embodiments of the invention the LNA gapmer is selected from the following uniform flank designs 4-10-4, 3-11-4, 4-11-4, 4-12-4 or 4-14-2.

In some embodiments of the invention the LNA gapmer is selected from the following alternating flanks designs 3-1-3-10-2, 1-3-4-6-1-3-2, 1-2-1-2-2-8-4, or 3-3-1-8-2-1-2.

Table 5 (Materials and Method section) lists preferred designs of each motif sequence.

In all instances the F-G-F' design may further include region D' and/or D" as described in the "Definitions" section under "Region D' or D" in an oligonucleotide". In some embodiments the oligonucleotide of the invention has 1, 2 or 3 phosphodiester linked nucleoside units, such as DNA units, at the 5' or 3' end of the gapmer region.

For some embodiments of the invention, the oligonucleotide is selected from the group of oligonucleotide compounds with CMP-ID-NO: 6_1; 7_1; 8_1; 9_1; 9_2; 9_3; 9_4; 9_5; 9_6; 9_7; 9_8; 9_9; 9_10; 9_11; 9_12; 9_13; 9_14; 9_15; 9_16; 9_17; 9_18; 9_19; 9_20; 9_21; 9_22; 9_23; 9_24; 9_25; 9_26; 9_27; 9_28; 9_29; 9_30; 9_31; 9_32; 9_33; 9_34; 9_35; 9_36; 9_37; 9_38; 9_39; 9_40; 9_41; 9_42; 9_43; 9_44; 9_45; 9_46; 9_47; 9_48; 9_49; 9_50; 9_51; 9_52; 9_53; 9_54; 9_55; 9_56; 9_57; 9_58; 9_59; 9_60; 9_61; 9_62; 9_63; 9_64; 9_65; 9_66; 9_67; 9_68; 9_69; 9_70; 9_71; 9_72; 9_73; 9_74; 9_75; 9_76; 9_77; 9_78; 9_79; 9_80; 9_81; 9_82; 9_83; 9_84; 9_85; 9_86; 9_87; 9_88; 9_89; 9_90; 9_91; 9_92; 9_93; 9_94; 9_95; 9_96; 9_97; 9_98; 9_99; 9_100; 9_101; 9_102; 9_103; 9_104; 9_105; 9_106; 10_1; 10_2; 10_3; 10_4; 10_5; 10_6; 10_7; 10_8; 10_9; 10_10; 10_11; 10_12; 10_13; 10_14; 10_15; 10_16; 10_17; 10_18; 10_19; 10_20; 10_21; 10_22; 10_23; 10_24; 10_25; 10_26; 10_27; 10_28; 10_29; 10_30; 10_31; 10_32; 10_33; 10_34; 10_35; 10_36; 10_37; 10_38; 10_39; 10_40; 10_41; 10_42; 10_43; 10_44; 10_45; 10_46; 10_47; 10_48; 10_49; 10_50; 10_51; 10_52; 10_53; 10_54; 10_55; 10_56; 10_57; 10_58; 10_59; 10_60; 10_61; 10_62; 10_63; 10_64; 10_65; 10_66; 10_67; 10_68; 10_69; 10_70; 10_71; 10_72; 10_73; 10_74; 10_75; 10_76; 10_77; 10_78; 10_79; 10_80; 10_81; 10_82; 10_83; 10_84; 10_85; 10_86; 10_87; 10_88; 10_89; 11_1; 12_1; 13_1; 14_1; 15_1; 16_1; 17_1; 18_1; 19_1; 20_1; 21_1; 22_1; 23_1; 24_1; 24_2; 24_3; 24_4; 24_5; 24_6; 24_7; 24_8; 24_9; 24_10; 24_11; 24_12; 24_13; 24_14; 24_15; 24_16; 24_17; 24_18; 24_19; 24_20; 24_21; 24_22; 24_23; 24_24; 24_25; 24_26; 24_27; 24_28; 24_29; 24_30; 24_31; 24_32; 24_33; 24_34; 24_35; 24_36; 24_37; 24_38; 24_39; 24_40; 24_41; 24_42; 24_43; 24_44; 24_45; 24_46; 24_47; 24_48; 24_49; 24_50; 24_51; 24_52; 24_53; 24_54; 24_55; 24_56; 24_57; 24_58; 24_59; 24_60; 24_61; 24_62; 25_1; 25_2; 25_3; 25_4; 25_5; 25_6; 25_7; 25_8; 25_9; 25_10; 25_11; 25_12; 25_13; 25_14; 25_15; 25_16; 25_17; 25_18; 25_19; 25_20; 25_21; 25_22; 25_23; 25_24; 25_25; 25_26; 25_27; 25_28; 25_29; 25_30; 25_31; 25_32; 25_33; 25_34; 25_35; 25_36; 25_37; 25_38; 25_39; 25_40; 25_41; 25_42; 25_43; 26_1; 26_2; 26_3; 26_4; 26_5; 26_6; 26_7; 26_8; 26_9; 26_10; 26_11; 26_12; 26_13; 26_14; 26_15; 26_16; 26_17; 26_18; 26_19; 26_20; 26_21; 26_22; 26_23; 26_24; 26_25; 26_26; 26_27; 26_28; 26_29; 26_30; 26_31; 27_1; 28_1; 28_2; 28_3; 28_4; 28_5; 28_6; 28_7; 28_8; 28_9; 28_10; 28_11; 28_12; 28_13; 28_14; 28_15; 28_16; 28_17; 28_18; 28_19; 28_20; 28_21; 28_22; 28_23; 28_24; 28_25; 28_26; 28_27; 28_28; 28_29; 28_30; 28_31; 28_32; 28_33; 29_1; 29_2; 29_3; 29_4; 29_5; 29_6; 29_7; 29_8; 29_9; 29_10; 29_11; 29_12; 29_13; 29_14; 30_1; 30_2; 30_3; 30_4; 30_5; 30_6; 30_7; 30_8; 30_9; 30_10; 30_11; 30_12; 30_13; 30_14; 30_15; 30_16; 30_17; 30_18; 30_19; 30_20; 30_21; 30_22; 30_23; 30_24; 30_25; 31_1; 31_2; 31_3; 32_1; 32_2; 32_3; 32_4; 32_5; 32_6; 32_7; 32_8; 32_9; 32_10; 32_11; 32_12; 32_13; 32_14; 32_15; 32_16; 32_17; 32_18; 32_19; 32_20; 32_21; 32_22; 32_23; 32_24; 32_25; 32_26; 32_27; 32_28; 32_29; 32_30; 32_31; 32_32; 32_33; 32_34; 32_35; 32_36; 32_37; 32_38; 32_39; 32_40; 32_41; 32_42; 32_43; 32_44; 32_45; 32_46; 32_47; 32_48; 32_49; 32_50; 32_51; 33_1; 33_2; 33_3; 33_4; 33_5; 33_6; 33_7; 33_8; 33_9; 33_10; 33_11; 33_12; 33_13; 33_14; 33_15; 33_16; 33_17; 33_18; 33_19; 33_20; 33_21; 33_22; 33_23; 33_24; 33_25; 33_26; 33_27; 33_28; 33_29; 33_30; 33_31; 33_32; 33_33; 34_1; 35_1; 35_2; 35_3; 36_1; 37_1; 38_1; 39_1; 40_1; 41_1; 42_1; 43_1; 44_1; 45_1; 46_1; 47_1; 48_1; 49_1; 49_2; 49_3; 49_4; 49_5; 49_6; 49_7; 49_8; 49_9; 49_10; 49_11; 49_12; 49_13; 49_14; 49_15; 49_16; 49_17; 49_18; 49_19; 49_20; 49_21; 49_22; 49_23; 49_24; 49_25; 49_26; 49_27; 49_28; 49_29; 49_30; 49_31; 49_32; 49_33; 49_34; 49_35; 49_36; 49_37; 49_38; 49_39; 49_40; 49_41; 49_42; 49_43; 49_44; 49_45; 49_46; 49_47; 49_48; 49_49; 49_50; 49_51; 49_52; 49_53; 49_54; 49_55; 49_56; 49_57; 49_58; 49_59; 49_60; 49_61; 49_62; 49_63; 49_64; 49_65; 49_66; 49_67; 49_68; 49_69; 49_70; 49_71; 49_72; 49_73; 49_74; 49_75; 49_76; 49_77; 49_78; 49_79; 49_80; 49_81; 49_82; 49_83; 49_84; 49_85; 49_86; 49_87; 49_88; 49_89; 49_90; 49_91; 49_92; 49_93; 49_94; 49_95; 49_96; 49_97; 49_98; 49_99; 49_100; 49_101; 49_102; 49_103; 49_104; 49_105; 49_106; 49_107; 49_108; 49_109; 49_110; 49_111; 49_112; 49_113; 49_114; 49_115; 49_116;

49_117; 49_118; 49_119; 49_120; 49_121; 49_122; 49_123; 49_124; 49_125; 49_126; 49_127; 49_128; 49_129; 49_130; 49_131; 49_132; 49_133; 49_134; 49_135; 49_136; 49_137; 49_138; 49_139; 49_140; 49_141; 49_142; 49_143; 49_144; 49_145; 49_146; 49_147; 49_148; 49_149; 49_150; 49_151; 49_152; 49_153; 49_154; 49_155; 49_156; 49_157; 49_158; 49_159; 49_160; 49_161; 49_162; 49_163; 49_164; 49_165; 49_166; 49_167; 49_168; 49_169; 49_170; 49_171; 49_172; 49_173; 49_174; 49_175; 49_176; 49_177; 49_178; 49_179; 49_180; 49_181; 49_182; 49_183; 49_184; 49_185; 49_186; 49_187; 49_188; 49_189; 49_190; 49_191; 49_192; 50_1; 51_1; 52_1; 53_1; 54_1; 55_1; 56_1; 57_1; 58_1; 59_1; 60_1; 61_1; 62_1; 63_1; 64_1 and 65_1.

For certain embodiments of the invention, the oligonucleotide is selected from the group of oligonucleotide compounds with CMP-ID-NO: 9_102; 9_103; 9_104; 11_1; 49_38; 49_51; 49_179; 49_189; 53_1; 56_1 and 62_1.

For certain embodiments of the invention, the oligonucleotide is selected from the group of oligonucleotide compounds with CMP-ID-NO: 9_102; 9_103; 9_104 and 11_1.

For certain embodiments of the invention, the oligonucleotide is selected from the group of oligonucleotide compounds with CMP-ID-NO: 49_38; 49_51; 49_179 and 49_189.

For certain embodiments of the invention, the oligonucleotide is selected from the group of oligonucleotide compounds with CMP-ID-NO: 53_1; 56_1 and 62_1.

A particular advantageous antisense oligonucleotide in the context of the invention is an oligonucleotide compound selected from the group consisting of

```
CMP ID NO: 9_102
                                          SEQ ID NO: 9
CTTtAATttaatcactcAT;

CMP ID NO: 9_103
                                          SEQ ID NO: 9
CTTTaatttaatcacTCAT;

CMP ID NO: 9_104
                                          SEQ ID NO: 9
CTTTaatttaatcaCtCAT;

CMP ID NO: 11_1
                                          SEQ ID NO: 11
CTTTaatttaatcaCTCA;

CMP ID NO: 49_38
                                          SEQ ID NO: 49
TtaaCTCAaatcaaTtctCA;

CMP ID NO: 49_51
                                          SEQ ID NO: 49
TtaActCAaatcaattCTCA;

CMP ID NO: 49_179
                                          SEQ ID NO: 49
TTAactCaaatcaatTCtCA;

CMP ID NO: 49_189
                                          SEQ ID NO: 49
TTAActcaaatcaattCTCA;

CMP ID NO: 53_1
                                          SEQ ID NO: 53
CAACaccttttaattcATTA;

CMP ID NO: 56_1
                                          SEQ ID NO: 56
CTCAtcaacaccttttaaTT;

CMP ID NO: 62_1
                                          SEQ ID NO: 62
TTAactcatcaacaCCTT;
``` wherein capital letters are beta-D-oxy LNA nucleosides, lowercase letters are DNA nucleosides, all LNA C are 5-methyl cytosine, all internucleoside linkages are phosphorothioate internucleoside linkages.

Figure 2:
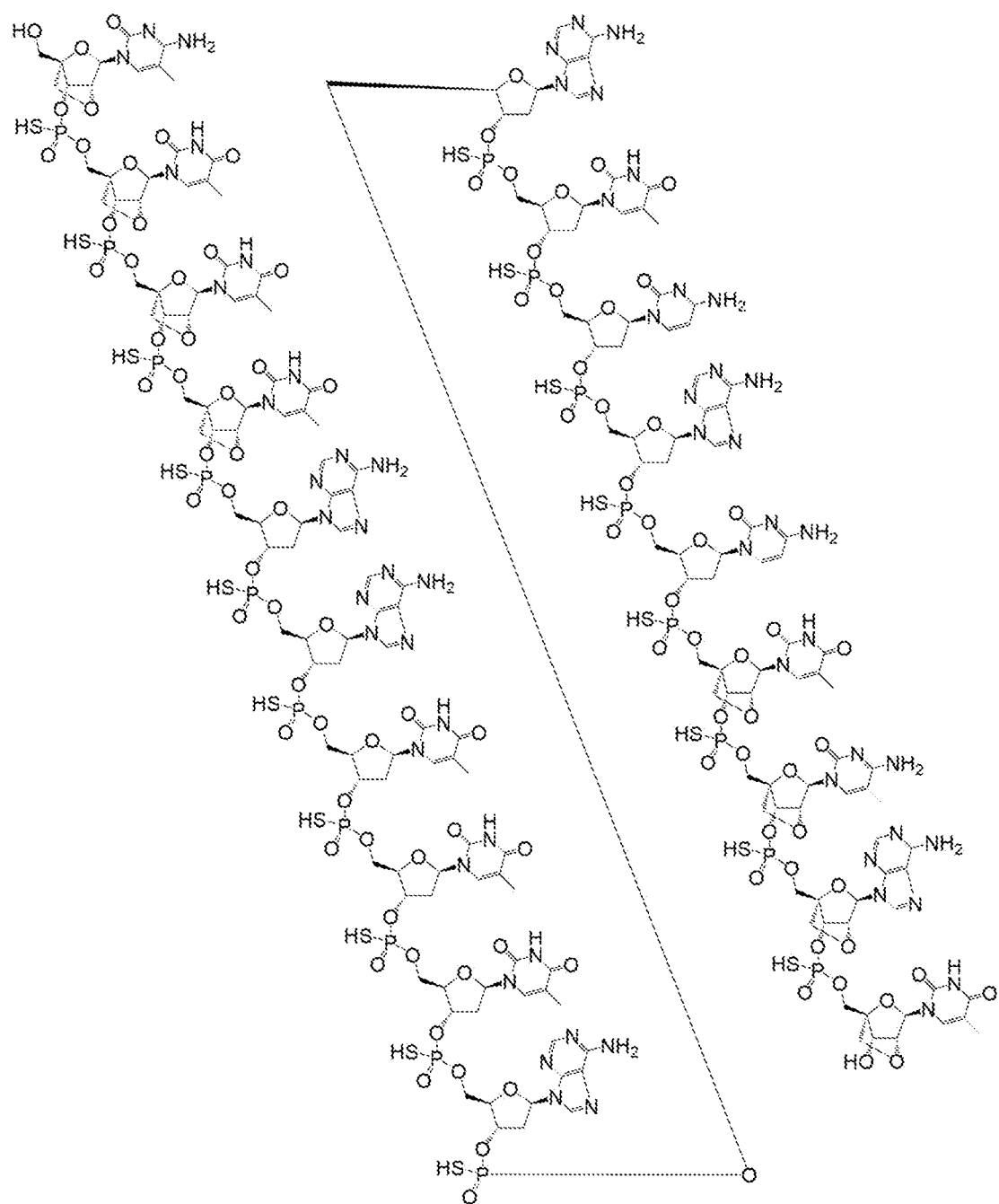
FIG. 2: Compound 9_103 (sequence of nucleobases is shown in SEQ ID NO 9)

In one embodiment the antisense oligonucleotide is CMP ID NO: 9_103 as shown in FIG. 2.

Figure 3:
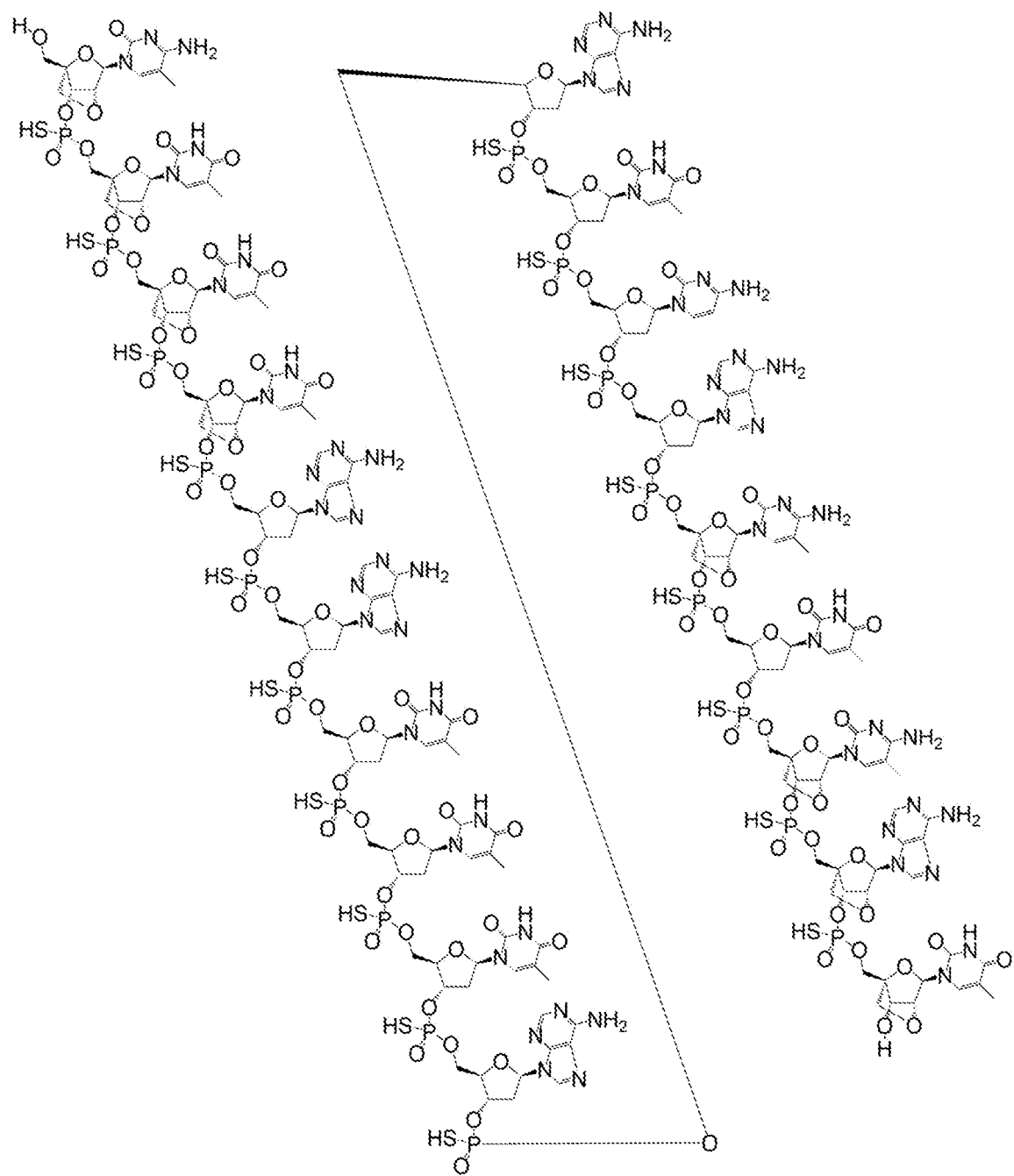
FIG. 3: Compound 9_104 (sequence of nucleobases is shown in SEQ ID NO 9)

In one embodiment the antisense oligonucleotide is CMP ID NO: 9_104 as shown in FIG. 3.

Figure 4:
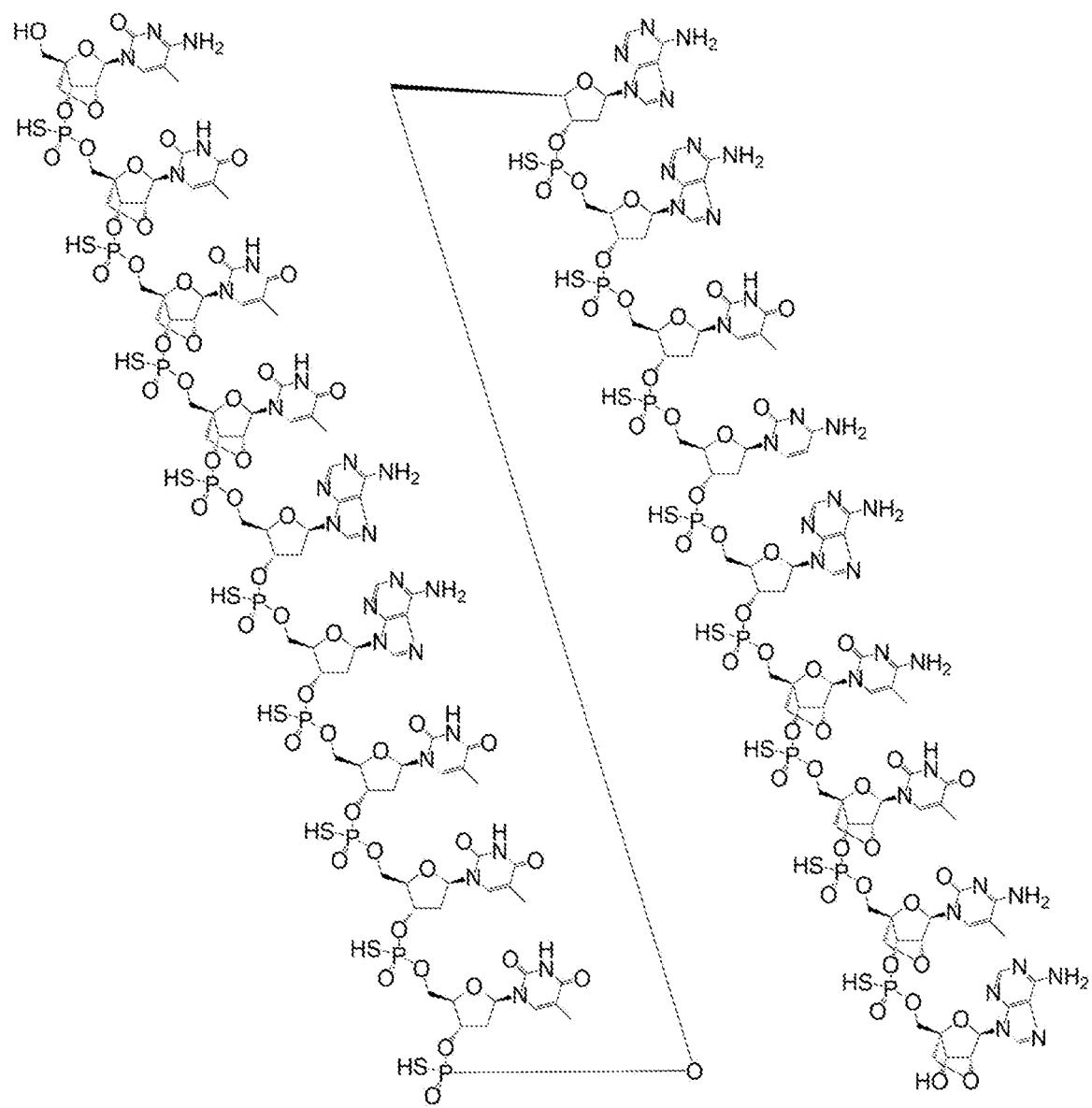
FIG. 4: Compound 11_1 (sequence of nucleobases is shown in SEQ ID NO 11)

In one embodiment the antisense oligonucleotide is CMP ID NO: 11_1 as shown in FIG. 4.

Figure 5:
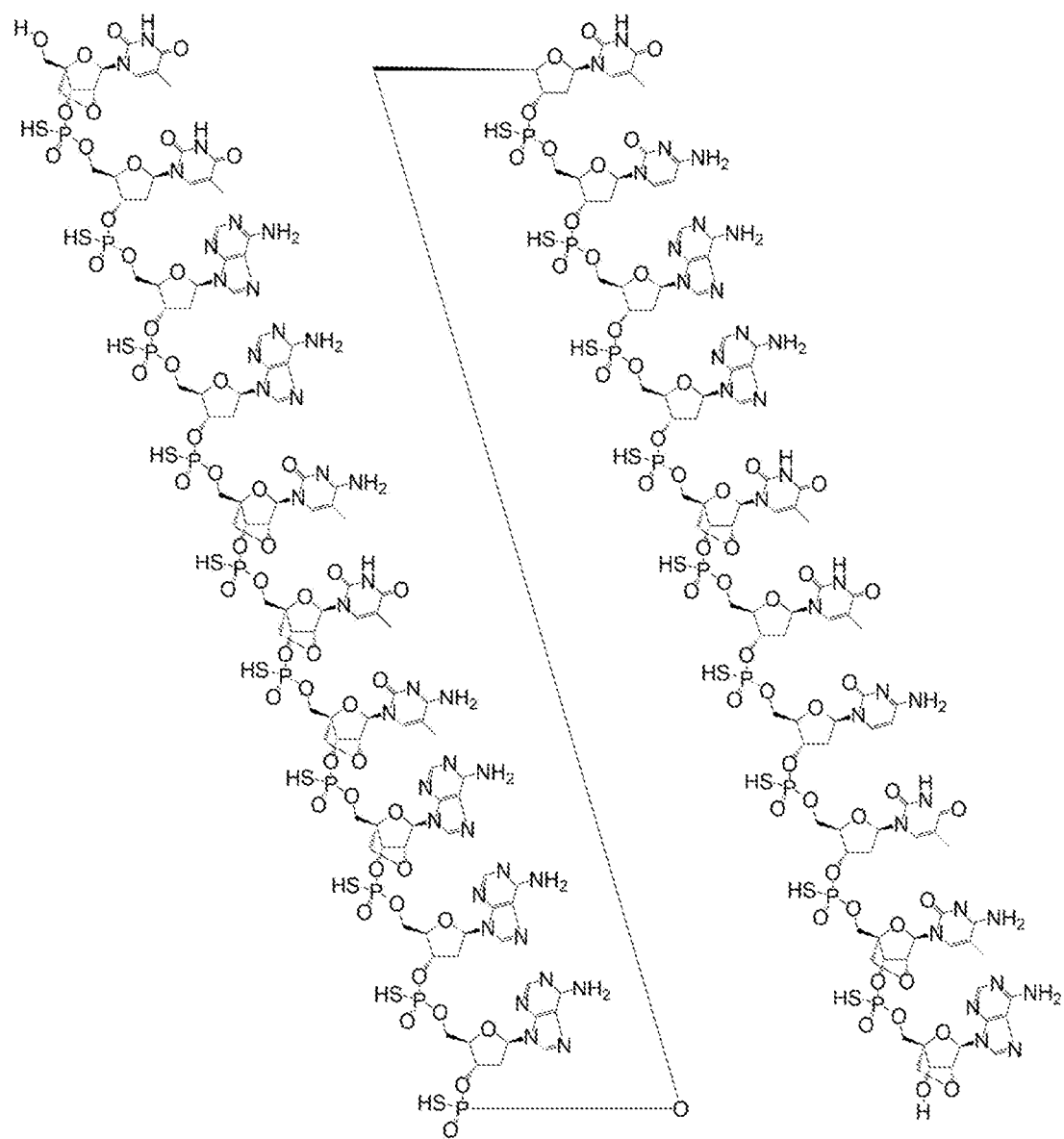
FIG. 5: Compound 49_38 (sequence of nucleobases is shown in SEQ ID NO 49)

In one embodiment the antisense oligonucleotide is CMP ID NO: 49_38 as shown in FIG. 5.

Figure 6:
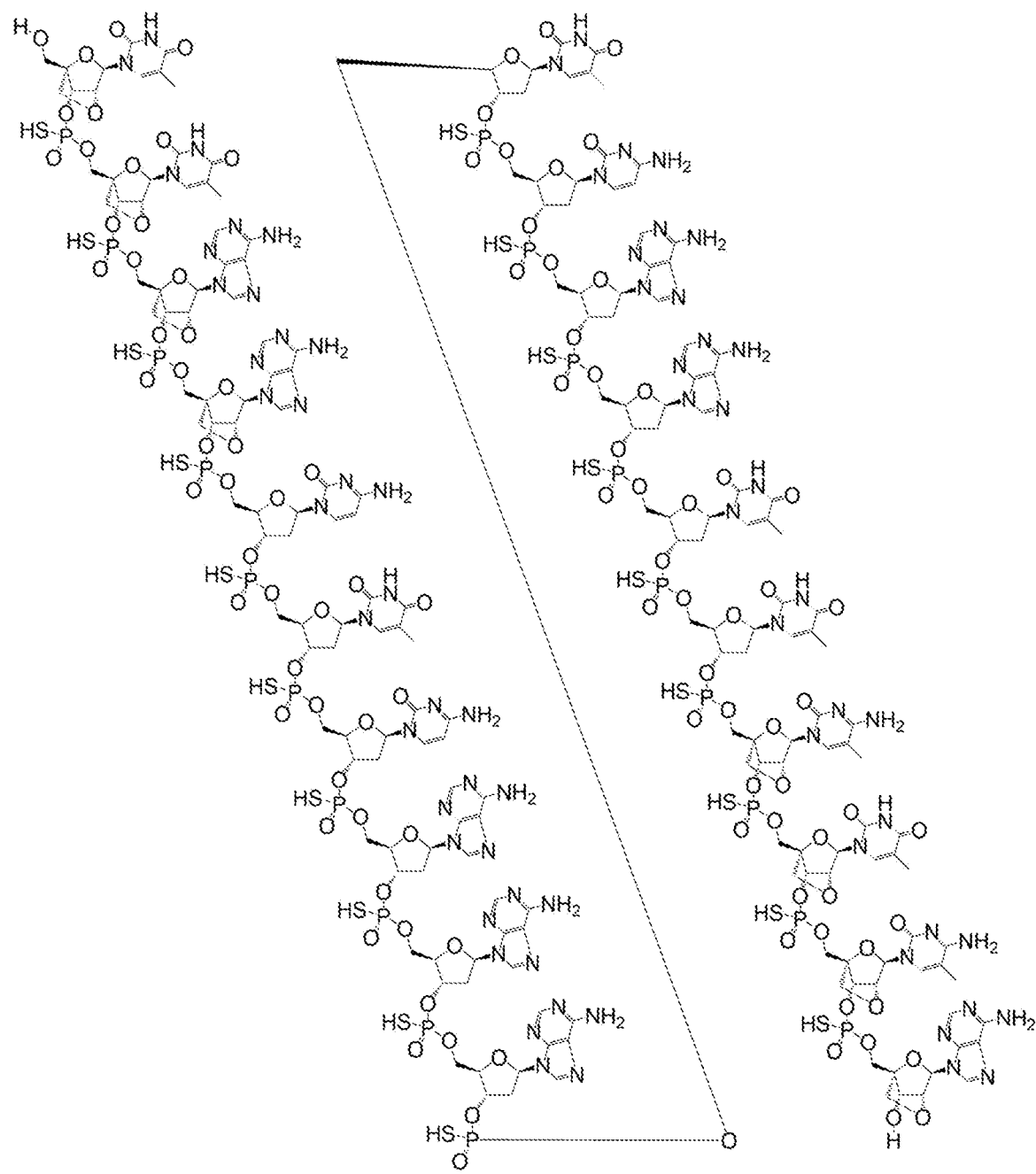
FIG. 6: Compound 49_189 (sequence of nucleobases is shown in SEQ ID NO 49)

In one embodiment the antisense oligonucleotide is CMP ID NO: 49_189 as shown in FIG. 6.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Salt

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect the invention provides a pharmaceutically acceptable salt of the antisense oligonucleotide or a conjugate thereof. In a preferred embodiment, the pharmaceutically acceptable salt is a sodium or a potassium salt.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 µM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5.

The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the oligonucleotide or oligonucleotide conjugate of the invention is a prodrug. In particular, with respect to oligonucleotide conjugates the conjugate moiety is cleaved off the oligonucleotide once the prodrug is delivered to the site of action, e.g. the target cell.

Applications

The oligonucleotides of the invention may be utilized as research reagents for, for example, diagnostics, therapeutics and prophylaxis.

In research, such oligonucleotides may be used to specifically modulate the synthesis of Tau protein in cells (e.g. in vitro cell cultures) and experimental animals thereby facilitating functional analysis of the target or an appraisal of its usefulness as a target for therapeutic intervention. Typically, the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

The present invention provides an in vivo or in vitro method for modulating Tau expression in a target cell which is expressing Tau, said method comprising administering an oligonucleotide of the invention in an effective amount to said cell.

In some embodiments, the target cell, is a mammalian cell in particular a human cell.

The target cell may be an in vitro cell culture or an in vivo cell forming part of a tissue in a mammal. In preferred embodiments the target cell is present in the brain or central nervous system. In particular cells in the brain stem, cerebellum, cerebral cortex, frontal cortex, medulla/pons and midbrain and spinal cord are relevant target regions. For the treatment of progressive supranuclear palsy (PSP) target reduction in the brain regions medulla/pons and midbrain are advantageous. For the treatment of Alzheimer target reduction in the brain regions cerebral cortex, medulla/pons and midbrain are advantageous. In particular, in neurons, nerves cells, axons and basal ganglia are relevant cell types.

In diagnostics the oligonucleotides may be used to detect and quantitate MAPT expression in cell and tissues by northern blotting, in-situ hybridisation or similar techniques.

For therapeutics, the oligonucleotides may be administered to an animal or a human, suspected of having a disease or disorder, which can be treated by modulating the expression of Tau.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The disease or disorder, as referred to herein, is associated with expression of Tau. In some embodiments disease or disorder may be associated with a mutation in the Tau gene or a gene whose protein product is associated with or interacts with Tau. Therefore, in some embodiments, the target nucleic acid is a mutated form of the Tau sequence and in other embodiments, the target nucleic acid is a regulator of the Tau sequence.

The methods of the invention are preferably employed for treatment or prophylaxis against diseases caused by abnormal levels and/or activity of Tau.

The invention further relates to use of an oligonucleotide, oligonucleotide conjugate or a pharmaceutical composition as defined herein for the manufacture of a medicament for the treatment of abnormal levels and/or activity of Tau.

In one embodiment, the invention relates to oligonucleotides, oligonucleotide conjugates or pharmaceutical compositions for use in the treatment of diseases or disorders selected from wherein the disease is selected from Tauopathies, Alzheimer's disease (AD), progressive supranuclear palsy (PSP), corticobasal ganglionic degeneration (CBD), chronic traumatic encephalopathy (CTE), fronto-temporal dementia (FTD), FTDP-17, Pick's disease (PiD), argyrophilic grain disease (AGD), tangle-predominant senile dementia (TPSD), primary age-related Tauopathy (PART), Down syndrome, lytico-bodig disease, infantile Tauopathies including hemimegalencephaly (HME), tuberous sclerosis complex, focal cortical dysplasia type 2b, ganglioglioma, Hallervorden-Spatz syndrome, neurodegeneration with brain iron accumulation type 1 (NBIA1), gangliocytomas, subacute sclerosing panencephalitis, seizure disorders (e.g., epilepsy), network dysfunction (e.g., depression) and movement disorders (e.g., Parkinson's disease).

In certain embodiments the disease is selected from Alzheimer's disease (AD), progressive supranuclear palsy (PSP), fronto-temporal dementia (FTD) or FTDP-17.

Administration

The oligonucleotides or pharmaceutical compositions of the present invention may be administered via parenteral (such as, intravenous, subcutaneous, intra-muscular, intracerebral, intracerebroventricular intraocular, or intrathecal administration).

In some embodiments, the administration is via intrathecal administration.

Advantageously, e.g. for treatment of neurological disorders, the oligonucleotide or pharmaceutical compositions of the present invention are administered intrathecally or intracranially, e.g. via intracerebral or intraventricular administration.

The invention also provides for the use of the oligonucleotide or conjugate thereof, such as pharmaceutical salts or compositions of the invention, for the manufacture of a medicament wherein the medicament is in a dosage form for subcutaneous administration.

The invention also provides for the use of the oligonucleotide of the invention, or conjugate thereof, such as pharmaceutical salts or compositions of the invention, for the manufacture of a medicament wherein the medicament is in a dosage form for intrathecal administration.

The invention also provides for the use of the oligonucleotide or oligonucleotide conjugate of the invention as described for the manufacture of a medicament wherein the medicament is in a dosage form for intrathecal administration.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

EMBODIMENTS

The following embodiments of the present invention may be used in combination with any other embodiments described herein.

1. An antisense oligonucleotide of 10 to 50 nucleotides in length, which comprises a contiguous nucleotide sequence of at least 10 nucleotides in length, such as 10-30 nucleotides in length, with at least 90% complementarity, such as 100% complementarity, to any target sequence in table 4 (R_1-R_2254).
2. The oligonucleotide of embodiment 1, wherein the target sequence is selected from one of the target regions R_223, R_738 or R_1298, corresponds to SEQ ID NO: 3, 4 or 5, respectively.
3. The oligonucleotide of embodiment 1 or 2, wherein the contiguous nucleotide sequence is 100% complementary to contiguous nucleotides within position 12051 to 12111, 39562 to 39593 or 72837 to 72940 of SEQ ID NO: 1.
4. The oligonucleotide of embodiment 1 to 3, wherein the contiguous nucleotide sequence is at last 16 nucleotides and 100% complementary, to contiguous nucleotides within position 12060 to 12078, position 39573 to 39592 or position 72862-72890 of SEQ ID NO: 1.
5. The oligonucleotide of embodiment 1 to 4, wherein the oligonucleotide comprises a sequence selected from the group consisting of SEQ ID NO: 6-65.
6. The oligonucleotide of embodiment 1 to 5, wherein the oligonucleotide comprises a sequence of SEQ ID NO: 9 or 11.
7. The oligonucleotide of embodiment 1 to 5, wherein the oligonucleotide comprises a sequence of SEQ ID NO: 49.
8. The oligonucleotide of embodiment 1 to 5, wherein the oligonucleotide comprises a sequence selected from the group consisting of SEQ ID NO: 53, 56 and 62.
9. The oligonucleotide of embodiment 1, 2 or 5 or 6, wherein the contiguous nucleotide sequence has zero to three mismatches compared to the target sequence it is complementary to.
10. The oligonucleotide of embodiment 9, wherein the contiguous nucleotide sequence has one mismatch compared to the target sequence.
11. The oligonucleotide of embodiment 9, wherein the contiguous nucleotide sequence has two mismatches compared to the target sequence.
12. The oligonucleotide of embodiment 9, wherein the contiguous nucleotide sequence is fully complementary to the target sequence.
13. The oligonucleotide of embodiment 1 to 12, wherein the oligonucleotide is capable of modulating expression of Tau.
14. The oligonucleotide of embodiment 13, wherein the oligonucleotide is capable of reducing expression of Tau.
15. The oligonucleotide of embodiment 1 to 14, wherein the oligonucleotide is capable of hybridizing to the target sequence with a $\Delta G°$ below $-10$ kcal.
16. The oligonucleotide of embodiment 1 to 15, wherein the target sequence is located in RNA.
17. The oligonucleotide of embodiment 16, wherein the RNA is mRNA.
18. The oligonucleotide of embodiment 17, wherein the mRNA is pre-mRNA.
19. The oligonucleotide of embodiment 1-18, wherein the contiguous nucleotide sequence comprises or consists of at least 14 contiguous nucleotides, particularly 15, 16, 17, 18, 19, 20, 21, or 22 contiguous nucleotides.
20. The oligonucleotide of embodiment 1-18, wherein the contiguous nucleotide sequence comprises or consists of from 16 to 22 nucleotides.
21. The oligonucleotide of embodiment 20, wherein the contiguous nucleotide sequence comprises or consists of from 18 to 20 nucleotides.
22. The oligonucleotide of embodiment 1-21, wherein the oligonucleotide comprises or consists of 14 to 30 nucleotides in length.

23. The oligonucleotide of embodiment 22, wherein the oligonucleotide comprises or consists of 16 to 24 nucleotides in length.
24. The oligonucleotide of embodiment 22 or 24, wherein the oligonucleotide comprises or consists of 18 to 20 nucleotides in length.
25. The oligonucleotide of embodiment 1-24, wherein the oligonucleotide or contiguous nucleotide sequence is single stranded.
26. The oligonucleotide of embodiment 1-25, wherein the oligonucleotide is not siRNA nor self-complementary.
27. The oligonucleotide of embodiment 1-26, comprising one or more modified nucleosides.
28. The oligonucleotide of embodiment 27, wherein the one or more modified nucleoside is a high-affinity modified nucleosides.
29. The oligonucleotide of embodiment 27 or 28, wherein the one or more modified nucleoside is a 2' sugar modified nucleoside.
30. The oligonucleotide of embodiment 29, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.
31. The oligonucleotide of embodiment 29 or 30, wherein the one or more 2' sugar modified nucleoside is a LNA nucleoside.
32. The antisense oligonucleotide of embodiment 31, wherein the LNA nucleoside is selected from oxy-LNA, amino-LNA, thio-LNA, cET, and ENA.
33. The antisense oligonucleotide of embodiment 31 or 32, wherein the modified LNA nucleoside is oxy-LNA with the following 2'-4' bridge —O—CH$_2$—.
34. The antisense oligonucleotide of embodiment 33, wherein the oxy-LNA is beta-D-oxy-LNA.
35. The antisense oligonucleotide of embodiment 31 or 32, wherein the modified LNA nucleoside is cET with the following 2'-4' bridge —O—CH(CH$_3$)—.
36. The antisense oligonucleotide of embodiment 35, wherein the cET is (S)cET, i.e. 6'(S)methyl-beta-D-oxy-LNA.
37. The antisense oligonucleotide of embodiment 31 or 32, wherein the LNA is ENA, with the following 2'-4' bridge —O—CH$_2$—CH$_2$—.
38. The oligonucleotide of embodiment 29 or 30, wherein the one or more 2' sugar modified nucleoside is a MOE nucleoside 39. The oligonucleotide of any one of embodiments 1-38, wherein the oligonucleotide comprises at least one modified internucleoside linkage.
40. The oligonucleotide of embodiment 39, wherein the modified internucleoside linkage is nuclease resistant.
41. The oligonucleotide of embodiment 39 or 40, wherein at least 50% of the internucleoside linkages within the contiguous nucleotide sequence are phosphorothioate internucleoside linkages or boranophosphate internucleoside linkages.
42. The oligonucleotide of embodiment 39 or 41, wherein 80% the internucleoside linkages within the contiguous nucleotide sequence are phosphorothioate internucleoside linkages.
43. The oligonucleotide of embodiment 39 to 42, wherein all the internucleoside linkages within the contiguous nucleotide sequence are phosphorothioate internucleoside linkages.
44. The oligonucleotide of embodiment 1-43, wherein the oligonucleotide is capable of recruiting RNase H.
45. The oligonucleotide of embodiment 44, wherein the oligonucleotide or the contiguous nucleotide sequence is a gapmer.
46. The oligonucleotide of embodiment 45, wherein the gapmer has the formula 5'-F-G-F'-3', where the F and F' wing regions independently comprise or consist of 1-8 nucleosides, of which 2-5 are 2' sugar modified nucleosides in accordance with embodiment 32 to 38 and G is a region between 6 and 16 nucleosides which are capable of recruiting RNaseH.
47. The antisense oligonucleotide of embodiment 46, wherein each wing region (F and F') is characterized by having at least one 2' sugar modified nucleoside at the 5' terminal and the 3' terminal of the wing and the G region has at least one DNA nucleoside adjacent to the wing regions (e.g. 5' and 3' terminal of the G region).
48. The oligonucleotide of embodiment 46 or 47, wherein all the 2' sugar modified nucleosides in region F and F' are identical LNA nucleosides.
49. The oligonucleotide of embodiment 48, wherein all the LNA nucleosides are oxy-LNA nucleosides.
50. The oligonucleotide of embodiment 46 or 47, wherein all the 2' sugar modified nucleosides in region F and F' are identical MOE nucleosides.
51. The oligonucleotide of embodiment 46-50, wherein
a. the F region is between 3 and 8 nucleotides in length and consists of 3-5 identical LNA nucleosides and 0-4 DNA nucleosides; and
b. the F' region is between 2 and 6 nucleotides in length and consists of 2-4 identical LNA nucleosides and 0-2 DNA nucleosides; and
c. region G is between 6 and 14 DNA nucleotides.
52. The oligonucleotide of embodiment 46 or 47, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.
53. The oligonucleotide of embodiment 46 to 50 or 52, wherein the RNaseH recruiting nucleosides in region G are independently selected from DNA, alpha-L-LNA, C4' alkylated DNA, ANA and 2'F-ANA and UNA.
54. The oligonucleotide of embodiment 53, wherein the nucleosides in region G is DNA and/or alpha-L-LNA nucleosides.
55. The oligonucleotide of embodiment 53 or 54, wherein region G consists of at least 75% DNA nucleosides.
56. The oligonucleotide of embodiment 53 to 55, wherein all the nucleotides in the G region are DNA.
57. The oligonucleotide of embodiment 1-56, wherein the oligonucleotide is selected from CMP ID NO: 9_102; 9_103; 9_104; 11_1; 49_38; 49_51; 49_179; 49_189; 53_1; 56_1 and 62_1.
58. The oligonucleotide of embodiment 57, wherein the oligonucleotide is a compound selected from the group consisting of

```
CMP ID NO: 9_102
                                   SEQ ID NO: 9
CTTtAATttaatcactcAT;

CMP ID NO: 9_103
                                   SEQ ID NO: 9
CTTTaatttaatcacTCAT;
```

-continued

```
CMP ID NO: 9_104
                                    SEQ ID NO: 9
CTTTaatttaatcaCtCAT;

CMP ID NO: 11_1
                                    SEQ ID NO: 11
CTTTaatttaatcaCTCA;

CMP ID NO: 49_38
                                    SEQ ID NO: 49
TtaaCTCAaatcaaTtctCA;

CMP ID NO: 49_51
                                    SEQ ID NO: 49
TtaActCAaatcaattCTCA;

CMP ID NO: 49_179
                                    SEQ ID NO: 49
TTAactCaaatcaatTCtCA;

CMP ID NO: 49_189
                                    SEQ ID NO: 49
TTAActcaaatcaattCTCA;

CMP ID NO: 53_1
                                    SEQ ID NO: 53
CAACaccttttaattcATTA;

CMP ID NO: 56_1
                                    SEQ ID NO: 56
CTCAtcaacaccttttaaTT;

CMP ID NO: 62_1
                                    SEQ ID NO: 62
TTAactcatcaacaCCTT;
``` wherein capital letters are beta-D-oxy LNA nucleosides, lowercase letters are DNA nucleosides, all LNA C are 5-methyl cytosine, all internucleoside linkages are phosphorothioate internucleoside linkages.

59. The antisense oligonucleotide according to any one of embodiments 1-58, wherein the antisense oligonucleotide is CMP ID NO: 9_103 as shown in FIG. 2.

60. The antisense oligonucleotide according to any one of embodiments 1-58, wherein the antisense oligonucleotide is CMP ID NO: 9_104 as shown in FIG. 3.

61. The antisense oligonucleotide according to any one of embodiments 1-58, wherein the antisense oligonucleotide is CMP ID NO: 11_1 as shown in FIG. 4.

62. The antisense oligonucleotide according to any one of embodiments 1-58, wherein the antisense oligonucleotide is CMP ID NO: 49_38 as shown in FIG. 5.

63. The antisense oligonucleotide according to any one of embodiments 1-58, wherein the antisense oligonucleotide is CMP ID NO: 49_189 as shown in FIG. 6.

64. A conjugate comprising the oligonucleotide according to any one of claims 1-58, and at least one conjugate moiety covalently attached to said oligonucleotide.

65. The oligonucleotide conjugate of embodiment 59, wherein the conjugate moiety is selected from carbohydrates, cell surface receptor ligands, drug substances, hormones, lipophilic substances, polymers, proteins, peptides, toxins, vitamins, viral proteins or combinations thereof.

66. The oligonucleotide conjugate of embodiment 59 or 65, wherein the conjugate facilitates delivery across the blood brain barrier.

67. The oligonucleotide conjugate of embodiment 66, wherein the conjugate is an antibody or antibody fragment targeting the transferrin receptor.

68. The oligonucleotide conjugate of embodiment 59-67, comprising a linker which is positioned between the oligonucleotide and the conjugate moiety.

69. The oligonucleotide conjugate of embodiment 68, wherein the linker is a physiologically labile linker.

70. A pharmaceutical composition comprising the oligonucleotide of embodiment 1-58 or a conjugate of embodiment 59-69 and a pharmaceutically acceptable diluent, carrier, salt and/or adjuvant.

71. A method for manufacturing the oligonucleotide of embodiment 1-58, comprising reacting nucleotide units thereby forming covalently linked contiguous nucleotide units comprised in the oligonucleotide.

72. The method of embodiment 71, further comprising reacting the contiguous nucleotide sequence with a non-nucleotide conjugation moiety.

73. A method for manufacturing the composition of embodiment 70, comprising mixing the oligonucleotide with a pharmaceutically acceptable diluent, carrier, salt and/or adjuvant.

74. An in vivo or in vitro method for modulating Tau expression in a target cell which is expressing Tau, said method comprising administering an oligonucleotide of embodiment 1-57 or a conjugate of embodiment 59-69 or the pharmaceutical composition of embodiment 70 in an effective amount to said cell.

75. A method for treating or preventing a disease comprising administering a therapeutically or prophylactically effective amount of an oligonucleotide of embodiment 1-58 or a conjugate of embodiment 59-69 or the pharmaceutical composition of embodiment 70 to a subject suffering from or susceptible to the disease.

76. The oligonucleotide of embodiment 1-57 or a conjugate of embodiment 59-69 or the pharmaceutical composition of embodiment 70, for use as a medicament for treatment or prevention of a disease in a subject.

77. Use of the oligonucleotide of oligonucleotide of embodiment 1-58 or a conjugate of embodiment 59-69 for the preparation of a medicament for treatment or prevention of a disease in a subject.

78. The method, the oligonucleotide or the use of embodiments 75-77, wherein the disease is associated with in vivo activity of Tau.

79. The method, the oligonucleotide or the use of embodiments 75-78, wherein the disease is associated with overexpression of Tau and/or abnormal levels of Tau.

80. The method, the oligonucleotide or the use of embodiments 79, wherein the Tau is reduced by at least 30%, or at least or at least 40%, or at least 50%, or at least 60%, or at least 70%, or at least 80%, or at least 90%, or at least 95% compared to the expression without the oligonucleotide of embodiment 1-58 or a conjugate of embodiment 59-69 or the pharmaceutical composition of embodiment 70.

81. The method, the oligonucleotide or the use of embodiments 75-79, wherein the disease is selected from Tauopathies, Alzheimer's disease (AD), progressive supranuclear palsy (PSP), corticobasal ganglionic degeneration (CBD), chronic traumatic encephalopathy (CTE), fronto-temporal dementia (FTD), FTDP-17, Pick's disease (PiD), argyrophilic grain disease (AGD), tangle-predominant senile dementia (TPSD), primary age-related Tauopathy (PART), Down syndrome, lytico-bodig disease, infantile Tauopathies including hemimegalencephaly (HME), tuberous sclerosis complex, focal cortical dysplasia type 2b, ganglioglioma, Hallervorden-Spatz syndrome, neurodegeneration with brain iron accumulation type 1 (NBIA1), gangliocytomas, subacute sclerosing panencephalitis, seizure disorders (e.g., epilepsy), network dysfunction (e.g., depression) and movement disorders (e.g., Parkinson's disease).
82. The method, the oligonucleotide or the use of embodiments 75-79 wherein the disease is selected from Alzheimer's disease (AD), progressive supranuclear palsy (PSP), fronto-temporal dementia (FTD) or FTDP-17.
83. The method, the oligonucleotide or the use of embodiments 75-82, wherein the subject is a mammal.
84. The method, the oligonucleotide or the use of embodiment 83, wherein the mammal is human.

EXAMPLES

Materials and Methods

Oligonucleotide Motif Sequences and Oligonucleotide Compounds

TABLE 5 list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 6 | tcactcatgccttaatc | 4-11-2 | TCACtcatgccttaaTC | 6_1 | 12051 | A |
| 7 | taatcactcatgcctta | 4-9-4 | TAATcactcatgcCTTA | 7_1 | 12054 | A |
| 8 | taatcactcatgcctt | 4-8-4 | TAATcactcatgCCTT | 8_1 | 12055 | A |
| 9 | ctttaatttaatcactcat | 1-10-1-2-1-1-3 | CtttaatttaaTcaCtCAT | 9_1 | 12060 | A |
| 9 | ctttaatttaatcactcat | 1-10-1-1-2-1-3 | CtttaatttaaTcACtCAT | 9_2 | 12060 | A |
| 9 | ctttaatttaatcactcat | 1-10-2-3-3 | CtttaatttaaTCactCAT | 9_3 | 12060 | A |
| 9 | ctttaatttaatcactcat | 1-10-2-2-4 | CtttaatttaaTCacTCAT | 9_4 | 12060 | A |
| 9 | ctttaatttaatcactcat | 1-10-2-1-1-2-2 | CtttaatttaaTCaCtcAT | 9_5 | 12060 | A |
| 9 | ctttaatttaatcactcat | 1-10-2-1-1-1-3 | CtttaatttaaTCaCtCAT | 9_6 | 12060 | A |
| 9 | ctttaatttaatcactcat | 1-10-3-3-2 | CtttaatttaaTCActcAT | 9_7 | 12060 | A |
| 9 | ctttaatttaatcactcat | 1-10-3-2-3 | CtttaatttaaTCActCAT | 9_8 | 12060 | A |
| 9 | ctttaatttaatcactcat | 1-10-3-1-4 | CtttaatttaaTCAcTCAT | 9_9 | 12060 | A |
| 9 | ctttaatttaatcactcat | 1-10-4-2-2 | CtttaatttaaTCACtcAT | 9_10 | 12060 | A |
| 9 | ctttaatttaatcactcat | 1-5-1-8-4 | CtttaaTttaatcacTCAT | 9_11 | 12060 | A |
| 9 | ctttaatttaatcactcat | 1-5-1-7-1-1-3 | CtttaaTttaatcaCtCAT | 9_12 | 12060 | A |
| 9 | ctttaatttaatcactcat | 1-5-1-6-1-2-3 | CtttaaTttaatcActCAT | 9_13 | 12060 | A |
| 9 | ctttaatttaatcactcat | 1-5-1-6-1-1-4 | CtttaaTttaatcAcTCAT | 9_14 | 12060 | A |
| 9 | ctttaatttaatcactcat | 1-5-1-6-2-1-3 | CtttaaTttaatcACtCAT | 9_15 | 12060 | A |
| 9 | ctttaatttaatcactcat | 1-4-1-9-4 | CtttaAtttaatcacTCAT | 9_16 | 12060 | A |
| 9 | ctttaatttaatcactcat | 1-4-2-8-4 | CtttaATttaatcacTCAT | 9_17 | 12060 | A |
| 9 | ctttaatttaatcactcat | 1-3-1-10-4 | CtttAatttaatcacTCAT | 9_18 | 12060 | A |
| 9 | ctttaatttaatcactcat | 1-3-1-9-1-1-3 | CtttAatttaatcaCtCAT | 9_19 | 12060 | A |
| 9 | ctttaatttaatcactcat | 1-3-1-1-1-8-4 | CtttAaTttaatcacTCAT | 9_20 | 12060 | A |
| 9 | ctttaatttaatcactcat | 1-3-2-9-4 | CtttAAtttaatcacTCAT | 9_21 | 12060 | A |
| 9 | ctttaatttaatcactcat | 1-3-3-8-4 | CtttAATttaatcacTCAT | 9_22 | 12060 | A |
| 9 | ctttaatttaatcactcat | 1-2-1-11-4 | CttTaatttaatcacTCAT | 9_23 | 12060 | A |
| 9 | ctttaatttaatcactcat | 1-2-1-10-1-1-3 | CttTaatttaatcaCtCAT | 9_24 | 12060 | A |
| 9 | ctttaatttaatcactcat | 1-2-1-2-1-8-4 | CttTaaTttaatcacTCAT | 9_25 | 12060 | A |
| 9 | ctttaatttaatcactcat | 1-2-1-1-1-9-4 | CttTaAtttaatcacTCAT | 9_26 | 12060 | A |
| 9 | ctttaatttaatcactcat | 1-2-1-1-2-8-4 | CttTaATttaatcacTCAT | 9_27 | 12060 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 9 | ctttaatttaatcactcat | 1-2-2-11-3 | CttTAatttaatcactCAT | 9_28 | 12060 | A |
| 9 | ctttaatttaatcactcat | 1-2-2-10-4 | CttTAatttaatcacTCAT | 9_29 | 12060 | A |
| 9 | ctttaatttaatcactcat | 1-2-2-9-1-2-2 | CttTAatttaatcaCtcAT | 9_30 | 12060 | A |
| 9 | ctttaatttaatcactcat | 1-2-2-9-1-1-3 | CttTAatttaatcaCtCAT | 9_31 | 12060 | A |
| 9 | ctttaatttaatcactcat | 1-2-2-1-1-8-4 | CttTAaTttaatcacTCAT | 9_32 | 12060 | A |
| 9 | ctttaatttaatcactcat | 1-2-3-9-4 | CttTAAtttaatcacTCAT | 9_33 | 12060 | A |
| 9 | ctttaatttaatcactcat | 1-2-4-10-2 | CttTAATttaatcactcAT | 9_34 | 12060 | A |
| 9 | ctttaatttaatcactcat | 1-2-4-8-4 | CttTAATttaatcacTCAT | 9_35 | 12060 | A |
| 9 | ctttaatttaatcactcat | 1-1-1-3-1-8-4 | CtTtaaTttaatcacTCAT | 9_36 | 12060 | A |
| 9 | ctttaatttaatcactcat | 1-1-1-2-1-9-4 | CtTtaAtttaatcacTCAT | 9_37 | 12060 | A |
| 9 | ctttaatttaatcactcat | 1-1-1-2-2-8-4 | CtTtaATttaatcacTCAT | 9_38 | 12060 | A |
| 9 | ctttaatttaatcactcat | 1-1-1-1-1-10-4 | CtTtAatttaatcacTCAT | 9_39 | 12060 | A |
| 9 | ctttaatttaatcactcat | 1-1-1-1-1-9-1-1-3 | CtTtAatttaatcaCtCAT | 9_40 | 12060 | A |
| 9 | ctttaatttaatcactcat | 1-1-1-1-1-1-1-8-4 | CtTtAaTttaatcacTCAT | 9_41 | 12060 | A |
| 9 | ctttaatttaatcactcat | 1-1-1-1-2-9-4 | CtTtAAtttaatcacTCAT | 9_42 | 12060 | A |
| 9 | ctttaatttaatcactcat | 1-1-1-1-3-8-4 | CtTtAATttaatcacTCAT | 9_43 | 12060 | A |
| 9 | ctttaatttaatcactcat | 1-1-2-11-4 | CtTTaatttaatcacTCAT | 9_44 | 12060 | A |
| 9 | ctttaatttaatcactcat | 1-1-2-10-1-2-2 | CtTTaatttaatcaCtcAT | 9_45 | 12060 | A |
| 9 | ctttaatttaatcactcat | 1-1-2-10-1-1-3 | CtTTaatttaatcaCtCAT | 9_46 | 12060 | A |
| 9 | ctttaatttaatcactcat | 1-1-2-2-1-8-4 | CtTTaaTttaatcacTCAT | 9_47 | 12060 | A |
| 9 | ctttaatttaatcactcat | 1-1-2-1-1-9-4 | CtTTaAtttaatcacTCAT | 9_48 | 12060 | A |
| 9 | ctttaatttaatcactcat | 1-1-2-1-2-10-2 | CtTTaATttaatcactcAT | 9_49 | 12060 | A |
| 9 | ctttaatttaatcactcat | 1-1-2-1-2-8-4 | CtTTaATttaatcacTCAT | 9_50 | 12060 | A |
| 9 | ctttaatttaatcactcat | 1-1-3-11-3 | CtTTAatttaatcactCAT | 9_51 | 12060 | A |
| 9 | ctttaatttaatcactcat | 1-1-3-10-4 | CtTTAatttaatcacTCAT | 9_52 | 12060 | A |
| 9 | ctttaatttaatcactcat | 1-1-3-9-1-2-2 | CtTTAatttaatcaCtcAT | 9_53 | 12060 | A |
| 9 | ctttaatttaatcactcat | 1-1-3-9-1-1-3 | CtTTAatttaatcaCtCAT | 9_54 | 12060 | A |
| 9 | ctttaatttaatcactcat | 1-1-3-1-1-10-2 | CtTTAaTttaatcactcAT | 9_55 | 12060 | A |
| 9 | ctttaatttaatcactcat | 1-1-3-1-1-8-4 | CtTTAaTttaatcacTCAT | 9_56 | 12060 | A |
| 9 | ctttaatttaatcactcat | 1-1-4-11-2 | CtTTAtttaatcactcAT | 9_57 | 12060 | A |
| 9 | ctttaatttaatcactcat | 1-1-4-9-4 | CtTTAtttaatcacTCAT | 9_58 | 12060 | A |
| 9 | ctttaatttaatcactcat | 2-11-1-2-3 | CTttaatttaatcActCAT | 9_59 | 12060 | A |
| 9 | ctttaatttaatcactcat | 2-11-1-1-4 | CTttaatttaatcAcTCAT | 9_60 | 12060 | A |
| 9 | ctttaatttaatcactcat | 2-11-2-1-3 | CTttaatttaatcACtCAT | 9_61 | 12060 | A |
| 9 | ctttaatttaatcactcat | 2-9-2-4-2 | CTttaatttaaTCactcAT | 9_62 | 12060 | A |
| 9 | ctttaatttaatcactcat | 2-9-2-3-3 | CTttaatttaaTCactCAT | 9_63 | 12060 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 9 | ctttaatttaatcactcat | 2-9-2-2-4 | CTttaatttaaTCacTCAT | 9_64 | 12060 | A |
| 9 | ctttaatttaatcactcat | 2-9-2-1-1-2-2 | CTttaatttaaTCaCtcAT | 9_65 | 12060 | A |
| 9 | ctttaatttaatcactcat | 2-9-2-1-1-1-3 | CTttaatttaaTCaCtCAT | 9_66 | 12060 | A |
| 9 | ctttaatttaatcactcat | 2-9-3-3-2 | CTttaatttaaTCActcAT | 9_67 | 12060 | A |
| 9 | ctttaatttaatcactcat | 2-9-3-2-3 | CTttaatttaaTCActCAT | 9_68 | 12060 | A |
| 9 | ctttaatttaatcactcat | 2-9-4-2-2 | CTttaatttaaTCACtcAT | 9_69 | 12060 | A |
| 9 | ctttaatttaatcactcat | 2-4-1-9-3 | CTttaaTttaatcactCAT | 9_70 | 12060 | A |
| 9 | ctttaatttaatcactcat | 2-4-1-8-4 | CTttaaTttaatcacTCAT | 9_71 | 12060 | A |
| 9 | ctttaatttaatcactcat | 2-4-1-7-1-2-2 | CTttaaTttaatcaCtcAT | 9_72 | 12060 | A |
| 9 | ctttaatttaatcactcat | 2-4-1-7-1-1-3 | CTttaaTttaatcaCtCAT | 9_73 | 12060 | A |
| 9 | ctttaatttaatcactcat | 2-4-1-6-1-2-3 | CTttaaTttaatcActCAT | 9_74 | 12060 | A |
| 9 | ctttaatttaatcactcat | 2-4-1-6-1-1-4 | CTttaaTttaatcAcTCAT | 9_75 | 12060 | A |
| 9 | ctttaatttaatcactcat | 2-4-1-6-2-2-2 | CTttaaTttaatcACtcAT | 9_76 | 12060 | A |
| 9 | ctttaatttaatcactcat | 2-4-1-6-2-1-3 | CTttaaTttaatcACtCAT | 9_77 | 12060 | A |
| 9 | ctttaatttaatcactcat | 2-2-1-11-3 | CTttAatttaatcactCAT | 9_78 | 12060 | A |
| 9 | ctttaatttaatcactcat | 2-2-1-10-4 | CTttAatttaatcacTCAT | 9_79 | 12060 | A |
| 9 | ctttaatttaatcactcat | 2-2-1-9-1-1-3 | CTttAatttaatcaCtCAT | 9_80 | 12060 | A |
| 9 | ctttaatttaatcactcat | 2-2-1-1-1-8-4 | CTttAaTttaatcacTCAT | 9_81 | 12060 | A |
| 9 | ctttaatttaatcactcat | 2-2-2-9-4 | CTttAAtttaatcacTCAT | 9_82 | 12060 | A |
| 9 | ctttaatttaatcactcat | 2-2-3-8-4 | CTttAATttaatcacTCAT | 9_83 | 12060 | A |
| 9 | ctttaatttaatcactcat | 2-1-1-10-1-2-2 | CTtTaatttaatcaCtcAT | 9_84 | 12060 | A |
| 9 | ctttaatttaatcactcat | 2-1-1-10-1-1-3 | CTtTaatttaatcaCtCAT | 9_85 | 12060 | A |
| 9 | ctttaatttaatcactcat | 2-1-1-1-1-9-4 | CTtTaAtttaatcacTCAT | 9_86 | 12060 | A |
| 9 | ctttaatttaatcactcat | 2-1-1-1-2-10-2 | CTtTaATttaatcactcAT | 9_87 | 12060 | A |
| 9 | ctttaatttaatcactcat | 2-1-2-11-3 | CTtTAatttaatcactCAT | 9_88 | 12060 | A |
| 9 | ctttaatttaatcactcat | 2-1-2-10-4 | CTtTAatttaatcacTCAT | 9_89 | 12060 | A |
| 9 | ctttaatttaatcactcat | 2-1-2-9-1-2-2 | CTtTAatttaatcaCtcAT | 9_90 | 12060 | A |
| 9 | ctttaatttaatcactcat | 2-1-2-9-1-1-3 | CTtTAatttaatcaCtCAT | 9_91 | 12060 | A |
| 9 | ctttaatttaatcactcat | 2-1-2-1-1-10-2 | CTtTAaTttaatcactcAT | 9_92 | 12060 | A |
| 9 | ctttaatttaatcactcat | 2-1-3-11-2 | CTtTAAtttaatcactcAT | 9_93 | 12060 | A |
| 9 | ctttaatttaatcactcat | 2-1-3-9-4 | CTtTAAtttaatcacTCAT | 9_94 | 12060 | A |
| 9 | ctttaatttaatcactcat | 2-1-4-10-2 | CTtTAATttaatcactcAT | 9_95 | 12060 | A |
| 9 | ctttaatttaatcactcat | 3-2-2-10-2 | CTTtaATttaatcactcAT | 9_96 | 12060 | A |
| 9 | ctttaatttaatcactcat | 3-1-1-11-3 | CTTtAatttaatcactCAT | 9_97 | 12060 | A |
| 9 | ctttaatttaatcactcat | 3-1-1-10-4 | CTTtAatttaatcacTCAT | 9_98 | 12060 | A |
| 9 | ctttaatttaatcactcat | 3-1-1-9-1-2-2 | CTTtAatttaatcaCtcAT | 9_99 | 12060 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 9 | ctttaatttaatcactcat | 3-1-1-9-1-1-3 | CTTtAatttaatcaCtCAT | 9_100 | 12060 | A |
| 9 | ctttaatttaatcactcat | 3-1-2-9-4 | CTTtAAtttaatcacTCAT | 9_101 | 12060 | A |
| 9 | ctttaatttaatcactcat | 3-1-3-10-2 | CTTtAATttaatcactcAT | 9_102 | 12060 | A |
| 9 | ctttaatttaatcactcat | 4-11-4 | CTTTaatttaatcacTCAT | 9_103 | 12060 | A |
| 9 | ctttaatttaatcactcat | 4-10-1-1-3 | CTTTaatttaatcaCtCAT | 9_104 | 12060 | A |
| 9 | ctttaatttaatcactcat | 4-2-1-10-2 | CTTTaaTttaatcactcAT | 9_105 | 12060 | A |
| 9 | ctttaatttaatcactcat | 4-1-1-9-4 | CTTTaAtttaatcacTCAT | 9_106 | 12060 | A |
| 10 | gctttaatttaatcactcat | 1-11-2-1-1-3 | GctttaatttaaTcaCtCAT | 10_1 | 12060 | A |
| 10 | gctttaatttaatcactcat | 1-11-2-4-2 | GctttaatttaaTCactcAT | 10_2 | 12060 | A |
| 10 | gctttaatttaatcactcat | 1-11-2-3-3 | GctttaatttaaTCactCAT | 10_3 | 12060 | A |
| 10 | gctttaatttaatcactcat | 1-11-2-2-4 | GctttaatttaaTCacTCAT | 10_4 | 12060 | A |
| 10 | gctttaatttaatcactcat | 1-11-2-1-1-2-2 | GctttaatttaaTCaCtcAT | 10_5 | 12060 | A |
| 10 | gctttaatttaatcactcat | 1-11-2-1-1-1-3 | GctttaatttaaTCaCtCAT | 10_6 | 12060 | A |
| 10 | gctttaatttaatcactcat | 1-11-3-3-2 | GctttaatttaaTCActcAT | 10_7 | 12060 | A |
| 10 | gctttaatttaatcactcat | 1-11-4-2-2 | GctttaatttaaTCACtcAT | 10_8 | 12060 | A |
| 10 | gctttaatttaatcactcat | 1-6-1-9-3 | GctttaaTttaatcactCAT | 10_9 | 12060 | A |
| 10 | gctttaatttaatcactcat | 1-6-1-8-4 | GctttaaTttaatcacTCAT | 10_10 | 12060 | A |
| 10 | gctttaatttaatcactcat | 1-6-1-7-1-2-2 | GctttaaTttaatcaCtcAT | 10_11 | 12060 | A |
| 10 | gctttaatttaatcactcat | 1-6-1-7-1-1-3 | GctttaaTttaatcaCtCAT | 10_12 | 12060 | A |
| 10 | gctttaatttaatcactcat | 1-6-1-4-1-2-1-1-3 | GctttaaTttaaTcaCtCAT | 10_13 | 12060 | A |
| 10 | gctttaatttaatcactcat | 1-6-1-4-2-3-3 | GctttaaTttaaTCactCAT | 10_14 | 12060 | A |
| 10 | gctttaatttaatcactcat | 1-6-1-4-2-1-1-2-2 | GctttaaTttaaTCaCtcAT | 10_15 | 12060 | A |
| 10 | gctttaatttaatcactcat | 1-6-1-4-3-3-2 | GctttaaTttaaTCActcAT | 10_16 | 12060 | A |
| 10 | gctttaatttaatcactcat | 1-5-1-9-4 | GctttaAtttaatcacTCAT | 10_17 | 12060 | A |
| 10 | gctttaatttaatcactcat | 1-4-1-10-4 | GctttAatttaatcacTCAT | 10_18 | 12060 | A |
| 10 | gctttaatttaatcactcat | 1-4-1-9-1-1-3 | GctttAatttaatcaCtCAT | 10_19 | 12060 | A |
| 10 | gctttaatttaatcactcat | 1-4-1-1-1-8-4 | GctttAaTttaatcacTCAT | 10_20 | 12060 | A |
| 10 | gctttaatttaatcactcat | 1-4-2-9-4 | GctttAAtttaatcacTCAT | 10_21 | 12060 | A |
| 10 | gctttaatttaatcactcat | 1-4-3-8-4 | GctttAATttaatcacTCAT | 10_22 | 12060 | A |
| 10 | gctttaatttaatcactcat | 1-3-1-11-4 | GctttTaatttaatcacTCAT | 10_23 | 12060 | A |
| 10 | gctttaatttaatcactcat | 1-3-1-10-1-2-2 | GcttTaatttaatcaCtcAT | 10_24 | 12060 | A |
| 10 | gctttaatttaatcactcat | 1-3-1-10-1-1-3 | GcttTaatttaatcaCtCAT | 10_25 | 12060 | A |
| 10 | gctttaatttaatcactcat | 1-3-1-2-1-8-4 | GcttTaaTttaatcacTCAT | 10_26 | 12060 | A |
| 10 | gctttaatttaatcactcat | 1-3-1-1-1-9-4 | GcttTaAtttaatcacTCAT | 10_27 | 12060 | A |
| 10 | gctttaatttaatcactcat | 1-3-2-10-4 | GcttTAatttaatcacTCAT | 10_28 | 12060 | A |
| 10 | gctttaatttaatcactcat | 1-3-2-9-1-2-2 | GcttTAatttaatcaCtcAT | 10_29 | 12060 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 10 | gctttaatttaatcactcat | 1-3-2-9-1-1-3 | GcttTAatttaatcaCtCAT | 10_30 | 12060 | A |
| 10 | gctttaatttaatcactcat | 1-2-1-3-1-8-4 | GctTtaaTttaatcacTCAT | 10_31 | 12060 | A |
| 10 | gctttaatttaatcactcat | 1-2-1-2-1-9-4 | GctTtaAtttaatcacTCAT | 10_32 | 12060 | A |
| 10 | gctttaatttaatcactcat | 1-2-1-1-1-10-4 | GctTtAatttaatcacTCAT | 10_33 | 12060 | A |
| 10 | gctttaatttaatcactcat | 1-2-1-1-1-9-1-2-2 | GctTtAatttaatcaCtcAT | 10_34 | 12060 | A |
| 10 | gctttaatttaatcactcat | 1-2-1-1-1-9-1-1-3 | GctTtAatttaatcaCtCAT | 10_35 | 12060 | A |
| 10 | gctttaatttaatcactcat | 1-2-1-1-1-1-1-8-4 | GctTtAaTttaatcacTCAT | 10_36 | 12060 | A |
| 10 | gctttaatttaatcactcat | 1-2-1-1-2-9-4 | GctTtAAtttaatcacTCAT | 10_37 | 12060 | A |
| 10 | gctttaatttaatcactcat | 1-2-2-11-4 | GctTTaatttaatcacTCAT | 10_38 | 12060 | A |
| 10 | gctttaatttaatcactcat | 1-2-2-10-1-2-2 | GctTTaatttaatcaCtcAT | 10_39 | 12060 | A |
| 10 | gctttaatttaatcactcat | 1-2-2-10-1-1-3 | GctTTaatttaatcaCtCAT | 10_40 | 12060 | A |
| 10 | gctttaatttaatcactcat | 1-2-2-1-1-9-4 | GctTTaAtttaatcacTCAT | 10_41 | 12060 | A |
| 10 | gctttaatttaatcactcat | 1-2-3-9-1-2-2 | GctTTAatttaatcaCtcAT | 10_42 | 12060 | A |
| 10 | gctttaatttaatcactcat | 1-1-1-9-2-4-2 | GcttaatttaaTCactcAT | 10_43 | 12060 | A |
| 10 | gctttaatttaatcactcat | 1-1-1-9-2-3-3 | GcttaatttaaTCactCAT | 10_44 | 12060 | A |
| 10 | gctttaatttaatcactcat | 1-1-1-9-2-1-1-2-2 | GcttaatttaaTCaCtcAT | 10_45 | 12060 | A |
| 10 | gctttaatttaatcactcat | 1-1-1-9-3-3-2 | GcttaatttaaTCActcAT | 10_46 | 12060 | A |
| 10 | gctttaatttaatcactcat | 1-1-1-4-1-9-3 | GcttaaTttaatcactCAT | 10_47 | 12060 | A |
| 10 | gctttaatttaatcactcat | 1-1-1-4-1-8-4 | GcttaaTttaatcacTCAT | 10_48 | 12060 | A |
| 10 | gctttaatttaatcactcat | 1-1-1-4-1-7-1-2-2 | GcttaaTttaatcaCtcAT | 10_49 | 12060 | A |
| 10 | gctttaatttaatcactcat | 1-1-1-4-1-7-1-1-3 | GcttaaTttaatcaCtCAT | 10_50 | 12060 | A |
| 10 | gctttaatttaatcactcat | 1-1-1-3-1-9-4 | GcttaAtttaatcacTCAT | 10_51 | 12060 | A |
| 10 | gctttaatttaatcactcat | 1-1-1-2-1-10-4 | GcttAatttaatcacTCAT | 10_52 | 12060 | A |
| 10 | gctttaatttaatcactcat | 1-1-1-2-1-9-1-2-2 | GcttAatttaatcaCtcAT | 10_53 | 12060 | A |
| 10 | gctttaatttaatcactcat | 1-1-1-2-1-9-1-1-3 | GcttAatttaatcaCtCAT | 10_54 | 12060 | A |
| 10 | gctttaatttaatcactcat | 1-1-1-2-1-1-1-8-4 | GcttAaTttaatcacTCAT | 10_55 | 12060 | A |
| 10 | gctttaatttaatcactcat | 1-1-1-2-2-9-4 | GcttAAtttaatcacTCAT | 10_56 | 12060 | A |
| 10 | gctttaatttaatcactcat | 1-1-1-1-1-11-4 | GctTaatttaatcacTCAT | 10_57 | 12060 | A |
| 10 | gctttaatttaatcactcat | 1-1-1-1-1-10-1-1-3 | GctTaatttaatcacCtCAT | 10_58 | 12060 | A |
| 10 | gctttaatttaatcactcat | 1-1-1-1-1-1-2-1-8-4 | GctTaaTttaatcacTCAT | 10_59 | 12060 | A |
| 10 | gctttaatttaatcactcat | 1-1-1-1-1-1-1-1-9-4 | GctTaAtttaatcacTCAT | 10_60 | 12060 | A |
| 10 | gctttaatttaatcactcat | 1-1-1-1-2-9-1-2-2 | GctTAatttaatcaCtcAT | 10_61 | 12060 | A |
| 10 | gctttaatttaatcactcat | 1-1-1-1-3-11-2 | GctTAAtttaatcactcAT | 10_62 | 12060 | A |
| 10 | gctttaatttaatcactcat | 1-1-2-3-1-8-4 | GaTtaaTttaatcacTCAT | 10_63 | 12060 | A |
| 10 | gctttaatttaatcactcat | 1-1-2-2-1-11-2 | GaTtaAtttaatcactcAT | 10_64 | 12060 | A |
| 10 | gctttaatttaatcactcat | 1-1-2-2-1-9-4 | GaTtaAtttaatcacTCAT | 10_65 | 12060 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 10 | gctttaatttaatcactcat | 1-1-2-1-1-10-4 | GaTtAatttaatcacTCAT | 10_66 | 12060 | A |
| 10 | gctttaatttaatcactcat | 1-1-2-1-1-9-1-1-3 | GcTTtAatttaatcaCtCAT | 10_67 | 12060 | A |
| 10 | gctttaatttaatcactcat | 1-1-2-1-2-11-2 | GcTTAAtttaatcactcAT | 10_68 | 12060 | A |
| 10 | gctttaatttaatcactcat | 1-1-3-10-2-1-2 | GcTTTaatttaatcaCTcAT | 10_69 | 12060 | A |
| 10 | gctttaatttaatcactcat | 1-1-4-9-1-2-2 | GcTTTAatttaatcaCtcAT | 10_70 | 12060 | A |
| 10 | gctttaatttaatcactcat | 2-11-1-4-2 | GCtttaatttaatCactcAT | 10_71 | 12060 | A |
| 10 | gctttaatttaatcactcat | 2-10-2-4-2 | GCtttaatttaaTCactcAT | 10_72 | 12060 | A |
| 10 | gctttaatttaatcactcat | 2-5-1-10-2 | GCtttaaTttaatcactcAT | 10_73 | 12060 | A |
| 10 | gctttaatttaatcactcat | 2-5-1-9-3 | GCtttaaTttaatcactCAT | 10_74 | 12060 | A |
| 10 | gctttaatttaatcactcat | 2-5-1-7-1-2-2 | GCtttaaTttaatcaCtcAT | 10_75 | 12060 | A |
| 10 | gctttaatttaatcactcat | 2-4-2-10-2 | GCtttaATttaatcactcAT | 10_76 | 12060 | A |
| 10 | gctttaatttaatcactcat | 2-3-1-9-1-2-2 | GCtttAatttaatcaCtcAT | 10_77 | 12060 | A |
| 10 | gctttaatttaatcactcat | 2-3-2-11-2 | GCtttAAtttaatcactcAT | 10_78 | 12060 | A |
| 10 | gctttaatttaatcactcat | 2-2-1-10-1-2-2 | GCttTaatttaatcaCtcAT | 10_79 | 12060 | A |
| 10 | gctttaatttaatcactcat | 2-2-1-1-1-11-2 | GCttTaAtttaatcactcAT | 10_80 | 12060 | A |
| 10 | gctttaatttaatcactcat | 2-2-3-11-2 | GCttTAAtttaatcactcAT | 10_81 | 12060 | A |
| 10 | gctttaatttaatcactcat | 2-1-2-1-11-2 | GCtTtaAtttaatcactcAT | 10_82 | 12060 | A |
| 10 | gctttaatttaatcactcat | 2-1-1-1-1-9-1-2-2 | GCtTtAatttaatcaCtcAT | 10_83 | 12060 | A |
| 10 | gctttaatttaatcactcat | 2-1-1-1-2-11-2 | GCtTtAAtttaatcactcAT | 10_84 | 12060 | A |
| 10 | gctttaatttaatcactcat | 3-10-1-4-2 | GCTttaatttaatCactcAT | 10_85 | 12060 | A |
| 10 | gctttaatttaatcactcat | 3-4-1-10-2 | GCTttaaTttaatcactcAT | 10_86 | 12060 | A |
| 10 | gctttaatttaatcactcat | 3-3-1-11-2 | GCTttaAtttaatcactcAT | 10_87 | 12060 | A |
| 10 | gctttaatttaatcactcat | 3-2-2-11-2 | GCTttAAtttaatcactcAT | 10_88 | 12060 | A |
| 10 | gctttaatttaatcactcat | 3-1-1-9-1-1-1-1-2 | GCTtTaatttaatcAcTcAT | 10_89 | 12060 | A |
| 11 | ctttaatttaatcactca | 4-10-4 | CTTTaatttaatcaCTCA | 11_1 | 12061 | A |
| 12 | ctttaatttaatcactc | 4-9-4 | CTTTaatttaatcACTC | 12_1 | 12062 | A |
| 13 | tccaagtcaatgcctggctt | 3-14-3 | TCCaagtcaatgcctggCTT | 13_1 | 12076 | A |
| 14 | atccaagtcaatgcctggct | 3-14-3 | ATCcaagtcaatgcctgGCT | 14_1 | 12077 | A |
| 15 | accatccaagtcaatgcctg | 3-14-3 | ACCatccaagtcaatgcCTG | 15_1 | 12080 | A |
| 16 | caccatccaagtcaatgcct | 3-14-3 | CACcatccaagtcaatgCCT | 16_1 | 12081 | A |
| 17 | tacaccatccaagtcaatgc | 3-14-3 | TACaccatccaagtcaaTGC | 17_1 | 12083 | A |
| 18 | ttacaccatccaagtcaatg | 3-14-3 | TTAcaccatccaagtcaATG | 18_1 | 12084 | A |
| 19 | acaccatccaagtcaat | 3-10-4 | ACAccatccaagtCAAT | 19_1 | 12085 | A |
| 20 | tacaccatccaagtcaa | 3-10-4 | TACaccatccaagTCAA | 20_1 | 12086 | A |
| 21 | ttacaccatccaagtca | 4-11-2 | TTACaccatccaagtCA | 21_1 | 12087 | A |
| 22 | ttacaccatccaagtc | 4-9-3 | TTACaccatccaaGTC | 22_1 | 12088 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 23 | aatattacaccatccaa | 4-9-4 | AATAttacaccatCCAA | 23_1 | 12091 | A |
| 24 | agaatattacaccatccaa | 1-3-1-10-4 | AgaaTattacaccatCCAA | 24_1 | 12091 | A |
| 24 | agaatattacaccatccaa | 1-3-1-9-1-1-3 | AgaaTattacaccaTcCAA | 24_2 | 12091 | A |
| 24 | agaatattacaccatccaa | 1-3-1-9-2-1-2 | AgaaTattacaccaTCcAA | 24_3 | 12091 | A |
| 24 | agaatattacaccatccaa | 1-3-1-8-1-2-3 | AgaaTattacaccAtcCAA | 24_4 | 12091 | A |
| 24 | agaatattacaccatccaa | 1-3-1-8-1-1-4 | AgaaTattacaccAtCCAA | 24_5 | 12091 | A |
| 24 | agaatattacaccatccaa | 1-3-1-8-2-1-3 | AgaaTattacaccATcCAA | 24_6 | 12091 | A |
| 24 | agaatattacaccatccaa | 1-3-1-8-3-1-2 | AgaaTattacaccATCcAA | 24_7 | 12091 | A |
| 24 | agaatattacaccatccaa | 1-3-1-7-1-1-2-1-2 | AgaaTattacacCaTCcAA | 24_8 | 12091 | A |
| 24 | agaatattacaccatccaa | 1-3-1-6-1-1-1-1-1-2 | AgaaTattacaCcAtCcAA | 24_9 | 12091 | A |
| 24 | agaatattacaccatccaa | 1-3-1-6-1-1-2-1-3 | AgaaTattacaCcATcCAA | 24_10 | 12091 | A |
| 24 | agaatattacaccatccaa | 1-2-1-11-4 | AgaAtattacaccatCCAA | 24_11 | 12091 | A |
| 24 | agaatattacaccatccaa | 1-2-1-10-1-1-3 | AgaAtattacaccaTcCAA | 24_12 | 12091 | A |
| 24 | agaatattacaccatccaa | 1-2-2-11-3 | AgaATattacaccatcCAA | 24_13 | 12091 | A |
| 24 | agaatattacaccatccaa | 1-2-2-9-2-1-2 | AgaATattacaccaTCcAA | 24_14 | 12091 | A |
| 24 | agaatattacaccatccaa | 1-2-2-8-1-2-3 | AgaATattacaccAtcCAA | 24_15 | 12091 | A |
| 24 | agaatattacaccatccaa | 1-2-2-8-1-1-1-1-2 | AgaATattacaccAtCcAA | 24_16 | 12091 | A |
| 24 | agaatattacaccatccaa | 1-2-2-8-3-1-2 | AgaATattacaccATCcAA | 24_17 | 12091 | A |
| 24 | agaatattacaccatccaa | 1-2-2-7-2-1-1-1-2 | AgaATattacacCAtCcAA | 24_18 | 12091 | A |
| 24 | agaatattacaccatccaa | 1-1-1-10-1-1-4 | AgAatattacaccAtCCAA | 24_19 | 12091 | A |
| 24 | agaatattacaccatccaa | 1-1-1-10-3-1-2 | AgAatattacaccATCcAA | 24_20 | 12091 | A |
| 24 | agaatattacaccatccaa | 1-1-1-1-1-11-3 | AgAaTattacaccatcCAA | 24_21 | 12091 | A |
| 24 | agaatattacaccatccaa | 1-1-1-1-1-9-2-1-2 | AgAaTattacaccaTCcAA | 24_22 | 12091 | A |
| 24 | agaatattacaccatccaa | 1-1-1-1-1-8-1-2-3 | AgAaTattacaccAtcCAA | 24_23 | 12091 | A |
| 24 | agaatattacaccatccaa | 1-1-1-1-1-8-1-1-1-2 | AgAaTattacaccAtCcAA | 24_24 | 12091 | A |
| 24 | agaatattacaccatccaa | 1-1-1-1-1-8-3-1-2 | AgAaTattacaccATCcAA | 24_25 | 12091 | A |
| 24 | agaatattacaccatccaa | 1-1-1-1-1-7-1-3-3 | AgAaTattacacCatcCAA | 24_26 | 12091 | A |
| 24 | agaatattacaccatccaa | 1-1-1-1-1-6-1-4-3 | AgAaTattacaCcatcCAA | 24_27 | 12091 | A |
| 24 | agaatattacaccatccaa | 1-1-1-1-2-6-2-3-2 | AgAaTAttacaCCAtccAA | 24_28 | 12091 | A |
| 24 | agaatattacaccatccaa | 1-1-2-10-2-1-2 | AgAAtattaccaTCcAA | 24_29 | 12091 | A |
| 24 | agaatattacaccatccaa | 1-1-3-11-3 | AgAAtattacaccatcCAA | 24_30 | 12091 | A |
| 24 | agaatattacaccatccaa | 1-1-3-10-1-1-2 | AgAAtattacaccatCcAA | 24_31 | 12091 | A |
| 24 | agaatattacaccatccaa | 1-1-3-9-2-1-2 | AgAAtattacaccaTCcAA | 24_32 | 12091 | A |
| 24 | agaatattacaccatccaa | 1-1-3-8-1-2-3 | AgAAtattacaccAtcCAA | 24_33 | 12091 | A |
| 24 | agaatattacaccatccaa | 1-1-3-8-1-1-1-1-2 | AgAAtattacaccAtCcAA | 24_34 | 12091 | A |
| 24 | agaatattacaccatccaa | 1-1-3-7-1-1-2-1-2 | AgAAtattacacCaTCcAA | 24_35 | 12091 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 24 | agaatattacaccatccaa | 2-3-1-8-2-1-2 | AGaatAttacaccaTCcAA | 24_36 | 12091 | A |
| 24 | agaatattacaccatccaa | 2-3-1-6-1-3-3 | AGaatAttacacCatcCAA | 24_37 | 12091 | A |
| 24 | agaatattacaccatccaa | 2-2-1-11-3 | AGaaTattacaccatcCAA | 24_38 | 12091 | A |
| 24 | agaatattacaccatccaa | 2-2-1-10-1-1-2 | AGaaTattacaccatCcAA | 24_39 | 12091 | A |
| 24 | agaatattacaccatccaa | 2-2-1-9-2-1-2 | AGaaTattacaccaTCcAA | 24_40 | 12091 | A |
| 24 | agaatattacaccatccaa | 2-2-1-8-1-2-3 | AGaaTattacaccAtcCAA | 24_41 | 12091 | A |
| 24 | agaatattacaccatccaa | 2-2-1-8-1-1-1-2 | AGaaTattacaccAtCcAA | 24_42 | 12091 | A |
| 24 | agaatattacaccatccaa | 2-2-1-8-3-1-2 | AGaaTattacaccATCcAA | 24_43 | 12091 | A |
| 24 | agaatattacaccatccaa | 2-2-1-6-1-1-1-1-1-2 | AGaaTattacaCcAtCcAA | 24_44 | 12091 | A |
| 24 | agaatattacaccatccaa | 2-2-2-6-1-2-1-1-2 | AGaaTAttacacCatCcAA | 24_45 | 12091 | A |
| 24 | agaatattacaccatccaa | 2-1-1-10-2-1-2 | AGaAtattacaccaTCcAA | 24_46 | 12091 | A |
| 24 | agaatattacaccatccaa | 2-1-1-1-1-6-1-1-2-1-2 | AGaAtAttacacCaTCcAA | 24_47 | 12091 | A |
| 24 | agaatattacaccatccaa | 2-1-2-11-3 | AGaATattacaccatcCAA | 24_48 | 12091 | A |
| 24 | agaatattacaccatccaa | 2-1-2-10-1-1-2 | AGaATattacaccatCcAA | 24_49 | 12091 | A |
| 24 | agaatattacaccatccaa | 2-1-2-9-2-1-2 | AGaATattacaccaTCcAA | 24_50 | 12091 | A |
| 24 | agaatattacaccatccaa | 2-1-2-8-1-2-3 | AGaATattacaccAtcCAA | 24_51 | 12091 | A |
| 24 | agaatattacaccatccaa | 2-1-2-8-1-1-1-2 | AGaATattacaccAtCcAA | 24_52 | 12091 | A |
| 24 | agaatattacaccatccaa | 2-1-3-9-1-1-2 | AGaATtattacaccatCcAA | 24_53 | 12091 | A |
| 24 | agaatattacaccatccaa | 3-11-2-1-2 | AGAatattacaccaTCcAA | 24_54 | 12091 | A |
| 24 | agaatattacaccatccaa | 3-10-1-2-3 | AGAatattacaccAtcCAA | 24_55 | 12091 | A |
| 24 | agaatattacaccatccaa | 3-10-1-1-1-2 | AGAatattacaccAtCcAA | 24_56 | 12091 | A |
| 24 | agaatattacaccatccaa | 3-1-1-10-1-1-2 | AGAaTattacaccatCcAA | 24_57 | 12091 | A |
| 24 | agaatattacaccatccaa | 3-1-1-8-1-3-2 | AGAaTattacaccAtccAA | 24_58 | 12091 | A |
| 24 | agaatattacaccatccaa | 3-1-1-8-1-1-1-2 | AGAaTattacaccAtCcAA | 24_59 | 12091 | A |
| 24 | agaatattacaccatccaa | 4-11-1-1-2 | AGAAtattacaccatCcAA | 24_60 | 12091 | A |
| 24 | agaatattacaccatccaa | 4-8-1-4-2 | AGAAtattacacCatccAA | 24_61 | 12091 | A |
| 24 | agaatattacaccatccaa | 4-1-1-9-1-1-2 | AGAAtAttacaccatCcAA | 24_62 | 12091 | A |
| 25 | cagaatattacaccatccaa1 | 4-1-9-1-1-3 | CagaaTattacaccaTcCAA | 25_1 | 12091 | A |
| 25 | cagaatattacaccatccaa1 | 4-1-9-2-1-2 | CagaaTattacaccaTCcAA | 25_2 | 12091 | A |
| 25 | cagaatattacaccatccaa1 | 4-1-7-1-2-1-1-2 | CagaaTattacacCatCcAA | 25_3 | 12091 | A |
| 25 | cagaatattacaccatccaa1 | 4-1-6-1-1-1-1-1-2 | CagaaTattacaCcAtCcAA | 25_4 | 12091 | A |
| 25 | cagaatattacaccatccaa1 | 3-1-10-2-1-2 | CagaAtattacaccaTCcAA | 25_5 | 12091 | A |
| 25 | cagaatattacaccatccaa1 | 3-1-1-1-6-2-3-2 | CagaAtAttacacCAtccAA | 25_7 | 12091 | A |
| 25 | cagaatattacaccatccaa1 | 3-1-1-1-6-2-3-2 | CagaAtAttacacCAtccAA | 25_7 | 12091 | A |
| 25 | cagaatattacaccatccaa1 | 3-2-11-3 | CagaATattacaccatcCAA | 25_8 | 12091 | A |
| 25 | cagaatattacaccatccaa1 | 3-2-10-1-1-2 | CagaATattacaccatCcAA | 25_9 | 12091 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 25 | cagaatattacaccatccaa | 1-3-2-9-2-1-2 | CagaATattacaccaTCcAA | 25_10 | 12091 | A |
| 25 | cagaatattacaccatccaa | 1-3-2-8-1-1-1-2 | CagaATattacaccAtCcAA | 25_11 | 12091 | A |
| 25 | cagaatattacaccatccaa | 1-2-1-11-2-1-2 | CagAatattacaccaTCcAA | 25_12 | 12091 | A |
| 25 | cagaatattacaccatccaa | 1-2-1-10-1-2-3 | CagAatattacaccAtcCAA | 25_13 | 12091 | A |
| 25 | cagaatattacaccatccaa | 1-2-1-2-1-6-1-1-2-1-2 | CagAatAttacacCaTCcAA | 25_14 | 12091 | A |
| 25 | cagaatattacaccatccaa | 1-2-1-1-1-11-3 | CagAaTattacaccatcCAA | 25_15 | 12091 | A |
| 25 | cagaatattacaccatccaa | 1-2-1-1-1-9-2-1-2 | CagAaTattacaccaTCcAA | 25_16 | 12091 | A |
| 25 | cagaatattacaccatccaa | 1-2-1-1-1-8-1-2-3 | CagAaTattacaccAtcCAA | 25_17 | 12091 | A |
| 25 | cagaatattacaccatccaa | 1-2-1-1-1-8-1-1-1-2 | CagAaTattacaccAtCcAA | 25_18 | 12091 | A |
| 25 | cagaatattacaccatccaa | 1-2-1-1-1-7-1-1-2-1-2 | CagAaTattacacCaTCcAA | 25_19 | 12091 | A |
| 25 | cagaatattacaccatccaa | 1-2-1-1-2-6-1-2-1-1-2 | CagAaTAttacacCatCcAA | 25_20 | 12091 | A |
| 25 | cagaatattacaccatccaa | 1-2-2-8-2-3-2 | CagAAtattacacCAtccAA | 25_21 | 12091 | A |
| 25 | cagaatattacaccatccaa | 1-2-2-8-2-1-1-2 | CagAAtattacacCAtCcAA | 25_22 | 12091 | A |
| 25 | cagaatattacaccatccaa | 1-1-1-2-1-11-3 | CaGaaTattacaccatcCAA | 25_23 | 12091 | A |
| 25 | cagaatattacaccatccaa | 1-1-1-2-1-10-1-1-2 | CaGaaTattacaccatCcAA | 25_24 | 12091 | A |
| 25 | cagaatattacaccatccaa | 1-1-1-2-1-9-2-1-2 | CaGaaTattacaccaTCcAA | 25_25 | 12091 | A |
| 25 | cagaatattacaccatccaa | 1-1-1-2-1-8-1-2-3 | CaGaaTattacaccAtcCAA | 25_26 | 12091 | A |
| 25 | cagaatattacaccatccaa | 1-1-1-2-1-8-1-1-1-2 | CaGaaTattacaccAtCcAA | 25_27 | 12091 | A |
| 25 | cagaatattacaccatccaa | 1-1-1-2-1-6-1-5-2 | CaGaaTattacaCcatccAA | 25_28 | 12091 | A |
| 25 | cagaatattacaccatccaa | 1-1-1-1-1-11-1-1-2 | CaGAatattacaccatCcAA | 25_29 | 12091 | A |
| 25 | cagaatattacaccatccaa | 1-1-1-1-1-10-2-1-2 | CaGaAtattacaccaTCcAA | 25_30 | 12091 | A |
| 25 | cagaatattacaccatccaa | 1-1-1-1-1-1-9-1-1-2 | CaGaAtAttacaccatCcAA | 25_31 | 12091 | A |
| 25 | cagaatattacaccatccaa | 1-1-1-1-1-1-6-2-3-2 | CaGaAtAttacacCAtccAA | 25_32 | 12091 | A |
| 25 | cagaatattacaccatccaa | 1-1-2-10-1-1-1-2 | CaGAatattacaccAtCcAA | 25_33 | 12091 | A |
| 25 | cagaatattacaccatccaa | 1-1-2-8-1-1-1-3-2 | CaGAatattacaCcAtccAA | 25_34 | 12091 | A |
| 25 | cagaatattacaccatccaa | 2-3-1-10-1-1-2 | CAgaaTattacaccatCcAA | 25_35 | 12091 | A |
| 25 | cagaatattacaccatccaa | 2-3-1-8-1-3-2 | CAgaaTattacaccAtccAA | 25_36 | 12091 | A |
| 25 | cagaatattacaccatccaa | 2-3-1-8-1-1-1-2 | CAgaaTattacaccAtCcAA | 25_37 | 12091 | A |
| 25 | cagaatattacaccatccaa | 2-2-1-11-1-1-2 | CAgAatattacaccatCcAA | 25_38 | 12091 | A |
| 25 | cagaatattacaccatccaa | 2-1-1-10-1-3-2 | CAgAatattacaccAtccAA | 25_39 | 12091 | A |
| 25 | cagaatattacaccatccaa | 2-1-1-10-1-1-1-2 | CAgAatattacaccAtCcAA | 25_40 | 12091 | A |
| 25 | cagaatattacaccatccaa | 2-1-1-1-1-8-1-3-2 | CAgAaTattacaccAtccAA | 25_41 | 12091 | A |
| 25 | cagaatattacaccatccaa | 2-1-1-1-1-7-1-4-2 | CAgAaTattacacCatccAA | 25_42 | 12091 | A |
| 25 | cagaatattacaccatccaa | 2-1-2-11-1-1-2 | CAgAAtattacaccatCcAA | 25_43 | 12091 | A |
| 26 | gaatattacaccatccaa | 1-10-2-1-4 | GaatattacacCAtCCAA | 26_1 | 12091 | A |
| 26 | gaatattacaccatccaa | 1-10-3-1-3 | GaatattacacCATcCAA | 26_2 | 12091 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 26 | gaatattacaccatccaa | 1-10-4-1-2 | GaatattacacCATCcAA | 26_3 | 12091 | A |
| 26 | gaatattacaccatccaa | 1-3-1-9-4 | GaatAttacaccatCCAA | 26_4 | 12091 | A |
| 26 | gaatattacaccatccaa | 1-2-1-10-4 | GaaTattacaccatCCAA | 26_5 | 12091 | A |
| 26 | gaatattacaccatccaa | 1-2-1-8-1-1-4 | GaaTattacaccAtCCAA | 26_6 | 12091 | A |
| 26 | gaatattacaccatccaa | 1-2-2-6-2-1-1-1-2 | GaaTAttacacCAtCcAA | 26_7 | 12091 | A |
| 26 | gaatattacaccatccaa | 1-1-1-11-4 | GaAtattacaccatCCAA | 26_8 | 12091 | A |
| 26 | gaatattacaccatccaa | 1-1-1-1-1-9-4 | GaAtAttacaccatCCAA | 26_9 | 12091 | A |
| 26 | gaatattacaccatccaa | 1-1-1-1-1-6-4-1-2 | GaAtAttacacCATCcAA | 26_10 | 12091 | A |
| 26 | gaatattacaccatccaa | 1-1-2-10-4 | GaATattacaccatCCAA | 26_11 | 12091 | A |
| 26 | gaatattacaccatccaa | 1-1-2-9-2-1-2 | GaATattacaccaTCcAA | 26_12 | 12091 | A |
| 26 | gaatattacaccatccaa | 1-1-2-8-1-1-4 | GaATattacaccAtCCAA | 26_13 | 12091 | A |
| 26 | gaatattacaccatccaa | 1-1-2-8-3-1-2 | GaATattacaccATCcAA | 26_14 | 12091 | A |
| 26 | gaatattacaccatccaa | 1-1-2-7-2-2-3 | GaATattacacCAtcCAA | 26_15 | 12091 | A |
| 26 | gaatattacaccatccaa | 2-10-1-1-4 | GAatattacaccAtCCAA | 26_16 | 12091 | A |
| 26 | gaatattacaccatccaa | 2-10-3-1-2 | GAatattacaccATCcAA | 26_17 | 12091 | A |
| 26 | gaatattacaccatccaa | 2-9-4-1-2 | GAatattacacCATCcAA | 26_18 | 12091 | A |
| 26 | gaatattacaccatccaa | 2-2-1-6-4-1-2 | GAatAttacacCATCcAA | 26_19 | 12091 | A |
| 26 | gaatattacaccatccaa | 2-1-1-11-3 | GAaTattacaccatcCAA | 26_20 | 12091 | A |
| 26 | gaatattacaccatccaa | 2-1-1-9-2-1-2 | GAaTattacaccaTCcAA | 26_21 | 12091 | A |
| 26 | gaatattacaccatccaa | 2-1-1-8-1-2-3 | GAaTattacaccAtcCAA | 26_22 | 12091 | A |
| 26 | gaatattacaccatccaa | 2-1-1-8-3-1-2 | GAaTattacaccATCcAA | 26_23 | 12091 | A |
| 26 | gaatattacaccatccaa | 2-1-1-7-1-3-3 | GAaTattacacCatcCAA | 26_24 | 12091 | A |
| 26 | gaatattacaccatccaa | 2-1-1-7-2-3-2 | GAaTattacacCAtccAA | 26_25 | 12091 | A |
| 26 | gaatattacaccatccaa | 3-11-4 | GAAtattacaccatCCAA | 26_26 | 12091 | A |
| 26 | gaatattacaccatccaa | 3-10-2-1-2 | GAAtattacaccaTCcAA | 26_27 | 12091 | A |
| 26 | gaatattacaccatccaa | 3-8-2-1-1-1-2 | GAAtattacacCAtCcAA | 26_28 | 12091 | A |
| 26 | gaatattacaccatccaa | 4-11-3 | GAATattacaccatcCAA | 26_29 | 12091 | A |
| 26 | gaatattacaccatccaa | 4-8-1-2-3 | GAATattacaccAtcCAA | 26_30 | 12091 | A |
| 26 | gaatattacaccatccaa | 4-7-1-1-2-1-2 | GAATattacacCaTCcAA | 26_31 | 12091 | A |
| 27 | aatattacaccatcca | 4-8-4 | AATAttacaccaTCCA | 27_1 | 12092 | A |
| 28 | agaatattacaccatcca | 1-3-1-10-3 | AgaaTattacaccatCCA | 28_1 | 12092 | A |
| 28 | agaatattacaccatcca | 1-3-1-9-1-1-2 | AgaaTattacaccaTcCA | 28_2 | 12092 | A |
| 28 | agaatattacaccatcca | 1-3-1-8-1-1-3 | AgaaTattacaccAtCCA | 28_3 | 12092 | A |
| 28 | agaatattacaccatcca | 1-3-1-8-2-1-2 | AgaaTattacaccATcCA | 28_4 | 12092 | A |
| 28 | agaatattacaccatcca | 1-2-1-11-3 | AgaAtattacaccatCCA | 28_5 | 12092 | A |
| 28 | agaatattacaccatcca | 1-2-1-10-4 | AgaAtattacaccaTCCA | 28_6 | 12092 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 28 | agaatattacaccatcca | 1-2-1-1-1-8-1-1-2 | AgaAtAttacaccaTcCA | 28_7 | 12092 | A |
| 28 | agaatattacaccatcca | 1-2-1-1-1-6-1-3-2 | AgaAtAttacacCatcCA | 28_8 | 12092 | A |
| 28 | agaatattacaccatcca | 1-2-2-11-2 | AgaATattacaccatcCA | 28_9 | 12092 | A |
| 28 | agaatattacaccatcca | 1-2-2-8-1-2-2 | AgaATattacaccAtcCA | 28_10 | 12092 | A |
| 28 | agaatattacaccatcca | 1-1-1-11-4 | AgAatattacaccaTCCA | 28_11 | 12092 | A |
| 28 | agaatattacaccatcca | 1-1-1-10-1-1-3 | AgAatattacaccAtCCA | 28_12 | 12092 | A |
| 28 | agaatattacaccatcca | 1-1-1-9-2-2-2 | AgAatattacacCAtcCA | 28_13 | 12092 | A |
| 28 | agaatattacaccatcca | 1-1-1-2-1-6-1-3-2 | AgAatAttacacCatcCA | 28_14 | 12092 | A |
| 28 | agaatattacaccatcca | 1-1-1-2-1-6-1-2-3 | AgAatAttacacCatCCA | 28_15 | 12092 | A |
| 28 | agaatattacaccatcca | 1-1-1-1-1-11-2 | AgAaTattacaccatcCA | 28_16 | 12092 | A |
| 28 | agaatattacaccatcca | 1-1-1-1-1-10-3 | AgAaTattacaccatCCA | 28_17 | 12092 | A |
| 28 | agaatattacaccatcca | 1-1-1-1-1-8-1-2-2 | AgAaTattacaccAtcCA | 28_18 | 12092 | A |
| 28 | agaatattacaccatcca | 1-1-1-1-1-8-1-1-3 | AgAaTattacaccAtCCA | 28_19 | 12092 | A |
| 28 | agaatattacaccatcca | 1-1-1-1-1-7-1-3-2 | AgAaTattacacCatcCA | 28_20 | 12092 | A |
| 28 | agaatattacaccatcca | 1-1-1-1-1-6-1-4-2 | AgAaTattacaCcatcCA | 28_21 | 12092 | A |
| 28 | agaatattacaccatcca | 1-1-1-1-2-6-1-3-2 | AgAaTAttacacCatcCA | 28_22 | 12092 | A |
| 28 | agaatattacaccatcca | 1-1-2-11-3 | AgAAtattacaccatCCA | 28_23 | 12092 | A |
| 28 | agaatattacaccatcca | 1-1-3-11-2 | AgAATattacaccatcCA | 28_24 | 12092 | A |
| 28 | agaatattacaccatcca | 1-1-3-8-1-2-2 | AgAATattacaccAtcCA | 28_25 | 12092 | A |
| 28 | agaatattacaccatcca | 2-2-1-11-2 | AGaaTattacaccatcCA | 28_26 | 12092 | A |
| 28 | agaatattacaccatcca | 2-2-1-8-1-2-2 | AGaaTattacaccAtcCA | 28_27 | 12092 | A |
| 28 | agaatattacaccatcca | 2-1-1-11-3 | AGaAtattacaccatCCA | 28_28 | 12092 | A |
| 28 | agaatattacaccatcca | 1-2-11-2 | AGaATattacaccatcCA | 28_29 | 12092 | A |
| 28 | agaatattacaccatcca | 2-1-2-8-1-2-2 | AGaATattacaccAtcCA | 28_30 | 12092 | A |
| 28 | agaatattacaccatcca | 3-10-1-2-2 | AGAatattacaccAtcCA | 28_31 | 12092 | A |
| 28 | agaatattacaccatcca | 3-1-1-11-2 | AGAaTattacaccatcCA | 28_32 | 12092 | A |
| 28 | agaatattacaccatcca | 3-1-1-8-1-2-2 | AGAaTattacaccAtcCA | 28_33 | 12092 | A |
| 29 | cagaatattacaccatcca | 1-4-1-9-1-1-2 | CagaaTattacaccaTcCA | 29_1 | 12092 | A |
| 29 | cagaatattacaccatcca | 1-3-1-11-3 | CagaAtattacaccatCCA | 29_2 | 12092 | A |
| 29 | cagaatattacaccatcca | 1-3-1-7-1-4-2 | CagaAtattacaCcatcCA | 29_3 | 12092 | A |
| 29 | cagaatattacaccatcca | 1-3-2-11-2 | CagaATattacaccatcCA | 29_4 | 12092 | A |
| 29 | cagaatattacaccatcca | 1-3-2-8-1-2-2 | CagaATattacaccAtcCA | 29_5 | 12092 | A |
| 29 | cagaatattacaccatcca | 1-3-2-7-1-3-2 | CagaATattacacCatcCA | 29_6 | 12092 | A |
| 29 | cagaatattacaccatcca | 1-2-1-1-1-11-2 | CagAaTattacaccatcCA | 29_7 | 12092 | A |
| 29 | cagaatattacaccatcca | 1-2-1-1-1-8-1-2-2 | CagAaTattacaccAtcCA | 29_8 | 12092 | A |
| 29 | cagaatattacaccatcca | 1-2-3-11-2 | CagAATattacaccatcCA | 29_9 | 12092 | A |

TABLE 5-continued list of oligonucleotide motif sequences (indicated by SEQ ID NO), designs of
these, as well as specific oligonucleotide compounds (indicated by CMP ID NO) designed
based on the motif sequence.

| SEQ ID NO | motif sequence | Design | Oligonucleotide Compound | CMP ID NO | Start on SEQ ID NO: 1 | Region |
|---|---|---|---|---|---|---|
| 29 | cagaatattacaccatcca | 1-1-1-2-1-11-2 | CaGaaTattacaccatcCA | 29_10 | 12092 | A |
| 29 | cagaatattacaccatcca | 1-1-1-2-1-8-1-2-2 | CaGaaTattacaccAtcCA | 29_11 | 12092 | A |
| 29 | cagaatattacaccatcca | 1-1-2-10-1-2-2 | CaGAatattacaccAtcCA | 29_12 | 12092 | A |
| 29 | cagaatattacaccatcca | 2-1-1-10-1-2-2 | CAgAatattacaccAtcCA | 29_13 | 12092 | A |
| 29 | cagaatattacaccatcca | 2-1-1-7-1-2-1-2-2 | CAgAatattacAccAtcCA | 29_14 | 12092 | A |
| 30 | gaatattacaccatcca | 1-10-2-1-3 | GaatattacacCAtCCA | 30_1 | 12092 | A |
| 30 | gaatattacaccatcca | 1-3-1-8-4 | GaatAttacaccaTCCA | 30_2 | 12092 | A |
| 30 | gaatattacaccatcca | 1-2-1-10-3 | GaaTattacaccatCCA | 30_3 | 12092 | A |
| 30 | gaatattacaccatcca | 1-2-1-8-1-1-3 | GaaTattacaccAtCCA | 30_4 | 12092 | A |
| 30 | gaatattacaccatcca | 1-1-1-11-3 | GaAtattacaccatCCA | 30_5 | 12092 | A |
| 30 | gaatattacaccatcca | 1-1-1-10-4 | GaAtattacaccaTCCA | 30_6 | 12092 | A |
| 30 | gaatattacaccatcca | 1-1-1-8-2-1-3 | GaAtattacacCAtCCA | 30_7 | 12092 | A |
| 30 | gaatattacaccatcca | 1-1-1-7-2-3-2 | GaAtattacaCCatcCA | 30_8 | 12092 | A |
| 30 | gaatattacaccatcca | 1-1-1-1-1-6-3-1-2 | GaAtAttacacCATcCA | 30_9 | 12092 | A |
| 30 | gaatattacaccatcca | 1-1-2-10-3 | GaATattacaccatCCA | 30_10 | 12092 | A |
| 30 | gaatattacaccatcca | 1-1-2-8-1-1-3 | GaATattacaccAtCCA | 30_11 | 12092 | A |
| 30 | gaatattacaccatcca | 2-11-4 | GAatattacaccaTCCA | 30_12 | 12092 | A |
| 30 | gaatattacaccatcca | 2-10-1-1-3 | GAatattacaccAtCCA | 30_13 | 12092 | A |
| 30 | gaatattacaccatcca | 2-2-1-9-3 | GAatAttacaccatCCA | 30_14 | 12092 | A |
| 30 | gaatattacaccatcca | 2-2-1-6-1-3-2 | GAatAttacacCatcCA | 30_15 | 12092 | A |
| 30 | gaatattacaccatcca | 2-1-1-11-2 | GAaTattacaccatcCA | 30_16 | 12092 | A |
| 30 | gaatattacaccatcca | 2-1-1-10-3 | GAaTattacaccatCCA | 30_17 | 12092 | A |
| 30 | gaatattacaccatcca | 2-1-1-8-1-2-2 | GAaTattacaccAtcCA | 30_18 | 12092 | A |
| 30 | gaatattacaccatcca | 2-1-1-8-1-1-3 | GAaTattacaccAtCCA | 30_19 | 12092 | A |
| 30 | gaatattacaccatcca | 2-1-1-7-2-2-2 | GAaTattacaCAtcCA | 30_20 | 12092 | A |
| 30 | gaatattacaccatcca | 2-1-1-6-1-4-2 | GAaTattacaCcatcCA | 30_21 | 12092 | A |
| 30 | gaatattacaccatcca | 3-11-3 | GAAtattacaccatCCA | 30_22 | 12092 | A |
| 30 | gaatattacaccatcca | 3-8-1-3-2 | GAAtattacaCCatcCA | 30_23 | 12092 | A |
| 30 | gaatattacaccatcca | 4-11-2 | GAATattacaccatcCA | 30_24 | 12092 | A |
| 30 | gaatattacaccatcca | 4-8-1-2-2 | GAATattacaccAtcCA | 30_25 | 12092 | A |
| 31 | tcagaatattacaccatcca | 1-1-1-3-1-11-2 | TcAgaaTattacaccatcCA | 31_1 | 12092 | A |
| 31 | tcagaatattacaccatcca | 1-1-1-3-1-8-1-2-2 | TcAgaaTattacaccAtcCA | 31_2 | 12092 | A |
| 31 | tcagaatattacaccatcca | 1-1-1-2-1-10-1-1-2 | TcAgaAtattacaccaTcCA | 31_3 | 12092 | A |
| 32 | agaatattacaccatcc | 1-3-1-9-3 | AgaaTattacaccaTCC | 32_1 | 12093 | A |
| 32 | agaatattacaccatcc | 1-3-1-8-4 | AgaaTattacaccATCC | 32_2 | 12093 | A |
| 32 | agaatattacaccatcc | 1-3-2-6-1-2-2 | AgaaTAttacacCatCC | 32_3 | 12093 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 32 | agaatattacaccatcc | 1-2-1-10-3 | AgaAtattacaccaTCC | 32_4 | 12093 | A |
| 32 | agaatattacaccatcc | 1-2-1-6-2-1-1-2 | AgaAtattacACcAtCC | 32_5 | 12093 | A |
| 32 | agaatattacaccatcc | 1-2-1-1-1-6-1-2-2 | AgaAtAttacacCatCC | 32_6 | 12093 | A |
| 32 | agaatattacaccatcc | 1-2-2-9-3 | AgaATattacaccaTCC | 32_7 | 12093 | A |
| 32 | agaatattacaccatcc | 1-2-2-8-1-1-2 | AgaATattacaccAtCC | 32_8 | 12093 | A |
| 32 | agaatattacaccatcc | 1-2-2-8-4 | AgaATattacaccATCC | 32_9 | 12093 | A |
| 32 | agaatattacaccatcc | 1-1-1-11-3 | AgAatattacaccaTCC | 32_10 | 12093 | A |
| 32 | agaatattacaccatcc | 1-1-1-10-4 | AgAatattacaccATCC | 32_11 | 12093 | A |
| 32 | agaatattacaccatcc | 1-1-1-8-1-1-1-2 | AgAatattacaCcAtCC | 32_12 | 12093 | A |
| 32 | agaatattacaccatcc | 1-1-1-8-1-1-4 | AgAatattacaCcATCC | 32_13 | 12093 | A |
| 32 | agaatattacaccatcc | 1-1-1-7-1-3-3 | AgAatattacAccaTCC | 32_14 | 12093 | A |
| 32 | agaatattacaccatcc | 1-1-1-7-2-3-2 | AgAatattacACcatCC | 32_15 | 12093 | A |
| 32 | agaatattacaccatcc | 1-1-1-7-3-2-2 | AgAatattacACCatCC | 32_16 | 12093 | A |
| 32 | agaatattacaccatcc | 1-1-1-1-1-9-3 | AgAaTattacaccaTCC | 32_17 | 12093 | A |
| 32 | agaatattacaccatcc | 1-1-1-1-1-8-1-1-2 | AgAaTattacaccAtCC | 32_18 | 12093 | A |
| 32 | agaatattacaccatcc | 1-1-1-1-1-8-4 | AgAaTattacaccATCC | 32_19 | 12093 | A |
| 32 | agaatattacaccatcc | 1-1-1-1-1-7-1-2-2 | AgAaTattacacCatCC | 32_20 | 12093 | A |
| 32 | agaatattacaccatcc | 1-1-1-1-1-6-1-1-1-2 | AgAaTattacaCcAtCC | 32_21 | 12093 | A |
| 32 | agaatattacaccatcc | 1-1-2-10-3 | AgAAtattacaccaTCC | 32_22 | 12093 | A |
| 32 | agaatattacaccatcc | 1-1-2-7-2-2-2 | AgAAtattacaCCatCC | 32_23 | 12093 | A |
| 32 | agaatattacaccatcc | 1-1-2-6-1-1-2-1-2 | AgAAtattacAcCAtCC | 32_24 | 12093 | A |
| 32 | agaatattacaccatcc | 1-1-3-10-2 | AgAATattacaccatCC | 32_25 | 12093 | A |
| 32 | agaatattacaccatcc | 1-1-3-9-3 | AgAATattacaccaTCC | 32_26 | 12093 | A |
| 32 | agaatattacaccatcc | 1-1-3-8-1-1-2 | AgAATattacaccAtCC | 32_27 | 12093 | A |
| 32 | agaatattacaccatcc | 1-1-3-8-4 | AgAATattacaccATCC | 32_28 | 12093 | A |
| 32 | agaatattacaccatcc | 1-1-3-6-1-1-1-2 | AgAATattacaCcAtCC | 32_29 | 12093 | A |
| 32 | agaatattacaccatcc | 2-2-1-10-2 | AGaaTattacaccatCC | 32_30 | 12093 | A |
| 32 | agaatattacaccatcc | 2-2-1-9-3 | AGaaTattacaccaTCC | 32_31 | 12093 | A |
| 32 | agaatattacaccatcc | 2-2-1-8-1-1-2 | AGaaTattacaccAtCC | 32_32 | 12093 | A |
| 32 | agaatattacaccatcc | 2-2-1-8-4 | AGaaTattacaccATCC | 32_33 | 12093 | A |
| 32 | agaatattacaccatcc | 2-1-1-11-2 | AGaAtattacaccatCC | 32_34 | 12093 | A |
| 32 | agaatattacaccatcc | 2-1-1-10-3 | AGaAtattacaccaTCC | 32_35 | 12093 | A |
| 32 | agaatattacaccatcc | 2-1-1-8-1-1-3 | AGaAtattacacCaTCC | 32_36 | 12093 | A |
| 32 | agaatattacaccatcc | 2-1-1-6-1-2-4 | AGaAtattacAccATCC | 32_37 | 12093 | A |
| 32 | agaatattacaccatcc | 2-1-2-10-2 | AGaATattacaccatCC | 32_38 | 12093 | A |
| 32 | agaatattacaccatcc | 2-1-2-8-1-1-2 | AGaATattacaccAtCC | 32_39 | 12093 | A |

TABLE 5-continued list of oligonucleotide motif sequences (indicated by SEQ ID NO), designs of
these, as well as specific oligonucleotide compounds (indicated by CMP ID NO) designed
based on the motif sequence.

| SEQ ID NO | motif sequence | Design | Oligonucleotide Compound | CMP ID NO | Start on SEQ ID NO: 1 | Region |
|---|---|---|---|---|---|---|
| 32 | agaatattacaccatcc | 3-11-3 | AGAatattacaccaTCC | 32_40 | 12093 | A |
| 32 | agaatattacaccatcc | 3-10-1-1-2 | AGAatattacaccAtCC | 32_41 | 12093 | A |
| 32 | agaatattacaccatcc | 3-7-1-3-3 | AGAatattacAccaTCC | 32_42 | 12093 | A |
| 32 | agaatattacaccatcc | 3-7-1-2-1-1-2 | AGAatattacAccAtCC | 32_43 | 12093 | A |
| 32 | agaatattacaccatcc | 3-7-1-1-1-2-2 | AGAatattacAcCatCC | 32_44 | 12093 | A |
| 32 | agaatattacaccatcc | 3-2-1-9-2 | AGAatAttacaccatCC | 32_45 | 12093 | A |
| 32 | agaatattacaccatcc | 3-1-1-10-2 | GAaTattacaccatCC | 32_46 | 12093 | A |
| 32 | agaatattacaccatcc | 3-1-1-8-1-1-2 | AGAaTattacaccAtCC | 32_47 | 12093 | A |
| 32 | agaatattacaccatcc | 4-11-2 | AGAAtattacaccatCC | 32_48 | 12093 | A |
| 32 | agaatattacaccatcc | 4-10-3 | AGAAtattacaccaTCC | 32_49 | 12093 | A |
| 32 | agaatattacaccatcc | 4-8-1-2-2 | AGAAtattacacCatCC | 32_50 | 12093 | A |
| 32 | agaatattacaccatcc | 4-6-1-1-1-2-2 | AGAAtattacAcCatCC | 32_51 | 12093 | A |
| 33 | cagaatattacaccatcc | 1-4-1-9-3 | CagaaTattacaccaTCC | 33_1 | 12093 | A |
| 33 | cagaatattacaccatcc | 1-3-1-10-3 | CagaAtattacaccaTCC | 33_2 | 12093 | A |
| 33 | cagaatattacaccatcc | 1-3-1-7-1-2-3 | CagaAtattacaCcaTCC | 33_3 | 12093 | A |
| 33 | cagaatattacaccatcc | 1-3-1-6-1-3-3 | CagaAtattacAccaTCC | 33_4 | 12093 | A |
| 33 | cagaatattacaccatcc | 1-3-1-6-2-3-2 | CagaAtattacACcatCC | 33_5 | 12093 | A |
| 33 | cagaatattacaccatcc | 1-3-2-10-2 | CagaATattacaccatCC | 33_6 | 12093 | A |
| 33 | cagaatattacaccatcc | 1-3-2-9-3 | CagaATattacaccaTCC | 33_7 | 12093 | A |
| 33 | cagaatattacaccatcc | 1-3-2-8-1-1-2 | CagaATattacaccAtCC | 33_8 | 12093 | A |
| 33 | cagaatattacaccatcc | 1-2-1-11-3 | CagAatattacaccaTCC | 33_9 | 12093 | A |
| 33 | cagaatattacaccatcc | 1-2-1-2-1-8-3 | CagAatAttacaccaTCC | 33_10 | 12093 | A |
| 33 | cagaatattacaccatcc | 1-2-1-1-1-9-3 | CagAaTattacaccaTCC | 33_11 | 12093 | A |
| 33 | cagaatattacaccatcc | 1-2-2-10-3 | CagAAtattacaccaTCC | 33_12 | 12093 | A |
| 33 | cagaatattacaccatcc | 1-2-2-8-1-1-3 | CagAAtattacacCaTCC | 33_13 | 12093 | A |
| 33 | cagaatattacaccatcc | 1-2-3-6-1-3-2 | CagAATattacaCcatCC | 33_14 | 12093 | A |
| 33 | cagaatattacaccatcc | 1-1-1-3-1-6-2-1-2 | CaGaatAttacacCAtCC | 33_15 | 12093 | A |
| 33 | cagaatattacaccatcc | 1-1-1-2-1-8-1-1-2 | CaGaaTattacaccAtCC | 33_16 | 12093 | A |
| 33 | cagaatattacaccatcc | 1-1-1-1-1-11-2 | CaGaAtattacaccatCC | 33_17 | 12093 | A |
| 33 | cagaatattacaccatcc | 1-1-1-1-1-10-3 | CaGaAtattacaccaTCC | 33_18 | 12093 | A |
| 33 | cagaatattacaccatcc | 1-1-1-1-1-7-1-3-2 | CaGaAtattacaCcatCC | 33_19 | 12093 | A |
| 33 | cagaatattacaccatcc | 1-1-1-1-1-6-2-1-1-2 | CaGaAtattacACcAtCC | 33_20 | 12093 | A |
| 33 | cagaatattacaccatcc | 1-1-2-10-1-1-2 | CaGAatattacaccAtCC | 33_21 | 12093 | A |
| 33 | cagaatattacaccatcc | 2-3-1-10-2 | CAgaaTattacaccatCC | 33_22 | 12093 | A |
| 33 | cagaatattacaccatcc | 2-3-1-8-1-1-2 | CAgaaTattacaccAtCC | 33_23 | 12093 | A |
| 33 | cagaatattacaccatcc | 2-2-1-11-2 | CAgaAtattacaccatCC | 33_24 | 12093 | A |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 33 | cagaatattacaccatcc | 2-2-1-10-3 | CAgaAtattacaccaTCC | 33_25 | 12093 | A |
| 33 | cagaatattacaccatcc | 2-2-1-1-1-6-1-2-2 | CAgaAtAttacacCatCC | 33_26 | 12093 | A |
| 33 | cagaatattacaccatcc | 2-1-1-11-3 | CAgAatattacaccaTCC | 33_27 | 12093 | A |
| 33 | cagaatattacaccatcc | 2-1-1-10-1-1-2 | CAgAatattacaccAtCC | 33_28 | 12093 | A |
| 33 | cagaatattacaccatcc | 2-1-1-1-1-10-2 | CAgAaTattacaccatCC | 33_29 | 12093 | A |
| 33 | cagaatattacaccatcc | 2-1-1-1-1-8-1-1-2 | CAgAaTattacaccAtCC | 33_30 | 12093 | A |
| 33 | cagaatattacaccatcc | 2-1-2-11-2 | CAgAAtattacaccatCC | 33_31 | 12093 | A |
| 33 | cagaatattacaccatcc | 2-1-2-6-1-4-2 | CAgAAtattacAccatCC | 33_32 | 12093 | A |
| 33 | cagaatattacaccatcc | 3-1-1-11-2 | CAGAatattacaccatCC | 33_33 | 12093 | A |
| 34 | gaatattacaccatcc | 4-8-4 | GAATattacaccATCC | 34_1 | 12093 | A |
| 35 | tcagaatattacaccatcc | 2-4-1-10-2 | TCagaaTattacaccatCC | 35_1 | 12093 | A |
| 35 | tcagaatattacaccatcc | 2-3-1-11-2 | TCagaAtattacaccatCC | 35_2 | 12093 | A |
| 35 | tcagaatattacaccatcc | 2-3-1-6-1-4-2 | TCagaAtattacAccatCC | 35_3 | 12093 | A |
| 36 | agaatattacaccatc | 4-8-4 | AGAAtattacacCATC | 36_1 | 12094 | A |
| 37 | cagaatattacaccat | 4-8-4 | CAGAatattacaCCAT | 37_1 | 12095 | A |
| 38 | caattctcatttcaaccttc | 2-14-4 | CAattctcatttcaacCTTC | 38_1 | 39562 | B |
| 39 | tcaattctcatttcaacctt | 2-15-3 | TCaattctcatttcaacCTT | 39_1 | 39563 | B |
| 40 | atcaattctcatttcaacct | 3-15-2 | ATCaattctcatttcaacCT | 40_1 | 39564 | B |
| 41 | aatcaattctcatttcaacc | 4-13-3 | AATCaattctcatttcaACC | 41_1 | 39565 | B |
| 42 | aaatcaattctcatttcaac | 4-12-4 | AAATcaattctcatttCAAC | 42_1 | 39566 | B |
| 43 | caaatcaattctcatttcaa | 4-12-4 | CAAAtcaattctcattTCAA | 43_1 | 39567 | B |
| 44 | tcaaatcaattctcatttca | 3-13-4 | TCAaatcaattctcatTTCA | 44_1 | 39568 | B |
| 45 | ctcaaatcaattctcatttc | 4-13-3 | CTCAaatcaattctcatTTC | 45_1 | 39569 | B |
| 46 | actcaaatcaattctcattt | 4-12-4 | ACTCaaatcaattctcATTT | 46_1 | 39570 | B |
| 47 | aactcaaatcaattctcatt | 4-12-4 | AACTcaaatcaattctCATT | 47_1 | 39571 | B |
| 48 | taactcaaatcaattctcat | 4-12-4 | TAACtcaaatcaattcTCAT | 48_1 | 39572 | B |
| 49 | ttaactcaaatcaattctca | 1-5-1-10-3 | TtaactCaaatcaattcTCA | 49_1 | 39573 | B |
| 49 | ttaactcaaatcaattctca | 1-5-2-10-2 | TtaactCAaatcaattctCA | 49_2 | 39573 | B |
| 49 | ttaactcaaatcaattctca | 1-5-2-9-3 | TtaactCAaatcaattcTCA | 49_3 | 39573 | B |
| 49 | ttaactcaaatcaattctca | 1-4-2-11-2 | TtaacTCaaatcaattctCA | 49_4 | 39573 | B |
| 49 | ttaactcaaatcaattctca | 1-4-3-10-2 | TtaacTCAaatcaattctCA | 49_5 | 39573 | B |
| 49 | taactcaaatcaattctca | 1-3-1-11-1-1-2 | TtaaCtcaaatcaattCtCA | 49_6 | 39573 | B |
| 49 | ttaactcaaatcaattctca | 1-3-1-11-4 | TtaaCtcaaatcaattCTCA | 49_7 | 39573 | B |
| 49 | ttaactcaaatcaattctca | 1-3-1-10-2-1-2 | TtaaCtcaaatcaatTCtCA | 49_8 | 39573 | B |
| 49 | ttaactcaaatcaattctca | 1-3-1-9-1-3-2 | TtaaCtcaaatcaaTtctCA | 49_9 | 39573 | B |
| 49 | ttaactcaaatcaattctca | 1-3-1-9-1-2-3 | TtaaCtcaaatcaaTtcTCA | 49_10 | 39573 | B |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-3-1-9-1-1-1-2 | TtaaCtcaaatcaaTtCtCA | 49_11 | 39573 | B |
| 49 | ttaactcaaatcaattctca | 1-3-1-9-1-1-4 | TtaaCtcaaatcaaTtCTCA | 49_12 | 39573 | B |
| 49 | ttaactcaaatcaattctca | 1-3-1-9-3-1-2 | TtaaCtcaaatcaaTTCtCA | 49_13 | 39573 | B |
| 49 | ttaactcaaatcaattctca | 1-3-1-7-1-4-3 | TtaaCtcaaatcAattcTCA | 49_14 | 39573 | B |
| 49 | ttaactcaaatcaattctca | 1-3-1-2-1-9-3 | TtaaCtcAaatcaattcTCA | 49_15 | 39573 | B |
| 49 | ttaactcaaatcaattctca | 1-3-1-2-1-8-1-1-2 | TtaaCtcAaatcaattCtCA | 49_16 | 39573 | B |
| 49 | ttaactcaaatcaattctca | 1-3-1-2-1-8-4 | TtaaCtcAaatcaattCTCA | 49_17 | 39573 | B |
| 49 | ttaactcaaatcaattctca | 1-3-1-2-1-7-1-2-2 | TtaaCtcAaatcaatTctCA | 49_18 | 39573 | B |
| 49 | ttaactcaaatcaattctca | 1-3-1-2-1-7-2-1-2 | TtaaCtcAaatcaatTCtCA | 49_19 | 39573 | B |
| 49 | ttaactcaaatcaattctca | 1-3-1-2-1-6-1-3-2 | TtaaCtcAaatcaaTtctCA | 49_20 | 39573 | B |
| 49 | ttaactcaaatcaattctca | 1-3-1-2-1-6-1-2-3 | TtaaCtcAaatcaaTtcTCA | 49_21 | 39573 | B |
| 49 | ttaactcaaatcaattctca | 1-3-1-2-1-6-1-1-1-2 | TtaaCtcAaatcaaTtCtCA | 49_22 | 39573 | B |
| 49 | ttaactcaaatcaattctca | 1-3-1-2-1-6-1-1-4 | TtaaCtcAaatcaaTtCTCA | 49_23 | 39573 | B |
| 49 | ttaactcaaatcaattctca | 1-3-1-2-1-6-3-1-2 | TtaaCtcAaatcaaTTCtCA | 49_24 | 39573 | B |
| 49 | ttaactcaaatcaattctca | 1-3-1-1-1-11-2 | TtaaCtCaaatcaattctCA | 49_25 | 39573 | B |
| 49 | ttaactcaaatcaattctca | 1-3-1-1-1-10-3 | TtaaCtCaaatcaattcTCA | 49_26 | 39573 | B |
| 49 | ttaactcaaatcaattctca | 1-3-1-1-1-9-1-1-2 | TtaaCtCaaatcaattCtCA | 49_27 | 39573 | B |
| 49 | ttaactcaaatcaattctca | 1-3-1-1-1-9-4 | TtaaCtCaaatcaattCTCA | 49_28 | 39573 | B |
| 49 | ttaactcaaatcaattctca | 1-3-1-1-1-8-2-1-2 | TtaaCtCaaatcaatTCtCA | 49_29 | 39573 | B |
| 49 | ttaactcaaatcaattctca | 1-3-1-1-2-10-2 | TtaaCtCAaatcaattctCA | 49_30 | 39573 | B |
| 49 | ttaactcaaatcaattctca | 1-3-1-1-2-9-3 | TtaaCtCAaatcaattcTCA | 49_31 | 39573 | B |
| 49 | ttaactcaaatcaattctca | 1-3-1-1-2-8-1-1-2 | TtaaCtCAaatcaattCtCA | 49_32 | 39573 | B |
| 49 | ttaactcaaatcaattctca | 1-3-1-1-2-6-1-3-2 | TtaaCtCAaatcaaTtctCA | 49_33 | 39573 | B |
| 49 | ttaactcaaatcaattctca | 1-3-1-1-2-6-1-1-1-2 | TtaaCtCAaatcaaTtCtCA | 49_34 | 39573 | B |
| 49 | ttaactcaaatcaattctca | 1-3-3-11-2 | TtaaCTCaaatcaattctCA | 49_35 | 39573 | B |
| 49 | ttaactcaaatcaattctca | 1-3-3-9-1-1-2 | TtaaCTCaaatcaattCtCA | 49_36 | 39573 | B |
| 49 | ttaactcaaatcaattctca | 1-3-4-10-2 | TtaaCTCAaatcaattctCA | 49_37 | 39573 | B |
| 49 | ttaactcaaatcaattctca | 1-3-4-6-1-3-2 | TtaaCTCAaatcaaTtctCA | 49_38 | 39573 | B |
| 49 | ttaactcaaatcaattctca | 1-2-1-11-2-1-2 | TtaActcaaatcaatTCtCA | 49_39 | 39573 | B |
| 49 | ttaactcaaatcaattctca | 1-2-1-10-1-1-1-1-2 | TtaActcaaatcaaTtCtCA | 49_40 | 39573 | B |
| 49 | ttaactcaaatcaattctca | 1-2-1-10-1-1-4 | TtaActcaaatcaaTtCTCA | 49_41 | 39573 | B |
| 49 | ttaactcaaatcaattctca | 1-2-1-3-1-8-1-1-2 | TtaActcAaatcaattCtCA | 49_42 | 39573 | B |
| 49 | ttaactcaaatcaattctca | 1-2-1-3-1-7-2-1-2 | TtaActcAaatcaatTCtCA | 49_43 | 39573 | B |
| 49 | ttaactcaaatcaattctca | 1-2-1-3-1-6-1-2-3 | TtaActcAaatcaaTtcTCA | 49_44 | 39573 | B |
| 49 | ttaactcaaatcaattctca | 1-2-1-3-1-6-1-1-1-2 | TtaActcAaatcaaTtCtCA | 49_45 | 39573 | B |
| 49 | ttaactcaaatcaattctca | 1-2-1-2-1-9-1-1-2 | TtaActCaaatcaattCtCA | 49_46 | 39573 | B |

TABLE 5-continued list of oligonucleotide motif sequences (indicated by SEQ ID NO), designs of
these, as well as specific oligonucleotide compounds (indicated by CMP ID NO) designed
based on the motif sequence.

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-2-1-2-1-9-4 | TtaActCaaatcaattCTCA | 49_47 | 39573 | B |
| 49 | ttaactcaaatcaattctca | 1-2-1-2-1-8-2-1-2 | TtaActCaaatcaatTCtCA | 49_48 | 39573 | B |
| 49 | ttaactcaaatcaattctca | 1-2-1-2-2-10-2 | TtaActCAaatcaattctCA | 49_49 | 39573 | B |
| 49 | ttaactcaaatcaattctca | 1-2-1-2-2-8-1-1-2 | TtaActCAaatcaattCtCA | 49_50 | 39573 | B |
| 49 | ttaactcaaatcaattctca | 1-2-1-2-2-8-4 | TtaActCAaatcaattCTCA | 49_51 | 39573 | B |
| 49 | ttaactcaaatcaattctca | 1-2-1-2-2-7-2-1-2 | TtaActCAaatcaatTCtCA | 49_52 | 39573 | B |
| 49 | ttaactcaaatcaattctca | 1-2-1-2-2-6-1-3-2 | TtaActCAaatcaaTtctCA | 49_53 | 39573 | B |
| 49 | ttaactcaaatcaattctca | 1-2-1-2-2-6-1-1-1-1-2 | TtaActCAaatcaaTtCtCA | 49_54 | 39573 | B |
| 49 | ttaactcaaatcaattctca | 1-2-1-1-2-9-1-1-2 | TtaAcTCaaatcaattCtCA | 49_55 | 39573 | B |
| 49 | ttaactcaaatcaattctca | 1-2-2-11-1-1-2 | TtaACtcaaatcaattCtCA | 49_56 | 39573 | B |
| 49 | ttaactcaaatcaattctca | 1-2-2-11-4 | TtaACtcaaatcaattCTCA | 49_57 | 39573 | B |
| 49 | ttaactcaaatcaattctca | 1-2-2-10-2-1-2 | TtaACtcaaatcaatTCtCA | 49_58 | 39573 | B |
| 49 | ttaactcaaatcaattctca | 1-2-2-9-1-3-2 | TtaACtcaaatcaaTtctCA | 49_59 | 39573 | B |
| 49 | ttaactcaaatcaattctca | 1-2-2-9-1-1-1-1-2 | TtaACtcaaatcaaTtCtCA | 49_60 | 39573 | B |
| 49 | ttaactcaaatcaattctca | 1-2-2-9-1-1-4 | TtaACtcaaatcaaTtCTCA | 49_61 | 39573 | B |
| 49 | ttaactcaaatcaattctca | 1-2-2-9-3-1-2 | TtaACtcaaatcaaTTCtCA | 49_62 | 39573 | B |
| 49 | ttaactcaaatcaattctca | 1-2-2-7-1-5-2 | TtaACtcaaatcAattctCA | 49_63 | 39573 | B |
| 49 | ttaactcaaatcaattctca | 1-2-2-2-1-10-2 | TtaACtcAaatcaattctCA | 49_64 | 39573 | B |
| 49 | ttaactcaaatcaattctca | 1-2-2-2-1-8-1-1-2 | TtaACtcAaatcaattCtCA | 49_65 | 39573 | B |
| 49 | ttaactcaaatcaattctca | 1-2-2-2-1-8-4 | TtaACtcAaatcaattCTCA | 49_66 | 39573 | B |
| 49 | ttaactcaaatcaattctca | 1-2-2-2-1-7-2-1-2 | TtaACtcAaatcaatTCtCA | 49_67 | 39573 | B |
| 49 | ttaactcaaatcaattctca | 1-2-2-2-1-6-1-3-2 | TtaACtcAaatcaaTtctCA | 49_68 | 39573 | B |
| 49 | ttaactcaaatcaattctca | 1-2-2-2-1-6-1-1-1-1-2 | TtaACtcAaatcaaTtCtCA | 49_69 | 39573 | B |
| 49 | ttaactcaaatcaattctca | 1-2-2-2-1-6-1-1-4 | TtaACtcAaatcaaTtCTCA | 49_70 | 39573 | B |
| 49 | ttaactcaaatcaattctca | 1-2-2-2-1-6-3-1-2 | TtaACtcAaatcaaTTCtCA | 49_71 | 39573 | B |
| 49 | ttaactcaaatcaattctca | 1-2-2-1-1-11-2 | TtaACtCaaatcaattctCA | 49_72 | 39573 | B |
| 49 | ttaactcaaatcaattctca | 1-2-2-1-1-9-1-1-2 | TtaACtCaaatcaattCtCA | 49_73 | 39573 | B |
| 49 | ttaactcaaatcaattctca | 1-2-2-1-1-9-4 | TtaACtCaaatcaattCTCA | 49_74 | 39573 | B |
| 49 | ttaactcaaatcaattctca | 1-2-2-1-1-8-2-1-2 | TtaACtCaaatcaatTCtCA | 49_75 | 39573 | B |
| 49 | ttaactcaaatcaattctca | 1-2-2-1-2-10-2 | TtaACtCAaatcaattctCA | 49_76 | 39573 | B |
| 49 | ttaactcaaatcaattctca | 1-2-2-1-2-8-1-1-2 | TtaACtCAaatcaattCtCA | 49_77 | 39573 | B |
| 49 | ttaactcaaatcaattctca | 1-2-2-1-2-6-1-3-2 | TtaACtCAaatcaaTtctCA | 49_78 | 39573 | B |
| 49 | ttaactcaaatcaattctca | 1-2-4-9-1-1-2 | TtaACTCaaatcaattCtCA | 49_79 | 39573 | B |
| 49 | ttaactcaaatcaattctca | 1-1-11-1-1-1-2 | TtAactcaaatcaaTtCtCA | 49_80 | 39573 | B |
| 49 | ttaactcaaatcaattctca | 1-1-10-1-2-1-1-2 | TtAactcaaatcaAttCtCA | 49_81 | 39573 | B |
| 49 | ttaactcaaatcaattctca | 1-1-10-1-1-2-1-2 | TtAactcaaatcaAtTCtCA | 49_82 | 39573 | B |

TABLE 5-continued list of oligonucleotide motif sequences (indicated by SEQ ID NO), designs of these, as well as specific oligonucleotide compounds (indicated by CMP ID NO) designed based on the motif sequence.

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-1-10-2-1-1-1-2 | TtAactcaaatcaATtCtCA | 49_83 | 39573 | B |
| 49 | ttaactcaaatcaattctca | 1-1-10-4-1-2 | TtAactcaaatcaATTCtCA | 49_84 | 39573 | B |
| 49 | ttaactcaaatcaattctca | 1-1-4-1-7-2-1-2 | TtAactcAaatcaatTCtCA | 49_85 | 39573 | B |
| 49 | ttaactcaaatcaattctca | 1-1-4-1-6-1-1-1-2 | TtAactcAaatcaaTtCtCA | 49_86 | 39573 | B |
| 49 | ttaactcaaatcaattctca | 1-1-3-1-9-1-1-2 | TtAactCaaatcaattCtCA | 49_87 | 39573 | B |
| 49 | ttaactcaaatcaattctca | 1-1-3-1-9-4 | TtAactCaaatcaattCTCA | 49_88 | 39573 | B |
| 49 | ttaactcaaatcaattctca | 1-1-3-1-8-2-1-2 | TtAactCaaatcaatTCtCA | 49_89 | 39573 | B |
| 49 | ttaactcaaatcaattctca | 1-1-3-2-8-1-1-2 | TtAactCAaatcaattCtCA | 49_90 | 39573 | B |
| 49 | ttaactcaaatcaattctca | 1-1-3-2-7-2-1-2 | TtAactCAaatcaatTCtCA | 49_91 | 39573 | B |
| 49 | ttaactcaaatcaattctca | 1-1-3-2-6-1-1-1-2 | TtAactCAaatcaaTtCtCA | 49_92 | 39573 | B |
| 49 | ttaactcaaatcaattctca | 1-1-3-2-6-3-1-2 | TtAactCAaatcaaTTCtCA | 49_93 | 39573 | B |
| 49 | ttaactcaaatcaattctca | 1-1-1-1-11-1-1-2 | TtAaCtcaaatcaattCtCA | 49_94 | 39573 | B |
| 49 | ttaactcaaatcaattctca | 1-1-1-1-10-2-1-2 | TtAaCtcaaatcaatTCtCA | 49_95 | 39573 | B |
| 49 | ttaactcaaatcaattctca | 1-1-1-1-9-1-3-2 | TtAaCtcaaatcaaTtctCA | 49_96 | 39573 | B |
| 49 | ttaactcaaatcaattctca | 1-1-1-1-9-1-1-1-2 | TtAaCtcaaatcaaTtCtCA | 49_97 | 39573 | B |
| 49 | ttaactcaaatcaattctca | 1-1-1-1-9-1-1-4 | TtAaCtcaaatcaaTtCTCA | 49_98 | 39573 | B |
| 49 | ttaactcaaatcaattctca | 1-1-1-1-9-3-1-2 | TtAaCtcaaatcaaTTCtCA | 49_99 | 39573 | B |
| 49 | ttaactcaaatcaattctca | 1-1-1-1-7-1-5-2 | TtAaCtcaaatcAattctCA | 49_100 | 39573 | B |
| 49 | ttaactcaaatcaattctca | 1-1-1-1-2-1-10-2 | TtAaCtcAaatcaattctCA | 49_101 | 39573 | B |
| 49 | ttaactcaaatcaattctca | 1-1-1-1-2-1-8-1-1-2 | TtAaCtcAaatcaattCtCA | 49_102 | 39573 | B |
| 49 | ttaactcaaatcaattctca | 1-1-1-1-2-1-8-4 | TtAaCtcAaatcaattCTCA | 49_103 | 39573 | B |
| 49 | ttaactcaaatcaattctca | 1-1-1-1-2-1-7-2-1-2 | TtAaCtcAaatcaatTCtCA | 49_104 | 39573 | B |
| 49 | ttaactcaaatcaattctca | 1-1-1-1-2-1-6-1-3-2 | TtAaCtcAaatcaaTtctCA | 49_105 | 39573 | B |
| 49 | ttaactcaaatcaattctca | 1-1-1-1-2-1-6-1-1-1-2 | TtAaCtcAaatcaaTtCtCA | 49_106 | 39573 | B |
| 49 | ttaactcaaatcaattctca | 1-1-1-1-2-1-6-1-1-4 | TtAaCtcAaatcaaTtCTCA | 49_107 | 39573 | B |
| 49 | ttaactcaaatcaattctca | 1-1-1-1-2-1-6-3-1-2 | TtAaCtcAaatcaaTTCtCA | 49_108 | 39573 | B |
| 49 | ttaactcaaatcaattctca | 1-1-1-1-1-11-2 | TtAaCtCaaatcaattctCA | 49_109 | 39573 | B |
| 49 | ttaactcaaatcaattctca | 1-1-1-1-1-9-1-1-2 | TtAaCtCaaatcaattCtCA | 49_110 | 39573 | B |
| 49 | ttaactcaaatcaattctca | 1-1-1-1-1-8-2-1-2 | TtAaCtCaaatcaatTCtCA | 49_111 | 39573 | B |
| 49 | ttaactcaaatcaattctca | 1-1-1-1-1-2-10-2 | TtAaCtCAaatcaattctCA | 49_112 | 39573 | B |
| 49 | ttaactcaaatcaattctca | 1-1-1-1-1-2-8-1-1-2 | TtAaCtCAaatcaattCtCA | 49_113 | 39573 | B |
| 49 | ttaactcaaatcaattctca | 1-1-1-1-1-2-6-1-3-2 | TtAaCtCAaatcaaTtctCA | 49_114 | 39573 | B |
| 49 | ttaactcaaatcaattctca | 1-2-11-2-1-2 | TtAActcaaatcaatTCtCA | 49_115 | 39573 | B |
| 49 | ttaactcaaatcaattctca | 1-2-10-1-1-1-2 | TtAActcaaatcaaTtCtCA | 49_116 | 39573 | B |
| 49 | ttaactcaaatcaattctca | 1-2-3-1-8-1-1-2 | TtAActcAaatcaattCtCA | 49_117 | 39573 | B |
| 49 | ttaactcaaatcaattctca | 1-2-3-1-7-2-1-2 | TtAActcAaatcaatTCtCA | 49_118 | 39573 | B |

TABLE 5-continued list of oligonucleotide motif sequences (indicated by SEQ ID NO), designs of
these, as well as specific oligonucleotide compounds (indicated by CMP ID NO) designed
based on the motif sequence.

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-1-2-3-1-6-1-1-1-2 | TtAActcAaatcaaTtCtCA | 49_119 | 39573 | B |
| 49 | ttaactcaaatcaattctca | 1-1-2-2-1-9-1-1-2 | TtAActCaaatcaattCtCA | 49_120 | 39573 | B |
| 49 | ttaactcaaatcaattctca | 1-1-2-2-1-8-2-1-2 | TtAActCaaatcaatTCtCA | 49_121 | 39573 | B |
| 49 | ttaactcaaatcaattctca | 1-1-2-2-2-8-1-1-2 | TtAActCAaatcaattCtCA | 49_122 | 39573 | B |
| 49 | ttaactcaaatcaattctca | 1-1-2-2-2-7-2-1-2 | TtAActCAaatcaatTCtCA | 49_123 | 39573 | B |
| 49 | ttaactcaaatcaattctca | 1-1-2-2-2-6-1-1-1-2 | TtAActCAaatcaaTtCtCA | 49_124 | 39573 | B |
| 49 | ttaactcaaatcaattctca | 1-1-3-11-1-1-2 | TtAACtcaaatcaattCtCA | 49_125 | 39573 | B |
| 49 | ttaactcaaatcaattctca | 1-1-3-11-4 | TtAACtcaaatcaattCTCA | 49_126 | 39573 | B |
| 49 | ttaactcaaatcaattctca | 1-1-3-10-2-1-2 | TtAACtcaaatcaatTCtCA | 49_127 | 39573 | B |
| 49 | ttaactcaaatcaattctca | 1-1-3-9-1-3-2 | TtAACtcaaatcaaTtctCA | 49_128 | 39573 | B |
| 49 | ttaactcaaatcaattctca | 1-1-3-9-1-1-1-2 | TtAACtcaaatcaaTtCtCA | 49_129 | 39573 | B |
| 49 | ttaactcaaatcaattctca | 1-1-3-9-3-1-2 | TtAACtcaaatcaaTTCtCA | 49_130 | 39573 | B |
| 49 | ttaactcaaatcaattctca | 1-1-3-7-1-5-2 | TtAACtcaaatcAattctCA | 49_131 | 39573 | B |
| 49 | ttaactcaaatcaattctca | 1-1-3-2-1-10-2 | TtAACtcAaatcaattctCA | 49_132 | 39573 | B |
| 49 | ttaactcaaatcaattctca | 1-1-3-2-1-8-1-1-2 | TtAACtcAaatcaattCtCA | 49_133 | 39573 | B |
| 49 | ttaactcaaatcaattctca | 1-1-3-2-1-7-2-1-2 | TtAACtcAaatcaatTCtCA | 49_134 | 39573 | B |
| 49 | ttaactcaaatcaattctca | 1-1-3-2-1-6-1-3-2 | TtAACtcAaatcaaTtctCA | 49_135 | 39573 | B |
| 49 | ttaactcaaatcaattctca | 1-1-3-2-1-6-1-1-1-2 | TtAACtcAaatcaaTtCtCA | 49_136 | 39573 | B |
| 49 | ttaactcaaatcaattctca | 1-1-3-2-1-6-3-1-2 | TtAACtcAaatcaaTTCtCA | 49_137 | 39573 | B |
| 49 | ttaactcaaatcaattctca | 1-1-3-1-1-11-2 | TtAACtCaaatcaattctCA | 49_138 | 39573 | B |
| 49 | ttaactcaaatcaattctca | 1-1-3-1-1-9-1-1-2 | TtAACtCaaatcaattCtCA | 49_139 | 39573 | B |
| 49 | ttaactcaaatcaattctca | 1-1-3-1-1-9-4 | TtAACtCaaatcaattCTCA | 49_140 | 39573 | B |
| 49 | ttaactcaaatcaattctca | 1-1-3-1-1-8-2-1-2 | TtAACtCaaatcaatTCtCA | 49_141 | 39573 | B |
| 49 | ttaactcaaatcaattctca | 1-1-3-1-2-8-1-1-2 | TtAACtCAaatcaattCtCA | 49_142 | 39573 | B |
| 49 | ttaactcaaatcaattctca | 1-1-3-1-2-6-1-3-2 | TtAACtCAaatcaaTtctCA | 49_143 | 39573 | B |
| 49 | ttaactcaaatcaattctca | 2-5-1-8-1-1-2 | TTaactcAaatcaattCtCA | 49_144 | 39573 | B |
| 49 | ttaactcaaatcaattctca | 2-5-1-7-2-1-2 | TTaactcAaatcaatTCtCA | 49_145 | 39573 | B |
| 49 | ttaactcaaatcaattctca | 2-5-1-6-1-1-1-2 | TTaactcAaatcaaTtCtCA | 49_146 | 39573 | B |
| 49 | ttaactcaaatcaattctca | 2-5-1-6-3-1-2 | TTaactcAaatcaaTTCtCA | 49_147 | 39573 | B |
| 49 | ttaactcaaatcaattctca | 2-4-2-8-1-1-2 | TTaactCAaatcaattCtCA | 49_148 | 39573 | B |
| 49 | ttaactcaaatcaattctca | 2-4-2-7-2-1-2 | TTaactCAaatcaatTCtCA | 49_149 | 39573 | B |
| 49 | ttaactcaaatcaattctca | 2-2-1-11-1-1-2 | TTaaCtcaaatcaattCtCA | 49_150 | 39573 | B |
| 49 | ttaactcaaatcaattctca | 2-2-1-11-4 | TTaaCtcaaatcaattCTCA | 49_151 | 39573 | B |
| 49 | ttaactcaaatcaattctca | 2-2-1-10-2-1-2 | TTaaCtcaaatcaatTCtCA | 49_152 | 39573 | B |
| 49 | ttaactcaaatcaattctca | 2-2-1-9-1-1-1-2 | TTaaCtcaaatcaaTtCtCA | 49_154 | 39573 | B |
| 49 | ttaactcaaatcaattctca | 2-2-1-7-1-5-2 | TTaaCtcaaatcAattctCA | 49_155 | 39573 | B |

TABLE 5-continued list of oligonucleotide motif sequences (indicated by SEQ ID NO), designs of
these, as well as specific oligonucleotide compounds (indicated by CMP ID NO) designed
based on the motif sequence.

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 2-2-1-2-1-10-2 | TTaaCtcAaatcaattctCA | 49_156 | 39573 | B |
| 49 | ttaactcaaatcaattctca | 2-2-1-2-1-8-1-1-2 | TTaaCtcAaatcaattCtCA | 49_157 | 39573 | B |
| 49 | ttaactcaaatcaattctca | 2-2-1-2-1-8-4 | TTaaCtcAaatcaattCTCA | 49_158 | 39573 | B |
| 49 | ttaactcaaatcaattctca | 2-2-1-2-1-7-2-1-2 | TTaaCtcAaatcaatTCtCA | 49_159 | 39573 | B |
| 49 | ttaactcaaatcaattctca | 2-2-1-2-1-6-1-3-2 | TTaaCtcAaatcaaTtctCA | 49_160 | 39573 | B |
| 49 | ttaactcaaatcaattctca | 2-2-1-2-1-6-1-1-1-2 | TTaaCtcAaatcaaTtCtCA | 49_161 | 39573 | B |
| 49 | ttaactcaaatcaattctca | 2-2-1-1-1-11-2 | TTaaCtCaaatcaattctCA | 49_162 | 39573 | B |
| 49 | ttaactcaaatcaattctca | 2-2-1-1-1-9-1-1-2 | TTaaCtCaaatcaattCtCA | 49_163 | 39573 | B |
| 49 | ttaactcaaatcaattctca | 2-2-1-1-2-10-2 | TTaaCtCAaatcaattctCA | 49_164 | 39573 | B |
| 49 | ttaactcaaatcaattctca | 2-2-1-1-2-6-1-3-2 | TTaaCtCAaatcaaTtctCA | 49_165 | 39573 | B |
| 49 | ttaactcaaatcaattctca | 2-1-1-10-1-1-1-2 | TTaActcaaatcaaTtCtCA | 49_166 | 39573 | B |
| 49 | ttaactcaaatcaattctca | 2-1-1-2-1-9-1-1-2 | TTaActCaaatcaattCtCA | 49_167 | 39573 | B |
| 49 | ttaactcaaatcaattctca | 2-1-1-2-2-8-1-1-2 | TTaActCAaatcaattCtCA | 49_168 | 39573 | B |
| 49 | ttaactcaaatcaattctca | 2-1-2-9-1-1-1-2 | TTaACtcaaatcaaTtCtCA | 49_169 | 39573 | B |
| 49 | ttaactcaaatcaattctca | 2-1-2-2-1-7-2-1-2 | TTaACtcAaatcaatTCtCA | 49_170 | 39573 | B |
| 49 | ttaactcaaatcaattctca | 2-1-2-2-1-6-1-1-1-2 | TTaACtcAaatcaaTtCtCA | 49_171 | 39573 | B |
| 49 | ttaactcaaatcaattctca | 3-11-1-1-1-2 | TTAactcaaatcaaTtCtCA | 49_172 | 39573 | B |
| 49 | ttaactcaaatcaattctca | 3-10-1-2-1-1-2 | TTAactcaaatcaAttCtCA | 49_173 | 39573 | B |
| 49 | ttaactcaaatcaattctca | 3-10-1-1-2-1-2 | TTAactcaaatcaAtTCtCA | 49_174 | 39573 | B |
| 49 | ttaactcaaatcaattctca | 3-4-1-7-2-1-2 | TTAactcAaatcaatTCtCA | 49_175 | 39573 | B |
| 49 | ttaactcaaatcaattctca | 3-4-1-6-1-1-1-1-2 | TTAactcAaatcaaTtCtCA | 49_176 | 39573 | B |
| 49 | ttaactcaaatcaattctca | 3-3-1-9-1-1-2 | TTAactCaaatcaattCtCA | 49_177 | 39573 | B |
| 49 | ttaactcaaatcaattctca | 3-3-1-9-4 | TTAactCaaatcaattCTCA | 49_178 | 39573 | B |
| 49 | ttaactcaaatcaattctca | 3-3-1-8-2-1-2 | TTAactCaaatcaatTCtCA | 49_179 | 39573 | B |
| 49 | ttaactcaaatcaattctca | 3-3-2-8-1-1-2 | TTAactCAaatcaattCtCA | 49_180 | 39573 | B |
| 49 | ttaactcaaatcaattctca | 3-1-1-11-1-1-2 | TTAaCtcaaatcaattCtCA | 49_181 | 39573 | B |
| 49 | ttaactcaaatcaattctca | 3-1-1-9-1-3-2 | TTAaCtcaaatcaaTtctCA | 49_182 | 39573 | B |
| 49 | ttaactcaaatcaattctca | 3-1-1-9-1-1-1-2 | TTAaCtcaaatcaaTtCtCA | 49_183 | 39573 | B |
| 49 | ttaactcaaatcaattctca | 3-1-1-7-1-5-2 | TTAaCtcaaatcAattctCA | 49_184 | 39573 | B |
| 49 | ttaactcaaatcaattctca | 3-1-1-2-1-10-2 | TTAaCtcAaatcaattctCA | 49_185 | 39573 | B |
| 49 | ttaactcaaatcaattctca | 3-1-1-2-1-8-1-1-2 | TTAaCtcAaatcaattCtCA | 49_186 | 39573 | B |
| 49 | ttaactcaaatcaattctca | 3-1-1-2-1-6-1-3-2 | TTAaCtcAaatcaaTtctCA | 49_187 | 39573 | B |
| 49 | ttaactcaaatcaattctca | 3-1-1-1-1-11-2 | TTAaCtCaaatcaattctCA | 49_188 | 39573 | B |
| 49 | ttaactcaaatcaattctca | 4-12-4 | TTAActcaaatcaattCTCA | 49_189 | 39573 | B |
| 49 | ttaactcaaatcaattctca | 4-11-2-1-2 | TTAActcaaatcaatTCtCA | 49_190 | 39573 | B |
| 49 | ttaactcaaatcaattctca | 4-3-1-7-2-1-2 | TTAActcAaatcaatTCtCA | 49_191 | 39573 | B |

TABLE 5-continued list of oligonucleotide motif sequences (indicated by SEQ ID NO), designs of
these, as well as specific oligonucleotide compounds (indicated by CMP ID NO) designed
based on the motif sequence.

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 4-2-1-9-1-1-2 | TTAActCaaatcaattCtCA | 49_192 | 39573 | B |
| 50 | tttaactcaaatcaattctc | 4-12-4 | TTTAactcaaatcaatTCTC | 50_1 | 39574 | B |
| 51 | tttaactcaaatcaattct | 4-11-4 | TTTAactcaaatcaaTTCT | 51_1 | 39575 | B |
| 52 | cctttttaattcattag | 4-8-4 | CCTTttaattcaTTAG | 52_1 | 72861 | C |
| 53 | caacacctttttaattcatta | 4-12-4 | CAACacctttttaattcATTA | 53_1 | 72862 | C |
| 54 | aacacctttttaattcatt | 4-10-4 | ACAcctttttaattCATT | 54_1 | 72863 | C |
| 55 | catcaacacctttttaattca | 2-14-4 | CAtcaacacctttttaaTTCA | 55_1 | 72865 | C |
| 56 | ctcatcaacacctttttaatt | 4-14-2 | CTCAtcaacacctttttaaTT | 56_1 | 72867 | C |
| 57 | actcatcaacacctttttaat | 2-14-4 | ACtcatcaacacctttTAAT | 57_1 | 72868 | C |
| 58 | aactcatcaacacctttttaa | 3-13-4 | AACtcatcaacacctttTTAA | 58_1 | 72869 | C |
| 59 | taactcatcaacacctttta | 4-14-2 | TAACtcatcaacacctttTA | 59_1 | 72870 | C |
| 60 | ttaactcatcaacaccttttt | 4-13-3 | TTAActcatcaacacctTTT | 60_1 | 72871 | C |
| 61 | ttaactcatcaacacctttt | 3-12-4 | TTAactcatcaacacCTTT | 61_1 | 72872 | C |
| 62 | ttaactcatcaacacctt | 3-11-4 | TTAactcatcaacaCCTT | 62_1 | 72873 | C |
| 63 | ttaactcatcaacacct | 4-9-4 | TTAActcatcaacACCT | 63_1 | 72874 | C |
| 64 | gttaactcatcaacacc | 4-10-3 | GTTAactcatcaacACC | 64_1 | 72875 | C |
| 65 | gttaactcatcaacac | 4-9-3 | GTTAactcatcaaCAC | 65_1 | 72876 | C |
| 66 | atttccaaattcacttttac | 1-1-3-10-2-1-2 | AtTTCcaaattcactTTtAC | 66_1 | 133964 | — |
| 67 | ccgttttcttaccaccct | 5-10-5 | CC$_o$GTTtttettaeeAC$_o$CCT | 67_1 | 114184 | — |

Motif sequences represent the contiguous sequence of nucleobases present in the oligonucleotide.

Designs refer to the gapmer design, F-G-F'. In classic gapmer design e.g. 3-10-3 all the nucleotides in the flanks (F and F') are constituted of the same 2'-sugar modified nucleoside, e.g. LNA, cET, or MOE, and a stretch of DNA in the middle forming the gap (G). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' [M]$_2$-[D]$_2$-[M] 3' and a 1-1-1-1-1 motif represents 5' [M]-[D]-[M]-[D]-[M] 3'. Both flanks have a 2' sugar modified nucleoside at the 5' and 3' terminal. The gap region (G), which is constituted of a number of DNA nucleosides (typically between 6 and 16), is located between the flanks. The heading "Oligonucleotide compound" in the table represents a specific design of the motif sequence. Capital letters represent beta-D-oxy LNA nucleosides, Underlined capital letter represent MOE nucleosides, lowercase letters represent DNA nucleosides, all LNA C are 5-methyl cytosine, e represents a 5-methyl cytosine DNA, all internucleoside linkages are phosphorothioate internucleoside linkages unless marked by a subscript letter between the nucleotides, subscript o represents a phosphodiester linkage.

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 µmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphodiester linkages can be introduced using 0.02 M iodine in THF/Pyridine/water 7:2:1. The rest of the reagents are the ones typically used for oligonucleotide synthesis.

For post solid phase synthesis conjugation a commercially available C6 amino linker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations:
DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Primary Neuronal Cell Cultures

Primary neuronal cultures were established from the forebrain of E18 transgenic mice expressing the human tau transgene on a mouse tau knockout background. (Andorfer et al. J Neurochem 86:582-590 (2003)). Primary neurons were generated by papain digestion according to manufacturer's protocol (Worthington Biochemical Corporation, LK0031050). Briefly, forebrains were dissected from hTau mouse E18 BAC-Tg embryos expressing the entire human microtubule-associated protein Tau (MAPT) gene on a murine MAPT-null background and were incubated at 37° C. for 30-45 minutes in papain/DNase/Earle's balanced salt solution (EBSS) solution. After trituration and centrifugation of cell pellet, the reaction was stopped by incubation with EBSS containing protease inhibitors, bovine serum albumin (BSA) and DNase. The cells were triturated and washed with Neurobasal (NB, Invitrogen) supplemented with 2% B-27, 100 μg/ml penicillin, 85 μg/ml streptomycin, and 0.5 mM glutamine.

Transgenic Tau Mouse (hTau Mouse)

Male and female transgenic mice (30-40 g) expressing a tau transgene derived from a human PAC, H1 haplotype driven by the tau promoter (Polydoro et. al., *J. Neurosci.* (2009) 29(34): 10741-9), and in which the native mouse Tau gene was deleted, were used to assess tolerability, pharmacodynamic endpoints and tissue drug concentrations.

Animals were held in colony rooms maintained at constant temperature (21±2° C.) and humidity (50±10%) and illuminated for 12 hours per day (lights on at 0600 hours). All animals had ad libitum access to food and water throughout the studies. Behavioral studies were conducted between 0700 and 1500 hours.

Intracerebroventricular (ICV) injections were performed using a Hamilton micro syringe fitted with a 27 or 30-gauge needle, according to the method of Haley and McCormick. The needle was equipped with a polyethylene guard at 2.5 mm from the tip in order to limit its penetration into the brain. Mice were anesthetized using isoflurane anesthetic (1.5-4%). The mouse to be injected was held by the loose skin at the back of the neck with the thumb and first fingers of one hand. Applying gentle but firm pressure, the head of the animal was then immobilized by pressing against a firm flat level surface. The needle tip was then inserted through the scalp and the skull, about 1 mm lateral and 1 mm caudal to bregma. Once the needle was positioned, ASO was given in a volume of 5 microliters in saline vehicle and injected into the right (or left) lateral ventricle over 20-30 seconds. The needle was left in place for 10 seconds before removal. This procedure requires no surgery or incision. Animals were warmed on heating pads until they recovered from the procedure.

3 days and/or 4 weeks post administration mice were sacrificed with isoflurane overdose followed by rapid decapitation and brain tissue (right, frontal cortical region) was collected on dry ice for later Tau qPCR.

Media Used for Cell Culturing and Differentiation of Human Stem Cell Derived Neurons N2B27+SFA Media=N2B27+S,F,A Cytokines

| Cytokines used | Ref | Provider | Stock | Final use in N2B27(dilution) |
|---|---|---|---|---|
| SHH (sonic hedgehog) | 100-45 | Peprotech | 100 ug/ml in PBS + 0.1% BSA | 1:500 (200 ng/ml) |
| FGF8 | 100-25 | Peprotech | 100 ug/ml in | 1:1000 (100 ng/ml) |
| AA (Aa2-P) | A8960 | Sigma | PBS + 0.1% BSA 100 mM in DMEM:F12 | 1:1000 |

N2B27+BGAA Media=N2B27+B,G,Aa,cA Cytokines+P/S+Laminin

| Cytokines used | Ref | Provider | Stock | Final use in N2B27(dilution) |
|---|---|---|---|---|
| BDNF | 450-02 | Peprotech | 20 ug/ml in PBS + 0.1% BSA | 1:1000 |
| GDNF | 450-10 | Peprotech | 10 ug/ml in PBS + 0.1% BSA | 1:1000 |
| AA (Aa2-P) | A8960 | Sigma | 100 mM in DMEM:F12 | 1:1000 |
| cAMP | D 009 | BIOLOG Life Science | 200 mM in water | 1:400 |
| PenStrep | 15140-122 | Gibco | | 1% |
| Laminin | 11243217001 | Roche | 1 mg/ml | 1:500 |

Example 1 In Vitro Screening of ASO's Targeting MAPT Introns

An antisense oligonucleotide (ASO) screening was performed in primary neuronal cells from humanized Tau mice with 807 ASO's targeting the MAPT introns.

The ability of ASOs to reduce MAPT mRNA in vitro was measured by QUANTIGENE® analysis. Each tau mRNA reduction was standardized by subtracting an assay background signal and normalizing each well via the housekeeping gene tubulin mRNA signal.

Primary neuronal cell cultures were prepared as described in the "Materials and Method" section and plated on poly-D-lysine coated 384 well plates at 10,000 cells per well and maintained in Neurobasal media containing B27, glutamax and Penicillin-Streptomycin. ASO's were diluted in water and added to cells at DIV01 to a final concentration of 0.5 µM. Following ASO addition, neurons were incubated at 37° C. and 5% $CO_2$ for 5 days to achieve steady state reduction of mRNA. Media was removed and cells were washed 1× in DPBS. Measurement of lysate messenger RNA was performed using the QUANTIGENE® 2.0 Reagent System (AFFYMETRIX®), which quantitates RNA using a branched DNA-signal amplification method reliant on the specifically designed RNA capture probe set. The cells were lysed using working cell lysis buffer solution made by adding 50 µl proteinase K to 5 ml of pre-warmed Lysis mix and diluted to 1:4 final dilution with $dH_2O$. The working lysis buffer was added to the plate (45 µl/well), triturated to mix, sealed and incubated for 30 min at 55° C. Following lysis the wells were stored at −80° C. or assayed immediately.

Lysates were diluted in lysis mix dependent on the specific capture probe used (tau or tubulin). 27 µl/well total was then added to the capture plate (384 well polystyrene plate coated with capture probes). Working probe sets reagents were generated by combining 2.2 ml of nuclease-free water, 1.2 ml of lysis mixture, 184 µl blocking reagent, and 66.8 µl of specific 2.0 probe set human MAPT catalogue #15486 and mouse beta 3 tubulin, catalogue #SB-17245, per manufacturer instructions (QUANTIGENE® 2.0 AFFYMETRIX®). Then 7 µl working probe set reagents were added to 27 µl lysate dilution (or 27 µl lysis mix for background samples) on the capture plate. Plates were centrifuged and then incubated for 16-20 hours at 55° C. to hybridize (target RNA capture). Signal amplification and detection of target RNA began by washing plates with buffer 3 times to remove unbound material. 2.0 Pre-Amplifier hybridization reagent (30 µl/well) was added, incubated at 55° C. for 1 hour then aspirated and wash buffer was added and aspirated 3 times. The 2.0 Amplifier hybridization reagent was then added as described (30 µl/well), incubated for 1 hour at 55° C. and the wash was repeated as described previously. The 2.0 Label Probe hybridization reagent was added next (30 µl/well), incubated for 1 hour at 50° C. and the wash was repeated as described previously. Lastly, the plates were centrifuged to remove any excess wash buffer and 2.0 Substrate was added (30 µl/well). Plates were incubated for 5 minutes at room temperature and plates were imaged on a PerkinElmer Envision multilabel reader in luminometer mode within 15 minutes.

For the gene of interest, the average assay background signal was subtracted from the average signal of each technical replicate. The background-subtracted, average signals for the gene of interest are divided by the background-subtracted average signal for the housekeeping tubulin RNA. The percent inhibition for the treated sample was calculated relative to untreated sample (i.e. the lower the value the larger the inhibition). Variability in background of untreated samples may result in percent inhibition of a treated sample that are equal to or higher than background, and in these cases, percent inhibition is expressed as 100% inhibition of control (i.e. no inhibition).

FIG. 1 shows the MAPT mRNA reduction achieved by all 807 ASO's. In the figure three regions A, B and C on the MAPT target nucleic acid are indicated. These regions have a high prevalence of ASO's that reduce the target to 40% or less compared to control (100%).

Example 2 In Vitro Screening of ASO's Targeting Selected Regions on MAPT

Based on the screening in Example 1, a new library of ASO's were designed to target region A, B and C as illustrated in FIG. 1. The motif sequences and the oligonucleotide compounds are shown in table 5 above.

The screening was conducted as described in Example 1. The results are shown in table 6.

TABLE 6 in vitro screening of anti-MAPT compounds

| CMP ID NO | Compound | % MAPT mRNA of control |
|---|---|---|
| 6_1 | TCACtcatgccttaaTC | 2 |
| 7_1 | TAATcactcatgcCTTA | 15 |
| 8_1 | TAATcactcatgCCTT | 34 |
| 9_1 | CtttaatttaaTcaCtCAT | 41 |
| 9_2 | CtttaatttaaTcACtCAT | 36 |
| 9_3 | CtttaatttaaTCactCAT | 28 |
| 9_4 | CtttaatttaaTCacTCAT | 31 |
| 9_5 | CtttaatttaaTCaCtCAT | 28 |
| 9_6 | CtttaatttaaTCaCtCAT | 55 |
| 9_7 | CtttaatttaaTCActcAT | 30 |
| 9_8 | CtttaatttaaTCActCAT | 21 |
| 9_9 | CtttaatttaaTCAcTCAT | 61 |
| 9_10 | CtttaatttaaTCACtCAT | 24 |
| 9_11 | CtttaaTttaatcacTCAT | 14 |
| 9_12 | CtttaaTttaatcaCtCAT | 22 |
| 9_13 | CtttaaTttaatcActCAT | 33 |
| 9_14 | CtttaaTttaatcAcTCAT | 9 |
| 9_15 | CtttaaTttaatcACtCAT | 20 |
| 9_16 | CtttaAtttaatcacTCAT | 17 |
| 9_18 | CtttAatttaatcacTCAT | 10 |
| 9_19 | CtttAatttaatcaCtCAT | 17 |
| 9_20 | CtttAaTttaatcacTCAT | 0 |
| 9_21 | CtttAAtttaatcacTCAT | 3 |
| 9_22 | CtttAATttaatcacTCAT | 1 |
| 9_23 | CttTaatttaatcacTCAT | 13 |
| 9_24 | CttTaatttaatcaCtCAT | 13 |
| 9_25 | CttTaaTttaatcacTCAT | 4 |
| 9_26 | CttTaAtttaatcacTCAT | 4 |

TABLE 6-continued in vitro screening of anti-MAPT compounds

| CMP ID NO | Compound | % MAPT mRNA of control |
|---|---|---|
| 9_27 | CttTaATttaatcacTCAT | 1 |
| 9_28 | CttTAatttaatcactCAT | 12 |
| 9_29 | CttTAatttaatcacTCAT | 1 |
| 9_30 | CttTAatttaatcaCtcAT | 15 |
| 9_31 | CttTAatttaatcaCtCAT | 4 |
| 9_32 | CttTAaTttaatcacTCAT | 1 |
| 9_33 | CttTAAtttaatcacTCAT | 1 |
| 9_34 | CttTAATttaatcactcAT | 4 |
| 9_35 | CttTAATttaatcacTCAT | 1 |
| 9_36 | CtTtaaTttaatcacTCAT | 5 |
| 9_37 | CtTtaAtttaatcacTCAT | 7 |
| 9_38 | CtTtaATttaatcacTCAT | 2 |
| 9_39 | CtTtAatttaatcacTCAT | 3 |
| 9_40 | CtTtAatttaatcaCtCAT | 9 |
| 9_41 | CtTtAaTttaatcacTCAT | 4 |
| 9_42 | CtTtAAtttaatcacTCAT | 1 |
| 9_43 | CtTtAATttaatcacTCAT | 1 |
| 9_44 | CtTTaatttaatcacTCAT | 2 |
| 9_45 | CtTTaatttaatcaCtcAT | 15 |
| 9_46 | CtTTaatttaatcaCtCAT | 3 |
| 9_47 | CtTTaaTttaatcacTCAT | 2 |
| 9_48 | CtTTaAtttaatcacTCAT | 1 |
| 9_49 | CtTTaATttaatcactcAT | 1 |
| 9_50 | CtTTaATttaatcacTCAT | 1 |
| 9_51 | CtTTAatttaatcactCAT | 1 |
| 9_52 | CtTTAatttaatcacTCAT | 1 |
| 9_53 | CtTTAatttaatcaCtCAT | 6 |
| 9_54 | CtTTAatttaatcaCtCAT | 2 |
| 9_56 | CtTTAaTttaatcacTCAT | 1 |
| 9_57 | CtTTAAtttaatcactcAT | 1 |
| 9_58 | CtTTAATttaatcacTCAT | 1 |
| 9_59 | CTttaatttaatcActCAT | 39 |
| 9_60 | CTttaatttaatcAcTCAT | 10 |
| 9_61 | CTttaatttaatcACtCAT | 20 |
| 9_62 | CTttaatttaaTCactcAT | 26 |
| 9_63 | CTttaatttaaTCactCAT | 14 |
| 9_64 | CTttaatttaaTCacTCAT | 14 |
| 9_65 | CTttaatttaaTCaCtcAT | 15 |
| 9_66 | CTttaatttaaTCaCtCAT | 38 |
| 9_67 | CTttaatttaaTCActcAT | 9 |
| 9_68 | CTttaatttaaTCActCAT | 12 |
| 9_69 | CTttaatttaaTCACtCAT | 9 |
| 9_70 | CTttaaTttaatcactCAT | 42 |
| 9_71 | CTttaaTttaatcacTCAT | 6 |
| 9_72 | CTttaaTttaatcaCtcAT | 49 |
| 9_73 | CTttaaTttaatcaCtCAT | 15 |
| 9_74 | CTttaaTttaatcActCAT | 16 |
| 9_75 | CTttaaTttaatcAcTCAT | 12 |
| 9_76 | CTttaaTttaatcACtCAT | 32 |
| 9_77 | CTttaaTttaatcACtCAT | 15 |
| 9_78 | CTttAatttaatcactCAT | 21 |
| 9_79 | CTttAatttaatcacTCAT | 3 |
| 9_80 | CTttAatttaatcaCtCAT | 10 |
| 9_81 | CTttAaTttaatcacTCAT | 2 |
| 9_82 | CTttAAtttaatcacTCAT | 1 |
| 9_84 | CTtTaatttaatcaCtcAT | 22 |
| 9_85 | CTtTaatttaatcaCtCAT | 8 |
| 9_86 | CTtTaAtttaatcacTCAT | 2 |
| 9_89 | CTtTAatttaatcacTCAT | 1 |
| 9_90 | CTtTAatttaatcaCtCAT | 5 |
| 9_92 | CTtTAaTttaatcactCAT | 1 |
| 9_94 | CTtTAAtttaatcacTCAT | 1 |
| 9_97 | CTTtAatttaatcactCAT | 0 |
| 9_98 | CTTtAatttaatcacTCAT | 1 |
| 9_99 | CTTtAatttaatcaCtCAT | 7 |
| 9_100 | CTTtAatttaatcaCtCAT | 3 |
| 9_101 | CTTtAAtttaatcacTCAT | 1 |
| 9_103 | CTTTaatttaatcacTCAT | 0 |
| 9_105 | CTTTaaTttaatcactcAT | 0 |
| 9_106 | CTTTaAtttaatcacTCAT | 1 |
| 10_1 | GctttaatttaaTcaCtCAT | 35 |
| 10_2 | GctttaatttaaTCactcAT | 56 |
| 10_3 | GctttaatttaaTCactCAT | 18 |
| 10_4 | GctttaatttaaTCacTCAT | 21 |
| 10_5 | GctttaatttaaTCaCtcAT | 16 |

TABLE 6-continued in vitro screening of anti-MAPT compounds

| CMP ID NO | Compound | % MAPT mRNA of control |
|---|---|---|
| 10_6 | GctttaatttaaTCaCtCAT | 35 |
| 10_7 | GctttaatttaaTCActcAT | 22 |
| 10_8 | GctttaatttaaTCACtcAT | 12 |
| 10_9 | GctttaaTttaatcactCAT | 61 |
| 10_10 | GctttaaTttaatcacTCAT | 19 |
| 10_11 | GctttaaTttaatcaCtcAT | 76 |
| 10_12 | GctttaaTttaatcaCtCAT | 12 |
| 10_13 | GctttaaTttaaTcaCtCAT | 15 |
| 10_14 | GctttaaTttaaTCactCAT | 7 |
| 10_15 | GctttaaTttaaTCaCtCAT | 14 |
| 10_16 | GctttaaTttaaTCActcAT | 10 |
| 10_17 | GctttaAtttaatcacTCAT | 28 |
| 10_18 | GctttAatttaatcacTCAT | 16 |
| 10_19 | GctttAatttaatcaCtCAT | 13 |
| 10_20 | GctttAaTttaatcacTCAT | 2 |
| 10_21 | GctttAAtttaatcacTCAT | 3 |
| 10_22 | GctttAATttaatcacTCAT | 1 |
| 10_23 | GcttTaatttaatcacTCAT | 18 |
| 10_24 | GcttTaatttaatcaCtcAT | 8i |
| 10_25 | GcttTaatttaatcaCtCAT | 8 |
| 10_26 | GcttTaaTttaatcacTCAT | 4 |
| 10_27 | GcttTaAtttaatcacTCAT | 3 |
| 10_28 | GcttTAatttaatcacTCAT | 2 |
| 10_29 | GcttTAatttaatcaCtcAT | 13 |
| 10_30 | GcttTAatttaatcaCtCAT | 3 |
| 10_31 | GctTtaaTttaatcacTCAT | 4 |
| 10_32 | GctTtaAtttaatcacTCAT | 6 |
| 10_33 | GctTtAatttaatcacTCAT | 3 |
| 10_34 | GctTtAatttaatcaCtcAT | 18 |
| 10_35 | GctTtAatttaatcaCtCAT | 6 |
| 10_36 | GctTtAaTttaatcacTCAT | 2 |
| 10_37 | GctTtAAtttaatcacTCAT | 1 |
| 10_38 | GctTTaatttaatcacTCAT | 1 |
| 10_39 | GctTTaatttaatcaCtcAT | 12 |
| 10_40 | GctTTaatttaatcaCtCAT | 3 |
| 10_41 | GctTTaAtttaatcacTCAT | 1 |
| 10_42 | GctTTAatttaatcaCtcAT | 5 |
| 10_43 | GcTttaatttaaTCactcAT | 15 |
| 10_44 | GcTttaatttaaTCactCAT | 11 |
| 10_45 | GcTttaatttaaTCaCtcAT | 15 |
| 10_46 | GcTttaatttaaTCActcAT | 7 |
| 10_47 | GcTttaaTttaatcactCAT | 23 |
| 10_48 | GcTttaaTttaatcacTCAT | 6 |
| 10_49 | GcTttaaTttaatcaCtcAT | 34 |
| 10_50 | GcTttaaTttaatcaCtCAT | 12 |
| 10_51 | GcTttaAtttaatcacTCAT | 10 |
| 10_52 | GcTttAatttaatcacTCAT | 5 |
| 10_53 | GcTttAatttaatcaCtcAT | 26 |
| 10_54 | GcTttAatttaatcaCtCAT | 10 |
| 10_55 | GcTttAaTttaatcacTCAT | 3 |
| 10_56 | GcTttAAtttaatcacTCAT | 2 |
| 10_57 | GcTtTaatttaatcacTCAT | 5 |
| 10_58 | GcTtTaatttaatcaCtCAT | 9 |
| 10_59 | GcTtTaaTttaatcacTCAT | 5 |
| 10_60 | GcTtTaAtttaatcacTCAT | 4 |
| 10_61 | GcTtTAatttaatcaCtcAT | 10 |
| 10_62 | GcTtTAatttaatcactcAT | 4 |
| 10_63 | GcTTtaaTttaatcacTCAT | 2 |
| 10_64 | GcTTtaAtttaatcactcAT | 21 |
| 10_65 | GcTTtaAtttaatcacTCAT | 2 |
| 10_66 | GcTTtAatttaatcacTCAT | 2 |
| 10_67 | GcTTtAatttaatcaCtCAT | 1 |
| 10_68 | GcTTtAAtttaatcactcAT | 4 |
| 10_69 | GcTTTaatttaatcaCTcAT | 1 |
| 10_70 | GcTTTAatttaatcaCtcAT | 5 |
| 10_71 | GCtttaatttaatCactcAT | 71 |
| 10_72 | GCtttaatttaaTCactcAT | 22 |
| 10_73 | GCtttaaTttaatcactcAT | 76 |
| 10_74 | GCtttaaTttaatcactCAT | 25 |
| 10_75 | GCtttaaTttaatcaCtcAT | 43 |
| 10_76 | GCtttaATttaatcactcAT | 25 |
| 10_77 | GCtttAatttaatcaCtcAT | 13 |
| 10_78 | GCtttAAtttaatcactcAT | 22 |
| 10_79 | GCttTaatttaatcaCtcAT | 16 |
| 10_80 | GCttTaAtttaatcactcAT | 8 |

TABLE 6-continued in vitro screening of anti-MAPT compounds

| CMP ID NO | Compound | % MAPT mRNA of control |
|---|---|---|
| 10_81 | GCttTAAtttaatcactcAT | 3 |
| 10_82 | GCtTtaAtttaatcactcAT | 21 |
| 10_83 | GCtTtAtttaatcaCtcAT | 7 |
| 10_84 | GCtTtAAtttaatcactcAT | 3 |
| 10_85 | GCTttaatttaatCactcAT | 29 |
| 10_86 | GCTttaaTttaatcactcAT | 32 |
| 10_87 | GCTttaAtttaatcactcAT | 38 |
| 10_88 | GCTttAAtttaatcactcAT | 6 |
| 10_89 | GCTtTaatttaatcAcTcAT | 9 |
| 11_1 | CTTTaatttaatcaCTCA | 0 |
| 12_1 | CTTTaatttaatcACTC | 0 |
| 19_1 | ACAccatccaagtCAAT | 20 |
| 20_1 | TACaccatccaagTCAA | 18 |
| 21_1 | TTAccatccaagtCA | 0 |
| 22_1 | TTACaccatccaaGTC | 5 |
| 23_1 | AATAttacaccatCCAA | 0 |
| 24_1 | AgaaTattacaccatCCAA | 11 |
| 24_2 | AgaaTattacaccaTcCAA | 8 |
| 24_3 | AgaaTattacaccaTCAA | 6 |
| 24_4 | AgaaTattacaccAtcAA | 11 |
| 24_5 | AgaaTattacaccAtCCAA | 14 |
| 24_6 | AgaaTattacaccATcAA | 6 |
| 24_7 | AgaaTattacaccATCAA | 2 |
| 24_8 | AgaaTattacacCaTCAA | 12 |
| 24_9 | AgaaTattacaCcAtCAA | 11 |
| 24_10 | AgaaTattacaCcATcAA | 18 |
| 24_11 | AgaAtattacaccatCCAA | 10 |
| 24_12 | AgaAtattacaccaTcAA | 12 |
| 24_13 | AgaATattacaccatcCAA | 1 |
| 24_14 | AgaATattacaccaTCAA | 1 |
| 24_15 | AgaATattacaccAtcAA | 9 |
| 24_16 | AgaATattacaccAtCAA | 0 |
| 24_17 | AgaATattacaccATcAA | 10 |
| 24_18 | AgaATattacaCAtCcAA | 3 |
| 24_19 | AgAatattacaccAtCAA | 10 |
| 24_20 | AgAatattacaccATCCAA | 13 |
| 24_21 | AgAaTattacaccatcCAA | 0 |
| 24_22 | AgAaTattacaccaTCcAA | 3 |
| 24_23 | AgAaTattacaccAtcCAA | 13 |
| 24_24 | AgAaTattacaccAtCCAA | 1 |
| 24_25 | AgAaTattacaccATCcAA | 8 |
| 24_26 | AgAaTattacacCatcCAA | 3 |
| 24_27 | AgAaTattacaCcatcCAA | 1 |
| 24_28 | AgAaTAttacacCAtcCAA | 5 |
| 24_29 | AgAAtattacaccaTCcAA | 13 |
| 24_30 | AgAATattacaccatcCAA | 10 |
| 24_31 | AgAATattacaccatCcAA | 4 |
| 24_32 | AgAATattacaccaTCcAA | 12 |
| 24_33 | AgAATattacaccAtcCAA | 13 |
| 24_34 | AgAATattacaccAtCcAA | 5 |
| 24_35 | AgAATattacacCaTCcAA | 4 |
| 24_36 | AGaatAttacaccaTCcAA | 5 |
| 24_37 | AGaatAttacacCatcCAA | 2 |
| 24_38 | AGaaTattacaccatcCAA | 11 |
| 24_39 | AGaaTattacaccatCcAA | 3 |
| 24_40 | AGaaTattacaccaTCcAA | 17 |
| 24_41 | AGaaTattacaccAtcCAA | 9 |
| 24_42 | AGaaTattacaccAtCcAA | 2 |
| 24_43 | AGaaTattacaccATCcAA | 5 |
| 24_44 | AGaaTattacaCcAtCcAA | 9 |
| 24_45 | AGaaTAttacacCatCcAA | 3 |
| 24_46 | AG aAtattacaccaTCcAA | 9 |
| 24_47 | AGaAtTattacacCaTCcAA | 26 |
| 24_48 | AGaATattacaccatcCAA | 8 |
| 24_49 | AGaATattacaccatCcAA | 0 |
| 24_50 | AGaATattacaccaTCcAA | 2 |
| 24_51 | AGaATattacaccAtcCAA | 4 |
| 24_52 | AGaATattacaccAtCcAA | 0 |
| 24_53 | AGaATAttacaccatCcAA | 1 |
| 24_54 | AGAatattacaccaTCcAA | 5 |
| 24_55 | AGAatattacaccAtcCAA | 1 |
| 24_56 | AGAatattacaccAtCcAA | 0 |
| 24_57 | AGAatattacaccatCcAA | 0 |
| 24_58 | AGAaTattacaccAtccAA | 13 |
| 24_59 | AGAaTattacaccAtCcAA | 11 |

TABLE 6-continued in vitro screening of anti-MAPT compounds

| CMP ID NO | Compound | % MAPT mRNA of control |
|---|---|---|
| 24_60 | AGAAtattacaccatCcAA | 11 |
| 24_61 | AGAAtattacacCatccAA | 56 |
| 24_62 | AGAAtAttacaccatCcAA | 4 |
| 25_1 | CagaaTattacaccaTcCAA | 8 |
| 25_2 | CagaaTattacaccaTCcAA | 11 |
| 25_3 | CagaaTattacacCatCcAA | 9 |
| 25_4 | CagaaTattacaCcAtCcAA | 12 |
| 25_5 | CagaAtattacaccaTCcAA | 20 |
| 25_6 | CagaAtattacaCCatccAA | 10 |
| 25_7 | CagaAtAttacacCAtccAA | 6 |
| 25_8 | CagaATattacaccatcCAA | 5 |
| 25_9 | CagaATattacaccatCcAA | 6 |
| 25_10 | CagaATattacaccaTCcAA | 9 |
| 25_11 | CagaATattacaccAtCcAA | 12 |
| 25_12 | CagAatattacaccaTCcAA | 11 |
| 25_13 | CagAatattacaccAtcCAA | 2 |
| 25_14 | CagAatAttacacCaTCcAA | 19 |
| 25_15 | CagAaTattacaccatcCAA | 13 |
| 25_16 | CagAaTattacaccaTCcAA | 7 |
| 25_17 | CagAaTattacaccAtcCAA | 0 |
| 25_18 | CagAaTattacaccAtCcAA | 13 |
| 25_19 | CagAaTattacacCaTCcAA | 6 |
| 25_20 | CagAaTAttacacCatCcAA | 12 |
| 25_21 | CagAAtattacacCAtccAA | 2 |
| 25_22 | CagAAtattacacCAtCcAA | 25 |
| 25_23 | CaGaaTattacaccatcCAA | 2 |
| 25_24 | CaGaaTattacaccatCcAA | 3 |
| 25_25 | CaGaaTattacaccaTCcAA | 5 |
| 25_26 | CaGaaTattacaccAtcCAA | 0 |
| 25_27 | CaGaaTattacaccAtCcAA | 10 |
| 25_28 | CaGaaTattacaCcatccAA | 4 |
| 25_29 | CaGaAtattacaccatCcAA | 6 |
| 25_30 | CaGaAtattacaccaTCcAA | 3 |
| 25_31 | CaGaAtAttacaccatCcAA | 6 |
| 25_32 | CaGaAtAttacaccAtCcAA | 2 |
| 25_33 | CaGAatattacacAtCcAA | 5 |
| 25_34 | CaGAatattacaCcAtccAA | 10 |
| 25_35 | CAgaaTattacaccatCcAA | 5 |
| 25_36 | CAgaaTattacaccAtccAA | 5 |
| 25_37 | CAgaaTattacaccAtCcAA | 3 |
| 25_38 | CAgaAtattacaccatCcAA | 26 |
| 25_39 | CAgAatattacaccAtccAA | 1 |
| 25_40 | CAgAatattacaccAtCcAA | 11 |
| 25_41 | CAgAaTattacaccAtccAA | 6 |
| 25_42 | CAgAaTattacacCatccAA | 73 |
| 25_43 | CAgAAtattacaccatCcAA | 1 |
| 26_1 | GaatattacacCAtCCAA | 11 |
| 26_2 | GaatattacacCATcCAA | 13 |
| 26_3 | GaatattacacCATCcAA | 10 |
| 26_4 | GaatAttacaccatCCAA | 0 |
| 26_5 | GaaTattacaccatCCAA | 2 |
| 26_6 | GaaTattacaccAtCCAA | 0 |
| 26_7 | GaaTAttacacCATCcAA | 8 |
| 26_8 | GaAtattacaccatCCAA | 1 |
| 26_9 | GaAtAttacaccatCCAA | 1 |
| 26_10 | GaAtAttacacCATCcAA | 22 |
| 26_11 | GaATattacaccatCCAA | 1 |
| 26_12 | GaATattacaccaTCcAA | 2 |
| 26_13 | GaATattacaccAtCCAA | 3 |
| 26_14 | GaATattacaccATCcAA | 3 |
| 26_15 | GaATattacacCAtcCAA | 1 |
| 26_16 | GAatattacaccAtCCAA | 0 |
| 26_17 | GAatattacaccATCcAA | 1 |
| 26_18 | GAatattacaCCATCcAA | 8 |
| 26_19 | GAatAttacacCATCcAA | 22 |
| 26_20 | GAaTattacaccatcCAA | 1 |
| 26_21 | GAaTattacaccaTCcAA | 1 |
| 26_22 | GAaTattacaccAtcCAA | 4 |
| 26_23 | GAaTattacaccATCcAA | 5 |
| 26_24 | GAaTattacacCatcCAA | 9 |
| 26_25 | GAaTattacacCAtccAA | 2 |
| 26_26 | GAAtattacaccatCCAA | 3 |
| 26_27 | GAAtattacaccaTCcAA | 3 |
| 26_28 | GAAtattacacCAtCcAA | 5 |
| 26_29 | GAATattacaccatcCAA | 0 |

TABLE 6-continued in vitro screening of anti-MAPT compounds

| CMP ID NO | Compound | % MAPT mRNA of control |
|---|---|---|
| 26_30 | GAATattacaccAtcCAA | 0 |
| 26_31 | GAATattacacCaTCcAA | 24 |
| 27_1 | AATAttacaccaTCCA | 0 |
| 28_1 | AgaaTattacaccatCCA | 1 |
| 28_2 | AgaaTattacaccaTcCA | 6 |
| 28_3 | AgaaTattacaccAtCCA | 1 |
| 28_4 | AgaaTattacaccATcCA | 5 |
| 28_5 | AgaAtattacaccatCCA | 5 |
| 28_6 | AgaAtattacaccaTCCA | 6 |
| 28_7 | AgaAtAttacaccaTcCA | 3 |
| 28_8 | AgaAtAttacacCatcCA | 4 |
| 28_9 | AgaAAtattacaccatcCA | 2 |
| 28_10 | AgaAAtattacaccAtcCA | 0 |
| 28_11 | AgAatattacaccaTCCA | 8 |
| 28_12 | AgAatattacaccAtCCA | 1 |
| 28_13 | AgAatattacacCAtcCA | 1 |
| 28_14 | AgAatAttacacCatcCA | 3 |
| 28_15 | AgAatAttacacCatCCA | 6 |
| 28_16 | AgAaTattacaccatcCA | 3 |
| 28_17 | AgAaTattacaccatCCA | 1 |
| 28_18 | AgAaTattacaccAtcCA | 3 |
| 28_19 | AgAaTattacaccAtCCA | 0 |
| 28_20 | AgAaTattacacCatcCA | 6 |
| 28_21 | AgAaTattacaCcatcCA | 3 |
| 28_22 | AgAaTAttacacCatcCA | 5 |
| 28_23 | AgAAtattacaccatCCA | 0 |
| 28_24 | AgAATattacaccatcCA | 2 |
| 28_25 | AgAATattacaccAtcCA | 3 |
| 28_26 | AGaaTattacaccatcCA | 2 |
| 28_27 | AGaaTattacaccAtcCA | 1 |
| 28_28 | AGaaTattacaccatCCA | 1 |
| 28_29 | AGaATattacaccatcCA | 0 |
| 28_30 | AGaATattacaccatcCA | 1 |
| 28_31 | AGAatattacaccAtcCA | 1 |
| 28_32 | AGAatattacaccatcCA | 1 |
| 28_33 | AGAatattacaccAtcCA | 5 |
| 29_1 | CagaaTattacaccaTcCA | 1 |
| 29_2 | CagaAtattacaccatCCA | 4 |
| 29_3 | CagaAtattacaCcatcCA | 15 |
| 29_4 | CagaATattacaccatcCA | 6 |
| 29_5 | CagaATattacaccAtcCA | 12 |
| 29_6 | CagaATattacacCatcCA | 3 |
| 29_7 | CagAaTattacaccatcCA | 2 |
| 29_8 | CagAaTattacaccAtcCA | 9 |
| 29_9 | CagAATattacaccatcCA | 0 |
| 29_10 | CaGaaTattacaccatcCA | 0 |
| 29_11 | CaGaaTattacaccAtcCA | 7 |
| 29_12 | CaGAatattacaccAtcCA | 4 |
| 29_13 | CAgAatattacaccAtcCA | 0 |
| 29_14 | CAgAatattacAccAtcCA | 2 |
| 30_1 | GaatattacacCAtCCA | 20 |
| 30_2 | GaatAttacaccaTCCA | 2 |
| 30_3 | GaaTattacaccatCCA | 1 |
| 30_4 | GaaTattacaccAtCCA | 1 |
| 30_5 | GaAtattacaccatCCA | 0 |
| 30_6 | GaAtattacaccaTCCA | 1 |
| 30_7 | GaAtattacacCAtCCA | 4 |
| 30_8 | GaAtattacaCCatcCA | 2 |
| 30_9 | GaAtAttacacCATcCA | 20 |
| 30_10 | GaATattacaccatCCA | 1 |
| 30_11 | GaATattacaccAtCCA | 4 |
| 30_12 | GAatattacaccaTCCA | 1 |
| 30_13 | GAatattacaccAtCCA | 1 |
| 30_14 | GAatAttacaccatCCA | 2 |
| 30_15 | GAatAttacacCatcCA | 3 |
| 30_16 | GAaTattacaccatcCA | 5 |
| 30_17 | GAaTattacaccatCCA | 0 |
| 30_18 | GAaTattacaccAtcCA | 5 |
| 30_19 | GAaTattacaccAtCCA | 3 |
| 30_20 | GAaTattacacCAtcCA | 2 |
| 30_21 | GAaTattacaCcatcCA | 2 |
| 30_22 | GAAtattacaccatCCA | 4 |
| 30_23 | GAAtattacacCatcCA | 2 |
| 30_24 | GAATattacaccatcCA | 1 |
| 30_25 | GAATattacaccAtcCA | 3 |

TABLE 6-continued in vitro screening of anti-MAPT compounds

| CMP ID NO | Compound | % MAPT mRNA of control |
|---|---|---|
| 31_1 | TcAgaaTattacaccatcCA | 10 |
| 31_2 | TcAgaaTattacaccAtcCA | 3 |
| 31_3 | TcAgaAtattacaccaTcCA | 7 |
| 32_1 | AgaaTattacaccaTCC | 1 |
| 32_2 | AgaaTattacaccATCC | 1 |
| 32_3 | AgaaTAttacacCatCC | 0 |
| 32_4 | AgaAtattacaccaTCC | 5 |
| 32_5 | AgaAtattacACcAtCC | 39 |
| 32_6 | AgaAtAttacacCatCC | 7 |
| 32_7 | AgaATattacaccaTCC | 1 |
| 32_8 | AgaATattacaccAtCC | 0 |
| 32_9 | AgaATattacaccATCC | 1 |
| 32_10 | AgAatattacaccaTCC | 1 |
| 32_11 | AgAatattacaccATCC | 5 |
| 32_12 | AgAatattacaCCAtCC | 5 |
| 32_13 | AgAatattacaCcATCC | 15 |
| 32_14 | AgAatattacAccaTCC | 3 |
| 32_15 | AgAatattacACcatCC | 0 |
| 32_16 | AgAatattacACCatCC | 18 |
| 32_17 | AgAaTattacaccaTCC | 4 |
| 32_18 | AgAaTattacaccAtCC | 3 |
| 32_19 | AgAaTattacaccATCC | 3 |
| 32_20 | AgAaTattacacCatCC | 10 |
| 32_21 | AgAaTattacaCcAtCC | 18 |
| 32_22 | AgAAtattacaccaTCC | 5 |
| 32_23 | AgAAtattacaCCatCC | 6 |
| 32_24 | AgAAtattacAcCAtCC | 34 |
| 32_25 | AgAATattacaccatCC | 1 |
| 32_26 | AgAATattacaccaTCC | 1 |
| 32_27 | AgAATattacaccAtCC | 2 |
| 32_28 | AgAATattacaccATCC | 2 |
| 32_29 | AgAATattacaCcAtCC | 13 |
| 32_30 | AGaaTattacaccatCC | 5 |
| 32_31 | AGaaTattacaccaTCC | 0 |
| 32_32 | AGaaTattacaccAtCC | 4 |
| 32_33 | AGaaTattacaccATCC | 1 |
| 32_34 | AGaAtattacaccatCC | 2 |
| 32_35 | AGaAtattacaccaTCC | 1 |
| 32_36 | AGaAtattacacCaTCC | 4 |
| 32_37 | AGaAtattacAccATCC | 11 |
| 32_38 | AGaATattacaccatCC | 0 |
| 32_39 | AGaATattacaccAtCC | 0 |
| 32_40 | AGAatattacaccaTCC | 4 |
| 32_41 | AGAatattacaccAtCC | 0 |
| 32_42 | AGAatattacAccaTCC | 2 |
| 32_43 | AGAatattacAccAtCC | 10 |
| 32_44 | AGAatattacAcCatCC | 12 |
| 32_45 | AGAatAttacaccatCC | 3 |
| 32_46 | AGAaTattacaccatCC | 1 |
| 32_47 | AGAaTattacaccAtCC | 1 |
| 32_48 | AGAAtattacaccatCC | 0 |
| 32_49 | AGAAtattacaccaTCC | 0 |
| 32_50 | AGAAtattacacCatCC | 0 |
| 32_51 | AGAAtattacAcCatCC | 5 |
| 33_1 | CagaaTattacaccaTCC | 7 |
| 33_2 | CagaAtattacaccaTCC | 55 |
| 33_3 | CagaAtattacaCcaTCC | 19 |
| 33_4 | CagaAtattacAccaTCC | 8 |
| 33_5 | CagaAtattacACcatCC | 20 |
| 33_6 | CagaATattacaccatCC | 1 |
| 33_7 | CagaATattacaccaTCC | 2 |
| 33_8 | CagaATattacaccAtCC | 3 |
| 33_9 | CagAatattacaccaTCC | 1 |
| 33_10 | CagAatAttacaccaTCC | 10 |
| 33_11 | CagAaTattacaccaTCC | 0 |
| 33_12 | CagAAtattacaccaTCC | 11 |
| 33_13 | CagAAtattacacCaTCC | 4 |
| 33_14 | CagAATattacaCcatCC | 3 |
| 33_15 | CaGaatAttacacCAtCC | 5 |
| 33_16 | CaGaaTattacaccAtCC | 1 |
| 33_17 | CaGaAtattacaccatCC | 1 |
| 33_18 | CaGaAtattacaccaTCC | 14 |
| 33_19 | CaGaAtattacaCcatCC | 6 |
| 33_20 | CaGaAtattacACcAtCC | 53 |
| 33_21 | CaGAatattacaccAtCC | 0 |

TABLE 6-continued in vitro screening of anti-MAPT compounds

| CMP ID NO | Compound | % MAPT mRNA of control |
|---|---|---|
| 33_22 | CAgaaTattacaccatCC | 0 |
| 33_23 | CAgaaTattacaccAtCC | 1 |
| 33_24 | CAgaAtattacaccatCC | 3 |
| 33_25 | CAgaAtattacaccaTCC | 61 |
| 33_26 | CAgaAtAttacacCatCC | 5 |
| 33_27 | CAgAatattacaccaTCC | 8 |
| 33_28 | CAgAatattacaccAtCC | 0 |
| 33_29 | CAgAaTattacaccatCC | 0 |
| 33_30 | CAgAaTattacaccAtCC | 1 |
| 33_31 | CAgAAtattacaccatCC | 13 |
| 33_32 | CAgAAtattacAccatCC | 1 |
| 33_33 | CAGaAtattacaccatCC | 10 |
| 34_1 | GAATattacaccATCC | 0 |
| 35_1 | TCagaaTattacaccatCC | 10 |
| 35_2 | TCagaAtattacaccatCC | 11 |
| 35_3 | TCagaAtattacAccatCC | 9 |
| 36_1 | AGAAtattacacCATC | 0 |
| 37_1 | CAGAatattacaCCAT | 0 |
| 38_1 | CAattctcatttcaacCTTC | 14 |
| 39_1 | TCaattctcatttcaacCTT | 35 |
| 40_1 | ATCaattctcatttcaacCT | 17 |
| 41_1 | AATCaattctcatttcaACC | 28 |
| 42_1 | AAATcaattctcatttCAAC | 38 |
| 43_1 | CAAAtcaattctcattTCAA | 22 |
| 44_1 | TCAaatcaattctcatTTCA | 0 |
| 45_1 | CTCAaatcaattctcatTTC | 6 |
| 46_1 | ACTCaaatcaattctcATTT | 5 |
| 47_1 | AACTcaaatcaattctCATT | 37 |
| 48_1 | TAACtcaaatcaattcTCAT | 20 |
| 49_1 | TtaactCaaatcaattcTCA | 46 |
| 49_2 | TtaactCAaatcaattctCA | 35 |
| 49_3 | TtaactCAaatcaattcTCA | 9 |
| 49_4 | TtaacTCaaatcaattctCA | 33 |
| 49_5 | TtaacTCAaatcaattctCA | 6 |
| 49_6 | TtaaCtcaaatcaattctCA | 63 |
| 49_7 | TtaaCtcaaatcaattcTCA | 18 |
| 49_8 | TtaaCtcaaatcaatTCtCA | 19 |
| 49_9 | TtaaCtcaaatcaaTtctCA | 80 |
| 49_10 | TtaaCtcaaatcaaTtcTCA | 26 |
| 49_11 | TtaaCtcaaatcaaTtCtCA | 30 |
| 49_12 | TtaaCtcaaatcaaTtCTCA | 18 |
| 49_13 | TtaaCtcaaatcaaTTCtCA | 32 |
| 49_14 | TtaaCtcaaatcAattcTCA | 22 |
| 49_15 | TtaaCtcAaatcaattcTCA | 20 |
| 49_16 | TtaaCtcAaatcaattCtCA | 28 |
| 49_17 | TtaaCtcAaatcaattCTCA | 7 |
| 49_18 | TtaaCtcAaatcaatTctCA | 19 |
| 49_19 | TtaaCtcAaatcaatTCtCA | 9 |
| 49_20 | TtaaCtcAaatcaaTtctCA | 33 |
| 49_21 | TtaaCtcAaatcaaTtcTCA | 13 |
| 49_22 | TtaaCtcAaatcaaTtCtCA | 16 |
| 49_23 | TtaaCtcAaatcaaTtCTCA | 12 |
| 49_24 | TtaaCtcAaatcaaTTCtCA | 19 |
| 49_25 | TtaaCtCaaatcaattctCA | 33 |
| 49_26 | TtaaCtCaaatcaattcTCA | 14 |
| 49_27 | TtaaCtCaaatcaattCtCA | 17 |
| 49_28 | TtaaCtCaaatcaattCTCA | 7 |
| 49_29 | TtaaCtCaaatcaatTCtCA | 7 |
| 49_30 | TtaaCtCAaatcaattctCA | 7 |
| 49_32 | TtaaCtCAaatcaattCtCA | 10 |
| 49_33 | TtaaCtCAaatcaaTtctCA | 10 |
| 49_34 | TtaaCtCAaatcaaTtCtCA | 6 |
| 49_35 | TtaaCTCaaatcaattctCA | 10 |
| 49_36 | TtaaCTCaaatcaattCtCA | 7 |
| 49_37 | TtaaCTCAaatcaattctCA | 4 |
| 49_39 | TtaActcaaatcaatTCtCA | 24 |
| 49_40 | TtaActcaaatcaaTtCtCA | 26 |
| 49_41 | TtaActcaaatcaaTtCTCA | 17 |
| 49_42 | TtaActcAaatcaattCtCA | 33 |
| 49_43 | TtaActcAaatcaatTCtCA | 11 |
| 49_44 | TtaActcAaatcaaTtcTCA | 15 |
| 49_45 | TtaActcAaatcaaTtCtCA | 24 |
| 49_46 | TtaActCaaatcaattCtCA | 20 |
| 49_47 | TtaActCaaatcaattCTCA | 6 |
| 49_48 | TtaActCaaatcaatTCtCA | 6 |

TABLE 6-continued in vitro screening of anti-MAPT compounds

| CMP ID NO | Compound | % MAPT mRNA of control |
|---|---|---|
| 49_49 | TtaActCAaatcaattctCA | 18 |
| 49_50 | TtaActCAaatcaattCtCA | 9 |
| 49_53 | TtaActCAaatcaaTtctCA | 12 |
| 49_54 | TtaActCAaatcaaTtCtCA | 6 |
| 49_55 | TtaAcTCaaatcaattctCA | 7 |
| 49_56 | TtaACtcaaatcaattCtCA | 30 |
| 49_57 | TtaACtcaaatcaattCTCA | 7 |
| 49_58 | TtaACtcaaatcaatTCtCA | 11 |
| 49_59 | TtaACtcaaatcaaTtctCA | 47 |
| 49_60 | TtaACtcaaatcaaTtCtCA | 18 |
| 49_61 | TtaACtcaaatcaaTtCTCA | 9 |
| 49_62 | TtaACtcaaatcaaTTCtCA | 17 |
| 49_63 | TtaACtcaaatcAattctCA | 40 |
| 49_64 | TtaACtcAaatcaattctCA | 23 |
| 49_65 | TtaACtcAaatcaattCtCA | 13 |
| 49_67 | TtaACtcAaatcaatTCtCA | 4 |
| 49_68 | TtaACtcAaatcaaTtctCA | 19 |
| 49_69 | TtaACtcAaatcaaTtCtCA | 12 |
| 49_70 | TtaACtcAaatcaaTtCTCA | 9 |
| 49_71 | TtaACtcAaatcaaTTCtCA | 16 |
| 49_72 | TtaACtCaaatcaattctCA | 12 |
| 49_73 | TtaACtCaaatcaattCtCA | 9 |
| 49_74 | TtaACtCaaatcaattCTCA | 4 |
| 49_75 | TtaACtCaaatcaatTCtCA | 4 |
| 49_76 | TtaACtCAaatcaattctCA | 3 |
| 49_78 | TtaACtCAaatcaaTtctCA | 3 |
| 49_79 | TtaACTCaaatcaattCtCA | 6 |
| 49_80 | TtAactcaaatcaaTtCtCA | 11 |
| 49_81 | TtAactcaaatcaAttCtCA | 35 |
| 49_82 | TtAactcaaatcaAtTCtCA | 18 |
| 49_83 | TtAactcaaatcaATtCtCA | 21 |
| 49_84 | TtAactcaaatcaATTCtCA | 36 |
| 49_85 | TtAactcaaatcaatTCtCA | 7 |
| 49_86 | TtAactcAaatcaaTtCtCA | 6 |
| 49_87 | TtAactCaaatcaattCtCA | 19 |
| 49_88 | TtAactCaaatcaattCTCA | 7 |
| 49_89 | TtAactCaaatcaatTCtCA | 6 |
| 49_90 | TtAactCAaatcaattCtCA | 9 |
| 49_92 | TtAactCAaatcaaTtCtCA | 3 |
| 49_93 | TtAactCAaatcaaTTCtCA | 11 |
| 49_94 | TtAaCtcaaatcaattCtCA | 34 |
| 49_95 | TtAaCtcaaatcaatTCtCA | 11 |
| 49_96 | TtAaCtcaaatcaaTtctCA | 56 |
| 49_97 | TtAaCtcaaatcaaTtCtCA | 15 |
| 49_98 | TtAaCtcaaatcaaTtCTCA | 14 |
| 49_99 | TtAaCtcaaatcaaTTCtCA | 30 |
| 49_100 | TtAaCtcaaatcAattctCA | 46 |
| 49_101 | TtAaCtcAaatcaattctCA | 24 |
| 49_102 | TtAaCtcAaatcaattCtCA | 22 |
| 49_103 | TtAaCtcAaatcaattCTCA | 8 |
| 49_104 | TtAaCtcAaatcaatTCtCA | 6 |
| 49_105 | TtAaCtcAaatcaaTtctCA | 28 |
| 49_106 | TtAaCtcAaatcaaTtCtCA | 31 |
| 49_107 | TtAaCtcAaatcaaTtCTCA | 29 |
| 49_108 | TtAaCtcAaatcaaTTCtCA | 38 |
| 49_109 | TtAaCtCaaatcaattctCA | 21 |
| 49_110 | TtAaCtCaaatcaattCtCA | 19 |
| 49_111 | TtAaCtCaaatcaatTCtCA | 9 |
| 49_112 | TtAaCtCAaatcaattctCA | 10 |
| 49_113 | TtAaCtCAaatcaattCtCA | 10 |
| 49_114 | TtAaCtCAaatcaaTtctCA | 6 |
| 49_115 | TtAActcaaatcaatTCtCA | 6 |
| 49_116 | TtAActcaaatcaaTtCtCA | 9 |
| 49_117 | TtAActcAaatcaattCtCA | 11 |
| 49_118 | TtAActcAaatcaatTCtCA | 3 |
| 49_119 | TtAActcAaatcaaTtCtCA | 11 |
| 49_120 | TtAActCaaatcaattCtCA | 33 |
| 49_121 | TtAActCaaatcaatTCtCA | 2 |
| 49_123 | TtAActCAaatcaatTCtCA | 1 |
| 49_125 | TtAACtcaaatcaattCtCA | 6 |
| 49_126 | TtAACtcaaatcaattCTCA | 5 |
| 49_127 | TtAACtcaaatcaatTCtCA | 9 |
| 49_128 | TtAACtcaaatcaaTtctCA | 33 |
| 49_129 | TtAACtcaaatcaaTtCtCA | 12 |
| 49_130 | TtAACtcaaatcaaTTCtCA | 19 |

TABLE 6-continued in vitro screening of anti-MAPT compounds

| CMP ID NO | Compound | % MAPT mRNA of control |
|---|---|---|
| 49_131 | TtAACtcaaatcAattctCA | 25 |
| 49_132 | TtAACtcAaatcaattctCA | 15 |
| 49_133 | TtAACtcAaatcaattCtCA | 6 |
| 49_134 | TtAACtcAaatcaatTCtCA | 10 |
| 49_135 | TtAACtcAaatcaaTtctCA | 15 |
| 49_136 | TtAACtcAaatcaaTtCtCA | 22 |
| 49_137 | TtAACtcAaatcaaTTCtCA | 33 |
| 49_138 | TtAACtCaaatcaattctCA | 8 |
| 49_139 | TtAACtCaaatcaattCtCA | 6 |
| 49_141 | TtAACtCaaatcaatTCtCA | 11 |
| 49_143 | TtAACtCAaatcaaTtctCA | 3 |
| 49_144 | TTaactcAaatcaattCtCA | 14 |
| 49_145 | TTaactcAaatcaatTCtCA | 6 |
| 49_146 | TTaactcAaatcaaTtCtCA | 6 |
| 49_147 | TTaactcAaatcaaTTCtCA | 9 |
| 49_148 | TTaactCAaatcaattCtCA | 6 |
| 49_149 | TTaactCAaatcaatTCtCA | 2 |
| 49_150 | TTaaCtcaaatcaattCtCA | 26 |
| 49_151 | TTaaCtcaaatcaattCTCA | 8 |
| 49_152 | TTaaCtcaaatcaatTCtCA | 11 |
| 49_153 | TTaaCtcaaatcaaTtctCA | 41 |
| 49_154 | TTaaCtcaaatcaaTtCtCA | 14 |
| 49_155 | TTaaCtcaaatcAattctCA | 38 |
| 49_156 | TTaaCtcAaatcaattctCA | 23 |
| 49_157 | TTaaCtcAaatcaattCtCA | 13 |
| 49_158 | TTaaCtcAaatcaattCTCA | 4 |
| 49_159 | TTaaCtcAaatcaatTCtCA | 6 |
| 49_160 | TTaaCtcAaatcaaTtctCA | 20 |
| 49_161 | TTaaCtcAaatcaaTtCtCA | 12 |
| 49_162 | TTaaCtCaaatcaattctCA | 18 |
| 49_163 | TTaaCtCaaatcaattCtCA | 10 |
| 49_164 | TTaaCtCAaatcaattctCA | 7 |
| 49_166 | TTaActcaaatcaaTtCtCA | 17 |
| 49_167 | TTaActCaaatcaattctCA | 7 |
| 49_168 | TTaActCAaatcaattctCA | 3 |
| 49_169 | TTaACtcaaatcaaTtCtCA | 12 |
| 49_170 | TTaACtcAaatcaaTtCtCA | 9 |
| 49_171 | TTaACtcAaatcaaTtCtCA | 25 |
| 49_172 | TTAactcaaatcaaTtCtCA | 16 |
| 49_173 | TTAactcaaatcaAttCtCA | 27 |
| 49_174 | TTAactcaaatcaAtTCtCA | 14 |
| 49_175 | TTAactcAaatcaatTCtCA | 5 |
| 49_176 | TTAactcAaatcaaTtCtCA | 6 |
| 49_177 | TTAactCaaatcaattCtCA | 15 |
| 49_178 | TTAactCaaatcaattCTCA | 4 |
| 49_180 | TTAactCAaatcaattCtCA | 6 |
| 49_181 | TTAaCtcaaatcaattCtCA | 23 |
| 49_182 | TTAaCtcaaatcaaTtctCA | 38 |
| 49_183 | TTAaCtCaaatcaaTtCtCA | 17 |
| 49_184 | TTAaCtCaaatcAattctCA | 40 |
| 49_185 | TTAaCtcAaatcaattctCA | 19 |
| 49_186 | TTAaCtCaaatcaattCtCA | 13 |
| 49_187 | TTAaCtcAaatcaaTtCtCA | 13 |
| 49_188 | TTAaCtCaaatcaattctCA | 18 |
| 49_189 | TTAActcaaatcaattCTCA | 3 |
| 49_190 | TTAActcaaatcaatTCtCA | 9 |
| 49_191 | TTAActcAaatcaatTCtCA | 3 |
| 49_192 | TTAActCaaatcaattCtCA | 6 |
| 50_1 | TTTAactcaaatcaatTCTC | 1 |
| 51_1 | TTTAactcaaatcaaTTCT | 10 |
| 52_1 | CCTTttaattcaTTAG | 72 |
| 53_1 | CAAccttttaattcATTA | 0 |
| 54_1 | AACccttttaattCATT | 27 |
| 55_1 | CAtcaacaccttttaaTTCA | 100 |
| 56_1 | CTCAtcaacaccttttaaTT | 15 |
| 57_1 | ACtcatcaacacctttTAAT | 37 |
| 58_1 | AACtcatcaacacctTTAA | 16 |
| 59_1 | TAACtcatcaacaccttttA | 18 |
| 60_1 | TTAActcatcaacaccTTTT | 12 |
| 61_1 | TTAactcatcaacacCTTT | 4 |
| 62_1 | TTAactcatcaacaCCTT | 3 |
| 63_1 | TTAActcatcaacACCT | 0 |
| 64_1 | GTTAactcatcaacACC | 29 |
| 65_1 | GTTAactcatcaaCAC | 78 |

Example 3 IC50 Values of Selected Oligonucleotides

The 1050 of some of the best performing oligonucleotides from Example 2 was determined in vitro in primary neuronal cells using a 96 well assay.

Primary neuronal cell cultures were prepared as described in the "Materials and Method" section and plated on poly-D-lysine coated 96 well plates at 50,000 cells per well and maintained in Neurobasal media containing B27, glutamax and Penicillin-Streptomycin. ASOs were diluted in water (for IC50 determinations) and added to cells at 1 day post plating (DIV01). For $IC_{50}$ determinations, neurons were treated with a top concentration of 0.5 to 5 μM and a concentration response dilution of about 1:4 was used to define the IC50. CMP ID NO: 66_1, corresponding to ASO-001933 in WO2016/126995, was included as a positive control. Following ASO treatment, neurons were incubated at 3700 for 5 days to achieve steady state reduction of mRNA. Media was removed and cells lysed as follows. Measurement of lysate messenger RNA was performed using the QUANTIGENE® 2.0 Reagent System (AF-FYMETRIX®), which quantitated RNA using a branched DNA-signal amplification method reliant on the specifically designed RNA capture probe set. The working cell lysis buffer solution was made by adding 50 μl proteinase K to 5 ml of pre-warmed Lysis mix and diluted to 1:4 final dilution with $dH_2O$. The working lysis buffer was added to the plate (150 μl/well), triturated to mix, sealed and incubated for 30 min at 55° C. Following lysis the wells were stored at −80° C. or assayed immediately.

Lysates were diluted in lysis mix dependent on the specific capture probe used (tau or tubulin). 80 μl/well total were then added to the capture plate (96 well polystyrene plate coated with capture probes). Working probe sets reagents were generated by combining nuclease-free water 12.1 μl, lysis mixture 6.6 μl, blocking reagent 1 μl, specific 2.0 probe set 0.3 μl human MAPT catalogue #15486 and either mouse beta 3 tubulin, catalogue #SB-17245, per manufacturer instructions (QUANTIGENE® 2.0 AFFYME-TRIX©). Then 20 μl working probe set reagents were added to 80 μl lysate dilution (or 80 μl lysis mix for background samples) on the capture plate. Plates were centrifuged and then incubated for 16-20 hours at 55° C. to hybridize (target RNA capture). Signal amplification and detection of target RNA was begun by washing plates with buffer 3 times to remove unbound material. 2.0 Pre-Amplifier hybridization reagent (100 μl/well) was added, incubated at 55° C. for 1 hour then aspirated and wash buffer was added and aspirated 3 times. The 2.0 Amplifier hybridization reagent was then added as described (100 μl/well), incubated for 1 hour at 55° C. and the wash was repeated as described previously. The 2.0 Label Probe hybridization reagent was added next (100 μl/well), incubated for 1 hour at 50° C. and the wash was repeated as described previously. Lastly, the plates were centrifuged to remove any excess wash buffer and 2.0 Substrate was added (100 μl/well). Plates were incubated for 5 minutes at room temperature and plates were imaged on a PerkinElmer Envision multilabel reader in luminometer mode within 15 minutes.

Data determination: For the gene of interest, the average assay background signal was subtracted from the average signal of each technical replicate. The background-subtracted, average signals for the gene of interest are divided by the background-subtracted average signal for the housekeeping tubulin RNA. The percent inhibition for the treated sample was calculated relative to untreated sample (i.e. the lower the value the larger the inhibition). Variability in background of untreated samples may result in percent inhibition of a treated sample that are equal to or higher than background, and in these cases, percent inhibition is expressed as 100% inhibition of control (i.e. no inhibition). The results are shown in table 7.

TABLE 7

IC50 of anti-MAPT compounds

| CMP ID NO | Compound | Region | IC50 (nM) |
|---|---|---|---|
| 9_103 | CTTTaatttaatcacTCAT | A | 12.2 |
| 11_1 | CTTTaatttaatcaCTCA | A | 9.4 |
| 34_1 | GAATattacaccATCC | A | 32.0 |
| 37_1 | CAGAatattacaCCAT | A | 15.6 |
| 49_189 | TTAActcaaatcaattCTCA | B | 11.8 |
| 56_1 | CTCAtcaacacctttaaTT | C | 44.0 |
| 62_1 | TTAactcatcaacaCCTT | C | 40.5 |
| 63_1 | TTAActcatcaacACCT | C | 37.1 |
| 66_1 | AtTTCcaaattcactTTtAC | — | 44.3 |

Example 4 In Vivo Tolerability and In Vivo Tau mRNA Reduction

Some of the best performing oligonucleotides from Example 2 were tested in vivo in a humanized Tau mouse to assess acute tolerability in CNS as well as MAPT mRNA reduction 3 days or 28 days after a single injection.

Transgenic Tau mice were administered with 100 μg ASO by intracerebroventricular (ICV) injection (see Materials and Method section, Transgenic Tau mouse). CMP ID NO: 66_1, corresponding to ASO-001933 in WO2016/126995, was included as a positive control. Animals were observed for behavioral side effects for one hour following the single injection of ASO ICV. The acute tolerability for the severity of side effects was scored on a scale of zero (no side effects) to 20 (convulsions resulting in euthanasia). The tolerability scale was divided into 5 neurobehavioral categories: 1) hyperactivity 2) decreased activity and arousal 3) motor dysfunction/ataxia 4) abnormal posture and breathing and 5) tremor/convulsions. Each category was scored on a scale of 0-4, with the worst possible total score of 20. Animals were observed for changes in behavior in the home cage, and then they were removed from the home cage for more detailed observations which included measurement of grip strength and righting reflex. Data from acute tolerability of ASO of the invention are presented in table 8.

The MAPT mRNA reduction in right, frontal cortical region was analyzed by qPCR as follows. Collected mouse brain tissue (see Materials and Methods section, Transgenic Tau mouse) was homogenized in a 10× volume of a high salt/sucrose buffer (10 mM Tris-HCl, pH 7.4, 800 mM NaCl, 10% sucrose (w/v), 1 mM EGTA) supplemented with phosphatase inhibitor cocktail sets 2 and 3, 1 mM PMSF (Sigma, Saint Louis, MO), and complete protease inhibitor cocktail EDTA-free (Roche, Indianapolis, IN) using a Quiagen TissueLyzer II. The homogenate was centrifuged at 20,000×g for 20 minutes at 4° C. The supernatant was centrifuged at 100,000×g for 1 hour at 4° C.

For cDNA synthesis and subsequent PCR, 300 ng of RNA from brain tissue supernatants was added to 1 well of a 96 well plate (Axygen, PCR-96-C-S). To each well 7.5 µl of master mix (5 µL of 2.5 mM NTP mix and 2.5 µL random primers per reaction) was added and the plate was centrifuged at 1000 rpm and placed in thermocycler for 3 min at 70° C. Plates were immediately cooled on ice and 4 µl of reaction master mix was added. Prior to PCR, plates were briefly centrifuged to collect sample in bottom of well. cDNA synthesis was carried out at 42° C. for 60 min, 95° C. for 10 min followed by a hold at 4° C. cDNA Samples were diluted 1:3 with molecular biology grade water and stored at −20° C. until further use.

For PCR, each sample was run in triplicate with two probe sets (MAPT: Taqman Expression assays Hs00902193_m1; GAPDH Taqman Expression assays Hs01922876_u1). To each reaction 4 µl of previously diluted cDNA and 6 µL of master mix was added and plates were centrifuged. Samples were incubated at 95° C. for 20 sec follow by 40 cycles at 95° C. for 1 sec and 60° C. for 20 sec.

Data were analyzed using the delta delta Ct method where each sample was first normalized to GAPDH and then expressed as percent of untreated control (percent inhibition). If the percent inhibition was equal to or higher than in control cells, percent inhibition was expressed as zero inhibition.

TABLE 8

Acute tolerability in hTau mice and MAPT mRNA reduction 3 days and 4 weeks post treatment in vivo

| CMP ID NO | Compound | Region | Acute tolerability | % MAPT mRNA of saline Day 3 | 4 weeks |
|---|---|---|---|---|---|
| 9_103 | CTTTaatttaatcacTCAT | A | 0.5 | 16 | 16 |
| 11_1 | CTTTaatttaatcaCTCA | A | 0.0 | 16 | 18 |
| 9_104 | CTTTaatttaatcaCtCAT | A | 0.25 | NA | 28 |
| 9_102 | CTTtAATtaatcactcAT | A | 1.75 | NA | 20 |
| 34_1 | GAATattacaccATCC | A | 0.0 | 36 | 20 |
| 9_91 | CTtTAatttaatcaCtCAT | A | 0.50 | NA | 84 |
| 9_83 | CTttAATttaatcacTCAT | A | 0.75 | NA | 31 |
| 9_17 | CtttaATttaatcacTCAT | A | 0.50 | NA | 65 |
| 9_88 | CTtTAatttaatcactCAT | A | 0.50 | NA | 43 |
| 9_96 | CTTtaATttaatcactcAT | A | 2.50 | NA | 54 |
| 9_95 | CTtTAATttaatcactcAT | A | 4.13 | NA | 34 |
| 9_93 | CTtTAAtttaatcactcAT | A | 1.88 | NA | 52 |
| 9_87 | CTtTaATttaatcactcAT | A | 1.63 | NA | 46 |
| 9_55 | CtTTAaTttaatcactcAT | A | 2.50 | NA | 54 |
| 37_1 | CAGAatattacaCCAT | A | 0.0 | 27 | NA |
| 49_189 | TTAActcaaatcaattCTCA | B | 0.0 | 29 | 29 |
| 49_38 | TtaaCTCAaatcaaTtctCA | B | 1.50 | NA | 18 |
| 49_179 | TTAactCaaatcaatTCtCA | B | 1.0 | NA | 32 |
| 49_51 | TtaActCAaatcaattCTCA | B | 1.25 | NA | 31 |
| 49_124 | TtAActCAaatcaaTtCtCA | B | 1.50 | NA | 48 |
| 49_165 | TTaaCtCAaatcaaTtctCA | B | 0.88 | NA | 44 |
| 49_91 | TtAactCAaatcaatTCTCA | B | 0.63 | NA | 60 |
| 49_52 | TtaActCAaatcaatTCtCA | B | 2.88 | NA | 56 |
| 49_140 | TtAACtCaaatcaattCTCA | B | 0.25 | NA | 43 |
| 49_66 | TtaActcAaatcaattCTCA | B | 0.0 | NA | 36 |
| 49_142 | TtAACtCAaatcaattCtCA | B | 0.5 | NA | 36 |
| 49_122 | TtAActCAaatcaattCtCA | B | 0.75 | NA | 56 |
| 49_77 | TtaACtCAaatcaattCtCA | B | 1.13 | NA | 55 |

TABLE 8-continued

Acute tolerability in hTau mice and MAPT mRNA reduction 3 days and 4 weeks post treatment in vivo

| CMP ID NO | Compound | Region | Acute tolerability | % MAPT mRNA of saline Day 3 | 4 weeks |
|---|---|---|---|---|---|
| 50_1 | TTTAactcaaatcaatTCTC | B | NA | 26 | NA |
| 53_1 | CAACaccttttaattcATTA | C | NA | 21 | NA |
| 56_1 | CTCAtcaacaccttttaaTT | C | 0.2 | 25 | NA |
| 62_1 | TTAactcatcaacaCCTT | C | 0.0 | 39 | 28 |
| 63_1 | TTAActcatcaacACCT | C | 0.5 | 13 | NA |
| 66_1 | AtTTCcaaattcactTTtAC | — | 0.83 | 37 | 44 |

NA = not assessed

Example 5: In Vitro Efficacy in Human Embryonic Stem Cell (hESC) Derived Neurons Selected ASO's from example 2 were tested at three different concentrations (200 nM, 8 nM and 0.32 nM) in an alternative in vitro assay using human embryonic stem cell (hESC) derived neurons. For comparative purposes two prior art oligonucleotides targeting MAPT were included, namely CMP ID NO: 66_1 corresponding to ASO-001933 in WO2016/126995 and CPM ID NO: 67:1 corresponding to compound No 814907 in WO2018/064593.

Culturing and ASO Treatment of Human Embryonic Stem Cells (ESCs):

Neural stem cells (NSCs) were derived from human ESCs according to published procedures (Chambers et al. 2009 Nat. Biotech. 7, 275-280). The neural stem cells (NSCs) were proliferated into ventralized progenitors during 1 week in SFA medium, and was then differentiated into neurons in BGAA medium during 6 weeks, for media content, please see the Materials and methods section.

Cells were seeded at a density of 10,000 cells/cm$^2$ in N2B27+SFA medium in a flask coated with poly-ornithine and laminin. Media was changed at day 4. After 7 days in N2B27+SFA medium cells were trypsinized, and seeded as ventralized progenitors in N2B27+BGAA media at a density of 50,000 cell/well in 96 well plates.

Media was changed twice a week and treatment with ASO was started at the first media change and continued for 6 weeks. Then cells were harvested as described below.

qPCR Analysis:

Treated neurons were harvested as follows: removal of media followed by addition of 125 µL PURELINK® Pro 96 Lysis buffer and 125 µL 70% ethanol. RNA was purified according to the manufacture's instruction and eluted in a final volume of 50 µL water, resulting in an RNA concentration of 10-20 ng/µL. Next, RNA was diluted 10 fold in water prior to the one-step qPCR reaction.

For the one-step qPCR reaction, qPCR-mix (qScriptTMXLE 1-step RT-qPCR TOUGHMIX® Low ROX from QauntaBio) was mixed with two Taqman probes at a ratio 10:1:1 (qPCR mix: probe1:probe2) to generate the mastermix. The qPCR was performed as technical replicates and Taqman probes were acquired from LifeTechnologies: MAPT_Hs00902193_m1; GAPDH 4325792 (house keeping gene used for normalization).

The mastermix (6 µL) and RNA (4 µL, 1-2 ng/µL) were then mixed in a qPCR plate (MICROAMP® optical 384 well, catalog no. 4309849). After sealing the plate, the plate was given a quick spin, 1000 g for 1 minute at RT, and transferred to a Viia™ 7 system (Applied Biosystems, Thermo). The following PCR conditions were used: 50° C. for 15 minutes; 95° C. for 3 minutes; 40 cycles of: 95° C. for 5 sec, followed by a temperature decrease of 1.6° C./sec, followed by 60° C. for 45 sec. The data was analyzed using the QuantStudio™ Real_time PCR Software. The percent inhibition for the ASO treated samples was calculated relative to the control treated samples (low values indicate high reduction of MAPT). The results are shown in table 9 as the average of the two technical repeats.

Tau Protein and pTau Protein Measurement in hESC Neurons:

PBS-washed cells were extracted into a buffer containing Cytobuster protein extraction reagent (Merck-Millipore #71009), 1% Phosphatase Inhibitor Cocktail 3 (Sigma #P0044), 1% Proteases Inhibitor Set III (Calbiochem #539134), 1% DNAse-I (Roche #4536282001) and 10 mM MgCl$_2$. The cell extract was lysed by pipetting up and down and then stored at −20° C. until use.

Total Tau levels in the cell extracts were measured by AlphaLISA using an in house assay format comprising the Tau-specific antibodies 5A6 (DSHB Antibody Registry ID: AB_528487) and Roche in house Tau monoclonal antibody Tau 4/2. The latter antibody was generated by immunizing mice with human full-length Tau i.e. longest human brain isoform, 441 amino acids. Tau 4/2 binds to an C-terminal epitope in Tau located between amino acids 369 and 441. Briefly, cell extracts were diluted into AlphaLISA Hi Block assay buffer (PerkinElmer AL004C) and mixed with biotinylated 5A6 and Tau 4/2-coated AlphaLISa acceptor beads. After incubation for 1 hr at room temperature, streptavidin-coated donor beads are added to the mixture. After incubation for 30 min, the samples were measured in an Envision plate reader (ex 680 nm, em 615 nm). A standard curve was constructed using recombinant human Tau (Merck-Millipore #AG960).

PhosphoTau (Tau-pS422) levels in the cell extracts were measured by AlphaLISA using the Roche in house assay format comprising Tau-specific antibody 5A6 (DSHB Antibody Registry ID: AB_528487) and Tau-pS422-specific antibody 5.6.11 (described in WO2010/142423 and Collin et al 2014 Brain vol 137 P 2834-2846). Cell extracts are diluted into assay buffer B before assay. Buffer B comprises 25 mM HEPES pH7.4, 0.5% Triton X-100, 0.1% Top Block (LuBio Science), 1 mg/ml Dextran500, 10% ELISA Blocking Reagent (Roche). A standard curve was prepared using ERK-phosphorylated Tau prepared as follows: recombinant human Tau was produced as described in Grueninger et al (Neurobiology of Disease 37 [2010] pp 294-306). Recombinant His-tagged ERK2 (produced in house) was activated by incubation with activated MEKK1 (produced in house). Activated ERK2 was then incubated with Tau at a molar ratio of 1:50 in buffer containing 2 mM ATP. ERk2 was subsequently removed by passage over Ni-NTA agarose (Qiagen). The extent of phosphorylation at S422 was subsequently determined by mass spectroscopy.

The results are shown in table 9.

TABLE 9

MAPT reduction and Tau protein reduction in hESC derived neurons following treatment at three different concentrations.

| CMP ID NO ASO conc | MAPT as % of control | | | Total Tau protein % of control | | | PhosphoTau protein % of control | | |
|---|---|---|---|---|---|---|---|---|---|
| (nM) | 200 | 8 | 0.32 | 200 | 8 | 0.32 | 200 | 8 | 0.32 |
| 9_104 | 5.4 | 36.6 | 100.9 | 7.0 | 40.3 | 88.3 | 0.6 | 12.0 | 54.0 |
| 9_103 | 1.2 | 15.6 | 71.8 | 1.8 | 23.2 | 66.2 | 0.1 | 19.8 | 92.9 |
| 11_1 | 1.0 | 12.5 | 72.3 | 1.5 | 25.9 | 65.1 | 0.1 | 17.5 | 70.4 |
| 49_38 | 5.7 | 36.3 | 83.5 | 6.8 | 45.5 | 79.6 | 1.3 | 51.6 | 116.6 |
| 49_189 | 7.0 | 36.5 | 90.2 | 10.4 | 48.1 | 102.9 | 5.0 | 59.6 | 137.3 |
| 53_1 | 4.8 | 32.9 | 79.4 | 8.8 | 45.7 | 79.0 | 3.1 | 48.6 | 127.6 |
| 66_1 | 11.0 | 40.2 | 81.9 | 10.9 | 48.4 | 69.9 | 3.6 | 57.9 | 94.2 |
| 9_102 | 2.0 | 34.9 | 99.0 | 3.0 | 44.3 | 87.4 | 0.3 | 37.7 | 113.8 |
| 49_179 | 10.5 | 53.6 | 96.4 | 12.4 | 70.7 | 91.7 | 3.5 | 76.0 | 112.0 |
| 49_51 | 6.7 | 39.8 | 76.1 | 5.9 | 60.2 | 92.2 | 1.3 | 68.2 | 161.6 |
| 56_1 | 2.8 | 36.8 | 93.2 | 3.6 | 49.3 | 96.6 | 0.3 | 37.9 | 111.9 |
| 62_1 | 4.5 | 38.6 | 86.2 | 5.8 | 48.4 | 88.1 | 1.5 | 47.8 | 119.0 |
| 67_1 | 31.1 | 57.0 | 86.0 | 35.9 | 58.4 | 79.2 | 26.2 | 65.8 | 115.5 |

Example 6: IC50 of Selected Compounds from Example 5

A selection of the efficacious ASO's from example 5 were tested in the same hESC derived neuron assay together with the two prior art controls (CMP ID 66_1 and CMP ID 67_1) to determine IC50 of the target mRNA reduction as well as the Tau protein reduction.

The experiment was conducted as described in example 5 using the following oligonucleotide concentrations: 1000, 200, 40, 8, 1.6, 0.32, 0.064, 0.0128, 0.00256 nM.

The IC50 values were fitted using the GraphPad PRISM software. The results are shown in table 10.

From these data it can be seen that CMP ID NO 9_103 and 49_38 of the invention are more efficacious and have a better IC50 than the prior art compounds on all parameter, whereas CMP ID NO 53_1 seems to have a better maximal knockdown than the prior art compounds and a similar IC50 as CMP ID NO: 66_1.

Example 7 In Vivo Activity in Specific Brain Regions of hTau Mouse

A selection of the ASO's from example 5 were tested for their ability to reduce the target in vivo in specific brain regions of a humanized Tau mouse (hTau mouse) four weeks after a single low dose ICV administration.

The humanized Tau mouse used in this example is an in house Roche hTau P301S transgenic mouse line which overexpresses human Tau (longest human brain isoform) with the point mutation P301S on a mouse Tau background.

Humanized Tau mice were administered with 25 µg ASO by intracerebroventricular (ICV) injection as described below. CMP ID NO: 66_1, corresponding to ASO-001933 in WO2016/126995, was included for comparative purposes.

In Vivo ICV Mouse Evaluation:

Animal Care:

Animals of mixed sex with a weight of 16-23-grams were held in colony rooms maintained at constant temperature (22±2° C.) and humidity (55±10%) and illuminated for 12 hours per day (lights on at 0600 hours). All animals had ad libitum access to food and water throughout the studies. All mouse protocols were approved by the Danish National Committee for Ethics in Animal Experiments.

Intra-Cerebroventricular Injections:

The compounds were administered to mice by intracerebroventricular (ICV) injections. 6-8 mice of mixed sexes were included in each treatment group. Prior to the ICV dosing, the mice were weighed and anaesthetized with isofluran or Propofol (30 mg/kg). Intracerebroventricular injections were performed using a Hamilton micro syringe with a FEP catheter fitted with a 23 gauge needle fixed in a stand adjusted to penetrate the correct distance (3.9 mm) through the skin and skull and into the right lateral ventricle. The mouse to be injected was held at the scruff of the neck with the thumb and first fingers of one hand. Applying gentle but firm pressure, the head was pressed upwards so that the needle pierced the skull 1-2 mm right of the midline (medio lateral) and 1-2 mm behind the eye. The 5 µl bolus of test

TABLE 10

IC50 and max efficacy (as % of control) with respect to MAPT and TAU protein

| CMP ID NO | Compound | IC50 MAPT (nM) | Max efficacy MAPT | IC50 TAU (nM) | Max efficacy MAPT |
|---|---|---|---|---|---|
| 9_103 | CTTTaatttaatcacTCAT | 2.0 | 0.6 | 1.4 | 1.1 |
| 49_38 | TtaaCTCAaatcaaTtctCA | 8.2 | 2.6 | 6.1 | 1.6 |
| 53_1 | CAACacctttaattcATTA | 7.6 | 1.7 | 15.0 | 1.9 |
| 66_1 | AtTTCcaaattcactTTtAC | 9.7 | 8.1 | 11.8 | 4.9 |
| 67_1 | CC₀GTTttcettacceeAC₀CCT | 17.7 | 22.6 | 43.3 | 23.4 | compound or vehicle was injected over 30 seconds with a previously determined infusion rate. To avoid reflux the mouse was held in this position for another 5 seconds before carefully being pulled downwards, away from the needle. This procedure required no surgery or incision. Animals were placed under a heating lamp until they recovered from the procedure.

At study termination (4 weeks), brain tissue (cortex, medulla/pons and midbrain) was collected on dry ice for analysis of tau mRNA and protein.

Tissue Homogenization:

Mouse brain tissue samples were homogenized in the MagNA Pure LC RNA Isolation Tissue Lysis Buffer (Roche, Indianapolis, IN) using a Qiagen TissueLyzer II. The homogenates were incubated for 30 minutes at room temperature for complete lysis. After lysis the homogenates were centrifuged for 3 minutes at 13000 rpm and the supernatant used for analysis.

RNA Purification from Tissue:

RNA was purified from 350 µL of supernatant using the MagNA Pure 96 instrument using the kit Cellular RNA Large Volume Kit (Roche, Indianapolis, IN). RNA samples were normalized to 2 ng/µL in RNase-Free water and stored at −20° C. until further use. MAPT mRNA levels were quantified as described in example 5.

Tau Protein Measurement from Mouse Brain Tissue:

Pre-weighed frozen tissue was extracted with 10 volumes (wt/vol) of extraction buffer comprising 10 mM TrisCl pH 7.4, 800 mM NaCl, 1 mM EGTA, 10% sucrose, 1% Phosphatase Inhibitor Cocktail 3 (Sigma #P0044), 1% Proteases Inhibitor Set III (Calbiochem #539134). A homogenate was prepared using the PreCellys tissue disruptor (20 sec, 6500 rpm). The homogenate was then centrifuged at 10'000×g for 20 min at 4° C. and the supernatant retained for analysis.

Tau levels in the extracts were measured by AlphaLISA using the total Tau AlphaLISA kit supplied by Perkin Elmer (Cat. Nr. AL271C). The antibodies used in this assay were BT2 and Tau-12 provided with the kit, both of which bind to the central region of tau. Extracts were diluted into HiBlock assay buffer and 5 µl of each sample was then used in assay. The assay was otherwise performed as described by the supplier Results from mRNA and protein quantification are shown in table 11

From these data it can be observed that even at the fairly low concertation of 25 µg, reduction of more than 20% is seen in most brain regions for the compounds of the invention, where as the control compound show virtually no reduction of the target at this concentration.

Example 8 In Vivo Dose Response and Time Course in the hTau Mouse

The dose response of two ASO's (CMP ID NO: 9103 and 49_189) was evaluated using three different doses (25, 50 and 100 µg) and target reduction was measure in specific brain regions 1 week and 4 weeks after administration. For comparative purposes two prior art compounds (CMP ID NO: 66_1_103 and 67_1) were included at some of the doses in the one-week study.

The experiment was essentially conducted as described in example 7. Tau protein was however not measured in the dose response study which was run for 1 week since the Tau protein has a half life beyond one week. The results are shown in Tables 12 and 13.

TABLE 12 in vivo efficacy in selected brain regions 1 week after a single ICV dose at 25 µg, 50 µg or 100 µg ASO or 4weeks after a single ICV dose at 100 µg ASO. MAPT mRNA as % control are shown for four brain regions.

| Brain region | ASO conc µg | | CMP ID NO | | | | | |
|---|---|---|---|---|---|---|---|---|
| | | | 9_103 | 49_38 | 66_1 | 67_1 | 9_103 | 49_38 |
| | | | Time | | | | | |
| | | | 1 week | | | | 4 weeks | |
| Cortex A1 | 25 | Avg | 51 | 69 | NA | NA | NA | NA |
| | | Std | 13 | 8 | NA | NA | NA | NA |
| | 50 | Avg | 52 | 52 | 68 | NA | NA | NA |
| | | Std | 12 | 14 | 14 | NA | NA | NA |
| | 100 | Avg | 33 | 39 | 60 | 71 | 36 | 37 |
| | | Std | 10 | 24 | 12 | 25 | 17 | 26 |
| Cortex A2 | 25 | Avg | 73 | 59 | NA | NA | NA | NA |
| | | Std | 12 | 12 | NA | NA | NA | NA |
| | 50 | Avg | 68 | 39 | 73 | NA | NA | NA |
| | | Std | 15 | 7 | 8 | NA | NA | NA |
| | 100 | Avg | 42 | 43 | 77 | 63 | 51 | 46 |
| | | Std | 21 | 30 | 12 | 20 | 13 | 30 |

TABLE 11 in vivo efficacy in selected brain regions 4 weeks after a single ICV dose of 25 µg ASO. MAPT mRNA as % control are shown for four brain regions and Tau protein as % of control is shown for one brain region

| | mRNA % ctrl | | | | | | | | Protein % ctrl | |
|---|---|---|---|---|---|---|---|---|---|---|
| | Cortex A1 | | Cortex A2 | | Medulla-Pons | | Midbrain | | CortexB2 | |
| CMP ID NO | Avg | Std | Avg | Std | Avg | Std | Avf | Std | Avg | Std |
| 9_104 | 74 | 12 | 77 | 14 | 68 | 19 | 65 | 18 | 73 | 18 |
| 9_103 | 80 | 13 | 80 | 10 | 66 | 17 | 64 | 12 | 69 | 16 |
| 11_1 | 58 | 12 | 62 | 15 | 54 | 16 | 48 | 19 | 63 | 11 |
| 49_38 | 63 | 12 | 67 | 9 | 55 | 18 | 49 | 16 | 76 | 15 |
| 49_189 | 75 | 5 | 70 | 10 | 54 | 4 | 55 | 6 | 84 | 13 |
| 53_1 | 80 | 10 | 93 | 7 | 81 | 12 | 81 | 16 | 101 | 11 |
| 66_1 | 94 | 20 | 98 | 6 | 101 | 4 | 99 | 11 | 112 | 8 |

TABLE 12-continued in vivo efficacy in selected brain regions 1 week after a single ICV dose at 25 μg, 50 μg or 100 μg ASO or 4weeks after a single ICV dose at 100 μg ASO. MAPT mRNA as % control are shown for four brain regions.

| Brain region | ASO conc μg | | CMP ID NO | | | | | |
|---|---|---|---|---|---|---|---|---|
| | | | 9_103 | 49_38 | 66_1 | 67_1 | 9_103 | 49_38 |
| | | | Time | | | | | |
| | | | 1 week | | | 4 weeks | | |
| Midbrain | 25 | Avg | 79 | 43 | NA | NA | NA | NA |
| | | Std | 20 | 4 | NA | NA | NA | NA |
| | 50 | Avg | 50 | 26 | 68 | NA | NA | NA |
| | | Std | 14 | 6 | 11 | NA | NA | NA |
| | 100 | Avg | 51 | 38 | 78 | 76 | 60 | 38 |
| | | Std | 29 | 31 | 21 | 27 | 28 | 35 |
| Medulla-Pons | 25 | Avg | 81 | 41 | | NA | NA | NA |
| | | Std | 21 | 6 | | NA | NA | NA |
| | 50 | Avg | 57 | 26 | 70 | NA | NA | NA |
| | | Std | 18 | 5 | 10 | NA | NA | NA |
| | 100 | Avg | 58 | 37 | 80 | 82 | 61 | 40 |
| | | Std | 34 | 31 | 23 | 28 | 29 | 33 |

NA = not assessed

TABLE 13 in vivo reduction of Tau protein as % of control 4 weeks after a single ICV dose at 100 μg ASO.

| Brain region | Cortex B1 | |
|---|---|---|
| CMP ID NO | Avg | Std |
| 9_103 | 56 | 18 |
| 49_38 | 43 | 35 |

From the data in table 12 and 13 it can be seen that the compounds of the invention perform significantly better than the prior art compounds, in particular when dosed at 100 μg. It can also be observed that the MAPT reduction is maintained over the 4 weeks. Furthermore, the compounds of the invention show a significant reduction of Tau protein after 4 weeks treatment with a single dose of 100 μg compound.

The invention claimed is:

1. An antisense oligonucleotide of 10 to 30 nucleotides in length, wherein the antisense oligonucleotide comprises a contiguous nucleotide sequence having SEQ ID NO: 9, or a pharmaceutically acceptable salt thereof.

2. The antisense oligonucleotide of claim 1, wherein the antisense oligonucleotide is capable of reducing the expression of Tau.

3. The antisense oligonucleotide of claim 1, wherein the contiguous nucleotide sequence comprises one or more 2' sugar modified nucleosides.

4. The antisense oligonucleotide of claim 1, wherein each of the one or more 2' sugar modified nucleosides is a 2'-O-alkyl-RNA nucleoside, a 2'-O-methyl-RNA nucleoside, a 2'-alkoxy-RNA nucleoside, a 2'-O-methoxyethyl-RNA nucleoside, a 2'-amino-DNA nucleoside, a 2'-fluoro-DNA nucleoside, an arabino nucleic acid (ANA) nucleoside, a 2'-fluoro-ANA nucleoside, or an LNA nucleoside.

5. The antisense oligonucleotide of claim 1, wherein the contiguous nucleotide sequence comprises 4 to 8 LNA nucleosides.

6. The antisense oligonucleotide of claim 1, wherein at least 80% of the internucleoside linkages within the contiguous nucleotide sequence are phosphorothioate internucleoside linkages.

7. The antisense oligonucleotide of claim 1, wherein the antisense oligonucleotide is capable of recruiting RNase H.

8. The antisense oligonucleotide of claim 1, wherein the antisense oligonucleotide, or contiguous nucleotide sequence thereof, comprises a gapmer of formula 5'-F-G-F'-3', wherein F and F' independently comprise 1-8 nucleosides, of which 2-5 are 2' sugar modified and defines the 5' and 3' end of the F and F' region, and the G is a region comprising between 6 and 16 nucleosides which are capable of recruiting RNaseH.

9. The antisense oligonucleotide of claim 8, wherein the antisense oligonucleotide, or contiguous nucleotide sequence thereof, consists of a gapmer of formula 5'-F-G-F'-3', wherein F and F' independently comprise 1-8 nucleosides, of which 2-5 are 2' sugar modified and defines the 5' and 3' end of the F and F' region, and the G is a region comprising between 6 and 16 nucleosides which are capable of recruiting RNaseH.

10. The antisense oligonucleotide of claim 8, wherein the antisense oligonucleotide, or contiguous nucleotide sequence thereof, comprises a gapmer of formula 5'-F-G-F'-3', wherein F and F' independently comprise 1-8 nucleosides, of which 2-5 are 2' sugar modified and defines the 5' and 3' end of the F and F' region, and the G is a region comprising between 6 and 16 DNA nucleosides which are capable of recruiting RNaseH.

11. The antisense oligonucleotide of claim 9, wherein the antisense oligonucleotide, or contiguous nucleotide sequence thereof, consists of a gapmer of formula 5'-F-G-F'-3', wherein F and F' independently comprise 1-8 nucleosides, of which 2-5 are 2' sugar modified and defines the 5' and 3' end of the F and F' region, and the G is a region comprising between 6 and 16 DNA nucleosides which are capable of recruiting RNaseH.

12. The antisense oligonucleotide of claim 1, wherein the antisense oligonucleotide is:

CTTtAATttaatcactcAT SEQ ID NO: 9; CMP ID NO: 9_102; or

CTTTaatttaatcaCtCAT SEQ ID NO: 9; CMP ID NO: 9_104 wherein capital letters are beta-D-oxy LNA nucleosides, lowercase letters are DNA nucleosides, all LNA C are 5-methyl cytosine, and all internucleoside linkages are phosphorothioate internucleoside linkages.

13. The antisense oligonucleotide of claim 1, wherein the antisense oligonucleotide is of formula:

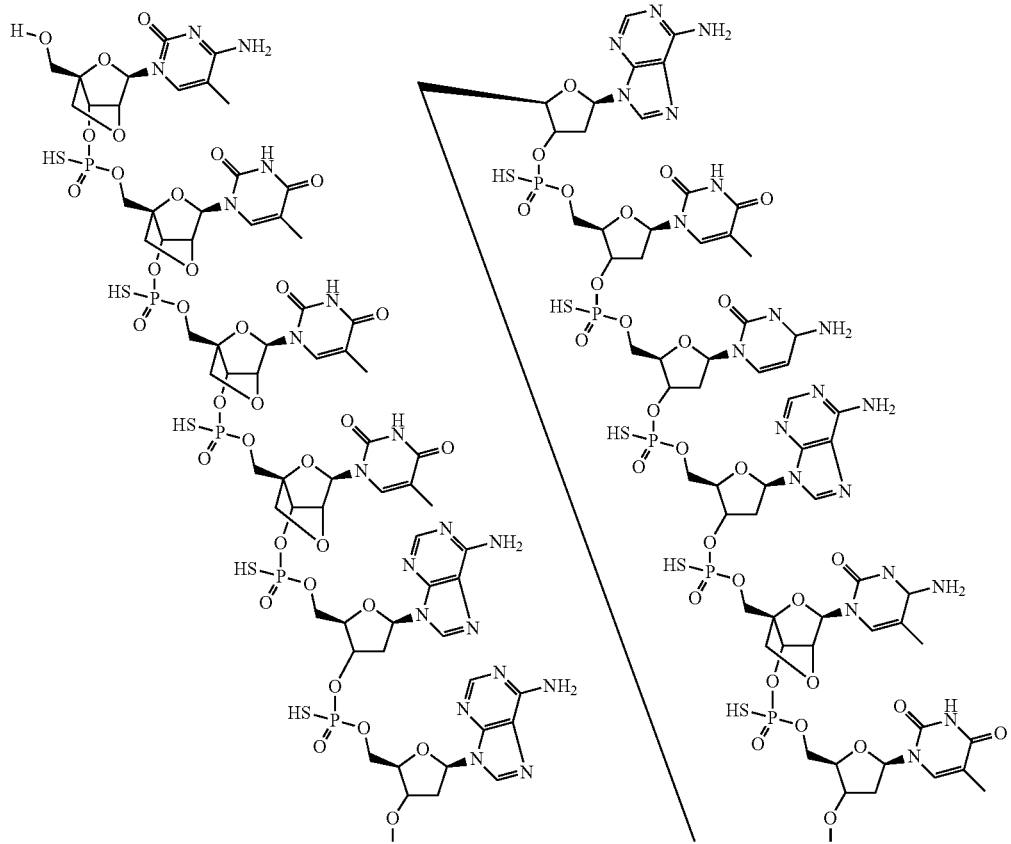

401
-continued
402
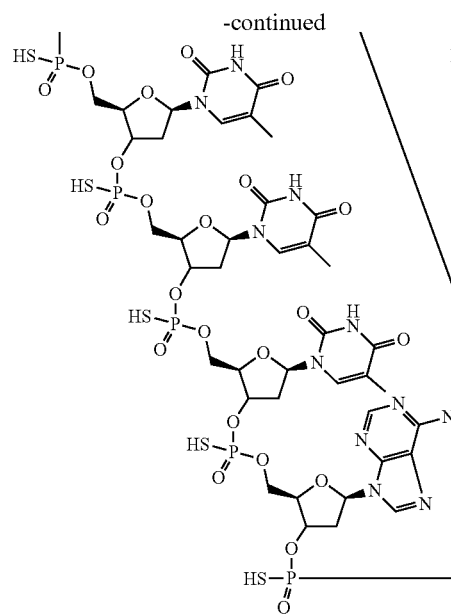
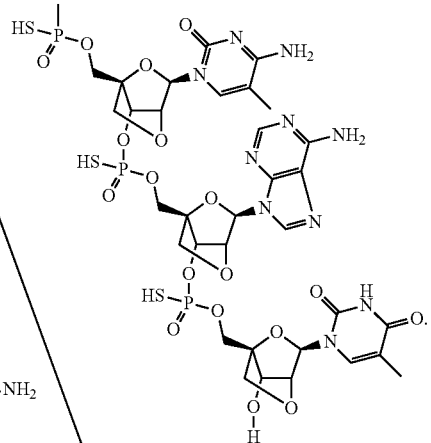
14. A conjugate comprising the antisense oligonucleotide of claim 1, and at least one conjugate moiety covalently attached to the antisense oligonucleotide.
15. A pharmaceutical composition comprising the antisense oligonucleotide of claim 1, and a pharmaceutically acceptable diluent, solvent, carrier, salt, and/or adjuvant.
* * * * *

SEQUENCE LISTING

<160> NUMBER OF SEQ ID NOS: 67

<210> SEQ ID NO 1
<211> LENGTH: 134004
<212> TYPE: DNA
<213> ORGANISM: Homo sapiens

<400> SEQUENCE: 1

```
acggccgagc ggcagggcgc tcgcgcgcgc ccactagtgg ccggaggaga aggctcccgc      60
ggaggccgcg ctgcccgccc cctcccctgg ggaggctcgc gttcccgctg ctcgcgcctg     120
cgccgcccgc cggcctcagg aacgcgccct cttcgccggc gcgcgccctc gcagtcaccg     180
ccacccacca gctccggcac caacagcagc gccgctgcca ccgcccacct tctgccgccg     240
ccaccacagc caccttctcc tcctccgctg tcctctcccg tcctcgcctc tgtcgactat     300
caggtaagcg ccgcggctcc gaaatctgcc tcgccgtccg cctctgtgca cccctgcgcc     360
gccgcccctc gccctccctc tccgcagact gggcttcgt gcgccgggca tcggtcgggg     420
ccaccgcagg gcccctccct gcctcccctg ctcggggct ggggccaggg cggcctggaa     480
agggacctga gcaagggatg cacgcacgcg tgagtgcgcg cgtgtgtgtg tgctggaggg     540
tcttcaccac cagattcgcg cagacccag gtggaggctg tgccggcagg gtgggcgcg      600 gcggcggtga cttgggggag ggggctgccc ttcactctcg actgcagcct tttgccgcaa     660
tgggcgtgtg tgtgtgtgtg tgtgtgtgtg tgtgtgtgtg tgtgtgtgtg gaggggtccg     720
ataacgaccc ccgaaaccga atctgaaatc cgctgtccct gccgctgttc gccatcagct     780
ctaagaaaga cgtggatcgg gttctagaaa agatgactcc ctgcacgccc ctccctgcac     840
ctcccgagca gtgattccga cagggccttc actgcccctg attttaggcg ggggccggcc     900
ccctcccctt ttcctccttc agaaaccgt aggggacatt tgggggctgg gagaaatcga     960
ggagatgggg agggtccac gcgctgtcac tttagttgcc cttccccctg cgcacgcctg    1020
gcacagagac gcgagcagcg ccgtgcctga gaacagtgcg cggatcccac tgtgcacgct    1080
cgcaaaggca gggttcacct ggcctggcga tgtgacgga ctcggcggcc gctggtcccc    1140
```

-continued

```
gttcgcgggc acgcacagcc gcagccacgc acggatgggc gcggggctgc aggtgcatct   1200
cggggcggat ttctttctca gcgctcggag cgcagggcgc ccggcgtgtg cgctccctgc   1260
cggaggcgcg gggctggcgc gcagggctcg cccctcactg cggcagtggg tgtggaccct   1320
ggtgggcgag gaaggggag ataggctgt gcctcctccc actcccgccc ccagcccccc    1380
ttttttttccc cctcggaacg cgaggtgcca tctttttcg gcgtgtcacg tctttacggt   1440
gccatgccaa accgggtggc cgggcttcat aggacagggc ggggcctggc attaaaggga   1500
gggggacaat cagcgctgaa atcttggcgt tttgctgctg cgggcgtgag cactgggggc   1560
gttcgcccag caccttcttc gggggctctt tgctttgtct gtagaggtta cgtgatctgc   1620
gctcccagcc ctggtttctg gcttttattc tgagggtgtt cagtcaacct cccccctacg   1680
cccatgcgcc tctctttcct ttttcgctcc tcatttccga gcccattgtt ggatctcgag   1740
gcttgctggg ttcgatgaac tcgagtcaac ccccgaccc ccggcacgca tggaacgggc    1800
gtgaccgcgc gcagcctcgt ctcggagtct gccggcgccg ggaagcttct gaagggatgg   1860
gattcgagtc tccgtgcgcg ctgcgggcgg cggcagaggg atctcgcccc tcctacacc    1920
ccaagtgtcc tgagggccac gccacaccag gttgcccagc gagggacgct ggctacccat   1980
ccggggatgg gtgggagcc ctggcgggc ctctccggct ttacgccctg ttgcttcgcc     2040
tggccggaga atgtgaggaa ggggcataag gttactggtg cttcggccac acccatcttt   2100
ctgagcccac tggactgggc gcagaggggg gattgccatg gaaaccacag gtgtccggag   2160
aggggatctt ggggctggcc tcacccttc cctgcggaga ttggggaccc tggggtaggg    2220
ggagccgcgc ccagtcggcc tcctggagga cacgggagga agcccgaac cccgcgcct     2280
gaggctgttt ctgattggcc cctggaggcc gcagacacgc agataggcgg ccctgggtgt   2340
attttattta atattatgtc cgtactgatt aatattattt atcttaaata aatttcaccc   2400
gtgtccaagt tcaccgcgcc cccaaaaccg agtctggggc ggcaggggga actcctggcc   2460
aacgaatcca tgcctcgccc tcctgtgatg aacctggtac gcacggtttt ctggttaatt   2520
ctatcgctga aaactggtgc gggggggcgca cttctgagac ggaagagcat ctaggagctg   2580
aatcctccac gcgggtcgcc caggttgatc tgaatttctg gggaatggct tggctgcccg   2640
cccgggacca ggccgacccct ccttgacggt ggcgtagagg gctggagcct gggtactgcg   2700
aggctcctcg catggctggg cccgccgcga ggggttgcag agcggctcag ggatcgattc   2760
aagcatcgtc tctcctccct cgccccaga cagagctggg cgcggggttc cccttccaga    2820
tggagcgagt gtctcggggt ggccccggaa aaggggagcc cgcggccacg gctacgtatt   2880
gccatctcgc gagcagagat gtcacctcct gcctttggag gaaagggagc ccggtgggga   2940
tgagcgcatt tagcccaatg ctgggaacaa agcgcactcc gcgcttctgc gatttcgctc   3000
cattttgaaa tgtgttggcg ctttggtggg gccgctgcgg tgggcaaggc cggggcgct    3060
gttaatggag gaacctcagg gggacggtcc ttcgtaggaa actctatcct ggctctgcgc   3120
gcgctttaag gaaatggctt ccctccagga cctcgaggga tgcagctttt gcgcggatga   3180
cggtggggtg ctgaaccagc cggtgcgcct ctggaaatgt ctgggcacgg atcctggggc   3240
catcgacgac tcctccccat tcccagcagg cgggagctct tacattccga gcagtgacc    3300
cctctcaccc tctggcgctc acacacctgt aactccaaac ctccgtctca gaatggtcca   3360
ggctggaagg gatgatgggg gctccgacag cgactgccta gctcacccct ctgcgtgctc   3420
aggctccagg ctcagcagga ccaatttgag ttctatctga tcccctcgg cccttaact    3480
gacccatcct acaggagaca gggaaatgtc tttcctaccg cggttgattc tggggtgtca   3540
```

```
ttttgtgttt tgtgatggct gcttatattt actgtataag cattgtattt actgtataag    3600
cattgtatta taattactgt ataagctgct tatatttact gtataagcat ctccaaatcc    3660
tccctctacg taaacaaatt aatggataaa cagataagtg tatccctgc ccccacccct     3720
gctacgcagg tccggagtga ctcttgaagc tcatacattc cttggccaag tttgcttctc    3780
taacagatgt ttatatagca ataacctggc ttggctcttg ggttcacctt tggacgattt    3840
ggggaagggg cttgttggct ttgctgggtt ttggatgagt gacagtccat gactgttcct    3900
gctggaaggg cgtgactttt aagtggtttc taatatcagg cattgctcct ccgacaggaa    3960
caaaagaaat ggatactgcc cataaattgt tagaaaactt agaatcgctt tgattgagga    4020
aaggttagat ttattccggt tggaaaaagt ggcctttcta ttaaacgtgc cctttgaccc    4080
tcatgccctt ggaggtcggt gccagcctgg agatgggata agattgtggt tttccttctg    4140
ccttttaac atctgttgtt acagtccatt tgttgaaaat ttaaagaaac tgttttattc     4200
cactttccct cagcatttat gtgtgtggtt tcagtagctc tgtggctata tgtacgaaca    4260
cgtgttattt ttccaattgg acatgtgata attttccaac tggaccttgc cttctattga    4320
tgtatttatt tagcatcttc cttactccct ccttgaaaaa gaatcactca aaaacaaata    4380
aaaacagccg taggggccta atacagtgct agacatacaa gaggtattcg gtccatacca    4440
aatggatttt atccatgaag gataaatggg gaaatacagt gggaagcagg tgggaaactg    4500
cgtttgactc tgctctttcc tccaccacca ctttcctcat caccgtgttc agagaccccc    4560
aaagccccct cacactccca gaaacacccc cctggccact cctaacttgc catgcccagg    4620
agttaggtgc ttccactagt gacatggagc tggcgtttgg ggggcacctc agcaggtgac    4680
gggaagagaa gaccccagcc tcaccagctg ggctgcagca gggagaggag tcctcatgtt    4740
ccagcaggga ctctcagctg ttttcctgta aaaccatggt tctcaactgg gggccactga    4800
gatgtctaga gagatgtttt tgttttcaca actcggggag ggtgctactg acatcttgtg    4860
ggtagaggcc aggaatgctg ttaaacatcc tacaaggaag gcacaggaca gtctcctaca    4920
tcaaaatatg acccagtccc aatgtcacca ctgctggggt tgacactggc actgctatct    4980
taattacatt cattgagtgt cttttaggag gccctattct aagtgcttgc taagattatc    5040
tcatttaatc ctcacaacac ttccgctatg tagcaggtgc tgttattatc tccgtgatgg    5100
ggaaactgaa gcacagagag ggttagtaac ttgctaaagg tcacagagcc agtgggtggt    5160
ggagctggtt gcctgacact agttccctcc cctctcagcc acatgtgggt ttacttggcc    5220
attgtggact agtctgggaa cccagatatg atctataaca ttgacccagt agaatattga    5280
ttccaaaacc actgtctcac aaatgaattt ttacaagagt ctgtaatcgg agcatgaccc    5340
agaataaggt tagggagatg tggagttaaa gctctcaatt tcttatctgg ccccgacaca    5400
gagagcaagg catttcactc tacattggtg ctctgtttat aaaacaaaga gcaaatatct    5460
cttcctaagg tccttaaacc tcttccccca atccagggtt tctggactgc tctgccatat    5520
gacggggcag ctggtttgat tgacccaggg aaggctggaa atcaagactg ggggatcaag    5580
acgtagattc agtgtggcca aggtcaagtc tctgaggttt agggacatca gatccccagc    5640
ttaggttctg tacctcggca aggtgaaagc gttggcgccc actgatgagg cctgctctga    5700
gattgtgggt gtgggttgag ttgggtgggc ataggcaagt cctcttgtaa gaatcttttg    5760
gcaaagatgg gcctgggagg cttttctcac ttcctgggc ccaggctttg caataagtat     5820
tccattatac tgtggtacct tggggctacc tgagaatcct ctgtctcgcc cctgttgcct    5880
```

```
tgccaaagag tttgctgtcc aagaattcct ttcctgtctc caggtgccat gctcctgcca    5940
cctctgccag gttccctgcc tgcccagatg gctcccaact gagtgtgagg aggaatttga    6000
gacaggtttt gagctttctg ggttctccag ttaggaaact ttctgtaagc atgcagatag    6060
aatgggcttc agcaaaatac aaactcgaac aacttccatg tatagtccct taatttctt    6120 tgctttttc atatttcatc aggctccatg ctgagcccaa tcagggaccc gatagaaatc    6180
caaacaccat gtcagcgagt ccccaagaaa tgcattttgt gccaaggcta ttcaaggaag    6240
gtttgggagc agctcaaggg cagacactgt taccctcccc caggtcccca gtgcagggca    6300
gtgttctgca tgtggaggca gtttggccta atggttaagg aggtaggctc tgatcgggcc    6360
tcctgggcac aaatcccagc tccctgctca ctgtgagacc taagccatat tgtttagctg    6420
cttggagagt tttttgtcat ccacaacttg gagtatgatg gtacctgtct cacgggttgc    6480
catggggttc acacaagcta acccggtact cactagggcc aagcacatag taactgctca    6540
gtaaatggca tcatcggcgg tgtcctgtgg atgagtgctt gtgattggct gaatgaccag    6600
aggggtctaa agatcctggt gatggaatca gttgtacaga taaattgtta cactgagtag    6660
ggatcaagat aggaaaagtc ggcaactacc cagctcccct gcaccaaact gggcagaagt    6720
ggatcctctg aaaattgcac acacccatgt ttaaatgtac acacgaact cttgccacag    6780 gcaagcggag atttgtcatc tgctgtccct gcctcatctt cttcctgaaa tccactccat    6840
gccaggaata aactgcatgc tctccaccag cccaaactga cctgccttcc cgccagccat    6900
cccgggcagg gtgacctggc ttagtacatc gggttcagag atctttccag tttactcgtt    6960
gaataaaaag tgagggctga tcgagaaagt aatggcagtc agggaaggcg aaggaggtaa    7020
agaagagatt ttacaaatga agtaattcaa cagagtgctg acattggtaa actggcaaac    7080
agatttcagg gtggttggtt gagagtagag tagaaaagga ttaaataaag caaacttgtg    7140
gtgtactgaa tcttaggaat tccatgtatc caataagtat agtcatttat gaattaataa    7200
attcggccta agaagccttc ttatcgctta aatcaagact aagtaacaat atatcagttt    7260 taaaagtca ttatatcaga aaatcattta aatgatacac atagatttcc aagattttac    7320
tttaaccgaa actatataaa tgtgaatttg ttcacccatc ttttgacaca gggctcaggt    7380
cttctcttgg tgtctggatc agccagttga aatttcttgt ctgttttgcc tatgccacat    7440
taataatgca ctgtctgggt cctccgattt cagtttggat tttgggttta cattgtggag    7500
tcatctgaat gcagaatcct tcagggattt tacttttttt tttttttttc atggtcttta    7560
ccatcccatt tgatagtaaa tattactcac ctttatgaag tctttccaaa acattcaact    7620
aaatttcttt aaaatcattg aatgatttga agagcttatt cctcagcact tttactccat    7680
cagcttgcac cttatttttt aatctttttt tgagacggag tctcgctcta tcgcccaggc    7740
ttaagtgcaa tggcgcgatc ttggctcact gcgacctcca cctcctgggt tcaagcaatt    7800
ccgcctcagc ctccgccgta gccgggacta caggtacaca ccataatgct cggctgattt    7860
ttgtattttt gtagggatgg ggtatcgcca tgttggccag gctggtcccg aacttctgac    7920
ccaagtgatc cacccacctc ggcctcccaa agtgctggga ttacaggtgt gagccaccgc    7980
gcccggccag cttgcacctt atttaggata tgtgattatt atagcaagtc tggtgtacat    8040
acaagatttt gaatgggcac agatgacctt tagtaagtgc ttggctgtga taagaggcag    8100
tcctgactgc agatcaggct gtgtggaccc cagccttgca tgtttacaga ccttcatgtc    8160
ttattcttac agggtatcag aagaacacct actggggaaa cttataaatt agtaaaaggt    8220
gggcattctc cccgcccatc ttctgtctgt ctgccaggac tagcacagca ctttgaagtc    8280
```

```
attcacatag aatcccaact taagagggta aaatcctcct caacagactg aaaataagtt    8340
taaattccct ttgctatatt aactcccctg aggaaagagt cttagatcaa tgtccaacac    8400
taaaaacagt tttaaatcag caagtgagaa ttaaatctga agcaattgat aataatgttt    8460
cattcattcc tctcctttgg ccccgtccac cctactgcta aatccaggca tcaaagagaa    8520
gagggacata attatctcta gtcccagctg ctggttttcc ttccagccta tggcccagtt    8580
ttctgtttta ctgagaaggc tggtgatgtt atcttgggat ctaagtctgc agtttcacca    8640 caaaagtcc  agggatgcac tttcatgctt gtgtcctcct ccctgggata gcaaggatat    8700
tagaagaccc ctggctctgt aattgcttgt catgtgctct acagacgcca cagaatgcca    8760
agaacgaagt gctgggaagg acaaattcat ggaaccgtgg gacggtgctc ctcccccagc    8820
gtaaaggaca gctcctcctc ctgaattgga gccagcgttc taaatcatgt gtcaacagag    8880
ttgtcctgga tcggatccag ttctgccatt gatttgcagg tcatttcagt ggtacctgtt    8940
tccagttgtt cttaattgaa cagtggcacc aaactattgt cttgcctcat cccctccca     9000 tggcctgtcc cccaaaaaga gacttcttgg gtaattaatc agggcaacat caggcagtct    9060
gggcgcggtg gctcacgcct gtaatcccag cactttggga ggccgaggcg ggcagatcat    9120
gaggttagga gattgagacc atcctggctt tgtgaaaccc cgtctctact aaaaatacaa    9180
aaaattagcc gggcgtggtg gcgggcgcct gtagtcccag ctactcgaga ggctgaggca    9240
ggggaatggc gtgaacccgg gaggtggagg ttgcagtgag ccgagatcgc accactgcac    9300
tctagcctgg gcgacagagc tagacttctt ctcaaaaaaa aaaaaaaaaa ggaatctctt    9360
tggttttata tattttttt  tatatatata atatatatta aaatataata tatatattta    9420
tataatataa tatataaata tattatatat tatatatttt tatatattat atattatata    9480
tattatatat tatatattta tatatttata tattatatat atttatatat tatatattta    9540
tatatattat atatttatat ataatatata ttatatatta tatattatat attatatatt    9600
atatatttat atatattata tattatatat attatatatt atatatttat atattatata    9660
tttatatata ttatatatta tatattatat atttatatat tatatatta  tatattatat    9720 atatttatat atattatata ttatatatta tatatgtata tattatatat gttatatatt    9780
atatatattt atatatataa tatattgtat atattatata tctaatatat tatatatatt    9840
atatatatta tatattataa tatatattat atattatata tattttata  tatataatat    9900 gtataatata taatatatat aaaaacatat ataatatata ttatatatta tatatatatt    9960
atatatatta tatattaa   atatatttta tatatattat atatattata tatattaaat   10020 atatttata  tatattatat atatatacac atatatatat ataaatgagg ccaggctcgg   10080
tggctcacac ttgtaatccc agcactgtgg gaggatcact tgaagccagg agtctgagac   10140
tagcctgggc aacaaaacaa gatcctgtct ctacaaaagg aaactgtaaa aattagctgg   10200
gcatgatggc atgtgtctgt agccctagct acttgggagg ccgaagcagg aggatcgctt   10260
gagcccagga gttcaaggct acagtgagct atgattgtcc catagcactc cagcctgggt   10320
aacacagcaa ggccctgtct ctaaacttt  ttttttttaat tctatttata tttacatgta   10380
tttaaatgtg aatattcact acctatttgt tgcatgcctg catttttat  actgggcttg   10440 ccaaaaaccc gaacagcttt ctactttgac aatgtatcag aatttaaatc agcaatatgt   10500
taataagcca agcaaaggtt atatatgcaa ataaaactgt tgtctataac ctcctgttac   10560
actggggcac agcaaaagtc atggtgtagt cgcatgtgaa cctgtccctt tcatagctgc   10620
```

```
tcattgccag gaaacatcag gaatagccat ttggaagagt catcagccct cccaccatcc   10680
gttttctgtc ttgtcttttc cctatgagca ggggaaattc cacgctggcc ccaatcccca   10740
gtgcagcggc tcagcctctg cctctgctgc tggtccccat gaggccagct tagaaacgga   10800
ggattttgca gaacatccct aaatccgctt gaataatgaa gtgatcattc ataaactcac   10860
ctgaacctta ttaaaaccta tttaatattt ttcctggata atcctatagg gataacttgc   10920
ctcctgggct tctctccacc gggttcagtt cttcctttag tggtgaagtt cctcccttct   10980
tagcatctca actgtgcctg agaaaaggcc agtggcggct gcactctgtt ccctgtggag   11040
tgttaataaa gactgaataa attgaaataa atccctttca atgtcattaa gtgctataaa   11100
taatcatgaa ccaatgttcg atggctgatg agaaatgcaa gaaaaatttt ttaatcagta   11160
ggattcataa gttgacaatc tgggccaagt taaaaaaaat aaaataaaa agacttttaa   11220 aaagatctta tcgtttgtta ccagtaagac tgaattccag aagcaagcta ctccctcatt   11280
tgtgggcccc tgttatcact ggctgcttag ggttgccaag ccctgaattc atttgtcaac   11340
taagagattt ttggccaaga ttaagatttc ccatgcctcc atatttccat ctgagaaatg   11400
gagattatac tgtcttcccc ctcagaatgg atgataatgt ggtctctctt ctgttcgcat   11460
agtcatgaaa ctgaaataaa acaacttaag agaattcctt tgagcttctc agaagtgctg   11520
cagggctggg ggatgcctcc caggagccgc agtcaggtgc tgatctgaag tctttggtgg   11580
gctgacttta gcctgacctg aaatagtata gctgctgcca cctggctccc ttagcgtcag   11640
tcagacggtg cagctggttc ctaggggtga gggctgagcc agcagggtcc gtgcccagga   11700
gggatgcatg ggtggccaca gcccagcctg cactgatctt gtctgtcccc ttctttggaa   11760
ggaaggagcc ccaaaccagg gtgcaagaca gtgggtgggg gtgccttgag catgacctca   11820
agtgatttcc agcccctgcc agtgctgact tctctgggga agggctggga cttccttctg   11880
ggctcaagtc acgacccttg gatggaattt cctgggagct tttctgtttt ttctggagtt   11940
ttcagttttt tcctaaccag acagggactt ggtacagaat ctcatattct aattatgcct   12000
aggagcagcc tctccccacc actcacagtg tttagcatgt gacaggaatc gattaaggca   12060
tgagtgatta aattaaagcc aggcattgac ttggatggtg taatattctg acatctgttt   12120
ggtgtcaaag gcacggggca ggcgcgttaa ttgaactgct tgcacctggc atttgaattg   12180
agccagagcg gggctaaagt cagtttgcct tcaccctgta aatggagggt ttctccggag   12240
cgtggatggt gggaggtatt tcagggtgta tgcataaccc ccaccctgac aatggcccat   12300
ctcttctcca gcgtggccag gtttgagtgc cagtcctggg tgtccagtgg ccccatagcc   12360
ttgcgtttta gtaaaatgct gccccccatta ccacctggtc tgtgcacttc ggtcactgga   12420
atttgccatc ttccagtccc gaatgtggca agccatggag ccttaagctc ttctcccctcc   12480 acatcctgga acagacccgc cagtttcttc caggcattgc ctcagtttgc ccctctgttt   12540
ccagtcacac tctcaccagc gataaaatga ttttagacct tatcatctca ccctcggatc   12600
cttatggaaa caataatgag ttgttccctg tttcaattcc aaaattcata tccaatccgt   12660
tttgcatgcc attgccaaat tcctcccaga gcaaccccgt cacctgccct ggccctctcc   12720
aagtgtggtc ctgccatggg catcgcctgc taagccaagc tggcctcgag ctgcctgccc   12780
gggtccccac accttggctc acctccctgc ccagtcccgc ctcctgccag cctgccctgt   12840
ggctccttca tagatgccgt gctctttctg cccttgctc acccatggca gccttgcccc   12900
tctctccctg ccccaccccc tatttaaatt gacctgacct tcctcagtgt ccatcttccc   12960
cgaagctttc cccagccttg gcactcaagg tccagaggct acgcgtttcc tctcacctgt   13020
```

```
ggcagcgccg tgctccccag tgcctcacag tttccttctt gccccgctt cctgtgtagg    13080 actcatctgc ccacaggttg cacgtcctgt gagggcaagg actgtgtctt atgtgacttt    13140
ccttctccag tcacagagct gggcacatag atagctcaaa accctcttta ttaacacagt    13200
tggatgttga gaaatcaaac aggccaatgt caaatgagct ctccttattt aaatcaagtc    13260
agttctccac ctcctagcac tcagttccag tactctatat acatggaaat aataaaaaac    13320
acatttcctt tgaaacattc tataatcgtt cctttgccct acttcagacc aacttaacgc    13380
actccccatt ggtccaaatg agttttgcta tacgaagatg ctgataataa tagcagcagt    13440
ggattattct gctaaaacca ttgcctcgtt aatcctcagt cccgaggtgg ggattattat    13500
cctcattttg cagagaagca aactgagact cagagatttc acagctgggg agggagccag    13560
ctcatccctc tgtccaggcc caagctctct cccgcttgcc ttcctgcctc tgcaacctca    13620
gagcatcccc catctggttc tactgcctgt gctagtcgtg caggagccaa aagacacgtc    13680
tttagtgcta aggactggag aagccatgcc ctccagcctc tgtgaatggg tcatatgtaa    13740
catgagcctg gagaaattat ttgaaaccaa aggcaagcct ctaaaccagg ctgctgcttc    13800
atggcgccgg tgacggcaga accaaattta gtgctgtggg caggtccaca cttatcaaat    13860
agagaagctc attttcttc cggctcacat caagcatgaa aaatgttcac ataccccc     13920 cacacacaca tgctttccgg aggggtccat gtggctagag gctggaagat gtggatgaga    13980
ggagcctggc aggtaagccc agggaagatg acattcagct tcccagacag catctacagg    14040
gagaaattta attaaaagtg gggcggtttc cctgagcaag gcagacaaag tcagccctct    14100
actgttaaga aaagggtca cagtgagagg ggaggtgagg agactgagtc tgtattttct    14160
agtctgttgg gctacactac ctgatccccc ttcctcaaaa atccacttta ctttccccat    14220
gtctacacca atgtggttca cactctggga ccaggaaaag ggggagtgat ggggaacaga    14280
gaagggagga gctcacacag ctgaggctgg ggttatgcat atcgaattac ttagaatttg    14340
caacctcaca gggtactttc atggcgttga aatacacttc ccacagccac cctccctcta    14400
actaaaagca agagtcattt ctcagttctg gtcttgcctc ccacgttctc ctccacattt    14460
aagaaaatcc accagctaca aagtgaagat accatatgtg atatcccacc ctagtttctg    14520
ttttatcagg gtttggagca ggtggagcag gcagagggat catttcagcc tataaattgt    14580
attaagggtg agtactgagt cattcttcaa gaaaagtttt agaagcatcc aaaactgaag    14640
ggtggagcca cctggagaca gtatcatcag tcctggcccc gagcatggcc tgcataggcc    14700
cccatggatc ccagcgggag ctgcagagtg cgggcacctt ggcacacagc cctgagtgca    14760
aaattaggag ctgggcagag ggcatctctc tgtcgccatt gggcagccca gggcacactg    14820
gtcatagcct tagaccacga acaccctgtg cccgggggac agatgcaacc agtgtgccct    14880
gggctgccca atggcaacag agagatcgac acctggaccc catgtcacgg ggactccact    14940
actaaggctc ctaagactgc caccttccag tgggataagc cctgcctcct actgggccca    15000
caatgtgcag agaacacttg ggactacctg gctttctgga tacacaaata ttgatccaat    15060
ctggactaat tagaaggtca gtcccaataa caaatcgaag tcagctgggc gtgatggctc    15120
actcctataa tcccagcact ttgggaggct gaggtgggca gatcatttga agccagaagt    15180
tcaagaccag cctgggcaac atagcaaaac cctgtctcta ctaaaaatac aaataattag    15240
gctgggtgtg gtggctcatg cctgtaatcc aacagtttg ggaggctgag gcaggtggtc    15300
acctgaggtc aggagtttga gaccagcctg gccaacaggg tgaaaccccg tgtctactaa    15360
```

| | |
|---|---|
| aaacataaaa attagccaag catgatggca tgtgcctata atcctggcta ctagggaggc | 15420 |
| tgagacagga gagaatcgct tgaatccagg aggtggttgc agtgagctga gatggtgcca | 15480 |
| ctgcactcca gcctggttga cagagcaaga ctctgtctca aaaaaaaaa aaaaaaaaa | 15540 |
| aaaagccatg cctggtggag cactacgtgt aatctcagct atttgggagg ctgaggcacg | 15600 |
| agaatcactt gaacctggga ggcagtggtt gcagtgagct gagatcgcgc cactgcactc | 15660 |
| cagcctgggc gacagagtga gtgagactcc atttcaaaaa aataataaat ctgagtcact | 15720 |
| ttaatattgt tatttggatg tcaacctcta ggtgtttgag acaggagagt gatatggggg | 15780 |
| cactggaaac acacaggcac ggggtgtcct cacacttggg tagcccacac gatgtgattt | 15840 |
| cagggtgctg ggaggtcccc ccactcccca aattactaac aagtggatag tactttacag | 15900 |
| tttatatgat ctcatttgat tcttaacatg agcctgtgag tgaaaaattc cttcccctct | 15960 |
| tctacagatt aggacgttga gattcaggga ggttcagagg gattcaggga agtcaagtgg | 16020 |
| cacctggagt cccgtggcta atttgaggcc ggtaggggat tcgaacccag gatttgtgct | 16080 |
| tcttatgcct gggcttctgc tccctggggc atggtcttcc ccctagcttt cccattcact | 16140 |
| gctttagcct aggggtccta ccctttatta aactgccagt gcctcactgc ttttctcccc | 16200 |
| caaagacaaa aaaaagtgt ttttgctttt gttttgtttt tcatgggcag agacctggaa | 16260 |
| tttcagcttg agaatttgtg ccatatgata aataaatcaa cagatggctt tttccttaaa | 16320 |
| aaaaaaaaa aaaaaacta agatgtattt gcagtgaggc ataatttgta ccaaaaagtg | 16380 |
| ctcaccacac tgtagtcatg ggggcaggag gcagccgcgg gtgaagggag aaatcttgga | 16440 |
| gtccaggcag cccccttctg ggctgaactg gggagctggg ggtgctgcca gccctgccag | 16500 |
| gttctcctag gaggcggcag ctcatatggc tgtgggagga ggcagaggga gcctcatatg | 16560 |
| cacccacatt tccagggatc tagaagacag aaggaggaaa accaccatca tgttaaagca | 16620 |
| gacagttagg taacacatcc tgtaatacaa gttatttttt ccacatctaa aggctaaaaa | 16680 |
| tagttgttag aatttaaaga taattggtaa atgagtttct atccttctag tttcacatca | 16740 |
| aatggaatca tgctgccttc acatcactag tgcccgttat ttgtgtttaa tttccacaat | 16800 |
| gttgtctaat tccactcttt gggcttcccc agggatccag cctccctcac tcgcccatcg | 16860 |
| cagggagatg ctttattcat ctttgtgtct tctgtgccgg gcatagcgca tggcacagaa | 16920 |
| taagcactca gtaattgatt cacgagtgaa taaatggatg agtgggtgag ttcaatattg | 16980 |
| actacaaaaa ccctaaggcc acactggtga gtggctgcgc ctgtagtccc agctgctggg | 17040 |
| gaatctgagg caggaggatc tcttgagccc aggagtttga aactagcctg ggcgatatag | 17100 |
| cgagaacctg tctcaaatga caaaaacagg gccaggtgca gtggctcacg cctggaatcc | 17160 |
| cagcacttta ggaggccaag atgggaggat cacttgaggc caggagtccg agaccagcct | 17220 |
| gggcaacata gggagaccct gtctctacaa aaatttttt aaaattagc tgggcatggc | 17280 |
| ggtgtgcgct tgtagtccca gctactcagg aggctgaggc aggaggatca cttgagccca | 17340 |
| ggaaattgag gctgcagcga gccatgatgg caccactgca ctgcagcctg ggcgtcagaa | 17400 |
| cgagacctgc tctcaaaaaa acaaacaaac aacaaaaaa aaggctttct taaagagact | 17460 |
| tgagaacaga aaggggaaca gatacataac ttatatattt atttgttcat ctttccacct | 17520 |
| tcctggaggg tggaggggaa caggtctgta tttggagttt tgaatgctaa aagtgggaat | 17580 |
| acatgtactg tttgccatga tctgttcaaa agttaagcca aatgccttag attctcctga | 17640 |
| aaactggaat gccactgtaa actataagcc ccacttcaaa gataaagat cttgatgaac | 17700 |
| agggctgggt ctgtggactg ggcctctccc caccacacaa ggaagggtgg tgccagttga | 17760 |

```
aggaaaatca cttaaatcct tgctgtctcc taataaggtg tggtcccagg tagggctgtc    17820
agaattagca aattaaaaca cagggcatct gtgaaaatta gaatttcaga taacaacaaa    17880
taattggcat aggctgcata atgtccctca aagatatcag gtcctaatct ccagaacctg    17940
taaatgtgat cttatttgga aaaggggtct ttgtagatgt ggttaaatta aggattttga    18000
gatgggggga ttatcctgta ttatctaggt aggtcctaaa tgcagtcaca ctcatccttg    18060
taagaggaag gaagagagag atggaaaaca cagaagagaa gacaatgtgg tgatggaggc    18120
agagattgga gtgaggtggc cacaagccaa ggactgctgg cagctaccag cagccagaaa    18180
agtccaggaa ccaattctct cttggagctc cagagggagt gtggccctgc tgacacctta    18240
gcttcaacct agtgatcctg attttggact ttggccttca gaagtgtgag ggaatgaata    18300
tctgttgttt taagccacca agtttatggt catttcctac agcagccaca ggaatcaaaa    18360
acagtaagta tgtcccatgc aatgtttgtg acacacacca aaaatattac ttgttgttca    18420
cctgaaattc aaatttaact gggtctcctg tattttattt ggccaaccta gttcccaggc    18480
ccaaagaaag aggcttttga aatttgcaag aaagctggtt ggagctgtca gaaagtggac    18540
tttgtaaaca cagtaccacc gaaccaattt gaactgtact acctctagac aaaagagagg    18600
gcagtcagac agttgttcgt gatttcttct ttcaacagtc atttgagcac ttactacaaa    18660
acagaagcta tgtgtaaggg tggaggcgtt agctgttaat caggacctcc aggctaagtt    18720
tctgtattag tccgttttca cgctgctgat aaagacatac ccgagactgg ggaatttaca    18780
aaagaaagag gtttaattgg acttacagtt ccaagtggct ggggaagcct cacaatcatg    18840
gcagaaggca aggaggagca agccacatct tacatggatg gcagcagaca gacagggaga    18900
gagagcttgt gcaggggaac tcctcttttt aaaaccatca gatctcgtta gacttattca    18960
ctatcaagag aacagcacag aaaagacctg cccccatgat tcagttactt cccaccagat    19020
ccctcccaca acatgtggga attcaagatg agatttgtta ccatatcagt taccaaccct    19080
tccagataaa tcacgtgaaa tatcgccatt aacagagtga gctcaggtgg ttcttcagtg    19140
catttctgat acctgaacct tccctgggaa tttcacagac catcaggctc tccacccttt    19200
gatagcagga tagcagggcc caggttctgc aggaggagat gttaccacag gcctgaaagg    19260
gagggagggg cagatgctac aggaagatgc tggctctgga ttcgctggag gagctttcaa    19320
gggaagtaga tacacactgt ctccatcatt tcatgtccat cacactctaa aatgctttgg    19380
acaagaagca aatgttaaag acaaatgtgg cccattttcc tgtacaaaga gggctgctcc    19440
catgccaggc tattggcact ggtgggcatg aggcttctct gctgccctgg ccgggggggtt    19500 ctctcactca ccattggctc tctgacacct ggagagacca ccacccttgg gctttcatga    19560
tgctcacaga atccacactg ttggagcttt aaggagcctg gatcaactgg aacaggcagg    19620
gagtactagg acagcccagc attgccccaa aatatccagg cctgataaaa gagaaaaaca    19680
ggtagctcac aggaaaagga taaaaaaagg aggaggggatt taacatgaaa aggtgcttga    19740
tctccctcat aataaaaaga ctgctgattc catccaggca agtgacagaa aaaaaaaatt    19800
taatttaaaa agactgctga taaaaccaca gcgagacact gctgctcagg gatctgaggg    19860
tgtgggcagc caggctgcca cgcatcatgg gtcggagagg aagaccacac ccctggagca    19920
gagggcggct gatctgtcag atgccctttg acagcacctc agcttccaag aattaaccct    19980
ttctatgtga gcagaggcat ccatgggggg acacactggt gaatcatctg ttatgtagaa    20040
gtctggaaaa catcaggatg gaactggtga ataagtgtg gcctctgacg gaatggagcg    20100
```

| | |
|---|---|
| gtccgtctgc actgctgcgg gtgcccctca gatcctgtgg gtcagtgaga aaagcagtga | 20160 |
| ggaacaaggc aggtactgtg tactgtcctc tgcgtgcaag gaaggccagc gcatgcaaca | 20220 |
| gagtccacac agacatagcc taactctgga aggaagaatg agaatgcagt ttcagtggtg | 20280 |
| gcctctggtg gggagaaact gggtgaaggg agatgtcatt tccatttctc tactattaat | 20340 |
| tttgtattac catgcttaaa tgttactttt tacctttttt ttttttttg agacagggtc | 20400 |
| tctctctgtt gcccaggcag gagtgcagtg gtacaatcat ggttcactgc agcctgaacc | 20460 |
| tcccaggctc aagcaatcct cccacctcag cctcctgagt agctgggact ataggcacgc | 20520 |
| ataccaccgt gcccagctat tttttttaat caagatggag ttttttctatg ttgcccaggc | 20580 |
| tggtctcaag ctcctggact caagcaatcc tcctgcctca gcctcccaaa gggctgagat | 20640 |
| taaaacgtga gtcaccctgc ccagccaatt gcttttaaa aaagattaaa tgcatgtata | 20700 |
| cgctcaggca tcagcacact tggaaaggat gaaaatatcc ggaagaaggg ttctttaaa | 20760 |
| aggctcctca agtgatgctg gcaggcatga cgaatgtccc tggtcacaaa agctctgatc | 20820 |
| tggcctaacc ctgtcatgtt agagactgga gtgcgtgtgt gtgcgcgcaa agtgtggggg | 20880 |
| gatgggggtg agtgtgtgtg gtgtgtaagc atgagtgtgt atgtgtgtgg tgtggggtg | 20940 |
| tgtgctgtgt gagcgtgtgt gagtctgtgt gtgtagtgtg tgtgtgaagt atgtggtgtg | 21000 |
| tatgtgtgac gtgaggtgtg tgtggtgtgt gagttgtgta tggtgtgtgc atgagcatgt | 21060 |
| gtgtgggcat gtgatgtgtg tgtggtgtgt aagcatgtgt gagtgtgtat gtttgagcat | 21120 |
| gtgtggtgtg ttgtgatatg tgtgtggtgt gtgagcatgt gtgtgtgatg tgtctgtgtg | 21180 |
| tggtgtgtgt gagcatgtgt gttgtgtgtg tggtgcatgt gtgtggcgtg tgagcgtgtg | 21240 |
| tgtgcattgt gtctgtgagc atgtgtgagt gtgtgtgtgt tcagcatata taaggcatgt | 21300 |
| aactgaacac agcactttag agggctctcc tggagtcaga gggggtgggt aggaggagaa | 21360 |
| gggaggtggg ctagtgtgct gaagtatcta ctccttgtca tagtctgtga caacccagac | 21420 |
| tagcccatga gccaccctgt tccctgcatt tccaatgaga cctcggtgga catgttccct | 21480 |
| gaggtgaggc tgactgatgt catttgacga tcttgatgcc aaatccttttt atatcaaaaa | 21540 |
| caaccagaac actctctttt ctcttagtgc tttcacccag atgaccacat ttcatcctcc | 21600 |
| cagccactct gggccaggtg gcactgctgg tttgaaaggg aggtctcccc tggagtaact | 21660 |
| tccgtgggcg gattcacacc ctgcccacag tcctgtccca gtcagcccac catggtggtc | 21720 |
| tccggttcct ccagaattcc cgcttttcag ctcatcccca cattcccgga gggactgaga | 21780 |
| gcgcagcccc agggccctgc tctttggggg ccgtctctac acccagagaa gcagcaaggc | 21840 |
| attcctaggt ttctctttca gatgcagaac ttcagtgttc agagatgttc ccactggtcc | 21900 |
| tgagagggct cagttcagct ttaatgactg cgctgttgcg tgtgctctgc agagggcggg | 21960 |
| tggcccagcg tggctgactg cagttttcct gacgtggagc ccgagcctgc cccgctgttt | 22020 |
| attaattaag gatcactctg cttgcagaac cctgaactcc ccagaactgt gaggtgggag | 22080 |
| aaccccgaga ggccacctgg ccccacttcc cacctgctgc ccaaacccccc tctctgcctt | 22140 |
| cctgacagtc accccaactc ccagtgatcc ccatcaacca tctgacaagg ggactgagag | 22200 |
| ggaagagaaa ggaggggccc aaagaggaag gtaaaactgt cgggaacagc ccccaaatgt | 22260 |
| gtgacagcct tcagtggagt tgcccacttt ccctttctc ctccctgcag gacctccctt | 22320 |
| ctccccagtc ctccccaact tctgaggtta cattgagaaa agtctgcaga gaggtgccag | 22380 |
| catcacaagg tgttaaggac cacgagtttg gcatttaac agatgccaga gccacttgag | 22440 |
| aaatgtggta actaagccca gagaggtaca gttaacctcc ccagagtcac acagcaggtt | 22500 |
| catggcaaag ctggactagc acaggtgtcc ttcccctgca gatcccctttc tgtgccccac | 22560 |

```
atcacctccc tccagtgtct gggccacctg gagatgggcc ctcagactca cccggccaga    22620
ggtgccatct catgggagag gtctggccag gaagcatcga tatttgagat cccaagaaat    22680
gaagacttgg cctgtcagat gacagacttc ggtcatggga acacgtgatc tgttttacac    22740
atgcgtcccc tcagcagcag ctttccagaa cattcccact ttcttctgta gtgagaagaa    22800
ctctttccct gcagcctcct gcccaactcc tccttcagtg tctttgcttc agtgtctttg    22860
ataaaccatt ctgctttgca gagtgcgagc tctgccttgc agggttcgca tctgcctgtg    22920
ctgagtaacc aacgctaagg tcgagtggtc ggtcacctct cataagagct agggttgtct    22980
catgctgatg actaggactt gccctcaagg agaaaaataa atcaaaacaa agcaaaaac    23040 agcaaacatg catctcttaa agaaggctct gagtccaggt aaatttcctt ccactgaagc    23100
agccaggctg aattcgaatt atctttgccc ctgcttaaaa actaatgcaa attttcctag    23160
agaatatcca ctaattcctg gaggggggcat gggcattcct gatgcccatg agaggaccat    23220
ttgctcttcc ctcagtatgc taaataacag aagcgacatt tgttgctgga agtatcagt    23280 gaagttaata aggttttttct tgcccagggt gagggaacag ttcccaatga caaatgctgt    23340
atgggaaggg gctgtagaac tgccagcccc tttggtccat ccgtaaagtg aactctgtgg    23400
atcctggagg attccagcgt ctttttttttt ttttctttttt tttaagaca gagccttgct    23460 gtcacccagg ctggagtgca gtggcacgat ctcagttcac tgcaacctcc gcctcccggg    23520
ttcaagcgat tctcatgtct cggcctcccg agcagcaaga ctacaggtgc gcaccaccat    23580
gcccgactaa ttttttgtatt attagtagag acgggggttt cactctgttg gccaggctgg    23640
tctcaaactc ctgacctcag gtgatccacc cgcctcagcc tcccaaagtg ctgggattac    23700
aggcatgagc caccatgccc agccagcatc tttcattttt ctgtctgctt tggccctttc    23760
ctctctcact gtcttccttt tccatttcca aagtcagtcc atctcactat tagcacaaaa    23820
actgctagag cgcttgtcat tggtcatctc tccctgcacc tggctggtct gttcttggcc    23880
actgaagcgt ttcccccagc tgttgcttta atcattttat tgttattatg ccttacttaa    23940
gaaatggata tgagatgcat ttacctgtct cttcctgcca ctctgcagag ccagtaagat    24000
gtggtggaaa gggcccaggc tttggaggag gctggctgg ggttggatct tggctgcccc    24060
ctactagctg tgtgaccttg ggtaagtagc tggacctctc tgagcctggt tcggaatcat    24120
agcacctctc tttcagggct gctgtaagga atagcagtgg tgtgtataaa gcagagcgca    24180
cagccagcaa ctggccccta gccacactgc tgagcaccta ctgtgataag ctgccattgt    24240
ggtgtgtgaa gcaaagggga aacatgcctg ctgtagtgag cttcctgtag ggcaggttgt    24300
agaaccagag gtgggttcca aggttacaaa gggactctta gtgtattagt ctgttctcac    24360
attactataa agacctacct gagactggat catttataaa gaaagaggt ttaattggct    24420 cacattggct gggtgcggtg gctcacgcct gtaatcccag cattttggga ggccaaggcc    24480
ggcggatcac ttgaggtcag gaatttgaga ccagcctggc caacatggtg aaaccctgtc    24540
tcttctaaaa taaaatacaa aaattagctg gccatggtgg tgtgcgcctg gaatcccagc    24600
tactcaggag gctgaggtgg aagaattgct tgagcccggg aggtggaggt tgcagtgagc    24660
caagatcgcc ccactgcact ctagcctggg cagcagactg agactctgtc tcaataaaaa    24720
aaaaaaaaaa gaaaagaaaa agaattgcaa gaaataaatt attgtttatg agctatatgg    24780
tctgtggtac cttgttgtgg gactgggagt cttggcgtct ccctgaccct gcctgttgct    24840
gcagcaccgc tcagccctgc ctgctcccta cctgcctccc ctcggcctct cctgcctcca    24900
```

```
ccgggcccct ggtgcctcct ctagagacag tcctcctggg accgattgtg ttctcactta    24960
cacgaggcat ccaggactac agataaccag aggaaggggc gccccccccg cctgccctcc    25020
tccctggcat cctcacgctg cagaggtcag agcctcatcc cagcccctta cctgcccta     25080 ctctgtggag aaccgtggtc agttcgccag gccggatcca cgaacggcct tgtggaagat    25140
ggtgagctca cacccagagc tggctccgat gaccctgtct cctttacatg tttctacctt    25200
cccctcccta ccttccccca ctgctgggcg cagagtggag gcagatgagg tttaaagctc    25260
agaagggctt aaacggggttg gggcgcagtg gctcatgcct gtaatcccgg cactttggga   25320
ggccaaggca gaggatcact tgagcccagg agttcgagac caacctgagc aacatagtga    25380
gaccgcgtct ctacaaaaaa taaaataaat aaaattagct ttgcagggtg gcatgcacct    25440
gcagtccctg ctactcagaa ggctgaggtg ggaggatcgc ttgtgcccag gagtttgagg    25500
ctgcagtgag ctatgctggc accacagcac tccagcctga gtaacagaat gagatcctgt    25560
ctcaaaacaa acaaacaaac aaacaaaaga aggcttaaag ggggctccag gtgggcttgg    25620
cagcacaaag ctatgaagtt ctatcttaga cacaagttct gttactgggc ctttgcaggc    25680
tggcctgggt acctggctgc catagacagg gaaccttcca gatgagctgc aggcgtggag    25740
cacaggagcc agggtgctct tcctgggctc tgtccacagg cagaacgtac acagtctttg    25800
tacacgtccg gcggctctgg tgcctatttt tgtttgtgtt tttcttttgt ttgggggggat   25860 ggatttggtt tcccccgagc cctctgtcct cctgtcacct ggctggtgct cggcaatgtt    25920
gaccagctgc ctggctggag ttggcagtgg ctaaggctgt gacagctaac atgttcctga    25980
gtcctctcat ttcttcacca taatgccctg ttgagtttgc agatactgtc tctgtttta    26040 tctcccgggg aaactgaggc tcagagtggc taggccacct tcccatggtc cctcagctca    26100
tgagggccac acagggcatt gcggtggcct tctcctcagc cttgaccctc cggccccagc    26160
attgctgcct caaggggtct cctctgctga gccgtgcacc ttctgcctgg cagctccaac    26220
tctgtggctg tgttcagtgg ctcagcactg ccccttgacc ctccctggcc ttctgcggat    26280
gccagactgg agcactctga caaggtctgg ggtggttgta tgggtcctgt gacctctata    26340
cacctcccag tgcctgggaa tcctgcagat acaccctcct tagccgtccc taaccataga    26400
ggacatttct gaggtccccg agagagtggg gcacccctgc aggatccaac tgctgggccc    26460
aggaaggata gcagcagcat gagggggttcc attagccaca aactcacggc atggaacctt    26520
cacccacctc gcccctcatc tgctgtttag cacctggcac gccgtgtata cttactgatt    26580
attcattttt aatggcaaat tatagtggca aacgtatgca tctttgcaca attgttgtac    26640
agcatgatga acaagtcatt aatagtaaag aataaatgtg aaagtgagaa aaatctgact    26700
gccaaagttt ttactccttc cttccctccc cagactttta aatgaaagtt tagggataat    26760
cccttagttg tcctgctagt aggacttgca attaaaagaa ttgggccaag aacacttcta    26820
cgcttctcct tttaggtttg ggtgtaaatt cggggtattt ctcactgatg aaagcctggt    26880
gcagggcaga ccgtgggaag cttctcatttc cggaatggac catcaacatc ccttggagaa    26940
gaattctctt ctccagaccc agacctggtg tcctggcacc cattgggcaa gtgggtccta    27000
gaagacaaac ctggtcagag cctggaggct gcttagcatt ccccacgcac attagcagct    27060
cggagagctc aggaagccgc agcccctcct tgcctcacca gcctggatca ggacagcatc    27120
ccctggaaga cacacagggc ctggcctctg attaccagc ctggagggaa agctcaatcg     27180
agcatcatgt cacccggtgc cccatgcag ggtggcactg gtgagacccc caagccaatg     27240
ataccacctc acaggagtgc aggcccattg tggccagatc atcttgactt ttcaagataa    27300
```

```
atcagaaatc gtatttccat gagatatccc tatttgcaag tgatggtgac taaattagaa    27360
gtttttgaat attgtaacat gttcgtaggc tgtttgtctg gtttaaactc tatctggagg    27420
aattcaagct agacttcagg aataacttct tgaggcaagg attttgagac cttagggaaa    27480
gaaggacgtc ttgggggtat tctgactgtt gtcctcctgg aagggaagaa cagagaacta    27540
gaagactgcc cttagcgaag ttcaaagcac ctaagcccgg gaccctcagc aagtgttctt    27600
gagtcacaga ttctccctga ggcgcctctt tctggctcca tagaatggct gattctgtaa    27660
ctcggtgagt ttgcttttttt tttttcctcc atcacccagg ctggagtgca gtgaagctgg    27720
agtgccgtgg agcgatcact gcaacctctg tctcccaggt tcaagcaatt ctccttcctc    27780
agcctcccaa gtagctggga ttacaagcat gcagcaccac acctggctaa ttttttgtgtt    27840 tttaatagag acgcccgaa gtgctaggat tacaggcatg agccaccgcg ccagccata    27900 actctgtgac tcttgttaca aaggccttat attttgctct ttgagggtgg ttttggtttg    27960
atgcctgttg gttgccatct tttaactagg gatgttttat caaaatgccc agccaaagtg    28020
tccaaacaaa ttataccttta aagtttgaaa atgtctggca cttctaattc aatgcctgtt    28080
gtgccaggca ctgggctgct gaggaactga gtcccgtccc tgcaggctag ctagagaaca    28140
cacacacaca cacacacaca cacacacaca gagtggtctt acaagtcagt tttatattct    28200
acctatatgc aataaaggta ttattatgtt gaggtgcctt gatataaaaa tttttcttaa    28260
aggagaggat gcctaaaaca ggcattacct gaaacctcct ctctccagca ttggttgtct    28320
tctgtcatga ctcagggttt tcactgagaa tgggatggaa atgtggtcta aagatagggc    28380
caatgttggg actggatccc ctctgggaag tcagaccagg ctagggcagg tccttgaagc    28440
catcaggaaa agcctctgga gccagaaaca aacaaaaaa aaaatggtgt taactaaact    28500
cagtctcaaa tcctgaatag gactcaagtc aagcaaaata attaaaggag ttagcaaagg    28560
gcaagtcaga gagaccgagc aacaccaatg tcttccggga gccctgtggc gagtgacaga    28620
gcctggactc tggagtagaa ctcatcttgt gtcttcttct gccactcgtt agctgggtga    28680
ccttgagcca agcccttaa cctcttggac cctatgttct tatctctaag tagggctgg    28740 taatatcttc ccctttgagg aatgccctct aagggggtgtt gtgaagattc ggtaaggtgg    28800
caggggtagg actcctggcc agaaacaggc acataataaa tgctaagtct ctccttctct    28860
ccacctgctg gatgctgtag atactaagga tttcgatgtg aatgagacaa aaccctgcc    28920 ttccaggagc ctttgagaat cagagaacta gacccatttc cagaacaagg ggatgcaggg    28980
tctggataaa gttttgggga tcaatagagc agagggctcc cagaggatcc catagggttg    29040
actcctaact caagggcatg agacaacccc caggaagggc accctggaag gggtccggct    29100
gtccctgatt tacttgtggg cactgggga atgcccggag ccatccagcc ctcagggctc    29160
tgtgtgattc tgggttcctc ccataaaaga taatcagatt cttttcacgtt aatgtctttc    29220 tccacctcat tgcacatcat gcagctattc attgactcag caagtatcag ctttgcatgc    29280
gaccttggcc tacccacttt agcttttagt aatagctccc ttcttgaata atacaaccag    29340
tggggaaaca gaacctaact cttacctctg ggaggcttat ttgctttgag aacatatgtc    29400
ctgcagtttt gttcatatgg cagtgaagtt tcgtgcacac actctagagc caggcagcct    29460
gggttcaaag cgcagctctg ccaggtccta actgcatgaa tttgggcaag tcgctcaacc    29520
tctccatgcc tgagtttcct catctgtaag attggagcaa tggtaatacc tgcttttttag    29580 ggttgagaag agaattaaat gaattaagat gggtaaagtg cttagagtgg agctttgcaa    29640
```

```
gtagtaagtg ctatgtaagt gttcgattta aaatgaaaga cccttaaata cattctttgt    29700
tcatttcaca agcccttcat ttcacaacct tacatttcac aaccaagctc tgtctcccct    29760
ggaatccagc cataactctg ctcacaagtg tgagacaggc cccagcagag ctgcacgaag    29820
aggagagaag gcagccccccc agactcccaa cccctgtcc aagatggcaa aaccagaaca    29880
cagcctctgt accaccccag caggtattca gaatctgcaa tctccaaagc ccacttcaat    29940
tgtaaatgta gagccacgtg cgctttaagt cacctgtcac tctggaggct cttttgctca    30000
gttcctcacc attagcaggg atgacaggga gtgcaggagt gcggtcgact cccagatatt    30060
ggagagcgct gggctagctg cccattctcc cggcctccac tcctctttgc tgtccagcca    30120
tcacttgctc tttgaaggca aacaaaacag aaaacagtgc caaaagtatg ggaagaaagc    30180
cagcttctcc cctggggtgc ctgtgatgcc atgcccaccc tccctgacca cgcagcccct    30240
gtggaccctc agggccccaa gcccccattt ccatcacatg cgtacaccca tgtgtgtcca    30300
tagccgccca tctcagtcaa taaggctgct cctgcccact tggaatagtg gtgacaacca    30360
ggagtggctt atgggaacta tcccaatggc ctgacacat gtccgctgca aaccgctgag    30420
gtaggacact gccctcatgt ctagctgatc agcaagaggc gcagttgctt tcttaggtaa    30480
cattgctgct gtgtcctggc cattgctggg gggtggcact taatctacac cagatttttc    30540
cctcctgtat cttccaagct gcttggatct tggtgctgaa ttaggttgga ctttgtcttg    30600
tggggaaggg aggactatag accctcaacg taagcaatgg tcagactatt ctaagaaaac    30660
tcgccgaatt aaagcatgag gtaaatttag ttctgacttc tgtccacccc actgccactg    30720
tcccctttta tcccatgatc ccttgctttt ctttcctcc tctctcccta tctcttgtgt    30780
ttgacgcatg ataggaattc agaaatatat gtttgtggat tgtttattc acgtagcaaa    30840 ccatttcttg agtgcctacc atgggccagg tagaatgggc ggccccgggc tgcagtggtt    30900
tcttcagccc ctctccaggg tttacactgt gcaagacggt ttgtgatggg tcctcccatc    30960
gaggaccaca ctcttctttc tctgtgcccc ttggtcctca gtctctgacc ccacttcaaa    31020
ggcagcattc actcagggaa gctcccatac aatgctagtc agagtaaaag tttggacaaa    31080
ttgccaggaa gcagcttgtc agtatgcata aacagccttt aaaatattac tactctttga    31140
cccagaattt cacttctagg aatctgtcct aaggaagtag tcacatgcaa aagatttatg    31200
taccaagatg ttcatcaaag tgttgtttta aacaggaag tctcagaagc tggataaata    31260
tccaacctct ggaaatggtt agatagaata gtatgtagcc attagaaaat tatgtctatg    31320
gggtttaaaa tgtcatggga aaacacttct gacataaaag agcatgagaa ctgtatattt    31380
agcataatct taactatgtt ttagaatgca caggaaaaaa atgtacaaac atattcatag    31440
tgatgtctct ggtggtagga ttatgatcag taagtacttc tgtctcttca tattttcctg    31500
tatttgataa tacatgcata tgttgttttt aaaataagaa aaattttaag tttaaaattg    31560
gagctgaaaa gtgttttag gtcaggcgag gtggctcaca cctgtaatag caccactttg    31620
ggaggctgag gcagtcagat cacttgagcc caggagttcg agaccagcct ggccaacatg    31680
gtgaaacccc atctctacta aaaataaaaa aattagccat gtgtggtggc acacatctgt    31740
aatcccagct acttgggagg ctgaggcatg agaattgctt gaaccagga ggtggaggtt    31800 gcagtgagcc aagatcgtgc cactgcactc tagtctgggc aacagagtaa gactctatgt    31860
caaagaaaaa aaaaaagaa aagccttttt aaacagtagc agacataact atataatcct    31920
tactaagctc tcggtcaaat ttttattat atatttattt tattcattta ttattttag     31980 acagggtctc actctgttgc ccaggctgga gtacagtggc gtgatcatgg ctctcttcaa    32040
```

-continued

```
acttgacctc ccgggctcaa gtgatcctcc catcttagcc tcccaagtag atgggaccac   32100
aggtgcatac caccacacct ggctaatttt ttttattttt tatttttaga gatggtgttt   32160
actatgttgc ccaggctagt ctcaaactcc tgggctcaag ctatcctccc acctcggcct   32220
cccgaagtgc tggggttacc agcatgagcc actgtaccca gccctcaaat ttttaaaaat   32280
ctataagaga cattattgga caattagaga aattcacata tggacttata atagtatcag   32340
agtgtgtggt gtgatggttc tggagggaat ggacttttc tttggagaca ggcttttcta   32400
tgcccaccct tttatcttgc taacttatca tcatccaggt tccagcagaa acattacttc   32460
ccccaggaaa tttcttaagg gtgcagtatc atgatgtctg cagcaaattc tcaaatagct   32520
caggaaaaaa gtacgtgtgt ggtatgagtg tgtgtatgta tgtgtgtata tatatacaca   32580
tatatacaca tatatataca tatatgtgta tatatataca tatatgtgta tatatataca   32640
cacacataca catatatata cacacacaca tacatacatg tatttttata taattatata   32700
tgcagagagt gcaaatgttg ccaagttaaa gattggtgag tctaggtgaa gggaatatgg   32760
tatttattgt attatttgtg caacttttct taagtttgaa aattttcaaa acaaaaaatt   32820
ggaggaagaa ggcatgccag tctaccccaa gccctccatt ggaatgctga aaatctaaac   32880
aatgtgattt ggcaatttca tttcttttct gttgtgggcc agtagtcctt agatgttggg   32940
gaagggggta gtcgctgagg tgtggttgac ttaggatgga agaagcagaa gtcaagactc   33000
ccagggtcaa agtggtttgc tctgctgacc caagtgtggg aggcccagag tcagcgtttc   33060
aggtgtgcta attcagcatg gttctattca cggccaaagt ccaccctggg cacctctctg   33120
gcagcaatct tgggtgactc tactaaggcc aggcctccat gacccctatgt ctggatccca   33180 tatctccacc tctcccactg tctcaggaac ggtgcttagc ttttttcttt ccctctcctg   33240
tcttctttgc cagcatgtag aaagtttaaa taattcccct ctttacaaca aacaaaaaca   33300
tacccccttc agtcaaccac cctagctctc ttctcctttt cccagccaga ttttttttaaa   33360 agcatcctag gccaggcgcg gtgactcacg cctgtaattc cagcactttg ggaggccaag   33420
gtgggtggat cacaaggtca ggagatcgag accatcctgg ctaacatggt gaaaccccat   33480
ctctactaaa aatacaaaaa agtagccggg agtggtggca ggtgcctgta gtcccagcta   33540
ctcgggaggc tgaggcagga gaatggcgtg aacctggtag gcggaggttg cagtgagccg   33600
agatggcgcc actgcactcc agcctgggtg acagagtgag actccgtctc aggaaaaaaa   33660
aaaaaaaaaa aaaaaaaagc atcctcagca ctttggcaac tccatctcct cccaacatgt   33720
ccctgttact ggaatccagc caggactcag ccccgatctt tctactctaa ccagttgtct   33780
cagttaacaa ggacaggttt atgctgcagt gacaaacaag atcccaaatt cttgtggctt   33840
cacacatctg gcaccacctc atcttccagc cttaggagtc atctttagt tccttgaaaa   33900 ctctttacag ttttctgttg gggccttgtc atatactatt ccctggaat gttctttcct   33960 atccctcccc tttcaccttg ctaacttgtg cccatcctc aggtctcagc agaaacatca   34020
cttccttggg gaagttttct ccaacaccca cactacacag gtgtcccatc tacactccta   34080
tgactttgtg gtacttgtct cacttcattt tccactgcct tccccacaag gcacctgcac   34140
aagggcaagg accgtaccac tgtacctatg tcactcattg ctgtggtcac ctgcactctg   34200
gctgcctacc ttaactacac attagaatca cctgaggagc ttttaaagcc acaatgcaag   34260
actccaccct aggccaattg gatccaaatc cctggggtag ggccagacat cagtggagtt   34320
atatatacat atatatattt tgtttgtttg tttgtttgtt tttgagaca gagttttgct   34380
```

```
ctgtcaccca ggctggagtg cagtggcgcg atcttggctc actgcaagct ccgcctctcg    34440
ggttcacacc attctcctgc ctcagcctcc tgagtggctg aactacaag tgctcgccac     34500 cacgcccagc taattttttt gtgtttttag tagagatggg gtttcaccgt gttagccagg    34560
atggtctcga tctcctgacc tcatgatctg cctgcctcat cagcctccca gagtgctggg    34620
attacaggca tgagccactg cacccggcca tcagtggata tattttaaa gcactgcaga     34680 gaattctgtt gcatcagctt gagaaccact gatctgcctt gtgcttcaca tttaaaactt    34740 tttttaatg aataaataaa ccccaaaaaa ttaatctccc taagcctccc tagaagatag     34800
gatggtaagg atattttcct aggtaaaaat atgttaattt catatttcat gaaatttcat    34860
gtttcatttc aatcaagctc tgtcatacac cttacatggg gcaagcccag tgcctgggca    34920
gggtgtaatt atactcatta cacaggcaag gaaaagtcac attaggtgat ggagcacaaa   34980
taggcagtta atggtttcag ggctagttag gatatgtttg tctttcaatt gcaagtaata   35040
gaagcccaaa gaaattggtt atttatataa tataattgat tggttcccaa atttgaaaaa   35100
ttcaggaata gacccagctt aggtacagct ggatccagtc actcaaacaa tgtcacaaag   35160
aaccctttga caggaatgta tcctgtgttg actctacttt gctctgagta gtctttcccc   35220
aggtgatgat aaaaatggtc atcatcgcca ggcttgtgtc ctgtttagta ggaatataca   35280
agaagagctc agtaaatgct ggccccacca ctaagcaaaa acaaaacttt tgttgttgtt   35340
attgttgttt taaataacag cttagacctt tcttctttcc ttgttattct ctttcatctg   35400
taatccagtt ttctacttct gaagtataga atgttctgat gatttattct tcattaccca   35460
caacttgcac atgtttattt aaaaatgcca ggattgcctg gccgttgtgt gctgttaacc   35520
tttgtttgct gttagtggat ccctgaagtt caggctccca ggggagcaga taatgggtat   35580
ccagttcctg caatatccac cctctggcaa gccaagttcc ttcctgggta aggttttgcc   35640
tacctgcatt cctagggaag tttctgggcc tgaccaccaa gccagctctg agaaggggtg   35700
cataagcccc accatgcttt ggctctgtcc ctatagaata ttttatgttg ttactgaaaa   35760
ctaaaggaag atgggtgcgg tggctcatgc ctgtaatccc agcactttgg gaggccaaga   35820
cagattgatc actcgatgcc aggagttcaa gaccagcctg gccaacatgg tgaaaccttg   35880
tctctacaaa aacaaaacaa aacaaaaatt agccgggtat ggtggcatgc acctgtggta   35940
ccagctactc aagaggctga ggcacaagaa tctcttgaac ctgggaggta gaggttgcag   36000
tgagccgaga tcgcactact gcattccagc ctgggtgaca gagcaagatt ctgtctccaa   36060
aaaaaaaaaa aaaagaaaa ggaaagctaa aggagagaga ctaaaatgat atcaggttcc    36120
tggagaacaa acagacatga ttttgcttca tggcaggaca gccggaagaa gtgggattat   36180
atcctcacat tacaaataag aaaactgaga ctcagaatgg ttaagtcact tgtcccaggc   36240
cacacagcca gtaaattaca gaaacagaat ttgaacccaa atcttccagc tccaaagctt   36300
gtgttctttt cactacctcc tgcttaattt tttaatttct aagattagac ccttcatcta   36360
tccatgacac ctgcctgtca tccctgaaa aaaggtgaac gccgttcaga aattttcta    36420 gcctgagctc actcccagtt cacttatttt tgctttgtca tggctgccca gtccccactt   36480
gtagaccagg aataggtcat ggctgcgggg actacgcgct gtcgctgctg caagggccgg   36540
cctctgtttc cggggctgag tgggggccag acctgccagg agcaccatct tctgtgggtc   36600
ctgcctggat gtcacatccc ggccccaaga agtcactgca aacctcgta ttattgagct    36660 tcacatccta gaatttgctg tcactgtggc tgctgcatga agttgtcctg agagaaacg    36720 gcattgtcat taacagggaa attgatggtc tgggggaaaa gtcatcctca ttctcttgca   36780
```

```
gatctatggg tgattgagac tggctgatgt tgaaggggtt tctcagccat cgtgtgccat    36840
gttatggaac agtggtgtag ccagccattt gacacccagc gctgaccttt gtttaacaac    36900
ctcacctata tatgacaaaa tgattgtcag aaataatcgt gtaatgaaat gactgtaata    36960
atggccagaa aagaaacgca gatagtaaaa tgtttctctt gttgaactct gtacatataa    37020
ttgcaccagg attttttca aataaaaagt aaatattata ctacaaaaaa gggaaaaagc    37080
acaagcattt attaaatagc tttctatatc tttctgagtt ttgatccttt gattgcagac    37140
tgatgtaata ttttatgtaa atcattgctt ggttactaag tgaactttaa gaaaagtgag    37200
acgtctgcag aagttgccca taatttagca gctactgtat tgtaccattg atgtacggct    37260
ttattttctt gattaattat ttaaacaata taattcacaa ttttaaaata ataaatttcc    37320
acttaaaatg gtatttaaac tcagcaaaat atatcatcta tgagtaaaat ttgtatttac    37380
caagcaaaaa tattacagtt tgtggttcac atgctgtctc actgttttaa attttaaata    37440
caaaaactcc aagtaggctg ggtgtggtgg ctcacacctg taatcccagt actttgggag    37500
gctgaggcag gcatatcgct tgagttcagg agttcaagat ttgcctgggc aacatagtga    37560
gatcctgtct ctactgaaaa caattagctg ggtgtggtgg cacatgcctg cggtcccagc    37620
tactcaggag gctgagatag gaggatcact tgaaccctgg gggacagagg ttgcagtgag    37680
gcaagattgc accactgcac tccagcctgg gtgacagatt gagaccctgt ctcaaaaaaa    37740
gaaaaaaaaa aagaaacac aaaaaactcca ggtggtcgca cagaatgaca ggactgaagt    37800
aacttagctc caatttctgt cttcataatc actgtcctac cattgtctgt gcttagaatc    37860
tacttgctta atgcaggaac atgtgttctc acagagatgg aaaatgcaaa tggcgccaga    37920
agcaagctgg aaattctgaa ccattaagaa tttactctct gccaggcacg gtggctcacg    37980
cctgtaatcc caggactttg ggaggctgag gcaggcagat catctgaggt caggagttca    38040
agaccagcct ggccaacatg gtgaaacttc atctctacaa aaatacaaaa attagccagg    38100
catgatggtg ggtgcctgta atcccagcta ctcgggaggc tgaggcagga gaatcgcttg    38160
cacctgagag gtggaggttg cagtgagccg agatctatct gcaccattgc acttcagcct    38220
gggagacaga gtaagactcc atctcaaaaa aaaaaaaaaa aaaaagaac ttactctcaa    38280 aataaatacg tgtggctgac tccacatatg gtagggccaa ctgtataact agaagttctc    38340
caaataactt ctgtggagaa aaaaaagttt attaaaggtt aacttttta aagtgctaac    38400 tagaaccta ctaacactga gatcgcacca attgtttata acttagacag gccgggtgc    38460 agtggctcat gcctataatc ccaacacttt gggaggccga ggcaggtgga tcacttgatg    38520
tcaggagttc gagaccagcc taaccaacat gatgaaaccc catctctact aaaaatacaa    38580
aaattagcca ggcacggtgg tacacgcctg taatcccagc tactggggag ggtgaggcag    38640
gagaatctct tgaacccagg aggcggagat tgcagtgggc caagatcgca ccattgcact    38700
ctagccccag caacaagagt gaaactctgt ttcaaacaaa caaacaaaaa aaaaacctc    38760 ttggaccagg aaaatatttt ttaagggagg agtattttat cactggcatt gtttaggatt    38820
gcaggcacat gatgctaatg aaaagcagac taactattag ttggttttat tactgttttt    38880
gaactctctc tctcccttt ttttttttt gagacagagt ctctctctct gtcacccagg    38940
ctggaatgca gtgactgcag tctcagctca ctacatcctc tgcctcctca gttcaagtga    39000
ttctcgtgcc tcagcctccc gagtagctgg gattacaggg caccacacca ggctaagttt    39060
ttgtattttt agtagaggca gggtttcacc atgttgccca ggctggtctc aaactcctgg    39120
```

| | |
|---|---|
| cctcaagcga tctgcccatc ttgacctccc aaagtgttgg gattacaggc gtgagccacc | 39180 |
| gtgcctagcc ctgttttttga actctctaga gacagtccag ccccttatta cttgtcctga | 39240 |
| ggcagctgct cccttcacct ggcccccgc attgtgttcc ggaccctgt cctggtggtg | 39300 |
| ctaaagaata tctctgtcga tcctttgggg actgggaaa ctgaggccca gtgccacgcg | 39360 |
| atgccatttg ttcagggaag attaggtcat ctgctaggtc cccagtcact tgaccttctt | 39420 |
| cccagacagg aagaagctgc tctgggtctc tcagtgctcc acgtgtcttt gcacattgaa | 39480 |
| atgttttctg attttttttt tttttttttt gctgttacat ttacttttaa aaataacaa | 39540 |
| gcaataaaat gttacatttg agaaggttga aatgagaatt gatttgagtt aaattctagc | 39600 |
| agattttttct tagaagaatg atatcatcat ctccagctac ctgcaattga tctactctga | 39660 |
| attaagaaag agacttccat ttgttgttta tattttgcac tcttgatgtg tttctttaaa | 39720 |
| ttatggtcat gggccaggtg taggagctca cacctgtaat cccagcacct tgggactctg | 39780 |
| aggagggagg atcactggag gccaggagtt caagacctcg tctgtacagt aaattttaaa | 39840 |
| aattagccag gcatggtagc attcacctgt agtcttagct acttgggagg ctgagatggg | 39900 |
| aggattgctt gagccagaac tttgaggcta cagtgagtta ttttcacgcc actgccctct | 39960 |
| agcctggctg acagagcaag acctgcctca aaaaaataag taaaaaataa attaaatttc | 40020 |
| aatcattagc agtcattagg atatttaaat acagtatgtt gaatcaaagt tacgcatgtg | 40080 |
| tgtattttt tttccagaga gttgtttatc atgtgggttt taatttaact ttaaaaaaat | 40140 |
| gttggctgga cagttgccca aatggtatca tcagccattt ggttgagaac gtatgtcctg | 40200 |
| cgggctcctc tgtcactgga gttttgctag ctgacagcca ctggctagtt agagactgca | 40260 |
| gtcagcacag atgcaggcgt ggacttgcgc acgtaaccat gtcaatgcaa agccatcact | 40320 |
| tcttaaaaat tctgaaccct gctgtctgag atggtggtgc agcggataga actctgctct | 40380 |
| aagaggcagt agctaattcc atgtcttctt tgcccttgac tagctgagtg actttgcaca | 40440 |
| tggggcttgc ctctctgttg ccttgtctgc aaagtggaat catcttttcc ttgctagaca | 40500 |
| gaaggtggac cctggaccta tggcctttt gagtttcccc cccgcttctt agaaggacct | 40560 |
| ctgatcctac tgagtttaat acccacgggt taataattgg gaaaagcaaa ggaagcgctt | 40620 |
| ctgtttaggt aattatatgc atgttttttgt cttttctgg ctggaaagat atccaagcca | 40680 |
| ctgggaaggt ccgtggctac ccagggtagc cctctctggg gagggctgct atatccaaga | 40740 |
| gccctcatg agaatttgaa aatcgaccat ggtagggcct gctgactttt gacagctaat | 40800 |
| ggtgtgctga gaattgtccc tccaaagatg cctttccatt ccctcgggag agtctgggca | 40860 |
| gcccctactg ggggctggga tgctggctct tccctcagcc tccaccccaa ctgctctctt | 40920 |
| ccctcctccc ctcccagcc ccctaatttc tctcacaagg ctttgttctg cagcaacctt | 40980 |
| tcctaatgca gtcctggcct cttcgcagct tcattacata accttccgtg gactcctggt | 41040 |
| ccaaggatca ccccagaaag ccagtcagag gtaggcacgc agctgggtc catttactta | 41100 |
| ccttccccac cccctcggaa ctcagaggtg gtgcaggaat ttggactcca agaattaaca | 41160 |
| gctccaccac catcaccaga gccaaaactc aggatgcatg tgcttcatct gctgcttatt | 41220 |
| tccagctgag agccagtggt gccatggttc cttagggagc cggtcccctg atgccggctc | 41280 |
| ctggccccaa atctctctga tccgggctct tccagaatgt cttgtctcca ccatcgcctt | 41340 |
| tgaccaatgg tgtcccttgt cctggtaatg tccccttttgc ctgatgatgg ccctgtcact | 41400 |
| cctctcttta gcacagagga ggctgtttca tcccttcaag cctgccctcc cttcaagtct | 41460 |
| tagctcaagt tcaccttctc cgcagagcct tctccaatct tcttgactac gtctcctctc | 41520 |

```
agctccagca acctctgtct ctggcactga ttccttactt agctaagaga atcacagaca    41580
cttggggctc aggacaatct gctttctctc ttcttaccca tggccttgga ctgtgtgtac    41640
ctctttgtct ccactcccaa acccaacccc cagagggcag agagcatgtt gtctgtccct    41700
ttgctcagca tgaagccatg cgtgtggtag atcggcagag ttccataact tgtgttgacc    41760
gaggggtcac tttgctctga aattacccct gtgtccttca gtatttgcac agatagcttc    41820
ctggccagac cgaatatatc caagggcatg cccacctct gctcctgttt ccaggtccct    41880
ggtgggggtt agttcatgcc ttcctcataa tctgcccact ggcctggtcc tcaaggtctt    41940
cccaactgct cagccagagt tgagaaaatg ggtcgctcca tcctgtttgt gtcgttctct    42000
ccttcctggc ccactctcct gcccacaggt atccaggggc tgcctgtagc attagaggac    42060
atacatgcac atgcgtgggc atgggacact cacgtagcct ccaagcacag catcaataat    42120
gcattctgtg ctttatagca tggaaagctg ctctaaactt tattacacag tggacatgtc    42180
tgaagcagct cccaaatcca cccctgagtg tgttggaatt ggcaagccta tcacttggga    42240
gtctagtttt tttgttcgtt aataatagat gcttcctgtg gccccagctt ggcaattttg    42300
atttaaagtg atcttaactg aagagactaa tggacgggtc tgaatttgtg cctttttaagc    42360
acaaagtatt gctcttaatt aactggattc tatcctttga gcaggcagag gccttccccc    42420
aagggcgtca ttaacgatcc acatctggac atcttccaaa gccttcttct gtttcaggcc    42480
aaccgcaggt gtgttcctga acacccagga ggctatgaga gccacatatg cctcccaaat    42540
acacacagtg tgcatgccca gggacataga gcagtgtgca aagtcccatt ccatctctct    42600
ccacctggga gaggatggct cttctgtctg attcatggct caaagtggta aaggagctcc    42660
ccactccccg tcccacgcct actcagagtc tgcaaatatg tatgcgatat gagagctcgt    42720
cagttagctg tcttcagtgt ggcgcacatt tgaggagtct gactcccctc cagcacaggc    42780
caatgtgcac tgctctccta tcttttgtacc cccactgttg cactgtgcag aggttggagc    42840
catagaagta ccagagctgt gaaaggagag gcccctctc acctctgccc tggtctccat    42900
ccccactttc tctaggaagc tagtaggtgc tgacagggga gagaagggag gggaggggtc    42960
cagaaacagt ggctcatgcc tgcaatccta gcactttggg aggctgaggc aggaggatca    43020
tttgaggtca ggagtttgag accagcctgg gcaatgtagc aagaccctat ctctacaaaa    43080
agaaaaaatg taattagctg ggtgtggtgg tgggcacctg tagtcctagc tacttgggag    43140
gatgaggtgg gaggattgct tgagcccaag agtttgaggt tacagtaagc tgtgattgca    43200
ccactgcact ccagcctggg caacagagct gagaccctat ctcaaaaaaa gaaaaaaaa    43260
aagaaaggag agagagagaa agaaaagaaa agaaaaaaaa aaagaagggg aagggaaagc    43320
ccagaagagt gtggggagag gaggcggccg tcattctggg gccctcagtg tgcacaacca    43380
gataacacat gctctgtggg cttttgtacc attttgcttg agcataaaga aaggaaggct    43440
gccccctaaat agaaagcact ctggaggcaa acaaatctga ctccaatcct ggccctgcca    43500
ctttcccagc tgaggactta gacaagcacc ctagcctctt ggacattctc agagccatct    43560
gctgcaagtg ggtgctgcca tacccacctt actgggcagg cttgggggac caagggtggt    43620
aaatggctca gtcttttcatg atgcggccac acagcaggtg cgccatccag gtccatttct    43680
ttccttcctt tccccaaat caagttgtca ttaaagtact agtccacatt aatgaaatca    43740
actgtattaa tttttctattt gctgctataa taaatcatca gaaatttagt ggcttaaacc    43800
aacacaaatg tattaccctta cagttctgga ggccagaagc cctccatagg tgtcactggg    43860
```

```
ctgaaatcaa ggttttggca aggttgcggt cctttctgga gggtccaggg gagaatccat   43920
tttcttcctt tttccagctt ctaaaggttt catgcattcc ttggctcatg atcttctata   43980
gctatagtca gaaaaatttt ccatcaatca tcttcaaagc cagcaatggc aggatgagtc   44040
ctcacatcac cttgctctga caccagttct ctgcctccct cttccacatg tcaggaccct   44100
catgattact ttgggctcac tctgataatc tgggatgatc tctctatttt agagtcagct   44160
gactgggaac cttaattcca tctacaaccc caattcctct tgccatgta cagtgacata   44220 ttcacaggtt ctggggatta ggacgagcct gtctctgaaa ggctacttta catgaaaatt   44280 catttttta attaagattt ttttttcctc ttgagacaag gtctcactct atggttcagg   44340
ctggagtgca gtggtatgat cacagctcac tgcagcctcg acgtctctgg gctcaggtga   44400
tcctcccacc tcagcttccc tagtagctgg aactacaggg gtgagccccc atgcccagct   44460 aattttttt ttttttttt tttgagacag agtctcactc agtcacccag gctggtgtgc   44520
agtggtgcaa tctcagctca cagcaacctc cgcctcctgg gttcaagtga ttcttgtgcc   44580
tcagcctccc aaggagctgg gactacaggt gtgcaccacc acgcccgact aattttgta   44640 tttttagtaa agatggggtt tcaccatgtt ggccaggctg gtctcaaact cctgatctca   44700
agtgatccac caacctcagc ctctcaaagt gctgggatta caggtgtaag ccaacatgcc   44760
cggccccagc taattttaa atatttttt tgtagagatg gggttttacc attttgtcta   44820
ggctggtctt gaactcctgg gctcaagcaa acctcccacc ttggtctccc aaagtgctgg   44880
gattacagca tgagccactg cactcggcct taagagaaga tttaataatt aatactttac   44940
aacaagatct ggaagaggtg ggatgagtaa ctaaatgagg atacaagtaa cccgggtcat   45000
atttgctaat acccttggtc acattgaact tgatatctta tcagattttc ctaatcagct   45060
cctttagcag cagtgttgca gcatcttatc tcattttgtt ttttgttttt ttgcctagca   45120
catgcctgta aatcactgga ttgaggtgtt tagatgtttg ttgtcctttg gatgcttctt   45180
ataaatccat atttcatggc tccctggaaa gtgctatgca aatgataagc tgcaaggatg   45240
gaaaggaaat tgcagtgctc ctgaattgta aatgggcttt tacgaggagg tttctaatta   45300
ctcgctcttt ctcttgaact gaggagttga agtgtaggtg gcagatccat aacagataat   45360
catgtgtgtg atgtgacttc agcctgagcg tcgaggacca agtcacagag caggaacagc   45420
cactctccag tgtccttggg gctacgtctg aggagaacct gggatttcat atatgacctg   45480
cactggctgg ggggctctct tgacgtaacg tgttccctct gagcatgtta cagattctga   45540
cattcttatg ttccttctgt ggagagacat gtacttagtg acctaactca ctttagcata   45600
tttttgctca tcgtttgtgt agcttaaagg aatcagataa ttacccctc cccactactt   45660 tcggaagcac aaatgcaatg ccctagaatt gtactgggga ctcaaaaaga aaagagagta   45720
gtaaaatcta ttaaggggga caaagacagc ctatatacta caagctttct attttatgg   45780 cagagaatgc catttctaa gtaaacagag aactgcattt gacctgcaat atcaaatgca   45840
tggatttgat gctttggaaa gcaactgttt tctgcgttaa tctgggtgtc ttccgtgaaa   45900
tgtcctcctg cctttggctt aaacactagc tttgtctaca gccattccat cctgaacctg   45960
cccaatcttg tctgaatcct ggtttcacca ctgacaagct gtgtgtcctt gggcaagtta   46020
cttcacctgt ctgtgcttca gagtcctcat ctgtgagttg gggaatctgg acagaatcta   46080
ccccataggg cgtagtgagg atgtgttgaa ttatcccaag tggctacaca gagtaagcac   46140
tcaaatgatg tcatcgttgt catgattgct gttaccagag cctagagttc attctgatac   46200
tcgagtctgt ggcccatcca gcccaggtaa ggaatagttg gaggagttgg gcatgttcag   46260
```

```
cttgaagagg agacgacagg ggatatggga tagttgaatc tgtgaagggc cccctgggat    46320
gaagaactgg catgttctgt gtggctccag ggcactgagc aggacccatt tgccaaagtc    46380
tcagggacac agtttctagc tatagacaga aaaattttct gtcactcaga ggatgaaaat    46440
agaatgagcc cccttaagag gtaatgagct ccctgtcatt ggaaggattc cagaagagct    46500
aggtaaccac tttaggtgct atcaagggc ttttttcttt aaagtccttt ccaaaagctt    46560
ctgagattgc ataaacaata ggaagccatc ttggtgcttt aacacaaact ctccccagtg    46620
atgagggttg agccaaagcc agattggcaa gcagagagga gacttgtgta caaggagttc    46680
ctcgagtcaa ttgcttttc cttgttctag ccagccagag ggctcctgtt ggaaaacagg    46740
agaccggaga ggctgaggcc tgaccaaacc agcttctgca ggccagctgg gaggccacaa    46800
ctcctaccta cgggaaaact gaagggcatc tctatttta gattagcaaa agaaaataaa    46860
tttaagtttg agtctccttt gcaacttta aaagacatct ttattgagat gatcattcac    46920
attctataaa attcccccac tttgagttac aattcagtgg ttttagtctt ccttgatgat    46980
tttgatggtc ttttcttaag gctcttggaa gacccagaag cctctcagac acaggtgggt    47040
gtggagggcg tagcacagag gcagacttct catttcctgg gtctcccctt taatgactct    47100 cagagaccc tccttccccc tgccctggc ttctacccca ggggtgtaga gttttgccat    47160
tttccaagca gaacttcatt tcctcttctg tgtctacact ctttgtgctt ctttcttgcc    47220
agctttttct cctttgcccg cccttccttc cttccttccc tccctccctc cttccctcct    47280
tccctctttc cctccttccc cccttccacc cttcccccct tcccccttc cctccttcct    47340 tccttccctc cttccttcct tccttcctgc cttccttcct tcctgccttc cttccttcct    47400
gccttccttc cttccttcct tccttccttc cttccttcct ggtatgtgac taatttctgt    47460
ttcaggacat aaatgttgtc caggctgttc tttggtcttt ctgttggata atggacattt    47520
ggcattgaga gaggctgctt tttctgaaat catgttcttg gggcccagaa cctaggtgtg    47580
tgcttctgac tttgttttct tcctgatcca aattctgata tgtccattta aattgatcta    47640
gacccacagg gcactgtggg acagatcctc agtggaacat gactctgtaa cgagagcatt    47700
ttgttttgtc aaaatgagaa catattattg cctttcatct gattgtaaac ataatacatg    47760
tttataaaac agtataatga gacaaaaatg tagacactaa taagggaaaa tctccctaat    47820
tgtatttctc ttcacagaga aagcccctgt tgggcatata tactctagtt tgtttatttg    47880
tttgactaca catatatgta ttcttttctt atgtataaaa attctgaaca tgcacatttc    47940
tgcaactact gttttcactt gatgatgcat ggacctctct agagtgtacg tttcttcttc    48000
cttacaaagc agttggcttc gcccagggta caccaggaca cggttttggc tctgtcccca    48060
gggtgtcacg ggaccagggg atgatctcac agggtctgcc atctgccctg cctggccgga    48120
ggctgcatcg agagggccaa ggggcaccac gtgtcgtggg tactgtcaaa caagagcctt    48180
cagagccttc cacagtcttt cttttgcttc ccagcattgc ttccccgctg gtggactctg    48240
aatctagaac tagctccagg cgcctctcca aattcagacg ggagctgggg cactattata    48300
atgcaaatct aggcaaagcc ctcccaatac caggatccag aatggggtgg ggccctttgc    48360
cctgaaaagc tgtttagttt gaaaatacaa acaggagaca gaaaagtttg ctaaattaa    48420 tggataaagt tttaacgatg gtaaccatag tagggttcat cgacagccag cgatggttct    48480
gaacacttga catgtattaa ctcacctaat ccccacattt tacagacaat gcaaaggagg    48540
ctctgggagg ttgagtgact tgccccaaag tcgcacagct cctaagtgaa ggattcggag    48600
```

```
tggactccag gcagcctggt ctgactccct gcactgcgct gtgcttatct ctggccccaa    48660
tgccgccatg cagaagtgtc tgggggcact ttgtctctgt cagacagaat tcggagatgt    48720
gtatgcttgc cctggtatgg cacttctctt tttttgagac agaatctcac tctgtcaccc    48780
tggctggagt gcagtggcat gatctcagct cactgcaacc tccgcctccc aggttcaagc    48840
aattcttgtg cctcagcctc ccaagtagct gggattatag atgtgcacca tcgtgcctag    48900
ctaaattttt gtacttttag taaagatgtt gttttgctgt gttggccaag ctgatctcga    48960
acttttggcc tcaagtgatc tgcctacctc agcctcccaa agtgctggga ttacaggcat    49020
gagccaccat gcctggcagt gtggcacttc ttacgtgtgt tcagcggaca ctgtttatct    49080
tctgtccctc caagacggtg ctgagctcag gtcgttcatt actggcagac aactgctgat    49140
ttccaacaga attgccatcc tcttctcccc tgcgactttc agagtgtgac ctcagactca    49200
aaaattagaa gtgaaaacat cttaaaaact atcaccttt cttcctaatc ctcctctccc    49260
ctccctgtct tccttgttgt ccccatctaa tgaactatca tggcaaaaag agcccatttc    49320
tggtcatttt ctgtggcctt tcaaactccc acctacccca ctgctcctgg gtgcattacc    49380
cgaaagctga gacttcagtg cagaaagtgc caggccctct gtcccccag atcgccttcc    49440 ttgtcttccc tgtgcttgcc tgtcacattg tgtgggttcc agcgctggaa ggaatgagga    49500
acagattctc tggttctcct tttgaagttt accttcgctc caccacttct gagaccttcc    49560
cggaagttgc cccttgtttc tctcctctcc agggctgccc cagagctgcc tctcacctct    49620
tcctgctgtc acccccaccac catcagggca gaagttggga caaagcctct cctactggct    49680
cctgcttttc tcccttaggt ccagcctcct cttctccatc ttcaggagtc tccttctcca    49740
ctcacacgtc atgacttcag cacctcgcat cagtccagaa tatgactgct tgttcaagtg    49800
ccacctttct catgcatttt tttctagtga caatcacagc caccctgtgg ggcaggagtg    49860
tcatcatccc catgtttcaa atgaagaatt gcagttcaga gagggcaagt gactggccca    49920
gcctcaacag ctagccagtg gaccccacca gggcttctga ctccagtccg ggttcccttt    49980
ccacccaaat ccatggaggg agctgagccg agaacaggtg tccttcagga agacgtgaag    50040
ccaaagcctc cacctccaaa ctcaggggcc cagggagtcc aggcacccat ccactcacaa    50100
ggctggatat ggtgcattcc aggagagggg ttggggggcga gtggcctctc tgtgtacccg    50160
tggggataga tgcgcaagtg gcatcgccac atcgtgagtc ctggcttcat gggtgagctc    50220
caggtccaac gagaagccaa gcaggggggcc cttcaagctc agctttgggc ccgggtcggg    50280
gtacagggta gagcgggcct ccccagcccc tgccatgagg ccaaggcagt gcatcgttcg    50340
cagcgtacat tcagaaacca aagcctagga gctggttatc attccggttt acagctgatg    50400
gaagagcagg tgcttccgag aacccacagt gctctttggc cagtgaccca agggtgcctc    50460
tgagaggcct cgcagcaccc ggaggtgctg ctgaggcaac gccctgactg taagaaggac    50520
cattcatcct cagagagtgg ccgtgatgct gctgcgacag tcccaccatc cctcccgact    50580
ctcactccca acagacttcc cactgtaaag ctgaactctc cagcaaatca cctctcgcca    50640
gactctctcc tcactctctc tgggtccact agaggttcct cagcctctct ttgccttggt    50700
tttcccagct gtaaaatgga gcaaagaggg cctatgtacc cacaaaggtg tggttggagc    50760
gactcctcct acattagggc ctcgagtggg gcttcatgat tggttggtgg aggtctccaa    50820
acccacccag tgccaccgaa ggctgagact gcagatgcaa tgccacaggt gtccttcctc    50880
agcctgggca gctgaacatc atgtgtaaaa cggggataat aagataataa cagccccttg    50940
cacctatgtg gctgtgagga ttaaacaaga taaatgtgta acagtgcctg gctatagaaa    51000
```

```
tatttactct tgttattaag ggaagaatat gtgtggctaa aaagggatcg aagatgtaaa   51060
agccaatccc tcccctcta gcatatttaa gggtaatgtt gagttggttt gtggaccatt    51120
tgctgcctgt tagagctgga aggtagggac cccctctcaa cagcgatgct acaaattata   51180
cccattggag gtcaaccaaa agacaaagct tattggctgg acatggtggc tcacacctgt   51240
aatcctagca ctttgggagg ccaaggcagg cggatcactt gagatcagga gttcgagacc   51300
agcctggcca acatggtgaa accccatccc tactaaaaat acaaaaatta gctgggcgtg   51360
gtggtgcaca cctgtaatcc cagctactca ggaggctgag gcaggagaat cactagaacc   51420
caggaggtga aggttgcagt gagccgagat cgcaccactg tactcaaacc gaggcaacag   51480
agggagacgc aatctcaaaa aaagaaaaa aagacaaagc ttgttaatac cagcatattg     51540
ttaagggaat aaagtaggct gcagaacaac tggtgtaata tggtgccatg tagggaaaat   51600
tacatgtgtg cataggagag gggtctgcaa ggttgtgccc taagatgtta gagtggttcc   51660
tttgcttttc tcttttataa ttttgtattt gacttttaaa taaggaccat aaatcacttt   51720
tataaaatac attctctcca gccctacta ctcctttaaa gaataagagt ggtttgccca    51780
agaaagacag ttttttttgc tctggttttc ttgattctga catcagagga aactccttct   51840
catccacttg gggctctggg ttcagggat tcatttcagg cagattaaag tggtgaccag    51900
gggcattcgt ggacacaggg agggacagga gcaccatcag tttgtctcac acaaccactg   51960
tcatcctcac tgaaggctgt tgcctgatca aaaacagtat tgggccaggc acggtggctc   52020
acacctgtaa taccaccact ttgggaggct gaggtgagtg gatcacttga ggtcaggagt   52080
tcgagatcaa cctggccaac atggtgaaac cttgtctcta ctaaaagttc aaaaattagc   52140
caggcgtggt gggtgcctgt agtcccagct acttgggagg ctgaggcagg agaattgctt   52200
gaacccgaga ggtagaggtt gcagtgagcc gagatggcac caccactc cagcctgggc     52260
gaccgagggg gactctgtct taaaaaaaaa aaaaaaaaa aaaatatat atatatat       52320
atgtcaaaaa tggggtagtt tttagatcta tagtagttct aaaacaaag gccatccaag    52380
catgacagat ttacaagcac tattggctat tccagtagtt acaatggagg agagaagctt   52440
ttagttaaaa caaacaaaca acacaacaaa cccagaaacc ttaggtcaaa accaaaattg   52500
tcctctcaga cacaatctgg gaattttctc atgacagtgg gcattagcca actgacatca   52560
gcagcaacca tccgtgtgca cacagtggca ccacctcctc ccaaaaagca gccttcatct   52620
atgccctcat acaatcgttg attattctct ttggattgag gcccggaatt atttaagttt   52680
cttcttgcca gcatgagtct ttcctttctg tatgctcctt atcttctctc tttaatttgg   52740
cagttctgct tgaaatctgg gtctttcatt agtagtagtt caatttggtt ccagaacatt   52800
ctgtggtgtg atgcaatgtg accagagctc acacttcaga gctcttcaag ggccagtctt   52860
actgagcacc tcccagtggc tgcctgtgtg ctgggcgcca cttgtggtgg gcaggagaga   52920
ggaggggaca caaaggaga cacagctcct tcttagaagc tcaaagttgg ggaccagctg     52980
ccacagaaga gtatgtttag catctgagac accaagatcc agcgtcacaa gggtgtttat   53040
taagcctcct catctctttc ttttttcttt tttttttttt tttcctcagg cagtcttact    53100
ctgtcaccca ggctggagtg cagtggcatg atctcggctc actgcatgca accaccacct   53160
cccgggttta agcaattctc ctgcctcagc ctcccagta gctgggatta caggtgccca    53220
ccaccacacc cagctaattt ttgtgttttt agtagagaca gggtttcacc atgttggtca   53280
ggctggtctc gaactcctga cctcagatga ttcacccacc tcggcctccc agtgtgctgg   53340
```

```
gattacaggt gtgagccacc gcgcctggcc ttgctgttga ttcatctata gtatgtttga   53400
cttgatgacc tccagttacc ttagacagag gttctcatct aagctccaac tttccatttc   53460
cttcgtcctc gtctttcccc ttaacccctc cacatttctc tcaaaatcac cccacttcta   53520
aaaaatactg tttatttttc ttttaaattt caaattatct atactcattg aaataaatca   53580
aaatagcatg gaataagcga aaaaaatgga tcccacccct ccccactccc attccctagg   53640
gctaaccata gttaaccatt taatgactag gttttttttgt tgttgttatt ttttatttat   53700
ttattttgag acagagtctt actctgtcac ccaggctgga gtgcagtggt gtgatctcgg   53760
ctcactgcaa cctctgcctc ccaggttcaa gcattctcct gcctctgcct cctgagtagc   53820
tgggattaca ggtgcctgcc accacacctg gctaattttt gtacttttgg tagagacagg   53880
gtttctcaat gttagccagg ctggtctcga actcctggcc tcaagtgatc tgcccacctt   53940
ggccttccaa aatactggga ttaaggtatg agccaccgca cccagccctc ctgggctctt   54000
ttcctttagt tgcactcgct ccccgctcct ggagtagagg gatttccgag agactgtggg   54060
ctccagcctt cacctaggcc caggactagg atgcctgccc taacatttat ctttatacct   54120
taaagcaaaa cagctggacc ataagcattc aagaacaaac tgtgaataag gagaaagttc   54180
tcccaggaaa caagagcttt agttatgttg gccagccct tatattcctt agctgttacc    54240
agtcactgct tgatttaatc tcggctatca cttggcctga caggtctgct gctggtgcca   54300
ggatgtctgg gttttgaagc ctggctccat tacatacttc ctgtgtgacc ttgggcaact   54360
tactcaacct gtctgttcct cagtttcccc agctgtatta tgtcagcata atagtttgtt   54420
gtgtgaatta aatgaggtaa taactggaaa tgcttcaaac atggttccta tcatgagaaa   54480
tcctgctttc cgcctaaatg tgctggaaaa ttcctggtgg tgcagaacag gagaccagag   54540
caaaggaaag acagggtgca gaagccaaaa attaccttgg agaacaaagc gcatgttaag   54600
gttatttttg gattctaggt ttatctctgc ttggtcttca gttacctaca agagatccat   54660
ttaggggatt tttgtttgtt tttaacgata gctttattga gatataattc atatgccata   54720
aaagtcactc ttttaaaatg tttccggtat attcacaagg ctgtgcagcc ttccctgtcc   54780
ttgattccag tctgagtttt taactgaagg gataaggagg accacgcttt ccccagacca   54840
gaaccgcggg ccagggggcg attccgctga gtcaccgcgg gcgcctggtg cgcggcggcg   54900
gagcccggga ccttccttgg ctgccccta gcgagggccg cagcgcagcc tgagacaccc   54960
gccggggccg ctccacggcc gtcggattta gactggaagc tcggtccagg tccccagctt   55020
gatgcgcccg cggtgtagga gaccagcccg actcgagctt cccctgagcc cctggactct   55080
tgactccagc agggcctggg taatgaacgt cagctcccct ttcccaaagg ggttgctctg   55140
ttgggaaggc acccgtttga tacagtagca tagagatggg ttttagcatc aaaatatcag   55200
aattcaagcc ttgctctctg cttactagct gtgtgaccct aaaaaggttt ctgaacgtct   55260
ctgagcttca gtttcctcat cattccttct cacggggtgg ttgtgagcat tacagagatc   55320
ctctctgtga agccctgtg agtggctcat cctgagggct gaaataaaca tgttattaat   55380
aatccaaaac tggcaaggga tgttgactgg tccccctccc ttgcccaagg agctttctag   55440
aacctgagtt atcattacca aactgtactg ccttgagtaa gaaagttaga aggaatggga   55500
aggatggtgg caggtggagg aaggcggatt ggtcatcacc tccttgcagc aagaaacagc   55560
cccagatcgt gggaaaccta cagacctgct agacagacta ggagcaaaag ctggggcttt   55620
aagaatcccc agggaggttc tcctgagaga gtagccagtt ggattttgta agcagagatt   55680
tgtttgggga ggaggtgaca acgtagggag cagaggggca aagctgtcgg gaatcctgcc   55740
```

-continued

```
ttgagggcag ggatgtgtgt tgggggagt tgggtcactg gggctcggtg gccttgggca    55800
agtttctacc tctcaggtcc tttacccacc tagggtcgcc atcctgccca cctcacaggt    55860
tacagtgagc ctggatgcac tgtcatgggc aggtgcccag gaaaatggca gacatgttcc    55920
aaacagcacg cagcattccc cagtgatgcc cagggtcacc ttggaggtgg gcgagatgcc    55980
tggggtttct cgtccacccc acaacacctc aggggacagc caaagctgtc ccttcaggta    56040
agctgcacag aagatgtgaa ctctgctgca aagactctat tctttgggag caaaagggac    56100
ccagggtctc acctgcacat ccctgtccct gagggcctag gggttcttgg aggcccagc    56160
cttggcaaaa tgaggaagaa ggtgaaggtt gtctgggccc ctgccaggct ccttcctcgg    56220
ccacgcactc cccttcctgc acacacaccc ttctccctcc accccatctc cattgttgtc    56280
agaaaagtca caataaaaag gtccatattg tctagttccc atacttttaa tttttaaaat    56340
tttatttatt tatttattta tgtattttt gagacagagt cttaacccag gctggagttc    56400
agtggcatga tctaggctca ctgcaacctc tccctcctgg gttcaagtga ttctcatgcc    56460
tcagcctccc gagtagctga gattacagat atgtgccact atgcccagct aattttgta    56520
tttttagtag agacggggtt tcaccatgtt ggccaggctg gtctcgaact cctggcctca    56580
agtgatctgc ctgcctgagc ctccggaagt gctgggattt caggtgtgag ccaccgcact    56640
cggctccaca cttttcactt attaaaagac tgtggtgtcc atcaatggat gaatgaataa    56700
accaatgtgg actatccctc ccattaccca aggaatgaag cacggagccg tgccaagatc    56760
tggattcaca gtgaaagaag ccagtcacca aaagccacgt gctgtgtgac ttcccttata    56820
cgaaatatcc agaagagata catccatggt gacagaaagt agatgagcag ctggggactg    56880
gcgaagggga gaagggggag cagctgtcta tgaggtccag cctttcttct gggtttggtg    56940
agaatgtttt ggaactagat agaggtgata gttgtacaac attgtgaatg tactaaatgc    57000
cactgaatca ttcattttaa atcgttcttt acgttgcatg aattttaagt caatcaaaaa    57060
cagttgtttg aaaagagaaa agcctatggg tagcggcagc agtgattgga tttatgattc    57120
gattccatgg ctcatccctc ccctgcctca cccctcgcc ctccgacgtc ttcttctttt    57180
actctgaact gttatctttg ttctcatctc tctctctctc tctcaaccct gcagacactt    57240
ttccctttct ttgtctgccc ccaccctcca gatttccgtg tctccagtgt ctccctacga    57300
ggcatgaatt gagactggga gggtgtgatt ctgaagaagg caccaacagt gactcagcta    57360
gccccttccc ccaccccgcc ccccgggcct caatttagct aaaaaaccac agggacggac    57420
tcaggaggca atacctttcc aagggtccct aaaaaatgtc ccattttagt gtccaggttt    57480
cactcaactt tagtgcctcc cctaaaatgt gttccttacc tcccacccca ctgcatctaa    57540
gtcactgcct gagaaaacag gattgaggaa aggagaaagg aagagagaga gagaggagga    57600
gagagagaga gagggaggaa ggctgatgga tttagaaaag aagaaaacaa gtggtctgag    57660
gaaaacagcc ttggtgtgtt tatttttcctg tctgtgtatc gcttctcggc cttttggcta    57720
agatcaagtg tattttcctg tctgtgtgtc tcgcttagat tacagggatc tgtgggtgat    57780
gacacgtctg gtccaggctg cgtagtcacc tcaagggcat gcttattgat gtgttttca    57840
attcactatc tttgcatggg agtcccaggc caagaggcac agctgcgcca tttgtctgtt    57900
ggtttagata tcctttatcc agttcttcca gagaaatcat cctgcccttc tggaggaggt    57960
gggcagcagg ggtcagagat gggagggaaa ggaaggagcc aggtccttgg ctaggatgcc    58020
agggtcccct gcctctcacc tggcctgggc tggaggcctc ctgctgtcct gtcactgatc    58080
```

-continued

| | | | | | |
|---|---|---|---|---|---|
|actacccgc|cccagcctcc|tgagttagaa|gacacaggct|aaagtagagt|atttcttcat|58140|
|tgaaaaaccc|atacaaaata|aaggttcata|aaaaataaaa|atttagactg|ggtgctgtgg|58200|
|ctcacacctg|tgatcccagc|actttgggag|gccaaggcag|gtggatcgct|tgagccctgg|58260|
|ggttcatgac|cagcctgggc|aacatagtga|aaccccatct|ctacaaaaaa|tacaaaaaat|58320|
|tagccaggca|tggtggtgca|tacctgtggt|cccagcttct|cagcctatgg|acccacatag|58380|
|aatacaatgt|cagcataaga|agggagccct|ggggtcacca|aatggtttgg|gcggcaaaga|58440|
|acctgaaggt|tgagagaagt|ggcttggtta|cccagctgtt|ggatgtgaga|cctggccact|58500|
|gcttcttcca|tacccctagac|ctgcaccctg|acatctcaag|taaaaagttg|ggggatgttt|58560|
|tatggtccag|gatgaaggaa|gggcagtgag|gggcagcgga|gcatcacttt|gcatttctgt|58620|
|ctgcctctta|ctggctgtgt|gacctggggc|aggtaacttc|ccagactcct|gggaatcata|58680|
|acacctatga|tgatgatgat|gatgatgatg|atgatgatga|tgacacctac|ctcaaggatt|58740|
|gccctgaagg|gtcacagaga|tgcctgcaag|gcacctgcat|ggagcaagcg|cccccttctct|58800|
|ggcaggtgct|gggtgagcac|tacctgctgc|caggccctgg|ggctatggca|ctgcgtgacc|58860|
|ctgcaagtcc|tacctggcga|agctgtcgtt|cttgtgctca|gtcagtgttg|gttgtaagac|58920|
|tgagaagagt|cacttcattt|tgctctccag|ggacatctttt|ctgggtccta|ttttctgcct|58980|
|atgtcaagta|gcgcctcaag|gatgctcctg|aaaatgggct|tgtctttctt|aacatggcag|59040|
|gtaggtccca|aagcattagc|atggggcagc|tgacctagcc|cagccaatgc|agtgcagtga|59100|
|ctcttgcaac|cgagtctaat|cagaaggtcc|atgaacctac|gagcatttcc|tgtcccagga|59160|
|tcagggtgga|ggctgagcct|ccctgcttag|agattcttcc|catgcattcc|acttttttcc|59220|
|ccaaaagaaa|atattgaccc|ttgagaggca|cacagtttat|ttattttgca|tagtaaatag|59280|
|tagcctgtat|tttaaggatg|agttgatttc|tgcatcagcc|cctgtaggtc|atcagccttc|59340|
|tattggtgca|tctgactctc|tctagccctg|cagggatggt|ggaggggggag|gggaaggagg|59400|
|gatctttatt|ggaaaccagg|acagtgagac|tcattgccct|gtcatctgct|ctgtggtgct|59460|
|gaatgaggca|gcccaacaga|gaaatacccct|gagcgagcat|ccccagcctc|caaaacagtg|59520|
|gcgcattgcc|ctgagtcctg|ggaatgacct|ttgattctcc|tgctcctgac|ttggaaccca|59580|
|tggaaacctc|tagaagcagc|tgaggaaaac|ccaacatgaa|aagcagaact|ccacactgag|59640|
|aatataggag|gtgatcggaa|catacaatga|ttccttgctaa|gaccgattca|cagttttttct|59700|
|ttttttttcga|tcgaagaaat|actggagaag|cctaaagaag|gagtctaaaa|actctggcac|59760|
|gtgggccaaa|actgtccttg|agctaagaat|gattttcaca|tttttaagtg|gttgaaaaat|59820|
|gaaataaaat|aagatgatgt|tttgtgacac|atgaaagcta|tgggaaattc|aaattctaat|59880|
|atctataaat|agtgttttat|cagaacacag|tcatgctcat|ttatttatgc|tcgatggctg|59940|
|ctttcccgct|acaattacgt|tgagcagtta|caacagagac|cacgtggccc|acaaagcctt|60000|
|acaatattta|ctatctggcc|ctttccagaa|aaaaatgtgc|cgactcttga|ccttaacctc|60060|
|agcaatttgg|gaggccgagg|caggcggatc|gcttgagctc|tggagttcat|gaccagcctg|60120|
|ggcaacatag|taagactcca|tctctacaaa|aaatacaaaa|cattagccag|gcatggtggt|60180|
|gcacacctgt|ggtcctagcc|actcgggaga|ctgaggtggg|aggatcgcct|gagcccagga|60240|
|agtcgaggct|gcagtgagct|gtgatggcac|cactgcacct|cagcctgggc|gacagagcaa|60300|
|gaccttgtct|ccaaataaat|aaataatgca|aagtaaaata|aataaaacca|tataaaaagg|60360|
|aatcaattta|aaattataat|gaaagctggc|cgggcatggt|ggctcacgcc|tgtaatccca|60420|
|gcactttggg|aggctgaggt|gggtggatca|cgaggccagg|agatcgagac|catcttggct|60480|

```
aacacggtga aacccogtct ctactaaaaa tacaaaaaaa aaattagccg ggcacagtgg   60540
cgggcgcctg tagtcccagc tactcgggag gctgaggcag gagaatgtct tgaacccggg   60600
aggtggagct tgcagtgagc cgagatcgtg ccacttgcag tccagcctgg gcgaaagagc   60660
gagactccgt ctcaaaaaca aaaacaaaaa caaaacaaa aaaaaattat aatgaaagcc    60720
aaggggcata gtagaacaaa ttttctagag ctcattaagt caaatgagtc accagttagt   60780
aaaacgcagt cacggggaag agagggcagg attctttgaa gcagcggctc tcctaaaaac   60840
aacccaccct tgtccagctg ccttccctcc tgagggtgtt ccctttgact gtgtgacccc   60900
catcccctat ttcccaaccg tccaagccca cctctagcat aatacgagct tttaatccct   60960
ctccctgacc ccaacccgat tttgaagccc agtctagtat tttctcaaat acacttcttg   61020
gctccattcc ttcctttcca tcacctctgc cttttcactg catgcttgga ccactgcagt   61080
cagctcccta tgaacagttg ctctctaccc atccaatcgg ccccgcctgc tgctgccaaa   61140
ttcaccgagg gcacctctgt ggtgctgcct gtggacaaag tccaagccag ccacctcacc   61200
cacctacagg tgagtgggga gcagccagcg tgtccagtgg tttaccccat cgccacagac   61260
ttggtgatgt gtcgatgtgc agagaagggg tgttggcagc cacaacacaa gcaacccgc    61320
cccatgtgag atctaagatg ggcgtgctgg gagccacctc tgagaatcca acagaaggca   61380
gaggggagaa cggctcacac ggcacaaaca ctccttcctt tttttttttt cttttcctt    61440
tttgaaagga gtctcactct attgcccagg caggagtgca gtggtgcaat ctcagctcac   61500
tgcaacctcc gcctcctagg ttcaagcgat tctccagcct cagcttccca gtagctggg    61560
attacaggta cactccacca tgcccggcta atttttgtgt ttttagtaga cacggggttt   61620
ccctatgttg gccaggctgg tcttgagctc ctgacctcag gtgatctgcc tgccttggcc   61680
tcccaaagtg ctgggattac aggtgtgagc catggggcct agcctccttc catttaaatg   61740
tatgcctaat ttgcccattg agaacggctg agacgcattt taagtggcca gggtctactt   61800
agagttagtg ctcatgacca ggcccaggtc aagcctggct ggccagatgg tgcctttgac   61860
ctgctctgtc tctgtgcaaa ggaatgagct gaaggatggg ggtgcagtgt gtgggcagtg   61920
ggctggggct ggcaggactc agtgactaag ggaagagaac tttcctcact accagcctgt   61980
cttttcaggg caccgcgggg ggctttggga cttggtgatg aacacagcac agagagctgt   62040
ccagcatgcg ggtccctggc ttctcacact tcccaggctc cttcagaggc tctctccaaa   62100
gggagctgct ctctctagaa cccatgaatt tggaatatag gcaaccactg cattggggac   62160
cactgacctc aaacatagag accagagcaa atggggctca tcacgtgaaa ctcatctgga   62220
actctagcag gttctttat atatatatat atatatat atttttttatt attatacttt    62280
aagttctagg gtacatgtgc acaacatgca ggtttgttac atatgtatac atgtgccatg   62340
ttggtgtgct gcacccatta attcatcatt tacattaggt atatctccta atgctatccc   62400
tccccactcc ccccacccca caacaggccc cagtgtgtga tgttcccctt cctgtgtcca   62460
agtgttctca ttgttcaatt cccacctacg agtgagaaca tgctgtgttt ggttttttg    62520
tccttgcgat agtttgctga gaatgatggt ttccagcttc atccatgtcc ctacaaagga   62580
catgaactca tcattttta tggctgcata gtattccatg gtgtatatgt gccacatttt   62640
cttaatccag tctatcattg ttggacattt gggttggttc caagtctttg ctattgtgaa   62700
tagtgccgca ataaacatac gtgtgcatgt gtctttataa cagcatgatt tatattcctt   62760
tggttatata cccagtaatg agatggctgg gtcaaatggt atttctagtt ctagatccct   62820
```

```
gaggaatcgc cacactgtct tccacaatgg ttgaactagt ttacagtcct accaacagtg    62880
taaaagtgtt cctatttctc cacatcctct ccagcagctg ttgtttcctg acttttaat    62940 gatcgccatt ctaactggtg tgagatgtta tctcatggtg gttttgattt gcatttctct    63000
gatggccagt gatgatgagc attttttcac atgtctgttg gcgaactcta gcagcttctt    63060
ttcacaagtt catggagaga ggtttcccac tgagggaatc acatctgtct gatcaaaaga    63120
ggcttgggaa atggctctcc tgttcattcc ctgaaaacct ctgatggaac cactgccact    63180
gtggcagccc cagcactggc accccagcca tgattggtgc cccagccaca tctctgctgt    63240
gagccccaga gccctggtta attaatcatc acgtgttga tggggagagg cccattcaca    63300
aaagcgacat aaagcccagg gagacgtggc cgtggcaaga agggtgtggg actacattcc    63360
gcccccaact gagagattca gaaaccagaa aaaatggaa aaacatactg tgctcttggg    63420
tgggaaaact aaatatcatg aagggagcaa ttttttatagt tttggcctat aatacaattc    63480
cagccgaaat cccagtggaa ctttgagaat ttgcaggaaa aaaaaaaatg tctaaagtac    63540
atctggaaga caaacttaca agaaggtcaa ataattttga aaagaaaat gatatctaag    63600 cccacctaga gaataagact tgagatccaa agctaaatca ggaggctcta gcaaaattga    63660
cagataagca ggacagagtg catggtgcat tcacctgggg aagagggcag attggtctac    63720
aaataggcct gggtccactg acttttagctg ttatatttgg ggagaaactt ttcaacctca    63780
ctccatctta aacctaaaaa tattccagat gaattaataa atataaaaa ttagaccact    63840 aaaaatgtag aagaaaatgg atgatctttc tataccatag agcaatggaa taaatcacaa    63900
aggaaaacag atttgactat ataaaactta aaccctgccc atcaaaaacc atcagaaacc    63960
aaaataaaag gcaaccaact ggagaagata gttgccacaa atatgatcaa gggttaatgt    64020
tattcataaa ttaagagccc acacaagtca ttagaataag cactgagacc tgaacagaca    64080
agcaaaaaga atgagagtgg gtcggcgcgg cggctcatgc ctgtaatccc agcactttgg    64140
aaggctgaag caggcggatc acttgatccc aggagttcca acaccagcct gagcaacatg    64200
gtgaaaccct gcctctacaa aagtcataaa tattagccgg gtgtgatggc acgcctgt    64260 agtcccagct actcaggagg ctgaggtggg tggatcactt gagcccggga ggtagagtct    64320
gcagtgagcc aagatcacac cgctgcactc cagctggagc aacagagtga ccctgact    64380 taaaagaaaa aaaaaaaaa agaggagaaa aatgctgatc tcactagtaa ttaaaacatc    64440
aggccaggcg cagtggctca cacctttaat cccagcactc tgggaggctg aggcaggcag    64500
atcacttgag atcaggagtt ctagaccagc ttggccaaca tggtgaaatc ccgtctctac    64560
aaaaaataca aaaattcgcc aagcgtggtg gcacatgcct gtgatcccag ctactcggga    64620
ggctgagaca ggagaattgc ttgaacacgg gaggcagagg ttgcagtaag ctgagatcgt    64680
accattccag tccagcctgg gctacagagc gagactctgt cccagaaaaa attaaaacat    64740
cacatattta acaactcta ggatatcatt taaaaaaaca ttaatagact gttttttaga    64800
gcacttttag gttcacagtg aaactgagtg gaaggtacag agacttcccg tatgttccct    64860
gccctccacg tacagcctcc cccactgcca acgtcctgca ccagagtggt acacttgtta    64920
caaccaatga atcctcatta acatatcatt atcacccaag ttcatagttt acattagtaa    64980
aacatcatct ttcatctata agcacaaaaa tttttttggca tttatttagg tgtatgatta    65040
actcagtgtt gacaagactc acacttcata cccacttgca ctgcatctga gaagcaattg    65100
gtgtctacag ccgctacacc ctcaacaagc ccgatcttgt ttgaaaagca attggtgatg    65160
cttctcaaaa ttctatggac aaagtcagcc gggcatggtg gctcatgcct gtaatcccta    65220
```

| | | | | |
|---|---|---|---|---|
| aactttggga | ggccgaggca | ggcagatcac | ctgaggtctg | gtgaaaccct gtctctacta | 65280 |
| aaaatgcaaa | aattacccag | gcatggtggc | tggggcctgt | aatcccagct actcgggagg | 65340 |
| ctgaggcagg | agaatcgctt | gaagcaagga | ggcggaggtt | tcagtgagcc aagattgcac | 65400 |
| cactgcactc | cagcctgggt | gacaagagtg | aaactccatc | taaaaaaaaa aaattatgga | 65460 |
| caaagttttt | caaaaagata | tttaatgcaa | ctttatttgt | aatattggaa catctgaggc | 65520 |
| catttcagtg | ctaactatta | ggggatggtt | aggaaaatat | ggtacatatg tggaaaggaa | 65580 |
| catttggtag | ttagtgcccc | tgatgtttac | aaaggctttt | agtgaccaac aaatgctcat | 65640 |
| gctataatct | tatgtgaaaa | aagcaagtag | cataattgca | actatatttt taatgcatag | 65700 |
| aataaaaggc | tagaaggaaa | tatcacagat | ccttgacata | cattcccaaa cctttgtaaa | 65760 |
| tccgcggatt | catgaaaaca | gacacatttg | cacaagtgcc | tgatcttttc tgttatacat | 65820 |
| tcattagaag | tcaagccctg | gtgccacaaa | gtatctgcct | tttcaaatgt gatcagaatg | 65880 |
| ttctcttttg | cttcaaggcc | attttttcacg | aagcagtggc | attttttgcct cttcatcaga | 65940 |
| gtcaccgtgt | gccctggagg | actgagaaca | gcagagccgt | tttaggatgg gacagggcag | 66000 |
| ccaggaggat | tgggctcact | ccctactgag | tgcctcactc | ccgtacagcc cccatagagg | 66060 |
| aagagggggtt | caaatttatt | cctcagccag | atggcatgtg | ccgcctgtcc tggaatttca | 66120 |
| catcacttat | gatggaccaa | aattccaaaa | gctgaatcca | tgattgtcaa agtctggtat | 66180 |
| ggcaggatgt | caacagtaat | cgtttctggg | cagagggatg | attttctctt cccatcttgc | 66240 |
| tttgtataaa | tacattttct | ataataaggt | tgtattactt | ttctcatcaa gaaatagcaa | 66300 |
| agtactgttt | tactcaaaat | atgaatagag | ccaggcatgg | tggcagctta tgcctgtaat | 66360 |
| cccaacactt | tgagaggcgg | atatgggagg | atcactttag | cccaggagtt tgagaccagc | 66420 |
| ctgggcaaca | tagtgagacc | cccgtcccca | ctcccccaaa | gaaaacccac aaagcattta | 66480 |
| tcctggatta | ttcacagggg | ccaaaaaaaa | aaaaaattc | aggcctccta tagccatgag | 66540 |
| ctacgaatat | gaaaatatgc | aaatgtgtaa | gaaaagccag | cacatccgat ttttactttt | 66600 |
| actttcacac | ctctgtccac | catgttccaa | gagaagaaac | ttggtcattg aaaggaatag | 66660 |
| atcaaatcca | aagaacaaaa | ccactgtgct | cattaaactt | cttagtgttc acaaagcttt | 66720 |
| agctgcaggt | tgaatggggc | aacccgaatt | ggctggctca | cctgggctgc agggagcaga | 66780 |
| gatcgcgaca | ctgcactcca | gcctgggcaa | caaagcgaga | ctctatctca aaaaaaaaaa | 66840 |
| agttcataaa | ttcaaagtta | tgaattattt | ttaaaataat | aataatttac aataaagatg | 66900 |
| aggacaaagt | gtgagtaaat | ggtggtttct | atccagctct | gttgagctga agtggcatct | 66960 |
| ccctgctggg | gcttttgggg | aagaagggtg | tgtgttgctc | ttcagatccc aagcctcatg | 67020 |
| cccctactgg | gccctgtggg | gtgcttctca | gccaccagg | agagccaccg ttggaacaca | 67080 |
| cacgtggggg | acctggtggg | tgccggtgtg | gtgaatgggg | gccacagcct gactccagga | 67140 |
| agccagcaaa | ctcggagctg | gaggagtcag | gacaccccg | atgagtcaag agttggtttt | 67200 |
| gctgccagtt | gacatctgat | tgaaccatct | cttcacttct | ccgtgcctca ctttccttac | 67260 |
| cagacaggct | ctgctgatgc | tgtccctctc | ctgttcagtc | gtgccctcac cgttaaagag | 67320 |
| aaagagcaaa | ctgctgggca | gcagcattga | tttttttaat | gaagtggaaa gagagctggg | 67380 |
| aataacaagt | cgggcccacc | tcacctgcct | cacctggtgg | gtttatttgt tttgtttttt | 67440 |
| ttttttttgtt | ttgagacaga | gtttcaccct | gtcacccagg | ctggagtgca gtggtgtaat | 67500 |
| ctcagctcac | tgcaacctcc | acctgccagg | ttcaattgat | tctcctgcct cagcctcccc | 67560 |

```
agtagctggg attacaggca cctgccacat gcctggctaa ttattgtatt tttagtagag   67620
atggggtttt accatgttgg ccaggctggt ctcgatctcc tgacctcagg tgatccaccc   67680
acctcggcct cccaaagtgc tgagatcaca ggcgtgagcc accatgcctg gccgtcacct   67740
ggtggtgttg aatatgaact gctgcggtgt tggtaaatta agcaagcaga tagatgtaaa   67800
taacgcttgg gcaggaatat ggagcacggg atgaggatgg gcggccaact gttagagagg   67860
gtagcaggga ggctgagatc tgcctgccat gaactgggag gagaggctcc tctctctctt   67920
cacccccact ctgcccccca acactcctca gaacttatcc tctcctcttc tttcccagg    67980 tgaactttga accaggatgg ctgagccccg ccaggagttc gaagtgatgg aagatcacgc   68040
tgggacgtac gggttggggg acaggaaaga tcaggggggc tacaccatgc accaagacca   68100
agagggtgac acggacgctg gcctgaaagg ttagtggaca gccatgcaca gcaggcccag   68160
atcactgcaa gccaaggggt ggcgggaaca gtttgcatcc agaattgcaa agaaatttta   68220
aatacattat tgtcttagac tgtcagtaaa gtaaagcctc attaatttga gtgggccaag   68280
ataactcaag cagtgagata atggccagac acggtggctc acgcctgtaa tcccagcact   68340
ttggaaggcc caggcaggag gatcccttga ggccaggaat ttgagaccgg cctgggcaac   68400
atagcaagac cccgtctcta aaataattta aaaattagcc aggtgttgtg gtgcatgtct   68460
atagtcctag ctactcagga tgctgaggca gaaggatcac ttgagcccag gagttcaagg   68520
ttgcagtaag ctgtgattat aaaactgcac tccagcctga gcaacagagc aagaccctgt   68580 caaaaaaaa agaaaagaaa aagaaagaa agaaatttac cttgagttac ccacatgagt    68640
gaatgtaggg acagagattt tagggcctta acaatctctc aaatacaggg tactttttga   68700
ggcattagcc acacctgtta gcttataaat cagtggtatt gattagcatg taaaatatgt   68760
gactttaaac attgcttttt atctcttact tagatcaggc ctgagtggcc tctcttagc    68820 aagagttggt tagccctggg attcttactg tagccacatt aataaacaac atcgacttct   68880
aaacattcta taataccatc ttttggccaa attgacttcg cctcttcctc tctctttcca   68940
aatgaaatgt gtttcatttc actgtcagac cacatggttg gggaccccac agagcacaca   69000
gccctccctc tgccttccca tgctggccct tcacccactg ctggagtgcc aggttggtcc   69060
aagggttgga ccaagttgtc tgaggttgtc tcaaggttgg tcgaggctgt ctccgcgctg   69120
ggttgtgcta caaggagccc ttcttttccat gggtgtggct ggcagtgagt gctcacagca   69180
acagcccaca gtgcagcccg agggcaggat ggactcagtc cctgcctcca tacccatttc   69240
taaggaggca aaatggcaaa cactctactt ttctcttta atgctaaaaa taagaaaaca    69300
ccttgcagcc cagggtatgg gtagtgcatg gaagccgtgg agttgtgagg tgggaagtga   69360
cctctgctgg atatgtctat tcaggaagat tgctggagtg ggtggggtct ctggaggtc    69420 ccctgagtgt gggaagctgg gaccaccagc tttctcgcac agggagtggc catcccagct   69480
tggagaggtt ccaggactgg ttgggaggca cgtttcagat ttctatctgt tgaatcagcg   69540
aagatattgg attatgagga atttgggaat taggaaagtg ggtgcaggtg ggttggggt    69600 aggtgaagga agacatgggc gtattggggg agcaggggct gctcagaggt gttccagaag   69660
ctctgggtga ggaggtgaga gggaccgggg aatgcagctc ggcccagcct ccctgcctga   69720
ggtcagccat cacgtggtga tggcaagatg gaaatgtgct ttctgactgc tccagccagt   69780
gctgccagat tcagctcccc agggagggca cctgagaggc tccaagccag gagatctgtt   69840 ttctccttg ttttgttttt tttgttttg ttttgtttta ttatacttta agttctaggg     69900
tacatgtgca caacgtgcag gtttgttaca tatgtataca tgtgccatgt tggtgtgctg   69960
```

```
cacccatcaa cttgtcattt acattaggta tatctcctaa tgctatccct ccccctccc   70020 cccacccct  gttttctcct ttgaatcctt cttagaggcc gggtgcggtg gctcacgcct   70080
gtaatcccag cactttggga ggctgcggca ggaggattgc ttgagcccag gagttccaga   70140
ccagcctggg caacatagtg agacctcgtc tctacagata ataattttaa aaattatccg   70200
ggcatagtgg catgcaccta tagtcccagc tactcaagag gcagaggcag gaggatcact   70260
tgagcccagg aggcggaggt tgccgtgagc caagatccca ccactgcact ccagcctggg   70320
cgacagagac ccccatgtca aataataata ataataaata aatccttctc agtcccttcc   70380
tcactgtgtc cccctccact gaattttcc  acctcctctc ccacttcccc cactcccgct   70440
ttccctctcc ttctctcccc actccatctt tttctttctc tgctgtttct cgtccctccc   70500
tcctctccat cccacaacac tgcctaccct gtccctgccc cacccggtg  ctcaggatgt   70560 gtgaagtgag gggtggtagc ccccaagacc tcaaccccga aggttagcct gttgaaacca   70620
cttctcccca gctgcccccc tggcagttgg tgctgctggg ggaaactggg attggggcc   70680 agattttgcc tcttttcctg acaaagagag atgaagagtt ctctcaccag gtgcctggga   70740
ctggggtgtg ggtgtcccag cctatcccag cgcatctgtt ctgcatcatg attaatagtg   70800
ctgctttcag ccgggcgcgg tggctcacac ctgtaatccc agcactttgg gaggctaagg   70860
tgggcagatc acaaggtcag gagttcgaga ccagcctggc caacatggtg aaacctcgtc   70920
tctactaaaa atacaaaaat taaccaggtg tggtggtggg tgcctgtagt cccagctact   70980
tgggaggctg aggcaggaga atcacttgaa tctgggaagc agaggttgca gtgagccaag   71040
atcgtgccac tgcactccag cctgggtgac agagcgagac tccgtcctaa aaaaaaagga   71100
gttttgctct gtcgcccagg ctggagtgta gtggcgccat ctcggctcac cgcaacctgc   71160
gcctcccggg tgcaagcgat tctcctgcct cagcctccca agtagctagg attacaggcg   71220
cctaccacca cgcccggcca gttcttgtat ttttagaaga gacggggttt cacccctgttg   71280 gccaggctcg tctgggactc ctgacctcag gtaatccgcc cacctcagcc tcccaaagtg   71340
ctgggattgc aggcatgagc caccgtgccc agtcaactcc ttctcaaaaa aaaaaaaata   71400
gtgctgcttt ctctttcaag tgtcctgatt tgggtgatag taaatgccac tctacttata   71460
agggatctac ctcagaatgc taattgggac attttttgtag cactctactg ttggcagcag   71520
gtgatgctca caacagcccg tgagggtgga tgacgtccgc ttcacagatg acaaaggagc   71580
ctcatgctca gaccgtgggc tgccagagca ggtccatggc tgcagcccca catggaccat   71640
atttccccct tgtcactctt tccaccaagc tcccttggaa cttcagttat taagctctct   71700
tgggtggaat ccaagttaga atcacaacat gtgcctcata tggattgtgc cagtgaaaaa   71760
tgacattcta tttagaggca gggcagcctg gcttagagtc agtttaaaat atgtattatg   71820
ctgcaacaaa tgtaccatga tcctgtaaga tgttcacaac aagggaactg gatgtgggt    71880 atactgtctg tactaacttc acaagttttc tgtaaatcta aaactgttcc aaaataacaa   71940
gttcgtttaa aattaactcc aggagaccag gtacggtagc taatgcctat aatcccagca   72000
cttcggaagg ctgaggcagg tggattgctt gagcccagga gtttgagaca agcctgggca   72060
acatggtgaa atcctgtctc taaaaaaaat cacaaaaatt agccaggtgt ggtggcgcat   72120
tcctgtagtc ccagctactt gcggggctga ggtgggagaa tcatctgagc ccaggagttt   72180
gaggctgcag tgagctgtga ttgtaccact gcactccaac ctgggcaaca gagcaagacc   72240
ctgtctcaaa aacaaaaaat gaaataaagt ccaggaaaga agtaggtttt accactctta   72300
```

| | |
|---|---|
| tttctgaag agaaaactaa atttaatgtg taaagtgagg acaagttcac caagttagtg | 72360 |
| tttgagttgc ctaaaatatg tttgctaaaa ctattcaaag cttcacata aaacatgatc | 72420 |
| agaagttcta tgccaaaaca tatgtgtgtg tatatatata tgcactatat atactgtata | 72480 |
| taaaaatgca aaatctaaat tgccaaccctt ttagaaattg ctctgaaagg aaagcatttc | 72540 |
| aagataattt gcttacccaa agaatatact ttccaagaaa gcaagtaata cttaaggtgt | 72600 |
| tcataatcct catcaaatta attcttgcta ctgaaagctt acaaggagct gttttgatgt | 72660 |
| cgggtgtgac aggtttgact tggcagaagg tgtcacttta ctaacaacat tttaaataag | 72720 |
| tgacagaaga caagaaacta cacgttaaat gccagaacaa agagtgtcta agtggatgct | 72780 |
| aagagttgaa atatggctgg atacctgccc aagagagctg aaaagtagat gaaagttggt | 72840 |
| tacctataaa ctagtgcacc ctaatgaatt aaaaggtgtt gatgagttaa cttgttatgc | 72900 |
| cttccagata agacatgcaa atgggcttc ttcctccttc actacttcca agggatttaa | 72960 |
| caaggagacc aatgcaaatg ataaggactg tagggctcaa gctggggaca gattggggaa | 73020 |
| agggggacca tcatgcccat atagatgtcc ctgtgccctg gcagtcaagg ctgctgaaaa | 73080 |
| ataacaaaac ccagaagtct gcgtgatgct gcctctccat ttgtccaaag ccttcttgcg | 73140 |
| gcagtttgca ggcttttgca aaagctccag gaccaaggag ctatgttcat gctggaagct | 73200 |
| tgttcaggat tagctgttct ttgtgggatg ggtgcagcca gggccaggtg tccagggaca | 73260 |
| gtgttttaac aaagggcatg aggtgtctga tctcacagtg gaactccact tgcctttttt | 73320 |
| tcatcttctc attctgcttc atgcacagaa ccagccccat cctgaaactg actctaaatt | 73380 |
| actcccgccc caggtggagt gccttttctcg gagttcaaca gagccttcct gtcgcccaag | 73440 |
| ggacaactcc actgaatgcc caagccacac ccaaaaccta acaagtaaaa accaaattct | 73500 |
| gtgctccccc atcctgggcc attcctggtt tctctactgc tgttggtgat accaccatca | 73560 |
| gcttgtccat catgaccctg gccagttcct cccacaaccc tccacagcac cagggaccct | 73620 |
| cacctccatt ccatccgaca cagatctcct caccacaaac cttggttttg caacagcagc | 73680 |
| catgagacct ttacaccctc cgcccttcat cctgtccccc actgaggccc cagagccatt | 73740 |
| ccttaaagca gcgcgccaca aactataacc cacaagccaa ttctggtacc cagcctgttt | 73800 |
| tgcacagcca gtgaactgac aatgatcttt tcatacagcc agaaaaacaa aacaaaacaa | 73860 |
| aaacaacaa aaaaaaaccc caccattctg agcatgtgac ttccatgttc aagatgtctc | 73920 |
| atgttcagaa aggcccctgg aaaaggagga aggggagctg ggcacaaagg gagaccctct | 73980 |
| cagctgagct cctcccatcc agacattttc ctggacttcc tatccaatga cttcccttag | 74040 |
| cttcttatca gccacccctg tctgcccagg aggctggaag atgtggcctt ttaactgggc | 74100 |
| acagctctgt cctctatcat atcagggctc tgttcccaag gagggtagag agaatggaca | 74160 |
| ccaggtggac cctcagcagt ctgtgccaca gagggagtgt ttgcaatttc cagactaaaa | 74220 |
| gtccccatgt gcttgacggg gtatgtgact acaacgtgat gcttgacttt tcctcatatg | 74280 |
| accagagcca ctttgtccat ctggtacaat gtcagctatc tgctagggc cctccaggat | 74340 |
| tcccagtcaa ttccatatct gcatcaccac cattggcact aaataaaata aaatactcaa | 74400 |
| gttcctgctg gtgagcatga gcagtgctac actgggccct tcaaccaagg tgacatgata | 74460 |
| atgactgaaa ataatcactg ccacttattg gggacgtctc atctgccagg catggtacaa | 74520 |
| agtgctttaa ataagcattc aacaatttca tgctgacaga agccctgtga gccagtggag | 74580 |
| ctactactat gcccattata caggggagaa aactgaggca gagagaggtt aggtaattcg | 74640 |
| ctcagcctca cacaaccaat aggtggtgga gccaggattt gggccccatc tgcctgactc | 74700 |

```
tctagaggct ctatcttcca gtcttccaga gttgagtcta agccatgaat aggacaatta   74760
gacagcagag gaaacccatt cagccaccat gtgcatgaag agtaaggaat ttctgtcata   74820
cagaggggag tgaattcact gagctgagag ctgaggaacc attgatctga tggctgagac   74880
accactggga agactggaga ggcttttctg ggcatgcagt gccaggcaca ggaggagctg   74940
agggaagatg actaagaggt actggcaaag aattcagaaa ttctgatgga agctttacat   75000
gttaccatca catccatcca tctatccacc catccatcca cccatatctt cctccctcca   75060
cccaatcatg catacatcca gtcatctata caccacccac ccacccatcc atccatccat   75120
ccatcccttc atccatccca tcatccatcc aattatacat acatccaatc atatatctgt   75180
acataatcca ttcttccctc ggttcatcca tccatccatt catccatcca tccacccatc   75240
ccttccttca tccttcctat catccatcca atcatatatc tgtacataat ccattcttcc   75300
ctcggttcat ccatccatcc attcatccat ccatccaccc atcccttcct tcatccttcc   75360
tatcatccat ccaatcatac atatatccaa tcatacatct gcacatcacc agctcatcca   75420
tctatccatt tatccatcca tccttccttc catccatcat tcatccatca tacatacatc   75480
taaccataca tctctacatc attcattctt ccatcgattc atccaattat ccatcattcc   75540
ttcctccatc catcccatta tccatttgat catacatata tcatctatac atcatccatt   75600
catccatcca tccatccatc cacccatatc ttcatccaat caatcataca tacatcgaat   75660
catctacaca tcacccatcc atccatccat ccattcatct atccacccat ccatccatcc   75720
atccatccat tcatctatcc acccatccat ccatccatcc atccatccat ccatgtaacc   75780
atccagtcat atatccaatt acacatccat ccagttatac attcatacat gcatctaatc   75840
attcaattat acatacacac atccatataa ttctacatcc aattataccct ccatccaatt   75900 acacattcat acacccacct aataaattat taattcatat atccatccat ataattatac   75960
atcaattata catccatcta atcattcagt aattcaccca ccatccagtc atctatccaa   76020
taatacattc atccaatcat ccatccatcc atccacccat tcatccatcc atccgtccgt   76080
ccacccatca tggtatgagc catgatttac cacgatggtc ccctgtggac agcccaggtg   76140
gggcagaact gaagggaagc ccagggctgc cccataaac atttgcctcc tttacatgga   76200
tgagaactag atccacatgt ataaatcctc atgatttgaa ggtgcttttta ccaacattca   76260 ctcatgggat tctcccagga gctctaggag gaggcaggta gagttgaggt catctcacgc   76320
attttacaga tgaggaaacg gaggccctga gaggcaggtc caaggccacc tgaccagaaa   76380
gaagtggaac tgggacttga acccagccat cttgccccct ggtcccatgc tctctagcct   76440
gtaactcctg cttcctggtg gggcatctcc aggaggaccc tatcggctgg ccatgggcct   76500
gccctggagt cttttgctct gtgtggccat ccttcctccc tcaggagagt gtgtgctccc   76560
agagcacagg ctgtatcttc tgagcatttt gtcccttccc agtacctagc actcagctct   76620
gtatacattg ggctctcaag aattctcaac cttccagagt gtaaggcctt gacctgctca   76680
gccctggata ctgcatgatg cattgataag cccataaaat aaccagggca gattgactcc   76740
cagtggccaa agtgccacag ggaagggaca attcagccct tctaggagga ggaggaggta   76800
gttttctcat ttctattaag gcaacaaaag ctgccttact aaggacattc ttggtggagg   76860
gcgtgactgt caaccactgt gatcatttgg gcctctcttg cccaggcttc ccattctgaa   76920
aggacagttt tattgtaggt acacatggct gccatttcaa atgtaactca cagcttgtcc   76980
atcagtcctt ggaggtctttt ctatgaaagg agcttggtgg cgtccaaaca ccacccaatg   77040
```

```
tccacttaga agtaagcacc gtgtctgccc tgagctgact ccttttccaa ggaaggggtt   77100
ggatcgctga gtgttttcc aggtgtctac ttgttgttaa ttaatagcaa tgacaaagca    77160
gaaggttcat gcgtagctcg gctttctggt atttgctgcc cgttgaccaa tggaagataa   77220
acctttgcct caggtggcac cactagctgg ttaagaggca ctttgtcctt tcacccagga   77280
gcaaacgcac atcacctgtg tcctcatctg atggccctgg tgtggggcac agtcgtgttg   77340
gcagggaggg aggtggggtt ggtcccctt gtgggtttgt tgcgaggccg tgttccagct    77400
gtttccacag ggagcgattt tcagctccac aggacactgc tccccagttc ctcctgagaa   77460 caaaagggg cgctggggag aggccaccgt tctgagggct cactgtatgt gttccagaat    77520
ctcccctgca gacccccact gaggacggat ctgaggaacc gggctctgaa acctctgatg   77580
ctaagagcac tccaacagcg gaaggtgggc ccccttcag acgcccctc catgcctcca     77640 gcctgtgctt agccgtgctt tgagcctccc tcctggctgc atctgctgct ccccctggct   77700
gagagatgtg ctcactcctt cggtgctttg caggacagcg tggtgggagc tgagccttgc   77760
gtcgatgcct tgcttgctgg tgctgagtgt gggcaccttc atcccgtgtg tgctctggag   77820
gcagccaccc ttggacagtc ccgcgcacag ctccacaaag ccccgctcca tacgattgtc   77880
ctcccacacc cccttcaaaa gcccctcct ctctctttct tcaggggcca gtaggtccca    77940
gagcagccat ttggctgagg aaggggcag gtcagtggac atctgatctt ggtttagtat    78000
ccttcatttt gggggctctg ggtgtggcct gggcctctgg actttggcca cggtgtttgt   78060 tccagcctt ctcctaacct gtcctttcca gacactcggc atctaggtta ttagcacctc    78120
gcatactttc tgacatgctc ctcagtcctg attttgacca tcttctcttg cttcccatct   78180
gtgtcagtca agactgcatt tggctgtaag aaacagaaac cccaactaac tgtggcattt   78240
acatgaagag gtttactttt ctcacataat cagatgtcta gacttggcca gcacctcaag   78300
ggtcattgat gctctcctgt ctttattttc tgtcatcttt agtggttgga ttgttgcctc   78360
atggttacaa agtggctgct gcacttccag gcatcacatc tgcctttgaa gcaggaacaa   78420
gttgcaaagt aaagtggcca aagggccct gaaactaaat gtgtccccctt aggaaagcag   78480 gagttttctt gcaagtggca atcttctgct tatgtctcat tggccagagc tgggtcttac   78540
ggccacccct tgctgcgagc aaggctggga cattgagcat tttgccgtcc aacctcttta   78600
gcagaataaa ccaaggggga agaacgttaa tagtggcttt tgagtcacta gttggcagta   78660
tctgcccctc tatctttcca tcctccccat ggagtttcaa ggttcctttc tcagtacttc   78720
ttcaggctct gcacgttcat ttggatcttg tgtcttgggg tgaaaaactg gcccaagtgt   78780
ctccccaagc atccaccttt ggattaattt ggaaaatggc tgtcaagtgc ccgcctcttg   78840
cttggtataa tgctacagct ttagaggacg cagcaggcat gggccttgcc gctgaggttc   78900
ttagcctcat gagaatatcc agatcagatt ctcttggctc cttcttagag ccagtgatgc   78960
aagacacttc ctgctcatct tgtcgggacg ttttacaag ttgcctgcca tcctgagaaa    79020
gtctacaaaa cgatgccaga cctcatgcca gcttcccaag ccttgactct cagtgctccc   79080
tcaacaggat tctggaagaa tctcccaaac aagtcgcaat cccctctgga ccctgtgcag   79140
gcatgagact caagagcatt ggctccacc cctggtggag gaacactgc tgggctggg     79200 atcttgcctg gttgctccgc ctgcacccaa gacaaccata attaaaatgt ccttcattga   79260
acttggaaag ccttcaaagc tgacaactcc ttatgtgtac ccggaaaggc ctgggagtgt   79320
gccagggcat tgctcgggag ggacgctgat ttggaagcat ttacctgatg agagactgac   79380
agcagctcct ggtagccgag cttttccctcc tgcctctgct gtgaaggtgg acccatccaa   79440
```

```
cagtcaaatg cctgactctg gacaggagcg gacctattta ttgccatgca agggactctg   79500 cactttgaa ttgtgggtca tgggcttgga tttaggggtt agagctggga gaagtcttgg   79560
aagtcaccta gagatgacac tgccattttg cagatgagga aaccgtccaa tcaaaatgga   79620
ccaaggactt gcccaaagcc tcacagcaaa accataggcc cccgcactaa ccccagagtc   79680
cctgtgctgt cttaagaatc aaatagttgt aagcaatcat ctggttttca gtatttcttc   79740 tttaaaatg cctggggcca tgcccagcag tctgtttcac tgcagcgttt acacagggct   79800
gccgggcttt cctggtggat gagctgggcg ttcatgagc cagaaccact cagcagcatg   79860
tcagtgtgct tcctggggag ctggtagcag gggctccggg ccctacttca gggctgcttt   79920
ctggcatatg gctgatcccc tcctcactcc tcctccctgc attgctcctg cgcaagaagc   79980
aaaggtgagg ggctgggtat ggctcgtcct ggcccctcta aggtggatct cggtggtttc   80040
tagatgtgac agcacccta gtggatgagg gagctcccgg caagcaggct gccgcgcagc   80100
cccacacgga gatcccagaa ggaaccacag gtgagggtaa gccccagaga cccccaggca   80160
gtcaaggccc tgctgggtgc cccagctgac ctgtgacaga agtgagggag ctttgcgtgt   80220
ttatcctcct gtggggcagg aacatggggtg gattctggct cctgggaatc ttgggttgtg   80280
agtagctcga tgccttggtg ctcagttacc tccctggctg cctgccagcc tctcagagca   80340
tttagggcct tctggacttc tagatgctcc tcatcttgcc tcagtcagcg cgtcagttcc   80400
agagacttct ctgcagggtt ttctggggca ggtggtggca gacccgtgcc ttcttgacac   80460
ctgaggtcag tccaccctcc tgctcagact gcccagcaca gggtcacctc caagggggtg   80520
gaccccaaga tcacctgagc gcacagaggg tgcagatgac tggaccacac cttttggtga   80580
tcttaatgag gtggtcccag aggagctcag acatgcaatc tagcatccag ttctgggact   80640
ctgtctcctt ttcaaacgta ttcatgtaga acaggcatga cgagaatgcc ttgtcaacat   80700
gggtgatggg gaatcaatca dacagggcgc cgggctcaag gctgcagtca cccaagagtg   80760
gctcagccca ccaggcccta ggaaacgcct gcacagcctg gagctcctgg agtcatttcc   80820
ttcatgtctt cttcactgca cttacgtaaa gatgccagcc attggtttgg tgatttggag   80880
ggtgcccagt tgcccaacaa gaaatgcaga agaggcctag ccaggatttc accagcagtg   80940
gagagtagag aagatgtggc cagaaaagag tttcctttcc ctcctaaaga tggtactccc   81000
tgcagctact ggggaagcct gcagcattct ctagggctct gtgtgttgag agcagcccca   81060
ccctggcccc ttctgagtgc atttctgctt tgtgacttga tccgtgaagt cccctgagat   81120
gggcagaggg gatgtcctcg aagctggggc agagcctcat ccttgaacgt gaaggacgtt   81180
tgaagactgt ggcatgatca caggatgaga tcacagggaa cttgagtttc tctcctcctc   81240
tcccttcaca gttatttcac tgagggaaat ccctccctg cccagaatga aaactctagc   81300
caactcttga cttttccatc actccaaagt agttgaaagt acattagtct ccacagtggc   81360
aaaacagtgt gcaaaagcta aataattaga acagccagtc ccatgtgaca gtcaaagctt   81420
ctaactccat tcaaagttgc agccattccc ctcgagggct ggcagggagg ggagggggtaa   81480 gagaaacagg aaggttctta ctgagttggt cctggtgtga gctgcgtcac actccctgca   81540
gaggtttcaa ggagactctc tctctctctg tctccatggg gaccttattt gaattcttct   81600
actcttaccc cagcctgcca tctccagcta tcctcccctg aagagccctt ctgctgcgct   81660
ggattctggt ggccatgtca tctcctcggc cccgtgggag tctgaagatc tggctgcagc   81720
ctcacctctg aggtcctgct agttgccacc tcttaaacat gatctgaggc tcccatgcac   81780
```

```
tctgacctgt gcccacatgg ggcccacggg aaacacgctg gcaagcaaac tgtgggtgtg    81840
cagacggttc tcagggctgc agcacctgtc ctttgctctg cccccaaagc aaggccagcc    81900
catcttccat cctctagtgt tccttggtgg ggccctgacc acagtccacc aggtccctaa    81960
ccagagggga cacacaccag gtgtcctcaa tgtattgcct tgaaacagtt gtgctgggac    82020
tgtgatgggg ggtggccatg tagccacccc caccaccccc aagccactct ctccaaggaa    82080
atcctcctaa agatcccttt acatcctcca tgtggtgggg aggttctaga gttgggtgca    82140
tgtgtcttca gctactgaca atgcagacct tagttggcac ctcgctctgg cctatcctgt    82200
ttgctgttct tggcgctcca gtgaaactcc ccatgggcca tccagttggg gtgcagtgtg    82260
gccaccccct tgcaggttcc tgccttgctg gagagcacag ggcctcctg gctcttgtaa    82320 aacactcccc atggtacaga gaggccagca gtgatgtgag gcccaacctc cctccatggt    82380
gttcccaagc agctcccttt ctggggtcaa ggggtggcaa agacagtgca gcgtccaatt    82440
tctgactcaa gccgggcctg gctatcgcag ctctgcactg tgtgtgacag caaggcaact    82500
cacccagtgc cgtggcagtg accgtgtccg aggaagcctc ctcacaccct ctgtctcaag    82560
gactctggca tttagctgga cttgctgtag ctctgagcct ttctgccatt gccatcacct    82620
tgtcagaaac tcaggccgaa tctgcactca gagttgtgcc caggcagttg agccaacact    82680
tgctcagcga tattgtcaca tgacaaggca ctgtcaccac tgggcgtcgt gggtagcgca    82740
gtgtcggctg gatggacccg gagggtgtct gtgtcatgct agtgctagtg atgggagccc    82800
cgtgagccca ttgcccgccc tcccatgccc tcagcagctg cctggggaca gccaatggcc    82860
tgggtgtttc tgaggctacc acatggcttc caggaaactc gagaaccttt ctctcccttg    82920
cctacactct tcacacaggc ctgtgctggc cagcggtggg gatccggcat tcctatctta    82980
ggtgcagaaa gtgactgact cattgcaggc ctggagata agactgatgg cccagccagc    83040
aagatgtatg gatttctcag aggcagtggc ctctgtcatt gtcctcagga aatgctggtg    83100
attctggtgg cctgaggtca atgcatgtca acgtggccaa cttgccttat aaactttttt    83160
tctggacaat tgcgtgcact gtcctgtaac agtgtcctgt tgtttatgat gcagaaatag    83220
gtgtttttaa agcctattga ttttggtact attaatgtgg tcaggaactt tctcagtctt    83280
tcttgtttgg ggtgagctgt ggcttcctaa acaggaaccc aagcacccc caaaagctgc    83340 tcaccagcac tgccagcctc cctcttacca agtagcaccc gttcaggaca ttctgcgaaa    83400
ggcatttgcc cagaagttgg gaggaaggaa atgtaacatt ttggggcacc taccatatgc    83460
caggcaccag gctaaacgtg ttcacacaaa ttctcttact aaccctcacc atccttctac    83520
aagacaaact agtatcttca tcttggggtt caagatgagg aaatggaggc tcagagaggt    83580
tgaatgaatg ccggtgcctg gatatgaacc ccatctgcct gactccgcaa cccaggcaaa    83640
gtctttcctt gaacttccca gcagccactg cttagacaca gcctccacaa ccatggctca    83700
gcagcaaatt gcttctctga cctcactcag cctgtgtgtc cttgttgagt gaggcattca    83760
ggaccctggt cccaaagtgg agaaagtctt tcctactagg tcatagctac acctgcatgt    83820
gggtgctgtg ccttttgttt agtgaacttt tatcaccagc atcctcagca atgacatttg    83880
cagagaagcc agagctgagg caccttggta ttccttggat gtgactttcc tgaatgttta    83940
agggaaaatg cccgaaggta cagagagctt ggtttctagt aaacaataac tgtcttgctt    84000 ttaccccccct tcatttgctg acacatacac cagctgaaga agcaggcatt ggagacaccc    84060
ccagcctgga agacgaagct gctggtcacg tgacccaagg tcagtgaact ggaattgcct    84120
gccatgactt gggggttggg gggagggaca tggggtgggc tctgccctga aaagatcatt    84180
```

```
tggacctgag ctctaattca caagtccagg agattttagg gagttggttc ttatcaaagg    84240
ttggctactc agatatagaa agagccctag tggttttttt ctaataccat ttctgggtaa    84300
ttcctaaggc atttagtgtt ctgaaagatg ctagccttgt ccagcctggg agttgagaat    84360
gaatgtctaa cagaaactct aggccgggcg tggtggctca cgcctctaat cccagcacta    84420
tgggagaccc aggtgggcag atcacctgag gtcaggagtt tgagaccagc ctggccaaca    84480
tgtgaaatcc tgtctcacta caaataaaaa aattagccgg gtgtggtggt aggtgcctat    84540
aatcccagct actcaggagg ctgaggcagg acaatcgctc gaacccagga ggtggacgtt    84600
gcagtgagcc gagatcgcat cattgcactc cagcctgggc aacaaaagca aaactccgtc    84660
tcaaaaaaaa aaaagaaact caaatatgtg tgacaggcga ttctcactgc aggctgccct    84720
gtggctgatc caggagcaag gccttaacca tgtcatcccc aagcgattgc ttgtaaactt    84780
tcttctgtgc agccttcaac ccttattatg attttcttct caggaaccaa actgctgtat    84840
tcaagaaagg cagctttgtg taatcattta tcataaatat cttaagaaaa atcctagaga    84900
ttcctaattt taggaaatgg gagacctatg gtactgatat aatgtgggct gggcttgttt    84960
tctgtcattt gctagataaa tgaacttgag agcctactgt aaaatgtgga agcttctaga    85020
ttgcagaagg gctggaaaga cactgttctt ttctcccgag tgatgggatc tgtccagtat    85080
ttagagctgc ctctgaggcc atctgattct aggagactct gcctcgttga ggatattttg    85140
aggcctaact acacattcct gccccagag aggtcacagc ctatagcagg ctgatgtttc    85200
tcatgtcaca tggcacagaa aggcacattt tcgttctcag gctaacaaag agcttcaaaa    85260
actattagaa gggacagtgg ctataagaga agaacctcag tcaatgtgtg aaattaacta    85320
ggaacctggc tcctgtttct tttaggtcat gttttttcagc ttaggtaaaa ctagaggctt    85380
tgataaagca tgacctctag aaatcattgc ttttcataaa tggaagtggg tttgagtttt    85440
ttctactgat tgttagtgca ggtgatgtct acatgccccc agaacatatt ccatgcaaca    85500 aaaaagccc aggtcaccgt ctttgctggg aacttgactt ttgtgctcac tgaattttaa    85560
gctttctgac agcagcctgg aatcatggag ggataaagta cctattagta agatggaaaa    85620
aggtgtttca ggttggagct gcagtctgtt gagagtaagc tatgggaagg cctgtatacg    85680
aggggtggac ttttcttctg taagtgtcca gagaccaggc ctcctgaaga gggcatgggg    85740
gcttaactta cctggactac tgtgtttaca atactcattt atcttgaact cctcctaacc    85800
cctgagaatt gctacattta gtatttgctg agtacttcct agcatcctag ggaatcaata    85860
gaacattctc ccaaccaggc tgggtgcggt ggctcatgtc tgtaatccca gcactttggg    85920
aggccaaggt aggcagatcc cttgaggcca ggagtgcaag actagcctgg ctgacatggt    85980 gaaacccgt ctttactaaa aatacaaaag ttagccaggc atggtggtac acacctgtaa    86040
tcccagctac atgggaggag taggaggcag gagaattgct tgaacctggg aggtggaggt    86100
tgctgtgagc cgagatcatg ccactgcact ccagcctggg cgacagagtg agtgagactc    86160
tgtttaaaaa aaaaaaaaaa aaagaacatt ctcctaacct ggcttcttcc tccaggggtg    86220
taattaatca tgtcagtttc ctcattgata cacacacaca cacactacaa tcctgtatcc    86280 attactttc aaggtacatt tactatttac gtttggggtc cttgtctctt ttttaatagt    86340
gtttcttaaa gtcttgtatt atatcagagt acagtaacat cccagtcaag agcactctag    86400
taagctctag gaggaaagcg acttccggaa ggcagtggag acctgtcctg ttggggcagc    86460
ataggggcag cccctgcctc tggtcagttc tggcgctcag gctcagggtt gcctctgggc    86520
```

```
tgttcttccc agagactgac aaagggctcc cataaggcac ctgcagagcc tgtgagaagc    86580
tgaagtcaat gttttcctga caccagttga tctgtgcagg atccattgat ttaaccacct    86640
gctgtgtggc atgcactgtg gtcgatgcca ggaacaggaa ttggaggggc ccatgagcat    86700
ggccagtatc acaggctgga ggtgctgctg cgctctgacc gggcctcttg gggatgagcc    86760
catgtcaacc accttgcctc cgatggggtc gggcccacag gttacctttg tgtgtccatg    86820
accacacctt cctccccgac ctcatccaaa tctctttctt ttccaagccc ctgaatcctt    86880
cagggctgca ggttttgttt aaagcagagc tggtgagttg cataggttgt tgcgttggga    86940
ctagatgggg tgttcaaaga gttgggagtt aaaaaacata aagggtattt attaggagaa    87000
ccaaggagtg taattctcct gttcttaata tgcggccagg ttaatgaatg tcacgtgaat    87060
gaaccagaaa aaaatgaagt gtgcccttga tcagctgggt tggtgtgcag caagctgtgt    87120
gaccagggga cagcagtggt cctgagggcc gtcactgtct gccgtgcaga gcccttcctc    87180
ccacgggggc ctacctcacc tgtgccaagg gcttgtctgt ggtcagtgac ctggatagat    87240
ctgaatgggg cttctttttc gaggagtctt atggcaggtc tctcagtaaa gactccattc    87300
ttgatgatca cacattttgg attttccaaa tctgtcagag aatgggcttg aggcggggtt    87360
tgtgggcact agtttcactg gtttcattta ccaaaaaggg gagcagaagt caagtatggt    87420
ggctcatccc tgtaatccca gaggcaagag aattgcttga gcccaggagt tcgagaccag    87480
cctgagcaac ataaggagac cccgtctcca caaaaatgaa aaataacatt ttagtcagac    87540
gtggtggcat gcatctgtgg tcccagctgc ttgggagggt gagatgggag ggttgtttga    87600
gccctggagt taaagttgca atgagctgtg attgcaccac tgcactctag cctgggtgac    87660
agaacgagac cctgtctcaa aaaaaaaaa aagaaagaa aaaaggaaa aaaaaactc       87720 atgcctgtaa tcccagcact ttggggaccg gggtgggcag atcacgaggt caggagatca    87780
agactatcct agccaacatg gtgaaacccc gtttctacta aaaatacaaa aattagccag    87840
gtgtggtggc acgtgcctgt aatcccagtt actcggagg ctgaggcagg agaatcgctt     87900
gaaccaggga gtcagaggtt gcagtgagct gagatcgtgc cactgtactc cagcctgggc    87960
gacagagtga gactctgtct caaaccaaaa aaaaggggtg ggggcgggg gcaggagaac     88020 agtgagaggt agggagagga aagggggattc tcgctacacc caaaccagat accatctaga    88080
ggctagaatc tttgggaggc tcaaattccc tagaaagcag gagaagcttc tgtagccctc    88140
ccgctttccc agtagattaa gcccagggcg gctccagatg tgtgacatgc tctgtgccca    88200
accagagccc atcataggca gaggaataac acccacacca gaagggccct cggaggtcac    88260
cacgtccaag aaccctcttt acagatgagg aaactgaggc ccagagaggg gagagccacc    88320
tagcgagctg gtggcggcta gaccaggaga gctgtcattc caagcaagca aaggcaacga    88380
gacgagccca gagctgtgct cccatctctt tgttaggggg cctgggatgc cctctcagtg    88440
tcattttgtc caggatgatg ctccctctct taagcgatta atgcgcccct gctaaccttt    88500
tgctatcgct gcctcttcaa accagaggag ttgagagttc cggccggca gaggaaggcg     88560 cctgaaaggc ccctggccaa tgagattagc gcccacgtcc agcctggacc ctgcggagag    88620
gcctctgggg tctctgggcc gtgcctcggg gagaaagagc cagaagctcc cgtcccgctg    88680
accgcgagcc ttcctcagca ccgtcccgtt tgcccagcgc ctcctccaac aggaggccct    88740
caggagccct ccctggagtg gggacaaaaa ggcggggact gggccgagaa gggtccggcc    88800
tttccgaagc ccgccaccac tgcgtatctc cacacagagc ctgaaagtgg taaggtggtc    88860
caggaaggct tcctccgaga gccaggcccc ccaggtctga gccaccagct catgtccggc    88920
```

```
atgcctgggg ctcccctcct gcctgagggc cccagagagg ccacacgcca accttcgggg   88980
acaggacctg aggacacaga gggcggccgc cacgcccctg agctgctcaa gcaccagctt   89040
ctaggagacc tgcaccagga ggggccgccg ctgaaggggg caggggggcaa agagaggccg   89100 gggagcaagg aggaggtgga tgaagaccgc gacgtcgatg agtcctcccc ccaagactcc   89160
cctccctcca aggcctcccc agcccaagat gggcggcctc cccagacagc cgccagagaa   89220
gccaccagca tcccaggctt cccagcgagg ggtgccatcc ccctccctgt ggatttcctc   89280
tccaaagttt ccacagagat cccagcctca gcccgacg ggcccagtgt agggcgggcc     89340
aaagggcagg atgccccct ggagttcacg tttcacgtgg aaatcacacc caacgtgcag    89400
aaggagcagg cgcactcgga ggagcatttg ggaagggctg catttccagg ggcccctgga   89460
gaggggccag aggcccgggg cccctctttt ggagaggaca caaagaggc tgaccttcca    89520 gagccctctg aaaagcagcc tgctgctgct ccgcggggga agcccgtcag ccgggtccct   89580
caactcaaag gtctgtgtct tgagcttctt cgctccttcc ctggggacct cccaggcctc   89640
ccaggctgcg ggcactgcca ctgagcttcc aggcctcccg actcctgctg cttctgacgt   89700
tcctaggacg ccactaaatc gacacctggg tgcagctgct ccactccctc ggcctcctcc   89760
cgtgctcagg ctgtggccgc acgcgcccct cacgcttgcc cgccactctg catgtcacca   89820 gcaccccgc tccgtgctcc ccaccttgtt tgactctctg gccacttgat ttgtccacaa    89880
cggcccatca gcccacagga ggtttggtgg gtgccttcca ccgacaggat gacgggtgcc   89940
ctcatggtgt ctagaactct ccaaccctcc catgtaggca taagcagccc cactttgcag   90000
atgaggaaac ggaggctcag agaagtacag taacttgccg aaggccaatg agtagtaagt   90060
gacagagcca ggtttgggat ccaggtaggt tgtctctgaa agacacgcct gtcctgcatc   90120
ccacaacgcc tcccaggagg tgctggagtg tggacgccta acacagagat gtgcagggca   90180
cacacagcag gtgacacaca cagcatccag aggtggccca gagctcatgc tgtgcctttg   90240
gcccagtgcc ctgcccccac ccactctgcc ttgtggcagg aagacaagga gcagacacaa   90300
gatctccctg gtccacatgc caccacctcc ctctgcagag acaaggggga tcctcatgct   90360
ggcattggag gggttgagc agggcccacc ttgagccctc aggagcacga ccacagcagc    90420
cctgcaggga gggattggtg ggaggagagt cccaagtatc agggagagga gagttggtgt   90480
cccacaggag acctcagagc cacaaggcga gcttgttcat aaatttggga cccttagcat   90540
ttcacagtta tttgcagagc ccagaaatgg atgttactga agctcacagt tgcaagcatc   90600
tgttaaattt ttattagatt ttacttttag ggaaaacttt gaaatgctat aaagaagcct   90660
gtgtttaaaa gttaagacag aggctggggg cgatggctca cgcctgtaat ctcagcactt   90720
tgggaggcca aggcaggtgg atcatttgag gttaggagtt cgagaccagc ctggccaaca   90780
tggtgagacc ctgtctctac taaaattaca aaaaattagc tgggcgtggt ggcgggcacc   90840
tgtagtccca gctactgggg aggctgaagc aggataagtg cttgaaccca ggaggcggag   90900
gttacagtga gccaagatca caccactgta ccctaagcct gggcgacaga gtgagactct   90960
gtctcaaaaa ataaaataaa ataaagttaa gagagaaaaa aatatatcct atatcctttg   91020
ttaaattcca aacagtagg ggacaaataa ctgacttgac aggttactac aatatttcct    91080
gaaatgatgt tttcttgaat actggcctac tagaggttca taggtgtgtt tggattaaaa   91140
aagagttcca tggcccagtg actgggggaa aaaataaaa gactaaagta agttaaacag    91200
gcttttctgc tgcaggactt gtcagagcct ttaatgtact aatggccatt gtgaccctct   91260
```

```
gagaaggtca cagagtgggt ttcccaaact tacttgattc tacctgctaa catttcctgg    91320
aggaagtttg ggaaatgccg atttagcaga ttcttttgtt gtgccgtgga tggtgctggt    91380
tgatgtgggc aaaacaaaga acacgtgagt cagatccgcc tggggctctt actaaagtgc    91440
aggttcccag gtgccacttt aggcttacag acccagttgt ggggtaagcc tgggagtctt    91500
ttagcaggtg attctgccac atagtatagt tggaaaacct ctgggcatac tcattgctgg    91560
tccctctaga aatccaggtg acaatagcca atgagaagct ccaagagacc cagttgtcca    91620
tggggtagag ggaatgtgat attgaaacca agaagaaaa tctatgatca gttttcagca     91680
gtgactgtca agagaaggag aagggtgagt tagcgctgat gctggctgac aggtcagcgg    91740
gttggtttca ccaaggagtg tgatgaaggc tgatgttgtc tgtgggaatg tatgatggta    91800
actggtttgt agctaatttg gggaagcagt gagaattcgt gcccttttgaa gaccagtaag   91860 tggcaagaaa cccaccaggc ctggctcagg gctgggctgg gcttggctcg tctcagagca    91920 gctgggctg gtggccaaag ccaccattag tgagggcag gccctggggg tacaaccagc      91980
aactagggga caaagacaac cctgccagcc tctcctattc tggaggcgtg tgaccagaaa    92040
tggagatggg ttggtcagca taagatggcc aggaaggtgg aaatcaggac tgctggcaat    92100
ctagccacat gggcagggga gccgggtggt tccaggcagt ttccaaggcc aagagggtga    92160
gcaggcacct cacagggaat cagggccaag cctggctgca gtgtggagac aatgcaccca    92220
cccccatcct tggatcttgc aggaggctgg gtcctcactg agctaccaac atccatggcc    92280
ctgaggcttt taaaacaccc atccatggag tggggctggt cccagtgggg tgaggctgac    92340
cctggcagaa acagggcagg agcctgtggg ttagggagac tgcaccttcc ttagatagcc    92400
tccatgccat catgtccccg tgacagtttc tgctgcgtcc cctctgcatg gtcccaccct    92460
cggccagcct gctgccccct cttgccaggt tgcgctaatc agtgaccccca gtgtgctgtg    92520 ttgatactaa caatgcgagg cctagcagat tcaagggaaa agagaaccaa ctgggtttcc    92580
accagaccca actaaacaaa catggaccta tcccagagaa atccagcttc accacagctg    92640
gctttctgtg aacagtgaaa atggagtgtg acaagcattc ttatttata ttttatcagc     92700 tcgcatggtc agtaaaagca aagacgggac tggaagcgat gacaaaaaag ccaaggtaag    92760
ctgacgatgc cacggagctc tgcagctggt caagtttaca gagaagctgt gctttatgtc    92820
tgattcattc tcatatataa tgtggggagt atttgtcact aaagtacagc tgtcatttaa    92880
agtgctttgt attttggggc aggcttttaa aaagtccagc atttattagt tttgatactt    92940
accccaggga agagcagttg gcaggttcat gaagtcatgc tcctaattcc agcttttctta   93000 gtgtactttc agtgagaccc tgacagtaaa tgaaggtgtg tttgaaaacc aaacccagga    93060
cagtaaatga aggtgtgttt gaaaccagcc ctaggacag taaatgaagc catcttctca     93120
ctgcataaac tgcacccaga tctttgccca tccttctcag tatttcactt cacccattgt    93180
ttactgtctc aatgactggg gaaatgtctg gggaaatgct cccgtaattg cacagtggcg    93240
tttttcctgg aaaatcccac catggctcta gataagacct attttttctta aaggtatcta   93300 aaatttccag cataaattct gtctgaaaca cctgaatttt aatcagtact ggagcccgga    93360
gggcatctcc agttgccaca tagctctgag cattcagtgg tgtgttgagg gctgctcccg    93420
gaagtgcctg cagagtcagg gctccccagc ctcatctagt gaggcagtgg aagggcctgt    93480
ggggatttgg agagctggcc tgggtctctg aagtgatagt gacagctgct tgtcaatcac    93540
ggtgcacatt tagtgccggg ggcagggggc agggaatacc agcctcatgc atgcatgcat    93600
tcatttgttc cttccttcat tcattcattc agtacacatg ggtacaacat ccctgccctg    93660
```

```
gagttgccca gagtctaggg aggggaaaga tctattaccc tgggcctcgg ccagctgggg    93720
agtgctgctg gtggagaggg gccgtgtgca gcgagggaag gaggagtcgt caataccccc    93780
accccagctt tgctttcttg tcatcagccc cagggcccca gcctgtgtcc ctcctctccc    93840
attgctactt catctcctgg gtcctcctta ccaagcctga ccacacagag ggccttggcc    93900
gcttccatgg ggaattggaa agcaataaga tagcatcccc tagaagccca gtgaagtctg    93960
ggacaggacc cttctctgag ctctgacttg ctcttggaaa cacttcgagg cttagcctcc    94020
ccactttgtt tcccaagagt gtgacctgtt cccctccaaa caccccttc tcctccaggg     94080 ccatgcccac ccgtcaaaat cccccacggg caggacgaac tgtgggtgtc agtcaccatc    94140
tatcctgcat cctggttcca gggccccccc cagccccgcc tccatagggga caggcgtgca    94200 gacaccgtc cctggctgct tcctcttgtg gaatgggttc aaaagtaagc agtgttgttt     94260
acactgacaa actgaaaaaa aagaaaaag ataacatt ggaggcttgg cacagtggct       94320
catgcctgta atcccagcac tttgggaggc taaggtggga ggatgtcccc agcccaagag    94380
ttctagacca gcctgggcaa catagcaaga ccccatctca aaaaaaaaat ttaattggcc    94440
aggcagaggt gggaggatca cttgaaccca aagggtggag gctgcagtga gccgtgatgg    94500
caccactgca ctccagccag ggcaacagag ggagaccctg tctctaaaac aaacaaacaa    94560
acaaacaaac aaaagagtta acattggcca gattaggatt caccagatag tgttaatatt    94620
agtttgattt gagactttaa tcagaaagca catgtgtggt gggggtgggt gtaacctaag    94680
tcaggtagaa tctttccaac ttgggggggg cacactcctg attgtagcca tatgagtctg    94740
tcagtgtggt ggaagagacc atgggttaat gggcaggtaa aaaagcacct tgcctggaat    94800
tgagtagaaa gtaaggccct tcagacccg tgacacactt ggggacattt tcttgagtaa     94860
catcctaaga ttcatgtacc ttgatgatct ccatcaactt actcatgtga agcacctta    94920 aaccagtcgt ctccaaattc aggggcacag taacatccaa caggctggag aaagaacgta    94980
ctagaacttc cattcctttt tcatgtcctc ttctaaaagc tttgtcaggg ccaggcgcgg    95040
tggctcacgc ctgtaatccc agcactttgg gaggccgaga cgggtggatc acgaggtcag    95100
gagatcgaga ccatcctggc taacacagtg aaaccccatc tctactaaaa atacaaaaaa    95160
acgagccggg cgtggtggtg ggcgcctgta gtcccagcta ctcgggaggc tgaggcagga    95220
gaatggcgtg aacccaggag gcagagcttg cagtgagccg agattgcacc actgcagtcc    95280
agcctgggcg acagagcgag actccgtctc aaaaagaaa agaaaaaga aaagaactg      95340 tgattgggga ggacggtcac tttcctgttc ttactgatca gaagggatat taagggtacc    95400
tgattcaaac agcctggaga tcactgcttt caaccattac ctgccttatt tatttttagt    95460
tactgtcctt ttttcagttt gtttccctcc tccatgtgct gacttttatt ttgattttat   95520
ttatgtttat gtttaagaca tccacacgtt cctctgctaa aaccttgaaa aataggcctt    95580
gccttagccc caaacacccc actcctggta gctcagaccc tctgatccaa ccctccagcc    95640
ctgctgtgtg cccagagcca ccttcctctc ctaaacacgt ctcttctgtc acttcccgaa    95700
ctggcagttc tggagcaaag gagatgaaac tcaaggtaag gaaaccacct ttgaaaagaa    95760
ccaggctgct ctgctgtggt ttgcaaatgt ggggtttgtt tatttgtttt ttagcctcaa    95820
agacctttct tcaaatgagt tctggcatag aagcaccgtg taaaatagtt agaattctgg    95880
gcaaagggga aaagagagct gggggccatc cctctcagca ccccacaggc tctcatagca    95940
gcagctccta agacacctgg tgggaccttg gtttcgaaat cgctactcta aggctgggca    96000
```

```
cggtggctca cacctgtaat cccagctctt taggaggccg aggagggtgg atcacctgag   96060
atcaggagtt cgagaccagc ctggctaaca tggcaaaacc ctgtctctac taaaaataca   96120
aaaattagcc gggcgtggtg ttatgcgtgg tggtaatcgc agctactcgg gaggctgagg   96180
cacaaggatt gcttgaaccc cagaggcaga ggttgtagtt agctccagct tgggcgacag   96240
agcaagaccc tgtcgcaaaa attgtttaaa aacaaaccc aaaattgcta ctctcattgg    96300
gttcctttgc ccattcctga ttttggcaag agaaatgctt ccagattgcc ctgatctggg   96360
taggacagca tcacgccata gcaacactgc cccgtgagct cactgccccc tcaactagct   96420
tgtggtcctt ggttaatgtc agtttctttt ttgagtttgt gttatgtcta agggtcatct   96480
gctgggtaac ggaacccagg gactgcccta gtccctagac tgtgccatgc ccgactctgc   96540
cagctttgtc agtgatgctg gtgctcgcct cctcgggtgc tcgcctggtc tgagcacacc   96600
caaggagttc ttgaggcctt agggttgttt gcgagagaat gaaagaacac gacctagctc   96660
tctttagcat ccttggtcag gttcaacact gcccccaggg gcctctggtg agccaacca    96720 ccatcagcca aataaatcca taattagagt cagaaaatgg atgtctgcat atgtgtagtg   96780
cactaatgtc ctgccgatga ttgacatgga gtggagagtg acctgatcat tgctgtgagc   96840
tctgctggcc ttggcacaac tcatgctgat aactaatgca cacagttcct ctgggaggaa   96900
atgtcctcag ggaacttgga gtttgggtgg ggatgtgggt ttgtgtgccc agcaagccct   96960
tgtggttgta gcagacacta gtggcatcta ggaggcaaag ggtcacccca gtcttagcca   97020
cgttttgagt caaggtggcg gagtggggct ggtgttgact cttggtggca gtaacttttc   97080
ccaatggtga aaaaccctc tatcatgttt catttacagg gggctgatgg taaaacgaag    97140
atcgccacac cgcggggagc agccctcca ggccagaagg gccaggccaa cgccaccagg     97200
attccagcaa aaacccgcc cgctccaaag acaccaccca gctctggtaa gaagaacgtt    97260
ctcttgaatc ttagaggaag ctgaagctct cagaggtaca gccttcattt taggaggcct   97320
taggccactg agaatgaata acccctggca gctggtcagc agcttgcagt ttactaagca   97380
ctggagtctt cattgccttc tcagtccttt tgatttctga ggcaaatgtt gaatccctac   97440
cttttttttt tttttttctt tgagacagag tttcgctttt gttatccagg ccggagtgca   97500
gtggtgtgat ctcagctcac tgcatcctcc acctcccagg ttcaagcgat tctcctacct   97560
cagcctccct agtagctggg attacaggca cctgccacta tgcccggcta attttttgta   97620 ttttagtag agacagggtt tcaccatgtt ggccaggctg gtctcgaacg cctgacctca    97680
ggtgatccac ctgcctcggc ctcccaaagt gctgggatta caggcatgag ccaccactcc   97740
cagcctgaat cctcactttt tatcaatgaa gaaattgagg ctgattctgc agcatgataa   97800
aaaaaaatac agaaaaagga aaaaaagaa agaaatcgag cctctgagag tttgcttgac    97860
tgagtctaac cagctcattt taaacccgag gaaaatgcag tcacatgact actaagtggc   97920
agctctcgga gcctctctgg ccccaagtcc agggttccat agaggcagcc ccagcatggc   97980
atgttttcag tccccaaatg agactctgga gacaaatgtc tctggagaca gagcagcagc   98040
ctggataagt cacaatgggt gacgtcactc agggctcaac ccctgggcag cttaacttgc   98100
tagggacgtt aggagtctgc tgcaaaacct gagggtctta gctgagcagt cacaggctgg   98160
gcccgttgcc ctgggctcct gtgagtaaaa cccagtcaat tttgagtacc cagtaaggca   98220
tccattgagt tattttgcag ccaggagtgc tattaagaac agtcgcggct gggcgtggtg   98280
gctcatgcct gtaatcccag cactttggga ggccaaggtg gcggatcac  ctgaggtcag   98340 gagttcgaga ccagcttggc caacatggca aaaccccgtc tctaataaaa atacaaaata   98400
```

```
attagctggg cgtggtggcg ggcgcctgta atcccagctt ctcaggaggg tgaggaagga   98460
gaatcacttg aacccaggag gcagaggttg cagtgagctg agatcgcacc attgcactcc   98520
agcctggatg acaaaagtga gattccttct caaaaaaaaa aaaaaaaaaa cagtcgtcct   98580 cttgggat  tagggacagc ctgcctgcct gcccgagcac ttctctcttc cattgcccca   98640
gtgaagtatt ccaggcccct gggtttagac tctgcaccat gtaggggtgt ctgacctgca   98700
cttgctcctt ggtggcacgg gcagcctatg gcacttgctg cgggctgtga ccaaagcctg   98760
gcctggatct tggatcttgg tgactctgct tctccctggc ctgagggagc tgcccagagc   98820
ctgcccacca cctgctgcgt gtcttgcgg tggcatttct cgcacacatg ccgtgcggtg   98880
gcacccccaa ggatggccat tcactaaggc ccattgtttt tgtcttttcg cttcgtgttt   98940
tctggcctgg tgttttctc atatacatgt gatccaggga taattcccag aattttgaca   99000
ggattttaag tagcgtttgg atcctgctgt tttttttca cttaacatcg ggccagttga   99060
ctcacactct gttttttgtt gttgttttt tgagacggag tctcactgtg tcacccaggc   99120
tgaagtgcag tggcacaatc ttggcatact gcaacctctg cttcccaaat tcaagcagtt   99180
ttcctgcctc agcctcctga gtagctggga ctacaggcac aggccaccac gccctgctaa   99240
tttttgtatt tttagtaaag acagggtttc accattttgg ccagcctagt ctcgaactcc   99300
tgacctcaag tgatccgccc acctcggcct cccaaagtgc tgggattaca ggggactcac   99360
actttgtaac aacctgaaac aacgtgatgc atttcccttt gggtcttacc tgctcttcgg   99420
tggctgcctg caggtggaga gaccctcccc cttgggcccc tcgaccttgt ttcagaatgg   99480
ggcccctgct gggccagctg tgggtgcctg ccacgtgaag gactcattaa ggccctgttt   99540
aagcctgatg ataataaggc tttcgtggat ttttctcttt aagcgactaa gcaagtccag   99600
agaagaccac cccctgcagg gcccagatct gagagaggta ctcgggagcc tacttcgctg   99660
ggagcagcct ccctttgcgt gtgtggccat tcactggctt gtgtttctag agccgggagg   99720
acccttttct gcaatgcagg gttcacacag ggttcgcagc ctgaagatgg agcagtccga   99780
attctcttcc ctgtgcagtt tgcgcagctg tgtttgtctg atgggctttc taatcctgtg   99840
tgctctcctt gacttcaggg acaatggcat tacaggcatg agccaccatg cctggctgtc   99900
tccctatgtt tcagatgaag acataggctt aaggaggtca ggtgacttgc ccacgaccac   99960
tctgtaaata agaggcatga aaagtatttg gagccaccac caccaagccc actggtcacc  100020
ctgggtctct gaagtcaggg aggcaggagg atgggaggtc tgaggaggca gagaggctga  100080
gcctggaggc cctggaggcc gaggccccat ctgttgtttc cttatgtgga aaataagagg  100140
cttcatttgt cctattgcca cagagcgtac tacttcagga acatccaaga catggaaatc  100200
cgcagggcac ggtggctcac gtctataatc ccggcacttt gggaggttga ggtgggaaa   100260 tcgcttgagg ccagaagttc aagaccagcc tgagcaacat agtcagaccc cgtctctata  100320
aaaaacatta tttttaaaaa agacatgaa  gtcaaattct aaaaactggt gctggctggg  100380
tgcggtggct catgcctata atcccagcac tttgggaggc cgaggcgggt ggatcacctg  100440
aggtcaggag ttcaagacca gcctggccaa catggtaaaa cctctactaa agaaatcttt  100500
actgaaaata caaaaatcca gtctctacta aaataagtct ctactaaaaa tacaaaaatt  100560
agccaggcgt ggtgctgcac acctgtaata tcagctactc gggaggctga ggcaggagac  100620
tcgcttgatc ccatgcagcg gaggttgcag tgagccgaga tcgccatt  gcactccagc  100680 ctgggcatca gaataagact ccgtctcaaa aaaaaaacca caaaaaaaca aacaacaac   100740
```

```
aaaagaaaac tagtgcttat tcgtcactgg ccaagctgcc cattggctac atgggtgctt   100800
caaagagctg cccttctcca ggtctggcca gcaggtatgt gttacagcaa atgcctgggg   100860
cagcggcagg ggcattgctg cgggaagctt ctggacttgc aggaaagcta agttctcaga   100920
ctgcagggga gctaagcaca cctcggcaca gggtgaggcc tgcggttctc agacttcagt   100980
ctttgtggag cttgagaaaa atgaggcttt gcaggtccca cccctagaga ttctgctcta   101040
tccactcttg aaggggatcg agaaatttgc attttgcaac tcccactttc ctccttgaaa   101100
gctccggaga ttctgacgca gggttccgtg ggccacactt tggaaaatac agacccatga   101160
gatagaatac cagactgttg aagtgtaacg ggggcctggg aagtgcagta acagaagcaa   101220
gtttgagggt aaaggacacc cagaggaggg agggacagca tctgcatgga gaggagaaga   101280
gacccccccag cagcttccag ggtgttggaa gggtgcgcta gtaactgcta tgcatggcag   101340
gtggggaact gtacgtcagg gcacagcagc atgaagcggt atggctcgtg tggacagcta   101400
gggacaggca ggcgtggagc aggcatcctg ttctgaaggc caaatcccac agaggagcca   101460
gggtgctggc aggagccctg aactagccga acagctgaac agctgaacat tcaccctgtg   101520
gggaaagggt cagaagcgtc caggcttgag ggcacagctg ggtctcgtca ctgcatcacc   101580
cttatttagg ataaaggccc tgaagaattg tattagaggt tggcaaagca tatctaccac   101640
ctcctggagc cacgctggcc gcagggatta taattatttc cattttcaaa ttaaggcctc   101700
tgagctcaga gaggggaagt tacttgtctg aggccacaca gcttgttgga gcccatctct   101760
tgacccaaag actgtggagc cgagttggcc acctctctgg gagcgggtat tggatggtgg   101820
ttgatggttt tccattgctt tcctgggaaa ggggtgtctc tgtccctaag caaaaaggca   101880
gggaggaaga gatgcttccc cagggcagcc gtctgctgta gctgcgcttc aacctggct    101940
tccacctgcc taacccagtg gtgagcctgg gaatggaccc acgggacagg cagccccag    102000
ggccttttct gaccccaccc actcgagtcc tggcttcact cccttccttc cttcccaggt   102060
gaacctccaa aatcagggga tcgcagcggc tacagcagcc ccggctcccc aggcactccc   102120
ggcagccgct cccgcacccc gtcccttcca accccaccca cccgggagcc caagaaggtg   102180
gcagtggtcc gtactccacc caagtcgccg tcttccgcca agagccgcct gcagacagcc   102240
cccgtgccca tgccagacct gaagaatgtc aagtccaaga tcggctccac tgagaacctg   102300
aagcaccagc cggaggcgg gaaggtgaga gtggctggct gcgcgtggag gtgtggggg    102360
ctgcgcctgg aggggtaggg ctgtgcctgg aagggtaggg ctgcgcctgg aggtgcgcgg   102420
ttgagcgtgg agtcgtggga ctgtgcatgg aggtgtgggg ctccccgcac ctgagcaccc   102480
ccgcataaca ccccagtccc ctctggaccc tcttcaagga agttcagttc tttattgggc   102540
tctccactac actgtgagtg ccctcctcag gcgagagaac gttctggctc ttctcttgcc   102600
ccttcagccc ctgttaatcg acagagatg gcagggctgt gtctccacgg ccggaggctc   102660
tcatagtcag ggcacccaca gcggttcccc acctgccttc tgggcagaat acactgccac   102720
ccataggtca gcatctccac tcgtgggcca tctgcttagg ttgggttcct ctggattctg   102780
gggagattgg gggttctgtt ttgatcagct gattcttctg ggagcaagtg ggtgctcgcg   102840
agctctccag cttcctaaag gtggagaagc acagacttcg ggggcctggc ctggatccct   102900
ttccccattc ctgtccctgt gccctcgtc tgggtgcgtt agggctgaca tacaaagcac    102960
cacagtgaaa gaacagcagt atgcctcctc actagccagg tgtgggcggg tgggtttctt   103020
ccaaggcctc tctgtggccg tgggtagcca cctctgtcct gcaccgctgc agtcttccct   103080
ctgtgtgtgc tcctggtagc tctgcgcatg ctcatcttct tataagaaca ccatggcagc   103140
```

```
tgggcgtagt ggctcacgcc tataatccca gcactttggg aggctgaggc aggcagatca 103200
cgaggtcagg agttcgagac caacctgacc aacagggtga aacctcgtct ctactaaaaa 103260
tacaaaaata cctgggcgtg gtggtggtgc gcgcctataa tcccagctac tcaggaggct 103320
gaggcaggag aatcgcttga acccaggagg cagaggttgc agtgagccga gatagtgcca 103380
ctgcactcca gtttgagcaa cagagcgaga ctctgtctca aaacaaaata aaacaaacca 103440
aaaaaaccca ccatggctta gggcccagcc tgatgacctc atttttcact tagtcacctc 103500
tctaaaggcc ctgtctccaa atagagtcac attctaaggt acggggtgt tggggagggg 103560 ggttagggct tcaacatgtg aatttgcggg gaccacaatt cagcccagga ccccgctccc 103620
gccacccagc actggggagc tggggaaggg tgaagaggag gctgggggtg agaaggacca 103680
cagctcactc tgaggctgca gatgtgctgg gccttctggg cactgggcct cggggagcta 103740
gggggctttc tggaaccctg ggcctgcgtg tcagcttgcc tcccccacgc aggcgctctc 103800
cacaccattg aagttcttat cacttgggtc tgagcctggg gcatttggac ggagggtggc 103860
caccagtgca catgggcacc ttgcctcaaa ccctgccacc tcccccacc caggatcccc 103920 cctgcccccg aacaagcttg tgagtgcagt gtcacatccc atcggatgg aaatggacgg 103980 tcgggttaaa agggacgcat gtgtagaccc tgcctctgtg catcaggcct cttttgagag 104040
tccctgcgtg ccaggcggtg cacagaggtg gagaagactc ggctgtgccc cagagcacct 104100
cctctcatcg aggaaaggac agacagtggc tcccctgtgg ctgtggggac aagggcagag 104160
ctccctggaa cacaggaggg agggaaggaa gagaacatct cagaatctcc ctcctgatgg 104220
caaacgatcc gggttaaatt aaggtccggc cttttcctgc tcaggcatgt ggagcttgta 104280
gtggaagagg ctctctggac cctcatccac cacagtggcc tggttagaga ccttgggaa 104340 ataactcaca ggtgacccag ggcctctgtc ctgtaccgca gctgagggaa actgtcctgc 104400
gcttccactg gggacaatgc gctccctcgt ctccagactt ccagtcctc attcggttct 104460 cgaaagtcgc ctccagaagc cccatcttgg gaccaccgtg actttcattc tccagggtgc 104520
ctggccttgg tgctgcccaa gaccccagag gggccctcac tggcctttcc tgccttttct 104580
cccattgccc acccatgcac ccccatcctg ctccagcacc cagactgcca tccaggatct 104640
cctcaagtca cataacaagc agcacccaca aggtgctccc ttcccctag cctgaatctg 104700 ctgctccccg tctggggttc cccgcccatg cacctctggg ggccctggg ttctgccata 104760 ccctgccctg tgtcccatgg tggggaatgt ccttctctcc ttatctcttc ccttccctta 104820
aatccaagtt cagttgccat ctcctccagg aagtcttcct ggattcccct ctctcttctt 104880
aaagcccctg taaactctga ccacactgag catgtgtctg ctgctcccta gtctgggcca 104940
tgagtgaggg tggaggccaa gtctcatgca ttttttgcagc cccacaaga ctgtgcaggt 105000 ggccggccct cattgaatgc ggggttaatt taactcagcc tctgtgtgag tggatgattc 105060
aggttgccag agacagaacc ctcagcttag catgggaagt agcttccctg ttgacccctga 105120 gttcatctga ggttggcttg aaggtgtgg gcaccatttg gcccagttct tacagctctg 105180
aagagagcag caggaatggg gctgagcagg aagacaact ttccattgaa ggccccttc 105240 agggccagaa ctgtccctcc cacccctgcag ctgccctgcc tctgcccatg aggggtgaga 105300
gtcaggcgac ctcatgccaa gtgtagaaag gggcagacgg gagccccagg ttatgacgtc 105360
accatgctgg gtgaggcag cacgtccaaa tctactaaag ggttaaagga gaaagggtga 105420
cttgactttt cttgagatat tttgggggac gaagtgtgga aaagtggcag aggacacagt 105480
```

-continued

```
cacagcctcc cttaaatgcc aggaaagcct agaaaaattg tctgaaacta aacctcagcc    105540
ataacaaaga ccaacacatg aatctccagg aaaaaagaaa aagaaaaatg tcatacaggg    105600
tccatgcaca agagccttta aaatgacccg ctgaagggtg tcaggcctcc tcctcctgga    105660
ctggcctgaa ggctccacga gcttttgctg agacctttgg gtccctgtgg cctcatgtag    105720
tacccagtat gcagtaagtg ctcaataaat gtttggctac aaagaggca aagctggcgg    105780
agtctgaaga atccctcaac cgtgccggaa cagatgctaa caccaaaggg aaaagagcag    105840
gagccaagtc acgtttggga acctgcagag gctgaaaact gccgcagatt gctgcaaatc    105900
attgggggaa aaacggaaaa cgtctgtttt cccctttgtg cttttctctg ttttcttctt    105960
tgtgcttttc tctgttttca ggatttgcta cagtgaacat agattgcttt ggggcccaa    106020
atggaattat tttgaaagga aaatgcagat aatcaggtgg ccgcactgga gcaccagctg    106080
ggtaggggta gagattgcag gcaaggagga ggagctgggt ggggtgccag gcaggaagag    106140
cccgtaggcc ccgccgatct tgtgggagtc gtggtggca gtgttccctc cagactgtaa    106200
aagggagcac ctggcgggaa gagggaattc ttttaaacat cattccagtg cccgagcctc    106260
ctggacctgt tgtcatcttg aggtgggcct ccctgggtg actctagtgt gcagcctggc    106320
tgagactcag tggccctggg ttcttactgc tgacacctac cctcaacctc aaccactgcg    106380
gcctcctgtg caccctgatc cagtggctca ttttccactt tcagtccag ctctatccct    106440
atttgcagtt tccaagtgcc tggtcctcag tcagctcaga cccagccagg ccagcccctg    106500
gttcccacat cccctttgcc aagctcatcc ccgccctgtt tggcctgcgg gagtgggagt    106560
gtgtccagac acagagacaa aggaccagct tttaaaacat tttgttgggg ccaggtgtgg    106620
tggctcacac ctaatcccaa cacctgggga ggccaaggca gaaggatcac ttgagtccag    106680
gagttcaaga ccagcctggg caacataggg agaccctgtc tctacaattt tttttttaat    106740
tagctgggcc tgttggcact ctcctgtagt tccagctact ctagaggctg aggtgggagg    106800
actgcttgag cctgggaggt cagggctgca atgagccatg ttcacaccac tgaacgccag    106860
cctgggcgag accctgtatc aaaaaagtaa agtaaaatga atcctgtacg ttatattaag    106920
gtgccccaaa ttgtacttag aaggatttca tagttttaaa tacttttgtt atttaaaaaa    106980
ttaaatgact gcagcatata aattaggttc ttaatggagg ggaaaaagag tacaagaaaa    107040
gaaataagaa tctagaaaca aagataagag cagaaataaa ccagaaaaca caaccttgca    107100
ctcctaactt aaaaaaaaaa atgaagaaaa cacaaccagt aaaacaacat ataacagcat    107160
taagagctgg ctcctggctg ggcgcggtgg cgcatgcctg taatcccaac actttgggag    107220
gccgatgctg gaggatcact tgagaccagg agttcaaggt tgcagtgagc tatgatcata    107280
ccactacacc ctagcctggg caacacagtg agactgagac tctattaaaa aaaaatgct    107340
ggttccttcc ttatttcatt cctttattca ttcattcaga caacatttat ggggcacttc    107400
tgagcaccag gctctgtgct aagagctttt gccccaggg tccaggccag ggacagggg    107460
caggtgagca gagaaacagg gccagtcaca gcagcaggag gaatgtagga tggagagctt    107520
ggccaggcaa ggacatgcag ggggagcagc ctgcacaagt cagcaagcca gagaagacag    107580
gcagacccctt gtttgggacc tgttcagtgg cctttgaaag gacagccccc acccggagtg    107640
ctgggtgcag gagctgaagg aggatagtgg aacactgcaa cgtggagctc ttcagagcaa    107700
aagcaaaata aacaactgga ggcagctggg gcagcagagg gtgtgtgttc agcactaagg    107760
ggtgtgaagc ttgagcgcta ggagagttca cactggcaga agagaggttg gggcagctgc    107820
aagcctctgg acatcgcccg acaggacaga gggtggtgga cggtggccct gaagagaggc    107880
```

```
tcagttcagc tggcagtggc cgtgggagtg ctgaagcagg caggctgtcg gcatctgctg   107940
gggacggtta agcagggtg agggcccagc ctcagcagcc cttcttgggg ggtcgctggg    108000
aaacatagag gagaactgaa gaagcaggga gtcccagggt ccatgcaggg cgagagagaa   108060
gttgctcatg tggggcccag gctgcaggat caggagaact ggggaccctg tgactgccag   108120
cggggagaag ggggtgtgca ggatcatgcc cagggaaggg cccagggggcc caagcatggg  108180 ggggcctggt tggctctgag aagatggagc taaagtcact ttctcggagg atgtccaggc   108240
caatagttgg gatgtgaaga cgtgaagcag cacagagcct ggaagcccag gatggacaga   108300
aacctacctg agcagtgggg cttgaaagc cttgggcgg ggggtgcaat attcaagatg      108360
gccacaagat ggcaatagaa tgctgtaact ttcttggttc tgggccgcag cctgggtggc   108420
tgcttccttc cctgtgtgta ttgatttgtt tctctttttt gagacagagt cttgctgggt   108480
tgcccaggct ggagtgcagt ggtgcgatca tagctcactg cagccttgaa gtcctgagct   108540
caagagatcc ttccacctca gcctcctgag tagttgggac cacaggcttg caccacagtg   108600
cccaactaat ttcttatatt ttttgtagag atggggtttc actgtgtcgc ccaggatggt   108660
cttgaactcc tgggctcaag tgatcctcct gcctcagcct cgcaaattgc tgggattaca   108720
ggtgtgagcc accatgccg accttctctt tttaagggcg tgtgtgtgtg tgtgtgtgtg    108780
tgggcgcact ctcgtcttca ccttccccca gccttgctct gtctctaccc agtcacctct   108840
gcccatctct ccgatctgtt tctctctcct tttaccctc tttcctccct cctcatacac    108900
cactgaccat tatagagaac tgagtattct aaaatacat tttatttatt tattttgaga    108960
cagagtctca ctctgtcacc caggctggag tgcagtggtg caatctcggc tcactgcaac   109020
ctccgcctcc caggttgaag caactctcct gcctcagcct ccctagtagc tgggattaca   109080
agcacacacc accatgccta gcaaatttt atattttag tagaggagga gtgtcaccat     109140
gtttgccaag ctggtctcaa actcctggcc tcaggtgatc tgcctacctt ggtctcccaa   109200
agtgctggga ttacaggtgt gagccaccac gcctgccctt aaaaatacat tatatttaat   109260
agcaaagccc cagttgtcac tttaaaaagc atctatgtag aacatttatg tggaataaat   109320
acagtgaatt tgtacgtgga atcgtttgcc tctcctcaat cagggccagg gatgcaggtg   109380
agcttgggct gagatgtcag acccccacagt aagtgggggg cagagccagg ctgggaccct  109440
cctctaggac agctctgtaa ctctgagacc ctccaggcat cttttcctgt acctcagtgc   109500
ttctgaaaaa tctgtgtgaa tcaaatcatt ttaaaggagc ttgggttcat cactgtttaa   109560
aggacagtgt aaataattct gaaggtgact ctaccctgtt atttgatctc ttctttggcc   109620
agctgactta acaggacata gacaggtttt cctgtgtcag ttcctaagct gatcaccttg   109680
gacttgaaga ggaggcttgt gtgggcatcc agtgcccacc ccgggttaaa ctcccagcag   109740
agtattgcac tgggcttgct gagcctggtg aggcaaagca cagcacagcg agcaccaggc   109800
agtgctggag acaggccaag tctgggccag cctgggagcc aactgtgagg cacggacggg   109860
gctgtggggc tgtggggctg caggcttggg gccagggagg gagggctggg ctctttggaa   109920
cagccttgag agaactgaac ccaaacaaaa ccagatcaag gtctagtgag agcttagggc   109980
tgctttgggt gctccaggaa attgattaaa ccaagtggac acacaccccc agccccacct   110040
caccacagcc tctccttcag ggtcaaactc tgaccacaga catttctccc ctgactagga   110100
gttccctgga tcaaaattgg gagcttgcaa cacatcgttc tctcccttga tggttttgt    110160 cagtgtctat ccagagctga agtgtaatat atatgttact gtagctgaga aattaaattt   110220
```

```
caggattctg atttcataat gacaaccatt cctcttttct ctcccttctg taaatctaag  110280
attctataaa cggtgttgac ttaatgtgac aattggcagt agttcaggtc tgctttgtaa  110340
ataccettgt gtctattgta aaatctcaca aaggcttgtt gcctttttg tggggttaga   110400
acaagaaaaa gccacatgga aaaaaaattt ctttttttgtt ttttttgttg cttgtttttt  110460
tgagacagag tttcactctg tcgcccaggc tggagtgcag tggtgcgatc tccgcccact  110520
gcaagctcca cctcccgggt tcatgctatt ctcctgtctc agcctcccaa gtagctggga  110580
ctgcaggtgc ccgccaccac acctggctaa tttttttgta ttttagtag agacggggtt    110640
tcaccgtgtt agccaggatg gtctcaatct cctgacctcg tcatctgcct gcctcggcct  110700
cccaaagtgc tgagattaca ggcgtgagcc accgtgcccg gccagaaaaa acatttcta   110760
agtatgtggc agatactgaa ttattgctta atgtcctttg attcatttgt ttaatttctt  110820
taatggatta gtacagaaaa caaagttctc ttccttgaaa aactggtaag ttttctttgt  110880
cagataagga gagttaaata acccatgaca tttcccttt tgcctcggct tccaggaagc    110940
tcaaagttaa atgtaatgat cactcttgta attatcagtg ttgatgccct tcccttcttc  111000
taatgttact ctttacattt tcctgcttta ttattgtgtg tgttttctaa ttctaagctg  111060
ttcccactcc tttctgaaag caggcaaatc ttctaagcct tatccactga aaagttatga  111120
ataaaaatg atcgtcaagc ctacaggtgc tgaggctact ccagaggctg aggccagagg    111180
accacttgag cccaggaatt tgagacctgg gctgggcagc atagcaagac tctatctcca  111240
ttaaaactat tttttttat ttaaaaaata atccgcaaag aaggagttta tgtgggattc    111300
cttaaaatcg gagggtggca tgaattgatt caaagacttg tgcagagggc gacagtgact  111360
ccttgagaag cagtgtgaga aagcctgtcc cacctccttc cgcagctcca gcctgggctg  111420
aggcactgtc acagtgtctc cttgctggca ggagagaatt tcaacattca ccaaaaagta  111480
gtattgtttt tattaggttt atgaggctgt agccttgagg acagcccagg caactttgt    111540
tgtcacatag atagcctgtg gctacaaact ctgagatcta gattcttctg cggctgcttc  111600
tgacctgaga aagttgcgga acctcagcga gcctcacatg gcctccttgt ccttaacgtg  111660
gggacggtgg gcaagaaagg tgatgtggca ctagagattt atccatctct aaaggaggag  111720
tggattgtac attgaaacac cagagaagga attacaaagg aagaatttga gtatctaaaa  111780
atgtaggtca ggcgctcctg tgttgattgc agggctattc acaatagcca agatttggaa  111840
gcaacccaag tgtccatcaa cagacaaatg gataaagaaa atgtggtgca tatacacaat  111900
ggaatactat tcagccatga aaagaatga gaatctgtca tttgaaacaa catggatgga   111960
actggaggac attatgttaa gtgaaataag ccagacagaa ggacagactt cacatgttct  112020
cacacatttg tgggagctaa aaattaaact catggagata gagagtagaa ggatggttac  112080
cagaggctga ggagggtgga ggggagcagg gagaaagtag ggatggttaa tgggtacaaa  112140
aacgtagtta gcatgcatag atctagtatt ggatagcaca gcagggtgac gacagccaac  112200
agtaatttat agtacattta aaacaacta aaagagtgta actggactgg ctaacatggt   112260
gaaaccccgt ctctactaaa aatacaaaaa ttagctgggc acggtggctc acgcctgtaa  112320
tcccagcact ttgggaggcc gaggcgggcc gatcacgagg tcaggagatc gagaccatcc  112380
tagctaacat ggtgaaaccc cgtctctact acaaatacaa aaaaagaaa aattagccg    112440
ggcatggtgg tgggcgcctg tagtcccagc tactcgggag gctgaggcag gagaatggcg  112500
tgaacccggg aggcggagct tgcagtgagc cgagatcgcg ccactgcact ccagcctggg  112560
cgacaaggca agattctatc tcaaaaaaat aaaaataaaa taaaataaaa taataaaata  112620
```

```
aaataaaata aaataaaata aaataaataa aataaaatgt ataattggaa tgtttataac 112680
acaagaaatg ataaatgctt gaggtgatag atacccatt caccgtgatg tgattattgc 112740
acaatgtatg tctgtatcta aatatctcat gtacccaca agtatataca cctactatgt 112800
acccatataa atttaaaatt aaaaaattat aaaacaaaaa taaataagta aattaaaatg 112860
taggctggac accgtggttc acgcctgtaa tcccagtgct tgtgaggct gaggtgagag 112920 aatcacttga gcccaggagt ttgagaccgg cctgggtgac atagcgagac ccatcatca 112980 caaagaattt ttaaaaatta gctgggcgtg gtagcacata ccggtagttc cagctacttg 113040
ggagaccgag gcaggaggat tgcttgagcc caggagttta aggctgcagt gagctacgat 113100
ggcgccactg cattccagcc tgggtgacag agtgagagct tgtctctatt ttaaaaataa 113160 taaaagaat aaataaaaat aaattaaaat gtaaatatgt gcatgttaga aaaatacac 113220 ccatcagcaa aagggggta aaggagcgat ttcagtcata attggagaga tgcagaataa 113280
gccagcaatg cagtttcttt tattttggtc aaaaaaata agcaaaacaa tgttgtaaac 113340
acccagtgct ggcagcaatg tggtgaggct ggctctctca ccagggctca cagggaaaac 113400
tcatgcaacc cttttagaaa gccatgtgga gagttgtacc gagaggtttt agaatattta 113460
taactttgac ccagaaattc tattctagga ctctgtgtta tgaaaataac ccatcatatg 113520
gaaaaagctc cttttcagaaa gaggttcatg ggaggctgtt tgtatttttt ttttctttgc 113580
atcaaatcca gctcctgcag gactgtttgt attattgaag tacaaagtgg aatcaataca 113640
aatgttggat agcaggggaa caatattcac aaaatggaat gggacatagt attaaacata 113700
gtgcttctga tgaccgtaga ccatagacaa tgcttaggat atgatatcac ttctttgtt 113760 gttttttgta ttttgagacg aagtctcatt ctgtcaccca ggctggagtt cagtggcgcc 113820
atctcagctc actgcaacct ccatctcccg ggttcaagct attctccttc ctcaacctcc 113880
cgagtagctg ggttgcgcac caccatgcct ggctaacttt tgtattttta gtacagacgg 113940
ggtttcacca cgttggccag gctgctcttg aactcctgac gtcaggtgat ccaccagcct 114000
tgacctccca aagtgctagg attacaggag ccactgtacc cagcctagga tatgatatca 114060
cttcttagag caagatacaa aattgcatgt gcacaataat tctaccaagt ataggtatac 114120
aggggtagtt atatataaat gagacttcaa ggaaatacaa caaatgcaa tcgtgattgt 114180 gttagggtgg taagaaaacg gttttgctt tgatgagctc tgtttttaa aatcgttata 114240 ttttctaata aaaatacata gtcttttgaa ggaacataaa agattatgaa gaaatgagtt 114300
agatattgat tcctattgaa gattcagaca agtaaaatta aggggaaaaa aaacgggatg 114360
aaccagaagt caggctggag ttccaacccc agatccgaca gcccaggctg atggggcctc 114420
cagggcagtg gtttccaccc agcattctca aaagagccac tgaggtctca gtgccatttt 114480
caagatttcg gaagcggcct gggcacggct ggtccttcac tgggatcacc acttggcaat 114540
tatttacacc tgagacgaat gaaaaccaga gtgctgagat tacaggcatg gtggcttacg 114600
cttgtaatcg gctttgggaa gccgaggtgg gctgattgct tgagcccagg agtttcaaac 114660
tatcctggac aacatagcat gacctcgtct ctacaaaaaa tacaaaaaat ttgccaggtg 114720
tggtggcatg tgcctgtggt cccagctact tgggaggctg aagtaggaga atcccctgag 114780
ccctgggaag tcgaggctgc actgagccgt gatggtgtca ctgcactcca gcctgggtga 114840
caaagtgaga ccctatctca caaagaaaaa aacaaaaca aaaacccaa agcacactgt 114900 ttccactgtt tccagagttc ctgagaggaa aggtcaccgg gtgaggaaga cgttctcact 114960
```

```
gatctggcag agaaaatgtc cagttttttcc aactccctaa accatggttt tctatttcat 115020
agttcttagg caaattggta aaaatcattt ctcatcaaaa cgctgatatt ttcacacctc 115080
cctggtgtct gcagaaagaa ccttccagaa atgcagtcgt gggagaccca tccaggccac 115140
ccctgcttat ggaagagctg agaaaaagcc cacgggagc atttgctcag cttccgttac 115200
gcacctagtg gcattgtggg tgggagaggg ctggtgggtg gatggaagga gaaggcacag 115260
cccccccttg cagggacaga gccctcgtac agaagggaca ccccacattt gtcttcccca 115320
caaagcggcc tgtgtcctgc ctacggggtc agggcttctc aaacctggct gtgtgtcaga 115380
atcaccaggg gaacttttca aaactagaga gactgaagcc agactcctag attctaattc 115440
taggtcaggg ctaggggctg agattgtaaa aatccacagg tgattctgat gcccggcagg 115500
cttgagaaca gccgcaggga gttctctggg aatgtgccgg tgggtctagc caggtgtgag 115560
tggagatgcc ggggaacttc ctattactca ctcgtcagtg tggccgaaca cattttttcac 115620 ttgacctcag gctggtgaac gctcccctct ggggttcagg cctcacgatg ccatccttttt 115680 gtgaagtgag gacctgcaat cccagcttcg taaagcccgc tggaaatcac tcacacttct 115740
gggatgcctt cagagcagcc ctctatccct tcagctcccc tgggatgtga ctcgacctcc 115800
cgtcactccc cagactgcct ctgccaagtc cgaaagtgga ggcatccttg cgagcaagta 115860
ggcgggtcca gggtggcgca tgtcactcat cgaaagtgga ggcgtccttg cgagcaagca 115920
ggcgggtcca gggtggcgtg tcactcatcc ttttttctgg ctaccaaagg tgcagataat 115980
taataagaag ctggatctta gcaacgtcca gtccaagtgt ggctcaaagg ataatatcaa 116040
acacgtcccg ggaggcggca gtgtgagtac cttcacacgt cccatgcgcc gtgctgtggc 116100
ttgaattatt aggaagtggt gtgagtgcgt acacttgcga gacactgcat agaataaatc 116160
cttcttgggc tctcaggatc tggctgcgac ctctgggtga atgtagcccg gctccccaca 116220
ttcccccaca cggtccactg ttcccagaag cccccttcctc atattctagg agggggtgtc 116280
ccagcatttc tgggtccccc agcctgcgca ggctgtgtgg acagaatagg gcagatgacg 116340
gaccctctct ccggaccctg cctgggaagc tgagaatacc catcaaagtc tccttccact 116400
catgcccagc cctgtcccca ggagccccat agcccattgg aagttgggct gaaggtggtg 116460
gcacctgaga ctgggctgcc gcctcctccc ccgacacctg ggcaggttga cgttgagtgg 116520
ctccactgtg gacaggtgac ccgtttgttc tgatgagcgg acaccaaggt cttactgtcc 116580
tgctcagctg ctgctcctac acgttcaagg caggagccga ttcctaagcc tccagcttat 116640
gcttagcctg cgccacccctc tggcagagac tccagatgca aagagccaaa ccaaagtgcg 116700
acaggtccct ctgcccagcg ttgaggtgtg gcagagaaat gctgcttttg gcccttttag 116760
atttggctgc ctcttgccag gagtggtggc tcgtgcctgt aattccagca ctttgggaga 116820
ctaaggcggg aggttcgctt gagcccagga gttcaagacc agcctgggca acaatgagac 116880
ccctgtgtct acaaaaagaa ttaaaattag ccaggtgtgg tggcacgcac ctgtagtccc 116940
agctacttgg gaggctgagg tgggaggatt gcctgagtcc gggaggcgga agttgcaagg 117000
agccatgatc gcgccactgc acttcaacct aggcaacaga gtgagacttt gtctcaaaaa 117060
acaatcatat aataattta aaataaatag atttggcttc ctctaaatgt ccccggggac 117120
tccgtgcatc ttctgtggag tgtctccgtg agattcggga ctcagatcct caagtgcaac 117180
tgacccaccc gataagctga ggcttcatca tcccctggcc ggtctatgtc gactgggcac 117240
ccgaggctcc tctcccacca gctctcttgg tcagctgaaa gcaaactgtt aacaccctgg 117300
ggagctggac gtatgagacc cttggggtgg gaggcgttga ttttttgagag caatcacctg 117360
```

```
gccctggctg gcagtaccgg gacactgctg tggctccggg gtgggctgtc tccagaaaat   117420
gcctggcctg aggcagccac ccgcatccag cccagagggt ttattcttgc aatgtgctgc   117480
tgcttcctgc cctgagcacc tggatcccgg cttctgccct gaggcccctt gagtcccaca   117540
ggtagcaagc gcttgccctg cggctgctgc atggggctaa ctaacgcttc ctcaccagtg   117600
tctgctaagt gtctcctctg tctcccacgc cctgctctcc tgtcccccca gtttgtctgc   117660
tgtgagggga cagaagaggt gtgtgccgcc cccaccctg cccgggccct tgttcctggg    117720
attgctgttt tcagctgttt gagctttgat cctggttctc tggcttcctc aaagtgagct   117780
cggccagagg aggaaggcca tgtgctttct ggttgaagtc aagtctggtg ccctggtgga   117840
ggctgtgctg ctgaggcgga gctggggaga gagtgcacac gggctgcgtg gccaacccct   117900
ctgggtagct gatgcccaaa gacgctgcag tgcccaggac atctgggacc tccctggggc   117960
ccgcccgtgt gtcccgcgct gtgttcatct gcgggctagc ctgtgacccg cgctgtgctc   118020
gtctgcgggc tagcctgtgt cccgcgctct gcttgtctgc ggtctagcct gtgacctggc   118080
agagagccac cagatgtccc gggctgagca ctgccctctg agcaccttca caggaagccc   118140
ttctcctggt gagaagagat gccagcccct ggcatctggg ggcactggat ccctggcctg   118200
agccctagcc tctccccagc ctgggggccc cttcccagca ggctggccct gctccttctc   118260
tacctgggac ccttctgcct cctggctgga ccctggaagc tctgcagggc ctgctgtccc   118320
cctccctgcc ctccaggtat cctgaccacc ggccctggct cccactgcca tccactcctc   118380
tcctttctgg ccgttccctg gtccctgtcc cagccccct ccccctctca cgagttacct    118440
cacccaggcc agagggaaga gggaaggagg ccctggtcat accagcacgt cctcccacct   118500
ccctcggccc tggtccaccc cctcagtgct ggcctcagag cacagctctc tccaagccag   118560
gccgcgcgcc atccatcctc cctgtccccc aacgtccttg ccacagatca tgtccgccct   118620
gacacacatg ggtctcagcc atctctgccc cagttaactc cccatccata aagagcacat   118680
gccagccgac accaaaataa ttcgggatgg ttccagttta gacctaagtg gaaggagaaa   118740
ccaccacctg ccctgcacct tgttttttgg tgaccttgat aaaccatctt cagccatgaa   118800
gccagctgtc tcccaggaag ctccagggcg gtgcttcctc gggagctgac tgataggtgg   118860
gaggtggctg ccccccttgca ccctcaggtg accccacaca aggccactgc tggaggccct   118920
ggggactcca ggaatgtcaa tcagtgacct gccccccagg ccccacacag ccatggctgc   118980
atagaggcct gcctccaagg gacctgtctg tctgccactg tggagtccct acagcgtgcc   119040
ccccacaggg gagctggttc tttgactgag atcagctggc agctcagggt catcattccc   119100
agagggagcg gtgccctgga ggccacaggc ctcctcatgt gtgtctgcgt ccgctcgagc   119160
ttactgagac actaaatctg ttggtttctg ctgtgccacc tacccaccct gttggtgttg   119220
ctttgttcct attgctaaag acaggaatgt ccaggacact gagtgtgcag gtgcctgctg   119280
gttctcacgt ccgagctgct gaactccgct gggtcctgct tactgatggt cttgctcta    119340 gtgctttcca gggtccgtgg aagcttttcc tggaataaag cccacgcatc gaccctcaca   119400
gcgcctcccc tctttgaggc ccagcagata ccccactcct gcctttccag caagattttt   119460
cagatgctgt gcatactcat catattgatc acttttttct tcatgcctga ttgtgatctg   119520
tcaatttcat gtcaggaaag ggagtgacat ttttacactt aagcgtttgc tgagcaaatg   119580
tctgggtctt gcacaatgac aatgggtccc tgttttcccc agaggctctt tgttctgca    119640 gggattgaag acactccagt cccacagtcc ccagctcccc tggggcaggg ttggcagaat   119700
```

```
ttcgacaaca catttttcca ccctgactag gatgtgctcc tcatggcagc tgggaaccac   119760
tgtccaataa gggcctgggc ttacacagct gcttctcatt gagttacacc cttaataaaa   119820
taatcccatt ttatccttt tgtctctctg tcttcctctc tctctgcctt tcctcttctc    119880
tctcctcctc tctcatctcc aggtgcaaat agtctacaaa ccagttgacc tgagcaaggt   119940
gacctccaag tgtggctcat taggcaacat ccatcataaa ccaggtagcc ctgtggaagg   120000
tgagggttgg gacgggaggg tgcaggggggt ggaggagtcc tggtgaggct ggaactgctc   120060
cagacttcag aaggggctgg aaaggatatt ttaggtagac ctacatcaag gaaagtgttg   120120
agtgtgaaac ttgcgggagc ccaggaggcg tggtggctcc agctcgctcc tgcccaggcc   120180
atgctgccca agacaaggtg aggcgggagt gaagtgaaat aaggcaggca cagaaagaaa   120240
gcacatattc tcggccgggc gctgtggctc acgcctgtaa ttccagcact ttgggaggcc   120300
aaggtgggtg gatcatgagg tcaggagatt gagaccatcc tggctaacac agtgaaaccc   120360
cgtctctact aaaaatacaa aaaattagcc gggcgtggtg gtgggcgcct gtagtcccag   120420
ctactccgga ggctgaggca ggaaaatggc gtgaacccgg aaggcggagc ttgcagtgag   120480
cggagtgagc agagatcgcg ccactgcact ccagcctggg cgacagagcg agactccgtc   120540
tcaaaaaaaa aaagcacatg ttctcgcttc tttgtgggat ccaggagata gagaataaga   120600
ggatggttac cagaggctgg aagggtagt gaggggatgg tgggggatg gtcaatgggt     120660 acaaaaaaaa tagaataaga cctagtattt gatagtgcaa caggggtgact atagtcaata   120720 ataatttaat tgtacattta aaataacta aagatagcc gggtgcagtg gcttacgtct      120780
gtaatcccag tactttggga ggctgaggtg gggcgtttgag accagcctgg ccaacatggt   120840
gaaaccccat ctctactaaa aatacaaaaa ttagccaggc atggtggcgg gcgcctgtaa   120900
tcccagctac tcgggaggct gaggcaggag aatcacttga acctgggagg cagaggttgc   120960
agtgagccga gatcttgcca ctgcactcca gcctgggtga cagtgaaact ccgtctcaaa   121020
aataaaaata aaaatacagc tgggcacggt ggctcacgcc tgtaatccca gcactttggg   121080
aggccgaggc gagcggatca caaggtcagg agatatagac catcctggct aacacggtga   121140
aacccggtct ctactaaaaa tacaaaaaat tagccaggcg tggtggcagg tgcctatagt   121200
cccagctact cacaaggctg aggcaggaga atggcatgaa cctgggaggc ggagcttgca   121260
gtgagccgag attgtgccac tgcactccag cctgggcgag agagtgagac tccgtctcaa   121320
aacaaaaaca aaacaaaaa caaaacaaa cacacaacaa aaacctaaaa gaatataaat    121380
ggattgtttg taacacaaag gacaaatgtt tgagggatg gataccccat tttccatgat    121440
gtgattatta tacattgtgt gtctgtatca aaacatctca tgagccccat aaatatatac   121500
acctaactat gtacccacaa aaattaaaaa aatatatttt ttaaggtgaa gagggaggcg   121560
agatgctggc cttaaccccct aacccgttgt tctccctgca agctgtccac agggcctctc   121620
agactcgagg ttcagctata tggatgcatg agcttggtcc ccagccaaca tgggagacac   121680
ttcaccatcg gcagcagcta cagcacagga accctgggtc actgccatgt cccctctgtg   121740
actttgttta acagaaaat gatgctctgg gccggctgtg gtggcccaca cctataatcc    121800
cagcaccttg ggaggcgggg gtgggcagat tgcctgaggt caggagttgg agatcagcct   121860
ggccgacatg gcgaaacccc atgtctacta aaaatacaaa aactagccag gcatggtggc   121920
acatgcctgt aatcccagct acttgggagg ctgaagcagg agaatcactt gaacccagga   121980
ggcagaggct gagtgagcca agatcgtgcc aatgcactcc agcttgggtg agggagtgag   122040
actccgtctc aaaaaaaaaa aaaagaaag aaaagaaaa gaaagtgatc ctactggaac   122100
```

```
catgcttact ccctccccca cctcacactg tgtagaaatt agtgctgtcg gccaggcgcg 122160
gtggctcatg cctgtaatcg cagcactttg ggaggccaag gcaggcggat cacgaggtca 122220
ggagatcaag accatcctgg ctaacacagt gaaaccctgt ctctactaaa aatacaaaaa 122280
attagccggg catggtggca ggcacctgta gtcccaacta cttgggaggc tgaggcagga 122340
gaatggcatg aacctgggag gcggagcttg cagtgagcca agatcgcgcc actgcatacc 122400
agcctaggtg acagagtgag actcagcaaa aaaagaaaga aagaaagaaa gaaatcagtg 122460
ctgtctatac ttctttctgc agtgatggaa atattctgta tctgtgctgt ccagtatagt 122520
agccactagc tacatgtggc acttgaaaca tggctggtac agttgaggaa gagtggctgc 122580
catatcggac gacacagcta tagattctgt caccccaccc cgagagtcca gagcggggac 122640
ttctgcctta ggccctattc agggctgatt tttacttgaa cccttactgt gggaagagaa 122700
ggccatgaga agttcagtct agaatgtgac tccttatttt ctggctccct tggacacttt 122760
gtgggattta gtctccctgt ggaaagtatt ccacaagtgg tgccactacc ccagctgtga 122820
gagcagctgg gagctgcttt tgtcatcttt ccctggaaag tcctgtgggc tgtctcttcc 122880
tcatgccttg tcccatgctt gggcatggtg tcaagcgtca ggagggagaa agggtcctta 122940
tttatttatt tagagaggga cccttcttct gttcccaggc tggagtgcag tggtgcgatc 123000
tcggctcact gcaacctccg cctcctgggt tcaagtgatt ctcctgcctc agcctcctga 123060
gtagctgaga ttacaggcac atgccaacat gcccggctaa tttttttttt tttttttttt 123120
tttttttttt tttttttttt gagatggagt tgtactctca ttgcccaggc tggaatgtaa 123180
tggcacaatc tcggctcact gcaacctcca cctcctggat tcaagcaatt ctcctgtctc 123240
agcttcccaa gtagctggga ttacaggtgc ccgccaccat gctcaactaa ttttttgtatt 123300 tttttttag tagagacgag gtttcaccat gttggtcaga ctggtctcaa actcctgacc 123360
tcaggtgatc cacctgcctc ggcctcccaa agtgctagga ttacaggcat gagccaccac 123420
gcccggcctg aaagggttct tatttagtgt gcattttgac attcaattta attccaaggt 123480 cttgtgtggggt catggtttac aggatgttga tatagaaaag acttcactta atgggccggg 123540
cgcagtggct catgcctgta atcccagcac tttgggaggc cgaggcaggc agatcaggag 123600
gtcaggagat tgagaccatc ctggctaaca cagtgaaacc ccatctctac tgaaaataca 123660
aaaaattagc tgggcgtggt ggcaggcacc tgtagtccca gccactcggt tggctgaggc 123720
aggagaatgg catgaacccg ggaggcggag cttgcagtga gcagagacca tgccactgca 123780
ctccagcctg ggcgacagag caagactctg tctcaagaaa aaaaaaaaaa aacagacttt 123840
acttactgga agccaaccaa tgtatattta gagtaatttt tcctgggctg agctgtcatt 123900
tacttttgca gtatctcaag aagaagagtt tacagtgtaa atatttgatg cacactttga 123960
ttatatagat gaagcaaact attttcaaga gctttgcaag gacttacttg tatccaaaca 124020
ccattctaaa aggagtctta cctacttcta aaggctggtc tctacttgga accacttgct 124080
tggccctggt tcaagtcctg ctgcaaacct ggaagtcctg tcattgtctt cttccctcca 124140
gagcagtggc acccaatcta attttttgctg tgccccagca gccccctggca ctttgccctg 124200 tagactgcag acctcatgta atgtatgtta agtccacaga accacagaag atgatggcaa 124260
gatgctcttg tgtgtgttgt gttctaggag gtggccaggt ggaagtaaaa tctgagaagc 124320
ttgacttcaa ggcagagtc cagtcgaaga ttgggtccct ggacaatatc acccacgtcc 124380
ctggcggagg aaataaaaag gtaaaggggg tagggtgggt tggatgctgc ccttgggtat 124440
```

```
atgggcatta atcaagttga gtggacaaag gctggtccag ttcccagagg aggaaaacag   124500
aggcttctgt gttgactggc tggatgtggg ccctcagcag catccagtgg gtctccactg   124560
cctgtctcaa tcacctggag ctttagcacg tttcacacct gggcccaac  ctggagaggc   124620 tgaccaatgg gtctcagggg cagctcggtt gctggagttt ttgtttttat ttatttttat   124680
gtatttaagg cagggtctct gtattagtcc attctcacac tgctaataaa gacataccca   124740
agactgggta atttataaag gaaagaggtt taatggactc acagttccac atggctgggg   124800
aggcctcaaa atcatggcgg aaggcaaagg agaagcaaag gcatttctta catggcgaca   124860
ggcaagagag cgtgtgcagg ggaactccca tttataaaac catcagacct catgagattt   124920
attcactatc atgagaacag catgggaaag acccgccccc atgattcagt tacctcccac   124980
tgggtccctc ccatgacaca tggaattatg ggagctacaa ttcaagatga gatttgggtg   125040
gggacacagc caaaccatat cagtctccct ctgtcatcca ggctggagtg cactggcatg   125100
atctcggctc actgcagcct ctacctccct gggtcaggtg atcttccac  ctcagcctcc   125160 caggtagctg gaactacagg tacctgccac tatgcctggc taaatatttt gtatttcctg   125220
tggagacgag gtttttgccac gttgcccagg ctggtcttga actcctgagg tcaagcaata   125280
tgcccacctc ggcctcccaa ggtgctggga ttacaggtgt gagccacagt gctcggccta   125340
agtcactgca gttttttaaag ctcccaggtg attcttcagt gcagtcaaaa gtgagaactg   125400
gctgggtgcg gtggctcatg cctgtaatcc cagcaccttg ggaggcgaag gtgggcagat   125460
ggcttgaggt caggagttca agaccagcct ggccaacatg gtaaaacccc atctctacta   125520
aaaatacaaa agttagctgg gtgtggtggt gcgtgcctgt aatcccagct acttgggagg   125580
ctgaggcatg agaattgctt gaacccaggg gacagaggtt gtagtgagcc gagatcgtgc   125640
cactgcactc cagcctgggc aacagagtga gattccatct cacaaaaaaa aaaaaaagcg   125700
agaaccactg tcctaggccc tgatgtttgc aggcaactaa aaaaggaagt ggacatcccc   125760
agtcagctgt ggcgcaccaa gaacaagtca tgggaacata acctaatttt ctaaatgggt   125820
tactaggcac ttagagcaaa acaatgatgc cgaaatcctg atttcagcaa agcctctgcc   125880
tgcctgtctt ggaagtatcc acatgaggct gctggggcct tggtgtcccc agcagtttct   125940
agtctctagg tcttgctgtg ggtgtctgtg cagtgagggt gtgtgtggcg ctgggtgagc   126000
tctgtctagg cctggcacag gatgcggtct ggtagctgct gcttctcttc tgcagaagcg   126060
cagccaagca ccctctgggg tttcaggccc acacccagcc tgaagttctg ggagtggctc   126120
actttccaac cttcagggtc tcccagcagc tgactgggga gtggtggagg gaaaagggat   126180
tgtattagtc cgttttcacg ccgctgatga agacataccc gatactgggc agtctaaaag   126240
atagaggtct gatggactca cagttccacg tgactgggga ggcctgacaa tcatggtgga   126300
aggtgaaagg cttgtctcac acggtggcag acaagagaaa agagcttgtg caggggaact   126360
cccctttata aaaccatcag atctcgggag acttattcac tatcatgaga acagcacggg   126420
aaagaccctc ctctatgatt caattacctc ccaccaggtc cctcccacaa catgtaggaa   126480
ttgtgggaac tacaattcaa gatgacattt gggtggggac acagccaaac catatcaggg   126540
cgtcccagaa agggtatagg gtctgagacc caagtcagca tgagaaagta tgcttctcat   126600
ggtggcccag ttgggtggaa gtggcagccg ggccgtcttt ccaccaggcc actcaagtag   126660
cagctgagag acccctgccc tggccagtcc ccgccctccc ctcttgccac tgcctctggt   126720
tctgaacaga tgggcaccct catccttgtat ttgtgattaa tgtctaacaa tgtagttttg   126780
tgagaagggt ttgctgatac agccttgctg cagatgctgc gaactgtggc ctgggcagga   126840
```

```
ccttacctcc agacacgccc tgaggcaggg gagggcactg gcccgtagct ggccgagagc    126900
tctcgggttg cgcgacaggg atactttca gcggctgggt cgctatccaa agtgagaaaa    126960
cgaggaggga ccaggaggct gtccgcctca agagatgtgg gggccaggtc cagttatctg    127020
gggaagcagt aagcttctct gctgtttcta accccaggcc tcccctggtc taaggcaggg    127080
cctcccagcc tcggggcact ttaaagatat ctgggcctgg ccccatcccc acagtctgac    127140
tgagtgggtc tggataggc  ctgagcattg gtgatttcct gggtgaaagg aggccctca     127200
cagtctctgg aagcttctct gtgttaggaa aagctctggg cttgactctg ctttgaaagt    127260
caagatccgc aaatcctctc agcctcagtt tctccttcag caagatgaaa tggaaatgct    127320
gtacctacgt cccggggtgg ttgtgagacc caaaaaagac aatgttctgg aaggttcctg    127380
gtgcgttgca gtcctctaag aacctgagtt agagccacgc tgagtctcag cttcttggct    127440
ccttctgttt caaactcgtc catgtgatag ctcaggaagg gtaggcaggg ccctgccccc    127500
tactcagaaa acaccatcct ggtcctgggg atccccgcag cattagtccc ctgttttccc    127560
agtgtattga gaaaaattgc taacaagcag tggggcacac caccagcctc ctgggttcct    127620
ttcagtttgg ggattttggg acattcccag gaatgtctta aaaacactt  caaaaaacat    127680
taacataaat atttttatca aagcctgtat taaatggtct ttcaagaaaa tacagtaaca    127740
ggtcaggcat ggtggctcat gcctgtaacc ccagcacttt gggaggccaa ggcaggcaga    127800
tcacctgaaa tcaggagttc aagaccaacc tggccaacac agccaaatcc catctctaca    127860
aaaaatacaa aaattagctg ggtgtggtgg cacacacctg tagtcccagc tacttgggag    127920
gccgaggcag gagaattgct tgatcccgga ggcggaggtt gcagtgagcc gagatcgtgc    127980
cactgcactc cagcgtgggt gacaaggtga atctttgtct caaaaaaaaa aaaaaaaaa     128040
agataaaata cagtatacag taatagagaa caatcctttt ttcaaagtag tgaccccaaa    128100
tgaacaaaat atgcatctag cttaaatgcg aacctggttt tctctacgcc cattcaagcc    128160
cctgcaatag gggcccttca ccccgcatcc atggactcct aaaattatat ggaaaatggc    128220
tgtgtgtgag tgtggatgga catgtgcaca catattttg  gctttaccag atgctcaaag    128280
agcctaggac ccaaaagggg ctgagaatga ccgtgtcggc cacttcaggg tcatcaggaa    128340
ttgctgtgca ctgctcactt ctccagtgaa cactttctgc ttctgtgttt cctggtatcc    128400
tttgggactc ctggctaggt catgtgtttc tctactttca aaagggcttc agccaggcac    128460
gatggcatga gcctgtagtc ccagttgctc tggaggttaa ggtgggaaga ttgcttgagc    128520
ccaggaattt gaggccagcc tgggcaagta gataggtaga tgattgatag atagatagat    128580
agataaatag atggatagat aagtcgctag acagtcatcc atccacccat ccacacataa    128640
aaaggccttt gtcatgtcat gttttgtggc ccacctgcca gtgttcccca cagttgctgc    128700
ccctccaaac tcatcagtca ctggcaaaca ggaggaatgt gtggctcatg tctgggcatc    128760
agtggctgtg ggagacatcc ttgatcttct ccagcttctc cttccacatt ttcctttgca    128820
atctggcaat atctattaaa ataaaatgtg catgccttt  gacctaagag cttcacttct    128880
aggacccact tacacgtgtg tgacatgatg ttcatacggg tttatttatc tgaggttgtt    128940
catacacacc attgcctgta atcactaaag gcggagcaga cctacacatc catccacaga    129000
ggagtagatg ccttttggta catccgtggc gacggaatac taagcagcct gtgtatctat    129060
acactcacac gtgtttgttt atgtgtggaa tatctctgga gggtacacaa gaaacttaaa    129120
atgatcactg tctctgggga gggtacctgg gtgcctggga ggcaggtcag ggaaggagtg    129180
```

```
ggcacaggta ttaccaattg aagacaata aaaacaacag ctcctggcca ggcgcagtgg   129240
ctcacgcctg taatggcagc actctgagag gctgaggcgg gcagattgct tgcgtccagg   129300
agttcaagac cagcctgggc aacatagcaa acccgttt ctattaaaaa tacaaaaaat     129360
tagccaggtg tggtggcatg cacctgtaat cccagctact cgggaggctg aggtgggaga   129420
atcacctgag cctgggaggt caaggctgca gtgaggtgag attgtgccac cgcactctag   129480
cctgggcgat agagcaagac cctgtctcaa aaacaaacaa aaaacagtcc ctggcactct   129540
gggccaggcc tggcagggca gttggcaggg ctggtctttc tctggcactt catctcaccc   129600
tccctccctt cctcttcttg cagattgaaa cccacaagct gaccttccgc gagaacgcca   129660
aagccaagac agaccacggg gcggagatcg tgtacaagtc gccagtggtg tctgggggaca  129720 cgtctccacg gcatctcagc aatgtctcct ccaccggcag catcgacatg gtagactcgc   129780
cccagctcgc cacgctagct gacgaggtgt ctgcctccct ggccaagcag ggtttgtgat   129840
caggcccctg gggcggtcaa taattgtgga gaggagagaa tgagagagtg tggaaaaaaa   129900
aagaataatg acccggcccc cgccctctgc ccccagctgc tcctcgcagt tcggttaatt   129960
ggttaatcac ttaacctgct tttgtcactc ggctttggct cgggacttca aaatcagtga   130020
tgggagtaag agcaaatttc atcttttccaa attgatgggt gggctagtaa taaaatattt   130080
aaaaaaaaac attcaaaaac atggccacat ccaacatttc ctcaggcaat ccttttgat    130140 tcttttttct tcccctcca tgtagaagag ggagaaggag aggctctgaa agctgcttct   130200
ggggggattc aagggactgg gggtgccaac cacctctggc cctgttgtgg gggtgtcaca   130260
gaggcagtgg cagcaacaaa ggatttgaaa cttggtgtgt tcgtggagcc acaggcagac   130320
gatgtcaacc ttgtgtgagt gtgacggggg ttggggtggg gcgggaggcc acggggagg    130380 ccgaggcagg ggctgggcag aggggagagg aagcacaaga agtgggagtg ggagaggaag   130440
ccacgtgctg gagagtagac atcccctcc ttgccgctgg gagagccaag gcctatgcca    130500
cctgcagcgt ctgagcggcc gcctgtcctt ggtggccggg ggtgggggcc tgctgtgggt   130560
cagtgtgcca ccctctgcag ggcagcctgt gggagaaggg acagcgggta aaaagagaag   130620
gcaagctggc aggagggtgg cacttcgtgg atgacctcct tagaaaagac tgaccttgat   130680
gtcttgagag cgctggcctc ttcctccctc cctgcagggt aggggcctg agttgagggg    130740 cttccctctg ctccacagaa accctgtttt attgagttct gaaggttgga actgctgcca   130800
tgattttggc cactttgcag acctgggact ttagggctaa ccagttctct ttgtaaggac   130860
ttgtgcctct tgggagacgt ccacccgttt ccaagcctgg gccactgtgca tctctggagt  130920 gtgtggggt ctgggaggca ggtcccgagc cccctgtcct tcccacggcc actgcagtca    130980
cccctgtctg cgccgctgtg ctgttgtctg ccgtgagagc ccaatcactg cctataccccc  131040 tcatcacacg tcacaatgtc ccgaattccc agcctcacca ccccttctca gtaatgaccc   131100
tggttggttg caggaggtac ctactccata ctgagggtga aattaaggga aggcaaagtc   131160
caggcacaag agtgggaccc cagcctctca ctctcagttc cactcatcca actgggaccc   131220
tcaccacgaa tctcatgatc tgattcggtt ccctgtctcc tcctcccgtc acagatgtga   131280
gccagggcac tgctcagctg tgaccctagg tgtttctgcc ttgttgacat ggagagagcc   131340 ctttccctg agaaggcctg gcccttcct gtgctgagcc cacagcagca ggctgggtgt     131400
cttggttgtc agtggtggca ccaggatgga agggcaaggc acccagggca ggcccacagt   131460
cccgctgtcc cccacttgca ccctagcttg tagctgccaa cctcccagac agcccagccc   131520
gctgctcagc tccacatgca tagtatcagc cctccacacc cgacaaaggg gaacacaccc   131580
```

```
ccttggaaat ggttctttc ccccagtccc agctggaagc catgctgtct gttctgctgg    131640
agcagctgaa catatacata gatgttgccc tgccctcccc atctgcaccc tgttgagttg    131700
tagttggatt tgtctgttta tgcttggatt caccagagtg actatgatag tgaaaagaaa    131760
aaaaaaaaaa aaaaggacg catgtatctt gaaatgcttg taaagaggtt tctaacccac     131820
cctcacgagg tgtctctcac ccccacactg ggactcgtgt ggcctgtgtg gtgccaccct    131880 gctgggcct cccaagtttt gaaaggcttt cctcagcacc tgggacccaa cagagaccag     131940
cttctagcag ctaaggaggc cgttcagctg tgacgaaggc ctgaagcaca ggattaggac    132000
tgaagcgatg atgtcccctt ccctacttcc ccttggggct ccctgtgtca gggcacagac    132060
taggtcttgt ggctggtctg gcttgcggcg cgaggatggt tctctctggt catagcccga    132120
agtctcatgg cagtcccaaa ggaggcttac aactcctgca tcacaagaaa aaggaagcca    132180
ctgccagctg gggggatctg cagctcccag aagctccgtg agcctcagcc acccctcaga    132240
ctgggttcct ctccaagctc gccctctgga ggggcagcgc agcctccac caagggccct     132300 gcgaccacag cagggattgg gatgaattgc ctgtcctgga tctgctctag aggcccaagc    132360
tgcctgcctg aggaaggatg acttgacaag tcaggagaca ctgttcccaa agccttgacc    132420
agagcacctc agcccgctga ccttgcacaa actccatctg ctgccatgag aaaagggaag    132480 ccgccttgc aaaacattgc tgcctaaaga aactcagcag cctcaggccc aattctgcca     132540
cttctggttt gggtacagtt aaaggcaacc ctgagggact tggcagtaga atccagggc     132600 ctcccctggg gctggcagct tcgtgtgcag ctagagcttt acctgaaagg aagtctctgg    132660
gcccagaact ctccaccaag agcctccctg ccgttcgctg agtcccagca attctcctaa    132720
gttgaaggga tctgagaagg agaaggaaat gtggggtaga tttggtggtg gttagagata    132780 tgccccctc attactgcca acagtttcgg ctgcatttct tcacgcacct cggttcctct     132840
tcctgaagtt cttgtgccct gctcttcagc accatgggcc ttcttatacg gaaggctctg    132900
ggatctcccc cttgtggggg caggctcttg gggccagcct aagatcatgg tttagggtga    132960
tcagtgctgg cagataaatt gaaaaggcac gctggcttgt gatcttaaat gaggacaatc    133020 ccccagggc tgggcactcc tcccctcccc tcacttctcc cacctgcaga gccagtgtcc     133080
ttgggtgggc tagataggat atactgtatg ccggctcctt caagctgctg actcacttta    133140
tcaatagttc catttaaatt gacttcagtg gtgagactgt atcctgtttg ctattgcttg    133200
ttgtgctatg gggggagggg ggaggaatgt gtaagatagt taacatgggc aaagggagat    133260
cttggggtgc agcacttaaa ctgcctcgta acccttttca tgatttcaac cacatttgct    133320
agagggaggg agcagccacg gagttagagg cccttggggt ttctctttc cactgacagg     133380 cttttcccagg cagctggcta gttcattccc tccccagcca ggtgcaggcg taggaatatg    133440
gacatctggt tgctttggcc tgctgccctc tttcaggggt cctaagccca caatcatgcc    133500
tccctaagac cttggcatcc ttccctctaa gccgttggca cctctgtgcc acctctcaca    133560
ctggctccag acacacagcc tgtgcttttg gagctgagat cactcgcttc accctcctca    133620
tctttgttct ccaagtaaag ccacgaggtc ggggcgaggg cagaggtgat cacctgcgtg    133680
tcccatctac agacctgcgg cttcataaaa cttctgattt ctcttcagct ttgaaaaggg    133740
ttaccctggg cactggccta gagcctcacc tcctaataga cttagcccca tgagtttgcc    133800
atgttgagca ggactatttc tggcacttgc aagtcccatg atttcttcgg taattctgag    133860
ggtgggggga gggacatgaa atcatcttag cttagctttc tgtctgtgaa tgtctatata    133920
```

```
gtgtattgtg tgttttaaca aatgatttac actgactgtt gctgtaaaag tgaatttgga    133980
aataaagtta ttactctgat taaa                                           134004
```

<210> SEQ ID NO 2
<211> LENGTH: 132218
<212> TYPE: DNA
<213> ORGANISM: Macaca fascicularis
<220> FEATURE:
<221> NAME/KEY: misc_feature
<222> LOCATION: (108730)..(108735)
<223> OTHER INFORMATION: n is a, c, g, or t

<400> SEQUENCE: 2

```
cgggaaaggg cagcgccgag aggaaccagc cgggaggcgc cggacagccg agcggcaggg      60
cgctcgcgcg cgcccactgg tggccggagg agaaggctcc cgcggaggcc gggctgcccg     120
ccccctcccc tggggaggct cgcgctcccg ctgctcgcgc ctgcgccgcc tgccggcctc     180
gggaacgcgc cctcttcccc ggcgcgcgcc ctcgcagtca ccgccaccca ccagctccgg     240
caccaacagc agcgccgctg ccaccgccca ccttctgccg ccgccaccac agccaccttc     300
tcctcctccg ctgtcctctc ccgtcctcgc ctctgtcgac tatcaggtaa gcgccgcggc     360
tccgaaatct gcctcgccgt ccgcccctgt gcaccctgc gccgccgccc ctcgccctca     420
gcctccacag actggggctt cgtgcgccgg gcatcggtcg gggcgaccgc agggcccctc     480
cttgcctccc ctgctcgggg gctggggcca gggcggcctg gaaagggacg tgagcaaggg     540
atgcacgcac gcctgagtgc gcgcgtgtgt gtgtgctgga gggtcttcac ccgcttcgcg     600
ctgaccccag gtgaggccg tgccggcagg gtggggcgcg gcgcggtga cttgggggag       660 ggggctgccc ttcactctcg accgcagtct tttgccgcaa tgggcgtgcg tggggggga     720 ggggtccgat aacgaccccc gaaaccgaac ctgaaatccg ctgtccctgc cgctgttcgc     780
catcagccct aaggaagatg tggatcgggt tctagaaaag atgactgact ccctgcacgc     840
ccctcccttt acctcccgag cagtgattcc gacaggcct tcactgcccc tgatttagg      900 cgggggccgg cccctccc ttttcctcct tcagaaaccc gtaggggaca tttgggggct      960
gggaggaatc gaggagatgg ggaggggtcc aggcgctgtc actttagttg ccccttccccc   1020 tgcgcacgcc tggcacagag acgcgagcag cgccgtgcct gagaacagtg cgaggatccc   1080
agtgtgcacg ctcgcaaagg caggggtcac ctggcctggc gatgtggacg gagtcggcgg    1140
ccgccggtcc ccgctcgcgg gcaggcacag cagcagccat gcactgacgg gcgcggggct    1200
gcaggtgcat ctcggggcgg gtttctttct cagcgctccg cgcgcagggt gcccggcgtg    1260
tgcgctccct gccggaggcg cggggctggc gcgcagggct cgcccctcac tgcggcagtg    1320
ggtgtggatc ctggtgggcg aggaggggg aggatagggc gtgcctcctc ccactcccga    1380
ggtgccatct ttttcggcg tgtcacgtct ttacggtgcc atgccaaacc gggtggccgg    1440
gcttcgtagg acagggcggg gcctggcatt aaagggaggg ggacaatcag cgctgaaatc   1500
ttggcgtttt gctgctgcgg gcgtgagcgc tgggggcgtt cacccagcac cttcttcggg   1560
ggctctttgc tttgtctgta gaggttacgt gatctgcgct cccagccctg gtttctggct   1620
tttattctga gggtgtttag ccaacctccc cccaccccca agcacctctt tccttttcg    1680 ttcctcattt ccgagcccat tgttggatct cgaggcttgc tggggtcgac gaacccgagt   1740
caaccccccg accccggca cgcatggaac gggcgtgacc gcgcgcagcc tcgtctcgga     1800
gtctgcgggc gccaggaagc ttctgaaggg atgggattcg agtctccgtg ctgcgctgcg    1860
ggcggcggca gagggatcac gcccctccca acaccccgag tgtcctgagg gccaagccac   1920
```

```
accaggttgc caacgagggg acgctggcta cccattcggg gatgggtggg gagcccggt    1980
ggggcctctc cagctttacg ccctgttgct tcgcctggcg ggagaatgtg aggagggggc    2040
ataaggttac tggtgctgcg gccacaccca tttttctgag cccactggag ggggcacaga    2100
gggggaattg ccatgggaac cacaggcgtc cggagagggg accttgggc tggcccccacc    2160
ccttccctgg ggagattggg gaccctgggg taggcggggc cgcgcccagt tggcctcctg    2220
gaggacacgg gaggaagccc ccaacccctg cacctgagac tctaattggc ctctggcggc    2280
cgcagatagg cagcccttgg gtgtattttt attaatatta tgtctgtact gattaatatt    2340
atttatcgta aatgcgggat ttcacccgta tccaagttca ccgtacccccc aaaaccgagt    2400
ctggggctgc aaggagaact cctggccaag gcatccgagc ctcgccctcc tgtgatgaac    2460
ctggtacgcg ccgttttctg gttaattcta tcgatgaaaa ctggtgcggg ggggcgcact    2520
tctgagacga acgagcatct aggagctgaa tcctccacgc gggctgccca ggttgatctg    2580
aatttccggg gaatggcttg actggggaac tagagcccgc ccgggaccag gctgaccttc    2640
ctcgacggtg gcgtcgaggg ctggagcctg agtgctgcga ggcttcccgc atggctgagc    2700
caccgcgagg ggttgcagag cggctcaggg gtcagttcaa gcatcttctc tcctccctcg    2760
cccccagaca gagctgggcg cgggattccg gttccagatg gagtgagggt ctcgggacgg    2820
ccctggaaaa ggggagccca cggtcaaggc tgcctattgc catctcgagc agagatgtca    2880
cctgctgccg ttggaggaaa gggagcccgg tggggatgag cgcatttagc ccaatgctgg    2940
gaacaaagca caatccgcgc ttctgcgatt tcgctccatt ttgaaatgtg ttggcgcttt    3000
ggttgggcca ctgcggtggg caaggccggg gaaggagggg gctgctgtta atggagaaac    3060
ctcaggggga cggtccttcg tgcaacaatt aggaaactcc atcctgactc tgtgcgcgct    3120
ttaaggaggt ggcttcgctc caggtcctcg agggatgcag ctttggcgcg gatgacggtg    3180
gggtgcttgc ctctggaaat gtctgggcac ggatcccggg gccatcgacg actcctcccc    3240
atccccagca ggcgggagct cttacattcc gagcgactgc tctcaccctc tggcgctcac    3300
acacctgtaa ctccaaacct ccgtctcaga atggtccggg ttggaaggga tgatgggggc    3360
tcggacagcg actgcccagc tcacccctct gcgcgctcag gctccaggct cagcaggacc    3420
aatttgagtt atatctgatc cccctgcccc cgtaactgac ccatcctaca ggagacaggg    3480
aaatgtcttt cctaccgcgg ttgattctag ggtgtcattt tgtgttttgc gatggctgct    3540
tatatttact acataagaat tgtttatttt ccatctccaa atcctccctc tacataaata    3600
aataaatgga taaacagata agtgtgtccc ccgcccccac ccccgctagg caggtctgga    3660
gtgacccttg aagctcatcc attccttggc caagtttgcc tccctaacag atatttatac    3720
agcaataacc cggcttggct cttgggttca ccttttagacg atttggggaa ggggcttgtt    3780
ggctttgctg gttttttggat gagtgacagt ccatgactgt tcctgctgga agggcgtggc    3840
ttttaagtgt tttctaatat caggcactgc tcctctgaga ggaacaaaag aaatggatac    3900
ctgcccataa attgctagaa aacttagaat tggtttgatt gaggaaaggt tagatttatt    3960
ccggttggaa aaagaggcct ttctattaaa ggggcccttt gaccctcatg cccttggagg    4020
tcagtgccag cctggagatg tgataagatt gtggttttcc ttctgccttt ttaacatccg    4080
ttgatacagt ccatttgttg aaaatttaa gaaacgtgtt ttattccact ttccctcagc    4140
atttatgtgt gtggcttcag tggctctgtg gctacatgta caaacacatg ttattttttcc    4200
aattggacat gttataattt tccaactgga ccttgccttc tattgatgta tttatttagc    4260
```

-continued

```
atcttcctta ctccctcctt gaaaaagact cactcaaaaa caagtaaaaa caaccgtagg    4320
ggcctaatac agtgctagac atacaagagg tatccggtcc ataccaaatg gattttatcc    4380
atgaaggata aatggggaaa cacaggttaa gagaaacaga aggtggggct ttatttatgg    4440
tcacggcaga aggaaggtct ggggacaaac tcagttcagt ctatcccagc cctgtgtccc    4500
agtgacgctc agctgcctgt gctcttgggc cacctcctcc cgccccctcc ccctccccac    4560
tgcagcactc ccatagcctg gtccctatgg cccacctccc tcttattggc cagaggtgaa    4620
gatgagagga aggagagag accaccctct accctaggga aggaagaccc tgccctggca    4680
ccttttggta cttggtgcag taggtcggtg ggaagcgggt gggaaaccac atttgactct    4740
gctccttcct ccgccaccac tttcctcatc accgtgttca gagaccccca aagccccttc    4800
acactcccag aaacagcccc ctggtcattc ctaacttgcc atgcccagga gttaggcgct    4860
tccactagtg acagggagct ggcgtttggg gggcacctca gcaggtgacg gggagagaag    4920
cctgcagcct caccagctgg gctgcagcag agagaggagc cctcatgttc cagcagggac    4980
tctcagctgt ttgcctgtaa aaccatgctt ctcacctggg ggccactgag atgtctagag    5040
agatgttttt cttttcacaa cttgaggagg gtgctactga catctcgtag atagaggcca    5100
gggatgctgc tgaacatcct acatggcaca ggacagtctc ctacatcaaa atatgaccca    5160
accccagtgt taccactgct ggggctgaca ctggcattgc taccttaatt acattcattg    5220
attgtcttct aggagccctg ttctaagtgc ttgtctcaga ttatctcatt taatcctcac    5280
aacaattccc ctatgtagca ggtgctgtta ttatctccat gctggggaaa ctgaagcaca    5340
gagagggtta gtaacttgct aaaggtcata gagccagtgg gtggtggagc tgggtgcctg    5400
ccactagctc cctcccctct cagccacacg tgggtttact tggccattgt ggactagtct    5460
gggaacccaa atatgatcta taacattgac ccagtagata ttgattctaa aaccactgtt    5520
tcacaaatga acttttacaa gagtctgtaa ttggagcatg acccagaata agtttaggga    5580
gatgtggagt ttaaagctct caatttctta tctggccccg acacagagag caaggcattt    5640
cactctacct tggtgctctg tttataaaac aaagagcaaa tatctcttcc caaggtcctt    5700
aaacttctac tccctaatgc agggtttctg gactgatctg ccagatgaag gggcagctgg    5760
tttgattgac ccagggaagg ctggaaatca agactggggg atcaagatgt agattcagtg    5820
tggccaagtc aagtctctgt ggtttaggga catcagatgc ccagcttagg ttctgtacct    5880
cggcaaggta aaagcgttgg tgcccactga tgaggccagc tctgagattg tgggtgtggg    5940
ttgagttggg tgggcatagg caagtcctca tgtgtaagaatc ccttggcaaa gataggcccg    6000
ggaggctttt ctcacttcct ggggcccagg ctttgcaata aatattccat tatactatgg    6060
tgccttgggg ctacctgaga atcctctgtc tcgcccctgt tgccttgcca aagaggttgc    6120
tgtccaagaa ttcctttcct gtctccagat gccatgctcc tgccacctct gccaggttcc    6180
ctgcctgccc agatggctcc cacctgagta tgaggaggag tttgaggctg gcccaggaca    6240
ggttttgagc tttctgggtt ctccggttag gaagctttct gtaagcatgc agatacaatg    6300
ggcatcagca aaatacaaac tggaacaatt ccaggtata ttcccttaat tttctttgct    6360
tttttcatat ttcatcaggc tccatgctga gcccaatcag ggacctgata aaaatccaaa    6420
caccatgtca gcgagtcccc aagaaatgca ttttgtgcca aggctattca aggaagtttt    6480
gggagcagct caagggcaga cactgttacc cttcccccag gtcccagtg cagggcagtg    6540 tcctgcatgt ggaggcagtt tggcctaatg gttaaggagg caggctctga ttgggcctcc    6600
tggacataag tcccagctcc ctgctcactg tgggacctaa gccatgttgt ttagctgttt    6660
```

```
ggagagtttt ttgtcatcca taacttggag tatgatggtg cctgtctcac gggttgccat    6720
ggggttcaaa caagctaacc tggtactcac cagggcccta cacatagtaa ctgctcagta    6780
aattgcatca ttggcagtgt cctatggata agtgcttgtg attggctgaa tgagcagagg    6840
ggtctaaaga ccctggtgat ggaatcagtt gtacagataa attgttacac tgagtaggga    6900
tcaagttagg aaaagtgggt aactgcccag ctcccctgca gccaaacttt gggcagacgt    6960
ggaccctctg aaaattgcac acacccatgt tttttttttgt ttttttgttt ttttttttt     7020 ttgagacaga gtctcgctct gtcgcccagg ctggagtgca gtggccggat ctcagctcac    7080
tgcaagctcc gcctcccggg tttacgccat tctcctgcct cagcctcctg agtagctggg    7140
actacaggcg cccgccacct cgcccggcta gttttttgta ttttagtag agacggggtt     7200 tcaccgtgtt agccaggatg gtctcgatct cctgacctcg tgatccgccc atctcggcct    7260
cccaaagtgc tgggattaca ggcttgagcc accgcgcccg gcctcacaca cccatgttta    7320
aatgtacaca cagaactctt gccacaggca agcagagatt tgtcatctgc tgtccctgct    7380
tcatattctt cctgaaatcc actccatgcc aggaataaac tgcatgctct ccaccagccc    7440
aaaccgacct gccctcccctc cagtcatccc gggaagggtg acctggctta gtacattggg    7500
ttcagagatc tttccagttt acttgttgaa taaaagtga gggctgatta agaaagtaat     7560
ggcagtcagg gaaggcgaag gaggtgaaga agagatttta caatgaagt aattcaacgg     7620 agtgctgacg ttggtaaact ggtgaacagg tttcagggtg gtcggttgag agtagagtag    7680
aaaagggtta aataaagcaa acttgtggtg tactgaatct taggaattcc atgtatccaa    7740
taagtatagt catttatgaa ttaataaatt aggcctaaga agccttctta tcccttaaat    7800
caagactgag taacaatata tcagttttaa aaagtcatta catcagaaaa taatgtaaat    7860
gatacacata gattttcaag attttacttt aactgaaact atataaatgt aaattcattc    7920
acccatcttt tcacacaggg cccaggtctt ctcttggtgt ctgatcagcc agttgaaatt    7980
tcgtgtctct cttgcctgtg ccatattaat aatgcactgt ctgggtcttc cgatttcagt    8040
ttggattttg gatttatatt gtggagtcat ctgaatgcag aatccctcag ggatttact     8100 tttttctttt tttgcatggt cttaccatc ctgtttgata gtaaatatta ctcacctttg     8160
tgaagtcttt ctaaaacatt caacttaatt ttcttaaaat cattgaatga tttgaagagc    8220
ttatccttcc ctctgcactt gtattccctc agcttgcacc ttattttatt atttattat     8280 ttatttattt attgagacag agtctcgctg tgtcgcccag gctcgagtgc agtggtgcga    8340
tctcggctca ctgcaacctc cacctcctgg gttcaagcaa ttctgcctca gcctccccag    8400
tagccgggac tacaagtaca caccataatg ctcgtttgat ttttgtattt ttgtagagat    8460
ggggttatgc catgttgtcc aggctggtcc tgaacttctg acccaggtga tccacccacc    8520
tcggcctccc aaagtgctgg gattacaggc gggagccacc atgcctggcc agcttgcacc    8580
ttagttaggg tatgtgatta ttatagcaag tctggtgtac gtagaagatt ttgaatgggc    8640
acagatgacc tttaggaagt gctgggctgt ggtaagaggc agtcctaact gcagatcagg    8700
ctgtgaggac cccagccttg catgttgaca gaccttcatg tcttattcgt acagggtatc    8760
agaagaacac ctactgggga aacttttaaa taagtaaaag gtgggcgtcc tccccgcctg    8820
tcttccgtct gtctgccagg actagcacag cactttgaag tcattcacat ggaatcccaa    8880
cttaagaggg cactacaaaa tcctctccat cagactgaaa ataagtttaa attccctttc    8940
ttatattaac tcccctgagg aaagagtctt agatcaatgt ccaatactaa aaacagtttt    9000
```

```
aaatcagcga gtgagaatta aatctgaaac cattgataat aacgtttcat tcattcctct    9060
cctttggcct catccaccct actgctaaat ccaggcatca aagagaagag ggacataatt    9120
atctctggtc ccagctgctg gttttccttc cagcctatgg cccagttttc cgttttactg    9180
agaaggctgg tgatgttggc ttgggatcta catctgcagt tgtaccacaa aaagtccagg    9240
gatgcacttg catccttgta tccgcctccc tgggatagca aggatattag aagaccectg    9300
gatccataat tgcttgtcac gttatctgca gacgccacag aatgccaaga acaaagtgct    9360
gggaaggacc aattcatgga accatgggac ggtgctcgtc ccccagcgta aaggacagct    9420
cctcctcctg aattgcagcc agcattctaa atcgtgtgtc aacagagttg tcctggatcg    9480
gatccagttc tcccattgat ttgcaggtca cttcaggggt gcctgttcca gttgttctta    9540
actgaatgct ggcagcaaac tgttgtctta cctcatccct ctaccacggc ctattcctcc    9600
aaaagagact tcttgggtaa tcacggcaac atcaggcagc cgggcgcggt ggctcacgcc    9660
tgtaatccca gcgctttggg aggcggaggc gggcggatca caaggttagg agattgagac    9720
catcctggtt aacacggtga aaccctgtct ctactaaaaa tacaaaaaat tagccaagcg    9780
tggtggcagg tgcctgtagt ctcagctact caggaggctg aggcgggaga atggcttgaa    9840
cccgggaggc ggagcttgca gtgagccgag attgtgccac tgtactctat cctgggtgac    9900
agagcaagat tcatctcaa aaagattctc tttggtttta tatgtatata agtgaggcca    9960
ggctcggtag ctcacacttg taatcccagc attgtgggag gatcgcttga agccaggagt   10020
ctgagactag cctgggcaac aaagcaagac cctgtcttta caaagaaaaa ctaaaaatta   10080
gctgggcgtg atggcatgct tctgtagccc tgtctacttg ggaggctgaa gcaggaggat   10140
cacttgagcc cgaagttcaa ggctacagtg aactatgatt gtcccactgc actccagcct   10200
gggtaacaca gcaaggtcct gtctctaaac atttttttaa aattctattt atatttacat   10260
gtatttaaat gtgaatattc actacctatt tgttgcatgc ctggattttt tatattgggc   10320
ttgctgaaaa cctgaacagc tttctacttg acaatgcatc agaatttaaa tcagcgtgtt   10380
aataagccaa gcaaaggtta tataggcaaa taaaactgtt gtctgtaacc tcctgtaaca   10440
ttggagcaca gcaaaaatca tggtatagac acatatgaac ctgtcccttt catagctgct   10500
cactgccagg aaacatcagg aatagccgtt tggaagagtc accggccctc ccaccatccg   10560
ttttctgtct tgtcttttcc ctatgagcag gggaaattcc ccactggccc caatccccgg   10620
tgcagcggct cagcctctgc ctctgccgcc gctttccatg aggccagctt agaaacagag   10680
gattttgcag aacatcccta aatccgcttg aataaaggag tgatcattca taaactcacc   10740
tgaaccttct taaaacctat ttaatatttt tcccggataa tcctatcgag ataacttgcc   10800
tcctgggctt ctctccacca ggttcagttc ttcctttagt ggtgaagttc ctcccttctt   10860
agcatctcag ctgtgcctga gaaaaggcca gcggtagctg cactctgttc cctgtggagt   10920
gttaataaag actgaataaa ttgaaataaa tcccttcaa tgtcactaaa gtgctataaa    10980
taatcatgaa ccaatgtttg atggcggatg agaaatgcaa gaaaaaattt ttaatcagta   11040
ggattcatgt tataagttga cagtctgggc caggttaaaa aaataaaaat aaaaagactt   11100
taagaaagat cttatcattt gttaccagca agactgaatt ccagaagcga gccacaccct   11160
cattttgtgg gcccctgtta tcactggctg cttaggggttg ccaagccctg aattcatttg   11220
tcaactaaga ggttttttggc caagattaag gtttcccatg cctccatatt tccatctgag   11280
aaatggagat tatgctgtct tcccctcag aatggatgat aatgtggtct ctcttctctt    11340
ctcatagtca tagaactgaa ataaaacaac ttaagagaat tcctttgagc ttctcaaaag   11400
```

```
tgctgcagga ctaggggatg cctcccggga gccgcagtcg ggtgctgatc tgaagtcttt    11460
ggtgggctga ctttagcctg acctgaaata gtatagctgc tgccacctgg ctcccttagt    11520
gccaaactgt gcagctggtt cctaggggtg agggctgagc cagcaaggtc tgtgcccagg    11580
agggatgcat gggtggccac agaacagcct gcactgatct tgtctgtccc ctgctttaga    11640
aggaaggaga cccaaaccag gatgcaagac agtgggtggc ggtgccttga gcatgacctc    11700
aagtgatttc cagcccctgc cagtgctgac ttctctgggg aagggctggg acttccttct    11760
gagctcaagt catgacccct acatagaatt cctgggagc ttttccattt ttctggagtt    11820
ttcagtttct tcctaaccag acagggactt ggtacagaat ctcatattct aattatgccc    11880
aggagcaacc tctccccacc acttacagcg tttagcatgt gacaggaatt gattaaggca    11940
tgagtgatta aattaaagcc aggcattgac ttggatggtg taatattctg atgactgttt    12000
ggtggcaaag gcacggggca gactcattaa ttgaactgct tgcacctgga atttgaattg    12060
agccagagcg gggctgaagt cagtttgcct tcaccctgtg aatggagggt ttctccggag    12120
cgtggatggt gggaggtatt tcaggatgta tgcgtaaccc ccaccctggc aatggcacat    12180
cttttctcca gcgtggccag gtttgagtgc cagtcctggg tgtccatagc cttgcgtttt    12240
agtaaaatgc tgcccccatt accacctggt ctgtccactt cggtcactgg aatttgccgt    12300
cttccagtcc ccagtgtggc aagccatgga gactcaagct cttcccctc cacatcctgg    12360 aacagacccg ccagtttctt ccaggcattg cctcagtttg ccctctctt tccagtcaca    12420 ctctcaccag cgataacatg atttaggcc ttatcacctc accctcggat ccttatggaa    12480
acaatgagtt gttccctgtt tcagttccaa aattcatatc caatccgttt tgcgtgccat    12540
tgccaaattc ttcccagagc aaccccgtca cctgccctgg ccctctccac gtgtggtcct    12600
gccatgagca tcacctgcta agccaagctg gcctcgagct gcctgcctgg gtccccacac    12660
cttggttcac ctcctgccc agtcccacct cccgcttcct gccagcctgc cctgtggctc    12720
cttcatagac gccgtgctct ttctgcccct tgctcaccca tggcagcttt gccctctct    12780 ccctgcccta ccccatatgt aaatcgccct gaccttcctc agtgtccatc ctccctgaag    12840
cttttcccag ccttgacact caaggtccag aggctgcgcg tttcctctta cctgtggcag    12900
agccgcgctc ctcagtgctc acagttcccc tcttgccccc gcttcctgtg taggactcat    12960
ctgcccacag gttgcacgtc ttatgaaggc aaggactgtg tcttacgtga ctttccttct    13020
ccagtcacag agctgggcac atatatagct caaaaccctc ttgattaaca caggtggatg    13080
ctgagaaatc aaacaggcga tgtcaaatga gctctcctta tttaaatcaa gtcagttctc    13140
cacctcctag ttactcagtt ccagtactgt atatacttgg aaataataaa aaccacattt    13200
cctttaaaac attctataat tgttccttg cccatacttca gactgactta acacactccc    13260
cattggtcca aatgagtttt gccatacgaa gatgctgata ataatagcag cagtggatta    13320
ttctactaaa accattgcct cgttaatcct cagtcccaac gaggtgggga ttattatcct    13380
cattttgcag agaagcaaac tgaggctcag agatttcaca gctggggagg gagccagatc    13440
atgcttctgt ccaggcccaa gctctccccc gcttgccttc ctgcctctgc aacctcagag    13500 catccccat ctggttccac tggctatgct agttgtgcgg gaaccaaaag ccccgtctct    13560
agtgctgagg actggagaag ccatggcctc caggctctgt gaatgggtca catgtaacct    13620
gagcctggag aaattgtttg aaactgaagg caagcctcta aaccaggctg ctgcttcatg    13680
gcgccggtga cggcagaacc aaatttagtg ctgtgggcag gtccacactt atcagaaaga    13740
```

```
gaagctcatt tttcttctgg ctcacatcaa gcatgaaaaa tgttcacaca cacaccccaa    13800
acacatacac actccggagg ggtccatgtg gctagaggct ggaagatgtg gatgagagga    13860
gcctggcggg taagcccagg gaagatgaca ttcagcttcc cagacagtgt ctacagggag    13920
aaatttaatt aaaagtgggg cgggttccct gagcaaggca gacaaagtca gccctctacg    13980
gttaagaaaa agggtcacag tgagaggaaa ggtgaagaga ctgagtctgt attttccagt    14040
ctgttgggcg acacgcctga tccccttcc tcaaaaatcc actttacttt ccccatgtct      14100
acaccagtgt ggttcacact ctgggacaag gaaaagggg agtgatgggg aacagagaag     14160
ggaggagctc acacagctga ggctgggtt atgcatatcg aattacttag aatttgcaac     14220
ctcacagggt acttttatgg cattgaaata cacttcccac agccaccctc cctctaacta    14280
aaagcaagag tcatttctca gttctggtct tgccgcccac cttctcctcc acattttaaa    14340
aaatccaccg gctgcaaagt gaagacacca tatgtgagat cccaccctag tttctgtttt    14400
atcagggttt ggagcaggtg gagcaggcag agggatcatt tcagcctgta cattgtatta    14460
agtattaagc gtgagtgctg agtcattctt caagaaaagt tttatgaagc acccaaaact    14520
gaagggtgga gccacctgga gacagtagcc tcagtcctgg ccctgagcac agcctgcata    14580
ggcccctctg gatcccggcg ggagctgcag agtgtgggca ccttggcaca cagccctgag    14640
tgcaaaatta ggagctgggc agagggcatc tctgtcgcca ttgggaagcc cagggcacac    14700
tggtcatagc cgtagaccac gagcacccta cacccggggg acagatgcaa ccagtgtgcc    14760
ctgggctgcc caatggcaac agagagattg acacctggat cccgtgtcac agggactcca    14820
ctaccaagac tcccgagact gccaccttcc agtgggataa gccctgcctc ctactgggcc    14880
cacaatgtac agagaacact tgggacgacc tggctttctg gatacacaaa tattgatcca    14940
atctgggcta attagaaggt cagtcccagt aaaaaatcaa agtcagctgg gtgtgaggct    15000
cactcctgta atcccagcac tttgaaaggg caaggcaggc agatcatttg aagccagaag    15060
ttcaagacca gcctgggcaa catagcaaaa ccctgtctct actaaaaata caaataatta    15120
ggctgggtgt ggtggctcat gcctataatc ccaacacttt gggaggccga ggcaggtaga    15180
cacctgaggt caggagtttg agaccagcct ggccaacaca gcaaaacccc gtctgtacta    15240
aaaacacaaa aattagccaa gcgtgatggc atgcacctgt aatcctggct accggggagg    15300
ctgagacagg agagaatcat ttgaatccag gaggcagagt tgcagtgagc tgagattgga    15360
ccattacact ccagcctggg tgatacagca agactctgtc tcaaaaaaa aaaaaaaaa     15420 aaaaaaaaa aagctggacc tggtggtgca ctacctgtaa tcccagctat ttggaggctg     15480
aggctcaaga atcacttgaa cccgggaggc agtggttgca gtgagccgag tccagcctgg    15540
gtgacagagt gagtgagact ccatttcaaa aaaataataa atctgagtca ctttaatatt    15600
cttatttgga tgtcaacctc taggtgtttg agacagggga gtgacatggg ggcacggtgt    15660
aacctcacac ttgggaagcc cacatgatgc gatatcaggg tgctgggagg tccccccact    15720
ccctaaatta ctaacaagtg gatagtactt tgcagtttat atgatcttat ttgattcttg    15780
acatgagcct gtgagtgaaa aattccttcc cctcttctac agattaggac attgagattc    15840
agggagcttc agcgggattc aggaagtcaa gtggcacctg gagtcccgcg gctaatttga    15900
ggctggtagg agagtcgaac ccaggacttg tgcttctcac gcctgggttt ctgcttccta    15960
gtgcatggtc ttcccctag ctttcccatt cactgcttta gcctagggct cttacccttt     16020
attaaactgc cagtgcctcc ctgctttct tgcccaaaga caaaaagtg ttttgtttc       16080 tgttttgttt ttcatagggc agagacctgg aatttcagct tgagaactta taccatatga    16140
```

```
taaataaatc atcaacagat ggcttttcc ttaaaaaaa aaaaaaaaaa aactctaaga    16200
tgtatatgca gggaggcata atttgtgcca aaaagtgctc accacactgt agtcatgggg    16260
gcaggaggca gccgcaggtg aagggagaaa tctcagagtc caagcagccc ccttctgggc    16320
tgaactgggg agctggggc actgccagcc ctgccaggtt ctcctaggag gcggcagttc    16380
atatggccgt gggaggaggc agggagcc tcatgtgtac ccacatttcc agggatccag    16440
aagacagaag gaggaaaact accatcatgt taaagcagac agttaggtaa cacatcctgt    16500
aatacaagtt attttttcca catctaaagg ctaaaaatag ttgctagaat ttaaagataa    16560
ttggtaaatg agtttctatc cttctagttt cacatcaaat ggaatcacgc tgccttcaca    16620
ttactagtgc ccgttatttg tgtttaattt ccacaatgtt gtctaattcc actctttggg    16680
cttccccagg gatccagact ccctcactcg cccgtcgcgg ggaaatgctt tatttatctt    16740
tgtgtcctct gagctgggca tagcacatgg cactgaataa gcactcagta attgattcgt    16800
gaatgaataa atggatgagt gggtgagttc aatatcgact acaaaccccc taaggccaca    16860
tgctagtgag tggctgcgcc tgtagtccca gctgctcggg aatctgaggc aggaggatct    16920
cttgagccca ggagtttgaa accagcctgg gcgatatagc gagaacctat ctcaaatgac    16980
aaaaacaggg ccaggtgcaa tggcttacgc ctggaatccc agcgctttag gagaccgaga    17040
tgggaggatc acttgaggcc aggagttcaa gaccagcctg gcaacatag ggagaccctg    17100 tcactacaat ttttttttt tttttaatt agctgggcat ggcggcgtgc acttgtagtt    17160
ccagatactc gggaagctga ggcaggcaga tcacttgagc ccaggaaatt aaggctgcag    17220
cgagccatga tggcaccact gcactgcagc ctgggcgtca gaatgagacc tgttctcaaa    17280
aaacaaacaa acaacaacaa aaaagtacag ccttctcttaa agagacttga gaacagaaag    17340
gggaacagat gcataactta tatatttatt tgttcatctt tccaccttcc tggaaggtag    17400
aggggaaccg gtctgcatt ggagttttga gtgctaaaag tgggaatcat gcactgtttg    17460
ccatgatctg ttcaaaagtt aagccaaatg ccttagattc tcctgaaaac tggaatgcca    17520
ctgtaagcta tgagccccac ttcaaagata aaagatcttg atgaacaggg ttgggtctgt    17580
ggactgggcc tctccctgcc aaacaaggaa gggtggtgac cagttgaagg caaatcactt    17640
aaatccttac cgtctcctaa taggtgtggt cccaggtagg gctgtcagaa ttagcaaatt    17700
aaaacatagg gcatctatgt aaattagaat ttcagataac aacaaataat tggcataggc    17760
tgcataatgt cccccaaaga tatcaggtcc taatctccag aacctgtaaa tgtgatctga    17820
tttggaaaag gggtctttgc agatgtggtt aaattaagga ttttgagatg ggggaattat    17880
cctgtattat ctaggcaggt cctaaatgca gtcacactca tccttgtaag aggaaggaag    17940
agggagatgg aaaacacaga agagaagacg atgtggtgat agaggcagag attggagtga    18000
tgtggccaca agccaaggac tgctggcagc caccagcagc cagaaaaggc caggaaccaa    18060
ttttctcttg gacctccaga gggagtgtgg ccctgctgac accttaactt caacctagtg    18120
atccttattt tggactttgg ccttcagaag tgtgagggaa tgaatatctg ttgttttaag    18180
acaccaagtt tatggtcctt tcctacagca gccacaggaa acaaaaacaa taagtatgcc    18240
ccatgcaatg tttgggacac acaccaaaaa tattgcttgt tgttcacctg aaattcaaat    18300
ttaactgggc atcctgtatt ttatttggcc aacctagtcc ccaggcccaa agaaagaggc    18360
ttttgaaatt tgcaagaaag ctggttggag ctgtcagaaa gtggactttg taaacacagt    18420
accactgaac caatttgaac cttactacct ctaggcaaaa gagagggcag tcagacagtt    18480
```

```
tttcgtgatt tattctttca acagtcattt gagtgcttac tacaaaacag aagctatgtg    18540
taagggtgga ggtgttagct gttaatcagg acctccaggc taagttactg tattagtcca    18600
ttttcatgct gctgataaag acatacccga gactgggcaa tttacagaag aaagaggttt    18660
aattggactt acagttccat gtgactgggg aagcctcaca tggtagaagg caaggaggag    18720
caagtcacat cttacatgga tggcagcagg caaagagaga gagagcgcac gcttgtgcag    18780
gagaactcct cttttttaaac ccatcagatc tcgttagact tattcactat caagataaca    18840
gcacagaaaa gacctgcccc catgattcag ttacctccca ctgggtccct cccacaacac    18900
gtgggaattc aaggtgagat tgttaccat gtcagttacc aactgttcca gataaatcac    18960
gtgaaatagc accattaaca gagtgagctc aggtggttct tcagtgcatt tctgatacct    19020
gagccttccc tgggaatttc acagcccatc aggctccccc tacttcgatg gcaggatggc    19080
agggcccagg ttaggcagga ggagatgtta tcacaggcct gaaaggcagg gaggggcaga    19140
tgctacagga aggtgctggc tctggattcc ctggcggagc tttcaaggga agtagatgca    19200
cactgtctcc atcatttcat gtccataaca ctctaaaatg ctttggacaa ggagcaaaag    19260
ttaaagacaa atgtggccca ttttcctgta caaagagggc tgcccccatg ccaggctgtt    19320
ggcatcagtg gcatgaggc ttttctgctg ccatagtggg ggggttctct cactcaccat    19380
tggctctctg acacctggag agaccccac ccttgggctt ttgtgatgct cacggaatcc    19440
acactgttgg agctttaagg cacctgggtc aactggaaca ggcagggat actaggacag    19500 cccagcattg ccccaaaata tccgggcctg ataaagaga aaacaggta gctcacagga    19560 aacgataaa aaaggaaga gggatttaac atgaaaggt gcttgatctc tctcataata    19620
aaaagactgc tgattccatc caggcaagtg acagaaaaaa aaaattttag tttaaaaga    19680 ttgctgataa aaccacagca agatgctgct gctcagggat ctgagggtgt gggcagccag    19740
gctgccacac atcatgagtg ggagaggaag accacacccc tggaacaaag ggcagctatc    19800
tgtcagatgt cctttgacag caccgcagct tccaagaatt aacccttcc atgtgagcag    19860 aggcatccat gcgggggaca cactggtgaa tcatctgtta tgcagaagtc tggaaaacat    19920
cagggtggaa ccggcgaaat aagtgtggcc tctgaaggaa tggagcggtc cctctgtgct    19980
gcttcgggtg ccctgagat cctgcgggcc agtgagaaag cagtgaggaa caaggcggat    20040
actgtgcact gtcctctgcg tgcaaggaag gctagtgcat gcgacggagt ccacacagac    20100
acagcctaac tctggaagga agaacaagaa tccagtttca gtggtggcct ctggcgggga    20160
gaaactgggt ggaggaagat gtcatttcca ttttctact attaattttt tattaccatg    20220
cttaaatatt acttttacc tttttttttt ttttttttga gacagggtat ctttctgttg    20280
cccaggcagg aatgcagtgg tgcagcctca acttcctagg ctcaagcaat cctcccacct    20340
cagcctcttg agtagctgag actacaggca cgcatgccac cacacccagc tatttttttt    20400
tttatcgaga tggaggcttt ctgtgttgcc cagggtggtc tcaaactcct ggactcaagc    20460
agtcctcctg cctcggcctc ccaaaggact gggattacaa cgtgagtcat cctgaccagc    20520
caattacttt tttaaaaaga ttaaatgcat gtatatgctc aggcatcagc acacttggaa    20580
aggacgagaa tatctggaag aagggttctt ttaaaggct cctcaagtga cgctggcagg    20640
cataacgaat gtccctggtc acaaaagctc tgatctggcc taaccctctc atattagaga    20700
ctggaaagag tgtgtgtgtg tgtggtgtgt gcaaagtgtg gaggatgggg gtgagtgtgt    20760
gtggtgtgta agcatgaatg tgtatgtgtg tggtgggggg gtgtgctgtg tgagcatgta    20820
tgtgagtctg tgtgtgtgta gtgtgtgtga gctatatggt gtgtatgtgt gatgtgtgtg    20880
```

```
aggtgtgtgt ggtgtgtgtg tatggtgtgt gtgtgatgtg tgtggtgtgt gagcatgtgt   20940
gaatgtgtga ttgtgtatgt ttgagaatat gtggtgtggt gtgatatgtg tgtgtggtgt   21000
gtgagcgtgt gtgtgtgatg tgtctgtatg tggtgtgtgt gagcgtgtgt gttgtgtgtg   21060
tgtggtgggt gtgtgcagta tgtgagtgtg tgtgtgcaat gtgtctgtga acatgtgtgt   21120
gcagtgtgtc tgtgagcatg tgtgagtgag tgtgtgagtg agtatgtata cagcatatat   21180
aaggcatgaa actgaacaca gcacctttag agtgctctcc tggagtcaga gggggtgggc   21240
aggaggagaa gggaggtggg ctagtgtgct gaagtgtcta ctccttgtca tggtttgtga   21300
caacccagat tagcccatga gccaccctgg tccctgcatt tccaatgaga cctcggtggt   21360
catgttctct gaggtgaggc tgactggtgt catttgatga tcttgatacc aaatcctttt   21420
gtatcaaaaa caaccggaac actctgtttt ctcttagtgc tttcacccag atgaccacat   21480
ttcatcctcc cagccactcc gggccaggtg gcactgctgg tttgaaaggg aagcctcccc   21540
tggagtaact tccgtgggcg gattcacacc ctacccacac tcctgtccca gtcggccac    21600 catggtggtc tctggttcct ccagaattcc cacttttcag ctcatcccca cattcccgga   21660
gggactgaga gcacagcccc caaggccctg ctctttgggg gcagtctcca cacccagaga   21720
agcagcaagg cattcctagg tttctctttc agatgcagaa cttcagtgct cagaggtgtt   21780
cccaccagtc ctcagagggc tcagttctgc tttaatgatc gtgctgttgc gtgggctcag   21840
cagagggcgg gtggcccagt gtggctgagt gcagttttcc tgacatggag tccgagcctg   21900
ccccgctgtt tattaattca ggatcactct ccttgcagaa ccctgaactc cccagaactg   21960
tgaggtggga gaaccccgag aggccacctg gccctgcttc ccacctactg cccacacccc   22020
ctctctgcct tcctgacagt caccccaact cccagtgatc cccatcaatc atctgacaag   22080
gggactgaga gggaagagaa aggaggggcc caaagagaaa ggtaaaagtg ttgggagcag   22140
cccccaaatg tgtgacatcc ttcagcagag ttgcccactt tccctttct cctccctgca    22200 ggacctccct tctcctcagt cctgcccaac ttctgaggtt acattgagaa aagtccgcag   22260
aggtgccagc atcacaaggt gttaaggacc acgagtttgg cattttaaca gatgccagag   22320
ccacttgaga aatgtggtaa ctaagcccag agaggtacag ttacctcccc agagtcacac   22380
agcaggttca tggcaaagca aaggtgtcct tccccctgca gatccctttc tgtgccccac   22440
atcatcttcc tccagtgtgt gggccacctg agacaggct ctcacactca cctggccaga    22500
ggtgccatct tgtgggaaag gcttggccag gaagcatcga tatttgagat cccaaaaaat   22560
gaaggcttgg cctgtcagat gacagacttc ggtcatgggg acgcatgatc tgttttacac   22620
acacgtcccc tcagcagcag ccttccagaa cattcccact ttcttctgta atgagaagaa   22680
ctctttccct gcagcctcct gcccatctcc tcctgggaga gccttgcttc agtgtctttg   22740
ataaatcatt ctgttttgca gagtgcgagc tctgcctcgg agggttcgca tccacctgtg   22800
ttgagtaacc aatacgaagg tcgagtggtc accctcata agagctaggg ttgtctcatg     22860
cctggggact aggacttgcc ctcaaggaaa aaaaaaaatc aaaacaaaag caaaacaac    22920 aaacatgcct ctctcaaaga aagtctgag tccaggtaaa tttccttcca ctgaagcagc     22980
caggctgaat ttgaattctc tttgcctctg cttaaaaact aatgcaaatt ttcctagaga   23040
atgcccacta attcctggag ggggcacggg cattcctgat gcccatgaga ggaccatttg   23100
ctcttccctc agtgtgctaa ataacagaag cgacatttgt tgctggaaag tatcagtgag   23160
gttaataagg tgtctcctgc ccagggtgag ggagcagttc ccaatgacaa atgctgtgtg   23220
```

-continued

```
ggaagggggcc ataaaactgc cagcccttt cgtccaccca taatgtggtg aaccctgtgg   23280
atcctggagg atttcagcat cttttttat ttttatttt attttttaga cggagtctcg    23340
ctctgttgcc caggctggag tgcagtggct ggatctcagc tcattgcaag ctccgcctcc   23400
cgggttcacg ccattctcct gcctcagcct cccgagtagc tgggactaca ggcacccgcc   23460
acctcgcccg gctagttttt tgtattttt agtagagatg gggtttcacc gtgttagcta   23520
ggatggtctt gatctcctga cctcgtgatc cgcccgtctt ggcctcccaa agtgctgggt   23580
ctcggcctcc caaagtgctg ggattacagg cttgagccac cgtgcccggc ctttttttct   23640
ttttcttttt tgagaaggag tctctctgtt gcccagactt gctctgttgc caggctggag   23700
ggcggaagtg cagtggcacg atctcggttc actgcaaccc ccgcctcctg ggttcaagcg   23760
attctcatgt ctcagcctcc cgagtagcta agattacagg tgcgcaccac catgcctgac   23820
taatttttgt attattagta gagggggtgtt tcattatgtt ggccaggctg gtctcaaact   23880
cctgacctca ggtgatccac ccagctcagc ctcccaaagt gatggaatta caggtatgaa   23940
ccaccacacc cagccagcat ctttcatttt tctgtccact ttggcccttt cctctctcac   24000
tgtcttcctt ttccatttcc aaagtcagtc catctcacta ttagcacaaa aactgctaga   24060
gcgctcgtca ttggtcatct ctccctgcac ctggctggtc tgttcttagg cactgaagtg   24120
tttcccccag ctgttgcttt aatcattttg ttatcatgcc ttacttaaga aatgaacatg   24180
agatgcattt atgtgtctct ttctgccact ctgcagagcc agtaagatgt ggtggaaagg   24240
gcccaggctt tggaggaggg ctggctgggg ttggatcttg gctgctccct actagctgtg   24300
tgaccttggg taagtagctg gacctctctg agcctggttc ggaatcatag cacctctctt   24360
tcagggctgc tgtaaggaat agcagcgatt tgtgtaaagc agagagcaca gctagcacct   24420
ggcccctagc cacactacag agcacttact gtgataagct gccattgtgg tgtgtgaagc   24480
aaaaggggaaa tgcctgctgt agtaagcttc ctgtagggca gttcgtagaa ccagagatgg   24540
gtttcaaggt tacaaaggga ctcttagtgt attagtccat tctcacatta ctataaagac   24600
ctacctgaga ctggatcatt tataaagaaa agaggtttaa ttggctcaca ctggctgggc   24660
acggtggctt acgcctgtaa tcccaacatt tgggagacc aaggccggcg gatctcttga   24720
gatcaggaat ttgagaccag cctggccaac atggtgaaac tctgtctctt ctaaaataaa   24780
atacaaaaat tatctgggca tggtggtgtg tgcctggaat cccagctact gggaggctg    24840
aggtgggaga actgcttgag cccaggaggc ggaagttgca atgagccaag atcgccccac   24900
tgcactccag cctgggcagc cgactgagac tccgtctcga aaaaagaaa agtaaaagaa   24960
ctgcaagaaa taaattgttg tttgtgagcc atatggtctg tggtacctcg ttgtggtact   25020
gggagtcttt tgtctccctg accctgcctg ttgctgcagc accgctcagc cctgcctgct   25080
ccctaccttc ctccccttgg cctctcctgc ctccactggg ccctggtgc ctcctctaga   25140
gacagtcctc ctgggaccag ttgtgttctc atttacacga ggcatccagg actacagaga   25200
accagaggaa ggggcgcccg cccgcccctcc tccctggcat cctcacgctg cagaggtcag   25260
agcctcatcc cggccccctta cctgccccta ccctgcagag aactgtggtc agttcctgag   25320
gccagatcca tgaacggcct tgtggaagat ggtgagctca cacccagagc tggctccgat   25380
gacccttct cctttacatg tttctacctt cccctcgtta ccttccccca ctgccaggca   25440
cagagtggag gcaggttggg tttaaagctc agaagggctt aaaggggtg gggcgcagtg   25500
gctcatgcct gtaatcccag cacttgggga ggccaaggca gaggatcact tgagcccagc   25560
agttcgagac cagcctgggc aacatagtga gaccgcgtct ctacaaaaaa taaaataaat   25620
```

```
aaaattagct tggcatggtg gcatgcacct gcagtccctg ctactcagaa ggctgaggtg   25680
ggaggatcac ttgtgcccag gagtttgagg ctgcagtggg ctgtgctggc accacagcac   25740
tccagcctga gtaacagaat gagatcctgt ctcaaaacaa acaaacaaaa aaagaaggct   25800 taaagggggac tccaggtggg cctggcagca caaagctatg aaggtctgtc ttagacacaa   25860
gctctgttac taggccttttg cacgctggcc tgggtacctg gctgccatag acagggaacc   25920
ttccagatga gctgtaggcg tggagcacag gagccagggt gctcttcctg ggctgtgtcc   25980
acaggcagta tgtacaccgg ctttgtacac gtccagcggg tccagtgcat attttttgttt   26040 gtgttttttct tttgtttcgg ggggtggatt tggttttccc ctgagtcctc tgtcctcctg   26100
tcacctggct ggtgctcggc aatgttgacc agctgcctgg ctggagttgg cagtggctga   26160
ggctgtgagc taacatgttc ctgagtcctc ccatttcttc accataatgc cctgttgagt   26220
ttgcagatac tgtctctgtt tttatctccc agggaaactg aggttcagag tggctaggcc   26280
accttcccac agtccctcag ctcatgaggg ccacacaggg cattgaggtg gcctcctcct   26340
cagccttgac tctctggccc catctttgct gcctcaaggg gtctcctctc ctgaactgtg   26400
caccttctgc ctggcagctc caactctatg gctgttttca gtggctcagc actgcccctt   26460
gaccttccct ggccctctgc agatgccagg ctggagcact ctggcaaggt ctggggtggt   26520
tacatgggtc ctgtcacttc tatacacctc ccagtgcctg ggaatcctgc agatacgccc   26580
tccttagcca tccctaacac atagaggaca tttctgaggt ccctgagaga gtggggcacc   26640
tctgcaggat ccaactgccg ggcccaggaa ggatagcagc agcgtgaggg gttccattag   26700
ccacaaactc atggcatgga gcctccaccc acctcgcccc tcatctgctg tttagcacct   26760
ggcacgctgt gtatacttac taattattat ataataatag caaattatag tggcaaatgt   26820
atgcatcttt gcacagttgt tatacagcac gatgagcaag tcattaatag taaggaataa   26880
atgtgaaggt gagaaaaatc tgactgccaa agttttttact ccttccttcc ctccccagac   26940
ttttaaatga aagttcaggg ataatccctt agttgtcctg gtagtaggac tcgtaattaa   27000
aataattggg ccaagaaccc ttctgtgctt ctcctttttag gtttgggtgt aaattcgggg   27060
tgtttctcac tggcgaaagc ctggtgcagg acagaccctg ggaagctttc tcttccagaa   27120
aggaccatca acatcccttg cagaagaatt ctcttctcca gactcagacc cggtgtcctg   27180
gcacccactg ggcaagtggg tcctagaaga caaacctggt cagagctgga ggctgcttag   27240
cattccccat gcacactagc agctcggaga gctcaggaag ccgcagcccc tccttgcctc   27300
accagcctgg gtcaggacag cgtccctgg aggatgcaca gggcctggcc tctggtcacc   27360
cagcctggag ggaaagctca atcgagcatc atgtcacccg gtgcccccat gcagggtggc   27420
actggtgaga ccccccaagcc aatgatacta cctcacagga gtgcgggccc agtgtggcca   27480
gatcaccttg acttttcaag ataaatcaga aatcgtattt ctgtgagata tccctatttt   27540
ccagtgatgg tgactaaatt agaagttgtt gaatttgta acatgctcct aggctgtttg   27600
tctggtttaa actctatctg gaggaattca agctagactt caggaataac ttcttgaggc   27660
aagggttttg agaccttagg gaaacaggga cgtctcgggg gtattctgac tgttgtcctc   27720
ctggaaggga agaacaggga actagaagat tgcccttagt gaagtccaaa gcacctaaac   27780
ccgggaccct cagcggtgtt cttaagtcac agattctccc tgaggcctct ctctggctcc   27840
atagaatggc tgattctgta actctgtgag tcttttttttt ttggagacag agtccttgcac   27900 tgtcacccag gctggagtgc agtggagctg gagtgccata gagcaatctt ggctcactgc   27960
```

```
aacctctgtc tcccaggttc aagcaactct cctacctcag cctcccaagt agctgggatt   28020
gcaagcatgc accaccacat ctggctaatt tttgtgtttt tagtactgat ggcccaaagt   28080
gctaggatta caggcatgag ccaccgtgtc cagccataac tcttgttatg taactcttgt   28140
tacaaaggcc ttatattttg ctctttgagg ttggttttag tttgatgcct gttggttgcc   28200 atctttaac tagggatgtt ttatcaaagt acccaaccaa agtatctaaa caaattatac   28260
tttaaagttt gaaaatgtcc agcatgtcta attgaatgcc tgttgtgcca ggcactgggc   28320
tgctgaggaa ctgagtccca tccctggagg ctagctagag aacacacaca cacacacaca   28380
gtggtctcac aagtcagttt tatattctac ctctatgcaa taagggtatt attatgttga   28440
ggtactttga cataaaaagt ttttcttaaa ggagaggatg cctagaacag gcattacctg   28500
aagcctcctc tctccagcat tggttgtctt ctgtcacgac tcagggtttt tcattgagaa   28560
tgggatggaa atgtggtcta aatatagggc ccatgttggg actggatccc ctctgggaag   28620
tcagaccagg ctagggcagg tccctagagt catcaggaaa agcctctgga gccagaaaca   28680
aaacaaaaca aaaaatgat gttaactaaa ctcagtccca aatcctgaat tggagtcagg   28740
tcaagcaaaa taatcaaagg agtcagcaaa gggcaagtca gagagaccaa gtgacaccag   28800
cgtcttccca ggagccctgt ggcgagtgac agagcctgga ctctggaata ggactcatct   28860
tgtgtctcct gccactcatt agctgggtga ccttgagcca agccccttaa cctgttggac   28920
cccatgttct tacctctaag tgggggctgg taatatcttc cccttcaagg aatgccctct   28980
aaggggtgtt gtgaagatca ggtaaggtgg caggggtggg acttctggcc aggaacagac   29040
gcataatcaa tgctaaatct ctcctcctct ccacctgctg gatgctgcag atcctaaaga   29100
tttcaatgtg aataagacaa aacccctgcc ctccaggagc ctttgagaat cagagaacta   29160
gacccattta cagaacaaag ggatgcagag tctggatgaa gttttgggga ttcatagagc   29220
agagggctac ccagccccag tctggacatc gctaggtcaa ctgtagcccc tcagtggctg   29280
atttagccca gaggatccca tagggttgac tcctaactca agggcatgag acaaccccca   29340
ggaaaggcac cgtggaaagg gtctggctgt ccctgattta cctgtgggca ctggggaat    29400 gccctcaggg ctctgtgtgg ttctgggttc ctccagtaaa aagtaatcaa attcttcac    29460 gttaatgtct ttctccacct cattgcacat catgcagcta ttcattgact cagcaactat   29520
cagctttgca tgcaaccttg cctacccgc tttagctttt agtaatagct cccctcttga    29580
gtaacacaaa ccagtgggga aacagaacct aactcttacc tctgggaggg ttatttgctt   29640
tgagaacatc tgtcctgcag tttcgctcat atggcagtga agttttgtgc acacactcta   29700
gagccaggga gcctgggttc aaaccccagc tctgccaggt cctaactgca tgaatttggg   29760
caagtcactc aacctctcca tgcttgagtt tcctcatctg taagattgga gcagtggtaa   29820
tacctgcttc ttagggttca gaagagaatt aaatgaatta agatgggtaa agtgcttaga   29880
atggagcgtt gcaagtagta agtgctatgt aagtgtttga tttaaaatga aagacccctta  29940 aatacattct ttgtgcattt cagaagccct tcattttgca tttcttttt tttttttttt   30000 tttttttttg agatggggtc ttgctctatc acccaggctg gagtgcagtg gcacgatctc   30060
agctcactgc aggtttcacc tcccgggttt acgctattct cctgcctcag cctcccgagt   30120
agctgggact ataggcaccc gccaccacgc ctggctaatt ttttgtatt ttcagtagag    30180 atgggggttc accgtgttag ccaggatagt ctcgatctcc tgacctcgtg atcctcccgt   30240
ctcagcctcc caaagtgctg ggattacaga catgagccac tgcgcccggc ctcattttgc   30300
atttcacaac caagctgtct cccctggaat ccagccataa ctctgctcac aagtgtgaga   30360
```

```
caggccccag cagagctgca cgaagaggag agaaggcagc cccccaggtc cccaactccc    30420
tgtccaagat ggcaaaacca gaacacagcc tcctccctac cccagcagga gttcagaatc    30480
tgcaatctcc aaaacccact tcaattttaa gtgtagagcc aggtgcgctt ttaagtcacc    30540
tgtcactctg gaggctcttt tgctcagttc ctcaccatta gcagggatga cagggagtgc    30600
aggagtacag ttggctccca gatattggag cgtgctgggc cagctgcccg ttctcccagc    30660
ctccactcct ctttgctgtc cagccatcac ttgctccttg aaggctaacg aaacaaaaaa    30720
cagtgccaag agcgtgggaa gaaagccagc ttctcccctg gggtagctgt gatatcatgc    30780
ccaccctccc tgaccacgca gcccctgggg accctcaggg ccccaagcac ccatttccat    30840
tgcacatgta cacccgtgtg cagccatggc cgcccatctc agtcaatagg gctgctcctg    30900
cccacttgga attgcggtga caaccaagag tggcttatgg gaactatccc aatgacctga    30960
cagcatgtcc gctgcaaacc gctgacgggg gacactgccc tcatctctag ctcatcagcg    31020
agaggcacag ttgctttctt aggtaacatt gctgctgtct ctgggcattg ctggggttg     31080 gcacttaatc tacaccgaat ttttccctcc tgtatcttcc gagctgcttg gatcttggtg    31140
ctgaattaga ttggacttta tcttgtgggg aagggaggac tataaacccc caacgtaagc    31200
aatggtcaga ctattctaag gaaacttgcc aaatttaaca tgaggtaaat ttagttctga    31260
cttctgtcca ccccactgct actgtccctt tttatcccat gatcccttgc ttttcttttc    31320
cttctctctc cctatctctt gggttcaaca catgatagga attcagaaat atatgtttgc    31380
gaatttgttt attcacgtag caaaccattt cttgagtgcc taccatgggc caggtagaat    31440
gggcagcccc gggatacagt ggtctctaca gcccctctcc tgggtttgta ctgtgcgaga    31500
tgatttagga tgggttctcc catcaaggac cacagtcttc tttctctgtg ccccttggtc    31560
ctcagtctct gaccccactt caaaggcagc attcactcag ggaagctccc atacggtgct    31620
agtcagagta aaagtttgga caaattgcca ggaagcagct tgtcagtatg cataaacagc    31680
cttaaaaata ttactactct tgacccagaa atttcacttc taggaatctg tcctaaggaa    31740
atagtcacat gcaaaagatt tataccag gatgttcatc aaagtgttgt ttataacagg     31800
aagtctcaga agctggttaa atatccaacc tctggaaatg gttatgcaga atagtatgta    31860
gctattagaa atttatgtct atggggttta aaatgtcatg ggaaaacact tctgacataa    31920
aagagcatga taattatata tttaacataa tcttaactat gttttagaat gtacaggaag    31980
aaagaaatgt acaaacatat tcattgtgat gtctctggtg gtaggattat gatcagtaag    32040
tgcttctgtc ttcatatttt cctgtgtttg ataatacatg catatgttgt ttataaaata    32100
agaaaaattt taagtttaaa attggagttg aaaagtcttt ttaggctggg cgaggtggct    32160
cacacctgta acaccagcac tttgggaggc tgaggtggtc agatcacttg agcccaggag    32220
tttgagacca gcctggctga catggtgaaa ccccatctct actaaaaatt aaaaattag     32280 ccatgtgtgg tggcgcacac ctgtaatccc agctacttgg gaggcagagg catgagaatt    32340
gcttgaaccc aggaggtgga ggttgcagtg agccaagatc gtgccactgc actccagtct    32400
gggcaacaga gtaagacttt atgtcaaaaa aaaaaaaaaa aaagacaagt ctttttaaac    32460
agtagcagcc ataactaaat ataatccata ctaagccctg atcaaatttt ttatttatgt    32520 atttattttta ttcatttatt attttttagac agggtctcac tctgttgcct gggctggagt    32580
acagtggcat gatcatggct catttcagac ttgacctcct gggctcaagc gatcctcaca    32640
tcttagcctg ccaagtacat gggaccacag gtgcatgcca ccacacctgg ctaatttatt    32700
```

```
ttatttattt ttttttagaga tggtgtttac tatgttgccc aggctggtct caaactcctg   32760
ggctcaagct atcctcccac ctcggcctcc caaagtgctg gggttaccag catgagccac   32820
tgtacccagc cctcaaattt taaaaaatct ataagggaca ttattggaca attagagaaa   32880
ttcgcatatg gacttataat agtatcagag tgtgtggtat gatggttctg gagggaatgg   32940 acttttctt taaagatagg cttttctatg cccacccttt taccttgcta acttatcatc   33000
atccaggttc cagcagaaac attacttcct ccaagaaagt tcttaagggt gcagtatctg   33060
cagcaaattc tcaaatagct caggaaaaaa gtatgtgtgt ggtatacaca cacacacata   33120
tatatacaca tacatacata tatttttatgt aattatatat gcagagagtg caaatgttgc   33180
caagttgaag attggtgaat ctaggtgaag agaatatggt atttattgta ttatctgtgc   33240 aactttttctt aggtttgaaa attttcaaaa caaaaaattg gaggaagaag acgtgccagt   33300
ctaccccaag ccctccactg gaatgctgga aatctaaaca atggcaattt catttctttt   33360
ctgttgtggg ccagtagtcc ttagatgttg gggaagcggg tagttgctgg ggtgtggttg   33420
acttaggatg gaagaagcag aagtcaagac tcccagggtc aaggtgcttt gctcttctga   33480
cccaagtgtg ggaggcccag agtcagcgtt tcaagtgtgc taattcagca tggttctgtt   33540
cacggccaaa gtccaccctg ggcacctctc tggcagcaat cttgggtgac tctactaagg   33600
tcaggcctcc ctgaccctat gtctggatcc catacctcca actctcccac tgtctcagga   33660
acagtgctta gcttttcttt tccctctcct gtcttccttg ccagcatcta gaaagtttaa   33720
ataattcccc tctttacaac aaaacaaaac atacccccctt cagtaaccca ccctagctct   33780
cttctccttt tcctagccag attttttttaa aagcatcctc agcactttgg caacctccat   33840
ctcctcccag catgccctat tactggaatc cagccaggac tcagccccaa tctttctact   33900
ctaaccactt gtctcagtta acaaggacag gtttatgctg cagtgacaaa caagacccaa   33960
attcctatgg cttcacacat ctggcactac ctcatcttcc agccttagga gtcatctttt   34020
agttccttga aaactctctg cagtttcctc ttggggcctt gtcatatgct attccctgg   34080 aaatgttctt tcctatcccc tccctttcac cttgctaact tgtgcccatc cttcaggtct   34140
cagcaaaaac atcactttct tgggggaagtt ttctccaata cccacactac acaggtgccc   34200
cattgacact cctatgactt tgtggcactt gtctcacttg atttcccact gccttcccca   34260
caagacacct ttacaagggc aaggaccgta ccactgtacc tatttcactc actgctgtgg   34320
tcacctgcac tctggctgcc taccttaact acacattaga atcacctgag gagcttttaa   34380
agccacaatg taagactcca ccctaggcca attggatcca aatccctggg gtagggccag   34440
ccatcagtgg agatatatat atatatatat attttttgaga cagagtttag ctgggactac   34500
aggtgctcac caccacccc agctaatttt tttgtgtttt tagtagagat ggggtttcac   34560
cgtaagcaag gatggtcttg atctccttac ctcatgatct acctgcctca gcctcccaaa   34620
gtgctggaat tacaggcgtg agccaccatg cctggccatc agtggatata ttttttaatgt   34680 actgcaggga attctgttgc atcagcttga gaaccactga tctgccttgt gcttcacatt   34740
taaaactttt tttctaatga ataaataaac ccctgaaaaa attaatctcc ctaagcctcc   34800
ctagaagata ggatggtaag gatattttcc taggtaaaaa tatgttaatt tcatatttca   34860
tgaaatttca tgtttcattt caatcaagct ctgtcataca ccttacatgg ggcaggccca   34920
gtgcctgagc agggtgtaat tattcaggca aggaaaagtc acattaggtg atggagcaca   34980
aataggcagt taatgttttc aggttagtt agaatatgtt tgtctttcaa ttgcaagtaa   35040
tagaagccca agaaattgg ttattcatat aatataattg attggttccc aaatttgaaa   35100
```

```
aattcaggaa tagacccagc ttaggtacag ctggatccag tcactcaaat aatgtcacaa   35160
tgaacccttt gacaggaatg taccgtgtct tgactctact ttgctctgag tagtctttgc   35220
ccaggtgatg ataaaaatgg ccatcatcat caggcttgtg tcctgtttac taggaatata   35280
caagaagagc tcagtaaatg ctggccccac cactaagcaa aaacaaaacc tttggggttg   35340
ttgttgttat tgttgtttta aatcacagct tagaccttcc ttctttcctt gttattctct   35400
ttcatctgta atccagtttt ctaattctga agtatagaat gttcagatca tttattcttc   35460
attacccaca acttgcacat gtttatttaa aatgccagga ttgcctggcc attgtgtgct   35520
gttaaccttt gtttgctgtt agtggatccc tgaagttcag ctcccaggg gagcagataa    35580 tgggtgtcta gttcctgcag tatctaccct ctggcaagcc aagttacttc ctgggtaagg   35640
ttttgcctac cctgcattcc cagggaagtt tctgggcctg accaccaagc cagctctgag   35700
gagaggtgca taagccccac catgctttgg ttctgtccct atagaatatt ttatgttgtt   35760
atcgaaaact aaaggaagat gggtgctgtg gctcaagcct gtaatcccag cactttggga   35820
ggccaagaca ggtggccagg agttcaagac cagcctggcc aacatggtga aaccctgtct   35880
ctacaaaaac aaaacaaaaa ttagccaggt atggtggtgt gcacctgtgg taccagctac   35940
tcaagaggct gaggcacaag aatctcttga acctgggagg tggagtttgc agcgagccga   36000
gatcgcacta ctgcattcca acctgggtaa cagagtgaga ctctgtctcc aaaaaaagaa   36060
aaagaaaagg aaaactaaag gaagggact aaaatgatat caggttcctg gagaacaaac    36120
agacatgatt ttgcttcatg gcaggacagc tggaagaggt gggattatat cctcacatta   36180
caaataagga aactgagact cagaatggtt aagtcacttg tcccaggcaa cacagccagt   36240
aaattacaga aacagaattt gaacccaaat cttccagctc caaagattgt gttttcacta   36300
cctcctgctt aattttttaa tttctaagat tagaccctac ttcatctatc catgatgcct   36360
acctgtcatc cccccaaaaa gggtgaacgc tgttcagaaa ttttctagc ctgagctcac    36420 tcccaattca cttattttg ctttgtcacg gctgcccagt ccccactggt agaccaggaa    36480
gtaggtcatg gctgcgggga ccacacgctg tcgctgctgc aagggctggc ctctgtttct   36540
ggggctgagt gggggtcaga cctgccagga gcaccacctt ctgtgggtcc tgcctggatg   36600
tcacatccca gccccaagaa gtcactgcaa acctttgtat tgttgagctt cacatcctag   36660
aattcactgt cactgtggct gctgcatgaa gtggtcctgg gagaaatggg cattggcatt   36720
aacagggaaa ttgatggtct ggggaaaaag tcatcctcat tctattgcag atctatgagt   36780
gattgagact ggctgatgtt gaagggtttt ctcagccatg atgtgccaca ttatggaaca   36840
gtggtgtagg cagccatttg acacccagcg ctgacctttg tttaacaacc tcacctatat   36900
atgacaaaat agttgtcaga aataatcatg taatgaaatg actgtaataa tggccagaaa   36960
agaaatgcag ataataaaat gtttctctta ttgaactctg tacatataat tgcaccagga   37020 ttttttttcaa ataaaagta aatatactac aaaaaggaa aaaagcacaa gtatttatta    37080
aatagctttt ctatatctt ctgagcttca atcctttgat tgcagactga tgtaatattt    37140
tatgtaaatc attgtttggt tactaagtga actttaagaa aagtaagatg tctgcaaaag   37200
ttgcccataa tttagtaact actgtattgt accattgatg tacagcttta ttttcttgat   37260 taattctttta aacaatataa ttcacaattt taaaataata aatttccact taaaatggta   37320
tttaaactca gcaaaatata taatctatga gtaaactttg tattactaag caaaaatatt   37380
acactttgtg gttcacatgc tgtctcactg tttaaattt taaatacaaa aactccaagt    37440
```

```
aggctgggtg tggtggctca cacctgtaat cccagtattt tgggaggctg aggcaggtgt  37500
atcacttgag ttcaggaatt cgagatttgc ctgggcaaca tgatgagatc ccgtctctac  37560
tgaaaataat tagctgggtg tggtagtgca catctgcggt cccagctact caggaggctg  37620
agatggggac agaggttgca gtgagccaag atcgcaccac cgtactccag cctgggtgac  37680
agactgagac cctgtctcaa aaaaaaaaa aaaaaaaaa agaaacaaaa attccaagtg  37740
gttgcacaga atgacaggac tgaagtaact tagctccagt ttctgtcttt ataatcactg  37800
tcctaccatt gtctgtgctt agaatctact tgcttaatgc aggaacatgt gttctcacag  37860
aggtggaaga tgcaaatggc acccgaagca ggctggaaat tctgaaccat taagaattta  37920
ctctctacca ggcacggtgg ctcacgcctg taatcccagg actttgggaa gatgaggcag  37980
gcagatcatc tgaggtcagg agttcaagac cagcctggcc aacatggtga atcccgtct  38040 ctacaaaaat acaaaaatta gccagacatg atggtgggtg cctataatcc cagctactcg  38100
ggagactgag gtgggagaat cgcttgaacc tgagatgcag aggttgcagt gatctgagat  38160
caatctgcac cattgcactc cagcctggga gacagagtaa gacccatctc aaaacaaaga  38220
aacagaacct actctcaaaa caaatacgtg tggctgactc cacatatggt agggccaact  38280
gtataactag aagttctcca ataacttct gtggagaaaa caaagtttat taaggatac  38340 tttttttttt taatttattt attattatta tactttaagt tgtagggtac atgtgcataa  38400
cgtgcaggtt tgttacatat gtatacttgt gccatgttgg tgtgctgcac ccatcaactc  38460
gtcatttaca tcaggtataa ctcccaatgc aatccttccc ccctccccccc tccccatgat  38520 aggcccctgt gtgtgatgtt ccccttcctg agtccaagtg atctcattgt tcagttccca  38580
cctatgagtg agaacatgca gtgtttggtt ttctgttctt gtgatagttt gctaagaatg  38640
atggtttcca gctgtatcca tgtccctaca aaggacacaa actcatcctt tttgatggct  38700
gcatagtatt ccatggtgta tatgtgccac attttcttaa tccaatctgt cactgatgga  38760
catttgggtt gattccaagt cttcgtgctatt gtgaatagtg ctgcaataaa catacgtgtg  38820
catgtgtctt tatagcagca taatttataa tcctttgggt atatacccag taatgggatg  38880
gctgggtcgt atggtacatc tagttctaga tccttgagga atcgccatac tgttttccat  38940
aatggttgaa ctagtttaca atcccaccaa cagtgtaaaa gtgttcctat ttctccacat  39000
cctctccagc acctgttgtt tcctgatttt ttaatgattg ccattctaac tggtgtgaga  39060
tggtatctca ttgtggtttt gatttgcatt tctctgatgg ccagtgatga tgagcatttt  39120
ttcatgtgtc tgttggctgt atgaatgtct tcttttgaga aatgtctgtt catatccttt  39180 gcccacttt tgatgggggtt gtttgttttt taaaggatac ttttttaaag tgctatctgt  39240
aactttacat atatattact aacactcaga gatcgcacca attgtttata acttagacca  39300
gggccgggca cagtggctca tgcctataat cccaacactt tgggaggctg aggcaggtgg  39360
atcacctgat gtcaggaatt caaaccagc ctaatctgca tgatgaaacc ccatctctac  39420
taaaaataca aaaattagcc aggcatggtg gtacacacct gtaatcccag ctgctgggga  39480
gggtgaggca ggagaatctc ctgaacccaa gaggcgaaga ttacagtggg ccgagattgc  39540
gccattgcac tccagcccaa gcaacaagag tgaaactctg tctcaaaaaa aaaaaaaaaa  39600
aaaaatctta gaccaggaaa attttttta agggaggagt attttatcac tggcattgtt  39660
taggattgct ggcacatgat gctaataaaa agcagactat tagttggttt tattactgtt  39720
tttgaacttt tttttttttt tttttttttt ttgagaaaga gtctcactct gttgcccagg  39780
ctggagcaca gtgactacga tctcagctcg ctacagcctc cgcctcctca gttcaagtga  39840
```

```
ttcttgtgcc tcagtctccc gagttgctgg gattacaggg caccacgcca ggctaagttt    39900
ttgtatttt  agtagagaca gggtttcgtc atattaccca ggctggtctc aaactcctgg    39960
cctcaagcga tctgcccacc ttgacctccc aaagtgttgg gattacaggc atgagccacc    40020
atgcccggcc ctgttttga  actctctaga gacagtccag ccctttatta cttctcctga    40080
ggcagctgct cccttcacct gggcccccgc attgtgttcc ggaccttgt  cctggtggtg    40140
ctgaagaata tctctgtcaa tccttttggg actggggaaa ctgaggccca gtgccacgcg    40200
atgccatttg ttcagggaac attaggtcac ctgctaggtc cccagtcact tgaccttctt    40260
cccagacagg aagaagctgc tctgggtctg agtcctgact ctctcagtgt cccatgtgtc    40320
tttgcacatt gaaatgtttt ctgatggttt tttgctgtta tatttacttt taaaaaataa    40380
ccagcaataa aatgttaggt ttgagaaggt tgaaatgaga attgatttga gttaaactct    40440
agcagatttt tcttagaaga atgatatcat ctccagccac ctgcaattga tctactctga    40500
attaagaaag aggcttccat atgttgttta tattttgcac tcttgatatg tttctttaaa    40560
ttatggtctt gggccaggta tagtagctca cgcctgtaat cccagcacct gggagtctg    40620
aggagggagg atcacttgag gccaggagtt cgagacctcg tctctacagt acatttaaa     40680
aattagccag gcatggtagc attcacctgt agttctagct acttgggagg ctgaggtggg    40740
aggatggctt gagccagaac tttgaggcta cagtgagtta ttgtcatgcc actgccctcc    40800
agcctcagtg acagagtgag acctgcctca aaaaaaataa gtaaaaaata aattaaattt    40860
caatcattag cagtcatcag gatatttaaa tacatttgtt gaatcaaagt tatgcatgtg    40920
tgtatttttt tttccagaga gttgtttata atgtggattt taatttaact ttaaaaaaat    40980
tttggctgga ctgttgccca aatggtatca ccagccattt ggttgagaac atatgtcctg    41040
caggctcttc tgtcactgga gttttgctag ctgacagcca ctggctagag actgtggtca    41100
gcacagaagc aggcgtggac ttgcgcacgt aagcaggtca atgcaaagcc atcacttctt    41160
aaaaattctg aaccctgctg tctgagatgg tggtgcagcc aatggagctc tgctctagga    41220
agcagaagct aattccatgt ctttgtttgc ccttgactag ctaggtgact ttgcacaccg    41280
ggcttgcctc tcttgttacc ttgtctgcaa agtggaatca tcttttcctt gctgacaga    41340
aggtggaccc tggacctatg ggcttttga gttttctcc ctcttagaag gacctctgat     41400
cctactgagt ttaacaccca tgggttaata attgggaaaa gcaaaggaag cgcttctgtt    41460
tagataatta tatgcatgtt tttgtctttt tctggctgga aagatgtcca agctactggg    41520
aaggtctgtg cctacccagg gtagccctct ctggggaggg ctgctgtatc caagatcccc    41580
tcaccggaat ttgaaaatca accatagtag ggcctgctga cttttgacag ctaatggtgt    41640
gctgagaatt gtccctccaa agacaccttt ccattccctc gggagagtct gggcagcccc    41700
tcctggggc  tgggatgctg gctcttccct cagcctccac cccaactgct ctcttccctc    41760
cttccctccc cagctcccta atttctctca caaggctttg ttccacagca acctttccta    41820
atgcagtcct ggccagggcc tcttcgcagc ctcattacat aaccttccac agactcctgg    41880
tccaaggatc accccagaaa gccagtcaga ggtaggcacg cagctggggt ccatttactt    41940
accttcccca ccccctcgga actcagaagt ggtgcaggaa tttggactcc aagaattaac    42000
agctccacca ctgtcaccag agccaaaact tcaggatgca tgctctacgt ctgctgctaa    42060
tttccagctg agagccagtg gcactgtggt tccttaggag ccggttccct gatgccggct    42120
cctggcccca aatccctctg atccgggctc ctccagaatg tcttgtctcc accatcccct    42180
```

```
ttgaccaatg gtgtctttgc ctggtaatgt cccctttgcc tgatgatggc cctgtcactc    42240
ctctgtctag cacagaggag gccgtttcat cccttcaagc ctgccctccc ttcaagtctt    42300
agctcaagtt caccttcttc acagagcctt ctccaatctt cttggctacg tctccgctca    42360
gctccagcaa cctctgtctc tggcactgat tccttactta gctcagagag tcacagacac    42420
ttgaggctca ggacaatctg ctttctctct tcttacccat agctttggac catgtgtatc    42480
tctttgtctc cactcccaaa cccaaccccc agagggcaga gagcatgttg tctgtccctt    42540
tgctcagcat gaagccctgt gtgtggtagg taggcagagt tgcataactc gtgttgacca    42600
aggggtcact ttgctctgaa attaccctg tgtccttcag tatttgcata gatagcttcc    42660
tggccagccc gaatatatcc aagggcatgg cccacctctg ctcctgtttc taggtccctg    42720
gtggagttag ttcatgcctt cctcataatc tgcccactgg cctggtcctc aaggtcttcc    42780
cagctgctca gctagagctg ggaaaatggg tcgctccatc ctgtttatgt cattctctcc    42840
ctgcctggcc cactctcctg cccacaggta tcctgggact gtctgtagga ttagaggaca    42900
tatgtgcaca tgcttgggca caggacactc acgcagcctc caagcacagc atcaataatg    42960
cattcggtgc attatagcgt ggaaagctgc tctaaacttt attacacagc ggacatgtct    43020
gaagcagctc ccaaatccac ccatgagtgt tttgcaattg gcaagcctat tacttgggag    43080
tccactttc tctgttcatt aataatagat gcttcctatg ccccagctt ggcaattttg    43140
atttaaagtg atcttaactg aagagactaa tggatgggtc tgaatttgtg cctttaagc    43200
acaaagtatt gctcttaatt aactggattc tatcctttaa gcaggcagag gctttccccc    43260
aatggcatca ttaatgaacc acatctggac atcttccaaa gccttcttct gtttcaggcc    43320
aatcacaggt gtgttcctga acacccagga ggctgtaaga gccacatatg cctcccaaat    43380
acacacaaca tgtgtgcctg gggacacaga gcagtgtgcg aagtcccatt ccatctctct    43440
ccacttggga gaggatggtt cttccatcta attcatggct caaagtggta aaggagctcc    43500
cccctcccca tgccatgccc actcagagtc tgcaaatatg tatgtgatat aagagctcgt    43560
cagttagctg tcatcagtgt ggcacacatt tgaggagtct gactcccctc cagcacaggc    43620
caatgtgcac tgcactcctt tctttgtgcc tccaccgttg cattgtgcag aagttgggt    43680
catagaagta ccagagctgt gaaaggagag gccccttctc acctctgccc tggtctccat    43740
ccccacttc tctaggaagc tggtaggtgc tgacatggga gagaagggag gggaggggc    43800
caggaacagt ggcttatgcc tgcaatccta gcactttggg aggctgaggc aggaggatca    43860
cttgaggcca ggagtttgag accaggctgg gcaatgtagc aagaccctat ctctacaaaa    43920
agaaaaaatg taattagctg ggtgtggtgg tgggcaccgg tagtcctagc tactcgggag    43980
gatgaggtgg gaggattgat tgagcccagg agtttgaggt tacagtgagc tgtgattgca    44040
ccactgcact ccagcctggg caacagagct gagaccctat ctctaaaaaa aagaaagaa    44100
agaaagacaa gacaaagaaa gaaagaaaga aagagagaga ggaaagaaag gaaaggaaag    44160
aaagaaaaaa aagagagaga gagagagaag ggaagggaaa gcccagaaga gtagaaggtg    44220
tggggagagg aggtggccgt cattctgggg ccctcagtgt gcactaccag ataacgcatt    44280
ctctgtgggc ttttgcacca ttttgcttga gcataaagaa aggaaggctg ccctaaata    44340
gaaagcactc tggaggcaaa gaaatctggc tccaatcctg gccctgccac tttcccagct    44400
gaggacttag acaagcaccc ttggacattc tcagagccat cagctgcaag tgggtgctgc    44460
catacccacc tcattgggca ggcttggggg accaagggtg gtaaatggct cggggtcttg    44520
catgatgcgg ccacacagca ggtgtgccat ccagatccat ttatttcctt cctttcccca    44580
```

```
aaatcaagtt gtcattaaag tgctagtcca cattaatgaa atctgtagac accaactgta    44640
ttagttttct gtttgctgct gtaacaaatc atcagaaatt tagtggctta aaccaacacg    44700
attgtattac tttacagttc tggaggccag aaaccctcca taggtgtccc tgggctgaaa    44760
tcaaggtgtt ggcaaggttg tggtcctttc tggagggtca agggaagagt ccattttctt    44820
ccttttccca gcttctaaag gtttcatgca ttccttggct catgatcttc tatagctata    44880
gaggaaaaaa aatttacatc aatcatcttc aaagccagcc atggcgggat aagtccttct    44940
cacatcacct tgctctgaca ccagctctcc gcctccctct tccacacgtc aggaccctcg    45000
tgattacttt gggctcactc tgataatctg ggatgatctc tctgtttgga agtcagctga    45060
cccagaacct taattccatc tacaacccca attcctcttt gccatgtata gtaacatatt    45120
cacaggttct ggggattagg acgagcctgt ctctgaaagg ctactttaca tgaaaattca    45180
ttttttaatt aagattttt tttttttcctc ttgagacaag gtctcactct atggtccagg    45240
ctggagtgca gtggagggat cacagctcgc tgtagccttg acgtctctgg gctcaggtga    45300
tcctcccacc tcagcttccc tagtagctgg aactataggt gtgagccacc acgcccagct    45360 aactttttt tttttttttt tttttttttt ttttttgaga cagagtctca ctcagtcacc    45420
caggccggag tgcagtggtg cgatctcagc tcacagcaac ctctgcctcc tgggttcaag    45480
tgattcttgt gcctcagcct cctgagtagc tgtgactaca gttgtgcacc accacgcccg    45540
actaattttt atatttttag tagagatggg gtttcaccat gttggccagg ctggtctcaa    45600
actcctgacc tcaagtgatc cacccacctc tcatattgct gggattacag gcgtgagcca    45660
ccgtgcgcag ccccagctaa ttttttaaata ttttttttgtg gagatggggt tttgtcatgt    45720
tgtccaggct ggtcttgaac tcctggactc aagcaatcct ctcaccttgg tctcccaaag    45780
tgctgggatt acaggcatga gccactgcac tcggccttaa gagaagattt aataattaat    45840
attttacaat attaattgta aagaggtagg atgagtaact aaattaggat acaagtaacc    45900
agggtcatat ttgctaatac ctttgatcac tttgcactgg atatcttatc agattttcct    45960
catcagctcc tttagcagca gtgtggcagc atcttatctc attttgtatt tttttgcata    46020
gcacacgcct ataaatcact ggattgaggt gtttagatgt tgttgtccc ttggatgctt    46080 cttacaaatc catattttat ggctcctgga aagtgctatg caaataataa gctgcaagaa    46140
tggaaaggaa attgcagtgc tcctgaattg taaatgggct tttacgagga ggtttctaat    46200
tactctgctc tttctcttga actgaggagt tgaagtgtaa gtggcagatc cataacagat    46260
aatcatgtgt gtgatgttac ttcagcctga gcctcgagga ccaagtcaca gagcaggaac    46320
agccactccc cagtgtccat ggggccacgt ctgaggagaa ctcagggatt tcatatgtga    46380
tctgcagtgg ctgggggct aagagagcat caagaggatg taatgtgtcc ctctgagtgt    46440
gttacagatt ctgacattct tatttttcctt ctgtggagag acatgtactc agtgacccaa    46500
ctcactttag catatgtttg ctcatcattt gtgtagcttg aaggaatcag atattacccc    46560
ctccccgcta tttggaagca cagatgcaat gccctagaat tgtactgggg gctcaaagag    46620
aaaagagagt agtaaaatct attaaagggg acaaagacag cctatatact acaagctttc    46680 tattttttgtg gcagagacgt tgtggtattt tctaagtaaa cagagtcgac ctgcaatatc    46740
aaatgcatgg atttgatgct ttggaaagca actgtcttct gtgttaatct gggtgtcttc    46800
tgtgaaatgt ccccctgcct ttggcttaaa cactagcttt gtctacagcc gctccatcct    46860
gaacctgccc attcttgtct gaatcctggc ttgaccactg acaagctgtg tgtccttggg    46920
```

```
caagttactt cacctctctg cttcagcgtc ctcatctgtg agttggggaa tctggacaga  46980
atctccccca tagggtatag tgaaggcttg ttgaattatc ccaagtggct acacagagta  47040
agcattcaac tgatgtcatc gttgtcatga ttgctgttac tggagcctag agttcattct  47100
gatactcaag gctgtggcgc atgtggcccc ggtaaggaac agttggagga gtcgggcatg  47160
ttcaacttga agaggagacg acagggaatg tgggatggtt gaatctgcga agggcccct   47220
gggatgaaga actggcatgt tctgtgtggc tccagggccc tgagcaggac ccatttacca  47280
aagtctcagg gacacagttt ctagctatag acagaaacat tttctgtcaa tcaaagaggg  47340
cgaaaataga atgagccccc ttaagaggta gtgagctccc tgtcattgga aggattccgg  47400
aagagctagg taaccactgt agtgctctca aggggctttt ttctttaaag tcctttccaa  47460
aaggttctga gagtacgtaa acaataggaa gccaccttgg tgctttaaca caaactctcc  47520
ccagtgatga ggtttgagcc aaagccagac tggcaagcag agaggaggct tgtgtacaag  47580
gagttcctcg ggtcaattgc tttttccttg ttctagccag ccagagggct cctgttggaa  47640
aacaggagac cagggaggcg gaggcctgac caaaccagcc tctgcaggcc agctgggaga  47700
ccacaactcc cacctgcggg aaaactgaag ggcatctcta ttttagatt gagcaaaaga  47760
aaataaattt aagtttgagc ctcctttgca acttctaaaa atcatcttta ttgagatgat  47820
cattcacatt ctataaaatt cccccacttt gagttacaat tcagtggttt tagtcttcct  47880
tgatgatgtt gatggtcttt tcataaggct cttggaagat ccagaagcct ctgagacaca  47940
ggtgggtgtg gagggcatag cacagaggca gacttctcat ttcctgggtc tccccttta   48000
tgactctcag agacccctcc ttcccctgcc gctggcttcc accccagggc tgtagagctt  48060
tgccactttc caagcagaac ttaatttcct cttctgtgtc tacactcttt gtgcttcttt  48120
cttgccagct ttttctcctt tgcccaccct ccctcccttc ttcccttctt ccttcctcc   48180
cttcctccct tccttcctgg tatgtgacta atttctgttt caggacatag atgttgtcca  48240
ggctgttctt cggcctttct gttggatgat ggacattggc attgagagag ctgcttttt   48300
ctgaaatcat gttttggggc ccaggaccta ggtgtgtgct tctggctttg ttttcttccc  48360
gatccaaatt ctgatatgtc catttaaatt gatgtagacc cacaggacac tgtgggacag  48420
atcctcagtg gaacatgact ccgtaacgag agcgttttgt tttgtcaaaa tgagaacata  48480
ttattgcttt tcatctgatt gtaaacataa tacatgtcta taagacagta taatgagaca  48540
aaaatgtaga cactaataag agaaaatctc cctaattgta tttgtattct cagagaaagc  48600
ccttgttggg catatatact ctagtttgtt tgtttgttta cacatatatg tactctttc   48660
ttatttataa aaattctgta catgtacatt tctgcaacta ctatttcact tgatgataca  48720
tagacctctc tagaccagcg tgtacatttc ttcctcctta caaagcagtt ggcttcgccc  48780
agggtgcacc aggacacagt tttggctctg tccccagggt gtcacgggac caggagatga  48840
tctcacaggg tctgccatct gccctgcctg gctggaggct gcatcgagag ggccaagggg  48900
caccacgtgt cgtggacact gtcaaacaag agcctttaga gctttccacg gtctttcttt  48960
tgcttcccag cattgcttcc ccgctggtgg actctgaatc tagaactagc tccaggcgcc  49020
tctccaaact cagacggagg ctgcggcatt attataatgc aaatctaggc aaagccctcc  49080
caataccagg atccagaatg gggtgggggcc ctttgcccta aaaagctgtt tggtttgaaa  49140
atacaaacag gagacagaaa ggtttggcta aattaatgga tgaagttta acaatggtaa   49200
ccatagtagg gttcactgac cgccagcgat ggttctgaat acttgacatg tattaactca  49260
tctaatcgcc acattttaca gacaatacaa aggaggctct gggaggttga atgacttgcc  49320
```

```
caaagtcgca cagctcctaa gtgaaggatt tggagtggac tccgggcagc ctggtctgac   49380
gccctgcact gcgctgtgct tatctctggc cccaatgccg ccatacagaa gtgtctgggg   49440
gcactttgtc tctgtcaaag agagaattcg gagatgcgta tgcttgccct ggtgtggcat   49500
ttctcttttt ttgagacaga atctcactct atcaccctgg ctcactgcaa cctccgcctc   49560
ccaggttcaa gcaattcttg tgcctcagcc tcctgagtag ctggaattac aggtgtgcac   49620
caccatgccc agctaatttt ttgtattgtt agtagagatg ttgttttgct gtgttggcca   49680
agctgatctc gaatttctgg cctcaagcga tccgcccacc tcagcttcca aagtgctggg   49740
agtacaggca tgagccacca cgcctggccg tgtggcactt tttacgtgtg ttcagcagac   49800
actgtttatc ttctgtcctt ccaagacagt gctgatcagg tcattcatta cagcagacaa   49860
ctgctgattt caaacagaat tgccatcctc ttctcccctg cgactttcag agtgtgacct   49920
cagactcaaa aatcagaagt gaaaacatct taaaaactat cacctttttct tcctaatcct   49980
cctctcccct ccctgtcttc cttgttgtcc ccatccaatg aactatcatg caaaaagag    50040
cccatttctg gccattttct gtggcctttc aaactcccac ctaccccact gcttctgggc   50100
tcattccctg aaagctgaga cttcggcgca gaaagtgcca ggccctctgt cccccccagat  50160
cgccttcctt gtcttccctg tgcttgcctg tcacattgtg tgggttccag cgctggaagg   50220
aatgagaaac agactctctg gttctccttt tgaagtttac cttcactcca ccacttctga   50280
gaccttccca gaagttgccc cttgtttctc tcccctccag ggctgaccca gagctgcccc   50340
tcacctcttc ctgctgtcac cccaccgcca tcagggcaga ggttgggaca aagcctctcc   50400
tactggctcc tgctattctc cctcaggtcc agcctcctct tctccatctt caggagtctc   50460
cctctccact cacatgtgat gacttcagca cctcgcatca gtccaggaca tcactacttg   50520
ttcaagtatc ttacccatgc attttttcca gtgacattca cagccaccct gtgagacagg   50580
agtgtcatca tctccatgtt tcaaatgaag aatctgcagt tcagagaggg caagtgactg   50640
gcccagcctc aacagccagc cagtggaccc cactaaaccc agggcttctg actgcagtcc   50700
gggttccctt tccacccaaa tccatggagg gaactgagcc gagaacaggt gtccttcagg   50760
aagacgtgaa gccaaagcct ccacctccaa actcaggggc ccaggagtc caggcaccca    50820
tccactcaca aggctggatg tggtgcattc caggagaggg gttgggggca agtggcctct   50880
ccgtgcaccc atgggatag atgcgcacgt ggcatctcca catcatgagg cctggcttcg    50940
tgggttagct ccaggtccat ggagaagcca agtagggggc cctccaagct cagctttggg   51000
cccaggtcag ggtgcaggat agagcaggcc tccctagcat ctgccatgag gccgaggcag   51060
tgcatcgttc acagggcaca ttcagaaacc acaacctaag agccggtcat cagtccgggt   51120
tacggctgat ggaagagcag gtgcttccaa gaacccacaa tgctctttgg ccagtggccc   51180
aaaggtgcct ccaagaggct tcacagcacc cggaggtgct gctgaggcaa cgccctgact   51240
gtaaggagga ccattcaccc tcagagagcg ccgtgatgc tgttgcgaca gtcctaccat     51300
ccctcccaac tctcactccc aacagacttc ccactctaaa gctgaactct ccagcaaatc   51360
acctctcgcc agactctccc ccgactctct ctgggtccac tggaggttcc tcagcctctc   51420
tgtgccttgg ttttcccagc tgtaaaatgg agcaaagagg gcctgtgtac ccccaaaggt   51480
gtggttggag cagctcctcc tacattaggg ccttgagtgg ggcttcgtga ttggttgatg   51540
gaggtctcca aacccaccca gtgccaccga agcctgggac tgcagatgca atgccacagg   51600
tgtccttcct cagcctgggc agctgcacat catgtgtaaa atgggggtaa taagataata   51660
```

```
acagccgctt gcacctatgt ggctatgagg attaaacaag ataaatgtgt aacagtgcct    51720
ggctatagaa atatttactc ctgttattaa gggaagaata tgcatggcta aaaagggagg    51780
gaagatgtaa aagccagtcc gtcccctct agcatattta agggtaatgt tgagttggtt    51840
tgtggaccat ttgctgccta ttagagccgg aaggtaggga cccctctca acagcgatgc    51900 tacaaattat acccattgga ggtcaaccaa aagacaaagc ttattggctg gacctggtgg    51960
ctcacgcctg taatcctagc actttgggag gccaaggcag gtggatcact tgagatcagg    52020
agttcgagac cagcctggct aacatggtga accccatct ctactaaaaa tacaaaaatt    52080
agctgggcgt ggtggtgcac gcctgtaatc ccagctactc aggaagctga ggcaggagaa    52140
tcactagaat ccaggaggtg gaggttgcag tgagccaagg tcatactact gtactccaac    52200
ctaggcaaca gagggagact caatctcaaa aaagaaaaa aagacaaagc ttgttaatac    52260
cagcatattg ttaagggaat aaagtaggct gcagaacagc tggtgtaata tggtgccatg    52320
tagggaaaat tacaagtgta cacaggagaa gagtctgcaa ggatgtgtcc taagatgtta    52380
gagtggtttg tttgctttt tcttttatca ttttgtattt gacttttaaa taaggaccat    52440
gaatcacttt tataaaatac attctctcca gcccctacta ctcctttaaa gaataagagt    52500
ggtttgccca agaaaggcag ttttttttgc tctggttttc ttgattctga catcaggga    52560 aactccttct catctacttg gggctctggg ttcaggggat tcatttcagg cagattaaag    52620
tggtgaccag ggacatttgt ggacacaggg agggacggga gcaccatcag tttgtctcac    52680
acaaccactg ccatcctcac tgaaggctgt tgcctgatca aaaaaagtat caggccaggc    52740
acggtgactc acgcctgtaa taccaccact ttgggaggct gaggtgagtg gatcacttga    52800
ggtcatgagt tcgagatcat cctggccaat atggtgaaac cccgtctcta ctaaaaatac    52860
aaaaattagc cgggcgtggt agtgggcgca tagtcccagc tacttgggag gctgaggcag    52920
gagaattgct tgaacccaag aggcagaggt tgcagtgagt ggagatggcc ccacctcact    52980
caagcctggg cgaccaggg agactctgtc taaaaatt atatatatat tatatatgtc    53040
aaaaatgggg tagttttag aactatagta gttctaaaaa caaaggccat ccaagcatga    53100
cagatttaca agcactttgg ttattccagt agttacaatg gaggatagaa gcttttagtt    53160
aaaacaaaca acacaacaaa cccagaaacc ttaggtcaaa accaaaattg tcctctcaga    53220
cacaatctgc gaattttctc atgacagtgg gcattagcca actgacatca gccgcaatca    53280
tccgtgtgca cacagtggca ccacctcctc ccaaaaagcg gccttcatcc atgctctcat    53340
acaatcgttg attattgtct ttggattgac gcccagaatt atttcagttt cttcttgcca    53400
gcatgaatct tttctttctg tatgctcctt atcttctctc tttaatttgg cagttctgct    53460
tgaaatctgg gtcttttcatt agtaatagtt cagtttggtt ccagaacatt ctgtggtgtg    53520
atgccatgtg accacaagct cacacttcag agctcttcgg gggccagtct taccgagcac    53580
ctctcagtgg ctgcctgtgt gctgggcgct acttgtggtg ggcaagagag aggagggac    53640 acaaaggag acacagctcc ttcttagaag ctcaaagttg gggaccagct gccacagaag    53700
agtatcttta gcatcccaga caccaagatc tggccttaca agggtgttta ttaagccttc    53760
tcagctcttt ttcttttttt tttttttttc agacagagtc tcactctatc acccaggctg    53820
gagtgcagtg ggaagatctc ggctcactgc atgcaaccac cacctcccgg gtttaagcga    53880
ttctctgcct cagcctcccc agtagctgag attacaggcg cccaacacca cacccagcta    53940 attttgtgt tttcagtaga cagggtttt caccatgttg gtcaggctgg tctcgaactc    54000
ctgacctcag atgatttgcc cacctcggcc tcccagtgtg ttgggattac aggcgtgagc    54060
```

```
cactgtgcct ggctttgctg ttgcttcagc aaaaagtatg tttgacttga tgacctccag    54120
ttaccttaga cagaggttct catctaagct ccaactttcc atttccattt tcctcgcctt    54180
tccccttaac ccctccacat ttctctcaaa atcaccccag ttctgtggcc gggtgcggtg    54240
gctcatgcct gtaatcccag cactttggga ggctgaggcg ggcgaatcac gaggtcagga    54300
gattgagacc atcctggcta acacggtgga accccgtctc tactgaaaat acaaaaaatt    54360
agccggacgt ggtggtggac gcctgtagtc ccagctactg ggaggctgag gcaggagaat    54420
ggcgtgaacc caggaggcgg agcttgcagt gagccgagat cgcgccactg caatccagcc    54480
tgggcgacag agtgagagac tccgtctcaa aaaaaaaaa aaaaaaaaa aaaatcaccc    54540 cagttctaaa aaatactctt cattttcctt ttaaatttca aattatactc attgaaataa    54600
atcaaaatag catagaataa gcaaaaaaaa tggatcccac ccttcctcac tcccattaca    54660
tagggctaac catagttaac catttaatta ctaggttttt ttgttgttat tatttattta    54720
tttatttatt tatttattta tttagagaca gagtctcatt ctgtcaccca ggctggagtg    54780
cagtggtgtg atctccgctc actgcaacct ccgcctccca ggttcaagca attctcctgc    54840
ctctgcctcc tgagtagctg agattacagg tgcccgccac cacacctggc taattttgt     54900 acttttggta gagacaaggt ttctccacgt tagccaagct ggtctccaac tcctggcctc    54960
aagttatccg cccaccttcg cctcccaaag tgctgggatt aaggcatgag ccaccacacc    55020
cagccctcct gggctctctt ttcctttagt tgcacacact cccctgttcc tggagtagag    55080
ggatttccta gagactgtgg gctccagcct tcacctaaac ccaggactag gatgcctgtc    55140
ctatcactta tctttataga ttaaagcaaa atagctggac cataagcatt cgagaacaaa    55200
tggtgaataa ggagaaagtt ctcccaggaa acaagagctt tacttcagtt gggccagtgt    55260
ccttatattc cttagctgtt gccagtcact gcttgattta atctcggcta tcacttggcc    55320
tgacaggtct gctgctggtg ccaggatgtc tgggttttta agcctggctc cattacatac    55380
ttcctgtgtg accttgggca acttactcag cctgtctgtt cctcagtttc ctcagctgta    55440
tgatgtcggc ataatagttt gttgtgtgaa ttaaatgagg caataactgg aaatgcttca    55500
aacatggttc ctattaggag aaatcctgct ttctgcctaa atgtgctgca aaattcctgg    55560
tggtgcagag caggagacca gagcaaagga aagacagggt gcagaagcca aaaattacct    55620
tggaggacaa agcgcatgtt aaggttaatt ttggattcta ggtttatctc tgcttggtct    55680
tcagttacct gcgagagatc catttagggg atttttgttt gttttttaacg atagctttat    55740 tgagatataa ttcatatgcc ataaaagtca ctcttttaaa atgtttccgg tatattcaca    55800
aggctgtgca ggcttccctg tgcttgattc cagtctgggt ttttaaccta gcgggtaagg    55860
gggaccagac cagaaccgcg ggccaggcgg cgattccgct gagtcaccgc gggcgcggt    55920 gcgcggcggc ggagcccggg accttccttg gctgcccct agcgagggcc gcagggcggc    55980
ctgagacacc ggccggggcc gccccacggc cgtcggattt agactggaag cttggtccag    56040
gtcaccagct tgatgcgccc gcggtatggg agaccagccc cactcgggct tcccctgagc    56100
gcccggactc ttgactccag cagggcctgg gttatgacca tcaactcccc tttgccaaag    56160
cgatgctctg ttgggaaggc acccatttga tacagtagcg tagagatggg ttttagcatc    56220
aaaatatcag aattcaaggc ttgctctctg cttactagct gtgtgaccct gaaaagattt    56280
ctgaacgtct ctgagcttca gtttcctcat cattccttct cacggggtgg ttgtgagcat    56340
tacagagatc ctctctggga agcccctgtg agtggctcat cctcagggct gaagtaaaca    56400
```

```
tgttattaat aatccaatac tggcaagggg tgttgactga tccccctccc ttccccaagg    56460
agctttctag aacctgagtt atcattacca aactgtgctg ccttgagtaa gaacgataga    56520
aggaacagga aggatggtgg caggtgcagg aaggcagatt ggtcctcgcc tccttgcagc    56580
aagaaacagc cccagatcgt gggaaaccta cagacctgcc agacagacta ggagcaaaag    56640
ctggggcgtt aagaatcccc agggaggttc tcctgaggga gcagccagtt ggattttgta    56700
agcagagatt tggctgggga ggagtgagga cgtggggagc agagggacaa aactgtcggg    56760
aatcctgcct tgagggcagg ggtgtgtgtt ggggggagtt aggtccctgg ggctcggtgg    56820
ccttgggcaa gtttctaccc ctcaggtctt ttacccatct agggactcca tctgtccacc    56880
tcacaggtta cagtgagcct ggatgcactg tcatgggcag gtgcccagga aaatggcaga    56940
catgttccaa atagcaagca gtgttcccca gtgacgtcca gggtcacctc ggaggtgggc    57000
aagatgcctg gggtttcttg tccacccccac aacacctcag gggacagcca aaactgtccc    57060
ttcaggtaag ctgcacagaa gacgtgaact ctgctgggaa gaccctcttc tttgggagca    57120
aaagggaccc agggtctcac ctgcacatcc ctgtccctga gggcctgggg gttcttggag    57180
gcccagcctt ggcaaaatga ggaagaatgt gagggttgtc caggcccctg ccaggctcct    57240
tccttagcca agcactcccc ttcctgcaca catacccttc tccctccact gcgtctccac    57300
tgttgtcaga aaagtcacaa taaaaaggtc cgtattatct agttcccaca cttttaattt    57360
ttttaatttt atttatttat ttatttattt atttatttat tgagacagag tctcactctg    57420
tcacccaggc tggagtgcag tggcacaatc taggctcact gcaacctctg cctcctgggt    57480
tcaagtgatt ctcatgcctc agcctctcaa gtagctgagg ttacaggtac gtgccaccat    57540
gcccagctaa ttttttgtatt tttggtagag atggagtttc accttgttgg ccaggctggt    57600
ctcaaactcc tggcctcaag tgatctgcct gcctcagcct ctcgaagtgc tgggatttca    57660
ggcgtcagcc actgcacccg gctccacact tttcacttat taaaagactg tggtgtccat    57720
caatggatga atgataaac caatgtggac tatccctccc attacccaag gaatgaagac    57780
ggaactttgc caagatgtgg attcacagtg aaagaagcca gtcaccaaaa gccacgtgct    57840
atgtgacttc ccttatacga aatatccaga agagatacat ccatggtgac agaaagtaga    57900
tgagcagctg ggggctggca gaggggagaa gggggagcag ctgtctatga gatccagcct    57960
ttcttctggg tttggtgaga atgttttgga actagagaga ggtgatagtt gtacaacatt    58020
gtgaatgtac taaatgccac tgaatcattc attttaaatc gttcgttgta tgttgcatga    58080
attttaagtc aatcaaaaac aattgtttga aaagggaaaa gccaatgggt agtggcagca    58140
gtgattggat tcatgattcg attccatggc tatccctccc cttaccctcc agcgtcttct    58200
tcttttactc tgcactgtca tctttgttcc catctctctc tctctcaacc ctgcagacac    58260
ttttcccttt ctttgtctgc cttcaccctc cagatttctc tgtctcccta tgaggcatga    58320
gttgaggctg ggagggtatg attctgaaga aggcactagg agtgactcag ctagcccctt    58380
cccctcccag ggcctcaatt tagctacaaa accacaggga gggactcagg aggcagtgcc    58440
tttccaaggg tccctaaaaa atgtcccatt ttagtgtcca gtttcactca actttagcgc    58500
ttcccctaaa atgtgttcgt tacctccac cccactgcct ctaagtcact gcctgagaaa    58560
acaggattga ggaaaggaga aaggaagaga gagagagagg aggagagaga gaaagggagg    58620
aaggctgatg gacttagaaa agcaagaaaa caagtggtct gaggaaaaca gccttggtgt    58680 gtttatttc ctgtctgtgt atcgcttctc ggcctttggg ctaagatcag gtgtattttt    58740
ctgtctgtgt gtctcactta gattacaggg atctgtgggt gataacatgt ctggtccagg    58800
```

```
ctgcgtagcc acctcaaggg catgcttatt tatgtgtttt tcaattcact atctttgctt   58860
gggagtccca ggccaagagg cacagctgcg ccatttgtct attggtttag atatccttta   58920
tccagttctt ccagagaaat catcctgccc ttggctctgg aggaggtggg cagtagcggt   58980
cagagagggg agggaaagga aggagccagg tccctggcta ggatgccagg gtcccctgcc   59040
tctcacctgg cctgggctgg agacctcctg ctgtcctgtc actgatcacc accccgcccc   59100
aggctcctga gttagaagac acaggctaaa gtagactatc tctccattga aaaacccata   59160
caaaataaag gttcataaaa aatagaaatt tagaccaagt gctgtggctc acacctgtga   59220
tcccagcact ttgggaagcc aaggcaggtg gattgcttga gccctggagt tcatgaccag   59280
cctgggcaac atagcgaaac tccatctcta caaaaaatac aaaaaattag ccaggcatgg   59340
tggtgcacgt ctgtggtccc agctactcag cctgtggacc tacatagaat acaatgtcag   59400
cataagaagg gagccctggg gtcaccaaat ggtttggggg gcaaagaact tgaaggttga   59460
gagaagtggt ttggtcaccc agctgtcggt tgtgagacct ggccactgct tcttccatac   59520
cctagacctg caccctgaca tctcaggtaa aaagttgggg aatgttttat ggtccaggat   59580
gaaggaacag gcagtgaggg gcagcggagt gtcactttgc atttctgtct gcctggtact   59640
ggctgtgtga cttggacagg taacttccca gactcctggg aatcataata tctatgatga   59700
tgatgatgat gatgacacct acctcaagga ctgccctgaa gggtcacaga gatgcctgca   59760
aggcacctgc atggagcaag cgccccttct ctggcaggtg ccaggtaagc acctcctgtt   59820
gccaggccct gaggctatgg cactgagtga ccctgcaaat cctacctggc gaggctggca   59880
ttcttgtgct cagtcagtgt tggttgtaag accaagagga gtcacttcat tttgctctcc   59940
aggaacatct ttctgggtcc tatttttgc ctatgtcaag cagagcctca aggatgctcc   60000
tgaaaatggg cttgtcttta ttaacatggc aggtaggtcc caaagcatta gcatgggca   60060
gctgacctcc cccagccaat gcagtgcagt gactcttgca accgagtcta atcaggtcca   60120
tgaacctacg agcatttcct gtccaggact ggggtgaagg ctgagcctct ctgcttagag   60180
attcttccca tgcattccac tatttctccc caaagaaaag tattgaccct cgagaggcac   60240
acagtttatt tcttttgcat agtaaatagt agcctgtatt ttaaggaaga attgatttct   60300
gcatcagccc ctgtaagtca tcagccttct attggtgcat ctgactctct ctagctctgc   60360
agggtgttg gaggggagg ggaaggaggg atctttatta gaaaccagaa tagtgagatc   60420
cattgccctg tcatctgttc catggcgctg aatgaggcgg cccagcagtg aaacaccgtg   60480
agcgagcatc cccagcctgc agaacagtgg ggcactgccc cgagtcctag gaatgaccct   60540
tgattctcct gctcctgact tggaacccat ggaaacctgt agaagcagct gaggaaaacc   60600
caacatgaaa agcagaactc cacactgaga atataggagg tgatcggaac atacagtgat   60660
tcttgctaag actgattcac tgttttatt ttttttcgat tgaagaaata ctggagaagc   60720
ctaaagaagg agtctaaaaa ctctggccca tgggccaaaa ttgtccttgt gctaagaata   60780
attttcacat tattaaatga ttgaaaaata aaataagaat gttttgtgac acatgaaagc   60840
tatgtgaaat tcaaattcca atatctataa atagtgtttt atcagaacac agtcatgctt   60900
attcattcat ctttgatggc tgctttccca ctgcaaccac gttgagcagt tacaacgag   60960
atcacgtggc ccacaaagtc ttacaatatt tactatctgg cccttccag aaaaaatgtg   61020
ctgactcttg accttgacct cagcactttg ggaggctgag gcaggtggat cgcttgagcc   61080
ctggagttca tgaccagcct ggacaatatt agtgagactc catctctaca aaaaatacaa   61140
```

```
aacattagcc aggcatggtg gtgcacacct gtggtcccag ccacttggga ggctgaggcg   61200
ggaggatagc ctgaacccag gaagttgaag ctgcagtgag ctgtgatagt gccattgcac   61260
ctcagcctgg atgacagagc aagaccttgt ctccaaataa ataaataata caaagtaaag   61320
taaataaaat aatataaaaa cgaatcaatt taaaattata atgaaagcca aggggcatag   61380
tagaacaaat tttctagagc tcattaagtc aaatgagtca ccagttagta aaacgcagtc   61440
aggggaaga gagggcagga ttctttgaag cagcggctct cctaaaaaca gaacccaccc   61500
ttgtccagct gccttccctc ctgagggtgt tcccttttgac catgtgaccc ccaccccta   61560
tttcccagcc atccaagccc acctctagca taatacgagc ttctaatccc tctccctgac   61620
cccatcccaa ttttgaagcc cagtctagta ttttctcaac tatacttctt ggctctgttc   61680
cttcctttct atcacctctg ccttttcact gcaagcttgg accactgcag tcacctccct   61740
accaacagtc gttccctacc catccagtcg gccccgcctg ctgctgcaaa attcacctag   61800
ggcacctctg tggtgctgcc cctgcctgtg acaaagtcc aagccagcca cctcacccac   61860
ctacaggtga gtggggagca gccagcgtgt ccagtggttt accccatcgc cacagacttg   61920
gtgatgtatt gatgtgcaga gaaggggtgt tcgcagccac aacacaagca atcctgcccc   61980
acgtgggacc taagatggac atgctgcaag ccacctctaa gaatccaaca taaggcagag   62040
gggagaatgg ctcacacggc acaaacactc ctttttgttt tgttttttt cttttgaga   62100
ggagtctcac tctattgccc aagcaggagt gcagtggcac aatctcagct caccgcaacc   62160
tccgcctccc aggttcaagc gattctccag cctcagcctt ccaagtagct gggatttcag   62220
gggtgcccca ccacacctgg ctaattttg tgttttggt agagacgggg tttcaccatg   62280
ttggccaggc tggtcttagc tcctgacctc aggtgatctg cctgccttga cctcccaaag   62340
tgctgggatt acaggtgtga gccatggggc ctagcctcct tccattttaa tgtatgccta   62400
atctgcccat tgagaatggt tgagacacat tttaggtggc cagggtctac ttagagttag   62460
tgctcatgat caggcccagg tccagcctgg ctggccaaat ggtgcctttg acctgctatg   62520
gctctgtgca aaggaatgag ctgatggatg ggggcgcagt gtgtgggcag tgggctgggg   62580
ctggcaggac tcagtgacca agggaagaga actttcctca ccaccaacct gtcttttcag   62640
ggcactgcag gggggctttg ggacttggtg atgaacacag catagtgagc tgtccagcat   62700
gtgggctcct ggattctcac agttcccggg ctccttcaga ggctctctct aaagagagct   62760
gctctctcta gaacccacac atttagaata taggcaacca ctgcaatggg gacaactgac   62820
ctcaaacata gagaccagag tagatggggc tcatcgtgtg aaactcatct tgaactctag   62880
cagcttcttt tcacaagttc atggagagag gttttccact gagggaatca catctgtctg   62940
atcaaacgag gcttgggaaa tggctctcct gttcattccc tggaaacctc tgatggaacc   63000
actgccactg tggcggcccc ggcactggca ccccagccat gattggtgcc ccagccacat   63060
ctctgctgtg agccctggtt aattaatcat ccgtgtgttg acggggagag gcccgttcac   63120
gaaagcggtg taaagcccag ggcgatgtgg ccatggcagg aagggtgcgg gactacgttc   63180
cacccccaac tgagagattc agaaaccaga agaaaatgga aaagcatact gtgctcttgg   63240
gtgggaaaac taaatatgaa gagagcaatt tttatagtgt tggcctataa tacaattcca   63300
gccgaaatcc caatggagct ttgagaattt gcaggaaaaa aaaaattcta aaatatatct   63360
ggaagacaaa acttacaaga aggtttcaaa ataatttg aaaagaaaa tgatatctga   63420
gcccacctag agaataagac ttgagatcca aagcttaaat caggaggctc tagcaccaaa   63480
actgacagat aaacgggaca gagtacatgg tgcattgacc tgggaaagag ggcagattgg   63540
```

```
tctgcaaata ggcctgggtc cattggcttt agctgttgtg tttggggaga aagttttcaa   63600
cctcactcca tcttaaacct aaaaatattc cagatgaatc agtaaatatg aaaaattaga   63660
ccactaaaaa cctagaagaa aatggatgat ctttctgtac catagagcaa tggaataaat   63720
cacaaaggaa aacagatttg actatataaa aattaaaccc tgcctatcaa aaaccatcag   63780
aaaccaaaat aaaaggcaac caactggaga agacagttgc cacaaatatg atcaagggtt   63840
aatgttattc ataaattaat agtccacaca agtcgttaga atgagcactg agacctgaac   63900
agagaagcaa aaagaatgtg agggggtcag cgcggaggct cacgcctata atcccagcac   63960
tttgggaggc caaggcaggc ggatcacgag gtcaggaaat tgcaactata tttttttaatg   64020 catagactaa gaggctagag ggaaatatca cagatcctta acatacattc ccaaacccttt   64080 gtaaatccac agattcatga aaacagacac gtttgcgcaa gtgcctgatc tttcctgtta   64140
tacattcatt agaagtcaag ccctcgtacc acacagtatc tgccttttca aatgtgatca   64200
aaatgttctc ttttgcttca aggccatttt tcataaggca atggcatttt tgcctcttca   64260
tcagagtcac tgtgtgccct ggaggactga aaacagcaga gccgtgttgg gatgggacag   64320
ggcagctggg aagattgggc tcattcccta ctaaatgcct cactcctgta ctgccccccat   64380 agaggaagag gggttcaaat ttattcctca gccagatggc atgtgccccc tctcctggaa   64440
tctcacgtca cttatgatgg accaaaattc caaaagctga atccatgact gtcaaagtct   64500
ggtatggcag gatgtcaaca gtaatcattt ctgggcagag ggatgatttt ctcttcccat   64560
cttgctttgt ataaatacat tttctataat aagattgtat tactttctc atgaggaaat    64620 agcaaagtac tgttttactc aaaatatgaa tagagccagg catgctagca gcttatgtca   64680
gtaatcccaa cacttttgga ggcggaaatg ggagggtcac tttagcccag gagtttgaga   64740
ccagcctggg taacatagtg agaccccgtc cctcctcccc ccaaaaaaat ctacaaagca   64800
tttatcctgg attattcaca ggggccaaaa aaaaaaagaa aaaaaaaaga aaattcaggc   64860
ctcttatagc catgagctat gaatatgaaa atatgcaaat gtgaaagaaa gccagcaca   64920 tctgagttttt acttttactt tcacacctct gtctaccata ttccaagagg agaaacttgg   64980
tcattgaaag gaatcgatca aatccaaaga acaaaactac tgtgttcatt aaacttctta   65040
gtgttcacaa gctttagct gcaggttgaa tgggacaccc cgaattgggc tcacctgggc    65100
tgcagggagc agagatagca ccactgcact ccagcctggg caacaaagcg agactctctc   65160
ttaaaaaaaa aacaaagttc agaaattcaa agttgtgagt tattttttaaa ataataataa   65220 ttataataat aaattcacaat aaagatgagg acaaagtgtg agcaaatggt ggtttctgtc   65280
cggctttgtt gagctgaagc agcctctccc tgctgggact tttggggaaa aagggtatgt   65340
gttgctcttc agatcccaag cctcatgccc ctactgggcc ctgtgtggtg cttctcagca   65400
cactgggaga gccaccgttg gaacgcacac ctgggggacc tggtgggtga cggtgcggtg   65460
agtgggggcc acagcctgac tccagggaag ccagcgagct cagagctgga ggagtcagga   65520 caccctgat gggtcaagag ttggttttgc tgccagttgg catctgattg aaccatccct    65580
tcacttctcc gtgcctcact ttccttacca gacgtgctct gctgatgcca ttctctcctg   65640
ttcagtccta ccttcaccat tgaagagaaa gagcaaactg ctaggcagca gcattgattt   65700
ttttaaggaa gtggaaagag agctgggaat aacaagtcag gctcacctcc cctacctcac   65760
ctggtgggtt tgtttgtttc gttttgtttt tgttttgaga ctgagtttcg ccctgtcacc   65820
caggctggag tgcagtggtg taatctcggc tcactgcaat ctccacctgc caggttcaat   65880
```

```
tgattctcct gcctcagtct cccgagtagc tgggattata ggcacctgcc acacgcctag   65940
ctaattcttg tattttagt agagatgggg tttcaccta ttggccaggt tggcctcgat     66000
cttctgacct caggtgatcc acccacctcg gcctcccaaa gtgctgggat tacaggcatg   66060
agccaccatg cctcgctctc acctggtggt tttgaatgtg aactgaatgt gttggtaaat   66120
taagcatgcg gatagacgta ataacactt gggcaggaat atggagcaag ggatgaggat    66180
gggtgcccag ctgttggaga gggtgatggg gaggctgcga tctgcctgcc atgaactggg   66240
aggaggggct cctctctctc ttcacccca ctctgccccc caacactccc tagaacttat    66300 cctccctct tctttcccca ggcgagcctt gaaccaggat ggctgagccc cgccaggagt    66360
tcgatgtgat ggaagatcac gctgggacgt acgggttggg ggacaggaaa gatcaagagg   66420
gctacaccat gctccaagac caagagggtg cacggacgc tggcctgaaa ggttagtgga    66480
cagccatgca cagcaggccc agatcactgc aagccaaggg gtggcaggaa caatttgcat   66540
ccagaattgt aaagacgttt taaatacatt attgtcttag attgtcagta gagtgaaacc   66600
tcattaattt gagtgggcca agataactca agcagtgaga taatggccag gcacagtggc   66660
tcacgcctat aatcccagca ctttggaagg cccaggcagg agaatcct gaggccacga    66720 atttgagacc agcctgggca acatagcaag accccgtctc taagaaaat ttaaaatta    66780 gctgggtgtt gtggtgcatg tctatagtcc tagctactca ggatgctgag gcggaagaat   66840
cacttgagcc caggagttca aggttgcagt aagctgtgat tatgaaactg cactccaacc   66900
tgagcaacag agcaagaccc tgttggaaaa aaaaaaagg aagaaattta ccttgagtta    66960
ccctcatgag tgaatgtacg gacaaagatt gcagggctt gacaatcttt caaatacagg    67020
gtactttttg aggcgttagc cacacctgtt ggcttataaa tcagtagtat tgattagcat   67080
gtaaaatatg tgacttttaaa cgttgctttt tatctcttcc ttagatcagg cctgactggc   67140
ctctctttag caagagttgg ttagccctgg gattcttact gtagccacat taataaacga   67200
catcaacttc taaatattct ataataccat cttttgggca aattgacttc gcctcttcct   67260
ttctctttcc aaatgaaatg tttcatttca ctgtcagacc acatggtccg ggaccccacg   67320
gagcacacag ccttccctcc gtctccccat gctggccctt cacccactgc tggagtgccg   67380
agttggtcca agggttggac caagttctca ggttgtctca aggttggtcc aggctgtctc   67440
agtgctggct tgtgctacaa ggagcccttc ttcccacggg tgtggcagtg agtgctcaca   67500
gcaacagccc acggtgcagc ccgagggcag ggtggactca gtccctgcct ccatacccat   67560
ttctaagcaa gcaaaatggc aaacactcta ctttctctt ttaatgctaa aaataagaaa    67620
acatgctgca gcccagggta tgggtagtgg atggaagcca tggagttcca aggtgggaag   67680
tgacctctac tggatgcgtc tattcaggaa gatcactgga gtgggtgggg tctctgggag   67740 gtccctgat tgtgggaagc tgggaccacc agctttctca cacagggagt ggccatccca    67800
gcttggagag gttccaggac tggtttcgac gctcgtttca gatttccatc tgttgaatca   67860
gggaaggtgt tggattatga ggaatttggg aattaggaaa gtgggtgcag gtaggttggg   67920
gggaggtgaa ggaagacatg ggcacattac aggaacaggg gctgctcaga ggtgtccgag   67980
aagctctggg tgaggaggtg agaggagag gggaatgcag cttggcgcag cctccctgcc    68040
tgaggtcagc catcacgtgg tgatggaaag agggaaatgt gctttctgac ggctccagcc   68100
agtgctgcca gattcagctc cccagggagg gcagctgagc ggctccaagc taggagatct   68160
gttttctcct ttgaatcctt cttagaggct gggcatggtg gctcacgcct gtaatcccag   68220
cactttggga ggctgtggcg ggaggatcgc ttgagcccag gagttccaga ccagcctggg   68280
```

```
caacataatg ggacctcgtc tctacagata ataatttta aaattacctg ggcatagtgg    68340
catgcaccta tagtcccagc tactcaagag gctgaggcag gaggatcgct tgagcccagg    68400
aggcagaggt tgcagtgagc caagatccca tcactgcact ccagcctagg caaaagagtg    68460
agactcccat gtccaattat aataataata aataaatctt tctcagtccc ttcctcactg    68520
tgtcccccte cactaaactt ttccaccacc tctcccactt ccctcgctcc cgctttccct    68580
ctccttctct ccccactcca tcttttttctt tctctgctgt ttcccacccc ttcctcctct    68640
ccatcctgca acactgccta ccctgtcccc gccccaccct ggtgctcagg atgtgttaag    68700
tgagggtggt agcctccaag acctcaaccc cgaaggttag cctgttgaaa ccactctccc    68760
agctgcccct cggcagttgg tgctgttggg ggaaactggg attgggagcc tcttttcctg    68820
acaaagagat gaagagttcc ctcaccaggt gcctgggact ggggtgtggg tgtcacagcc    68880
tatcccagcg catctgtttg catcatgatt aatagtgcta ctttcaactg ggggcggtgg    68940
ctcacgcctg taatcccagc actttgggag gctgaggtgg gtggatcacg aggtcaggag    69000
ttcaagacca gcctggccaa catggtgaaa tcccgtctct actaaaaata caaaaactaa    69060
ccgggtatgg tggtgggcgc ctgtagtccc agttactcag gacgctgagg caggaggatc    69120
aattgaacct gagaggtgga ggttgcagtg agcctagatc atgccactgc actccagcct    69180
gggcaataag cgcaaaactc catctcaaga gaaaaaaaaa atagtgctgc tttcagcctg    69240
ggcacggtgg ctcatgcctg caatcccagc actttgggag gccgatgtgg gtggatcacg    69300
aggtcaggag tccaagacga gcctggttaa catggtgaaa ccatgtcaag agagactcc    69360
ttctctctct ctcttttttt tttttttttt taagacagag tttcgctctg tcgccaaggc    69420
tggagtgcag tggcaccatc tcggctcact gcaacctccg cctcctgggt tcaagcgatt    69480
ctgctgcctc agtctcccaa gtagctagga ttacaggtgc ccgccaccac gcccagctaa    69540
ttttttgtatt tttagtagag acagggtttt accatgttgg ccaggctgat ctcggactcc    69600
tgacctcatg atctgcccac ctcggcctcc cgaagtgctg gctttacacg cacgagccac    69660
tacgcccaat caactccttc tcaaaagaaa aaaaaatagt gctgctttct ctttcaagtg    69720
tcctgatttg agtgatagta aatgccaccc tacttataag ggaactacct cagaatgcta    69780
attgggacat ttttgtagca ctctactatt ggcaataggt gatgctcaca acagcccgtg    69840
agggtggatg acatccactt cacagatgac aaaggagcct cgtggtcaga ccgtgggctg    69900
ccggagcagg tccatggctg cagccccaca tgggccatat ttccccttg tcactgtttc    69960
caccaagccc ccttggaact tcagttatta aactctcttg ggtggaattc aagttagaat    70020
cacaacagat gcctcatatg aattgtgcca gtgaaaaatg acattctatt tagaggcagg    70080
gcagcctggc ttagagtaag tttaaaatat gtgttatgct gcagcaaatg taccatgatc    70140
ctgtaagatg ttcacaacag gggaactgga tgtggggtat attctctgta ctaacttcgc    70200
aagttttcta taaatctaaa actgttccaa aataacaagt tccttaaaaa ttaactccag    70260
gagaccagat gcagtggcta atgcctgtaa tcccagcact ttggaaggct gaggcaggtg    70320
gattgcttga gcccaggagt ttgaggccag cctgggcaac gtggtgaaat cccatctcta    70380
caaaaaatac aaaaattagc caggtgtggt ggcgcactcc tgtagtccca gctacttggg    70440
ggactgaggt gggagaatca tctgagccca ggagtttgag gctgcagtga gctatgatta    70500
taccactgca ctccaacctg gcaacagag cgagaccctg tctcaaaaaa caaaaatgaa    70560
ataaagtctg ggaaagaagt gggttttacc actcttattt tctgaagaga aactaaattt    70620
```

```
aatgtgtaaa gtgaggacaa gttcaccaag ttagtgtttg agttgcctaa aatatgtttg    70680
ctaaaactat tcaatgcttt cacataaaac atgatcagaa gttctatgcc aaaacatatg    70740
tgtgtgtgta tatatatatg cactatatat actgtatgca aaaatgcaaa atctaaattg    70800
ccaacctttt tgaaactgct ctgaagggaa agcatttgaa gataaattgc ttacccaaag    70860
aacatacttt ccaagaaagc aagtaatact taaggtgttc atagtcctca tcaaattaat    70920
tcttgctact gaaagcttac aaggagctgt ttttatgtcg ggtgtgacag gtttgacttg    70980
gcagaaggtg tcactttact aacaacattt taaataagtg acagaagaca agaaactaca    71040
tgttaaatac cagaacaaag agtgtctaag tggatgctaa gagttgaaat atggctggat    71100
acctgcccaa gacagctgaa aagtagatga aagttggtta cctataaact agtgcaccct    71160
aatgaattaa aaggtgttga tgagttaact tgttatgcct tccagataag acatgcaaat    71220
ggggcttctt cctccttccc tccttccaag gaatttaaca aggagaccaa tgcaaatgat    71280
aagaactgta gggctcaagc tgggaacaga ttggggaaag ggggaccatc atgcccatat    71340
agatgcccct gtgccctggc agtcaaggct tctgaaaaat aacgaaaccc agaagtctgc    71400
atgatgctgc cttatcattt gtccaaagcc ttcttgcggc agtttgcagg ctcttgcgag    71460
ctccaggacc aaggagctat gttcgtgctg gaagcttgtt taggacgagc tgttctttgt    71520
gggatgggtg cagccaaggc caggtgtcca gggatggtgt tttaacaaag cgtgtgaggt    71580
gtctgatctc acagtgcact tgaattccac ttgcattttt ttcatcttct cattctgttt    71640
catgcacaga accagcccca tcctgaaagt gactctaaat tactcctgcc ccaggtggag    71700
tgcctttctc agagttcaac agagccttcc tgtcgcccaa gggacaactc cactgaatgc    71760
ccaggcctaa caaataaaaa ccaaactctg tgctccccca tcctgggcca ttactggttt    71820
ctctactgct gttggtggta ccaccatcaa cttgtccatc atgaccctgg ccagttcctc    71880
ccacaaccct ccacagcacc cagggacctc acctccattc catccgacac agacctcctc    71940
accacaaacc ttggttttgc aacagcagcc ctgagacctt tacaccctcc tcccttcatc    72000
ctgtccccca ccaaggcccc agagccattc cttaaagcag ggctccacaa actatgagcc    72060
acaggccaat tctggtaccc agcctgtttt gcacagccag tgaactgaca atgatctttt    72120
catacaacca gaaaaaaaaa aaaaaaagc ccaccattct gagtatgtga cttccatgtt    72180
caagatgtct catgttcaga aaggcccctg gaaaaggagg aagggtatga gctgggcaca    72240
aagggagacc ctctcagctg agctcctccc atccagacat tttcctggac ttcctatcca    72300
atgacttccc ttagcttctc atcagccacc cctgcctgcc caggaagctg gcagatgtgg    72360
ccttttaact gggcacagct ctgttctata tcatatcagg gctctgttcc caaggaaggt    72420
agagagaatg gacaccaggt ggaccctcag cagtctgtgc cacagaggga gtgtttgcag    72480
tttccacact aaaagtcccc atgtgcttga cgggatctgt gactacaacg tgatgcttga    72540
cttttcctca tatgaccaga gccactttgt ccatctggtg caatggtcag ctacctgcta    72600
ggggccctcc aggattccca gttgattcca tatctgcatc accaccatca gcactaaata    72660
aaatactcaa gttcctgctg gtgagcatga gcagtgctac attgggccct tcaaccaagg    72720
tgacaaggac tgaaaataat cactgccact tattgggggc ttctcatctg ccaggcatgg    72780
tacaaagtgc tttaaataag cattcaacag tttcatgctg acagaagccc tgtgagccag    72840
tggagctact tccatgccca ttatacaagg gagaaaactg aggcagaggg aggttaggta    72900
attcggtcag catcacacaa ccaataggtg gtggagccag gatttgggcc ccatctgcct    72960
gactctctag aggctctgat ctatccagag ttgagtctaa gccatgaata gggcaattag    73020
```

```
aaagcagagg aaacccattc agccaccatg tgcatgagag tgaggaattt ctgtcataca    73080
gaggggagtg aattcactga gctgagagct gaggaaccac tgatctgatg gctgagacac    73140
cactgggaag actggagagg cttttctggg catgcattgc caggcacagg agaagctgag    73200
ggaagatgac taagaggtac tggcaaagaa ctcagaaatt ctgatggaag ctttacatgc    73260
taccatcaca tccatccatc tatccaccca tccatccacc catatcttcc tccatccacc    73320
caatcataca tacatccagt catctgtaca ccacccaccc atccatccat ccatccatcc    73380
atccatccat ccatccatcc atccatccat ccatccattc cttcatccat cccatcatcc    73440
atccaattat acatacatcc aatcatatat atctgtacat catccattct ccctccatt    73500 catccatcca tccacccatc ccttccttca tccttctcat catccatcca atcatacata    73560
tatccagtca tatatctgta catcaccagc tccatctatc catttatcca tccatccttt    73620
ctttcatcca tcaatcatcc atccatcata catacatcca accatacatc tctacatcat    73680
tcattcttcc atcgattcat ccaattatcc atctattcct tcctgtatct atcccattat    73740
ccatttgatc atacatacat catctataca tcatccattc atccaaccat ccattcatcc    73800
atccatccat ccacccatat cttcatccaa tcaatcatac atacatccaa tcatctacac    73860
atcacccatc catccatcca tccacccatc catccaccca tccatccatc catccatcca    73920
tccaatcatc cagtcgtata ttcaattaca catccatcca attatacatt catacatgca    73980
tctaatcatt caattataca tatacacatc catataatta tacatccaat catacctcta    74040
tccaattata cattcataca tccaactaat aaattattaa ttcatatatc catccttata    74100
attatacatc catctaatca ttcagtaatt cacccatcca tccagtcatc tatccaataa    74160
tacattcatc caatcatcca tccatccatc cacccatcca tccatccacc cattcatcca    74220
tccatccatc cacccaccca tcatggtttg agccatgatt tactaccatg gtccactgtg    74280
gacagcccag gtgggattga attgaagaga agcccagggc tgcccccata aacatttggc    74340
tcctttacat cgatgagaac tagatccaca tgtataaatc ctcatgattt gaaggtgctt    74400
ttaccaacat tcactcatgg gattctccca gcagctctag gaggtagagt tgaggtcatc    74460
tcacccattt tacaaatgag gaaacagagg ccctgagagg caggtccaag tccacctgac    74520
cagaaagaag tggaactggg acttgaaccc agccatcttg ccccttggtc ccgtgctctc    74580
tagcctataa ctcccgcttc ctggtagggc acctccagga ggaccctatc ggctggcctt    74640
gggcctgcct ttgagtcttt tgctgtgtgt ggccatcctt cctccctcag gagagtgtgt    74700
actcccagag cacagactgt atcttctgag cattttgtcc cttcccagta cctagcactc    74760
agctctgtat acatcaggct ctcaagaagt ctcaagcttc cagagggtaa ggtcttgacc    74820
tgctctgccc cggatactgc aggatgcatt gataagccca taaataaccc agggcagatt    74880
gactcccagt ggccaaagta ccacagggaa gggacaattc agtccttcta ggaggaggaa    74940
gtagttttct aatttctatt aagccaacaa aagctgcctt actaagggca ttattggtgg    75000
agggtgtgac tgtcaaccac tgtgatcatt tgggcctctc ttgcccaagc ttcccattct    75060
gaaaggacag ttttcttgta ggtacccatg gctgccattt caaatgtaac tcacagcttg    75120
tccatcagtc cttggagatc tttctgtgga cgcttgatgg catccaaaca ccacctaatg    75180
tccacttaga agtaagcacc gtgtctgccc tgagctgact ccttttccaa ggaaggggtt    75240
ggatctctga gtgttttcct aggtgtctgc ttgttaatta atagcaataa acaaagcaga    75300
aggttcatgc gtagctgggc tttctggtat ttgctgcccg ttgaccaatg gaagataaac    75360
```

```
ctttgcctca ggtggcacca ctagctggtt aagaggcact ttctcctgtc acccaggagc    75420
aaacgcacat cacctgtgtc ctcgtctgat ggccctggtg tggggcacag tcgtgttggc    75480
agggaaggag gtggggttgg tccctttgt gggtttgtca caaggccgtg ttccaactgt    75540
ttccatgggg agcaattttc agctccacaa gacactgctc cccagttcct cctgagatta    75600 aaaggggggcg ctggggagag gccgccgttc tgaggcctca ccatgtgtgt tccagaatct    75660
cccctgcaga ccccgctga ggatggatct gaggaactgg gctctgaaac ctctgatgct    75720
aagagcactc caacggcgga aggtgggccc cgcttcagac gcccctcca tgcctccagc    75780 ctgtgcttag ctgtgctttg agcctcctc ctggctgcat ctgctgctcc cctggctga    75840 gaaatgtgct cactcattcg gtgctttgca ggacagtgtg gcgggagctg agccctgctt    75900
cgatgccttg cttgctggtg ctgagcgtgg gcaccttcat cccatgtgtg ctctggaggc    75960 agccacccctt ggagagtccc gcgcacagct ccacaaaacc ccgctccata cgattgtcct    76020
cccatacccc cttcaaaagc cacctcttct ctctttcttc aggggccagc aggtcccaga    76080
gcagccattt ggctgaggga aggggcaggt cagtgcacat ctgatcttgg cttagtatct    76140
ttcattttgg gggttctggg tgtggcctgg gcctctggac tttggccacg atgtttgttc    76200
cggcccttct aacctgtcct ttccagacac tcagcatcta ggttattagg actcacatac    76260
ttcctgacgt gctcctcagt cctgattttg accatcttct cttgcttccc atctgtatca    76320
gtcaagactg catttggctg taagaaacag aaaccccaac taactgtggc atttacatga    76380
agaggtttac ttttctcaca taatcagatg cctgaacttg gccagcacct caagggtcac    76440
tgatgctctc ccgtctttat tttctgtcat ctttagtggt tggattgttg cctcatggtt    76500
acaaagtggc tgctgcactt ccaggcatca catctgcctt tgaagcagga atgagttgca    76560
aagtaaagtg gccaaaaggg ccctgaaact aaatgcgtcc ccttaggaaa acaggagttt    76620
tcttgcaagt ggcagtcttc cacttatgtc tcatcagcca gagctgggtc ttatggccac    76680 ccccttgctgc aggcaaggct aggacattga gcattttgcc ttccagcctc tttagcagaa    76740
taaatcaagg gagaagaatg ttaataatgg ctttcaagtg actagttggc agtatctgcc    76800
cgtctgtctc tccatcctcc ccttggaggt tcaaggttcc tttcttagca cttcttcagg    76860
ctctgcacat tcatttggat cttgtgtctt ggggtgaaaa acttgcccaa gtgtctctgc    76920
aagcatctac ctttgatga atttggaaag tggctgtcaa gtgcccgccc cttgcttggt    76980
acaatgctgc atctttagag gatgcagcag gcgtgggcct tgctgctgag gttcttagcc    77040
tcataagaat atccaggtta gattctcttg gctccttctt agagctagtg atgcaagaca    77100
cttcctgttc atcttgtcgg gatggttttg caagttgcct gccatcctga gaaagtctac    77160
aaaacgatgc cagacctcat gccagcttcc caagccttgg ctctcagtgc tccctcaaca    77220
gtctggaaga atctcccaaa caagtctcaa tgccctctgg accctgtgca ggcgtgagac    77280
tcaagagcac tggctcccac ccctggtgga gggagccctg ctggggctgg atcttgcct    77340 ggttgctctg cctgcaccca agacaaccat aattaaaatg tccttcattg aacttggaaa    77400
gccttcaaag ctgacaactc cttacgtgta cctggagtgg cctgggagtg tgccagggca    77460
ttgcttgaga ggaacactga tttgaagcg tttaccttga tgagagactg acagcagctc    77520
ctggtagccg agctttccct cctgcctctg ctgtgaaggt ggaccatgc gacagtcaaa    77580 tgcctgactt tggataggac cggaccatt tattgccatg caaggactc tgcatttttg    77640 aattatgggt catgggcttg gagacagggg ttagagctgg gagaagtctt ggaagtcacc    77700
tagagaagac actgccattt tgcagatgag gaaactgtcc aatcaaaatg gaccaaggat    77760
```

```
ttgcccaaag tctcacagca aaaccatagc ccccgcccta accccccccag tccccgtgct   77820
gtctcagttg taattctcgc cttaaggatc aaatagttat gagcaatcat ctggttttca   77880
gtattctttt aaaatgcctg gggccatgcc cagcagtccc tttcactggg gtttagacag   77940
ggctgccggg ctttcctggt ggatgagctg ggcagttcat gagccagtag cactcagcag   78000
catgtcagtg tgcttcctgg ggagctggca gcaggggctt caggccctgc ttcagggctg   78060
cttcttgca tatggctgat cccctcctca ctcctcctcc ctgcattgct cctgcacaag    78120
aagcaaaggt gatgggcatg gctcatcctg gctcctctaa ggtggttctc ggtggtttcc   78180
agatgtgaca gcgcccttag tggatgagag agctcccggc gagcaggctg ccgcccagcc   78240
ccacatggag atcccagaag gaaccacagg tgagggtgag ccccagagac ccccaggcag   78300
tcaaggccct gcccggtgcc ccagctgacc tgcgacagaa gtgagggcac tttgcgtgtt   78360
tatcctcctg tggggcagga acatgggtgg attctggctc ctgggaatct tgggttgtga   78420
gtagcttgat gtcttggtgc ccagctacct ccctggctgc ctgccagcct tcagagcat    78480
ttagggcctt ctggacttct tctagacgct cctcatcttg cctcagtcag cgcatcagtt   78540
ccagggagtt ctctgcagga ttttctgggg caggtggtgg cagacccgtg ccttcttggc   78600
acctgaggtc agccacccctc ctgctcagac tgtccggcac agggccacct cccaaggggt  78660
ggacccaaag atcacctgag cgcacagagg gtgcagatga ctggaccgca tcttttggtg   78720
atcttaatga ggtggtccca gaggagctga gacatgtgat ctagcatcca gttctgggac   78780
tctgtctcct tttcaaacat attcgtgtag gacaggcatg acgagaatgc cttgtcaaca   78840
cgggtgatgg ggaattgatc ggacagggcg ctgggctcaa ggctgcagtc acccaagagt   78900
ggctcagctc cccaggccct aggaaacgcc cgcacagcct ggagctcctg gagtcatttc   78960
cttcatgtct cttcactgca cttacgtaaa gatgccagcc attggtctgg tgatttggag   79020
ggtgcccagt tgcccaacaa gaaatgcaga agaggcctag acaggatttc atcagcaatg   79080
gagagcaggg aagatgtgcc cagaaaagag tttcttttcc ttcctaaaga tggtgctccc   79140
tgcagctact ggggaagcct gcagcgttct ctagggctct gtgtgttgag accagcccca   79200
ccctggcccc ttctgagtgc atttctgctt tgtgacttga tccgtgaggt cccctgagat   79260
gggcagaggg gatgtcctcg aagctggggc agagcctcat ccttgaacgt gaaggatgtt   79320
tgaagaccgt ggcacgatca cgggatgcga tcacggggaa cttcagtttc tctcctcctc   79380
tcccttcagt tatttcactg ggggaaatcc ctcccctgcc cagaatgaaa actctagcca   79440
actcttgact tttccatcac tccaaagtaa ttgaaagtac gttagtctcc acagtggcaa   79500
aacacagtgt gcaaatgcta ataattaga acagccagtc ccatgtgaca gtcaaagctt    79560
ctaactccat tcaaagttgc cgccattccc cttgggggct ggcggggaag ggaggggtag   79620
gagaaacagg aaggttctta ctgagtcggt cctggtgtga gccatgtcac actccctgca   79680
taggtttcaa ggagatactc tttctctctc tctccatggg gaccttatt gaattcttct    79740
agactcttcc cccagcctgc catctccagc tatcctcccc tgaagagccc ttcctctgca   79800
ctggattctg gtggccgtgt catctccggcc ctgtgggagt ctgaagatct ggctgcagcc  79860
tcacctctga ggtcctgctg gttgccacct cttagacatg atctgaggct cccatgcact   79920
ctctctgacc tgtgcccaca tggggcccac gggaaacatg ctggcaagca aactgtgggt   79980
gtgcggacag ttctcaggac tgtagcatct gtcctttgct ctgcccccaa agcaaggcca   80040
gcccatcttc catctgagaa tgggcagatt ctcagtgttc cttggtgggg ccctgatcat   80100
```

```
agaccaccag gtccctaacc agagggggaca tgcaccacat gtcctcaacg tattgacttg    80160
aaacattgta ctgggactgt gatggggggtg gccatgtagc cactcccacc accccccaagc    80220 cactctctcc aaggaaatcc tcctaaagat ccctttacac cctccgtgtg gtgggggtggt    80280 tctagagttg ggtgcatgtg tcttcagcta ctgacaatgc agaccttagt tggcacctcg    80340
ctctggccca tcctatttgc tgttcttggc actccagtga aactccccat gggccatcca    80400
gttagggtgc agagtggcca ccccccttgca ggatcctgcc ttgctggaga gcacagggcc    80460
ctcctggctc ttgtaaaaca ttccgcaggg tacagagagg ccattggtga tgtgaggtcc    80520
aacctccact gtgccctccc tccctccttg ttgtttccaa gcagctccct tgctggggtc    80580
aagcggtggc aaagacagca cagcctccaa tttctgactc acgccaggcc cggctatcac    80640
agctctgcgc tggtgtgtga cagcaaggtg actcacccag tgccgtggca gtgacagtgt    80700
ccagggaagc ctccacatgc tctctgtctc aaggactctg gcatttagtg ggatttgctg    80760
tcactctgag cctttctacc attgccatca ccttgtcaga aactcaggcc gaatctgcac    80820
tcagagctgt gcccaggcag ttgagccaac actcgctcag tgatgttgtt gcatgacaag    80880
gcactgtcac cactgggcct cgtgggcagc gcagtgtcgg ctggatggac ccggagggtg    80940
tctgtgtcat gctagtgcta gtgatgggag ccccctgagc ccattgccta ccctcccatc    81000
cccttagcag ctgcctgggg acagccaatg gcctgggtgt ttctgaggct accacatggc    81060
taccaggaac ctcgagaacc tttctctccc ttgcctacag tcttcacaca ggcctgtgct    81120
ggccagtggt gggggatccag cattcctgtc ttaggtgcag agagtgactg actcattgca    81180
ggcctgggag ataagactga tggcccaacc agcaacatgt atgcatttct cagaggcagt    81240
gacctctatc actgccctca ggaaatgctg gtgattctgg tggcctgagg tcaatgcatg    81300
tcaacgtggc caacttgcct tataaactct tcttctgaac aattgcatgc attgtcctgt    81360
aacagtgtcc tgttgtttat gatgcagaaa ttggtgtttt taaagcacgt tgattttggt    81420
actattgatg tggtcaggaa ctttctcagt cttttcttgtt tggggtgagc tgtggcttcc    81480
taaacaggaa cccaagatac ccccaaaaac tgctcagtag cactgccagc tccctcttta    81540
ccaagtagca cccattcagg gcattctgtg aaaggcattt acccagaagt tgggaggaag    81600
gaaacgtaac attttggggc acctaccata tgccaggcac caggctaaac gtgttcacac    81660
aaattctctt actaaccctc accatccttc tacaagacaa actagtatct tcatctgggg    81720
ttctagatga ggaaatggag gctcagagag gttgaatgaa tgctggtgcc tggatacgaa    81780
ctccgtctgc ctgactccac aacccaggca aagtctttcc ttgaacttcc cagcagccac    81840
tgcttagaca cagtctccac gaccacggct cagcagcaaa ctgcttctct gacctcactc    81900
agcctgtgtg tccttgtgga gtggggcatt cagggcccca gtggagaaag tctttcctac    81960
taggtcatag ccacacctgc atgtgggtgc tgtgcatttt acttagtgaa cttttaccac    82020
cagcatcctc agcaatgaca tttgcagaga agccagagct gaggcacctt agtattcttg    82080
ggacgtgact ttcctgaatg ttttagggaa ataccagaa gacacagaga gcttggtttc    82140
tagcaaacaa taactgtttt gcttttaccc cccttcattt gctgacacat acaccagctg    82200
aggaagcagg catcggagac accccagcc tggaagacga agctgctggt cacgtgaccc    82260
aaggtcagtg aactggaatt gcctgccgtg actttggggt tgggaggagg gacatggggt    82320
gggctctgcc ctgaaaagat catttaaatg gacccgagcc ctaattcaca aatccaggag    82380
attctaggga gttggttctt atcaaaggtt ggctactcag atatagaaag agccctggtg    82440
gtttttttct aataccattt ctgggcaatt cctaaggcat ttagagttct gaaagaccta    82500
```

| | | | | |
|---|---|---|---|---|
| gtccgacctg | ggagctgaga | atgaatgtct | aacaggaact | ctaggctggg tatggtgact 82560 |
| cacaccacta | atcccaacac | aggcgggccg | atcacctgag | gtcaggcgtt tgagaccagc 82620 |
| ctggccaaca | tggtgaattc | ctgtctcact | acaaataaaa | aaattagcca ggtgtccatg 82680 |
| ctggctaaca | cggtgaaacc | ccatctctac | taaaaataca | aaaaattagc caggtgtggt 82740 |
| ggcgggtgcc | tgttgtccca | gctactcggg | aagctgaggc | aggagaatgg cctgaacccg 82800 |
| ggaggcggag | cttacagtga | gccgaggtcg | cgccactgca | ctccagcctg ggcgacagag 82860 |
| cgagactcca | tctcaaaaaa | aaaaaaaaaa | ttagctgggc | gtggtggtgg gtgcctgtaa 82920 |
| tcccagctac | tcaggaggct | gaggcaggac | aatcgctcga | acccaagagg cggacattgc 82980 |
| agggagccga | gatcatgcac | tccagcctgg | gcaacaagag | cgaaactctg tctcaaaaag 83040 |
| aaaaaagaaa | ctcaaataca | gcgattctca | gtgcaggctg | ccctctggcc gatccaggag 83100 |
| caaggcctta | accatgtcac | ccccaagcga | ttgcttttaa | actttcttct ctgcagcctt 83160 |
| caaccccttat | gattttcttc | tcaggtatca | gactgctgtg | ttcaagaaag acagctttgt 83220 |
| gtaatcattt | atcataaata | tcttaagaac | tttaaaaatc | ctagagattc ctaactttag 83280 |
| gaaatgggag | acctgtgata | ctgatataat | gtgggctggg | cttgttttct gtcatttgct 83340 |
| agataaatga | acttgaaagc | ctactgtaaa | atgtggaagc | ttctagattg caaaagggct 83400 |
| gggaagatgc | tgttctttc | tcctgagtga | tgggctctgt | ccagtgttca gagctgcctc 83460 |
| tgaggccgtc | tgatcctagg | agactctgcc | tcgttgaggg | aattttgagg cctaactaca 83520 |
| cattcctgcc | cccagagagg | tcacagccta | tagcaggctg | acgtttctca tctcacatgg 83580 |
| cacagaaagg | cacattttca | ttcttaggct | aacaaagagc | ttcaaaaact agaagcttgg 83640 |
| ctcctgtttc | ttttaggtca | tgttttcaa | cttaggtaaa | actagaggtt ttgataacgt 83700 |
| atgacctcta | gaaatcattg | ctttccataa | acagaagtgg | atctgagttt tttctactga 83760 |
| tttttagtgc | aggctatgtc | tacatgccca | cagaacatat | tccatgcaag agaaaaagcc 83820 |
| caggccacca | tctttgctgg | gaacttgact | tttgcgctca | ctgaattta agctttctga 83880 |
| cagcagcctg | gaatcatgga | gggataaagt | acctattagt | aagatggaaa aaggtgtttc 83940 |
| aggatggagc | tgcagtcttt | tgagagtaag | ccatgggaag | gcctgtatac gatgggtggg 84000 |
| cttttcttct | gtaagtgtct | agagaccagg | cctcctgaag | agggcatggg ggcttaactt 84060 |
| acctggacta | ctgtgtttac | aatactcatt | tatctcgaac | tcctcctaac ccctgagaat 84120 |
| tgctacattt | aatatttgct | gagtacttcc | tagcattctc | ccaaccaggc tgggtgccgt 84180 |
| ggctcatgtc | tgtaatccca | gcactttggg | aggccaaggc | aggcagattt cttgaggcca 84240 |
| gaagtgtgag | actagcctgg | ctgacatcgt | aaaatcccat | ctctactaaa aatacaaaag 84300 |
| ttagccgggc | atggtggtac | acacctgtaa | tcccagctac | atgggaggag taggaggcag 84360 |
| gagagttgct | actgaggcag | gagaattgct | tgaacctggg | aggtggaggt tgctgtgagc 84420 |
| cgagatcata | ccactgcact | ccagcctggg | cgacagagtg | agcgagagtc tgtctcaaaa 84480 |
| aaaaaaaaaa | aaaagaacgt | tctcctaacc | tggcttcttc | ctccaggggt gtaattaatc 84540 |
| atgtcagttt | cctcattgat | acacacacac | ccccacacct | acacgctg tacaatcctg 84600 |
| tatccattac | ttttcaaggt | acgtttacta | tttatgtttg | ggatccttgt ctcttttta 84660 |
| atagtgtttc | ttaaagtctt | gtattatatc | agagtactgt | aacatcacag tcaagagcac 84720 |
| tctagtaagc | tctaggagga | aagcgcctta | tggaaggcag | tggagacctg tcctgttggg 84780 |
| gcggcatagg | ggcagcccct | gtctctggtc | agttctggcg | ctcaggctca gggtttcctg 84840 |

```
taggctgctc ttcccagaga ctgaccaagg gctctcataa ggcacctgca gaccctgtaa    84900
gaagcagaag tcagtgtttc ctgacaccag ttgatacgtt caggatccac tgattaaact    84960
acctgctgtg tggcatgcat tgtggtcgat gccagaaata ggaattggag gggcccatga    85020
gcatggccag tatcagactg aaggtgctgc tggaggtgct gctgcgctgt gaccaggcct    85080
cttggggatg agcccgtggc aaccaccctg cctccgatgg ggtgggccca catgttacct    85140
gtgtgtgtcc atgaccacac cttcctcccc cacctcatcc aaatttcttt cttttccaag    85200
cccccgaatc cttcagggct gcaggttttg tttaaagcag agctggtgag ttgcatgggt    85260
ggttgtgttg cgactagatg gggtgttcaa agagttggga gttaaaaaac ataaaggggtg   85320 cttattagga gaaccaagga gtataattgt cctgttctta atatgcagcc agattaatga    85380
atgtcacatg aatgaaccag aaaaacatga aatgtgccct tgatcagctg ggttggtgtg    85440
cagcaagctg tgtgaccaag ggacagcagt gctcctgagg gccgtcactg tctgctgtgc    85500
agagcccttc ctcccacggg agcctacctc acctgtgcaa ggggcttgtc tgtggtcagt    85560
gacctggata gatctgaatg gggcttattt tttgaggagt cttatggcag gtctatcagt    85620
aaagactcta ttcttgatga tcacacattt tggattttcc aaatctatca gaggatgggc    85680
ttgaggcaga gtttgtagac actagtttca ctggtttcat ttaccaaaaa ggggagcaga    85740
agtcaagtat ggtggctcat gcctgtaatc ccagaggcag gagaactgct tgagcccagg    85800
aattcgagac cagcctaagc aacataagga gacctgtctc tacaaaaata aaaataata    85860 tcttagtcag acgtggtggc gtgcctctgt ggtcccagct actcgggaga gtgagatggg    85920
aggatcgttt gagccctgga gttaaagttg caatgagctg tgattgcacc actgcactct    85980
agcctgggtg acagagcgag accctgtctc aaaaaaaaaa aaaaaaaaga aagaaaaga    86040 aaaagaaaag aaaaaaactc atgcctgtaa tcccagcagt ttgggggggct ggggtgggcg    86100 gatcacaagg tcaggagatc gagaccatcc tggccaacat ggtgaaactc catctctact    86160
aaaaacacaa aaattagccg ggtgcggtgg cgtgtgccta taatcccagc tactcaggag    86220
gctgaggcag gagaatcact tgaaccaggg agccggaggt tgcagtgagc cgagatcgcg    86280
ccactgcact ccagcctcgg caacagagtg aaactctgtc tcaaaaaaaa gggaggcggg    86340
ggaacagtga gaggtaggga gaggaaaggg gattctcgct acacccaagc caggtaccat    86400
ctagaggcta gactctttgg gaagctcaaa ttccctagaa agcaggagaa gcttccttag    86460
ccctcccgct ttcccagtag attaagccca tgagcccaag gcggctctag atgtgtgaca    86520
tgctctgtgc acaaccagag cccatcacag gcagaggaat aacacccaca ccagaagggc    86580
cctcagaggt caccacgtcc aggaaccctc cttacagatg aggaaactga ggcccagaga    86640
ggggaggacc cagggagctg gtggcagcta gaccaggaga gttgtcattc caagcaagca    86700
aaggcaacga gatgagccca gagctgtgct cccatctctt tgttaggggg ctaggatgcc    86760
ctctcaatgt cattttgtcc aggatgatgc tccctctctt aagcaattaa tgcgcccttg    86820
ttaacctttt gctatcgctg cctcttcaaa ccagaggagt tgagagttcc gggccagcag    86880
aggaaggcac ctgaaaggcc cctggccaat gagattagtg ctcacgtcca gcctggaccc    86940
tgcaaagagg cctctgggt ctctgggctg tgcatggggg agaaagagcc agaagctccc    87000
atcccactga ccgcgagcct tcctcagcac cgtcccattt gctcagcgcc tcctccaaca    87060
ggaggccctc gagagccctc ccaggagtgg ggacgaaaag gtggggactg ggccgagaag    87120
ggtccgacct ttccgaagtc cgccaccct gcgtatctcc acacagagcc tgaaagtggt    87180
aaggtggtcc aggaagtctt cctcggagag ccaggccccc caggtctgag ccaccagctc    87240
```

```
gtgtccagca tgcctggggc tcccctcctg cctgagggcc ccagagaggc cacacgccag    87300
ccttcaggga caggacctga ggacacagag ggtggccaac acgcccctga gctgctcaag    87360
caccagcttc tgggagacct gcaccaggag gggccgccac tgaagggagc cggggggcaaa   87420 gagaggctgg ggagcaagga ggaggtggat gaagaccgcg acgtcgatga gtcctccccg    87480
caagactccc ctccatccag ggtctcccca gtccaagatg ggcagcctcc ccagacagcc    87540
gccagagaag ccaccagcgt cccaggcttc cagcggagg gtgccattgc cctccctgtg     87600
gatttcctct ccagagtttc cacagagatc ccagcctctg agcccgaggg gcccagtgca    87660
gggtgggctg aagggcagga catgcccct gagttcacgt tccacgtgga aatcacaccc     87720
aacgtgcaga aggagcaggc gcacccggag gaggattcgg aagggctgc atttccaggg    87780 gctcctggag aggagccaga ggcccgggc ccctctttgg gagaggacac aaaagaggct    87840
gagcttccag agcccactga aaagcagcct gctgctgctc cgcggggaaa acccgtcagc    87900
cgggtccctc aactcaaagg tctgtgtctt gagcttcctc gctccttccc tggggacctc    87960
ccgggcctcc caggctgcgg ttactgccac tgagcttcag gccttcccaa ctcctgctgc    88020
ttccgacatt cctaggacgc cactaaaccg actcctgggt gcagctgctc cactccctcg    88080
gtctcctccc gtgctcaggc tgtggccaca cgcgcccctc acgcttgcct gccactctgc    88140
atgtcaccag cacccccacc gcgtgctccc caccttgttt gactctctgg ccacttgatg    88200
tgtccacaat ggcccatcag cccacaggag gttggtgggt gccctccacc ggcagggtgg    88260
cagcttccct cacggtgtct agaactcgcc aaccctccca tgtaggcaca agcagcccca    88320
ctttgcagat gaggaaacgg aggcccagag aagtgcagta acttgccgaa ggtcactgag    88380
tagtaagtga cagagccagg tttgggatcc aggtaggttg gctctgaaag acatacctgt    88440
cctgcatccc acagcaggac aaccctccca ggaggtgctg gagtgtggac tcctaacacg    88500
gagatgggca gggtacacac agcaggcgac acacacagca ttcagaggtg gcccagagcc    88560
cacactgtgc ctttggccca gcaccctgcc cccacccgct ctgccttgtg gcaggaagat    88620
gaggagcaga cacaagatct ccctggtcca catgccgcca cctccctcag cagaggacga    88680
ggagatccac atgctggcat gcagggggc tgagcagggc ccatcttgag ccctcaggag    88740
catgaccaca gcagccccac agggtgggat tggtgtgggg agagtcccaa gtatcaggga    88800
gaggagagtt ggtgtcccgc gggagacctc atagccacaa ggcaagcttg tccataaatt    88860
tggggcccct tggaatttcac agttatttgc caagcccaga aatggatgtt actgaagctc    88920
acagttgcaa gcatctgtta aattttatt agattttact tttagagaaa actttgaaat    88980
gctatagata aagaagcctg tgttgaaaag ttaagacaga ggccaggcac ggtggctcat    89040
gcctgtaatc tcagcacttt gggaggccga ggcaggtgga tcacttgtgg ttagaagttc    89100
gagaccagtc tggccaacat ggtgagaccc tgtctctact aaaaatacaa aaaattagc    89160 tgggcgtggt gacgggcacc tgtagtccca actacggggg aggctaaagc agaagtgctt    89220
gaacccagga ggcagcagtt acagtgagcc aagatcacac caccgtaccc caagcctggg    89280
cgacagagca agactctgtc tcaaaaaatg aaatgaagta aaataaaata aagttaagag    89340
agaaaaagta tatcctatat cctataacag taggggacaa ataactgacc tgacaggtta    89400
ctacaatatt tcctgaaatg atgttttctt gactaccagc ctactggagg tgtgtctggg    89460
ttaaaaaaga gttccatggc ccagtgactg cgggaaaaaa aaaaaaaaca gactaaacta    89520
agttaaacag gcttttctgc tgctggactt gtcagaacct ttaacgtact aacagtcatt    89580
```

-continued

```
gtgaccctct gagaaggtca caagtgggtt tcccaaactt actcgattct acctgctaac    89640
atttcctgga ggaggacttg ttcagtgctt ctgcagtttg ggaaatgttg atttagcagg    89700
ggatgttgtt gtgccatgga tggtgctggc tgatatgggc aaaggaaaga acacgtgagt    89760
cagattcgcc tggggctctt attaaagtgc aggttaccgg ggccactttc ggcttacaaa    89820
cccagttgtg gggtaagcct gggagtcttt gagcaggtga ttctgccata tagtatagtt    89880
ggaaaacctc tgggcatact cattgctggt ccctctagaa atccaggtga caatagccaa    89940
cgagaagctc caagagaccc gattgtctgt ggggtagagg gaatatgata ttaaaaccaa    90000
agaaaaaaat ctatcatcag ttttcagcag tgactgtcaa gagaaggaga agggtgagtt    90060
agcactgatg ctggcagaca ggccagtggg ttggtttcac cagggagtgt gatgaaggct    90120
gatgttatct gggatgatgt atgatggtaa ctggtttgta gctaactggg ggaagcggtg    90180
aggatttgtg cccttcgaag accagcaagt ggcaagaaac ccaccaggcc tggctcagcg    90240
ctaggccggg cttggctcgt ctgagagcag ctggggctgg tggccaaagc ccctattagt    90300
gaggggtaag ctttgggggt acaaccagca actaggggac aaagacaagc ctgccaggct    90360
ctcctattct ggaggcaggt gaccaggaat ggagatgggg tggtcagcat aagatggcca    90420
ggaaggtggg aatcagggct gctggcaatc tagccgcatg ggcaagggag ctgggtgact    90480
ccaggcagtt tccaaggccc agagggtgag caggcacctc gcaggaacc agggccaagc    90540 ctggctgcag tgtggagaca actcacccac ccccgtcctt ggatcttgca ggaggctggg    90600
tcctcactga gctaccaata tccatggccc tgaggctttt aaaacacctg tccgtggagt    90660
ggggctggtc ccagtggggt gaggctgacc ctggcagaaa cagggcagga gcctgtgggt    90720
tagggagact gcaccttcct tagatagcct ccgtgtcatc atgtccctgt gacagtttct    90780
gctgcgtccc ttctgcatgg tcccaccctc agccagcctg ctgcccctc ttgccaggtt    90840 gctctaatca gtgaccccag tgtgctatgc tgatactaac aatgtgagac ctagcacatt    90900
caagggagaa gagaaccaac tggtttccac cagacccaac taaacaaaac acggacctat    90960
cccagagaaa tgcaacttca ccacagctgg ctgtttctgt gaacagtgaa aatggagtgt    91020
gacaagcatt cttatttat attttatcag ctcgcatggt cagtaaaagc aaagacggga    91080
ctggaagcga tgacaaaaaa gccaaggtaa gctgacgatg ccacggaact ctgcagctgg    91140
tccagtttac agagaagctg tgctttatgt ctgattcatt ctcatatata atgtggggag    91200
catttgtcac taaagcacag ctgtcattta aagtgctttg tattttgggg caggcttttt    91260
aaaagtccag catttattag ttttgatact taccccaggg aagagaagtt ggcaggttca    91320
tgaagtcatg ctgctaattc cagctttctt agtgtagttt cagtgagacc ctgacagtaa    91380
atgaaggtgt gtttgaaaac caaccccagg acagtaaatg aagttgtgtt tgaaaaccaa    91440
ccccaggaca gtaaatgaag ccatctgctc actgcataaa ctgcaccctg atctttgccc    91500
atccttctca gtatttcact tcacccatcg tttactccct caatgacttg gtgtctggga    91560
aaatgctccc gtaattgcac agtggcgttt ttcctggaaa atcccaccat ggctctagat    91620
aagacctatt tttcttaaag gtatctaaaa tttccagcat aaattctgtc tgaaacagct    91680
gaattttaat cagtcctgga gcccagaggg catctccagt tgccacatag ctctgagcat    91740
tcggtggtgt gttggtgtgt tgggggctgc tcccggaagt gcctgcagag tcagggctcc    91800
ccagcctcac ctagtgaggc agcggaaggg cctgcgggaa tttggagagc tgcccttttgg   91860 gtccctgaag tgatagtgac agctgcttgt caatcatggt gcacatttag tgccggggc    91920 aggggtcagg gaataccagc ctcatgcatg catgcattcg ttcattcatt catgcagcac    91980
```

```
acatgggtac gacatccctg ccctggagtt gcctagattc tagggagggg aaagatctat    92040
taccgtggac ctcggccagg tggggagtgc tgctggtgga gaggggccat gtgcagcgag    92100
gaaggagggg tcatcaatac ccccaccca  gctttgcttt cttgtcatca gccccagggc    92160
cccagcctgt gtccctcctc tcccactact gcttcatctc ctgggttctc cttaccaagc    92220
ctggccacac agagggtctc ggccgcttcc atggggaatt ggaaagcaat aagataacat    92280
ccccaagaag cccaatgaag tctgggtcag gacccttctc tgagctgact cgctctcgga    92340
aacactttga ggcttagcct ccccactttg ttttctgaga gcgctacctc ttcccctcca    92400
aacatcccct tctcctctgg ggccatgccc acccatcaaa atcccccatg ggtaggatga    92460
attgtgggtg tcagtcacca tctatcccac atcccggttc caggtccccc caccccccgc    92520
cgcctccaca gggacaggta tgcagacacg tgtctctggc tgcttcctca tgtggaatgg    92580
gttcaaaagt tagcagtgtt gtttacactg gcaaactgaa aaagagaaaa cattggaggc    92640
ttggcacagt ggctcatgcc tgtaatccca gcactttggg aggctaaggt gggaggacct    92700
cccgagccca agagttctag accagcctgg gcaacatagc aagaccccat ctctaaaacg    92760
aaaatttaat tggccaggca gaggtgggag gatcacttga gcccaaaagg tagaggctgc    92820
agtgagccgt gatggcacca ctgcactcca gccagggcaa cagagggaga ccctgtctct    92880
aaaaccaaca atgacaaaaa aagagttaac attggccaga ttaggattca ccaaatagtg    92940
ttaatattag tttgatttga gactttaatc agaaagcaca tgtgtggtgg gggtgggcat    93000
aacctaagat agaatctttc caacgtgggg tgggcacact cctgattgag tctatcagtg    93060
tggtggaaga ggccatgggt taatgggcag gcaaaaaagc cccttgcctg gaattgagta    93120
gaaagtaagg cccttcagac ccatgacaca cttggcgaca ttttcttgag taacatccta    93180
agattcatgt accttgatga tctccatcaa cttactcatg tgaagcaccc ttacaccagt    93240
ggtctccaaa ttcaggggca caatcacatc taacaggctg gagaaagaac atactagaac    93300
ttccattcct ttgtcatgtc ctcttctaaa gctttgtcag atgtgagttg agtaagttgg    93360
tcatataaga agtatgactg gggaggatgg tcactttcct gttcttactg atcagatggg    93420
atgttaaggg tacctgattc aaacagcctg gagatcactc ctttcaacca ttacctgcct    93480
tatttatttt tagttactgt cctttttca  gtttgttttc ctcctccatg tgctgacttt    93540
tattttgatt ttatttatgt ttatgtttaa gacatccaca cgttcctctg ctaaaacctt    93600
gaaaaatagg ccttgcctta gccccaaaca ccccactcct ggtagctcag accctctgat    93660
ccaaccctcc agccctgccg tgtgcccaga gccaccttcc tctcctaaat acgtctcttc    93720
tgtcactccc cgaactggca gttctggagc aaaggagatg aaactcaagg taaggaaacc    93780 accctttgaaa agaaccaggc tgctctgctg tggtttgcaa atgtggggtg ttttttgttt    93840 tttgttttt  tagcctcaaa gacctttctt caaatgagct ctgacacaga agcaccgtgt    93900
aaatagttag aattctgggc aaagaggaaa agagagctgg gggccatacc tttcagcacc    93960
ccacaggctc tcatagcagc agcccctcag acacctggtg ggaccttggt ttcgaaattg    94020
ctactctaag gctgggcgcg gtggctcaca ctgtaatccc agctctttgg gaggccgagg    94080
agggtggatc acctgaggtc aggagttcga gaccagcctg gccaacatag tgaaaccctg    94140
tctctactat aaatacaaaa attagccgag catggtggtg tgcacctgta attgcagcta    94200
ctcgggaggc tgaggcacaa gaattgctcg aactccagta gcagaggttg cagtgagcca    94260
agattgtgcc actgggctcc agcttgggtg acagagcaag actctgtcgc aaaatttttt    94320
```

| | |
|---|---|
| ttaaaaacaa acccaaaatg gctactctca ttgggttcct ttgcccattc ctgattttgg | 94380 |
| taacagaaat gcttccagat tgccctgatc tgggtaggac agcatcaggc cacagcaaca | 94440 |
| ctgccctgtg agcccactcc ccctggact agcttgtggt ccttagttaa tgtcagtttc | 94500 |
| ttctttgagt ttgtgttatg tctaagggtc atctgctggg tagccgaacc cagggactgc | 94560 |
| cctagtccct agactatgcc atgcccgact ctgccagctt tgtcagtgat gctggtgctc | 94620 |
| ccctcctcgg gtgctcacct gctctgagca cacccaagga gttcctgacg ccttagggtt | 94680 |
| gtatgggaga gaatgaaaga acacaacgta gctctcttta gcatccttgg ccaggttcaa | 94740 |
| cactgtctcc aagggcctct ggtggaacca accaccatca gccaaataaa tccataatta | 94800 |
| gagtcagaaa atggatgtcc gcctatgcat agtgcactaa tgtcctgccg attgattgac | 94860 |
| atggagtgga gagtgacttg atcattgctg taagctctgc tggccttggc acaactcatg | 94920 |
| ctgataacca gtgcacatag ttcctctgag aggaaatgtc ctcagggaac ttggagtttg | 94980 |
| ggtggggatg tggatttgtg tgcccagcaa gccctcatga ttgtagcaga cacttgtggc | 95040 |
| atctagaagg caaagggtca ccccagtctt aaccgcgttt tgagtcaagg tgcggagtgg | 95100 |
| ggctggtgtt gactcggtgg cagcaacttt tcccaatggt gaaaaaaccc tcgaccctgt | 95160 |
| ttcatttaca gggggctgat gggaaaacga agatcgccac accccgggga gcggcccctc | 95220 |
| caggccagaa gggccaagcc aacgccacca ggattccagc aaaaacccg cccgccccaa | 95280 |
| agacaccacc cagctctggt aagaagaatg ttctcttgaa tcttagagga agctgaagct | 95340 |
| ctcagaggta tagccttcat tttaggaggc cttaggccac tgagagtgaa cggcccctgg | 95400 |
| cagctggtca gcaccttgca gttcactaag caccagagtc ttcatttcct tcgcagttct | 95460 |
| tctgatttct gaggcagatg ttgaatcccc acgttttgt ttgtttgttt tgttttgttt | 95520 |
| ttgagatgga gtttcgctct tgttgcccag gctggagtgt ggtggcgcaa tctcagctca | 95580 |
| ctgcaacctc cacctcctgg gtttaagcaa ttctcctacc tcagcctccc tagtagctgg | 95640 |
| cattacaggc acctgccacc acgcctggct aattttttgt attttttaata gagacggggt | 95700 |
| ttcgccatgt tggccaggct ggtctcgaac tcctgacctc aggtgatcca cttgccttga | 95760 |
| cctcccatag tgctgggatt acaggcgtga gccaccactg ccagcctgaa tcctcacttt | 95820 |
| ttatcagtga agaaattgag gctgattctg cagcacgata aaaaaatata tagaaaaagg | 95880 |
| aaaaaaaaaa gaaagaaatc gagcctctga gagtttgctt gactgagtct aaccagctca | 95940 |
| ttttaagcct gaggaaaatg tggtcatatg gctactaaat ggcagctctt ggagcctctc | 96000 |
| tggccccaag tccagggttc cacagaggca gccccagcat ggtgtgtttg cagtccccaa | 96060 |
| atgcgaccgg agacaaatgt ctctggagac agagcagcag cctggatagg tcacaatggg | 96120 |
| tgatgtcact tagggctcaa cccccaggca gcttaacttg ctggggacgt taggagtctg | 96180 |
| ctgcaaaacc tgagggtctt agctgagcag tcgcaggctg ggcccattgc cctgggctcc | 96240 |
| tgtgagtaaa acccagtcag ttttgagtac ccagtaaggc atccatctag ttattttgca | 96300 |
| gccggggtgc tattaagaat agtcacggct gggcatggtg gctcacgcct gtaatcccag | 96360 |
| cactttggag gctgaggagg gtggatcacc tgaggtcagg agttcgagac cagcctggcc | 96420 |
| aacatggcga aaccgtctct actaaaaata caaaaaagtt agctgggcgt ggtagcagat | 96480 |
| gcctgtaatc ccaactactc aggaagctga ggcaggagaa tcgcttgaac ccgggaggcg | 96540 |
| gaggttgcag cgagccgaga tcatgccatt gcactccagc ctgagcaaca aaagtgtgag | 96600 |
| actctttctc gaaaacaaac aaaacaaaca ggccgggcac agtggctcat gcctgtaatc | 96660 |
| ccagcacttt gggaggccga ggcgggcgga tcacaaggtc aggaggtcaa gaccatcctg | 96720 |

```
gctaactcag tgaaatcctg tctactaaaa atacaaaaaa ttagccaggc ttggtggtgg    96780
gcacccgtag tcccagctac tcaggaggct gaggcaggag aatggcgtga acccgggagg    96840
cggagcttgc agtgagccaa gatcgcacca ctgcactcca gcctgggcaa cagagtgaga    96900
cagagtgaga ctcaaaacaa acaaacaaaa aaacgaagaa aacagtcatc ctctttgggg    96960
attagggaca gcctgcctga gcacttctct ctcccattgc cccagtgaag tgttccacca    97020
ttgggtttag accctgcacc acgtaggggt gtctgacctg cacttgctcc ttggcagtgt    97080
gcaggcagcc tgtggctctt gctgcaggct gtggccaaag cctggcctgg atcttggtga    97140
ctctacttct ccctggcctg agggagctgc ccagagcctg cctgtcacct gctgcctgtc    97200
tttgcagtgg catttcacac acacgtggtg cggtggcagc cccaaggatg gccgttcact    97260
aaggcccgtt gttttttgtct ttttgcttcg tgttttctgg cctggtgttt ttctcatata    97320
cgtggtgatc cagggataat tcccagaatt ttgacaggat tttaggtagg gtttggatcc    97380
tgctgttttt tcacttaaca tggggctagt tgactcacac gctgtttttt gttgttgttg    97440
ttttgtgtcg cccactgtgt cgcccaggct ggagtgcagt ggcatgatct tggctcactg    97500
caacctcttc ttcccaggtt caagcaattc tcctgcctca gcctcctgag tagctaggac    97560
tataagcaca ggccaccaag ccctgctaat ttttgtattt ttagtaaaga cagggtttca    97620
ccatgttgac caggctggtc tcgaactcct gacctcaagt gatctgtcca cctcggcctc    97680
ccaaagtgct ggaattacag gggactcaca ctttgtaaca acctgaaaca aggtcatgca    97740 tttcccttttg ggtcttacct gctcttcggt ggctgcctgc atgtggagag accctcccccc   97800 ttgggcctcc tccaccttgt ttcagaacgg ggcctctgct gggccggccg tgggtgcctg    97860
ccatgtgaag gactcattaa ggccccgttt aaacctgatg ataatgaggt ttttgtggat    97920
ttttctcttt aagcgaccaa gcaagtgcag agaaaaccac cccctgcaga gcccacatct    97980
gagagaggta ctcaggagcc tgcttcactg ggagcagcct ccctttgcat gtgtggctgt    98040
tcactggctt gtgttcctag agccgacagg accctttttct gcaatgcagg gttcacacag    98100
ggttcgcagc ttgaagatgg agcagtccga attctcttcc ccagattttg tgcagctgtg    98160
tttgtccgat gggctttcta atcctgtgtg ctctccttga cttcagggac aatggcatta    98220
caggcatgaa ccaccatgca tggctgtctc cctattttt tcagctgaag acataggctt    98280
agggaggtca ggtgacttgc ccaagacctc tctgcaagta agaggcatga aaaggatttg    98340
gagccaccac caccaagccc attggtcacc ctgggtctct gaagtcaggg aagcaggagg    98400
atgggagatc tcaggaggca gagaggctga gcctggaggc cctggaggcc gaggccccat    98460
ctgttgtttc cttatgtgga aaagaagagg cttcgtgtgt tctattgcca caaagcttga    98520
ctacttcagg aacatccaag acatggaaat cagcagggca cggtggctaa tgtctataat    98580
cctggcactt tgggaggctg aggtgggaga attgcttgag gccagaagtt caagaccagc    98640
ctgcgtaaca tagtcagacc ccgtctctat aaaaaacatt atttaggccg ggcgcggtgg    98700
ctcaagcctg taatcccagc actgtgggag gcagagacgg gtggatcacg aggtcaggag    98760
atcgagacca tcctggctaa cagggtgaaa ccccgtctct actaaaaaat acaaaaaact    98820
agccgggcga ggtggcgggc gcctgtagtc ccagatactc aggaggctga ggcaggaaa    98880 tggcgtaaac ccgggaggcg gagcttgcag tgagctgaga tccggccact gcactccagc    98940
ctgggcgaca gagcgagact ccgtctcaaa aacaaaacaa aacaaacaaa caaaaaaaaa    99000
cattatttaa aaaagagaca tggaattctt taaatcctaa aaactggtgc tggctgggcg    99060
```

```
tggtagctca cgcctgtatt cccagcactt tgggaggctg aggcaggtgg atcacctgag   99120
gtcaggagtt caagaccagc ctggccaaca tgataaaacc tctactaaag aagtctctac   99180
tggcccggcg tggtggctca cgcctgtaat cccagcagtt tgggaggcgg aggcgggcag   99240
atcaggagat caagaccatc ctggctaaca cggtgaaacc ccgtctctac taaaaataca   99300
aaaaattatc caggcgtagt ggcgggcgcc tgtagtccca gctactcggg aggctgaggc   99360
aggagaatgg tgtaaaccca ggaggcggag cttgcagtga gccaagattg cgccactgca   99420
ctccagcctg ggcaacaaag cgagactcca tctcaaaaaa aagaagtct ctactaaaaa    99480
tacaaaaata cagtctctac taaagtctct actaaaaata caaaaattag ccgggcatgg   99540
cactgcattc ctgtaatccc aggattccca ggattctcct cccagccacg ggaggctgag   99600
gcaggagaat cgcttgaacc cgggaggcgg agcttgcagt gagccgagat cacgccactg   99660
cactccagcc tgggtgacag agcgagactc catctcaaaa caaacaaaa caaacaata    99720
acaacaacaa aactagtgct tattcgtcgc tgaccaagct gcccattggc tacatgggtg   99780
cttcaaacaa agagctgccc ttctccagct ctggccagca ggtatgtgtt acagcgaatg   99840
ccaggggcag cggcagggggc attcttgtgg gaagcttcca gaccagcagg aaagctaagt   99900
tctcagactg caggggagca aagcacacct gggcacagag tgaggcctgc agttctcaga   99960
cttcagtctt tggggagctt gagaaaaatg agcttttcag gccccacccc tagagattct  100020
gctctatcca ctctcagtgg ggcccagaaa tgtgcacttt acaagtccta ctttcctcct  100080
tgaaagctcc agagattctg atgcagggtt ccgtgggcca gacttcggaa acatggacc   100140
catgagacag aatagcagag tgttgaagtg taacagggac ctgggaagtg cagtaacaga  100200
agcaaatctg ggggtaaagg acacccagag gaggaaggga cagcatctgc gtggagagga  100260
gacccccccag cagcttctgg ggtgttggaa aggtgcactt actgctatgc atggcaggtg  100320
gggaactgta tggcagggca cagcagcatg aagtggcatg gctcatgtgg acagttaggg  100380
acaagcaggt atggagcagg catcctgttc tggagcccag atcccacaga ggagccaggg  100440
agctggcagg agccctgaac tagccgaaca gctgaacatt caccctgtgg agaaagggtc  100500
agaagcgtcc aggcttgagg gcacagctgg gtcccgtcac tgtgtcaccc ttatttagga  100560
taaaggccct aaagaattgc actagagatt ggcaaagcat atctaccacc tcctggagcc  100620
accctggctg cagggattat aattatatcc attttcaaat taaggcctct gagctcagag  100680
aggagaagtg acttgtctga ccacacacag cttgttggag cccatctctt gacccaaaga  100740
ccgaggggcc gagttggcca cctctctggg aactggtgtt gtatagtggt tgatggtttt  100800
ccattgcttt cctgggaaag gggtgtctct gtccctaagc aaaaaggcag ggaggaggag  100860
atgcttctcc agggcggccg cctcctgctg ctgtagctgc gcttccaacc tggcttccac  100920
ctgcctaacc cagtggtgag cctgggaatg gacctgcggg acgggcagcc cccagggcct  100980
tttctgaccc ccacctgagt cctggcttca ctcccttcct tcctcccag gtgaacctcc   101040
aaaatcaggg gatcgcagtg gctacagcag ccccggctcc ccgggcactc ccggcagccg  101100
ctcccgcacc ccgtcccttc caaccctcc agcccgggag cccaagaagg tggcggtggt  101160
ccgtactcca cctaagtcgc cgtcttccgc caagagccgc ctgcagacag ccccgtgcc   101220
catgccagac ctgaagaacg tcaagtccaa gatcggctcc accgagaacc tgaagcacca  101280
gccgggaggc gggaaggtaa gagaggctgg ctgcgcgtgg agatgtgggg ggctgcgcct  101340
ggaggggtag ggctgcgcct ggaagggtag ggctgcgcct ggagggggtag ggctgcgcct  101400
ggaggggtag ggctgcgcct ggaggggtag ggctgcacgt ggaggtacgc ggctgaacgt  101460
```

```
ggagccatgg ggctgcgcac ggagacatgg ggctgcgcgt ggaggtgcgc ggctgcgtct    101520
ggaggtatgg ggctccccgc acctgggctc ggctaccacc cccgcataac accccggtcc    101580
catccagacc ctcttcaagg aaatttagtt ctttattggg ctctccacta cactgagagt    101640
gctctcctca ggcgagagta cgttctggct cttctcttgc cccttcagcc cctgttaatc    101700
ggacagagat ggcagggctg tgtctccacg gccggaagct ctcatagggc acccacaggg    101760
gctccccacc ttccttctgg gtagaacacg ctgctacccg taggtgggca tctccactta    101820
tgggccatct gcttaggttg ggttcctctg gattctggga agattggggg ttctgttttc    101880
atcagctgat tcttctgggg gcaagtgggt gctcgccagc tctccagctt cctaaaggtg    101940
gagaagcacg gacttccagg ggcctggcct ggaccccttt ctctgctcct gtccctgtgc    102000
ccctcatctg ggtgcgttag gctgacatac aaagcaccgc agtgaaagag cagcagtgtg    102060
cctcctcacc agccagatgt gggcggtggg tatcttccaa ggcctctctg tggcggtgcg    102120
tagccacctc cgccctgcgc cgccagggtc ttctctctgt gtgtgctcct ggtggctctg    102180
cacacgctca tcttataaga acaccatggc ggctgggcgt gatggctcat gcctgtaatc    102240
ccagcatttt ggggaggccga gggggggcgga tcatgaggtc aggagttcga gaccagcctg    102300
agcaacagag tggaacctcg tctctactaa aaatacaaaa attagctggg cgtggtggta    102360
gcgcatgcct gtaatcccag ctactcagga ggttgaggca ggagaaccgc ttgaacccag    102420
gaggcagagg ttgccgtgag ctgagatagt gccattgcac tccagtctgc gcgacagagt    102480
gagactccat ctcaaaacaa gaaaagaaaa aagaaagaaa gaaagaacg ccgttgctta    102540 gggcccagcc tgatgacctc atatttcact taatcacctc tctaaaggcc ctgtctccaa    102600
atagagtcac attctaaggt acgggggtt agggcttcaa catatgaatt tgtgggacc    102660 acagttcagc ccaggacccc cttcccacca cccagcagag ctggggaagg gtgaagagga    102720
ggctgggggt gcagaggacc acggctcact ctgaggctgc agatgtgctg ggccttctgg    102780
gcactgggcc tcggggagct aagggggcttt ctgaaaccct gggcctgtgt gtcagcttgc    102840
cgcccccacg caggcgctct ccacaccgtt gaatttcttt tttttttttt tttttttgag    102900
acggagtctt gctctgtcgc ccaggctgga gtgcagtggc cggatctcag ctcactgcaa    102960
gctccgcctc ccgggttcac gccattctcc tgcctcagcc tcccgagtag ctgggactac    103020
aggcacccgc cacatcgccc ggctagtttt ttgtattttt tagtagagac ggggtttcac    103080
cgtgttagcc aggatggtct cgatctcctg acctcgtgat ccacccgtct cggcctccca    103140
aagtgctggg attacaggct tgagccaccg cgcccgccg aatttcttat cacttgggcc    103200
tgagcctggg ccatgtggag ggagggtggc caccagtgca tgtgagcacc ttgcctcaaa    103260
ccctgccacc taccctggcc caggcttcga tgcaggagcc ccctgcccc tgaacaagcc    103320 tgtgggtgca gcatcgcatc ccgtcaggat ggaaatggac ggttgggtta aaagagatgc    103380
atgtgtagac cctgcctctc tgcatcaagc ctcctttgag tgcccctgcg tgccagaccg    103440
tgcatagagg tggagaagac tcagctgtgc cccggagcac ctcctctcat cgaggaaagg    103500
acagacagtg gctcccctgt ggccgtgggg acaagggcag agctccctgg aacacaggag    103560
ggagggaagg aagagaacat ctcaggatct ccctcttgat ggcaaatgat ctgggttaaa    103620
ttaaaagtcc ggcctctccc tgcttaggca tgtggagctt gtagtggaag agggtctctg    103680
gaccctcacc taccacaatg gcctggttag aggccttggg gaaataactc acaggcgacc    103740
cagggcctct gtcctgtacc acagctgagg gaaactgtcc tgcgcttcca ctgggataa    103800
```

```
tgcgctccct cgtctccaga cttttccagtc ctcattcggt tctcgaaagt cgcctccaga  103860
agccccatct cgggaccatt gtgaccttca ttctccaggg tgcctggccc tggtgctgcc  103920
caagaaccca gagggggccct cactggcctt tcctgccttt tctcccattg cccacccatg  103980
tacccccatc ctgctccagc atccagactg ccatccacgc atacccagga tctcctcaag  104040
tcacatgaca ggcagtaccc tcaaagtgct cccttccccc cagtctgaat ctgctgctcg  104100
ctgtctgggg ttccccgccc atgcaccccc ggggcccct gggttctgcc atgccctgcc  104160
cagtgtccca cagcagggaa tgtccttctc tccttatctc ttcccttccc ttaaacccaa  104220
gttcagttgc catctcctcc aggaagtctt cctggatttc cctctctctt ctcaaagccc  104280
ctgaaaaccc tgacgacact gaacatgcgt gtgctgctcc ctagtctggg ccgtgactga  104340
gggtgaaggc cgagtctcac gcgttttgt agcccccaca agactgcgca ggtggccggc  104400
cctcactgaa tgcggggtta atttaactcg ggctctgtgt gagtggatga ttcaggttgc  104460
cagagacaga accctcagct tagcatggga ggtagctccg ctcttgaccc tgagttcatc  104520
tgaggttgac ttggaaggtg tgggcaccat ttggcccagt tcttacagct ctgaagagat  104580
cagcaggaat ggggctgagc agccaagaca gctttccatc cagaactgtc cctcccactc  104640
tgtgactgcc ctgcctgtgc ccatgagggg tgagagtcag gcgacctcat gccaagtata  104700
gaaaggggca cggccgggcg cggtggctca gcctgtaat cccagcactt gggaggccg  104760 agacgggtgg atcacgaggt caggagatcg agaccatcct ggcgaacatg gtgaaacccc  104820
gtctctacta aaaatacaa aaaactagcc gggcgaggta gcgggcgcct gtggtcccag  104880
ctactcggga ggctgaggca ggagaatggc gtgaacccgg gaggcggagc ttgcagtgag  104940
ctgcgatctg gtcactgcac tgcagcctgg gcgacagagc aagactccgt ctcaaaaaaa  105000
aaaaaaaaaa gaaaggggca gacagggtcc caggttacga cgtcatcacg ctgggcgag  105060 acggcacatc caaatgtact aaagggttaa aggagaaagg gtgactttat ttttcttgag  105120
atattttggg ggacgaagta tggaaaagtg gcagaggaca cagtcacagc ctcccttaaa  105180
tgccaggaaa gcctagaaaa attgtctgaa accaaacctc agccatcaca aagaccaaca  105240
catgaatctc caggaaagaa gaaaaaaaag tcatacgggg tccacgcaca agggcctta  105300 aaacgacccg ctggagggtc tcaggcctcc tcctcctcct agactggcct gaagtctcca  105360
cgaggttttg ctgagacctt tgggtccctg tggcctcatg tagtgcccag catacagtaa  105420
gtgctcaata aatgtttggc tacaaaagag acaaagctgg aggagtctga agaatcactc  105480
agtcctgccg gaacagatgc tcacactgaa gacagaagag caggagccaa gtcaggtttg  105540
ggaacctgta gaggctgaaa accaccgcag atcgctgtaa atcgtttggg aacaaaacag  105600
aaaacgtctg ttttctcctt tgtgcttgtc tctgttttcg ggatgtgcta cagtgaacat  105660
gtattgcttt gggggcccca aatggaatta tttttaaagg aaaatgcaga tgatcgggtg  105720
gccacactgg agcactgact gggtagggt ggagattgca gggaaggaag aagagctggg  105780
tgggatgcca ggcaggaaaa gcccatagac ccccaccgat cttgtggtga gccgtgggca  105840
gcggtgttcc atcctaactg caaaagggag cacctggggg gaagagggga ttcttttaaa  105900
caccattcca gtgcccgagc cccccggacc tgttgtcatc ttgggttggc ttcccctggg  105960
tgactccagt gtgcagctgg ctgagactca gtgaccctgg gttcttactg ctgacaccta  106020 cccctcaacct caaccactgt ggcctcctgt gcaccctgat ctccagtgac tcattttcca  106080
ctttcagtcc caactctatt cctatttgca gattccaagc gcctggctcc tcagtcaact  106140
cagacccagc caggccagcc catgggtccc acatgcccct tgccaaggtt gtccccgccc  106200
```

```
tgtctggcct gcgagggtgg gggtatgtcc agacacagag acaaaggacc agcttttaaa    106260
acattttgtt ggagccaggt gtggtgactc acacttaatc ccaacacttg gggaggccaa    106320
ggcagaagga tcacttgagt ccaggagttc gagaccagcc tgggcaacat acggagaccc    106380
tgtctttaca cttttttttt ttttttttaat tagctgggca tgttggcact cgcctgtagt    106440
tccagctact ccagaggctg aggtgggagg actgcttgag cctgggaggt caaggctgca    106500
atgagccatg ttcacgccac tgaacgccag cctgggcgag accctgtgtc aaaaagtaa    106560 agtaaaatga atcctgtaca ttacattaag gcgccccaaa ttgtacttag aaggatttca    106620
tagttttaaa tacttttgtt atttaaaaaa ttaaataact gcagcatata aattaggttc    106680
ttaatggagg gggaaaagaa tacaaggaaa aaaagaatc tagaaacaaa gataagagca    106740
gaaataaata aaaaaacaca accttgcact cctaacttta aaaaaaaaaa aagtgaagaa    106800
aacacaacca gtaaaacaga acatataaca gcatcaaaag ctgactcctg gctgggcgca    106860
gtggtgcatg cctgtaatcc cagcactttg ccaggctgat gctggaggat cgcttgagac    106920
caggagttca aggttgcagt gagctatgat cacaccacta caccccagcc tgggcaatag    106980
agcgagactg agacctattt aaaaaaaaag aagaaagaa cagaaaagct ggttccttcc    107040
ttatttcatt cctttattca ttcattcaga caacatttat ggggtacctc tgaacaccag    107100
gctctgtgct aagagctttt gcccccaggg cccaggccag gggacagggg cagatgagca    107160
gagaaacagg gccagttgca gcagcaggag gaattaggat ggagagcttg gccaggaaag    107220
gacatgcaag gggagcaacc cgcacaagtc agcaagccag agaagacaga cagacccttg    107280
tttgggacct gttcagtggc ctttgaaagg acagccccca cccagactgc tgggtgcagg    107340
agctgaagga ggatagtgga acacggtaac gtggagctct tcagagcaaa agcaaaataa    107400
agctagaact ggaggcggct ggagcagccg agggcgtgtg tccagcgtta aggggtgtga    107460
agcttgggcg ctaggagagt tcacactggc agaagagagg ttgcggctgc tgcgagccgc    107520
tggacatcgc ccaataggac agagggtggt ggagggggggg cctgaagaga ggctcagttc    107580
agctgcagtg gccgtgggag tgctgaagtg ggcgggctgt gggcagctgc tgggagggt    107640 tacgcggggg tgagggccca gcaacagcaa cccttcttgg ggggtcactg ggaaacaaag    107700
aggagagctg aagaagcagg gagtcccagg ggccatgcag ggcaagagag aatttgctca    107760 tatgggccc aggctgcagg atcaggagaa ctggggaccc tgtggctgcc agcagggaga    107820
agggagtgta caggatcatg gccaggaaag ggcccggggg ctatgggggg gcctggttgg    107880
ctccgagaag ttggagctga agtcactttc tcggaggatg tccaggccag tagttgggat    107940
gtgaagacct gaagcagcac agagcctgga agcccaggat ggacagaaac ctacctgagc    108000
agtgggcctt tgaaagcctt gagtgtgcaa tattgaagat ggccacaaga tggcgataga    108060
atgctgtaac tgtttcttgg ttctgggccg cagcctgggt ggcttgcttc cttccctgtg    108120
tgtgttgatt tgtttctctt ttttgagaca gggtcttgct gagttgccca ggctggagtg    108180
cagtggtgcg atcgtagctc actgcaacct tgaagtcctg agctcaagcg atccttccac    108240
ctcagcctcc tgagtagttg ggaccacagg cttgcaccac agtgcccggc taatttcttg    108300
tattttttgc agagatgtgg tttcactgtg ttgcccagga tggtcttgaa cgcctgggct    108360
caagtgatcc tcctgcctca gcctcccaaa ctgctggtgt gagccaccat gcccgacctt    108420
cacttttttt tttttgaga cagagtctcg ctctgtcgcc caggctggag tgcagtggcc    108480
ggatctcagc tcactgcaag ctccgcctcc cgggtttacg ccattctcct gcctcagcct    108540
```

```
cccgagtagc tgggactaca ggcgcccgcc acctcgcccg gctagttttt tgtatttttt 108600
tttagtagag acgggttttc accgtgttcg ccaggatggt ctcgatctcc tgacctcgtg 108660
atccgcccgt ctcggcctcc caaagtgctg ggattagagg cttgagccac cacgcccggc 108720
cctcttctcn nnnnngggcg tctgtgtgtg cgcctgtgtg cgcgtgtgtg cgtgtgcgtg 108780
cgcctgtgtg tgtgcacgtg cgtgtgtgcg tacgtgcatg tgcgcgcata cgtgtgcgcg 108840
cacacactcg tcttcacctt ctcccagcct tgctctctct ctacccagtc acctctgccc 108900
atctctctga tctatttctc tctcctttta cccctctttc ctcccttctc atacaccact 108960
gacaattata gagaactgag tattctaaaa atactttctt tatttatttt gagacagagt 109020
ctcactctgt catccaggct ggagtgcgat ggtgcaatct cggctcactg caacctccgc 109080
ctcccaggtt caagcaactc tcctgcctca gcctccctag tagctgggat tacagacgcg 109140
caccaccacg cctggctaat ttttatattt gtagtagaga cagggtttca ccatgttggc 109200
caagctggtc tcaaactcct ggcctcaggt gatctgcctg ccctggcctc ccaaagtact 109260
gggattgcag gcctgagtca ccgtgcctgg ccttaaaaat acattatatt taatatcaaa 109320
gccccagttg tcacttttaaa aagcatctat gtagaactta tgtggaataa atacagtgaa 109380
tttgtacgtg ggatcgtttg cctctccttc tcaatcaggg ccaggatgc aggtgagctt 109440 gggctgagat gtcagactcc acagtaagtg gggggcagtg ccaggctggg accctcctct 109500
aggacagatc tgtaactctg agaccctcca ggcatctttc cctgtacatc agtgcttctg 109560
aaaaatcttg tgtaaatcaa atcattttaa aggagcttgt ttaaaggaca gtgtaaataa 109620
ttctgaaggt gactctaccc tgttatttga tctcttcctt ggccggttga cttgacagga 109680
catagacagg ttttcctgtg tcagttccca agctgatcac cttggacttg aagagaaggc 109740
ttgtgtgggc atccagtgtc caccccgggt taaattccca gcagagcatt gcactggccc 109800
tgctgagcct ggtgaggcaa agcgcagctc agcaagcagg cagcgctgga gacaggccaa 109860
gcctgggcca gcctggggagc caactgtgag gcacggggct gtgggctgc aggcttgagg 109920 ccagggagag agggctgggc tctttggagt agccttgaga gacctgaacc caaacaaaac 109980
cagatcaagg tctagtgaga gcttagggct gctttgggtg ctccaggaaa ttgattaaac 110040
caagtggaca cacaccccca gccccacctc accacagcct ctccttcagg gtcaaactct 110100
gactcagaca tttctcccct gactgggagt tccctggatc caaattggga gcttgcaacg 110160
ctttgttctc tcccttgatg gttttttgtca gtgcctcccc agagccgaag tgtaatatat 110220
atgtttctgt agctgagaaa ttcaatttca ggattctgat ttcataatga cagccattcc 110280 cctttttctct cccttctgta aatctaagat tctgtaaagg atgttgactt aatgtgacaa 110340
ttggcagtag ttcatgtctg cttttgtaaat acccttgtgt ctattgcaaa atctcataaa 110400
ggcttgttga ctttttttgtg gggttagaac aagaaaaagc cacatggaaa aaaatttctt 110460
ttttgttttt tgtttgtttg tttgcgacag agtctcactc tgtcgcccag actggagtgc 110520
agtggcacga tctcggctca ctgcaagttc tgcctcctgg ggtcatgcta ttctcctgcc 110580
tcagcctcct gagtagctag gactacaggc gcctgccatc acacctggct aattttttttg 110640 tatttttttag tagagacagg gtttcaccgt gttaaccagg atggtctcga tctcatgacc 110700
tcatgatctg cctgccttgg cttcccaaaa tgctgggatt acaggcgtga gccaccgcgc 110760
ccagctggaa aaaacatttc tatgtatgtg acagacactg agttattgct taatgtcctt 110820
tgattcattt gcttaatttc ttttatggat tagtacagaa aacaaagttc tcttccttga 110880
aaaactggta agtttccttt gtcagataag gagagttatg taacccatga catttccctt 110940
```

```
tttgccttgg cttctaggaa gctcaaagct aaatggaatg atcactcttg taattgtcag 111000
tattgatgcc ctccccttct tctaatgtta ctctttacgt tttcctgttt tattattgtg 111060
agtgtgtgtt ttctaattct aagctgttcc cactccttt tgaaagcagg caaatcggcc 111120
gggcgcggtg gctcaagcct gtaatcccag cactttggga ggctgagacg gcggatcac 111180 gaggtcagga gatcgagacc atcctggcga acacggtgaa accccgtctc tactaaaaag 111240
tacaaaaaaa ctagccgggc aaggtggcgg gcgcctgtag tcccagctac tcggaggct 111300 gaggcaggag aatggtgtaa acccgggagg cggagcttgc agtgagctga gatccggcca 111360
ctgcactcca gcctacgcga cagagcgaga ctctgtctca aaaaaaaaaa aaaaaaaga 111420 aagcaggcaa atcttcttct aagacttatc cagtgaaaag ttatgaataa aaaatgatca 111480
tcaagtctac aggtgctgag gctactacag aggctgaggc cagaggacta cttgagccca 111540
ggaatttgag acctgggctg gcaacatag caagacccca tctccattaa aactattttt 111600
tattaaaaaa ataatccgca aaggagttta tgtggggttc cttaaaatcg gagggtgaca 111660
tgaattgatt caaagacttg tgcaaagggc gacagcaact ccttgagaag cagtatgaga 111720
aatcctgtcc tacctcctcc cccagctcca gcctgggctg aggcactgtc acagtgtctc 111780
cttgctggca ggagagaatt tcagtgttca ccaaaaagta gtattgtttt tattaggttt 111840
atgaggctgt agccttgagg acaacccagg acaactttgt tgtcacaaag gtagcctgcg 111900
gctacgggaa ctctgagatc tagattcttc tgtggctgct tctgacctga gaaagttgca 111960
gaacctctgt gggcctcaca tggcctcctt gtcctttatg aggggatggt gggcaagaaa 112020
ggtgatgtga cattagagat ttatccatct ctaagggagg agtggattgt acgttgaaac 112080
accagagaag gaattacaaa ggaagaattt gagtatctaa aactgtaggt cggacactcc 112140
tgtattgatt gcagcactat tcacaatagc caagatttgg aagcaacacg agtgtccatc 112200
agcagacgaa tggagaaaga aaatgtggtt catatatgca atggagtatt cagccatgaa 112260
aaagaataag attctgtcat ttgaaacaac atggatggaa ctggaggaca tcatgttaag 112320
tgaaataagc cagacagagg gacagacttc acatgttctc acacatttgt gggagctaaa 112380
aattaaactc atggagacag aaagtagaag gatggttacc agaggctgag aagggtggag 112440
gggagtgggg agaaagtggg gatggttaat gggcacaaaa acatagttag catgaataga 112500
tctagtattg gatagcacaa catcgtgact acagtcaaca ggaatttata gtacatttta 112560
aaacaactaa aagagtgtaa ttggaatgtt cataacacaa gaaatgatca gtgcttgagg 112620
tgatggatac cccatcaccc tgatgtgatt attacacaat gtatgtctgt ttctaaatat 112680
ctcatgtacc ccacaagtat atacacctac tatgtaccca tataaattta aaattaaaaa 112740
tttataaaac acacataaat aagtacattc aaatgtaggc tggacactgt ggttcacacc 112800
tgtaatccca gtgctttgag aggctgaggt gagagaatca cttgagccca ggagtttgag 112860
acctcatcac cacaaagaat ttttaaaaat tagctgggtg ttgtggcaca taccggtagt 112920
cccagctact ggggagacgg aggcaggagg atcgcttgag cccaggagtt taaggctgca 112980
gtgagctacg atggcgccac tgcattccag cctggatgac agagtgagac cctgtctcta 113040
ttttaaaaat aataaaaaga ataaataata aaaataaatt aaaatgtaag tatttgtatg 113100
ttagaaaaaa tacacccatc agccaaaggg gtaaaggagt gatttcagtc ataatcagat 113160
gcaggataag ccagcaatgc agtttctttt attttggtca aagaaataag caaaacaata 113220
ttgtaaacac ccagtcagtg ctggcagcaa tatgaggctg gctctctcac cagggctcac 113280
```

```
agggggaaact catgcaaccc ttttagaaag ccatgtggag agttgtactg agaggttttc   113340
gaatatttat aactttgacc cagaaattct attctaggac tctgtgttat gaaaataacc   113400
catcatatgg aaaaagctcc tttcagaaag aggttcatgg gaggctgttt gtattttttct  113460 ttctttgcat caaatccagc tcctgcagga ctgtttgtat tattggagta caaaatggaa   113520
tcaatacaaa tgttggctag caggggggaaa atattcacaa aatggaatgg aacatattat  113580
taaacatagt gcttctgatg accgtagacc atacagaatg cttaggatat gatatcactt   113640
cttttgttct tttttgtttt ttgagacaaa atctccttct gtcacctggg ctggagttca   113700
gtggcacgat ctcagctgac tgcaacttcc atctcccagg ttctcctgcc tcaacctccc   113760
aagtagctgg gactacagtt gcttgccacc atgcccggct aacttttgta ttttttacta   113820
tagacagggt ttcaccttgt tggccaggct gttctcgaac tcctgacctc cggtgatcca   113880
cctgccttgg cctcccaaag tgctgggatt accggtgtga gccaccgcgc ccagcctagg   113940
atatgatatc acttcttaga gcaagataca aaattgcatg tgcacagtaa ttctcccaag   114000
tttaggtaca cagggatggt tacatctaaa cgagacttaa aggaaataca aaaaatgcaa   114060
tcctgattgt gttagggtgg taagaaaacg gttttgtttt tgctttgatg agctgttttt   114120
taaaattgtt atattttcta ataaaaatac atagtgtgtt tgaaggaata taaaagatta   114180
tgaagagatg agttagatgt tgattcatat tgaagattca gatgagtaaa attaaggggg   114240
aaaaacggga tgaaccagaa gccaggctgg agtcccagtc ccagacccga cagcccaggc   114300
tgatggggcc tccagggcag tggtctccac ccagcattct caaaagagcc actgagctct   114360 tgccatttc aagatttcag aaaccacctt ggcatggctg gtctttcact gggatctcca   114420
cttggcaatt atttacatct gagacgaata aaaaccaaag tgctgagatt acatgcgcag   114480
tggctcaggc ttgtaatccc agcactttgg gaagctgagg tgggctgatt gcttgagccc   114540
aggagtttca gaccatcctg gacaacatag cgtgacctca tctctacaaa aaatacaaaa   114600 aaaattgccag gtgtggtggc atgtgcctgt ggtcccagct acttgggagg ctgaagtagg   114660
agaatccctt gagtccaggg aggtcgaggc tgcagtgtgc cgggaagatg tcactgcact   114720
ccagcctggg ggacaaagtg agaccctgtc tcactaagaa aaaaaaaaa aaaaagcact   114780 gtttccagag ttcctgaggg gaaggtcacc gggtgaggaa gacgttctca ctgatctggc   114840
agacaaaatg tcaagttttt ccaactccct aaacccctggt tttctatttc atagttttta   114900
ggcaaattgg taaaaatcat ttctcatcaa aacgctgatt tttcgtacct cccgggtgtc   114960
tacagaaaga accttccaga aatgcagtcg cgggagaccc atccaggcca ccctgctta   115020 tggaagagct gagaaaaagc cccacggggcg catttgctca gcttccgtta cgcacctggt  115080
ggcactgtgg gtgggaggggg gctggtgggt ggatggaagg agaaggcact gccccccttgc 115140 agggacagag ccctcttaca gaggggacac cccgcatttg tcttccccac aaagcggcct   115200
gtgtcctgcc tgcgggctca gggcttctta aacctggctg tgtgtcagaa tcaccagggg   115260
aacttttcaa aaccagaggg actggaaaga ctcctccaga tttgaattct aggttagggc   115320
tggggtctga gatttttaaaa atccacaggt gattcccatg cccaacaggc ttgagaacag   115380
ccacaggaag ttctctggga atgttccggt gggtctagct aggggtgagt ggagatgcca   115440
gggaacttcc tgttactcac tcatcagtgt ggcctaacac gttttcact gaccccaggc    115500 tggtgaacgc tcccctctgg ggttcgggcc tgacgatgcc atcctttttgt gaagtgagtc   115560 cctgcccctg aggacctgca atcccagctt cgtaaagccc gcggggaatc actcacagtt   115620
ccgggatgcc ttcggggcag ccctctctct gtcccttcag ctccccctgggg gtgtgactca  115680
```

```
atctcccgcc actccccaga ctgcctctgc caagtccaaa agtggaggca tcctttcgag   115740
caagcaggcg ggtccagggt gacgcgtgtc actcatcgaa aatggaggcg tccttgtgag   115800
aaagcaggcg ggtccagggt gacgcgtgtc actcatcgaa aatggaggcg tccttgtgag   115860
aaagcaggcg ggtccagggt ggtgtgtgtc actcatcaaa agtggaggca tccttgcgag   115920
caagcaggcg ggtccagggt gacgtgtcac tcatcctttt ttctggctat caaaggtgca   115980
gataattaat aagaagctgg atcttagcaa cgtccagtcc aagtgtggct caaaggataa   116040
tatcaaacac gtcccgggag gcggcagtgt gagtaccttc acacgtcccg tgcgccgtgc   116100
tgtggcttga atttttagga agtggcgtga gtgcgtacac ttgcgagaca ctgcatagaa   116160
taaatcctcc ttgggctctg aggatctggc tgcgcccct gggtgaatgt agcccggctc    116220
cccacattcc ctcacacagt caactgttcc cagaagcccc ctcctcatgt tctaggaggg   116280
agtgtcccag catttctggg tccccaggcc gtgcaggctg cgtgtacaga atagggtgtc   116340
tgacggaccc tctctccagc ccctgcctgg gaagctgaga atacccgtca aggtctccct   116400
ccactcacac ccagccctgt ccccaggagc cccatagcgc attgaaagtt gggctgaagg   116460
tggtggcacc tgagactggg ctgccgcctc cacccccgac acctgggcag gttgacgttg   116520
actggctcca ctgtggacag gtgacccgtt tgttctgatg agtggacacc aaggtcttac   116580
cttcctgctc agctgtgcct cctatgtgtt caaggcagga gcggattcct aagcctccaa   116640
cttatgctta gcctgcacca ccctctggca gagactccag atgcaaagag ccaaaccaaa   116700
gtgtgacagg tccctctgcc cagcgttgag gtatggcaga gaaatgctgc ttttggccct   116760
tttagatttg gctgcctctg gtcagaagcg gtggctcatg cctgtaatcc cagcactttg   116820
ggagatgaag acggtaggtt tgcttgagcc caggagttca agtccagcct gggcaacagt   116880
gagacccctg tctctacaaa aaaaatttaa attacccagg tgtggtggtg tgcacctgta   116940
gtcccagcta cttgggaggc tgaggtggga ggatcacctg agtccgggag gcagaggttg   117000
taaggagcca tgatcgcgcc actgcacttc aactgaggca acagagcgag actttgtctc   117060
aaaaaacaat ggtataataa ttttaaaata aatagatttg gcttcctgta aatgtccctg   117120
gtgagattcg ggactcagat cctcaagtcc cactgactca cccgatgagc tgaggcttca   117180
tcatcccctg gccggtctat gtccacgggg caccggaggc tcctctccca ccagcagtct   117240
tggtgagctg aaagcaaact gttaacaccc tggggagctg gaggtatgag accctcgagg   117300 tccacccccaa gggaggcgtt gattttgag agcaatcacc tgaccctggc tggcagtacc   117360
aggacactgc tgtggctctg gggcgggctg tctccggaaa atgcctggcc tggggcagcc   117420
acccgcatcc agcccagagg gtttattctt gcaatgtgct gctgcttcct gcactgagca   117480
cctggatcct ggcttctgcc ctgaggcccc tggagtccca caagtagcaa gcgcttggcc   117540
tgcggctgct gcatggggct actaacgctt cctccaccagt gtctgctaag tgtctcctct   117600
gtctcccacg ccctgctctc ctgtcgcccc agtttgtctg ctgtgagggg acaaaagaga   117660
tgtgtgcccc caccccctgcc caggtccttg ttcctgggat tgctgttcag ctgtttgagc   117720
tttgatcctg gttctctggc ttcctcaaag tgggctcggc cagaggagga aggccatgtg   117780 cttttctggtt aaagtcgagt ctggtggcct ggtgagact cgctcctga ggcggagctg     117840 gggatagagc actcatgggc tgcgtggcca accctctgg tagctgatgc ccaaagacgc    117900
tgcagtgccc aggacatccg ggacctccct ggggcccgcc cgtgtgtcct acgctgtgct    117960
cgtctgtggg ctagcctgtg acccgcgctg tgctcatctg tgggctagcc tgtgacctgg   118020
```

```
cagagagcca ccagatgtcc cgggctgagc accgccctct gagcaccttc acaggaagcc 118080
tttctcctgg tgagaagaga tgccagcctc tggcatctgg gggcactgga tccctggcgg 118140
cggctagggc taggtggccc tagtctctcc ccagcctggg ggccccttcc cagcaggttg 118200
gccctgctcc ttctccacct gggacccttc ttcctcctgg ctgggccctg gaagttctgc 118260
aggacctgcc gtccccctcc ctggcctcca ggtatcttga ccaccgccct ggctcccact 118320
gccacccact cctctcctat ctggccgttc cctggtccct gtcccagccc cctcccccct 118380
ctcatgagtt tcctcaccaa ggccagaggg aagagggaag gaggccctgg tcataccagc 118440
acgtccttcc acctccctca gccctggtcc accccttgg cgccagcctc agagcacagc 118500
tctctccaac ccaggccgca caccgtccgt cctccctgcc cccacgtcct tgccgcagat 118560
cctgtccgcc ctgacacaca ttggcctcag ccatctctgc cccagttaac tccccatcca 118620
taaagagcac acgccagctg acgttaaaat aatttgggat ggttccagtg tagacctaag 118680
tagaagcggg aaccgctgcc cccactgcac cttggttcct ggtggccttg ataaaccatc 118740
ttcagccatg aagccagctg tctcccaggc agctccaggg cagggcttcc tggggagctg 118800
actgataggt ggggaggtggc tgccccctgg cacctcagg tgacccacac aaggccactg 118860
ccggaggccc tggggactcc agaatgtcag tcatgacccg cccccaggcc gcacacagcc 118920
acggtttcac agatgccggc ctccagggga cctgtctgtc tgccactcgg agtccccaca 118980
gggtgccccc ccaggggagc tggctctcgg actgagatca gctggcagtc cggactgtca 119040
ttccccgagg gagcggtgcc ctggatccca caggcctccg catgtgtgtc tgtgtccgtt 119100
cgagcttgct gagacattca atctgttggt ttctgttgtg ccgcctaccc accctgtcga 119160
tgatgctttg ctcctgttgc taaagacagg aatgcccagg accctgagtg tgcaggtgcc 119220
cgctggctct cacgtccgag ctgctgaact ccgctgggtc ctgcttactg accgtctttg 119280
ctctagtgct gtccgtggaa gcttttcctg gaataaagcc cacccatcaa ccctcacagc 119340
gcctcccctc tttgaggccc agcagatagc gcactccagc cttccagca agattttca 119400
gatgctgtgc atactcatca tattgatcac ttttttcttc atgtctgatt gtgatctgtc 119460
gatttcatgt taggaaaagg agtgactttt ttacccttaa gcctttgctg agcaaatgtc 119520
tgggccttgc acaatgacaa cgggtccctg ttttcccag aggctctttt gttctgcagg 119580
gattgaagac actccaatcc cacagtcccc agctcccctg gagcagggtt ggcagaattt 119640
cgacaacaca ttttccacc ctgaataggg tgcgctcctc atggcagctg gaaccactg 119700
tccaatcagg gcctgggctt acacagctgc ttctcattgc attacacccct taataaaata 119760
atcccatttt atcctctttg tctctctgtc ttcttctctc tctgcctctc ctcttctcgc 119820
tcctctctca tctccaggtg caaatagtct acaaaccagt tgacctgagc aaggtgacct 119880
ccaagtgtgg ctcattaggc aacatccatc ataaaccagg tagccctgtg gaaggcgagg 119940
gttgggatgg gaaggtgcac ggggtggagg agtcctggcg aggctggaac tgccccagac 120000
ttcgaaaggg gctggaaagg atttgctggg tagaccatca aggagagttg agtgtggaac 120060
ttgcgggagc ccaggaggcg tggtggctcc agctcgctcc tgcccaggcc atgctggcca 120120
agacaaggta aggcgggagt gaagtcaaat aaggcaagca cagaaagaaa gcacatgttc 120180
ttggctgggc gcggtggctc acacctgtaa tcccagcact ttgggaggcc aaggcaggcg 120240
gatcacgagg tcaggagatt gagaccatcc tggctaacac ggtgaaaccc catctctact 120300
aaaattacaa aaaattagcc gggcatggtg gcgggcacct gtagtcccag ctactcagaa 120360
agctgaggca ggaaaatggc atgaacccag gaggcggagc ttgcagtgag ccgagatggc 120420
```

```
gccactgcac tccagcctgg gtgacagagc gagactctgt ctcaaaaaaa aaaaaaacac 120480
acacacatgt tctcgcttat ttgtgggatc caggagatag ataatagaag gatgattatc 120540
agaggctggg aagggtagtg aggggatggt ggggagatgg ttaatgggta caaaaaaaaa 120600
tagaataaga cctagtattt gatagtgcaa cagggtgact atagtcaata ataatttaat 120660
tgtacattta aaataaacta aaagatagcc agatgcactg gcttacgtct gtactcccag 120720
cactttggga ggccgaggtg ggcatttgag accagcctgg ccaacatggt aaaaccccat 120780
ctctactaaa aatacaaaaa ttagctgggc gtggtggcgg gcacctgtaa tcccagctac 120840
tcgagaggct gaggcaggag aatcacttga acctggaggc agaggttgca gtgagccaag 120900
atcttgccac tacactccag cctgggtgac agagcgaaac tctgtctcaa aataaaaat 120960 aactaaaaga atataaatgg attgtttgta acacaaagga caaatgtttg cgggatgga 121020 taccccattt tccatgatgt gattattaca cattgtgttt ctgcatcaaa acatctcatg 121080
aaccccataa atatatatac ctactatgta cccataaaca ttttttttaaa aaattttttc 121140 aaggtgaaga gggaggcaag atgctggcct taagccctaa cccgggattc tcccagcaag 121200
ctgtccacag gtcttctcag gcttgaggtg cagctatatg gatgtgtgag cttggtcccc 121260
agccaacatg gagacacttc actatcggca gcagctacag cacaggaacc ctgggtcact 121320
gccgtgtccc ctctgtgact ttgtttaaac agaaaatgat gctctgggct ggccgcggtg 121380
gctcacgcct ataattccag cactttggga ggctgaggtg ggcagatcat gaggtcagga 121440
gatcgagact atcctggcta acacggtgaa accccatctc tgctaaaaat acaaaaaact 121500
agccgggcgt ggtggcgggc gcctgtagtc ccagctactt gggaggctga ggcaggagaa 121560
tggcgtgaac ccaggaggca gagctgcagt gagctgagat cgcgccactg cactccagcc 121620
tgggtgacag agtgagactc catctcaaag aaaaaataaa ataaaaaaat acttgactta 121680
ctggaagcca accaatgtat aatttagaat aatttctcct gggttgagct gtcacttacc 121740
tttgcagtat ctcaagagga agagttcact gtgtaaatat tgatgcatac tttgattaga 121800
tagatgaagc aaactatttt caagcacttt tcaaggactt acttgtatcc aaacagcatt 121860
ctaaaggaaa gtcttaccta cttctaaagg ctggtctcta cttgaaacct cttgcttggc 121920
cctggttcaa gtcctgctgc aaacctggaa gtcccgtcac tgtcttcttc cctgcagagc 121980
agtggctccc gatctaattt ttgctgtgcc ccagcagccc ctggcacttt gccctgtaga 122040
ccacagacct catgtaatgt gtgctaagtc cacggaactg cggaagatga tggcaagatg 122100
ctcttgtgtg tgttgtgttc taggaggtgg ccaggtggaa gtaaaatctg agaagctgga 122160
cttcaaggac agagtgcagt cgaagatcgg gtccctggac aatatcaccc atgtccctgg 122220
cggaggaaat aaaaggtaa aggggcgggt ttggatgctg cacttgggta tgggcattaa 122280
tcaagtcgag tggacaaaga ctggtccagt tcccagagga ggaaaacaga ggcttctgtg 122340
ttgactggct ggatgtgggc cctcagcagc atccagtggg tctcgactgc ctgtctcaat 122400
caccttcacc aggagcttta gcacatttca cagctgggct ccaacctgga gaggctgact 122460
gatcggtctt aggtgcagct cagttgctgg agttttttgtt tttatttatt tttaagtatt 122520
tgaggcaggg tctctgtatt agtctgttct cacactgcta ataaagacat acccaagact 122580
gcgtaattta taaggaaag aggtttaatg gactcacagt tccacatggc tggggaggcc 122640
tcaaaatcat ggtggaaagc aaaggagaag caaaggcatg tcttacatag cagcaggcaa 122700
gagagcgtgt gcagggcaac tcccatttat aaaaccatca gacctcatga gacttattca 122760
```

```
ctatcatgag aacggcatgg gaaagacccg cccccatgat tcagttacct cccactgggt 122820
ccctcccatg atacatggaa ttatgggaac tacaattcaa gatgagattt gggtggggac 122880
acagccagcc cgtatcattc tccctctgtc atccaggctg gagtgcatta gcatgatctc 122940
agctcactgc agcctctacc tccctgggtc aggtgatcct cccacctcag cctcccaagt 123000
agctggaact acaggtatct gccactatgc ccggctaaat attttgtatt tcctgtggag 123060
acgaggtttt gccatgttgc ccaggctggt cttgaactcc tgaggtcaag caatatgccc 123120
acctcagcct cccaaggtgc tgggattaca ggtgtgagcc acagtgcttg gcctaagtgg 123180
ctgcagtttt taaagctccc aggtgattct ttagtgcagt caaaagtgag aactagctgg 123240
gtgcggtggc tcatgcctgt aatcccagca ccttgggagg ccaaggtggg cagatggttt 123300
agtagagatg atctctacta aaaatacaaa agttagctgg gtgtggtggt gcatgcctgt 123360
aatcccagct acttgggagg ctgaggcatg agaatcgctt taacccaggt ggcagaggtt 123420
gtagtgagcc aagatcatgc cactgcactc cagtctgggg aacagagtga gactccatct 123480
caaaaaaaaa aaaaaaaaa atgagaacca ctgtcctagg ccctgatgtt tgcagacaac 123540
taaaaaagga agtggacatc cccagtcacc tgtggcgcac caagaacaca tgggaacata 123600
atctaattt ctaaatgggt tactaggcac ttagagcaaa acaatgatgc tgaaatcctg 123660
atttcaggaa agcctctgcc tgcctgttgt ggaagtgtcc acacgaggct cctgggcct 123720
tggtgtcccc agcagtttct agtctccagg tcttgctgtg ggtgtctgtg cagtgagggt 123780
gtgtgtggcg ctaagcgaga tctgtctagg gctggcacag gatgcggtct ggtagctgct 123840
gcttctcttc tgcagaagcg cagccaagca ccctctgggg tttcctgccc acacccagcc 123900
tgaagttctg ggagtggctc actttccaac cttcagggtc tcccaggagc tgactggggc 123960
gtggtagagg gaaaaggatt gtattagtct gttttcatgc tgccgatgaa gacctatccg 124020
atactgggca atttacaaaa gaaagaggtc tgatggagtt acagttccac gtggctgggg 124080
aggcctcaca atcatggcgg aaggtgagag gcttgtttca catggtggca gacaagaaaa 124140
gagagcttgt gcaggggaac tcccctttat aaagccatca gatctcggga gacttactat 124200
catgagaaca gcactatcat gagaacatag gggcagggaa aacccgcccc tacgattcaa 124260
tcctctccca tcgggtccct cccacaacgt gtaggaattg tgggaactat aattcaagat 124320
gagatttggg tggggtcaca gccaaaccgt atcgggtgt cccagaaagg gtgtgggatc 124380
tgagacccag ctcggcgtga ggaagtttgc ttctcgaggt ggcccagtcg ggtggaagtg 124440
gcaaccaggc tgtctctcca ccaggccact caggtggcag ctgagagacc cctgccctgg 124500
tcagtctccg ccctcccctc ttgccactgc atctggttct gaacagatgg gcaccctcat 124560
cttgtgtttg tgataaatgt ctaaccatgt agttttgtga gaagtgtttg ccgcagatgc 124620
tgtaaactgt ggcctggggc agacctcacc tccagacagg ccctgaggct ggcgagggca 124680
ctggcccata gtagctggcc gagagctctc aggttgtgcc acgcaggaca cagggatact 124740
tttcagtgcc tgggtcacta tccaaagtga gaaaacagcg ggggaccagg aggctgcccg 124800
cctcaaggga tgtgggggcc gggcccagtt atctgaggaa gcagtcagct tctctgctgt 124860
ttccaccagc caggcctccc ctggtctaag gcagggcctc ccagccttgg ggcgctttaa 124920
agatacctgg gcctggcccc atcccacag tctgactgag tgggtcggga taggggcatg 124980
ggcattggcg atttcctggg tgaagggagg cccgctgcag tctctggaag cttctctgtg 125040
ttaggaagag ctctgggctt gactctgctc ggagagtcaa gatccgcaaa tcctctcagc 125100
ctcagtttct ccttcagcaa gatgaaatgg aaatgctgta cctacgtccc agggtggttg 125160
```

```
tgagaccccc ccccccaaaa aaaacaatgt tctggaaggt tcctggtgcg ttgcagtcct   125220
ctaagaacct gagttagagc catgctgagt ctcagcttct tggctccttc tgtttccaac   125280
ttgtccatgt gatggctcag gaaggtgggc agggccctgc ccctactcag aaaacatcat   125340
cctggtccca gggatccccg cagcgttagt cccgttttcc gtgtgttgag aaaaattgct   125400
aacaagcagt ggggcacacc accagcctcc tgggttcttt tcagtttggg gattttggga   125460
cattcccagg aatgtcaact ttctcttaaa aaacacttca aaaaacatta acataaatat   125520
ttttatcaaa gcttgtatta aatggtcttt caagaaaata cagtaacagg ccaggcatgg   125580
tggctcacgc ctgtaacccc agcactttgg gaggccaagg caggcagatc acctgaaatc   125640
aggagttcga caccagcccg gccaatgcag cagaaccccg tctctacaaa aaatacaaaa   125700
attagctggg tgtggtggca cacctgta gtcccagcta ctcgggaggc cgaggcagaa   125760
ttgcttgatc ccaggaggtg gaggttgcag tgagctgaga ttgcgccact gcactccagc   125820
ctgggtgaca agagtgaaac tttgtctaaa aaaaaaaaa aaagaaaaa gaaaatacac   125880 taatagagaa caatctgttt ttcaaagtag tgactgcaaa tgaacaaaat atgcatctag   125940
cttaaacggg agcatggttt tctctatgcc cattcaagcc tgctgcaata ggggcccttc   126000
agcctggatc catggactcc taaaattata tggaaaatgg ctgtgtgggt gtgagcgtgg   126060
gtggacatgt gcacacatat ttttggcttt accagatgct caaagagcct aggacccaac   126120
aagggctgag gataaccctg tcggccgctt cagggtcatc aggaattcct gtgcgctgct   126180
cacttctcca gtgagcgcct tctgcttccg cgtttcctgg tatccttcgg ggctcctggc   126240
taggtcatgt gtttctctac tttcttttt tttctttttt tttttttgag acggagtctc   126300
gctctgccgc ccagactgga gtgcagtggc tggatctcag ctcactgcaa gctccgcctc   126360
ccgggttcac gccattctcc tgcctcagcc tcccgagtag ctgggactac aggcgcccgc   126420
cacctcgccc ggctagtttt ttgtattttt tttttagtag agacggggtt tcaccgtgtt   126480
agccaggatg gtcttgatct cctgacctcg tgatccgccc atctcggcct cccaaagtgc   126540
tgggattaca ggcttgagcc accgcgcctg gcctgtttct ctactttcaa aagggcttca   126600
gccaggcacg gtggcatgag cctgtagtcc cagctgcccg ggaggttcag gtgggaagat   126660
tgcttgagcc caggaatttg aggccagcct gggcaagtag atagataggt agatgataga   126720
tagatagata gatagataga tagatagata gatagataga tagatagata gatgataga   126780 tagatagata gatgtataat agatggatag ataagtcgct agacagactc catcctaaat   126840
cacccatcca cctacccaca cataaaaagg cctttgtcat gtcatgtttt gtggcccacc   126900
tgccagtgct gcccacagtt gctgcccctc caaactcatc agtcactggc aaacaggagg   126960
aatgtgtgtg gctcatgtct gggcatcagt ggctgtggga gacatccttg atcttctcca   127020
gcttctcctt ccacatttc ctttgcaatc tggcaatatc tatcaaaata aaatgcgcat   127080 gcctttgac ctaagagctc cacttctagg acacacttac aggtgtgtga catgatgttc   127140
attcagggtt atttatctga ggttgttcat acacaccatt gcctgtaatc actaaaggcg   127200
ggagcagcct aggcatccat tcacagagga gtagacgcct ttggatacat ccgtggtgac   127260
ggaatactaa gcagcctgtg tacatataca ctcacacatg tgtttgttta tgtgtggaat   127320
atctctgcag gatacacaag aaacttaaaa tgatcactgt ctctggggag ggtacctggg   127380
tgcctgggag gcaggtcagg ggaggagtgg gcacagggat tacgaattgg aagacaataa   127440
aaacaacagc ttctggccag gcacagtggc tcacgcctgt aatggcagca ctctgagagg   127500
```

```
ccgaggcggg cggattgctt ccgcccaaga gttcgagacc agcctgggca acatagtgaa 127560
accccgtttc tattaaaaat acaaaaaact agccaggtgt ggtggcatgc acctgtaatc 127620
ccagctaccc gggaggctga ggtgggagaa tcacctgagc ctgggaggtt gaggctgcag 127680
tgaggtgaga ttgcaccacc tcactctagc ctgggtgata gagcaagacc ctgtctcaaa 127740
aacaaacaaa caacagtccc tggcactgtg ggccaggcct ggcagggcag ttggcagggc 127800
tggtctttct ctggcacttc atctcaccct ccctcccttc ctcttctcct tgcagattga 127860
aacccacaag ctgaccttcc gcgagaacgc caaagccaag acagaccacg ggcggaaat 127920
cgtgtacaag tcgccggtgg tgtctgggga cacgtctcca cggcacctca gcaatgtctc 127980
ctccaccggc agcatcgaca tggtagactc gccccagctc gccacgctag ccgacgaggt 128040
gtctgcctcc ctggccaagc agggtttgtg atcaggcccc cggggcggtc aataatcgtg 128100
gagagaagag agagtgagag tgtggaaaaa aaagaataa tgacccggcc ccgccctctg 128160
cccccagctg ctcctcgcag ttcggttaat cggttcatca cttaaccggc ttttatcgct 128220
cggctttggc tcgggacttc aaaatcagtg atgggaataa gagcaaattg catctttcca 128280
aattgatcgg tgggctaata ataaaatatt ttttaaaaaa cattcaaaaa catggccaca 128340
cccaacattt cctcgggcaa ttcctttga ttctttttttt ttcccccctcc atgtagaaga 128400
gggagaagga gaggctgtga aagctgcttc gggggggattt caagagactg ggggtgccca 128460
ccgcctctgg ccctgtcgtg gggtgtcac agaggcagcg gcagcaacaa aggatttgaa 128520
acttggtgtg ttcgtggagc cacaggcaga cgatgtcaac cttgtgtgag tgtgacgggt 128580
gggggtgggg cggaggcca tggggaggc caaggcaggg gctgggcaga ggggagagga 128640
aggacgagaa gggggagtgg gagaggaagc cacatgctgg agaggagatg ccctcctccg 128700
cgccactggg agggccaagg cctccgccac ctgcagtgtc tcagactgag cggctgcctg 128760
tccttggtgg ccagggtctg ctgcgagttg atgtgccacc ctctgcaggg cagcctgtgg 128820
gagaagggc ggcgggtaag aagagaaggc aagctggcgg gagggtggca ccccgtggat 128880
gacctccttg gaaaagactg accttgatgt cggagggcgc tggcctcttc ctccctccct 128940
gcagggtagg gggcctgagc cgaggggctt ccctctgctc cacagaaacc ctgttttatt 129000
gagttctgaa ggttggaact gcagccatga ttttggccac tttgcagacc tgggacttta 129060
gggctaacca gttctctttg taaggacttg tgcctcttgg gagacgtcca cccgtttcca 129120
agcctgggcc accggcatct ctggagtgtg caggggtctg ggaggcgggt cccgagcccc 129180
ctgtccttcc cacggccact gcagtcaccc ctgtctgccc cactgtgctg tcgtctgcca 129240
tgagaaccca gtcactgcct ataccctca tcacgtcaca atgtccaaat tcccagcctc 129300
accacccccc ttctcagtaa ggaccctggt tggctgtggg aggcacctac tccatactga 129360
gggtgaaatt aagggaaggt aaagtccagg cacaagagtg ggaccccagc ctctcactct 129420
cagttccact catccaactg ggtccctcac cacgaatctc acgacctgat tcggttccct 129480
gcctcctcct cccatcacag atgtgagcca ggcactgct cagctgtgac cctcggtgtt 129540
tctgccttgt tgacatagag agagcccttt cccccgaga aggcctggcc ccttcctgtg 129600
ctgagcccgc agcaggaggc tgggtgtcct ggttgtcggt gacggcacca ggatgggcgg 129660
gcaaggcacc cagggcaggc ccacagtccc gctgtccccc acttgcaccc cagcttgtgg 129720
ctgccagcct cccagacagc ccagcccgct gctcagctcc acatgcatag aatcagccct 129780
ccacatccca aaaggggaa cacaccccct tcgaaatggt tttctccccg gtcccagctg 129840
gaagccatgc tgtctgttct gctggagcag ctgaacatat acatagatgt tgccctgccc 129900
```

```
tccccatctg cacectgttg cgttgtagtt ggatttgtct gtttatgctt ggattcacca  129960
gagtgactat gatagtgaaa agaaaaaaaa aaaaaaaaa aggacgcatg tatcttgaaa  130020
tgcttgtaaa gaggtttcta acccaccctc acaaggtgtc tctcacccce acgctgggac  130080
gcgtgtggcc tgtgtggcgc cgccctgctg gggcctccca aggtttgaaa ggctttcctc  130140
agcatccggg acccaacaga gaccagattc tagcatctaa ggaggccgtt cagctgtgaa  130200
gaaggcctga agcacaggat taggactgaa gcgatgacat ctccttccct acttcccctt  130260
ggggctctct gtgtcagggc agagagtagg tcttgtggct ggtctggctt gcggcacgag  130320
gatggttctc tctggtcaca gcccgaagtc ccacagcagt cctaaaggag gcttacaact  130380
cctgcatcac aagaagaagg aagccagtgc cagctggggg gatctgcagc tcccagaagc  130440
tccatgagcc tcagccaccc cgcagactgg gttcctcgcc aagctcgccc tctggagggg  130500
cagccagcct cccaccaagg gccctgcgac cacagcaggg attgggatga atggcctatc  130560
ctggatctgc tccagaggcc cgagccacct gcctgaggaa ggataagtca ggagacaccg  130620
ttcccaaagc cttgaccaga gcacctcagc ccactgacct tgcacaaact ccatctgctg  130680
ccatgagaaa agggaagccg cctttgcaaa aaattgctgc ctaaagaaac tcagcagcct  130740
caggctcaat tctgccgctt ctggtttggg tacagttaaa ggcaaccctg agggacttgg  130800
cagtagaaat ccagggcatc ccctagggct ggcaacttcg tgtgcagcta gagctttccc  130860
tgcaagaagt ttctgggccc agaactctcc accaggaagc tccctgctgt tcgctaagtc  130920
ccagcaattc tctaagtgaa gggatctgag aatgaggagg aaatgtgggg tagagatttg  130980
gtggtggtta gagacatgcc cccctcatta ctgccaacag tttcggctgc atttttcacg  131040
tacctcggtt cctcttcctg aagttcttgt gccctgctct tcagcaccgt gggccttatc  131100
cggtaggctc tgggatctcc cccttgtggg gcaggctctt ggggccagcc taagatcatg  131160
gtttagggtg atcagtgctg gcagataaat tgcaaaggca cgctggcttg tgacctcaaa  131220
tgacaatccc cccagggctg ggcactcctc ccctcccctc acttctccca cctgcagagc  131280
cagtgtccgt gggtgggcta gataggatat actgtatgcc ggctccttca agctgttgac  131340
tcactttatc aatagttcca tttaaattga cttcaatggt gagactgtat cctgtttgct  131400
attgcttatt gtgctatggg gggaggggg aggaatgtgt aacatagtta acatgggtaa  131460
agggagatct tggggtgcag cacttcaatt gcctcgtaac ccttttcatc atttcaacca  131520
catttgctaa agggagggag cagccacgcg gttagaggcc cttggggttt ctcttttcca  131580
ctgacagcct ttcccaggca gctggccagt tccccattcc ctccccagcc aggtgcaggc  131640
gtagcaatat ggacatctgg ttgctttggc ctgctgccct cttcagggg tcctaagccc  131700
acaatcatgc ctccctaaga ccctggcatc cttccttta agccgttggc acctctgtgc  131760
cacctctcac actggctcca gacacagcct gtgcttctgg cagctgagat cactcacttc  131820
ccctcctca tctttgttgg agctccaagt caagccacga ggtcagggcg agggcagagg  131880
tggtcaccag cgtgtcccat ctacagacct gtggcttcgt aagacttctg atttctcttc  131940
agctttgaaa agggttaccc tgggcactgg cctagagtct cacctcctaa tagacttacc  132000
cccatgagtt tgccatgttg agcaggacaa tttctggcac ttgcaagtcc catgatttct  132060
tcggtaattg tgagggtggg gggagggaca tgaaatcatc ttagcttagc ttcctgtctg  132120
tgaatgtcta tatagtgtat tgtgtgtttt aacaaatgat ttacactgac tgttgccgta  132180
aaagtgaatt tggaaataaa gttattactc tgattaaa                          132218
```

```
<210> SEQ ID NO 3
<211> LENGTH: 61
<212> TYPE: DNA
<213> ORGANISM: Artificial
<220> FEATURE:
<223> OTHER INFORMATION: Target region

<400> SEQUENCE: 3
gattaaggca tgagtgatta aattaaagcc aggcattgac ttggatggtg taatattctg    60
a                                                                    61

<210> SEQ ID NO 4
<211> LENGTH: 32
<212> TYPE: DNA
<213> ORGANISM: Artificial
<220> FEATURE:
<223> OTHER INFORMATION: Target region

<400> SEQUENCE: 4
gaaggttgaa atgagaattg atttgagtta aa                                  32

<210> SEQ ID NO 5
<211> LENGTH: 104
<212> TYPE: DNA
<213> ORGANISM: Artificial
<220> FEATURE:
<223> OTHER INFORMATION: Target region

<400> SEQUENCE: 5
tggttaccta taaactagtg caccctaatg aattaaaagg tgttgatgag ttaacttgtt    60
atgccttcca gataagacat gcaaatgggg cttcttcctc cttc                    104

<210> SEQ ID NO 6
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 6
tcactcatgc cttaatc                                                   17

<210> SEQ ID NO 7
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 7
taatcactca tgcctta                                                   17

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
taatcactca tgcctt                                                    16

<210> SEQ ID NO 9
<211> LENGTH: 19
```

```
<212> TYPE: DNA
<213> ORGANISM: Artificial sequence
<220> FEATURE:
<223> OTHER INFORMATION: Synthetic oligonucleotide

<400> SEQUENCE: 9
ctttaattta atcactcat                                                19

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gctttaattt aatcactcat                                               20

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
ctttaattta atcactca                                                 18

<210> SEQ ID NO 12
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 12
ctttaattta atcactc                                                  17

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tccaagtcaa tgcctggctt                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
atccaagtca atgcctggct                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
```

| | |
|---|---|
| accatccaag tcaatgcctg | 20 |

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16

| | |
|---|---|
| caccatccaa gtcaatgcct | 20 |

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17

| | |
|---|---|
| tacaccatcc aagtcaatgc | 20 |

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18

| | |
|---|---|
| ttacaccatc caagtcaatg | 20 |

<210> SEQ ID NO 19
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 19

| | |
|---|---|
| acaccatcca agtcaat | 17 |

<210> SEQ ID NO 20
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 20

| | |
|---|---|
| tacaccatcc aagtcaa | 17 |

<210> SEQ ID NO 21
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 21

| | |
|---|---|
| ttacaccatc caagtca | 17 |

<210> SEQ ID NO 22
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 22
ttacaccatc caagtc                                                      16

<210> SEQ ID NO 23
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 23
aatattacac catccaa                                                     17

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
agaatattac accatccaa                                                   19

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cagaatatta caccatccaa                                                  20

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
gaatattaca ccatccaa                                                    18

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
aatattacac catcca                                                      16

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
agaatattac accatcca                                                    18
```

<210> SEQ ID NO 29
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 29
cagaatatta caccatcca                                                19

<210> SEQ ID NO 30
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 30
gaatattaca ccatcca                                                  17

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tcagaatatt acaccatcca                                               20

<210> SEQ ID NO 32
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 32
agaatattac accatcc                                                  17

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
cagaatatta caccatcc                                                 18

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
gaatattaca ccatcc                                                   16

<210> SEQ ID NO 35
<211> LENGTH: 19
<212> TYPE: DNA
<213> ORGANISM: Artificial sequence
<220> FEATURE:
<223> OTHER INFORMATION: Synthetic oligonucleotide -continued

```
<400> SEQUENCE: 35
tcagaatatt acaccatcc                                               19

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
agaatattac accatc                                                  16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
cagaatatta caccat                                                  16

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
caattctcat ttcaaccttc                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tcaattctca tttcaacctt                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
atcaattctc atttcaacct                                              20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aatcaattct catttcaacc                                              20

<210> SEQ ID NO 42
```

-continued

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
aaatcaattc tcatttcaac                                                    20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
caaatcaatt ctcatttcaa                                                    20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
tcaaatcaat tctcatttca                                                    20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
ctcaaatcaa ttctcatttc                                                    20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
actcaaatca attctcattt                                                    20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
aactcaaatc aattctcatt                                                    20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48

```
taactcaaat caattctcat                                        20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ttaactcaaa tcaattctca                                        20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tttaactcaa atcaattctc                                        20

<210> SEQ ID NO 51
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 51
tttaactcaa atcaattct                                         19

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
ccttttaatt cattag                                            16

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
caacaccttt taattcatta                                        20

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
aacacctttt aattcatt                                          18

<210> SEQ ID NO 55
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 55
catcaacacc ttttaattca                                              20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ctcatcaaca ccttttaatt                                              20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
actcatcaac accttttaat                                              20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
aactcatcaa caccttttaa                                              20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
taactcatca acacctttta                                              20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
ttaactcatc aacacctttt                                              20

<210> SEQ ID NO 61
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 61
ttaactcatc aacaccttt                                               19
```

<210> SEQ ID NO 62
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 62
ttaactcatc aacacctt                                                 18

<210> SEQ ID NO 63
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 63
ttaactcatc aacacct                                                  17

<210> SEQ ID NO 64
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 64
gttaactcat caacacc                                                  17

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
gttaactcat caacac                                                   16

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
atttccaaat tcacttttac                                               20

<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 67 ccgtttctt accaccct                                                  18